US012617773B2

(12) United States Patent
Allemann et al.

(10) Patent No.: US 12,617,773 B2
(45) Date of Patent: May 5, 2026

(54) AZETIDIN-3-YLMETHANOL DERIVATIVES AS CCR6 RECEPTOR MODULATORS

(71) Applicant: Idorsia Pharmaceuticals Ltd, Allschwil (CH)

(72) Inventors: Oliver Allemann, Allschwil (CH); Eva Caroff, Allschwil (CH); Alexia Chavanton-Arpel, Allschwil (CH); Andrew Croxford, Zurich (CH); Francis Hubler, Allschwil (CH); Loïc Jacob, Allschwil (CH); Emmanuel Meyer, Allschwil (CH); Sylvia Richard-Bildstein, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 680 days.

(21) Appl. No.: 17/997,531

(22) PCT Filed: Apr. 30, 2021

(86) PCT No.: PCT/EP2021/061401
§ 371 (c)(1),
(2) Date: Oct. 28, 2022

(87) PCT Pub. No.: WO2021/219849
PCT Pub. Date: Nov. 4, 2021

(65) Prior Publication Data

US 2023/0174514 A1 Jun. 8, 2023

(30) Foreign Application Priority Data

Apr. 30, 2020 (WO) ................. PCT/EP2020/062103

(51) Int. Cl.

| | |
|---|---|
| ***C07D 401/14*** | (2006.01) |
| ***A61K 31/4427*** | (2006.01) |
| ***A61K 31/4439*** | (2006.01) |
| ***A61P 29/00*** | (2006.01) |
| ***A61P 35/00*** | (2006.01) |
| ***A61P 37/00*** | (2006.01) |
| ***C07D 401/12*** | (2006.01) |
| ***C07D 405/14*** | (2006.01) |
| ***C07D 413/14*** | (2006.01) |
| ***C07D 417/14*** | (2006.01) |

(52) U.S. Cl.
CPC ........ *C07D 401/14* (2013.01); *A61K 31/4427* (2013.01); *A61K 31/4439* (2013.01); *A61P 29/00* (2018.01); *A61P 35/00* (2018.01); *A61P 37/00* (2018.01); *C07D 401/12* (2013.01); *C07D 405/14* (2013.01); *C07D 413/14* (2013.01); *C07D 417/14* (2013.01)

(58) Field of Classification Search
None
See application file for complete search history.

(56) References Cited

U.S. PATENT DOCUMENTS

| | | | | |
|---|---|---|---|---|
| 3,458,635 | A | 7/1969 | Lunsford et al. | |
| 3,479,370 | A | 11/1969 | Lunsford et al. | |
| 3,489,769 | A | 1/1970 | Helsley et al. | |
| 3,499,002 | A | 3/1970 | Helsley et al. | |
| 3,542,807 | A | 11/1970 | Lunsford et al. | |
| 3,651,085 | A | 3/1972 | Lunsford et al. | |
| 2003/0119806 | A1 * | 6/2003 | Lindell ................ | C07D 403/10 514/210.01 |
| 2014/0296254 | A1 | 10/2014 | Musicki et al. | |
| 2014/0309208 | A1 | 10/2014 | Musicki et al. | |
| 2015/0105366 | A1 | 4/2015 | Leonard et al. | |
| 2025/0011313 | A1 | 1/2025 | Alleman et al. | |
| 2025/0042881 | A1 | 2/2025 | Alleman et al. | |

FOREIGN PATENT DOCUMENTS

| | | | |
|---|---|---|---|
| CN | 103588697 | A | 2/2014 |
| GB | 1304650 | A | 1/1973 |
| WO | WO 91/13359 | A1 | 9/1991 |
| WO | WO 1993/020063 | A1 | 10/1993 |
| WO | WO 99/43664 | A1 | 9/1999 |
| WO | WO 03/022808 | A1 | 3/2003 |
| WO | WO 2006/136830 | A1 | 12/2006 |
| WO | WO 2007/022351 | A2 | 2/2007 |
| WO | WO 2008/103426 | A1 | 8/2008 |
| WO | WO 2010/131145 | A1 | 11/2010 |
| WO | WO 2013/061004 | A1 | 5/2013 |

(Continued)

OTHER PUBLICATIONS

Abe, F. et al., "Histone deacetylase inhibitors inhibit metastasis by restoring a tumor suppressive microRNA-150 in advanced cutaneous T-cell lymphoma," Oncotarget, 2017, 8 (5), 7572-7585.
Abraham, M. et al., "Natural and induce immunization against CCL20 ameliorate experimental autoimmune encephalitis and may confer protection against multiple sclerosis," Clinical Immunology, 2017, 183, 316-324.
Acosta-Rodriguez, E. et al., "Surface phenotype and antigenic specificity of human interleukin 17-producing T helper memory cells," Nature Immunology, 2007, 8 (6) 639-646.
Baeten, D. et al., "Secukinumab, an Interleukin-17A Inhibitor, in Ankylosing Spondylitis," The New England Journal of Medicine, 2015, 373 (26), 2534-2548.

(Continued)

*Primary Examiner* — Kortney L. Klinkel
*Assistant Examiner* — Dawanna Shar-Day White
(74) *Attorney, Agent, or Firm* — Hoxie & Associates LLC

(57) ABSTRACT

The present invention relates to compounds of Formula (I), their synthesis and use as CCR6 receptor modulators for the treatment or prevention of various diseases, conditions or disorders.

Formula (I)

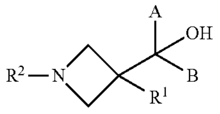

30 Claims, No Drawings

(56) References Cited

FOREIGN PATENT DOCUMENTS

| | | | |
|---|---|---|---|
| WO | WO 2013/061005 | A1 | 5/2013 |
| WO | WO 2014/062658 | A1 | 4/2014 |
| WO | WO 2014/075580 | A1 | 5/2014 |
| WO | WO 2015/057205 | A1 | 4/2015 |
| WO | WO 2015/057626 | A1 | 4/2015 |
| WO | WO 2015/084842 | A1 | 6/2015 |
| WO | WO 2017/087607 | A1 | 5/2017 |
| WO | WO 2019/036374 | A1 | 2/2019 |
| WO | WO 2019/105915 | A1 | 6/2019 |
| WO | WO 2019/136370 | A2 | 7/2019 |
| WO | WO 2019/147862 | A1 | 8/2019 |
| WO | WO 2020/058869 | A1 | 3/2020 |
| WO | WO 2023/057548 | A1 | 4/2023 |
| WO | WO 2023/072924 | A1 | 5/2023 |
| WO | WO 2023/073082 | A1 | 5/2023 |
| WO | WO 2024/121138 | A1 | 6/2024 |

OTHER PUBLICATIONS

Blokland, S. et al., "Decreased circulating CXCR3 + CCR9+T helper cells are associated with elevated levels of their ligands CXCL10 and CCL25 in the salivary gland of patients with Sjögren's syndrome to facilitate their concerted migration," Scandinavian Journal of Immunology, 2020, 91:e12852, 8 pages, https://doi.org/10.1111/sji.12852.

Bonelli, M. et al., "CCR6 controls autoimmune but not innate immunity-driven experimental arthritis," Journal of Cellular and Molecular Medicine, 2018, 22, 5278-5285.

Buhl, T. et al., "Molecular and Morphological Characterization of Inflammatory Infiltrate in Rosacea Reveals Activation of Th1/Th17 Pathways," Journal of Investigative Dermatology, 2015, 135, 2198-2208.

Campbell, J. et al.,"IL-17-Secreting γδ T Cells Are Completely Dependent upon. CCR6 for Homing to Inflamed Skin," The Journal of Immunology, 2017, 199, 3129-3136.

Campell, J. et al., "Efficacy of Chemokine Receptor Inhibition in Treating IL-36α-Induced Psoriasiform Inflammation," The Journal of Immunology, 2019, 202, 1687-1692.

Castro, G. et al., "RORγt and RORα signature genes in human Th17 cells," PLoS ONE, 2017, 12(8): e0181868, 22 pages, https://doi.org/10.1371/journal.pone.0181868.

Chabaud, M. et al., "Enhancing Effect of IL-1, IL-17, and TNF-α on Macrophage Inflammatory Protein-3α Production in Rheumatoid Arthritis: Regulation by Soluble Receptors and Th2 Cytokines," The Journal of Immunology, 2001, 167, 6015-6020.

Chang, H., et al., "CCR6 is a Predicting Biomarker of Radiosensitivity and Potential Target of Radiosensitization in Rectal Cancer," Cancer Research and Treatment, 2018, 50 (4), 1203-1213.

Chen, W. et al., "CCL20 Triggered by Chemotherapy Hinders the Therapeutic Efficacy of Breast Cancer," PLoS Biology, 2018, 16(7):e2005869, 27 pages, https://doi.org/10.1371/journal.pbio.2005869.

Chevrel, G. et al., "Addition of interleukin 1 (IL1) and IL17 soluble receptors to a tumour necrosis factor α soluble receptor more effectively reduces the production of IL6 and macrophage inhibitory protein-3x and increases that of collagen in an in vitro model of rheumatoid synoviocyte activation," Annals of Rheumatic Diseases, 2002, 61, 730-733.

Chew, V. et al., "Delineation of an immunosuppressive gradient in hepatocellular carcinoma using high-dimensional proteomic and transcriptomic analyses," PNAS Early Edition, 2017, 10 pages, www.pnas.org/cgi/doi/10.1073/pnas.1706559114.

Cohen, S., "Rituximab for Rheumatoid Arthritis Refractory to Anti-Tumor Necrosis Factor Therapy," Arthritis & Rheumatism, 2006, 54 (9), 2793-2806.

Cook, D. et al., "CCR6 Mediates Dendritic Cell Localization, Lymphocyte Homeostasis, and Immune Responses in Mucosal Tissue," Immunity, 2000, 12, 495-503.

Coperchini, F. et al., "TNF-α increases the membrane expression of the chemokine receptor CCR6 in thyroid tumor cells, but not in normal thyrocytes: potential role in the metastatic spread of thyroid cancer," Tumor Biology, 2016, 37, 5569-5575.

Cua, D. et al., "Innate IL-17-producing cells: the sentinels of the immune system," Nature Reviews, Immunology, 2010, 10, 479-489 and corrigendum.

Ding, X., et al., "High Expression of CCL20 is Associated with Poor Prognosis in Patients with Hepatocellular Carcinoma after Curative Resection," Journal of Gastrointestinal Surgery, 2012, 16, 828-836.

Dohlman, T. et al., "The CCR6/CCL20 Axis Mediates Th17 Cell Migration to the Ocular Surface in Dry Eye Disease," Immunology and Microbiology, 2013, 54 (6), 4081-4091.

Dolcino, M. et al., "Gene Expression Profiling in Peripheral Blood Cells and Synovial Membranes of Patients with Psoriatic Arthritis," PLoS ONE, 2015, 10(6): e0128262, 33 pages, doi: 10.1371/journal.pone.0128262.

El Sharkawi, F. et al., "The combined effect of IL-17F and CCL20 gene polymorphism in susceptibility to multiple sclerosis in Egypt," Gene, 2019, 685, 164-169.

Elhofy, A. et al., "Mice deficient for CCR6 fail to control chronic experimental autoimmune encephalomyelitis," NIH Public Access, Author Manuscript, Available in PMC 2010, 19 pages, doi: 10.1016/j.jneuroim.2009.05.011, face of article states: Published in final edited form as: *J Neuroimmunol.* 2009, 213(1-2), 91-99.

Ghadjar, P. et al., "Chemokine receptor CCR6 expression level and aggressiveness of prostate cancer," Journal of Cancer Research and Clinical Oncology, 2008, 134 (11), 1181-1189.

Giuliani, N. et al., "CC-Chemokine Ligand 20/Macrophage Inflammatory Protein-3α and CC-Chemokine Receptor 6 Are Overexpressed in Myeloma Microenvironment Related to Osteolytic Bone Lesions," Cancer Research, 2008, 68 (16), 6840-6850.

Greaves, D. et al., "CCR6, a CC Chemokine Receptor that Interacts with Macrophage Inflammatory Protein 3α and Is Highly Expressed in Human Dendritic Cells," Journal of Experimental Medicine, 1997, 186 (6), 837-844.

Greene, T. et al., Eds., Protective Groups in Organic Synthesis, Wiley-Interscience, 1999.

Guo, W. et al., "DEPDC1 drives hepatocellular carcinoma cell proliferation, invasion and angiogenesis by regulating the CCL20/CCR6 signaling pathway," Oncology Reports, 2019, 15 pages, doi: 10.3982/or.2019.7221.

Harasawa, H. et al., "Survey of chemokine receptor expression reveals frequent co-expression of skin-homing CCR4 and CCR10 in adult T-cell leukemia/lymphoma," Leukemia & Lymphoma, 2006, 47 (10), 2163-2173.

Harper, E. et al., "Th17 Cytokines Stimulate CCL20 Expression in Keratinocytes In Vitro and In Vivo: Implications for Psoriasis Pathogenesis," NIH Public Access, Author Manuscript, Available in PMC 2010, 16 pages, doi: 10.1038/jid.2009.64, face of article states: Published in final edited form as: *J Invest Dermatol.* 2009, 129(9), 2175-2183.

Hashikawa, K. et al., "Microarray analysis of gene expression by microdissected epidermis and dermis in mycosis fungoides and adult T-cell leukemia/lymphoma," Internal Journal of Oncology, 2014, 45, 1200-1208.

Hattori, T. et al., "Gene Expression Profiling of IL-17A-Treated Synovial Fibroblasts from the Human Temporomandibular Joint," Mediators of Inflammation, 2015, Article ID 436067, 12 pages, http://dx.doi.org/10.1155/2015/436067.

He, H. et al., "CCR6+ B lymphocytes responding to tumor cell-derived CCL20 support hepatocellular carcinoma progression via enhancing angiogenesis," American Journal of Cancer Research, 2017, 7 (5), 1151-1163 and supplementary tables and figures.

Hedrick, M et al., "CCR6 is required for IL-23-induced psoriasis-like inflammation in mice," The Journal of Clinical Investigation, 2009, 119 (8), 2317-2329.

Hedrick, M. et al., "CCR6 as a possible therapeutic target in psoriasis," NIH Public Access, Author Manuscript, Available in PMC 2013, 19 pages, doi: 10.1517/14728222.2010.504716, face of article states: Published in final edited form as: *Expert Opin Ther Targets.* 2010, 14(9), 911-922.

(56) References Cited

OTHER PUBLICATIONS

Hirota, K. et al., "Preferential recruitment of CCR6-expressing Th17 cells to inflamed joints via CCL20 in rheumatoid arthritis and its animal model," The Journal of Experimental Medicine, 2007, 204 (12), 2803-2812.

Ivanov, I. et al., "The Orphan Nuclear Receptor RORγt Directs the Differentiation Program of Proinflammatory IL-17$^{+}$ T Helper Cells," Cell, 2006, 126, 1121-1133.

Jin, P. et al., "Astrocyte-derived CCL2-reinforces HIF-1-mediated hypoxic responses in glioblastoma by stimulating the CCR6-NF-γB signaling pathway," Oncogene, 2018, 37, 3070-3087.

Kang, M. et al., "Interleukin-17 in Various Ocular Surface Inflammatory Diseases," Journal of Korean Medical Science, 2011, 26, 938-944.

Kenna, K. et al., "Enrichment of Circulating Interleukin-17-Secreting Interleukin-23 Receptor-Positive γ/δ T Cells in Patients With Active Ankylosing Spondylitis," Arthritis & Rheumatism, 2012, 64 (5), 1420-1429.

Kirshberg, S. et al. "Involvement of CCR6/CCL20/IL-17 Axis in NSCLC Disease Progression," PLoS ONE, 2011, 6(9): e24856, 10 pages, doi.10.1371/journal.pone.0024856.

Kleeff, J. et al., "Detection and localization of MIP-3αLARC/EXODUS, a macrophage proinflammatory chemokine, and its CCR6 receptor in human pancreatic cancer," International Journal of Cancer, 1999, 8, 650-657.

Kohler, R. et al., "A Role for Macrophage Inflammatory Protein-3α/CC Chemokine Ligand 20 in Immune Priming During T Cell-Mediated Inflammation of the Central Nervous System," The Journal of Immunology, 2003, 170, 6298-6306.

Kwon, J. et al., "Colonic epithelial cells are a major site of macrophage inflammatory protein 3α(MIP-3α) production in normal colon and inflammatory bowel disease," Gut, 2002, 51, 818-826.

Lee, A. et al., "Expression of CCR6 on B cells in systemic lupus erythematosus patients," Clinical Rheumatology, 2017, 36, 1453-1456.

Lee, H-J. et al., "Increased Expression of MIP-3α/CCL20 in Peripheral Blood Mononuclear Cells From Patients With Ulcerative Colitis and Its Down-regulation by Sulfasalazine and Glucocorticoid Treatment," Inflammatory Bowel Disease, 2005, 11 (12), 1070-1079.

Lee, J-J. et al., "Enrichment of Human CCR6$^{+}$ Regulatory T cells with Superior Suppressive Activity in Oral Cancer," The Journal of Immunology, 2017, 199, 467-476.

Lee, S. et al., "Human antigen R-regulated CCL20 contributes to osteolytic breast cancer bone metastasis," Scientific Reports, 2017, 7: 9610, 13 pages, doi: 10.1038/s41598-017-09040-4.

Leipe, J., et al., "Role of Th17 Cells in Human Autoimmune Arthritis," Arthritis & Rheumatism, 2010, 62 (10), 2876-2885.

Liu, J. et al., "Tumor-Associated Macrophages Recruit CCR6$^{+}$ Regulatory T Cells and Promote the Development of Colorectal Cancer via Enhancing CCL20 Production in Mice," PLoS ONE, 2011, 6(4): e19495, doi: 10.1371/journal.pone.0019495, 13 pages.

Liu, J. et al., "CCR6 is a Prognostic Marker for Overall Survival in Patients with Colorectal Cancer, and Its Overexpression Enhances Metastasis In Vivo," PLoS ONE, 2014, 9(6): e101137, 13 pages, doi: 10.1371/journal.pone.0101137.

Liu, W. et al., "Cisplatin-stimulated macrophages promote ovarian cancer migration via the CCL20-CCR6 axis," Cancer Letters, 2020, 473, 59-69.

Lu, E et al., "CCL20/CCR6 promotes cell proliferation and metastasis in laryngeal cancer by activating p38 pathway," Biomedicine & Pharmacotherapy, 2017, 85, 486-492.

Mabuchi, T. et al., "Chemokine receptors in the pathogenesis and therapy of psoriasis," Journal of Dermatological Science, 2012, 65, 4-11.

Matsui, T. et al., "Selective recruitment of CCR6-expressing cells by increased production of MIP-3α in rheumatoid arthritis," Clinical & Experimental Immunology, 2001, 125, 155-161.

Maung, H. et al., "Common transcriptional programs and the role of chemokine (C-C motif) ligand 20 (*CCL20*) in cell migration of cholangiocarcinoma," EXCLI Journal, 2020, 19, 154-166.

Mays, A. et al., "Chemokine and Chemokine Receptor Profiles in Metastatic Salivary Adenoid Cystic Carcinoma," Anticancer Research, 2016, 36, 4013-4018.

Meares, G. et al., "Regulation of CCL20 Expression in Astrocytes by IL-6 and IL-17," Gila, 2012, 60, 771-781.

Meissner, A. et al., "CC chemokine ligand 20 partially controls adhesion of naive B cells to activated endothelial cells under shear stress," Blood, 2003, 102 (8), 2724-2727.

Melis, L. et al., "Systemic levels of IL-23 are strongly associated with disease activity in rheumatoid arthritis but not spondyloarthritis," Annals of Rheumatic Diseases, 2010, 69, 618-623.

Miyagaki, T. et al., "IL-22, but Not IL-17, Dominant Environment in Cutaneous T-cell Lymphoma," Clinical Cancer Research, 2011, 17 (24), 7529-7538.

Möller, C et al., "Expression and function of chemokine receptors in human multiple myeloma," Leukemia, 2003, 17, 203-210.

Montresor, C. et al., "Chemokines and the signaling modules regulating integrin affinity," Frontiers in Immunology, 2012, 3, Article 127, 10 pages, doi: 10.3389.fimmu.2012.00127.

Mony, J. et al., "Chemokine receptor expression by inflammatory T cells in EAE," Frontiers in Cellular Neuroscience, 2014, 8, Article 187, 9 pages, doi: 10.3389/fncel.2014.00187.

Moody, S. et al., "Novel *GPR34* and *CCR6* mutation and distinct genetic profiles in MALT lymphomas of different sites," Haematologica, 2018, 103 (8), 1329-1336.

Mrizak, D. et al., "Effect of Nasopharyngeal Carcinoma-Derived Exosomes on Human Regulatory T Cells," Journal of the National Cancer Institute, 2015, 107 (1): dju363, 13 pages, doi: 10.1093/jnci/dju363.

Nandi, B. et al., "CCR6, the Sole Receptor for the Chemokine CCL20, Promotes Spontaneous Intestinal Tumorigenesis," PLoS ONE, 2014, 9(5): e97566, 10 pages, doi: 10.1371/journal.pone.0097566.

Nistala, K., et al., "Interleukin-17-Producing T Cells Are Enriched in the Joints of Children With Arthritis, but Have a Reciprocal Relationship to Regulatory T Cell Numbers," Arthritis & Rheumatism, 2008, 58 (3), 875-887.

Papp, K. et al., "Brodalumab, an Anti-Interleukin-17-receptor Antibody for Psoriasis," The New England Journal of Medicine, 2012, 336 (13), 1181-1189.

Paul, C. et al., "Efficacy, safety and usability of secukinumab administration by autoinjector/pen in psoriasis: a randomized, controlled trial (Juncture)," Journal of European Academy of Dermatology and Venereology, 2015, 29, 1082-1090.

Ranasingh, R. et al., "Modulation of the CCR6-CCL20 Axis: A Potential Therapeutic Target in Inflammation and Cancer," Medicina, 2018, 54, 88, 12 pages, doi: 10.3390/medicina54050088.

Reboldi, A. et al., "C-C chemokine receptor 6-regulated entry of $T_H$-17 cells into the CNS through the choroid plexus is required for the initiation of EAE," Nature Immunology, 2009, 10 (5), 514-23.

Reboldi, A. et al., "IgA production requires B cell interaction with subepithelial dendritic cells in Peyer's patches," HHS Public Access, Author Manuscript, Available in PMC 2016, 25 pages, doi: 10.1126/science.aaf4822, face of article states: Published in final edited form as: *Science*. 2016, 352(6287): aaf4822.

Reich, K. et al., "Guselkumab versus secukinumab for the treatment of moderate-to-severe psoriasis (Eclipse): results from a phase 3, randomised controlled trial," Lancet, 2019, 394, 831-839.

Remington, The Science and Practice of Pharmacy, 21st Edition, 2005, Part 5, "Pharmaceutical Manufacturing," published by Lippincott Williams & Wilkins.

Robert, R., et al., "Essential role for CCR6 in certain inflammatory diseases demonstrated using specific antagonist and knockin mic," JCI Insight, 2017, 2(15):394821, 17 pages, https://doi.org/10.1172/jci.insight.94821.

Rubie, C. et al., "Chemokine expression in hepatocellular carcinoma versus colorectal liver metastases," World Journal of Gastroenterology, 2006, 12 (41), 6627- 6633.

(56) References Cited

OTHER PUBLICATIONS

Rubie, C. et al., "CCL20/CCR6 expression in profile in pancreatic cancer," Journal of Translational Medicine, 2010, 8:45, 8 pages, doi: 10.1186/1479-5876-8-45.
Schutyser, E. et al., "The CC chemokine CCL20 and its receptor CCR6," Cytokine & Growth Factor Reviews, 2003, 14, 409-426.
Shen, H. et al., "Frequency and Phenotype of Peripheral Blood Th17 Cells in Ankylosing Spondylitis and Rheumatoid Arthritis," Arthritis & Rheumatism, 2009, 60 (6), 1647-1656.
Singh, S. et al., "Human T Cells That Are Able to Produce IL-17 Express the Chemokine Receptor CCR6," The Journal of Immunology, 2008, 180, 214-221.
Skepner, J., et al., "Pharmacologic Inhibition of RORγt Regulates Th17 Signature Gene Expression and Suppresses Cutaneous Inflammation In Vivo," The Journal of Immunology, 2014, 192, 2564-2575.
Skovdahl, H. et al., "Expression of CCL20 and Its Corresponding Receptor CCR6 Is Enhanced in Active Inflammatory Bowel Disease, and TLR3 Mediates CCL20 Expression in Colonic Epithelial Cells," PLoS ONE, 2015, 10(11): e0141710, 17 pages, doi: 10.1371/journal.pone.0141710.
Stahl, P. et al., Eds., Handbook of Pharmaceutical Salts, Properties, Selection, and Use, Wiley-VCH, 2008.
Suan, D. et al., "CCR6 Defines Memory B Cell Precursors in Mouse and Human Germinal Centers, Revealing Light-Zone Location and Predominant Low Antigen Affinity," Immunity, 2017, 47, 1142-1153 and e1-e4.
Sucur, A., et al., "Combined manual and automated immunophenotypisation identified disease-specific peripheral blood immune subpopulations in rheumatoid arthritis, ankylosing spondylitis and psoriatic arthritis," Clinical and Experimental Rheumatology, 2019, 17 pages.
Tanis, V. et al., "3-Substituted Quinolines as RORγt Inverse Agonists," Bioorganic & Medicinal Chemistry Letters, 2019, 29, 1463-1470.
Tawaraishi, T. et al., "Identification of a novel series of potent and elective CCR6 inhibitors as biological probes," Bioorganic & Medicinal Chemistry Letters, 2018, 28, 3067-3072.
Tsaur, I. et al., "CCL2 Chemokine as a Potential Biomarker for Prostate Cancer: A Pilot Study," Cancer Research Treatment, 2015, 47 (2), 306-312.
Uchida, K. et al., "The Increased Expression of CCL20 and CCR6 in Rectal Mucosa Correlated to Severe Inflammation in Pediatric Ulcerative Colitis," Gastroenterology Research and Practice, 2015, Article ID 856532, 6 pages, http://dx.doi.org/10.1155/2015/856352.
Van Hamburg, J. et al., "Th17 Cells, but Not Th1 Cells, From Patients With Early Rheumatoid Arthritis Are Potent Inducers of Matrix Metalloproteinases and Proinflammatory Cytokines Upon Synovial Fibroblast Interaction, Including Autocrine Interleukin-17A Production," Arthritis & Rheumatism, 2011, 63 (1), 73-83.
Van Langelaar, J. et al., "T helper 17.1 cells associate with multiple sclerosis disease activity: perspectives for early intervention," Brain, 2018, 141, 1334-1349.
Varona, R. et al., "CCR6 has a non-redundant role in the development of inflammatory bowel disease," European Journal of Immunology, 2003, 33, 2937-2946.
Wallace, A. et al., "Chemokine (C-C) motif ligand 20 is regulated by $PGF_{2\alpha}$- F-prostanoid receptor signalling in endometrial adenocarcinoma and promotes cell proliferation," Molecular and Cellular Endocrinology, 2011, 331, 129-135.
Wang, L. et al., "Overexpression of CCL20 and its receptor CCR6 predicts poor clinical prognosis in human gliomas," Medical Oncology, 2012, 29, 3491-3497.
Yu, S. et al., "Is CCR6 Required for the Development of Psoriasiform Dermatitis in Mice?" HHS Public Access, Author Manuscript, Available in PMC 2019, 6 pages, doi:10.1016/j.jid.2018.07.036, face of article states: Published in final edited form as: *J Invest Dermatol*. 2019, 139(2): 485-488.
Zhang, C., et al., "The role of CCL20/CCR6 axis in recruiting Treg cells to tumor sites of NSCLC patients," Biomedicine & Pharmacotherapy, 2015, 69, 242-248.
Zhang, X-P. et al., "Role of CCL20/CCR6 and the ERK signaling pathway in lung adenocarcinoma," Oncology Letters, 2017, 14, 8183-8189.
Zhao, X. et al., "Synergistic association of FOXP3+ tumor infiltrating lymphocytes with CCL20 expressions with poor prognosis of primary breast cancer: A retrospective cohort study," Medicine, 2019, 98:50(e18403), 11 pages.
Al-Mossawi, M. et al., "Unique transcriptome signatures and GM-CSF expression in lymphocytes from patients with spondyloarthritis," Nature Communications, 2017, 8:1510, 11 pages, doi: 10.1038/s41467-017-01771-2.
Dellacasagrande, J. et al., "Liver Metastasis of Cancer Racilitated by Chemokine Receptor CCR6," Scandinavian Journal of Immunology, 2003, 57, 534-544.
Elgueta, R. et al., "CCR6-Dependent Positioning of Memory B Cells Is Essential for Their Ability To Mount a Recall Response to Antigen," The Journal of Immunology, 2015, 194 (2), 505-513.
Getschman, A. et al., "Protein engineering of the chemokine CCL20 prevents psoriasiform dermatitis in an IL-23-dependent murine model," PNAS, 2017, 117 (47), 12460-12465.
Ikeda, S. et al., "Disruption of CCL20-CCR6 interaction inhibits metastasis of advanced cutaneous T-cell lymphoma," Oncotarget, 2016, 7 (12), 13563-13574.
Ito, M. et al., "MicroRNA-150 inhibits tumor invasion and metastasis by targeting the chemokine receptor CCR6, in advanced cutaneous T-cell lymphoma," Blood, 2014, 123 (10), 1499-1511.
Iwamoto, S. et al., "TNF-α is essential in the induction of fatal autoimmune hepatitis in mice through upregulation of hepatic CCL20 expression," Clinical Immunology, 2013, 146, 15-25.
Kadomoto, S. et al., "Tumor-Associated Macrophages Induce Migration of Renal Cell Carcinoma Cells via Activation of the CCL20-CCR6 Axis," Cancers, 2020, 12, 89, 13 pages, doi: 10.3390/cancers12010089.
Lin, Y-L. et al., "CCR6 Deficiency Impairs IgA Production and Dysregulates Antimicrobial Peptide Production, Altering the Intestinal Flora," Frontiers in Immunology, 2017, 8:805, 20 pages, doi: 10.3389/fimmu.2017.00805.
Marsigliante, S. et al., "Paracrine CCL20 Loop Induces Epithelial-Mesenchymal Transition In Breast Epithelial Cells," Molecular Carcinogenesis, 2016, 55, 1175-1186.
Wang, G-Z. et al., "Tobacco smoke induces production of chemokine CCL20 to promote lung cancer," Cancer Letters, 2015, 363, 60-70.
Wang, L-X. et al., "Network-based co-expression analysis for exploring the potential diagnostic biomarkers of metastatic melanoma," PLoS One, 2018, 13(1): e0190447, 16 pages, http://doi.org/10.1371/journal.pone.0190447.
Wouters, J. et al., Eds., Pharmaceutical Salts and Co-crystals, RSC Publishing, 2012.
Wu, Q. et al., "Blocking Triggering Receptor Expressed on Myeloid Cells-1-Positive Tumor-Associated Macrophages Induced by Hypoxia Reverses Immunosuppression and Anti-Programmed Cell Death Ligand 1 Resistance in Liver Cancer," Hepatology, 2019, 70 (1), 198-214.
Zhong, W. et al., "CCR6+ Th cell distribution differenciates systemic lupus erythematosus patents based on anti-dsDNA antibody status," PeerJ, 2018, 6:e4294, 19 pages, doi: 10.7717/peerj.4294.
Zhu, C. et al., "CCR6 promotes tumor angiogenesis via the AKT/NF-kB/VEGF pathway in colorectal cancer," BBA—Molecular Basis of Disease, 2018, 1864, 387-397.
U.S. Appl. No. 18/704,588, filed Apr. 25, 2024 (371(c) Date), Alleman et al.
U.S. Appl. No. 18/705,346, filed Apr. 26, 2024 (371(c) Date), Alleman et al.
U.S. Appl. No. 19/136,271, filed Jun. 5, 2025 (371(c) Date), Fleischer et al.
Kulig, P. et al., "Efficacy of IDOR-1117-2520, a novel, orally available CCR6 antagonist in preclinical models of skin dermatitis," British Journal of Pharmacology, 2025, 24 pages, DOI: 10.1111/bph.70025.
Meyer, E. et al., "Discovery of the Clinical Candidate IDOR-1117-2520: A Potent and Selective Antagonist of CCR6 for Autoimmune Diseases," Journal of Medicinal Chemistry, 2024, 67, 8077-8098.

(56) References Cited

OTHER PUBLICATIONS

Meyer, E., "Discovery of the Clinical Candidate IDOR-1117-2520: A Potent and Selective Antagonist of CCR6 for Autoimmune Diseases," RICT Conference Presentation, 2024, 30 pages.

* cited by examiner

AZETIDIN-3-YLMETHANOL DERIVATIVES AS CCR6 RECEPTOR MODULATORS

CROSS REFERENCE TO RELATED APPLICATIONS

This application is the National Stage Entry under 35 U.S.C. § 371 of International Application No. PCT/EP2021/061401 filed Apr. 30, 2021, which claims priority to International Application No. PCT/EP2020/062103 filed Apr. 30, 2020, the contents of each of which are hereby incorporated by reference in their entireties.

The present invention relates to novel compounds of Formula (I), or pharmaceutically acceptable salts thereof, and their use as CCR6 receptor modulators in the treatment or prevention of various diseases, conditions or disorders ameliorated by modulating said receptor. Furthermore, the present invention concerns related aspects such as pharmaceutical compositions containing one or more compounds of Formula (I) and processes for the preparation of said compounds.

Chemokine receptors comprise a family G-protein coupled receptors (GPCRs) that recognize and bind to peptide chemokine ligands. The predominant functions of chemokine receptors and their ligands are to induce leukocyte trafficking to-and-from lymphoid organs and tissues in the steady state, as well as in the context of an infection or inflammation. Additionally, chemokine signaling events can induce the activation of integrin molecules on the surface of immune cells, allowing firm adhesion to activated endothelium, facilitating migration from blood into inflamed tissue (Montresor A, Frontiers in Imm., 2012; Meissner A, Blood, 2003). Chemokine receptor 6 (CCR6, aliases BN-1, C-C CKR-6, CD196, CKRL3, CMKBR6, DCR2, DRY6, GPR29, GPRCY4, STRL22) is a GPCR mainly expressed on effector CD4+ T helper cells, but is also present on B cells, CD8+ cytotoxic T cells, regulatory T cells (Treg), immature dendritic cells (DC) and type 3 innate lymphoid cells (ILC3) (Cua D J, Nat Rev Immunol. 2010 July; 10(7):479-89. doi: 10.1038/nri2800). CCR6 binds to the chemokine CCL20 (chemokine (C—C motif) ligand 20) (Greaves D R, J Exp Med. 1997 Sep. 15; 186(6):837-44. doi: 10.1084/jem.186.6.837). CCL20 is also called macrophage inflammatory protein 3a (MIP-3a), liver and activation-regulated chemokine (LARC), or Exodus-1 (Schutyser E, Cytokine Growth Factor Rev. 2003 October; 1-((5):409-26. doi: 10.1016/s1359-6101(03)00049-2). CCR6/CCL20 interactions dictate the humoral response in the intestinal mucosa and are required for lymphocyte homeostasis in the mucosa of the small intestine (Cook D N, Immunity. 2000 May; 12(5):495-503. doi: 10.1016/s1074-7613(00)80201-0). Under steady state conditions, CCR6 and CCL20 regulate production of IgA in the intestine, where CCL20 expressed in Peyer's patches guides CCR6+IgA+ B cells to the mucosa and secretory IgA can be released into the gut lumen (Lin Y L, Front Immunol. 2017; 8:805. doi: 10.3389/fimmu.2017.00805; Reboldi A, Science. 2016 May 13; 352(6287):aaf4822. doi: 10.1126/science.aaf4822). Under inflammatory conditions, expression of CCL20 is highly upregulated by proinflammatory cytokines including IL-17A, TNFa and IL-1b in both endothelial and epithelial cells (Harper E G, J Invest Dermatol. 2009 September; 129(9):2175-83. doi: 10.1038/jid.2009.65; PLoS One. 2015; 10(11):e0141710. doi: 10.1371/journal.pone.0141710) and tissue fibroblasts (Hattori T, Mediators Inflamm. 2015; 2015:436067. doi: 10.1155/2015/436067). Interleukin (IL)-17A expression is restricted to cells expressing the transcription factor RORgt (Cell. 2006 Sep. 22; 126(6):1121-33. doi: 10.1016/j.cell.2006.07.035). IL-17A expression has been shown to segregate with CCR6 expression on human T cells (Singh S P, J Immunol. 2008 Jan. 1; 180(1):214-21. doi: 10.4049/jimmunol.180.1.214; Nat Immunol. 2007 June; 8(6):639-46. doi: 10.1038/ni1467). CCR6 was also described as a target gene of RORgt (PLoS One. 2017; 12(8):e0181868. doi: 10.1371/journal.pone.0181868; Skepner J, J Immunol. 2014 Mar. 15; 192(6):2564-75. doi: 10.4049/jimmunol.1302190), thus clarifying the co-expression of IL-17A and CCR6 in RORgt+ cell types.

Certain disclosures in the prior art may be regarded as relating to modulation of CCR6. For instance, Tawaraishia et al. (Bioorganic & Medicinal Chemistry Letters, Volume 28, Issue 18, 2018, Pages 3067-3072, ISSN 0960-894X, https://doi.org/10.1016/j.bmcl.2018.07.042) disclose a series of benzenesulfonyl-aminocyclohexane derivatives as selective CCR6 inhibitors. CN103588697 teaches sulfonamide derivatives as CCR6 antagonists and their use in treating CCR6-mediated diseases such as autoimmune diseases, inflammation, psoriasis, multiple sclerosis or cancer. WO2014/075580 describes the use of aurintricarboxylic acid for targeting chemokine receptors. WO2015/084842 teaches certain sulfonamides which may be used in treating CCR6 related diseases. WO2017/087607, WO2010/131145, WO2013/061004, WO2013/061005, WO2019/036374 and WO2020/058869 provide certain cyclobutenediones for use in the treatment of chemokine/CCR6 related diseases. WO2019/136370 teaches a method of treating a certain type of psoriasis. WO2019/147862 proposes azetidine derivatives which may be used as chemokine modulators.

Further, WO1999/43664 discloses certain pyrrolidinones with anti-inflammatory and analgesic properties. In WO2019/105915 certain heterocyclic compounds are provided which may be used as MAGL inhibitors. WO2015/057626, US2015/0105366, WO2014/062658, WO2015/057205 and Tanis V M et al. (Bioorg Med Chem Lett. 2019 Jun. 15; 29(12):1463-1470. doi: 10.1016/j.bmcl.2019.04.021) relate to modulators of the RORγt receptor which may be used in treating rheumatoid arthritis or psoriasis. WO03/022808 proposes certain azetidine derivatives for use as pesticides. WO2008/103426 and WO2007/022351 disclose certain quaternary ammonium compounds useful as muscarinic receptor antagonists. WO2006/136830 teaches certain heteroaryl-alkylamines as protein kinase inhibitors. WO91/13359 proposes heterocyclic cholinergic enhancers. US28141 teaches certain pyrrolidines which may be used for treating depression. GB 1304650 discloses spasmolytic pyrrolidines. U.S. Pat. Nos. 3,479,370, 3,489,769, 3,499,002, 3,542,807 and 3,651,085 relate to certain pyrrolidines with analgesic/tranquilizing activity.

The present CCR6 modulators may be useful, alone, or in combination in the treatment or prevention of the following diseases or disorders: Rheumatoid arthritis (RA) causes chronic inflammation of the joints and chemokines regulate infiltration of the inflamed synovium by inflammatory cells. RA is characterized by the increased release of CCL20 and the subsequent recruitment of CCR6+ T cells to the inflamed joints. CCL20 is highly expressed in the synovial fluid of RA (Hirota, J Exp Med. 2007 Nov. 26; 204(12):2803-12. doi: 10.1084/jem.20071397; Matsui T, Clin Exp Immunol. 2001 July; 125(1):155-61. doi: 10.1046/j.1365-2249.2001.01542.x). In patients with RA, CCR6+ Th cells have been found in the inflamed synovium and increased proportions of peripheral blood CCR6+ Th cells have been found in patients with early RA (van Hamburg J P, Arthritis Rheum. 2011 January; 63(1):73-83. doi: 10.1002/art.30093; Leipe J Arthritis Rheum. 2010 October; 62(10):2876-85. doi: 10.1002/art.27622; Nistala K, Arthritis Rheum. 2008 March; 58(3):875-87. doi: 10.1002/art.23291). The production of CCL20 is known to be up-regulated in synovium explants or fibroblast-like synoviocytes from RA patients after stimulation of TNF-a, IL-1b and IL-17 (Matsui T, Clin Exp Immunol. 2001 July; 125(1):155-61. doi: 10.1046/j.1365-2249.2001.01542.x; J Immunol. 2001 Nov. 15; 167 (10):6015-20. doi: 10.4049/jimmunol.167.10.6015; Chevrel G, Ann Rheum Dis. 2002 August; 61(8):730-3. doi: 10.1136/ard.61.8.730). CCR6+ B cells in RA synovium have been reported, contributing to pathogenesis by antigen presentation, autoantibody production and/or inflammatory cytokine production. Furthermore, Rituximab is an efficacious therapy for RA (Cohen S B, Arthritis Rheum. 2006 September; 54(9):2793-806. doi: 10.1002/art.22025), supporting a role for CCR6+ B cells in RA pathogenesis. Additionally, CCR6-deficient mice have impaired IgG1-dependent memory B cell responses (J Immunol. 2015 Jan. 15; 194 (2):505-13. doi: 10.4049/jimmunol.1401553). Preclinical rodent models showed that CCR6-deficient mice developed a less severe joint inflammation in the collagen-induced arthritis (CIA) model. Reduced production of collagen-specific antibodies in CCR6-deficient mice were observed compared to WT mice, and arthritic inflammation was also reduced (J Cell Mol Med. 2018 November; 22(11):5278-5285. doi: 10.1111/jcmm.13783). Furthermore, depletion of CCR6+ cells reduced the severity of SKG arthritis (Hirota K, J Exp Med. 2007 Nov. 26; 204(12):2803-12. doi: 10.1084/jem.20071397).

CCR6+ Th17 are increased in peripheral blood in ankylosing spondylitis patients (Shen H, Arthritis Rheum. 2009 June; 60(6):1647-56. doi: 10.1002/art.24568). Circulating interleukin-17-secreting interleukin-23 receptor-positive y/6 T cells were also reported in patients with active ankylosing spondylitis (Kenna T J, Arthritis Rheum. 2012 May; 64(5): 1420-9. doi: 10.1002/art.33507). Secukinumab, an IL-17A inhibitor, in was shown to be efficacious in ankylosing spondylitis (AS) (Baeten D, N Engl J Med. 2015 Dec. 24; 373(26):2534-48. doi: 10.1056/NEJMoa1505066). CD32B expression on memory B cells in AS was increased and was associated with disease activity. Furthermore, CCR6+ cytotoxic T-cells and CD32B' memory B-cells were highly enriched within the synovial compartment of AS patients (Sucur A, Clin Exp Rheumatol. 2019 Nov. 20; PMID: 31820725).

Psoriasis is a commonly occurring autoimmune skin disease. The role of Th17-associated cytokines has been clinically validated and their role in psoriatic inflammation confirmed (Paul C, J Eur Acad Dermatol Venereol. 2015 June; 29(6):1082-90. doi: 10.1111/jdv.12751). An IL-17R-blocking antibody (brodalumab, AMG 827) were shown to reduce clinical manifestations of psoriasis and also to reduce CCL20 expression in skin biopsies from psoriasis patients (Papp K A, N Engl J Med. 2012 Mar. 29; 366(13):1181-9. doi: 10.1056/NEJMoa1109017). Also, an IL-23 neutralizing antibody (guselkumab) was shown to be efficacious in reducing psoriatic inflammation (Reich K, Lancet. 2019 Sep. 7; 394(10201):831-839. doi: 10.1016/S0140-6736(19) 31773-8). CCR6-deficient mice failed to develop psoriasiform skin lesions following intradermal IL-23 injections (Hedrick M N, J Clin Invest. 2009 August; 119(8):2317-29. doi: 10.1172/jci37378). Small molecule CCR6 antagonists have also been shown to be efficacious in the Aldara and IL-36a-injection mouse psoriasis models (Campbell J J, J Immunol. 2019 Mar. 15; 202(6):1687-1692. doi: 10.4049/jimmunol.1801519; Campbell J J, J Immunol. 2017 Nov. 1; 199(9):3129-3136. doi: 10.4049/jimmunol.1700826). Furthermore, CCR6-deficient mice have been shown to be protected from imiquimod-induced ear swelling (Yu S, J Invest Dermatol. 2019 February; 139(2): 485-488. doi: 10.1016/j.jid.2018.07.036).

Anti-CCR6 neutralizing antibodies have also shown efficacy in Aldara induced ear swelling in mice (Robert R, JCI Insight. 2017 Aug. 3; 2(15): e94821. Published online 2017 Aug. 3. doi: 10.1172/jci.insight.94821). An engineered disulfide-linked CCL20 dimer, which binds CCR6 but inhibits T cell migration, was shown to reduce skin swelling in an IL-23-dependent mouse model of psoriasis (Getschman A E, Proc Natl Acad Sci USA. 2017 Nov. 21; 114(47):12460-12465. doi: 10.1073/pnas.1704958114). Collectively, these data show that a positive feedback consisting of epidermal and dermal production of CCL20, potent recruitment of CCR6+ T cells or into inflamed psoriatic skin, their activation by IL-23 and their expression of IL-17A and IL-22, drives a pathogenic Th17 response in psoriatic skin lesions. Inhibition of CCR6 has therefore been recognized as a potential therapeutic pathway to treat psoriasis (Hedrick M N, Expert Opin Ther Targets. 2010 September; 1-((9):911-22. doi: 10.1517/14728222.2010.504716; Mabuchi T, J Dermatol Sci. 2012 January; 65(1):4-11. doi: 10.1016/j.jdermsci.2011.11.007). CCR6 expression was shown to be upregulated in synovial membranes of psoriatic arthritis (PsA) patients (Dolcino M, PLoS One. 2015 Jun. 18; 10(6): e0128262. doi: 10.1371/journal.pone.0128262). IL-17A- and GM-CSF-expressing CD4+ T cells isolated from synovial fluid of PsA patients also expressed CCR6 (Al-Mossawi et al., Nat Commun. 2017 Nov. 15; 8(1):1510. doi: 10.1038/s41467-017-01771-2). CCL20 was shown to be highly upregulated in synovial fluid retrieved from PsA patients (Melis L, Ann Rheum Dis. 2010 March; 69(3):618-23. doi: 10.1136/ard.2009.107649).

Additional inflammatory skin disorders including rosacea have been shown to have highly elevated levels of CCL20 in inflamed skin (Buhl T, JID, 2015).

CCR6 and CCL20 are highly elevated in active Crohn's disease (CD) and ulcerative colitis (UC) (Skovdahl et al., PLoS One. 2015 Nov. 4; 10(11):e0141710. doi: 10.1371/journal.pone.0141710). Increased enterocyte CCL20 production has been proposed to play an important role in lymphocyte recruitment to the colonic epithelium in irritable bowel disease (IBD) (Kwon J H, Gut. 2002 December; 51(6):818-26. doi: 10.1136/gut.51.6.818). CCL20 and CCR6 expression are also correlated with histological severity in rectum resected from UC patients. CCL20 expression in chronic UC is higher than that in acute UC after pathological examination (Uchida K, Gastroenterol Res Pract. 2015; 2015:856532. doi: 10.1155/2015/856532). Expression of CCL20 was significantly up-regulated in the PBMCs of patients with UC compared with those of normal healthy controls. UC groups treated with sulfasalazine and GC showed decreases of CCL20 expression in PBMCs, accompanied by ameliorated disease. INFO or IL-1β-induced CCL20 secretion was strongly reduced by sulfasalazine and/or GC treatment of human intestinal epithelial cell lines (Lee H J, 2 Inflamm Bowel Dis. 2005 December; 11(12): 1070-9. doi: 10.1097/01.mib.0000187576.26043.ac). CCR6 deficiency resulted in reduced intestinal pathology in mice treated with dextran sodium sulfate (DSS) to induce colonic inflammation (Verona R, Eur J Immunol. 2003 October; 33(10):2937-46. doi: 10.1002/eji.200324347).

Th17 cells expressing CCR6 were shown to be important effectors mediating dry eye disease (DED), an inflammatory state at the ocular surface, potentially resulting in corneal perforation. Antibody-mediated neutralization of CCL20 in a DED mouse model reduced Th17 recruitment into the ocular surface, resulting in improved clinical readouts (Dohlman T H, Invest Ophthalmol Vis Sci. 2013 Jun. 12; 54(6):4081-91. doi: 10.1167/iovs.12-11216). Inhibition of the CCR6/CCL20 axis was therefore proposed as a therapeutic mechanism to treat DED.

CCR6 expression has been described on T cells isolated from the cerebrospinal fluid of multiple sclerosis (MS) patients (van Langelaar J, Brain, 2018 May 1; 141(5):1334-1349. doi: 10.1093/brain/awy069). CCR6 expression was also shown on T cells infiltrating the inflamed CNS in experimental autoimmune encephalomyelitis (EAE) (Mony J T, Front Cell Neurosci. 2014; 8:187. doi: 10.3389/fncel.2014.00187). Furthermore, CCL20 gene polymorphisms have been shown to be associated with MS patient cohorts (El Sharkey et al., Gene. 2019 Feb. 15; 685:164-169. doi: 10.1016/j.gene.2018.11.006). Preclinical data has shown that CCR6 is important for development of EAE (Reboldi A, Nat Immunol. 2009 May; 10(5):514-23. doi: 10.1038/ni.1716). This finding was confirmed in later study, showing that CCR6-deficient mice were resistant to disease induction with reduced peak severity. In the same study, vaccination with hCCL20 produced an anti-mouse CCL20 response in the host mice, which was sufficient to reduce clinical scores (Abraham M, Clin Immunol. 2017 October; 183:316-324. doi: 10.1016/j.clim.2017.09.018). However, conflicting data exists concerning the role for CCR6 in EAE development (J Neuroimmunol. 2009 Aug. 18; 213(1-2):91-9. doi: 10.1016/j.jneuroim.2009.05.011). EAE severity and histopathology were significantly reduced after injection of anti-CCL20 upon first clinical manifestations (Kohler R E, J Immunol. 2003 Jun. 15; 170(12):6298-306. doi: 10.4049/jimmunol.170.12.6298). Anti-CCR6 neutralizing antibodies were shown to reduce the severity of EAE in mice (Robert R, JCI Insight. 2017 Aug. 3; 2(15): e94821. Published online 2017 Aug. 3. doi: 10.1172/jci.insight.94821). IL-6 and IL-17 increase the expression of CCL20 from murine astrocytes (Meares G P, Glia. 2012 May; 60(5):771-81. doi: 10.1002/glia.22307).

CCR6 and CCL20 are proposed to influence kinetics of germinal center (GC) formation and B cell responses and CCR6 is considered a marker memory B cell precursors in both mouse and human germinal centers (Suan D, Immunity. 2017 Dec. 19; 47(6):1142-1153.e4. doi: 10.1016/j.immuni.2017.11.022). Expression of CCR6 on naive, pre-GC, GC/plasma cell and memory B cells in peripheral B cells of systemic lupus erythematosus (SLE) patients was increased (Lee A Y S, Clin Rheumatol. 2017 June; 36(6):1453-1456. doi: 10.1007/s10067-017-3652-3).CD4+CCR6+ cells may also contribute to disease severity in SLE patients and were shown to be increased in anti-DNA+ SLE patients, which correlated with disease severity and erythrocyte sedimentation rate (Zhong W, PeerJ. 2018; 6:e4294. doi: 10.7717/peerj.4294). Increased CCR6 expression in the salivary glands of patients with primary Sjögren's syndrome (pSS) was demonstrated [Scand J Immunol. 2020 March; 91(3): e12852. doi: 10.1111/sji.12852]. A trend towards increased CCL20 mRNA expression was also observed. Significant reductions in CCR6+ Th cells (both CCR9− and CCR9+) in the circulation of patients with pSS as compared with healthy controls (HCs) were demonstrated [Scand J Immunol. 2020 March; 91(3):e12852. doi: 10.1111/sji.12852].

In an animal model of autoimmune hepatitis (AIH), administering anti-TNF-α suppressed hepatic CCL20 expression. Mice receiving anti-CCL20 showed reduced AIH. Furthermore, TNFα stimulation enhanced CCL20 expression in hepatocytes. These findings suggest that TNFα is essential in the induction of AIH through upregulation of hepatic CCL20 expression, which recruits CCR6+ T cells which drive pathology (Clin Immunol. 2013 January; 146(1):15-25. doi: 10.1016/j.dim.2012.10.008).

The present CCR6 modulators may be useful, alone, or in combination in the treatment or prevention of autoimmune diseases or disorders including Posterior uveitis, allergic conjunctivitis, allergic disease in the gastrointestinal tract, type I diabetes and endometriosis (Medicina (Kaunas). 2018 Nov. 16; 54(5). doi: 10.3390/medicina54050088). CCR6 modulators may also be useful, alone or in combination, to treat diseases of the ocular surface in which elevated levels of IL-17A have been recorded, including meibomian gland dysfunction; GVHD, graft-versus host disease; autoimmune keratitis, filamentary keratitis, dry eye syndrome with rheumatic arthritis; dry eye syndrome without systemic disease; Stevens-Johnson syndrome. (J Korean Med Sci. 2011 July; 26(7):938-44. doi: 10.3346/jkms.2011.26.7.938).

The present CCR6 modulators may be useful, alone, or in combination in the treatment or prevention of malignant diseases. Modulation of the CCR6/CCL20 axis using siRNA, shRNA, CCR6 knock-out animals, CCL20 ligand treatment or antibodies has been shown to alter tumor growth and metastatic processes in experimental disease models as single agents, or in combination with immunotherapy (such as especially PD1 and/or PDL1 blockade) for the prevention/prophylaxis or treatment of cancers.

The therapeutic potential of modulating this axis for the treatment of malignancies has been described in tumor mouse models using small interfering RNA (siRNA) or small hairpin RNA (shRNA)-mediated silencing of CCR6 or CCL20. Specifically, in a mouse model of cutaneous T cell lymphoma (My-La cells), Abe et al. reported that the administration of a CCR6-targeted siRNA prolonged survival of animals when compared with control animals (Oncotarget. 2017 Jan. 31; 8(5):7572-7585. doi: 10.18632/oncotarget.13810). Using another approach, Ito and colleagues demonstrated that mice, injected with T lymphoma cells (My-La) harboring a CCR6 silencing siRNA construct, survived significantly longer than mice injected with control cells (Blood. 2014 Mar. 6; 123(10):1499-511. doi: 10.1182/blood-2013-09-527739). Zhu and co-workers demonstrated that, the average volume and weight of tumor nodules in mice injected subcutaneously with a set of colorectal cancer cell lines was decreased when CCR6 was silenced in the cancer cells by means of shRNA (PMID Biochim Biophys Acta Mol Basis Dis. 2018 February; 1864(2):387-397. doi: 10.1016/j.bbadis.2017.10.033). In glioblastoma xenograft models using patient-derived glioblastoma cell lines, mice injected with cells harboring a shRNA construct silencing CCR6 expression survived longer than those injected with control cells. In addition, histology and immunohistochemistry revealed that tumors formed by glioma cells with CCR6-targeting shRNA were much smaller, and tumor vessel formation was significantly lower versus control tumors. Collectively, these data further support the notion that CCR6 signaling enhances the oncogenic potential of malignancies including lymphoma, colorectal tumors and glioblastoma (Oncogene. 2018 June; 37(23):3070-3087. doi: 10.1038/s41388-018-0182-7). Specifically, the implication of the CCR6/CCL20 axis in tumorigenesis using CCR6 knock-out animals was reported in the literature. In the CMT93 mouse model of colorectal cancer (CRC), the infiltration of T regulatory cells was completely prevented in tumors of mice deficient in CCR6 in comparison to wildtype animals. The reported data further suggest that the homing and trafficking of tumor-infiltrating T regulatory cells to the tumor mass is dependent on the chemokine receptor CCR6 in vivo (PLoS One. 2011 Apr. 29; 6(4):e19495. doi: 10.1371/journal.pone.0019495). According to Nandi and colleagues, in a mouse model of spontaneous intestinal tumorigenesis [APCMIN/+ mice, heterozygous for a mutation in the adenomatous polyposis coli (APC) gene], mice deficient in CCR6 had a lower occurrence of spontaneous intestinal tumorigenesis (PLoS One. 2014; 9(5):e97566. doi: 10.1371/journal.pone.0097566).

The potential role of the CCR6/CCL20 axis in tumorigenesis was also demonstrated by administrating the recombinant CCL20 chemokine. Specifically, in a mouse model of colorectal cancer (CMT93 cells), Liu and colleagues showed that tumor size was significantly increased in mice treated with recombinant mouse CCL20 compared with PBS controls, suggesting a critical role for CCL20 in colorectal cancer growth and development (PLoS One. 2011 Apr. 29; 6(4):e19495. doi: 10.1371/journal.pone.0019495).

Specifically, using neutralizing CCL20 antibodies, the potential role of the CCR6/CCL20 axis in tumor promotion was demonstrated in the literature using mouse models. Ikeda and co-workers used a specific cutaneous T cell lymphoma (CTCL) mouse model in which animals succumb to metastasis of CTCL cells into multiple organs. However, administration of a neutralizing CCL20 antibody significantly prolonged the survival of the xenografted mice (Oncotarget. 2016 Mar. 22; 7(12):13563-74. doi: 10.18632/oncotarget.6916). Lee and co-workers described in a mouse model of metastatic breast cancer (MDA-MB-231 cells were injected into the left cardiac ventricles of nude mice) that the administration of an anti-CCL20 antibody prevented the development of bone metastasis, one of the major site of breast cancer metastasis in human disease (Sci Rep. 2017 Aug. 29; 7(1):9610. doi: 10.1038/s41598-017-09040-4). In a humanized mouse model of nasopharyngeal carcinoma, Mrizak et al. observed a significant decrease of T regulatory cell recruitment into the tumor when mice were injected with anti-CCL20 monoclinal antibody in comparison to sham treated animals (J Natl Cancer Inst. 2015 January; 107(1):363. doi: 10.1093/jnci/dju363). In addition, in a mouse model of hepatocarcinoma (Hepa1-6 cells), blockade of CCL20 activity in immunocompetent mice using an anti-CCL20 antibody, attenuated tumor incidence, restrained tumor growth and distal metastasis. Moreover, the authors reported that in this mouse model, tumor angiogenesis was significantly inhibited upon CCL20 neutralization. (He at al., PMID 28560063—Am J Cancer Res. 2017; 7(5):1151-1163). Using the same mouse model, the administration of the anti-CCL20 neutralizing antibody remarkably reduced the infiltration of T regulatory cells into the tumor, especially CCR6 positive T regulatory cells, and significantly decreased tumor growth. Antitumor efficacy was further enhanced when the mice were co-treated with an anti-PDL-1 antibody. Collectively these data sets suggest that CCL20 blockade could abrogate anti-PD-L1 resistance in a mouse model of hepatocarcinoma by inhibiting T regulatory recruitment to the tumor (Hepatology. 2019 July; 70(1):198-214. doi: 10.1002/hep.30593).

Specifically, the potential role of the CCR6/CCL20 axis in tumor metastasis was described in the literature. Dellacasagrande and colleagues reported that, in a mouse model of plasmacytoma, tumor cells that disseminated to the liver overexpressed functional CCR6 in comparison with tumor cells of the primary tumor (from s.c. injection of mouse plasmacytoma (MOPC315)). The same authors found that CCR6 was overexpressed in small liver metastases of colon, thyroid and ovarian carcinomas compared with normal liver (Scand J Immunol. 2003 June; 57(6):534-44. doi: 10.1046/j.1365-3083.2003.01263.x).

Furthermore, the present CCR6 modulators may be useful, alone, or in combination in the treatment or prevention of cancers where the expression of CCR6 and/or CCL20 correlates with disease progression and resistance to standard treatment care. Specifically, the correlation of CCR6 expression with disease progression was described in the literature for numerous cancer indications. For example, in renal cell carcinoma CCR6 expression is associated with a lower overall survival (Cancers (Basel). 2019 Dec. 30; 12(1). doi: 10.3390/cancers12010089). In colorectal cancer, tumor expression of CCR6 positively correlates with metastasis and upregulated CCR6 predicts poor survival, shorter disease-free survival (PLoS One. 2014; 9(6):e101137. doi: 10.1371/journal.pone.0101137), and poorer 5-year overall survival (Biochim Biophys Acta Mol Basis Dis. 2018 February; 1864(2):387-397. doi: 10.1016/j.bbadis.2017.10.033). In ovarian cancer high CCR6 mRNA expression was also associated with a worse prognosis (Cancer Lett. 2020 Mar. 1; 472:59-69. doi: 10.1016/j.canlet.2019.12.024). CCR6 expression was associated with rectal cancer aggressiveness, indeed, high-level expression of CCR6 protein was more common in non-responders to radiotherapy than in responders (Cancer Res Treat. 2018 October; 50(4):1203-1213. doi: 10.4143/crt.2017.538). The expression level of CCR6 in prostate cancer was associated with clinical and pathologic features of more advanced and aggressive disease (J Cancer Res Clin Oncol. 2008 November; 134(11):1181-9. doi: 10.1007/s00432-008-0403-5). In non-small cell lung cancer (NSCLC) high CCR6 expression was associated with shorter disease-free survival and conferred a disease stage-independent 5-fold increased risk for disease recurrence (PLoS One. 2011; 6(9):e24856. doi: 10.1371/journal.pone.0024856). Hepatocarcinoma patients with increased infiltrated CCR6 positive immune cells in tumor tissues showed a poorer prognosis (Am J Cancer Res. 2017; 7(5):1151-1163).

Analogous to CCR6, expression of its ligand CCL20 has been reported to correlate with poorer disease outcome for several indications. Specifically, in breast cancer, elevated CCL20 expression significantly correlated with lower overall free survival, lower percent metastasis free survival (Sci Rep. 2017 Aug. 29; 7(1):9610. doi: 10.1038/s41598-017-09040-4), with higher histological grade, higher Ki67 index, and axillary lymph node metastases. Moreover, breast tumor CCL20 expression positively correlated with expression of FOXP3, a marker of T regulatory cells. Patients with axillary lymph node metastases, and concomitant elevation in CCL20 expression and FOXP3-positive T regulatory cells, had the worst overall survival. (Medicine (Baltimore). 2019 December; 98(50):e18403. doi: 10.1097/MD.0000000000018403). In NSCLC higher expression of CCL20 was associated with a lower overall survival (Biomed Pharmacother. 2015 February; 69:242-8. doi: 10.1016/j.biopha.2014.12.008.)(Cancer Lett. 2015 Jul. 10; 363(1):60-70. doi: 10.1016/j.canlet.2015.04.005). Analogous to NSCLC, hepatocellular carcinoma patients with high CCL20 expression had poorer overall survival and poorer recurrence-free survival. The same authors described that CCL20 expression was significantly associated with tumor size, tumor number, vascular invasion, tumor differentiation and tumor recurrence (J Gastrointest Surg. 2012 April; 16(4):828-36. doi: 10.1007/s11605-011-1775-4). In addition to CCR6 or CCL20 alone, correlation of CCR6/

CCL20 co-expression with disease progression is stated in literature. Indeed, overexpression of both, CCL20 and CCR6, was detected in high-grade glioma tissues as compared to low-grade tissues and increased with ascending tumor World Health Organization (WHO) grades. Particularly glioma patients with CCL20/CCR6 co-expression had the shortest overall survival (Med Oncol. 2012 December; 29(5):3491-7. doi: 10.1007/s12032-012-0314-9).

Besides, CCR6 and/or CCL20 expression correlates with enhance chemotherapeutic resistance and is associated with metastasis. Indeed, CCL20 expression can increase the chemotherapeutic resistance of breast cancer cells (PLoS Biol. 2018 July; 16(7):e2005869. doi: 10.1371/journal.pbio.2005869). Rubie and colleagues describe that in colorectal liver metastases (CRLM) and in human samples of hepatocellular carcinoma (HCC), significant up-regulation of CCL20/CCR6 was detected (RT-PCR). Moreover, CCL20 was significantly overexpression in colorectal liver metastases as compared to the primary HCC, indicating an involvement of the CCL20/CCR6 ligand-receptor pair in the carcinogenesis and progression of hepatic malignancies (World J Gastroenterol. 2006 Nov. 7; 12(41):6627-33. doi: 10.3748/wjg.v12.i41.6627).

The present CCR6 modulators may be useful, alone, or in combination in the treatment or prevention of diseases or disorders where CCR6 and/or CCL20 are expressed or overexpressed in patient samples or cancer cell lines. Specifically, the chemokine receptor CCR6 is described to be expressed in several cancer types or cancer cell lines in the literature. Lu and coworkers describe that CCR6 expression was higher in laryngeal cancer tissues compared with their normal controls. The authors reported that CCR6 was also expressed in commonly used laryngeal cancer cells such as TU212, M4E, M2E and Hep-2 (Biomed Pharmacother. 2017 January; 85:486-492. doi: 10.1016/j.biopha.2016.11.055). Based on gene expression data from malignant melanoma, among the biological networks reported CCR6 gene was described and characterized as a valuable factor involved in immune responses and tumor progression (PLoS One. 2018; 13(1):e0190447. doi: 10.1371/journal.pone.0190447.) Whole exome sequencing in 21 MALT lymphomas of the salivary gland and thyroid revealed that CCR6 was expressed (Haematologica. 2018 August; 103(8):1329-1336. doi: 10.3324/haematol.2018.191601). In samples of adult human T-cell leukemia/lymphoma (ATLL) transcripts of CCR6 were detected, and CCR6 was further found at the protein level using flow cytometric analysis (Leuk Lymphoma. 2006 October; 47(10):2163-73. doi: 10.1080/10428190600775599). In patient-derived prostate cancer samples the gene expression of CCR6 (mRNA) was significantly higher in tumor tissue as compared to adjacent normal tissue (Cancer Res Treat. 2015 April; 47(2):306-12. doi: 10.4143/crt.2014.015). CCR6 expression was detected in commonly used cancer cell lines, indeed, according to Mays and co-workers, in salivary adenoid cystic carcinoma cells SACC-83, among other CC chemokine receptors, CCR6 was expressed using RT-PCR gene analysis (Anticancer Res. 2016 August; 36(8):4013-8). According to Möller and colleagues, in multiple myeloma (MM) cell lines including U266 1970, U-266 1984, U-1958, Karpas 707, LP-1,28 L-363, HL407E and HL407L.3, CCR6 was also expressed (Leukemia. 2003 January; 17(1):203-10. doi: 10.1038/sj.leu.2402717).

Analogous to CCR6, the ligand CCL20 was reported to be expressed in multiple tumor samples and tumor cell lines in the literature. For example, Zhang and co-workers demonstrated that in samples from NSCLC patients, using RT-PCR, CCL20 showed higher expression in tumor samples than in samples of adjacent tissue, this was also verified at the protein level using immunohistochemistry (Biomed Pharmacother. 2015 February; 69:242-8. doi: 10.1016/j.biopha.2014.12.008). Gene expression analysis of cholangiocarcinoma samples and corresponding normal tissue revealed CCL20 to be one of the genes most significantly over-expressed in malignant vs healthy tissue (EXCLI J. 2020; 19:154-166. doi: 10.17179/excli2019-1893). CCL20 expression was also reported in multiple myeloma (MM) human samples (Cancer Res. 2008 Aug. 15; 68(16):6840-50. doi: 10.1158/0008-5472.CAN-08-0402). Besides, according to Rubies et al., CCL20 mRNA and protein was significantly up-regulated in pancreatic carcinoma (8-fold) as compared to matched normal pancreas in which CCL20 was weakly expressed (J Transl Med. 2010 May 10; 8:45. doi: 10.1186/1479-5876-8-45). CCL20 is also expressed in oral squamous cell carcinoma (IHC staining) and Lee et al. reported that expression is enriched in human CCR6+ regulatory T cells with superior suppressive activity (J Immunol. 2017 Jul. 15; 199(2):467-476. doi: 10.4049/jimmunol.1601815).

In addition to CCR6 or CCL20 alone, the co-expression of both CCR6 and CCL20 is reported for samples of cancer patients and cancer cells lines in literature. Both genes have been described to be expressed in adult T-cell leukemia/lymphoma patient samples (Microarray and IHC protein staining) (Int J Oncol. 2014 September; 45(3):1200-8. doi: 10.3892/ijo.2014.2524) and in CTCL. In the latter, CCL20 and CCR6 were detected at the mRNA and protein levels (Clin Cancer Res. 2011 Dec. 15; 17(24):7529-38. doi: 10.1158/1078-0432.CCR-11-1192). Transcriptomic analysis (nanostring) of samples of hepatocellular carcinoma revealed CCR6 and CCL20 expression. Moreover, a chemotactic gradient between non-tumor and tumor tissues was reported and a recruitment process of T regulatory cells, tumor associated macrophages and natural killer cells involving the CCR6/CCL20 axis suggested (Proc Natl Acad Sci USA. 2017 Jul. 18; 114(29):E5900-E5909. doi: 10.1073/pnas.1706559114). Similarly, Guo and co-workers reported CCR6 and CCL20 upregulation in hepatocarcinoma lesions compared to healthy tissue as well as CCR6 and CCL20 expression in hepatocarcinoma cell lines (L02, Li-/, Huh-7, SNU-387, Hep3B) (Oncol Rep. 2019 September; 42(3):1075-1089. doi: 10.3892/or.2019.7221). In human colorectal cancer, both CCL20 and CCR6 are expressed according to Nandi et al. (IHC protein staining). Both, CCR6 and CCL20, were found to be highly expressed in samples of NSCLC (protein and mRNA) (Oncol Lett. 2017 December; 1-((6):8183-8189. doi: 10.3892/01.2017.7253). Using in situ hybridization, both CCL20 and CCR6 mRNA moieties were strongly expressed in all pancreatic cancer samples analysed. In contrast, in healthy pancreas CCL20 and CCR6 expression was low (Int J Cancer. 1999 May 17; 81(4):650-7. doi: 10.1002/(sici)1097-0215(19990517)81:4<650::aid-ijc23>3.0.co; 2-#). Jin and co-workers examined CCR6 and CCL20 expression in glioblastoma using publicly available datasets. The authors used the GEO dataset GSE2223 to compare the mRNA levels of CCL20 and CCR6, between normal brain and glioblastoma tissues. Again, CCR6 and CCL20 expression levels were significantly higher in glioblastoma tissues than in normal brain tissues (Oncogene. 2018 June; 37(23):3070-3087. doi: 10.1038/s41388-018-0182-7). In addition, Wallace and colleagues observed that in endometrial adenocarcinoma explants and cell lines, expression of CCL20 and its receptor CCR6 were higher compared to non-malignant endometrium (mRNA, RT-PCR) (Mol Cell Endocrinol. 2011 Jan. 1; 331(1):129-35.

doi: 10.1016/j.mce.2010.08.018). CCL20/CCR6 axis may play a role in breast cancer, cholangiocarcinoma, and thyroid cancer since expression of CCR6/CCL20 genes and/or proteins was reported in patient derived breast cancer cells (Mol Carcinog. 2016 July; 55(7):1175-86. doi: 10.1002/mc.22360), in HuCCT1 and TFK-1 cholangiocarcinoma cell lines ( )(Win et al., PMID 32194362) (EXCLI J. 2020; 19:154-166. doi: 10.17179/excli2019-1893) and thyroid cancer cell lines such as TPC-1, BCPAP, FTC-133, and SW1736 (Tumour Biol. 2016 April; 37(4):5569-75. doi: 10.1007/s13277-015-4418-7). Furthermore, the present CCR6 modulators may be useful, alone, or in combination in the treatment or prevention of cancers where the expression and/or evidence of CCR6/CCL20 axis activity has been reported, or where CCR6+ regulatory T cells have been identified inside the tumor microenvironment.

1) One aspect of the present invention relates to compounds of Formula (I), wherein Formula (I)

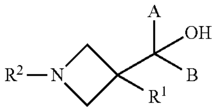

A represents a 6-membered heteroaryl containing from one to three ring nitrogen atom(s) (notably one or two ring nitrogen atoms; especially one or two ring nitrogen atoms in meta-position(s) and/or para-position of A with respect to the point of attachment of A to the rest of the molecule), wherein said 6-membered heteroaryl is independently unsubstituted, mono-, di- or tri-substituted (notably mono- or di-substituted in meta- and/or para-position of A with respect to the point of attachment of A to the rest of the molecule), wherein the substituent(s), if any, is(are) independently selected from halogen (especially fluorine);

cyano;

hydroxy-$C_{1-6}$-alkyl which is optionally further substituted with one to three fluorine atoms (wherein notably the hydroxy group is separated from any one fluorine atom by at least two carbon atoms; especially such hydroxy-$C_{1-6}$-alkyl represents 3-hydroxy-propyl, 4-hydroxy-butyl, 3-hydroxy-butyl, 3-hydroxy-3-methyl-butyl, 3-hydroxy-4-methyl-pentyl, 3-hydroxy-3-trifluoromethyl-butyl, or 2,2-difluoro-3-hydroxy-prop-1-yl);

$C_{1-5}$-alkyl (notably methyl, ethyl, propyl, isopropyl, butyl, or isobutyl) which is unsubstituted or mono-substituted with $C_{1-3}$-alkoxy (especially methoxy);

$C_{3-6}$-cycloalkyl which is optionally fused with a pyridine ring (notably at positions 2 and 3 adjacent to the nitrogen atom of said pyridine ring), wherein said $C_{3-6}$-cycloalkyl is unsubstituted or mono-substituted with hydroxy (notably at the point of attachment of the $C_{3-6}$-cycloalkyl to the $C_{1-4}$-alkyl);

—O—$R^{O1}$, wherein $R^{O1}$ represents $C_{3-6}$-cycloalkyl (especially cyclopentyl) or pyrrolidinyl (especially pyrrolidin-2-yl) which is independently unsubstituted or mono-substituted with $C_{1-3}$-alkyl (especially methyl) or $C_{1-4}$-alkyl-carbonyl (especially acetyl);

phenyl-$L^1$-, wherein said phenyl is unsubstituted or mono-substituted with fluorine, $C_{1-4}$-alkoxy-carbonyl (especially methoxy-carbonyl), or hydroxy-$C_{1-4}$-alkyl (especially hydroxy-methyl); wherein -$L^1$- represents a bond (i.e. the phenyl is attached directly to said alkyl), oxygen (i.e. the phenyl is attached via oxygen to said alkyl), or the group —$CH_2$—O— (wherein the phenyl is attached to the methylene group);

$C_{4-6}$-heterocyclyl containing one or two ring heteroatoms independently selected from nitrogen and oxygen (notably azetidinyl, imidazolidinyl, pyrrolidinyl, oxazolidinyl, piperidinyl, or tetrahydropyranyl; especially azetidin-3-yl, tetrahydropyran-4-yl, imidazolidin-1-yl, pyrrolidin-1-yl, oxazolidin-3-yl, pyrrolidin-2-yl, pyrrolidin-3-yl, piperidin-4-yl), wherein said $C_{4-6}$-heterocyclyl is unsubstituted, mono-, or di-substituted with oxo, hydroxy, $C_{1-3}$-alkyl (especially methyl), $C_{1-4}$-alkyl-carbonyl (especially acetyl), or $C_{1-4}$-alkoxy-carbonyl (especially tert-butoxy-carbonyl);

[in particular such $C_{4-6}$-heterocyclyl represents 1-(tert-butoxy-carbonyl)-3-hydroxy-azetidin-3-yl, tetrahydropyran-4-yl, 4-hydroxy-tetrahydropyran-4-yl, 2-oxo-imidazolidin-1-yl, 2-oxo-3-methyl-imidazolidin-1-yl, 2-oxo-pyrrolidin-1-yl, 2-oxo-oxazolidin-3-yl, 2-oxo-oxazolidin-3-yl, N-acetyl-2-methyl-pyrrolidin-2-yl, N-(tert-butoxy-carbonyl)-3-hydroxy-pyrrolidin-3-yl, N-acetyl-piperidin-4-yl, or N-(tert-butoxy-carbonyl)-piperidin-4-yl]

5-membered heteroaryl containing one or two ring nitrogen atoms (notably pyrazolyl; especially pyrazol-4-yl), wherein said 5-membered heteroaryl is unsubstituted or mono-substituted with $C_{1-3}$-alkyl (especially methyl);

—$NR^{N1}R^{N1}$ wherein $R^{N1}$ represents hydrogen and $R^{N2}$ represents $C_{1-3}$-alkyl-carbonyl (especially acetyl) or hydroxy-$C_{1-3}$-alkyl-carbonyl (especially hydroxymethyl-carbonyl) [in particular such —$NR^{N1}R^{N2}$ represent acetyl-amino or hydroxymethyl-carbonyl-amino];

indolyl (especially indol-2-yl);

pyrrolopyridinyl (especially 1H-pyrrolo[2,3-b]pyridin-2-yl));

N—($C_{1-3}$-alkyl)amino-carbonyl-oxy; or 1-hydroxy-1-$C_{3-5}$-cycloalkyl-1-(pyridinyl)-methyl (especially 1-hydroxy-1-cyclopropyl-1-(pyridin-2-yl)-methyl);

[in particular such $C_{1-4}$-alkyl represents methyl, ethyl, isopropyl, cyclopentyl-oxy-methyl, 2-(1-hydroxy-cyclopropyl)-ethyl, 2-(1-hydroxy-cyclobutyl)-ethyl, 2-(1-hydroxy-cyclopentyl)-ethyl, 3-methoxy-propyl, 4-fluoro-phenoxy-methyl, 2-(2-(methoxy-carbonyl)-phenyl)-ethyl, benzyl-oxy-methyl, N-(isopropyl)-amino-carbonyl-oxy-methyl, 2-(1-(tert-butoxy-carbonyl)-3-hydroxyazetidin-3-yl)-ethyl, 3-methyl-3-(2-oxo-imidazolidin-1-yl)-butyl, 3-methyl-3-(2-oxo-3-methyl-imidazolidin-1-yl)-butyl, 3-methyl-3-(2-oxo-pyrrolidin-1-yl)-butyl, 2-(N-(tert-butoxy-carbonyl)-3-hydroxy-pyrrolidin-3-yl)-ethyl, 3-methyl-3-(2-oxo-oxazolidin-3-yl)-butyl, 2-(1-methyl-1H-pyrazol-4-yl)-ethyl, 2-(2-hydroxymethyl-phenyl)ethyl, 2-(tetrahydropyran-4-yl)-ethyl, 2-(4-hydroxy-tetrahydropyran-4-yl)-ethyl, 2-(indol-2-yl)-ethyl, 2-(8-hydroxy-5,6,7,8-tetrahydroquinolin-8-yl)ethyl, 2-(7-hydroxy-6,7-dihydro-5H-cyclopenta[b]pyridin-7-yl)-ethyl, 2-(N-acetyl-piperidin-4-yl)-ethyl, 2-(N-(tert-butoxy-carbonyl)-piperidin-4-yl)-ethyl, N-acetyl-2-methyl-pyrrolidin-2-yl-oxy-methyl, acetyl-amino-isopropyl, N-(hydroxymethyl-carbonyl)-aminomethyl, 3-hydroxy-3-cyclopropyl-3-(pyridin-2-yl)-propyl, 2-(indol-2-yl)-ethyl, or 2-(1H-pyrrolo[2,3-b]pyridin-2-yl)-ethyl]

$C_{3-5}$-alkyl (especially n-propyl, n-butyl, or n-pentyl) which is substituted with hydroxy and $R^{A1}$, wherein said substituents are both at position 3 with respect to the point of attachment of said $C_{3-5}$-alkyl to the rest of the molecule; wherein $R^{A1}$ represents tetrahydropyranyl (especially tetrahydropyran-4-yl);

phenyl which is unsubstituted or mono-substituted with fluorine (especially 3-fluoro-phenyl) or $C_{1-3}$-alkoxy (especially 2-methoxy-phenyl or 4-methoxy-phenyl);

5- or 6-membered heteroaryl containing one or two ring heteroatom(s) being independently selected from nitrogen or sulfur (notably thiazolyl, pyrazolyl, pyridinyl, pyrazinyl, or pyrimidinyl; especially thiazol-4-yl, thiazol-5-yl, pyrazol-3-yl, pyrazol-4-yl, pyridin-2-yl, pyridin-3-yl, pyrimidin-2-yl, pyrazin-2-yl, or pyrimidin-4-yl), wherein said 5- or 6-membered heteroaryl is independently unsubstituted, mono- or di-substituted, and wherein the substituent(s), if any, is(are) independently selected from $C_{1-3}$-alkyl (especially methyl), $C_{3-5}$-cycloalkyl (especially cyclopropyl), or $C_{1-3}$-alkoxy (especially methoxy); or indazolyl (especially indazol-3-yl);

[in particular such $C_{3-5}$-alkyl which represents 3-hydroxy-3-(tetrahydropyran-4-yl)-propyl, 3-hydroxy-3-phenyl-propyl, 3-hydroxy-3-phenyl-butyl, 3-hydroxy-3-(3-fluoro-phenyl)-butyl, 3-hydroxy-3-(2-methoxy-phenyl)-butyl, 3-hydroxy-3-(4-methoxy-phenyl)-butyl, 3-hydroxy-3-(1,5-dimethyl-pyrazol-3-yl)-butyl, 3-hydroxy-3-(1-methyl-pyrazol-3-yl)-butyl, 3-hydroxy-3-(1-cyclopropyl-1H-pyrazol-3-yl)-butyl, 3-hydroxy-3-(1,5-dimethyl-pyrazol-3-yl)-propyl, 3-hydroxy-3-(2-methyl-thiazol-4-yl)-butyl, 3-hydroxy-3-(2-methyl-thiazol-5-yl)-butyl, 3-hydroxy-3-(6-methoxy-pyridin-2-yl)-butyl, 3-hydroxy-3-(5-methyl-pyridin-3-yl)-butyl, 3-hydroxy-3-(pyridin-2-yl)-butyl, 3-hydroxy-3-(6-methyl-pyridin-2-yl)-butyl, 3-hydroxy-3-(pyrimidin-2-yl)-butyl, 3-hydroxy-3-(6-methoxy-pyrimidin-4-yl)-butyl, 3-hydroxy-3-(6-methyl-pyrimidin-4-yl)-pentyl, 3-hydroxy-3-(2-methyl-pyrimidin-4-yl)-butyl, 3-hydroxy-3-(5-methyl-pyrazin-2-yl)-butyl, 3-hydroxy-3-(1H-indazol-3-yl)-butyl, 3-hydroxy-3-(1,3-dimethyl-pyrazol-4-yl)-propyl, 3-hydroxy-3-(2-methyl-thiazol-4-yl)-propyl, 3-hydroxy-3-(pyridin-2-yl)-pentyl, or 3-hydroxy-3-(6-methoxy-pyridin-2-yl)-pentyl]

$C_{3-5}$-alkenyl which is unsubstituted (especially isopropenyl) or mono-substituted with hydroxy (especially 4-hydroxy-but-1-en-2-yl);

$C_{4-6}$-cycloalkenyl (notably cyclopentenyl; especially cyclopent-1-en-1-yl) which is unsubstituted, mono-, or di-substituted with $C_{1-3}$-alkyl, oxo, or hydroxy; wherein optionally one ring carbon atom of said $C_{4-6}$-cycloalkenyl is replaced by an oxygen atom;

[in particular such $C_{4-6}$-cycloalkenyl represents cyclopent-1-en-1-yl, 3-oxo-cyclopent-1-en-1-yl, 3-hydroxy-cyclopent-1-en-1-yl, 3-hydroxy-3-methyl-cyclopent-1-en-1-yl, or 2,3-dihydro-furan-3-yl]

$C_{3-6}$-cycloalkyl which is unsubstituted, mono-, or di-substituted with $C_{1-3}$-alkyl (especially methyl, ethyl, isopropyl), hydroxy or hydroxy-$C_{1-3}$-alkyl (especially 1-hydroxy-1-methyl-ethyl), wherein optionally one ring carbon atom of said $C_{3-6}$-cycloalkyl is replaced by an oxygen atom;

[in particular such $C_{3-6}$-cycloalkyl represents cyclopropyl, cyclopentyl, 3-hydroxy-cyclopentyl, 3-hydroxy-3-methyl-cyclopentyl, 3-hydroxy-3-ethyl-cyclopentyl, 3-hydroxy-3-isopropyl-cyclopentyl, 2-(2-hydroxy-isopropyl)-cyclopropyl, 4-hydroxy-cyclohexyl, 4-hydroxy-4-methyl-cyclohexyl, oxetan-3-yl, tetrahydrofuran-3-yl, tetrahydrofuran-2-yl, tetrahydropyran-4-yl, 5-methyl-tetrahydrofuran-2-yl, or 5,5-dimethyl-tetrahydrofuran-2-yl]

—O—$R^{O2}$, wherein $R^{O2}$ represents $C_{1-4}$-alkyl (especially methyl, ethyl, isopropyl, sec-butyl, or isobutyl);

$C_{2-5}$-alkyl which is mono-substituted with hydroxy or $C_{1-3}$-alkoxy (especially methoxy);

[in particular such $C_{2-5}$-alkyl represents 2-hydroxy-ethyl, 3-hydroxy-propyl, 2-hydroxy-2-methyl-propyl, 3-hydroxy-3-methyl-butyl, or 2-methoxy-ethyl]

-$L^2$-$CY^2$, wherein

-$L^2$- independently represents a bond (i.e. the $CY^2$ is directly attached to the rest of the molecule), —$CH_2$—, or —$CH_2$—$CH_2$—; and $CY^2$ independently represents phenyl which is unsubstituted or mono-substituted with hydroxy-$C_{1-3}$-alkyl (especially 2-hydroxy-ethyl);

benzyl-oxy;

5- to 6-membered heteroaryl containing one to three ring heteroatom(s) being independently selected from nitrogen, oxygen, or sulfur (notably pyridinyl, oxadiazolyl, or triazolyl); especially pyridin-2-yl, 1,2,4-oxadiazol-5-yl, or 1,2,4-triazol-1-yl), wherein said 5- or 6-membered heteroaryl is independently unsubstituted, mono- or di-substituted; wherein the substituent(s), if any, is(are) independently selected from $C_{1-3}$-alkyl (especially methyl) or $C_{1-3}$-cycloalkyl (especially cyclopropyl);

$C_{3-6}$-cycloalkyl, wherein optionally one carbon ring atom is replaced by one heteroatom selected from oxygen and nitrogen (especially oxetanyl, cyclopentyl or cyclohexyl); wherein said $C_{3-6}$-cycloalkyl is unsubstituted, mono-, or di-substituted, wherein the substituents are selected from $C_{1-3}$-alkyl (especially methyl), hydroxy, fluoro, oxo, $C_{1-3}$-alkyl-carbonyl (especially acetyl), and $C_{1-3}$-alkoxy (especially methoxy);

benzooxazolonyl (especially 3H-benzooxazol-2-on-6-yl);

chromanyl (especially chroman-6-yl);

[in particular such -$L^2$-$CY^2$ represents phenyl, 4-(2-hydroxy-ethyl)-phenyl, 2-(2-hydroxy-ethyl)-phenyl, benzyl, 2-(benzyl-oxy)-ethyl, 2-(pyridin-2-yl)-ethyl, 3-cyclopropyl-1,2,4-oxadiazol-5-yl-methyl, 2-(3,5-dimethyl-1,2,4-triazol-1-yl)-ethyl, oxetan-3-yl-methyl, 2,2-dimethyl-cyclopentyl, 3,3-difluoro-cyclopentyl, 3-methoxy-cyclopentyl, cyclohexyl, 4-hydroxy-cyclohexyl, 4-methyl-4-hydroxy-cyclohexyl, 4-oxo-cyclohexyl, tetrahydrofuran-3-yl, tetrahydropyran-4-yl, tetrahydropyran-4-yl-methyl, N-acetyl-piperidin-4-yl-methyl, 3H-benzooxazol-2-on-6-yl, or chroman-6-yl]

[in particular such —O—$R^{O2}$ represents methoxy, ethoxy, isopropoxy, isobutoxy, sec-butoxy, phenoxy, 4-(2-hydroxy-ethyl)-phenoxy, 2-(2-hydroxy-ethyl)-phenoxy, benzyl-oxy, 2-(benzyl-oxy)-ethoxy, 2-methoxy-ethoxy, 3-hydroxy-propoxy, 2-hydroxy-2-methyl-propoxy, 2-hydroxy-ethoxy, 3-hydroxy-3-methyl-butoxy, 2,2-dimethyl-cyclopentyl-oxy, 3,3-difluoro-cyclopentyl-oxy, cyclohexyl-oxy, 4-hydroxy-cyclohexyl-oxy, 4-methyl-4-hydroxy-cyclohexyl-oxy, 4-oxo-cyclohexyl-oxy, tetrahydrofuran-3-yl-oxy, tetrahydropyran-4-yl-oxy, tetrahydropyran-4-yl-methoxy, 3-methoxy-cyclopentyl-oxy, oxetan-3-yl-methoxy, 2-(pyridin-2-yl)-ethyl-oxy, (3-cyclopropyl-1,2,4-oxadiazol-5-yl)-methoxy, 2-(3,5-dimethyl-1,2,4-triazol-1-yl)-ethoxy, N-acetyl-piperidin-4-yl-methyl-oxy, 3H-benzooxazol-2-on-6-yl, or chroman-6-yl-oxy]

—C≡C—$R^{T1}$, wherein $R^{T1}$ represents $C_{1-4}$-alkyl (notably methyl, ethyl, isopropyl, or isobutyl), wherein said $C_{1-4}$-alkyl independently is mono-substituted with hydroxy;

[in particular said $C_{1-4}$-alkyl represents hydroxy-methyl, 1-hydroxy-ethyl, 2-hydroxy-ethyl, 1-hydroxy-2-methyl-propyl, 1-hydroxy-1-methyl-ethyl, or 1-hydroxy-1-trifluoromethyl-ethyl];

$C_{1-3}$-alkoxy (especially methoxy);

—S(=O)$_2$—$R^{SOT}$, wherein $R^{SOT}$ represents $C_{1-3}$-alkyl, $C_{1-3}$-alkyl-amino, or $C_{3-5}$-cycloalkyl (especially such —S(=O)$_2$—$R^{SOT}$ represents methyl-sulfonyl, methyl-amino-sulfonyl or cyclopropyl-sulfonyl);

—$NR^{NT1}R^{NT2}$ wherein $R^{NT1}$ represents hydrogen and $R^{NT2}$ represents $C_{1-3}$-alkyl-carbonyl, $C_{1-3}$-alkoxy-$C_{1-3}$-alkyl-carbonyl, or $C_{3-5}$-cycloalkyl-carbonyl (especially such —$NR^{NT1}R^{NT2}$ represent acetyl-amino, isopropyl-carbonyl-amino, methoxy-methyl-carbonyl-amino, or cyclopropyl-carbonyl-amino);

$C_{4-6}$-heterocyclyl containing one or two ring heteroatom(s) independently selected from nitrogen and oxygen (notably oxazolidinyl, imidazolidinyl, or pyrrolidinyl; especially oxazolidin-3-yl, imidazolidin-3-yl, or pyrrolidin-1-yl); wherein said $C_{4-6}$-heterocyclyl is mono-substituted with oxo; or di-substituted with oxo and $C_{1-3}$-alkyl (especially methyl); (especially such $C_{4-6}$-heterocyclyl represents oxazolidin-2-on-3-yl, imidazolidin-2-on-3-yl, 1-methyl-imidazolidin-2-on-3-yl, or pyrrolidin-2-on-1-yl); or N—($C_{1-3}$-alkyl-carbonyl)-piperidinyl-$C_{1-3}$-alkyl (especially N-acetyl-piperidin-4-yl-methyl);

$C_{3-6}$-cycloalkyl (especially cyclopropyl) which is mono-substituted (especially at the point of attachment of the $C_{3-6}$-cycloalkyl to the rest of the molecule) with hydroxy;

amino-sulfonyl which is optionally di-substituted with methyl;

phenyl which is mono-substituted with halogen (especially 4-fluoro-phenyl);

pyridinyl (especially pyridine-2-yl);

pyrimidinyl which is mono-substituted with $C_{1-3}$-alkyl (especially 6-methyl-pyrimidin-4-yl);

oxazolidinonyl (especially oxazolidin-2-on-3-yl);

[in particular such $C_{3-6}$-cycloalkyl represents 1-hydroxy-cyclopropyl, 1-hydroxy-cyclobutyl, 1-hydroxy-cyclopenty, 1-(amino-sulfonyl)-cyclopropyl, 1-(dimethyl-amino-sulfonyl)-cyclopropyl, 1-(6-methyl-pyrimidin-4-yl)-cyclopropyl, 1-(pyridine-2-yl)-cyclopropyl, 1-(4-fluoro-phenyl)-cyclopropyl, 1-(pyridine-2-yl)-cyclopropyl, or 1-(oxazolidin-2-on-3-yl)-cyclopropyl];

$C_{3-6}$-cycloalkyl (notably cyclopentyl or cyclohexyl) fused with a pyridine ring (notably at positions 2 and 3 of the pyridine ring), wherein said $C_{3-6}$-cycloalkyl is mono-substituted with hydroxy (notably at position 1 of the $C_{3-6}$-cycloalkyl ring); wherein optionally one ring carbon atom in said $C_{3-6}$-cycloalkyl is replaced with one oxygen atom;

[in particular such $C_{3-6}$-cycloalkyl represents 8-hydroxy-5,6,7,8-tetrahydroquinolin-8-yl, 7-hydroxy-6,7-dihydro-5H-cyclopenta[b]pyridin-7-yl, or 4-hydroxy-3,4-dihydro-2H-pyrano[3,2-b]pyridin-4-yl);

$C_{4-6}$-heterocyclyl containing one ring heteroatom independently selected from nitrogen and oxygen (notably azetidinyl, pyrrolidinyl, piperidinyl, tetrahydropyranyl; especially azetidin-3-yl, piperidin-4-yl, pyrrolidin-3-yl, pyrrolidin-2-yl, pyrrolidine-1-yl, or tetrahydropyran-4-yl); wherein said $C_{4-6}$-heterocyclyl is mono-, di-, or tri-substituted (especially mono- or di-substituted), wherein the substituent(s) is(are) independently selected from $C_{1-3}$-alkyl (especially methyl), hydroxy, oxo, $C_{1-3}$-alkyl-carbonyl (especially acetyl), $C_{1-3}$-alkoxy-carbonyl (especially tert-butoxy-carbonyl), $C_{1-3}$-alkyl-sulfonyl (especially methyl-sulfonyl), and $C_{1-3}$-alkyl-amino-sulfonyl (especially methyl-amino-sulfonyl);

[in particular such $C_{4-6}$-heterocyclyl represents N-(isopropyl-carbonyl)-3-hydroxy-azetidin-3-yl, N-(tert-butoxy-carbonyl)-3-hydroxy-azetidin-3-yl, N-methyl-3-hydroxy-pyrrolidin-2-one-3-yl, N-acetyl-2-methyl-pyrrolidin-2-yl, 3-hydroxy-N-(tert-butoxy-carbonyl)-pyrrolidin-3-yl, 2-oxo-pyrrolidine-1-yl, N-acetyl-piperidin-4-yl, N-acetyl-4-methyl-piperidin-4-yl, N-(methyl-amino-sulfonyl)-4-methyl-piperidin-4-yl, N-acetyl-4-hydroxy-piperidin-4-yl, N-(methyl-sulfonyl)-piperidin-4-yl, N-(tert-butoxy-carbonyl)piperidin-4-yl, 3-hydroxy-2-oxo-1-methyl-pyrrolidin-2-yl, or 4-hydroxy-tetrahydropyran-4-yl);

pyrazolyl (notably 1H-pyrazol-4-yl) which is N-substituted with methyl;

indolyl (especially indol-2-yl);

3-hydroxy-1-methyl-1,3-dihydro-indol-2-on-3-yl; or 4-hydroxy-3,4-dihydro-2H-pyrano[3,2-b]pyridin-4-yl;

[in particular such —C≡C—$R^{T1}$ represents 3-hydroxy-3-trifluoromethyl-but-1-yn-1-yl, 3-hydroxy-prop-1-yn-1-yl, 4-hydroxy-but-1-yn-1-yl, 3-hydroxy-but-1-yn-1-yl, 3-hydroxy-3-methyl-but-1-yn-1-yl, 3-methyl-3-(pyrrolidin-2-on-1-yl)-but-1-yn-1-yl, 3-methyl-3-(cyclopropyl-sulfonyl)-but-1-yn-1-yl, 3-methyl-3-(acetyl-amino)-but-1-yn-1-yl, 3-methyl-3-(oxazolidin-2-on-3-yl)-but-1-yn-1-yl, 3-methyl-3-(imidazolidin-2-on-3-yl)-but-1-yn-1-yl, 3-methyl-3-(1-methyl-imidazolidin-2-on-3-yl)-but-1-yn-1-yl, 3-methyl-3-(2-oxopyrrolidine-1-yl)-but-1-yn-1-yl, 3-methyl-3-(methyl-sulfonyl)-but-1-yn-1-yl, 3-methyl-3-(cyclopropyl-carbonyl-amino)-but-1-yn-1-yl, 3-methyl-3-(isopropyl-carbonyl-amino)-but-1-yn-1-yl, 3-methyl-3-(methoxy-methyl-carbonyl-amino)-but-1-yn-1-yl, 3-hydroxy-4-methyl-pent-1-yn-1-yl, 3-methoxy-prop-1-yn-1-yl, 3-(N-acetyl-piperidin-4-yl)-prop-1-yn-1-yl, (1-hydroxy-cyclopropyl)-ethynyl, (1-hydroxy-cyclobutyl)-ethynyl, (1-hydroxy-cyclopentyl)-ethynyl, (8-hydroxy-5,6,7,8-tetrahydroquinolin-8-yl)-ethynyl, (7-hydroxy-6,7-dihydro-5H-cyclopenta[b]pyridin-7-yl)-ethynyl, (1-methyl-pyrazol-4-yl)-ethynyl, (tetrahydropyran-4-yl)-ethynyl, (4-hydroxy-tetrahydropyran-4-yl)-ethynyl, indol-2-yl-ethynyl, (1-(isopropyl-carbonyl)-3-hydroxy-azetidin-3-yl)-ethynyl, (1-(tert-butoxy-carbonyl)-3-hydroxy-azetidin-3-yl)-ethynyl, (1-(6-methyl-pyrimidin-4-yl)-cyclopropyl)-ethynyl, (N-acetyl-4-methyl-piperidin-4-yl)-ethynyl, (N-acetyl-4-hydroxy-piperidin-4-yl)-ethynyl, (1-(4-fluoro-phenyl)-cyclopropyl)-ethynyl, (N-acetyl-piperidin-4-yl)-ethynyl, (N-(methyl-sulfonyl)-piperidin-4-yl)-ethynyl, (1-(dimethyl-amino-sulfonyl)-cyclopropyl)-ethynyl, (1-(amino-sulfonyl)-cyclopropyl)-ethynyl, (N-(methyl-amino-sulfonyl)-4-methyl-piperidin-4-yl)-ethynyl, (1-(pyridine-2-yl)-cyclopropyl)-ethynyl, (3-hydroxy-N-(tert-butoxy-carbonyl)-pyrrolidin-3-yl)-ethynyl, (1-(oxazolidin-2-on-3-yl)-cyclopropyl)-ethynyl, (3-hydroxy-1-methyl-1,3-dihydro-indol-2-on-3-yl)-ethynyl, (4-hydroxy-3,4-dihydro-2H-pyrano[3,2-b]pyridin-4-yl)-ethynyl, (N-(tert-butoxy-carbonyl)piperidin-4-yl)-ethynyl, (N-acetyl-2-methyl-pyrrolidin-2-yl)-ethynyl, or (3-hydroxy-2-oxo-1-methyl-pyrrolidin-3-yl)-ethynyl]

—C≡C—C(OH)($R^{T2}$)($R^{T3}$), wherein $R^{T2}$ represents hydrogen or $C_{1-3}$-alkyl (notably methyl or ethyl; especially methyl);

$R^{T3}$ represents phenyl which is unsubstituted or mono-substituted, wherein the substituent, if any, is selected from $C_{1-3}$-alkoxy (notably methoxy) or halogen (notably fluorine);

[in particular such phenyl which is unsubstituted or mono-substituted is 2-fluoro-phenyl, 4-methoxy-phenyl, or 2-methoxy-phenyl]

5- to 6-membered heteroaryl containing one or two ring heteroatom(s) being independently selected from nitrogen, oxygen, or sulfur (notably thiophenyl, thiazolyl, pyrrolyl, pyrazolyl, isoxazolyl, pyridinyl, pyrazinyl, or pyrimidinyl; especially thiophen-2-yl, thiazol-4-yl, thiazol-5-yl, pyrrol-2-yl, pyrazol-3-yl, pyrazol-4-yl, isoxazol-5-yl, pyridin-2-yl, pyrimidin-2-yl, pyrazin-2-yl, or pyrimidin-4-yl), wherein said 5- or 6-membered heteroaryl is independently unsubstituted, mono- or di-substituted, and wherein the substituent(s), if any, is(are) independently selected from $C_{1-3}$-alkyl (especially methyl), $C_{1-3}$-cycloalkyl (especially cyclopropyl), $C_{1-3}$-fluoroalkyl (notably $C_1$-fluoroalkyl; especially difluoromethyl or trifluoromethyl), and $C_{1-3}$-alkoxy (especially methoxy);

[in particular such 5- to 6-membered heteroaryl is 5-methyl-thiophen-2-yl, 2-methyl-thiazol-5-yl, 1-methyl-1H-pyrrol-2-yl, 1-cyclopropyl-1H-pyrazol-3-yl, 1-methyl-1H-pyrazol-3-yl, 1,3-dimethyl-pyrazol-4-yl, 1,5-dimethyl-1H-pyrazol-3-yl, 2-methyl-thiazol-4-yl, 3-methyl-isoxazol-5-yl, 1-methyl-1H-imidazol-2-yl, pyridin-2-yl, 6-methoxy-pyridin-2-yl, 6-methyl-pyridin-2-yl, pyrimidin-2-yl, 2-methoxy-pyrimidin-4-yl, 6-methoxy-pyrimidin-4-yl, pyrimidin-4-yl, 2-methyl-pyrimidin-4-yl, 6-methyl-pyrimidin-4-yl, 2,6-dimethyl-pyrimidin-4-yl, 2,6-dimethoxy-pyrimidin-4-yl, 2-methyl-6-methoxy-pyrimidin-4-yl, 2-methoxy-6-methyl-pyrimidin-4-yl, 5-methyl-pyrazin-2-yl, 1-cyclopropyl-1H-pyrazol-3-yl, 6-cyclopropyl-pyrimidin-4-yl, 6-difluoromethyl-pyrimidin-4-yl, 2-trifluoromethyl-pyrimidin-4-yl, 6-trifluoromethyl-pyrimidin-4-yl, or 1,5-dimethyl-1H-pyrazol-3-yl]

$C_{4-7}$-heterocyclyl containing one ring heteroatom selected from nitrogen and oxygen; wherein said $C_{4-7}$-heterocyclyl is unsubstituted, mono-, or di-substituted, wherein the substituent(s), if any, is(are) independently selected from $C_{1-3}$-alkyl (especially methyl) or $C_{1-3}$-alkyl-carbonyl (especially acetyl); or

[in particular such $C_{4-7}$-heterocyclyl represents N-acetyl-piperidin-4-yl, N-acetyl-4-methyl-piperidin-4-yl, or tetrahydropyran-4-yl]

indazolyl (especially indazol-3-yl);

[in particular such —C≡C—C(OH)($R^{T2}$)($R^{T3}$) represents 3-hydroxy-3-(5-methyl-thiophen-2-yl)-but-1-yn-1-yl, 3-hydroxy-3-(2-methyl-thiazol-5-yl)-but-1-yn-1-yl, 3-hydroxy-3-(1-methyl-1H-pyrrol-2-yl)-but-1-yn-1-yl, 3-hydroxy-3-(3-methyl-isoxazol-5-yl)-but-1-yn-1-yl, 3-hydroxy-3-(1-methyl-1H-pyrrol-2-yl)-but-1-yn-1-yl, 3-hydroxy-3-(1-methyl-1H-imidazol-2-yl)-but-1-yn-1-yl, 3-hydroxy-3-(5-methyl-pyrazin-2-yl)-but-1-yn-1-yl, 3-hydroxy-3-(tetrahydropyran-4-yl)-prop-1-yn-1-yl, 3-hydroxy-3-(N-acetyl-piperidin-4-yl)-prop-1-yn-1-yl, 3-hydroxy-3-(N-acetyl-4-methyl-piperidin-4-yl)-but-1-yn-1-yl, 3-hydroxy-3-phenyl-prop-1-yn-1-yl, 3-hydroxy-3-(2-methyl-thiazol-4-yl)-prop-1-yn-1-yl, 3-hydroxy-3-(1,3-dimethyl-pyrazol-4-yl)-prop-1-yn-1-yl, 3-hydroxy-3-phenyl-but-1-yn-1-yl, 3-hydroxy-3-(1-methyl-1H-pyrazol-3-yl)-but-1-yn-1-yl, 3-hydroxy-3-(1-cyclopropyl-1H-pyrazol-3-yl)-but-1-yn-1-yl, 3-hydroxy-3-(1,5-dimethyl-1H-pyrazol-3-yl)-but-1-yn-1-yl, 3-hydroxy-3-(1-methyl-pyrazol-3-yl)-but-1-yn-1-yl, 3-hydroxy-3-(pyrimidin-2-yl)-but-1-yn-1-yl, 3-hydroxy-3-(1-methyl-pyrazol-3-yl)-but-1-yn-1-yl, 3-hydroxy-3-(3-fluoro-phenyl)-but-1-yn-1-yl, 3-hydroxy-3-(6-methyl-pyrimidin-4-yl)-but-1-yn-1-yl, 3-hydroxy-3-(2-methoxy-pyrimidin-4-yl)-but-1-yn-1-yl, 3-hydroxy-3-(2-methoxy-6-methyl-pyrimidin-4-yl)-but-1-yn-1-yl, 3-hydroxy-3-(6-methoxy-pyrimidin-4-yl)-but-1-yn-1-yl, 3-hydroxy-3-(2,6-dimethoxy-pyrimidin-4-yl)-but-1-yn-1-yl, 3-hydroxy-3-(2-methyl-pyrimidin-4-yl)-but-1-yn-1-yl, 3-hydroxy-3-(6-methoxy-2-methyl-pyrimidin-4-yl)-but-1-yn-1-yl, 3-hydroxy-3-(pyridin-2-yl)-pent-1-yn-1-yl, 3-hydroxy-3-(6-methoxy-pyridin-2-yl)-but-1-yn-1-yl, 3-hydroxy-3-(6-methyl-pyridin-2-yl)-but-1-yn-1-yl, 3-hydroxy-3-(6-methyl-pyridin-2-yl)-pent-1-yn-1-yl, 3-hydroxy-3-(2,6-dimethyl-pyrimidin-4-yl)-but-1-yn-1-yl, 3-hydroxy-3-(6-methoxy-pyridin-2-yl)-pent-1-yn-1-yl, 3-hydroxy-3-(1H-indazol-3-yl)-but-1-yn-1-yl, 3-hydroxy-3-(6-cyclopropyl-pyrimidin-4-yl)-but-1-yn-1-yl, 3-hydroxy-3-(6-difluoromethyl-pyrimidin-4-yl)-but-1-yn-1-yl, 3-hydroxy-3-(2-trifluoromethyl-pyrimidin-4-yl)-but-1-yn-1-yl, 3-hydroxy-3-(6-trifluoromethyl-pyrimidin-4-yl)-but-1-yn-1-yl, 3-hydroxy-3-(indazol-3-yl)-but-1-yn-1-yl, 3-hydroxy-3-(4-methoxy-phenyl)-but-1-yn-1-yl, or 3-hydroxy-3-(2-methoxy-phenyl)-but-1-yn-1-yl]

—$NR^{N3}R^{N4}$ wherein $R^{N3}$ represents $C_{1-3}$-alkyl (especially methyl); and $R^{N4}$ represents hydroxy-$C_{1-3}$-alkyl (especially 2-hydroxy-ethyl) or 2-(benzyl-oxy)-$C_{1-3}$-alkyl (especially 2-(benzyl-oxy)-ethyl); or $R^{N3}$ and $R^{N4}$ form, together with the nitrogen to which they are attached, a heterocyclic ring of 4 to 6 members (notably 5 to 6 members), wherein the members needed to complete said heterocyclic ring are each independently selected from —$CH_2$—, —O—, —(C═O)—, —$CHR^X$— and —$C(R^Y)_2$—; wherein said heterocyclic ring does not contain more than one member independently selected from the group consisting of —O— and —(C═O)—; wherein said heterocyclic ring does not contain more than two members selected from the group consisting of —$CHR^X$—; and wherein said heterocyclic ring does not contain more than two members selected from the group consisting of —$C(R^Y)_2$—; wherein $R^X$ independently represents fluorine, methyl, isopropyl, isobutyl, tert-butyl, hydroxy, trifluoromethyl, hydroxy-methyl, 1-hydroxy-ethyl, 1-hydroxy-1-methyl-ethyl, cyclopropyl, 2-methoxy-ethyl, 2-methyl-thiazol-5-yl, 4-methyl-thiazol-2-yl, phenyl, benzyl, tetrahydropyran-4-yl, N-acetyl-piperidin-4-yl, 1,2,4-oxadiazolyl, 3-methyl-1,2,4-oxadiazol-5-yl, 2-methyl-2H-[1,2,3]triazol-4-yl, 1-methyl-1H-pyrazol-4-yl, 1-difluoromethyl-1H-pyrazol-4-yl, 1,3-dimethyl-1H-pyrazol-4-yl, pyridin-2-yl, 6-methyl-pyridin-3-yl, 6-isopropyl-pyridin-2-yl, 6-trifluoromethyl-pyridin-3-yl, 2-isopropyl-pyrimidin-4-yl, or 1-methoxy-methyl; and wherein $R^Y$ independently represents fluorine, hydroxy, cyclopropyl, methyl, hydroxy-methyl, or trifluoromethyl [notably such —$NR^{N3}R^{N4}$ is pyrrolidinyl; 2-pyrrolidonyl; oxazolidinonyl (especially 1,3-oxazolidin-2-on-3-yl); piperidinyl; or morpholinyl, optionally independently substituted with one or two substituents independently selected from a group consisting of $R^X$ and $R^Y$];

[in particular such —$NR^{N3}R^{N4}$ represents pyrrolidin-1-yl, 3-fluoro-pyrrolidin-1-yl, 3,3-difluoro-pyrrolidin-1-yl, 3,4-difluoro-pyrrolidin-1-yl, 3-isopropyl-pyrrolidin-1-yl, 3,3-dimethyl-pyrrolidin-1-yl, 3-hydroxy-pyrrolidin-1-yl, 2-methyl-pyrrolidin-1-yl, 3-hydroxy-3-methyl-pyrrolidin-1-yl, 3-(hydroxy-methyl)-pyrrolidin-1-yl, 2-(hydroxy-methyl)-pyrrolidin-1-yl, 3-(1-hydroxy-ethyl)-pyrrolidin-1-yl, 3-hydroxy-3-cyclopropyl-pyrrolidin-1-yl, 3-hydroxy-3-trifluoromethyl-pyrrolidin-1-yl, 3-trifluoromethyl-pyrrolidin-1-yl, 3-(1-hydroxy-1-methyl-ethyl)-pyrrolidin-1-yl, 3-(1-hydroxy-ethyl)-pyrrolidin-1-yl, 3-(hydroxy-methyl)-3-methyl-pyrrolidin-1-yl, 1,3-oxazolidin-2-on-3-yl, 5-(tert-butyl)-1,3-oxazolidin-2-on-3-yl, 5-phenyl-1,3-oxazolidin-2-on-3-yl, 5-benzyl-1,3-oxazolidin-2-on-3-yl, 5-isopropyl-1,3-oxazolidin-2-on-3-yl, 5-(tetrahydropyran-4-yl)-1,3-oxazolidin-2-on-3-yl, 5,5-dimethyl-1,3-oxazolidin-2-on-3-yl, morpholin-4-yl, piperidin-1-yl, 4-hydroxy-piperidin-1-yl, 3-hydroxy-piperidin-1-yl, 3-(tetrahydropyran-4-yl)-pyrrolid-2-on-1-yl, N-methyl-N-(2-(benzyl-oxy)-ethyl)-amino, N-methyl-N-(2-hydroxy-ethyl)-amino, pyrrolidin-2-on-1-yl, 4-phenyl-pyrrolidin-2-on-1-yl, 4-(N-acetyl-piperidin-4-yl)-pyrrolidin-2-on-1-yl, 4-(pyridin-2-yl)-pyrrolidin-2-on-1-yl, 4-(6-methyl-pyridin-3-yl)-pyrrolidin-2-on-1-yl, 4-(2-isopropyl-pyrimidin-4-yl)-pyrrolidin-2-on-1-yl, 4-(6-isopropyl-pyridin-2-yl)-pyrrolidin-2-on-1-yl, 4-(6-trifluoromethyl-pyridin-3-yl)-pyrrolidin-2-on-1-yl, 4-methyl-pyrrolidin-2-on-1-yl, 4-isopropyl-pyrrolidin-2-on-1-yl, 3-isopropyl-pyrrolidin-2-on-1-yl, 3,3-dimethyl-pyrrolidin-2-on-1-yl, 4,4-dimethyl-pyrrolidin-2-on-1-yl, 3-(piperidin-4-yl)-pyrrolidin-2-on-1-yl, 4-(1-methyl-1H-pyrazol-4-yl)-pyrrolidin-2-on-1-yl, 4-(1-difluoromethyl-1H-pyrazol-4-yl)-pyrrolidin-2-on-1-yl, 4-(1,3-dimethyl-1H-pyrazol-4-yl)-pyrrolidin-2-on-1-yl, 4-(6-isopropyl-pyridin-2-yl)-pyrrolidin-2-on-1-yl, 4-isobutyl-pyrrolidin-2-on-1-yl, 4-cyclopropyl-pyrrolidin-2-on-1-yl, 4-trifluoromethyl-pyrrolidin-2-on-1-yl, 3-(2-methoxy-ethyl)-pyrrolidin-2-on-1-yl, 4-(2-methoxy-ethyl)-pyrrolidin-2-on-1-yl, 2,2,6,6-tetrafluoro-morpholin-4-yl, 2,6-dimethyl-morpholin-4-yl, 2-(methoxy-methyl)morpholin-4-yl, 3-(3-methyl-1,2,4-oxadiazol-5-yl)-pyrrolidin-1-yl, 4-(2-methyl-thiazol-5-yl)-pyrrolidin-2-on-1-yl, 4-(2-methyl-2H-[1,2,3]triazol-4-yl)-pyrrolidin-2-on-1-yl, 3-(4-methyl-thiazol-2-yl)-pyrrolidin-1-yl, or 3-(phenyl)-pyrrolidin-1-yl]

—(C═O)—$N(R^{N5})(R^{N6})$, wherein $R^{N5}$ represents hydrogen; and $R^{N6}$ represents $C_{3-6}$-cycloalkyl (especially cyclopentyl) or tetrahydropyranyl (especially tetrahydropyran-4-yl); or $R^{N5}$ and $R^{N6}$ form, together with the nitrogen to which they are attached, pyrrolidinyl;

[in particular such —(C═O)—$N(R^{N5})(R^{N6})$ represents N-cyclopentyl-amino-carbonyl, N-(tetrahydropyran-4-yl)-amino-carbonyl, or pyrrolidinyl-carbonyl]

piperidin-4-yl or pyrrolidin-3-yl which are mono-substituted at the nitrogen ring atom, wherein the substituent is independently selected from $C_{1-4}$-alkoxy-carbonyl (especially tert-butoxy-carbonyl), pyridinyl (especially pyridin-2-yl), phenyl and (4-methylphenyl)-sulfonyl;

[in particular such piperidin-4-yl or pyrrolidin-3-yl are N-(tert-butoxy-carbonyl)-piperidin-4-yl, N-(tert-butoxy-carbonyl)-pyrrolidin-3-yl, N-(pyridin-2-yl)-piperidin-4-yl, N-(phenyl)-piperidin-4-yl, or N4(4-methylphenyl)-sulfonyl)-piperidin-4-yl]

5- or 6-membered heteroaryl containing from one to three (notably two or three; especially three) ring heteroatom(s) independently selected from nitrogen, oxygen and sulfur (notably pyrazolyl, triazolyl, oxazolyl, thiazolyl, oxadiazolyl, pyrimidinyl, or pyridinyl; especially pyrazol-1-yl, 1H-1,2,3-triazol-1-yl, oxazol-2-yl, thiazol-2-yl, 1,2,4-oxadiazol-5-yl, 1,2,4-oxadiazol-3-yl, pyrimidin-2-yl, or pyridin-2-yl); wherein said 5- or 6-membered heteroaryl is independently unsubstituted, mono-, di-, or tri-substituted (notably mono-substituted; especially mono-substituted in position 3 with respect to the point of attachment of said 5- or 6-membered heteroaryl to A), wherein the substituent(s), if any, is(are) independently selected from $C_{1-4}$-alkyl (notably methyl, ethyl, propyl, isopropyl, or tert-butyl) which is unsubstituted; or mono-substituted with hydroxy;

$C_{1-4}$-alkoxy (especially methoxy and tert-butoxy); or

—$N(R^{N7})(R^{N8})$, wherein $R^{N7}$ represents hydrogen or $C_{1-3}$-alkyl (especially methyl); and $R^{N8}$ independently represent $C_{3-5}$-cycloalkyl-carbonyl (especially cyclopropyl-carbonyl), $C_{1-3}$-alkyl (especially methyl), $C_{1-3}$-alkyl-carbonyl including deuterated $C_{1-3}$-alkyl-carbonyl (especially acetyl, ethyl-carbonyl, isopropyl-carbonyl, or acetyl-2,2,2-$d_3$), $C_{1-3}$-alkoxy-$C_{1-3}$-alkyl-carbonyl (especially methoxy-methyl-carbonyl), tetrahydropyranyl-carbonyl (especially tetrahydropyran-4-yl-carbonyl), or hydroxy-$C_{1-3}$-alkyl-carbonyl (especially hydroxy-methyl-carbonyl);

di-substituted, wherein one substituent is hydroxy, and the other substituent is trifluoromethyl; or both substituents are hydroxy; or di- or tri-substituted, wherein two substituents are fluorine and, if present, a further substituent is hydroxy (wherein especially the hydroxy group is separated by at least two carbon atoms from any of said fluorine substituents);

[in particular such $C_{1-4}$-alkyl represents methyl, isopropyl, hydroxy-methyl, 1-hydroxy-1-methyl-ethyl, 2-hydroxy-2-methyl-propyl, 2-hydroxy-1,1-dimethyl-ethyl, methoxy-methyl, 2-methoxy-ethyl, 1-methoxy-1-methyl-ethyl, 2-methoxy-2-methyl-propyl, 2-methoxy-1,1-dimethyl-ethyl, tert-butoxy-methyl; 1,2-dihydroxy-ethyl, N-acetyl-2-amino-ethyl, N-(acetyl-2,2,2-$d_3$)-2-amino-ethyl, 2-(methylcarboxamido)-2-methyl-propyl, 2-(ethylcarboxamido)-2-methyl-propyl, 2-(cyclopropyl-carboxamido)-2-methyl-propyl, 2-(tetrahydropyran-4-yl-carboxamido)-2-methyl-propyl, 2-(methoxy-methyl-carboxamido)-2-methyl-propyl, 2-(ethyl-carboxamido)-2-methyl-propyl, 2-(isopropyl-carboxamido)-2-methyl-propyl, 2-(methyl-d3-carboxamido)-2-methyl-propyl, N-methyl-N-(hydroxy-methyl-carbonyl)-2-amino-ethyl, N-methyl-N-acetyl-2-amino-ethyl, 2,2,2-trifluoro-1-hydroxy-1-methyl-ethyl, 1,1-difluoro-2-hydroxy-ethyl, 1,1-difluoro-ethyl, or N-methyl-N-(acetyl-2,2,2-$d_3$)-2-amino-ethyl; in particular such $C_{1-4}$-alkyl group is 1-hydroxy-1-methyl-ethyl, 2-hydroxy-2-methyl-propyl, or 2-hydroxy-1,1-dimethyl-ethyl]

-$L^3$-$CY^3$, wherein

-$L^3$- independently represents a bond (i.e. the $CY^3$ is directly attached to the rest of the molecule), —$CH_2$—, —$CH_2$—$CH_2$—, —$C(CH_3)_2$—, —CH(OH)—, or —O—$CH_2$—, wherein when -$L^3$- is —O—$CH_2$—, said $CY^3$ is attached to the oxygen atom of said —O—$CH_2$—; and $CY^3$ independently represents $C_{3-6}$-cycloalkyl or $C_{4-6}$-heterocyclyl, said $C_{4-6}$-heterocyclyl containing one or two ring heteroatoms independently selected from nitrogen and oxygen (especially $CY^3$ represents cyclopropyl, cyclobutyl, oxetanyl, azetidinyl, pyrrolidinyl, tetrahydropyranyl, tetrahydrofuranyl, morpholinyl, imidazolidinyl, piperidinyl, or piperazinyl); wherein said $CY^3$ independently is unsubstituted, mono-, di-, or tri-substituted, wherein the substituents is selected from halogen (especially fluorine);

oxo;

hydroxy;

$C_{1-3}$-alkyl which is optionally mono-substituted with $C_{1-3}$-alkoxy (especially such $C_{1-3}$-alkyl represents methyl, ethyl, isopropyl, or methoxy-methyl);

$C_{1-3}$-alkoxy (especially methoxy);

—(C═O)—$R^{CO}$, wherein $R^{CO}$ represents $C_{1-3}$-alkyl which is optionally mono-substituted with hydroxy or $C_{1-3}$-alkoxy (especially methyl, ethyl, n-propyl, isopropyl, tert-butyl, hydroxy-methyl, methoxy-methyl, benzyl-oxy, or 2-methoxy-ethyl);

$C_{1-3}$-fluoroalkyl (especially 2,2,2-trifluoro-ethyl);

$C_{1-3}$-alkoxy, wherein said $C_{1-3}$-alkoxy is optionally mono-substituted with $C_{1-3}$-alkoxy (especially methoxy, ethoxy, or 2-methoxy-ethoxy);

$C_{3-6}$-cycloalkyl-$(CH_2)_n$—, wherein optionally one or two carbon ring atom(s) is/are replaced by one or two oxygen ring atom(s); wherein n represents the integer 0, 1, or 2 (especially such $C_{3-5}$-cycloalkyl-$(CH_2)_n$— represents cyclopropyl, cyclopentyl, oxetan-3-yl, oxetan-3-yl-methyl, 1,4-dioxan-2-yl, or tetrahydropyran-4-yl); or phenyl;

[especially such —(C═O)—$R^{CO}$ represents acetyl, ethyl-carbonyl, n-propyl-carbonyl, isopropyl-carbonyl, tert-butyl-carbonyl, hydroxymethyl-carbonyl, 2,2,2-trifluoro-ethyl-carbonyl, methoxy-methyl-carbonyl, 2-methoxy-ethyl-carbonyl, methoxy-carbonyl, ethoxy-carbonyl, 2-methoxy-ethoxy-carbonyl, cyclopropyl-carbonyl, cyclopentyl-carbonyl, oxetan-3-yl-carbonyl, oxetan-3-yl-methyl-carbonyl, phenyl-carbonyl, or tetrahydropyran-4-yl-carbonyl, methoxy-methyl-carbonyl, or 1,4-dioxan-2-yl-carbonyl]

—N($R^{N9}$)($R^{N10}$), wherein $R^{N9}$ represents hydrogen or $C_{1-3}$-alkyl (especially methyl); and $R^{N10}$ represents $C_{1-3}$-alkyl (especially methyl), $C_{1-3}$-alkyl-carbonyl (especially acetyl), $C_{1-3}$-alkyl-sulfonyl (especially methyl-sulfonyl), $C_{1-3}$-alkoxy-carbonyl (especially ethoxy-carbonyl), $C_{1-3}$-alkoxy-$C_{1-3}$-alkyl-carbonyl (especially methoxy-methyl-carbonyl), or tetrahydropyranyl-carbonyl (especially tetrahydropyran-4-yl-carbonyl);

—S(═O)$_2$—$R^{SO}$, wherein $R^{SO}$ represents $C_{1-3}$-alkyl which is optionally mono-substituted with hydroxy, $C_{1-3}$-alkoxy, or amino (especially such $C_{1-3}$-alkyl is methyl, n-propyl, isopropyl, 2-hydroxy-ethyl, 2-methoxy-ethyl, or methyl-amino); or $C_{3-5}$-cycloalkyl, wherein optionally one carbon ring atom is replaced by one oxygen ring atom (especially represents cyclopropyl, cyclopentyl, or tetrahydropyranyl);

[especially such —S(═O)$_2$—$R^{SO}$ represents methyl-sulfonyl, n-propyl-sulfonyl, isopropyl-sulfonyl, 2-hydroxyethyl-sulfonyl, cyclopropyl-sulfonyl, cyclopentyl-sulfonyl, 2-methoxy-ethyl-sulfonyl, methyl-amino-sulfonyl, or tetrahydropyran-4-yl-sulfonyl]

5-membered heteroaryl containing one ring heteroatom selected from nitrogen, oxygen, and sulfur (notably oxygen); wherein said 5-membered heteroaryl is unsubstituted (notably furanyl; especially furan-2-yl); and phenyl-$(CH_2)_p$—, wherein p represents the integer 0, 1, or 2 (especially such phenyl-$(CH_2)_p$— represents phenyl or benzyl);

[in particular such -$L^3$-$CY^3$ represents1-hydroxy-cyclopropyl, 1-(methyl-amino)-cyclopropyl, 1-(acetyl-amino)-cycloprop-1-yl-methyl, 1-(N-acetyl-N-methyl-amino)-cycloprop-1-yl-methyl, 1-(N-(methoxy-methyl-carbonyl)-amino)-cycloprop-1-yl-methyl, 1-(N-(ethoxy-carbonyl)-N-methyl-amino)-cycloprop-1-yl, 1-(N-methylacetamido)-cycloprop-1-yl (including 14N-methylacet-d3-amidoy cycloprop-1-yl), 1-(1-(methoxy-methyl)-cyclopropylymethyl, 1-(tetrahydropyran-4-yl-carbonyl-amino)-cyclopropyl-methyl, cyclobutyl-oxy-methyl, 1-hydroxy-cyclobutyl, 3-hydroxy-cyclobutyl, 1-methoxy-cyclobutyl, 1-hydroxy-cyclopentyl, 3-hydroxy-3-methyl-cyclopentyl, 1-hydroxy-cyclohexyl, 4-hydroxy-cyclohexyl, (1-hydroxy-cyclohexyl)-methyl, (1-hydroxy-cyclobutyp-methyl, 1-hydroxy-1-cyclohexyl-methyl, 1-methoxy-cyclopentyl, oxetan-3-yl, tetrahydrofuran-2-yl-methyl, tetrahydrofuran-2-yl, tetrahydrofuran-3-yl, tetrahydro-pyran-3-yl, tetrahydropyran-4-yl, 4-hydroxy-tetrahydropyran-4-yl, 4-hydroxy-tetrahydropyran-4-yl-methyl, 4-methyl-tetrahydropyran-4-yl-methyl, 4-methyl-tetrahydropyran-4-yl, 2,6-dimethyl-tetrahydropyran-4-yl, 4-methoxy-tetrahydropyran-4-yl, 4-fluoro-tetrahydropyran-4-yl, tetrahydropyran-4-yl-methyl, 2-(tetrahydropyran-4-yl)-ethyl, 1-(tetrahydro-pyran-4-yl)-1-methyl-ethyl, tetrahydropyran-4-yl-oxy-methyl, (4-methyl-tetrahydropyran-4-yl)oxy-methyl, N-acetyl-3-fluoro-azetidin-3-yl (including N-acetyl-d3-3-fluoro-azetidin-3-yl), N-acetyl-3-methyl-azetidin-3-yl (including N-acetyl-d3-3-methyl-azetidin-3-yl), 2-oxo-azetidin-3-yl, 2-oxo-azetidin-4-yl, N-acetyl-azetidin-3-yl, 5-oxo-pyrrolidin-2-yl, N-phenyl-5-oxo-pyrrolidin-2-yl, N-phenyl-5-oxo-pyrrolidin-3-yl, N-benzyl-5-oxo-pyrrolidin-3-yl, N-benzyl-2-oxo-pyrrolidin-3-yl, 5-oxo-pyrrolidin-3-yl, N-(furan-2-yl-methyl)-5-oxo-pyrrolidin-3-yl, 3-methyl-5-oxo-pyrrolidin-3-yl, 1-methyl-5-oxo-pyrrolidin-3-yl, 1-isopropyl-5-oxo-pyrrolidin-3-yl, 1,3-dimethyl-2-oxo-pyrrolidin-3-yl, 2-oxo-pyrrolidin-1-yl-methyl, 2-oxo-pyrrolidin-1-yl-methyl, 1-ethyl-5-oxo-pyrrolidin-3-yl, 1-isobutyl-5-oxo-pyrrolidin-3-yl, N-acetyl-pyrrolidin-3-yl, N-acetyl-pyrrolidin-3-yl-methyl, 2,5-dioxo-3,3-dimethyl-pyrrolidin-1-yl-methyl, 2-oxo-imidazolidin-1-yl-methyl, 2-oxo-oxazolidin-3-yl-methyl, piperidin-4-yl, 1-methyl-2,6-dioxo-piperidin-4-yl, 4-methyl-piperidin-4-yl, 4-fluoro-piperidin-4-yl, 2-oxo-piperidin-4-yl, 6-oxo-piperidin-2-yl, 6-oxo-piperidin-3-yl, 1-methyl-6-oxo-piperidin-3-yl, 3-methyl-6-oxo-piperidin-3-yl, N-acetyl-piperidin-4-yl, N-acetyl-piperidin-4-yl-methyl, N-acetyl-2-methyl-piperidin-4-yl, N-acetyl-4-fluoro-piperidin-4-yl, N-acetyl-3-methyl-piperidin-4-yl, N-acetyl-4-methyl-piperidin-4-yl, N-acetyl-4-hydroxy-piperidin-4-yl, N-acetyl-4-methoxy-piperidin-4-yl, N-acetyl-piperidin-3-yl, N-acetyl-piperidin-3-yl-methyl, N-acetyl-3-methyl-piperidin-3-yl, N-acetyl-3-hydroxy-piperidin-3-yl, N-(isopropyl-carbonyl)-4-hydroxy-piperidin-4-yl, N-(tert-butyl-carbonyl)-piperidin-4-yl, N-[2-methoxy-ethoxy-carbonyl)-piperidin-4-yl, N-(hydroxymethyl-carbonyl)-piperidin-4-yl, N-(cyclopropyl-sulfonyl)-piperidin-4-yl, N-(methyl-sulfonyl)-piperidin-4-yl, N-(n-propyl-sulfonyl)-piperidin-4-yl, N-(isopropyl-sulfonyl)-piperidin-4-yl, N-(2-hydroxy-ethyl-sulfonyl)-piperidin-4-yl, N-(cyclopentyl-sulfonyl)-piperidin-4-yl, N-(methoxy-carbonyl)-piperidin-4-yl, N-(cyclopropyl-carbonyl)-piperidin-4-yl, N-(cyclopentyl-carbonyl)-piperidin-4-yl, N-(methyl-amino-sulfonyl)-piperidin-4-yl, N-(2-methoxy-ethyl-sulfonyl)piperidin-4-yl, N-(ethyl-carbonyl)-4-hydroxy-piperidin-4-yl, N-(methoxy-methyl-carbonyl)piperidin-4-yl, N-(ethoxy-carbonyl)-piperidin-4-yl, N-acetyl-4-ethyl-piperidin-4-yl, N-(n-propyl-carbonyl)piperidin-4-yl, N-(2-methoxy-ethyl-carbonyl)-piperidin-4-yl, N-(oxetan-3-yl-carbonyl)piperidin-4-yl, N-(oxetan-3-yl-methyl-carbonyl)-piperidin-4-yl, N-(2,2,2-trifluoro-ethyl-carbonyl)-piperidin-4-yl, N-(tetrahydropyran-4-yl-carbonyl)-piperidin-4-yl, N-(phenyl-carbonyl)-piperidin-4-yl, N-(tetrahydropyran-4-yl-sulfonyl)-piperidin-4-yl, N-(benzyl-oxy-carbonyl)-piperidin-4-yl, N-(methoxy-methyl-carbonyl)-4-isopropyl-piperidin-4-yl, N-(1,4-dioxan-2-yl-carbonyl)-piperidin-4-yl, morpholin-4-yl, morpholin-4-yl-methyl, 1-methyl-1-(morpholin-4-yl)-ethyl, (2,6-dimethyl-morpholin-4-yl)-methyl, 2,4-dioxo-imidazolidin-1-yl-methyl, 2,5-dioxo-imidazolidin-1-yl-methyl, 2,5-dioxo-3-methyl-imidazolidin-1-yl-methyl, 2,4-dioxo-3-methyl-imidazolidin-1-yl-methyl, 2-oxo-3-methyl-imidazolidin-1-yl-methyl, 2-oxo-3-cyclopropyl-imidazolidin-1-yl-methyl, 2,5-dioxo-pyrrolidin-1-yl-methyl, N-acetyl-pyrrolidin-3-yl, or 4-acetyl-piperazin-1-yl];

phenyl or 6-membered heteroaryl containing one or two ring nitrogen atom(s) (notably pyridinyl or pyrimidinyl; especially pyridin-3-yl or pyrimidin-4-yl); wherein said phenyl or 6-membered heteroaryl is independently unsubstituted or mono-substituted with $C_{1-3}$-alkyl (especially methyl) or $C_{1-3}$-alkoxy (especially methoxy);

[in particular such phenyl or 6-membered heteroaryl is 3-methoxy-phenyl, pyridin-3-yl, or 6-methyl-pirimidin-4-yl]

pyrazolyl-$C_{1-3}$-alkyl (especially 2-(pyrazol-1-yl)-ethyl);

$C_{1-3}$-alkyl-sulfonyl-$C_{1-3}$-alkyl (especially methyl-sulfonyl-methyl);

3-hydroxymethyl-bicyclo[1.1.1]pent-1-yl;

7-oxa-bicyclo[2.2.1]hept-2-yl; and 6-oxa-spiro[2.5]oct-1-yl;

5-oxo-4-oxa-6-azaspiro[2.4]hept-6-yl, 5-aza-spiro[2.4]heptan-6-on-5yl, 2,2-dimethyl-6-oxo-5-oxa-7-azaspiro[3.4]oct-7-yl, 2-cyclopropyl-6-oxo-5-oxa-7-azaspiro[3.4]oct-7-yl, 2-oxo-1-oxa-3-azaspiro[4.4]non-3-yl, 8,8-difluoro-2-oxo-1-oxa-3-azaspiro[4.5]dec-3-yl, or 8-oxo-7-oxa-9-azadispiro[3.1.4.1]undec-9-yl;

7-aza-bicyclo[2.2.1]hept-7-yl, 2-oxa-5-aza-bicyclo[2.2.1]hept-5-yl, 6-oxa-3-aza-bicyclo[3.1.1]hept-3-yl, or 8-oxa-3-azabicyclo[3.2.1]oct-3-yl;

5-oxo-6-azaspiro[3.4]oct-6-yl, 3-oxo-2-azaspiro[4.4]non-2-yl, 1-oxa-3-aza-spiro[4.5]decan-2-on-3-yl, 1-oxo-2-azaspiro[4.5]dec-2-yl, 1-oxo-8-oxa-2-azaspiro[4.5]dec-2-yl, 3-oxo-8-oxa-2-azaspiro[4.5]dec-2-yl, or 4-oxo-hexahydro-5H-furo[2,3-c]pyrrol-5-yl;

3-(7-hydroxy-6,7-dihydro-5H-cyclopenta[b]pyridin-7-yl)propyl or 3-(8-hydroxy-5,6,7,8-tetrahydroquinolin-8-yl)propyl);

6-acetyl-7,8-dihydro-5H-pyrido[4,3-d]pyrimidin-2-yl;

6-acetyl-5,6,7,8-tetrahydro-1,6-naphthyridine-2-yl;

2-(6,7-dihydro-5H-[1]pyrindin-7-ol)-ethyl;

2-(8-hydroxy-5,6,7,8-tetrahydro-quinolin-8-yl)-ethyl;

7,8-dihydro-5H-[1,6]naphthyridin-6-yl;

2,3-dihydro-isoindol-1-on-2-yl;

7,8-dihydro-5H-pyrido[4,3-d]pyrimidin-6-yl; and 6-acetyl-7,8-dihydro-5H-pyrido[4,3-d]pyrimidin-2-yl;

B represents phenyl, which is unsubstituted, mono-, di- or tri-substituted, wherein a first substituent (especially in para-position with respect to the point of attachment of B to the rest of molecule), if present, is selected from halogen (especially bromine);

$C_{1-5}$-alkyl (notably methyl, ethyl, n-propyl, isopropyl, n-butyl, isobutyl, tert-butyl, 1-ethyl-propyl, 2,2-dimethyl-propyl, 1,1-dimethyl-propyl; especially methyl, ethyl, or isopropyl; in particular isopropyl);

$C_{2-4}$-alkenyl (especially prop-1-en-2-yl);

$C_{1-3}$-alkoxy (especially methoxy, ethoxy, or isopropoxy);

$C_{1-3}$-alkoxy-$C_{1-4}$-alkyl (especially 3-methoxy-propyl);

$C_{1-4}$-fluoroalkyl (especially trifluoromethyl, 1-methyl-1-fluoro-ethyl, 1,1-difluoro-ethyl, 2,2,2-trifluoro-ethyl, 1,1-dimethyl-1-trifluoromethyl-methyl, 1,1,2,2,2-pentafluoro-ethyl, or 1,2,2,2-tetrafluoro-1-trifluoromethyl-ethyl);

$C_{3-5}$-cycloalkyl (especially cyclopropyl or cyclobutyl) which independently is unsubstituted or mono-substituted (notably at the point of attachment of said $C_{3-5}$-cycloalkyl to the rest of the molecule) with $C_{1-3}$-alkyl (especially methyl) or $C_{1-3}$-fluoroalkyl (especially trifluoromethyl);

—$SF_5$;

bicyclo[1.1.1]pent-1-yl;

$C_{3-5}$-cycloalkoxy (especially cyclopropoxy or cyclobutoxy); and $C_{1-3}$-fluoroalkoxy (especially trifluoromethoxy);

and the remaining substituent/s of B, if present, independently is/are selected from halogen (notably fluorine or chlorine; especially said remaining substituent(s) are in meta-position with respect to the point of attachment of B to the rest of molecule) and $C_{1-3}$-alkyl (especially methyl);

or B represents benzothiophenyl (notably 1-benzothiophenyl; especially 1-benzothiophen-5-yl) or naphthalenyl (especially naphthalen-2-yl);

[in particular such B is phenyl, 4-bromo-phenyl, 4-methyl-phenyl, 4-ethyl-phenyl, 4-propyl-phenyl, 4-isopropyl-phenyl, 4-butyl-phenyl, 4-isobutyl-phenyl, 4-tert-butyl-phenyl, 4-(1-ethyl-propyl)-phenyl, 4-(1,1-dimethyl-propyl)-phenyl, 4-(2,2-dimethyl-propyl)-phenyl, 3-chloro-4-isopropyl-phenyl, 3-fluoro-4-isopropyl-phenyl, 3,5-difluoro-4-isopropyl-phenyl, 3-methyl-4-isopropyl-phenyl, 4-(prop-1-en-2-yl)-phenyl, 4-cyclopropyl-phenyl, 4-methoxy-phenyl, 4-ethoxy-phenyl, 4-isopropoxy-phenyl, 4-trifluoromethyl-phenyl, 4-(1-methyl-1-fluoro-ethyl)-phenyl, 4-(1,1-difluoro-ethyl)phenyl, 4-(2,2,2-trifluoro-ethyl)-phenyl, 4-(1,1-dimethyl-1-trifluoromethyl-methyl)phenyl, 4-(1,1,2,2,2-pentafluoro-ethyl)-phenyl, 4-(1,2,2,2-tetrafluoro-1-trifluoromethyl-ethyl)-phenyl, 4-trifluoromethoxy-phenyl, 4-(1-methyl-cyclopropyl)-phenyl, 4-cyclobutyl-phenyl, 4-(pentafluoro-l6-sulfaneyl)-phenyl, 4-(bicyclo[1.1.1]pent-1-yl)-phenyl, 4-cyclopropoxy-phenyl, 4-cyclobutoxy-phenyl, 4-(trifluoromethoxy)-phenyl, 4-(3-methoxy-propyl)-phenyl, 4-(1-trifluoromethyl-cyclopropyl)-phenyl, naphthalen-2-yl, or 1-benzothiophen-5-yl]

$R^1$ represents $C_{1-3}$-alkyl (especially methyl or ethyl), cyano, or halogen (especially fluorine);

$R^2$ represents $C_{1-4}$-alkyl (especially methyl, ethyl, n-propyl, isopropyl, tert-butyl or isobutyl), $C_{3-5}$-cycloalkyl (especially cyclopropyl or cyclobutyl), $C_{3-5}$-cycloalkyl-$C_{1-3}$-alkyl (especially cyclopropyl-methyl), hydroxy-$C_{1-3}$-alkyl (especially 2-hydroxy-ethyl), $C_{1-3}$-alkoxy-$C_{1-3}$-alkyl (especially 2-methoxy-ethyl), or $C_{1-3}$-fluoroalkyl (especially 2,2-difluoro-ethyl, 3,3,3-trifluoro-propyl, or 2-fluoroethyl).

Definitions provided herein are intended to apply uniformly to the compounds of Formula (I) as defined in any one of embodiments 1) to 53), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein. If not explicitly defined otherwise in the respective embodiment or claim, groups defined herein are unsubstituted.

The term "halogen", used alone or in combination, means fluorine, chlorine, bromine, or iodine; notably fluorine or chlorine; especially fluorine.

The term "cyano", used alone or in combination, refers to a group —CN.

The term "oxy", used alone or in combination, refers to a group —O—.

The term "oxo", used alone or in combination, refers to the group =O.

The term "amino", used alone or in combination, refers to the group —$NH_2$.

The term "amino-carbonyl", used alone or in combination, refers to the group —C(=O)—$NH_2$.

The term "amino-carbonyl-oxy", used alone or in combination, refers to the group —O—C(=O)—$NH_2$, wherein substitutions to the amino group may be further defined. For example, N—($C_{1-3}$-alkyl)-amino-carbonyl-oxy- means that the amino group of said amino-carbonyl-oxy group is substituted with a $C_{1-3}$-alkyl group, said $C_{1-3}$-alkyl group being defined hereinbelow. An example of N—($C_{1-3}$-alkyl)amino-carbonyl-oxy- is N-(isopropyl)amino-carbonyl-oxy.

The term "alkyl", used alone or in combination, refers to a saturated straight or branched hydrocarbon chain group containing one to six carbon atoms. The term "$C_{x-y}$-alkyl" (x and y each being an integer), refers to an alkyl group as defined before, containing x toy carbon atoms. In case a $C_{x-y}$-alkyl group is used in combination with another substituent, the term means that said substituent is linked through a $C_{x-y}$-alkyl group to the rest of the molecule. For example, a $C_{1-6}$-alkyl group contains from one to six carbon atoms. Examples of $C_{1-6}$-alkyl groups are the $C_{1-4}$-alkyl groups methyl, ethyl, n-propyl, isopropyl, n-butyl, sec-butyl, tert-butyl, and isobutyl, as well as n-pentyl, and isopentyl. A preferred example of a $C_{1-3}$-alkyl as used for the substituent $R^1$ is methyl. A preferred example of a $C_{1-4}$-alkyl as used for the substituent $R^2$ is ethyl or methyl; most preferably methyl. A particularly preferred example of a $C_{1-6}$-alkyl as used for the substituent of B is isopropyl.

The term "amino-alkyl", used alone or in combination, refers to an alkyl group as defined before, wherein one hydrogen atom has been replaced by an amino group. The term "amino-$C_{x-y}$-alkyl" (x and y each being an integer), used alone or in combination, refers to an amino-alkyl group as defined before wherein the alkyl group contains x to y carbon atoms. For example, amino-$C_{1-4}$-alkyl is an amino-alkyl group containing from one to four carbon atoms. Examples of such amino-$C_{1-4}$-alkyl groups are amino-methyl, 1-amino-ethyl, 2-amino-ethyl and 2-amino-2,2-dimethyl-ethyl.

The term "hydroxyalkyl", used alone or in combination, refers to an alkyl group as defined before, wherein one hydrogen atom has been replaced by a hydroxy group. The term "hydroxy-$C_{x-y}$-alkyl" (x and y each being an integer), used alone or in combination, refers to a hydroxyalkyl group as defined before wherein the alkyl group contains x toy carbon atoms. For example, a hydroxy-$C_{1-6}$-alkyl group is a hydroxyalkyl group as defined before which contains from one to six carbon atoms.

The term "hydroxy-alkyl" refers to an alkyl group as defined herein, wherein one hydrogen atom is replaced by one hydroxy group.

The term "oxetanyl-alkyl", used alone or in combination, refers to an alkyl group as defined before, wherein one hydrogen atom has been replaced by an oxetanyl group;

especially such oxetanyl group is oxetan-3-yl. The term "oxetanyl-$C_{x-y}$-alkyl" (x and y each being an integer), used alone or in combination, refers to an oxetanyl-alkyl group as defined before, wherein the alkyl group contains x to y carbon atoms. For example, an oxetanyl-$C_{1-3}$-alkyl group is an oxetanyl-alkyl group as defined before which contains from one to three carbon atoms.

The term "pyridinyl-alkyl", used alone or in combination, refers to an alkyl group as defined before, wherein one hydrogen atom has been replaced by a pyridinyl group; especially such pyridinyl group is pyridin-2-yl. The term "pyridinyl-$C_{x-y}$-alkyl" (x and y each being an integer), used alone or in combination, refers to a pyridinyl-alkyl group as defined before, wherein the alkyl group contains x to y carbon atoms. For example, a pyridinyl-$C_{1-3}$-alkyl group is a pyridinyl-alkyl group as defined before which contains from one to three carbon atoms.

The term "pyrazolyl-alkyl", used alone or in combination, refers to an alkyl group as defined before, wherein one hydrogen atom has been replaced by a pyrazolyl group; especially such pyrazolyl group is pyrazol-1-yl. The term "pyrazolyl-$C_{x-y}$-alkyl" (x and y each being an integer), used alone or in combination, refers to a pyrazolyl-alkyl group as defined before, wherein the alkyl group contains x to y carbon atoms. For example, a pyrazolyl-$C_{1-3}$-alkyl group is a pyrazolyl-alkyl group as defined before which contains from one to three carbon atoms.

The term "benzyl-oxy-alkyl", used alone or in combination, refers to an alkyl group as defined before, wherein one hydrogen atom has been replaced by the group $C_6H_5$—$CH_2$—O—. The term "benzyl-oxy-$C_{x-y}$-alkyl" (x and y each being an integer), used alone or in combination, refers to a benzyl-oxy-alkyl group as defined before, wherein the alkyl group contains x to y carbon atoms. For example, a benzyl-oxy-$C_{1-3}$-alkyl group is benzyl-oxy-alkyl group as defined before which contains from one to three carbon atoms.

The term "alkyl-carbonyl", used alone or in combination, refers to an alkyl group as defined before, wherein one hydrogen atom has been replaced by the group —C(═O)—. The term "$C_{x-y}$-alkyl-carbonyl" (x and y each being an integer), used alone or in combination, refers to an alkyl-carbonyl group as defined before, wherein the alkyl group contains x to y carbon atoms. For example, a $C_{1-3}$-alkyl-carbonyl group is an alkyl-carbonyl group as defined before which contains from one to three carbon atoms.

The term "amino-carbonyl-oxy", used alone or in combination, refers to the group $H_2N$—C(═O)—O—, wherein substitutions to the amino group may be further defined.

The term "(hydroxy-alkyl)-carbonyl", used alone or in combination, refers to a hydroxy-alkyl group as defined before, wherein one hydrogen atom of the alkyl has been replaced by the group —C(═O)—. The term "(hydroxy-$C_{x-y}$-alkyl)-carbonyl" (x and y each being an integer), used alone or in combination, refers to (hydroxy-alkyl)-carbonyl group as defined before, wherein the alkyl group contains x to y carbon atoms. For example, a (hydroxy-$C_{1-3}$-alkyl)-carbonyl group is an (hydroxy-alkyl)-carbonyl group as defined before which contains from one to three carbon atoms.

The term "alkyl-sulfonyl-alkyl", used alone or in combination, refers to an alkyl group as defined before, wherein one hydrogen atom has been replaced by an alkyl-sulfonyl group, wherein the alkyl part of the said alkyl-sulfonyl is as defined before. The term "$C_{x1-y1}$-alkyl-sulfonyl-$C_{x2-y2}$-alkyl" (x1, x2, y1 and y2 each being an integer), used alone or in combination, refers to an alkyl-sulfonyl-alkyl group as defined before, wherein the alkyl groups contain independently from one another x1 to y1 and x2 to y2 carbon atoms. For example, a $C_{1-3}$-alkyl-sulfonyl-$C_{1-3}$-alkyl is an alkyl-sulfonyl-alkyl group as defined before which contains in both alkyl pats independently from one to three carbon atoms.

The term "fluoroalkyl", used alone or in combination, refers to an alkyl group as defined before in which one or more (and possibly all) hydrogen atoms have been replaced by fluorine. The term "$C_{x-y}$-fluoroalkyl" (x and y each being an integer) refers to a fluoroalkyl group as defined before containing x to y carbon atoms. For example, a $C_{1-3}$-fluoroalkyl group contains from one to three carbon atoms in which one to seven hydrogen atoms have been replaced with fluorine. Examples of $C_{1-3}$-fluoroalkyl groups are trifluoromethyl, 2-fluoroethyl, 2,2-difluoroethyl and 2,2,2-trifluoroethyl.

The term "alkenyl", used alone or in combination, refers to a straight or branched hydrocarbon chain an alkyl group as defined before, wherein said chain comprises one double bond. The term "$C_{x-y}$-alkenyl" (x and y each being an integer), used alone or in combination, refers to an alkenyl group as defined before, containing from x to y carbon atoms. For example, the term $C_{3-5}$-alkenyl, used alone or in combination, refers to an alkenyl group as defined before containing from 3 to 5 carbon atoms. Examples of $C_{3-5}$-alkenyl groups are —CH═$CH_2$, —CH═$CH_2$—$CH_3$, —$CH_2$—CH═$CH_2$, and —C($CH_3$)═$CH_2$.

The term "alkylene", used alone or in combination, refers to a saturated, branched or straight, bivalent aliphatic hydrocarbon group, regarded as derived from an alkane by removal of two hydrogen atoms. The term "$C_{x-y}$-alkylene" (x and y each being an integer), used alone or in combination, refers to an alkylene group as defined before containing x to y carbon atoms. For example, a $C_{1-2}$-alkylene is an alkylene group as defined above containing one or two carbon atoms. Examples of $C_{1-2}$-alkylene groups are —$CH_2$—, —$(CH_2)_2$— and —CH($CH_3$)—.

The term "hydroxy-alkylene", used alone or in combination, refers to an alkylene group as defined before, wherein one hydrogen atom has been replaced with a hydroxy group. The term "hydroxy-$C_{x-y}$-alkylene" (x and y each being an integer), used alone or in combination, refers to a hydroxy-alkylene group as defined before containing x to y carbon atoms. For example, a hydroxy-$C_{1-2}$-alkylene is a hydroxy-alkylene group as defined above containing one or two carbon atoms. Examples of hydroxy-$C_{1-2}$-alkylene groups are —CH(OH)—, —CH(OH)—$CH_2$—, and —C(OH)($CH_3$)—; preferably —CH(OH)—.

The term oxy-$C_{1-2}$-alkylene, used alone or in combination, refers to the group —O—$C_{1-2}$-alkylene, wherein $C_{1-2}$-alkylene is defined above. Preferably, oxy-$C_{1-2}$-alkylene is the group —O—$CH_2$—.

The term "alkoxy", used alone or in combination, refers to an alkyl group as defined before, wherein one hydrogen atom has been replaced by —O—. The term "$C_{x-y}$-alkoxy" (x and y each being an integer), used alone or in combination, refers to an alkoxy group as defined before, wherein the alkoxy group contains x to y carbon atoms. For example, a $C_{1-3}$-alkoxy group is an alkoxy group as defined before which contains from one to three carbon atoms. Examples of $C_{1-3}$-alkoxy groups are methoxy, ethoxy, n-propoxy, or isopropoxy; notably methoxy.

The term "alkoxy-alkyl", used alone or in combination, refers to an alkyl group as defined before, wherein one hydrogen atom has been replaced by an alkoxy group as defined before. The term "$C_{x1-y1}$-alkoxy-$C_{x2-y2}$-alkyl" (x1, x2, y1 and y2 each being an integer), used alone or in combination, refers to an alkoxy-alkyl group as defined before, wherein the two hydrocarbon parts of the group contain independently from one another x1 to y1 and x2 to y2 carbon atoms. For example, a $C_{1-3}$-alkoxy-$C_{1-3}$-alkyl is an alkoxy-alkyl group as defined before which contains in the two hydrocarbon parts of the group independently from one to three carbon atoms. Examples of $C_{1-3}$-alkoxy-$C_{1-3}$-alkyl groups are methoxy-methyl or ethoxy-ethyl.

The term "fluoroalkoxy", used alone or in combination, refers to an alkoxy group as defined before containing one to three carbon atoms in which one or more (and possibly all) hydrogen atoms have been replaced with fluorine. The term "$C_{x-y}$-fluoroalkoxy" (x and y each being an integer) refers to a fluoroalkoxy group as defined before containing x to y carbon atoms. For example, a $C_{1-3}$-fluoroalkoxy group contains from one to three carbon atoms in which one to seven hydrogen atoms have been replaced by fluorine. Examples of $C_{1-3}$-fluoroalkoxy groups include trifluoromethoxy, difluoromethoxy, 2-fluoroethoxy, 2,2-difluoroethoxy and 2,2,2-trifluoroethoxy.

The term "$C_{1-4}$-alkoxy-carbonyl" refers to an alkoxy group as defined before attached to a carbonyl group (i.e. $C_{1-4}$-alkoxy-C(═O)—).

The term "cycloalkyl", used alone or in combination, refers to a saturated monocyclic hydrocarbon ring containing three to seven carbon atoms (preferably three to six carbon atoms). The term "$C_{x-y}$-cycloalkyl" (x and y each being an integer), refers to a saturated monocyclic hydrocarbon ring containing x to y carbon atoms. For example, a $C_{3-6}$-cycloalkyl group contains from three to six carbon atoms. Examples of $C_{3-6}$-cycloalkyl groups are cyclopropyl, cyclobutyl, cyclopentyl and cyclohexyl.

Likewise, the term "$C_{x-y}$-heterocyclyl" refers to a cycloalkyl group as define above containing x to y ring atoms, wherein in said group one or more ring carbon atoms are replaced by heteroatoms as explicitly defined.

The term "cycloalkenyl", used alone or in combination, refers to an unsaturated monocyclic hydrocarbon ring containing one double carbon-carbon ring bond, said ring containing four to six carbon (preferably five) atoms. The term "$C_{x-y}$-cycloalkenyl" (x and y each being an integer), refers to a cycloalkenyl ring as defined before containing x to y carbon atoms. For example, a $C_{4-6}$-cycloalkenyl group contains from four to six carbon atoms. Examples of $C_{4-6}$-cycloalkenyl groups are cyclobutenyl, cyclopentenyl and cyclohexenyl; notably cyclopentenyl; especially cyclopent-1-en-1-yl.

The term "cycloalkoxy", used alone or in combination, refers to an cycloalkyl group as defined before, wherein one hydrogen atom has been replaced by —O—. The term "$C_{x-y}$-cycloalkoxy" (x and y each being an integer), used alone or in combination, refers to a cycloalkoxy group as defined before, wherein the cycloalkoxy group contains x to y carbon atoms. For example, a $C_{3-5}$-cycloalkoxy group is a cycloalkoxy group as defined before which contains from three to five carbon atoms. Examples of $C_{3-5}$-cycloalkoxy groups are cyclopropoxy, cyclobutoxy, or cyclopentoxy.

The term "cycloalkyl-sulfonyl", used alone or in combination, refers to a cycloalkyl group as defined before, wherein one hydrogen atom is replaced by a sulfonyl group (i.e. —S(═O)$_2$—). The term "$C_{x-y}$-cycloalkyl-sulfonyl" (x and y each being an integer), refers to a cycloalkyl group containing x to y carbon atoms. For example, a $C_{3-5}$-cycloalkyl-sulfonyl group contains from three to six carbon atoms. Examples of $C_{3-5}$-cycloalkyl-sulfonyl groups are cyclopropyl-sulfonyl, cyclobutyl-sulfonyl and cyclopentyl-sulfonyl.

The term "cycloalkyl-alkyl", used alone or in combination, refers to an alkyl group as defined before, wherein one hydrogen atom has been replaced by a cycloalkyl group as defined before. The term "$C_{x1-y1}$-cycloalkyl-$C_{x2-y2}$-alkyl" (x1, x2, y1 and y2 each being an integer), used alone or in combination, refers to an cycloalkyl-alkyl group as defined before, wherein the two hydrocarbon parts of the group contain independently from one another x1 to y1 and x2 to y2 carbon atoms. For example, $C_{3-5}$-cycloalkyl-$C_{1-3}$-alkyl is a cycloalkyl-alkyl group as defined before which contains in the cycloalkyl part from three to five carbon atoms, and an alkyl part which contains from one to three carbon atoms. Examples of $C_{3-5}$-cycloalkyl-$C_{1-3}$-alkyl groups are cyclopropyl-methyl or cyclopropyl-ethyl.

The term "$C_{3-6}$-cycloalkyl fused with a pyridine ring", used alone or in combination, refers to a $C_{3-6}$-cycloalkyl group as defined before which is fused with a pyridine ring. Examples of $C_{3-6}$-cycloalkyl fused with a pyridine ring are the following groups:

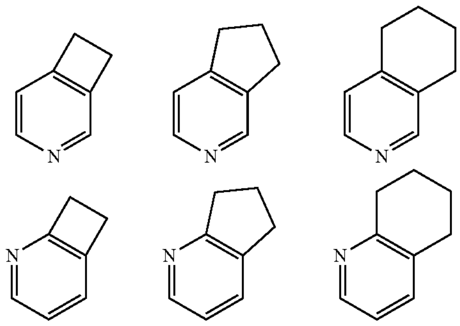
;

preferably the last two groups from left to right. It is understood that when a substituent is referred to as "$C_{3-6}$-cycloalkyl fused with a pyridine ring" the point of attachment of said substituent to the rest of the molecule is in the $C_{3-6}$-cycloalkyl part of the substituent and not in the fused pyridine ring.

The term "hydroxy-azetidinyl", used alone or in combination, refers to an azetidinyl group substituted with a hydroxy group. Preferably, the term hydroxy-azetidinyl refers to 3-hydroxy-azetidin-3-yl.

The term "heteroaryl", used alone or in combination, means a 5- to 10-membered monocyclic or bicyclic aromatic ring containing one to a maximum of four heteroatoms (notably containing one to a maximum of three heteroatoms), each independently selected from oxygen, nitrogen and sulfur. Examples of such heteroaryl groups are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, pyridinyl, pyrimidinyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl/heteroarylene groups are unsubstituted or substituted as explicitly defined.

The term "5- to 6-membered heteroaryl", used alone or in combination, refers to a 5- to 6-membered monocyclic aromatic ring and containing one to a maximum of four ring heteroatoms (preferably one to a maximum of three ring heteroatoms), each independently selected from oxygen, nitrogen and sulfur. Examples of 5-membered groups are 5-membered heteroaryl groups such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl, tetrazolyl; notably pyrazolyl, triazolyl, oxazolyl, thiazolyl, oxadiazolyl; especially pyrazol-1-yl, 1,2,3-triazol-1-yl, oxazol-2-yl, thiazol-2-yl, 1,2,4-oxadiazol-5-yl or 1,2,4-oxadiazol-3-yl; most preferably 1,2,4-oxadiazol-5-yl or 1,2,4-oxadiazol-3-yl. Examples of 6-membered heteroaryl groups are groups such as pyridinyl, pyrimidinyl, pyridazinyl, pyrazinyl. The above-mentioned heteroaryl groups are unsubstituted or substituted as explicitly defined.

In the context of mono-substituted 5-membered heteroaryl groups, it is understood that a substitution in position 3 with respect to the point of attachment of a 5-membered heteroaryl to A means that the substituent in position 3 and the point of attachment to A are in a relative 1,3-arrangement. Preferred examples of such 5-membered heteroaryl groups which are mono-substituted in position 3 with respect to the point of attachment of said 5-membered heteroaryl to A are selected from a group consisting of

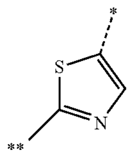
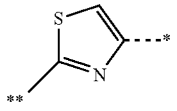
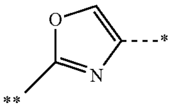
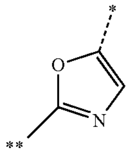
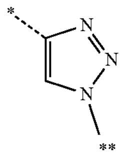
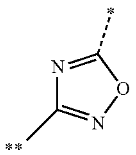
and
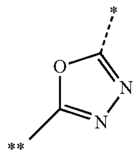

wherein one asterisk (*) denotes the attachment point to the substituent and two asterisks (**) denote the attachment point to A. Especially preferred are the last two (from left to right) 5-membered heteroaryl groups.

Further embodiments of the invention are presented hereinafter:

2) One embodiment relates to compounds according to embodiment 1), wherein A represents pyridinyl, pyrimidinyl, pyrazinyl, or pyridazinyl (notably pyridazinyl or pyridinyl; especially pyridin-2-yl, pyridin-3-yl, pyridin-4-yl, pyrimidin-5-yl, pyrazin-2-yl, or pyridazin-4-yl), wherein A is independently unsubstituted, mono-, di- or tri-substituted (notably mono- or di-substituted in meta- and/or para-position of A with respect to the point of attachment of A to the rest of the molecule; especially mono-substituted in meta-position of A with respect to the point of attachment of A to the rest of the molecule), wherein the substituent(s), if any, is(are) as defined in embodiment 1).

3) Another embodiment relates to compounds according to embodiment 1), wherein A represents pyridin-3-yl, pyridin-4-yl, or pyridazin-4-yl (in particular pyridin-3-yl or pyridazin-4-yl), wherein A is independently unsubstituted, mono-, di- or tri-substituted (notably mono- or di-substituted in meta- and/or para-position of A with respect to the point of attachment of A to the rest of the molecule; especially mono-substituted in meta-position of A with respect to the point of attachment of A to the rest of the molecule), wherein the substituent(s), if any, is(are) as defined in embodiment 1).

In a sub-embodiment, A is independently
- unsubstituted;
- mono-substituted (notably in meta-position of A with respect to the point of attachment of A to the rest of the molecule), wherein the substituent is as defined in embodiment 1); or
- di-substituted, wherein a first substituent is (notably in meta-position of A with respect to the point of attachment of A to the rest of the molecule) selected from the substituents defined in embodiment 1) (especially excluding halogen (especially fluorine) or cyano); and a second substituent is (notably in para-position of A with respect to the point of attachment of A to the rest of the molecule) selected from halogen (especially fluorine) and cyano.

4) Another embodiment relates to compounds according to embodiment 1), wherein A represents pyridin-3-yl, pyridin-4-yl, or pyridazin-4-yl (especially pyridin-3-yl or pyridazin-4-yl; in particular pyridin-3-yl), wherein A is mono-substituted (notably in meta-position of A with respect to the point of attachment of A to the rest of the molecule), wherein the substituent is as defined in embodiment 1).

5) Another embodiment relates to compounds according to any one of embodiments 1) to 4), wherein said substituent of A/at least one of said substituents of A is —O—$R^{O2}$ as defined in embodiment 1).

6) Another embodiment relates to compounds according to embodiment 5), wherein said substituent of A/at least one of said substituents of A is —O—$R^{O2}$, wherein $R^{O2}$ represents

- $C_{1-4}$-alkyl (especially isopropyl, sec-butyl, or isobutyl);
- $C_{2-5}$-alkyl which is mono-substituted with hydroxy or $C_{1-3}$-alkoxy (especially methoxy);
- [in particular such $C_{2-5}$-alkyl represents 2-hydroxy-ethyl, 3-hydroxy-propyl, 2-hydroxy-2-methyl-propyl, 3-hydroxy-3-methyl-butyl, or 2-methoxy-ethyl]
- -$L^2$-$CY^2$, wherein
  - -$L^2$- independently represents a bond (i.e. the $CY^2$ is directly attached to the rest of the molecule); and
  - $CY^2$ independently represents
    - $C_{3-6}$-cycloalkyl (especially oxetanyl, cyclopentyl or cyclohexyl), wherein optionally one carbon ring atom is replaced by one oxygen atom; wherein said $C_{3-6}$-cycloalkyl is unsubstituted, mono-, or di-substituted, wherein the substituents are selected from $C_{1-3}$-alkyl (especially methyl), hydroxy, fluoro, oxo, $C_{1-3}$-alkyl-carbonyl (especially acetyl), and $C_{1-3}$-alkoxy (especially methoxy);

chromanyl (especially chroman-6-yl);

[in particular such -$L^2$-$CY^2$ represents 2-(benzyl-oxy)-ethyl, 2,2-dimethyl-cyclopentyl, 3,3-difluoro-cyclopentyl, 3-methoxy-cyclopentyl, cyclohexyl, 4-hydroxy-cyclohexyl, 4-methyl-4-hydroxy-cyclohexyl, 4-oxo-cyclohexyl, tetrahydrofuran-3-yl, tetrahydropyran-4-yl, tetrahydropyran-4-yl-methyl, or chroman-6-yl]

[in particular such —O—$R^{O2}$ represents isopropoxy, isobutoxy, sec-butoxy, 2-(benzyl-oxy)-ethoxy, 2-methoxy-ethoxy, 3-hydroxy-propoxy, 2-hydroxy-2-methyl-propoxy, 2-hydroxy-ethoxy, 3-hydroxy-3-methyl-butoxy, 2,2-dimethyl-cyclopentyl-oxy, 3,3-difluoro-cyclopentyl-oxy, cyclohexyl-oxy, 4-hydroxy-cyclohexyl-oxy, 4-methyl-4-hydroxy-cyclohexyl-oxy, 4-oxo-cyclohexyl-oxy, tetrahydrofuran-3-yl-oxy, tetrahydropyran-4-yl-oxy, tetrahydropyran-4-yl-methoxy, 3-methoxy-cyclopentyl-oxy, or chroman-6-yl-oxy]

7) Another embodiment relates to compounds according to any one of embodiments 1) to 4), wherein said substituent of A/at least one of said substituents of A is $C_{3-5}$-alkyl as defined in embodiment 1).

8) Another embodiment relates to compounds according to embodiment 7), wherein said substituent of A/at least one of said substituents of A is $C_{3-5}$-alkyl (especially n-propyl, n-butyl, or n-pentyl) which is substituted with hydroxy and $R^{A1}$, wherein said substituents are both at position 3 with respect to the point of attachment of said $C_{3-5}$-alkyl to the rest of the molecule; wherein $R^{A1}$ represents phenyl which is unsubstituted or mono-substituted with fluorine (especially 3-fluoro-phenyl) or $C_{1-3}$-alkoxy (especially 2-methoxy-phenyl or 4-methoxy-phenyl);

6-membered heteroaryl containing one or two ring nitrogen heteroatom(s) (notably pyridin-2-yl, pyridin-3-yl, pyrimidin-2-yl, pyrazin-2-yl, or pyrimidin-4-yl), wherein said 5- or 6-membered heteroaryl is independently unsubstituted, mono- or di-substituted, and wherein the substituent(s), if any, is(are) independently selected from $C_{1-3}$-alkyl (especially methyl), $C_{3-5}$-cycloalkyl (especially cyclopropyl), or $C_{1-3}$-alkoxy (especially methoxy); or

[in particular such $C_{3-5}$-alkyl which represents 3-hydroxy-3-phenyl-propyl, 3-hydroxy-3-phenyl-butyl, 3-hydroxy-3-(3-fluoro-phenyl)-butyl, 3-hydroxy-3-(2-methoxy-phenyl)-butyl, 3-hydroxy-3-(4-methoxy-phenyl)-butyl, 3-hydroxy-3-(6-methoxy-pyridin-2-yl)-butyl, 3-hydroxy-3-(5-methyl-pyridin-3-yl)-butyl, 3-hydroxy-3-(pyridin-2-yl)-butyl, 3-hydroxy-3-(6-methyl-pyridin-2-yl)-butyl, 3-hydroxy-3-(pyrimidin-2-yl)-butyl, 3-hydroxy-3-(6-methoxy-pyrimidin-4-yl)-butyl, 3-hydroxy-3-(6-methyl-pyrimidin-4-yl)-pentyl, 3-hydroxy-3-(2-methyl-pyrimidin-4-yl)-butyl, 3-hydroxy-3-(5-methyl-pyrazin-2-yl)-butyl, 3-hydroxy-3-(pyridin-2-yl)-pentyl, or 3-hydroxy-3-(6-methoxy-pyridin-2-yl)-pentyl]

9) Another embodiment relates to compounds according to any one of embodiments 1) to 4), wherein said substituent of A/at least one of said substituents of A is —$NR^{N3}R^{N4}$, wherein $R^{N3}$ and $R^{N4}$ form, together with the nitrogen to which they are attached, a heterocyclic ring as defined in embodiment 1).

10) Another embodiment relates to compounds according to embodiment 9), wherein said substituent of A/at least one of said substituents of A is —$NR^{N3}R^{N4}$ wherein $R^{N3}$ and $R^{N4}$ form, together with the nitrogen to which they are attached, a heterocyclic ring of 4 to 6 members (notably 5 to 6 members), wherein the members needed to complete said heterocyclic ring are each independently selected from —$CH_2$—, —O—, —(C═O)—, —$CHR^X$— and —$C(R^Y)_2$—; wherein said heterocyclic ring does not contain more than one member independently selected from the group consisting of —O— and —(C═O)—; wherein said heterocyclic ring does not contain more than two members selected from the group consisting of —$CHR^X$—; and wherein said heterocyclic ring does not contain more than two members selected from the group consisting of —$C(R^Y)_2$—; wherein $R^X$ independently represents fluorine, methyl, isopropyl, hydroxy, trifluoromethyl, cyclopropyl, phenyl, 3-methyl-1,2,4-oxadiazol-5-yl; and wherein $R^Y$ independently represents fluorine, hydroxy, cyclopropyl, methyl, or trifluoromethyl [notably such —$NR^{N3}R^{N4}$ is pyrrolidinyl; 2-pyrrolidonyl; oxazolidinonyl (especially 1,3-oxazolidin-2-on-3-yl); piperidinyl; or morpholinyl, optionally independently substituted with one or two substituents independently selected from a group consisting of $R^X$ and $R^Y$].

[in particular such —$NR^{N3}R^{N4}$ represents pyrrolidin-1-yl, 3-fluoro-pyrrolidin-1-yl, 3,3-difluoro-pyrrolidin-1-yl, 3,4-difluoro-pyrrolidin-1-yl, 3-isopropyl-pyrrolidin-1-yl, 3,3-dimethyl-pyrrolidin-1-yl, 3-hydroxy-pyrrolidin-1-yl, 2-methyl-pyrrolidin-1-yl, 3-hydroxy-3-methyl-pyrrolidin-1-yl, 3-hydroxy-3-trifluoromethyl-pyrrolidin-1-yl, 3-trifluoromethyl-pyrrolidin-1-yl, morpholin-4-yl, 3-(tetrahydropyran-4-yl)-pyrrolid-2-on-1-yl, pyrrolidin-2-on-1-yl, 4-phenyl-pyrrolidin-2-on-1-yl, 4-(pyridin-2-yl)-pyrrolidin-2-on-1-yl, 4-(6-methyl-pyridin-3-yl)-pyrrolidin-2-on-1-yl, 4-(2-isopropyl-pyrimidin-4-yl)-pyrrolidin-2-on-1-yl, 4-(6-isopropyl-pyridin-2-yl)-pyrrolidin-2-on-1-yl, 4-(6-trifluoromethyl-pyridin-3-yl)-pyrrolidin-2-on-1-yl, 4-methyl-pyrrolidin-2-on-1-yl, 4-isopropyl-pyrrolidin-2-on-1-yl, 3-isopropyl-pyrrolidin-2-on-1-yl, 3,3-dimethyl-pyrrolidin-2-on-1-yl, 4,4-dimethyl-pyrrolidin-2-on-1-yl, 3-(piperidin-4-yl)-pyrrolidin-2-on-1-yl, 4-(6-isopropyl-pyridin-2-yl)-pyrrolidin-2-on-1-yl, 4-isobutyl-pyrrolidin-2-on-1-yl, 4-cyclopropyl-pyrrolidin-2-on-1-yl, 4-trifluoromethyl-pyrrolidin-2-on-1-yl, 2,2,6,6-tetrafluoro-morpholin-4-yl, 2,6-dimethyl-morpholin-4-yl, 3-(3-methyl-1,2,4-oxadiazol-5-yl)-pyrrolidin-1-yl, or 3-(phenyl)-pyrrolidin-1-yl]

11) Another embodiment relates to compounds according to any one of embodiments 1) to 4), wherein said substituent of A/at least one of said substituents of A is 5- or 6-membered heteroaryl as defined in embodiment 1), wherein the substituent(s) of said 5- or 6-membered heteroaryl, if any, is(are) independently selected from $C_{1-4}$-alkyl as defined in embodiment 1).

12) Another embodiment relates to compounds according to embodiment 11), wherein said substituent of A/at least one of said substituents of A is 5- or 6-membered heteroaryl containing from one to three (notably two or three; especially three) ring heteroatom(s) independently selected from nitrogen, oxygen and sulfur (notably pyrazolyl, oxazolyl, thiazolyl, oxadiazolyl, pyrimidinyl, or pyridinyl; especially pyrazol-1-yl, 1H-1,2,3-triazol-1-yl, oxazol-2-yl, thiazol-2-yl, 1,2,4-oxadiazol-5-yl, 1,2,4-oxadiazol-3-yl, pyrimidin-2-yl, or pyridin-2-yl; notably 1,2,4-oxadiazol-5-yl or 1,2,4-oxadiazol-3-yl; especially 1,2,4-oxadiazol-3-yl); wherein said 5- or 6-membered heteroaryl is independently unsubstituted, mono-, di-, or tri-substituted (notably mono-substituted; especially mono-substituted in position 3 with respect to the point of attachment of said 5- or 6-membered heteroaryl to A), wherein the substituent(s), if any, is(are) independently selected from $C_{1-4}$-alkyl (especially methyl, ethyl, propyl, isopropyl, or tert-butyl) which is
  unsubstituted;
  mono-substituted with
    hydroxy; or
    $C_{1-4}$-alkoxy (especially methoxy and tert-butoxy); or
    [in particular such $C_{1-4}$-alkyl represents methyl, isopropyl, hydroxy-methyl, 1-hydroxy-1-methyl-ethyl, 2-hydroxy-2-methyl-propyl, 2-hydroxy-1,1-dimethyl-ethyl, methoxy-methyl, 2-methoxy-ethyl, 1-methoxy-1-methyl-ethyl, 2-methoxy-2-methyl-propyl, 2-methoxy-1,1-dimethyl-ethyl, or tert-butoxy-methyl; in particular such $C_{1-4}$-alkyl represents 1-hydroxy-1-methyl-ethyl, 2-hydroxy-2-methyl-propyl, or 2-hydroxy-1,1-dimethyl-ethyl]
  di-substituted, wherein one substituent is hydroxy, and another substituent is trifluoromethyl; or two substituents are hydroxy;
  di- or tri-substituted, wherein two substituents are fluorine and, if present, one substituent is hydroxy (wherein the hydroxy group is separated by at least two carbon atoms from any of said fluorine substituents);

[in particular such $C_{1-4}$-alkyl represents methyl, isopropyl, hydroxy-methyl, 1-hydroxy-1-methyl-ethyl, 2-hydroxy-2-methyl-propyl, 2-hydroxy-1,1-dimethyl-ethyl, methoxy-methyl, 2-methoxy-ethyl, 1-methoxy-1-methyl-ethyl, 2-methoxy-2-methyl-propyl, 2-methoxy-1,1-dimethyl-ethyl, tert-butoxy-methyl; 1,2-di hydroxy-ethyl, N-acetyl-2-amino-ethyl, N-(acetyl-2,2,2-$d_3$)-2-amino-ethyl, 2-(methylcarboxamido)-2-methyl-propyl, 2-(ethylcarboxamido)-2-methyl-propyl, 2-(cyclopropyl-carboxamido)-2-methyl-propyl, 2-(tetrahydropyran-4-yl-carboxamido)-2-methyl-propyl, 2-(methoxy-methyl-carboxamido)-2-methyl-propyl, 2-(ethyl-carboxamido)-2-methyl-propyl, 2-(isopropyl-carboxamido)-2-methyl-propyl, 2-(methyl-d3-carboxamido)-2-methyl-propyl, N-methyl-N-(hydroxy-methyl-carbonyl)-2-amino-ethyl, N-methyl-N-acetyl-2-amino-ethyl, 2,2,2-trifluoro-1-hydroxy-1-methyl-ethyl, 1,1-difluoro-2-hydroxy-ethyl, 1,1-difluoro-ethyl, or N-methyl-N-(acetyl-2,2,2-$d_3$)-2-amino-ethyl; in particular such $C_{1-4}$-alkyl group is 1-hydroxy-1-methyl-ethyl, 2-hydroxy-2-methyl-propyl, or 2-hydroxy-1,1-dimethyl-ethyl]

13) Another embodiment relates to compounds according to embodiment 11), wherein said substituent of A/at least one of said substituents of A is 1,2,4-oxadiazol-5-yl or 1,2,4-oxadiazol-3-yl (especially 1,2,4-oxadiazol-3-yl), wherein said oxadiazolyl groups are mono-substituted, wherein the substituent is independently selected from
  $C_{1-4}$-alkyl (especially methyl, ethyl, propyl, isopropyl, of tetrt-butyl) which is
    mono-substituted with
      hydroxy; or
      $C_{1-4}$-alkoxy (especially methoxy and tert-butoxy).
      [in particular such $C_{1-4}$-alkyl represents hydroxy-methyl, 1-hydroxy-1-methyl-ethyl, 2-hydroxy-2-methyl-propyl, 2-hydroxy-1,1-dimethyl-ethyl, methoxy-methyl, 2-methoxy-ethyl, 1-methoxy-1-methyl-ethyl, 2-methoxy-2-methyl-propyl, 2-methoxy-1,1-dimethyl-ethyl, or tert-butoxy-methyl; in particular such $C_{1-4}$-alkyl represents 1-hydroxy-1-methyl-ethyl, 2-hydroxy-2-methyl-propyl, or 2-hydroxy-1,1-dimethyl-ethyl]

14) Another embodiment relates to compounds according to embodiment 11), wherein said substituent of A/at least one of said substituents of A is 1,2,4-oxadiazol-3-yl, which is mono-substituted (especially in position 3 with respect to the point of attachment of said oxadiazolyl to A), wherein the substituent is
  $C_{1-4}$-alkyl (especially methyl, ethyl, propyl, isopropyl, or tert-butyl) which is
    mono-substituted with
      hydroxy;
      [in particular such $C_{1-4}$-alkyl represents hydroxy-methyl, 1-hydroxy-1-methyl-ethyl, 2-hydroxy-2-methyl-propyl, 2-hydroxy-1,1-dimethyl-ethyl, in particular such $C_{1-4}$-alkyl represents 1-hydroxy-1-methyl-ethyl, 2-hydroxy-2-methyl-propyl, or 2-hydroxy-1,1-dimethyl-ethyl]

15) Another embodiment relates to compounds according to embodiment 11), wherein A represents pyridin-3-yl, wherein said pyridin-3-yl is mono-substituted in meta-position with respect to the point of attachment of said pyridin-3-yl to the rest of the molecule, wherein the substituent is 1,2,4-oxadiazol-3-yl, which is mono-substituted (especially in position 3 with respect to the point of attachment of said oxadiazolyl to A), wherein the substituent is hydroxy-methyl, 1-hydroxy-1-methyl-ethyl, 2-hydroxy-2-methyl-propyl, or 2-hydroxy-1,1-dimethyl-ethyl.

[in particular such 1,2,4-oxadiazol-3-yl represents 5-(hydroxy-methyl)-1,2,4-oxadiazol-3-yl, 5-(1-hydroxy-1-methyl-ethyl)-1,2,4-oxadiazol-3-yl, 5-(2-hydroxy-2-methyl-propyl)-1,2,4-oxadiazol-3-yl, or 5-(2-hydroxy-1,1-dimethyl-ethyl)-1,2,4-oxadiazol-3-yl]

16) Another embodiment relates to compounds according to any one of embodiments 1) to 4), wherein said substituent of A/at least one of said substituents of A is 5- or 6-membered heteroaryl as defined in embodiment 1), wherein the substituent(s) of said 5- or 6-membered heteroaryl, if any, is(are) independently selected from $L^3$-$CY^3$ as defined in embodiment 1).

17) Another embodiment relates to compounds according to embodiment 16), wherein said substituent of A/at least one of said substituents of A is 5- or 6-membered heteroaryl containing from one to three (notably two or three; especially three) ring heteroatom(s) independently selected from nitrogen, oxygen and sulfur (notably pyrazolyl, oxazolyl, thiazolyl, oxadiazolyl, pyrimidinyl, or pyridinyl; especially pyrazol-1-yl, 1H-1,2,3-triazol-1-yl, oxazol-2-yl, thiazol-2-yl, 1,2,4-oxadiazol-5-yl, 1,2,4-oxadiazol-3-yl, pyrimidin-2-yl, or pyridin-2-yl; notably 1,2,4-oxadiazol-5-yl or 1,2,4-oxadiazol-3-yl; especially 1,2,4-oxadiazol-3-yl); wherein said 5- or 6-membered heteroaryl is independently unsubstituted, mono-, di-, or tri-substituted (notably mono-substituted; especially mono-substituted in position 3 with respect to the point of attachment of said 5- or 6-membered heteroaryl to A), wherein the substituent(s), if any, is(are) independently selected from $L^3$-$CY^3$, wherein -$L^3$- independently represents a bond (i.e. the $CY^3$ is directly attached to the rest of the molecule), —$CH_2$—, —$CH_2$—$CH_2$—, —$C(CH_3)_2$—, —CH(OH)—, or —O—$CH_2$—, wherein when -$L^3$- is —O—$CH_2$—, said $CY^3$ is attached to the oxygen atom of said —O—$CH_2$—; and $CY^3$ independently represents piperidinyl; wherein said piperidinyl independently is unsubstituted, mono-, di-, or tri-substituted as defined in embodiment 1).

18) Another embodiment relates to compounds according to embodiment 16), wherein said substituent of A/at least one of said substituents of A is 1,2,4-oxadiazol-5-yl or 1,2,4-oxadiazol-3-yl (especially 1,2,4-oxadiazol-3-yl), wherein said oxadiazolyl groups are mono-substituted, wherein the substituent is independently selected from -$L^3$-$CY^3$, wherein -$L^3$- independently represents a bond (i.e. the $CY^3$ is directly attached to the rest of the molecule), —$CH_2$—, —$CH_2$—$CH_2$—, —$C(CH_3)_2$—, —CH(OH)—, or —O—$CH_2$—, wherein when -$L^3$- is —O—$CH_2$—, said $CY^3$ is attached to the oxygen atom of said —O—$CH_2$—; and $CY^3$ independently represents piperidinyl (notably piperidin-2-yl, piperidin-3-yl, or piperidin-4-yl; especially piperidin-4-yl) wherein said piperidinyl independently is unsubstituted, mono-, di-, or tri-substituted (especially unsubstituted, mono-, or di-substituted) with halogen (especially fluorine);

oxo;

hydroxy;

$C_{1-3}$-alkyl which is optionally mono-substituted with $C_{1-3}$-alkoxy (especially such $C_{1-3}$-alkyl represents methyl, ethyl, propyl, isopropyl, or methoxy-methyl);

$C_{1-3}$-alkoxy (especially methoxy);

—(C═O)—$R^{CO}$, wherein $R^{CO}$ represents $C_{1-3}$-alkyl which is optionally mono-substituted with hydroxy or $C_{1-3}$-alkoxy (especially methyl, ethyl, n-propyl, isopropyl, tert-butyl, hydroxy-methyl, methoxy-methyl, benzyl-oxy, or 2-methoxy-ethyl; in particular said —(C═O)—$R^{CO}$ is acetyl);

$C_{1-3}$-fluoroalkyl (especially 2,2,2-trifluoro-ethyl);

$C_{1-3}$-alkoxy (especially methoxy);

$C_{3-6}$-cycloalkyl-$(CH_2)_n$—, wherein optionally one or two carbon ring atom(s) is/are replaced by one or two oxygen ring atom(s); wherein n represents the integer 0, or 1 (especially such $C_{3-5}$-cycloalkyl-$(CH_2)_n$— represents cyclopropyl, cyclopentyl, oxetan-3-yl, oxetan-3-yl-methyl, 1,4-dioxan-2-yl, or tetrahydropyran-4-yl); or phenyl;

[especially such —(C═O)—$R^{CO}$ represents acetyl, ethyl-carbonyl, n-propyl-carbonyl, isopropyl-carbonyl, tert-butyl-carbonyl, hydroxymethyl-carbonyl, 2,2,2-trifluoro-ethyl-carbonyl, methoxy-methyl-carbonyl, 2-methoxy-ethyl-carbonyl, methoxy-carbonyl, ethoxy-carbonyl, 2-methoxy-ethoxy-carbonyl, cyclopropyl-carbonyl, cyclopentyl-carbonyl, oxetan-3-yl-carbonyl, oxetan-3-yl-methyl-carbonyl, phenyl-carbonyl, or tetrahydropyran-4-yl-carbonyl, methoxy-methyl-carbonyl, or 1,4-dioxan-2-yl-carbonyl]

—S(═O)$_2$—$R^{SO}$, wherein $R^{SO}$ represents $C_{1-3}$-alkyl which is optionally mono-substituted with hydroxy, $C_{1-3}$-alkoxy, or amino (especially methyl, n-propyl, isopropyl, 2-hydroxy-ethyl, 2-methoxy-ethyl, or methyl-amino); or $C_{3-5}$-cycloalkyl, wherein optionally one carbon ring atom is replaced by one oxygen ring atom (especially represents cyclopropyl, cyclopentyl, or tetrahydropyran-4-yl);

[especially such —S(═O)$_2$—$R^{SO}$ represents methyl-sulfonyl, n-propyl-sulfonyl, isopropyl-sulfonyl, 2-hydroxyethyl-sulfonyl, cyclopropyl-sulfonyl, cyclopentyl-sulfonyl, 2-methoxy-ethyl-sulfonyl, methyl-amino-sulfonyl, or tetrahydropyran-4-yl-sulfonyl]

[in particular such -$L^3$-$CY^3$ piperidin-4-yl, 1-methyl-2,6-dioxo-piperidin-4-yl, 4-methyl-piperidin-4-yl, 4-fluoro-piperidin-4-yl, 2-oxo-piperidin-4-yl, 6-oxo-piperidin-2-yl, 6-oxo-piperidin-3-yl, 1-methyl-6-oxo-piperidin-3-yl, 3-methyl-6-oxo-piperidin-3-yl, N-acetyl-piperidin-4-yl, N-acetyl-piperidin-4-yl-methyl, N-acetyl-2-methyl-piperidin-4-yl, N-acetyl-4-fluoro-piperidin-4-yl, N-acetyl-3-methyl-piperidin-4-yl, N-acetyl-4-methyl-piperidin-4-yl, N-acetyl-4-hydroxy-piperidin-4-yl, N-acetyl-4-methoxy-piperidin-4-yl, N-acetyl-piperidin-3-yl, N-acetyl-piperidin-3-yl-methyl, N-acetyl-3-methyl-piperidin-3-yl, N-acetyl-3-hydroxy-piperidin-3-yl, N-(isopropyl-carbonyl)-4-hydroxy-piperidin-4-yl, N-(tert-butyl-carbonyl)-piperidin-4-yl, N-(2-methoxy-ethoxy-carbonyl)piperidin-4-yl, N-(hydroxymethyl-carbonyl)-piperidin-4-yl, N-(cyclopropyl-sulfonyl)-piperidin-4-yl, N-(methyl-sulfonyl)-piperidin-4-yl, N-(n-propyl-sulfonyl)-piperidin-4-yl, N-(isopropyl-sulfonyl)-piperidin-4-yl, N-(2-hydroxy-ethyl-sulfonyl)piperidin-4-yl, N-(cyclopentyl-sulfonyl)-piperidin-4-yl, N-(methoxy-carbonyl)piperidin-4-yl, N-(cyclopropyl-carbonyl)-piperidin-4-yl, N-(cyclopentyl-carbonyl)-piperidin-4-yl, N-(methyl-amino-sulfonyl)-piperidin-4-yl, N-(2-methoxy-ethyl-sulfonyl)-piperidin-4-yl, N-(ethyl-carbonyl)-4-hydroxy-piperidin-4-yl, N-(methoxy-methyl-carbonyl)-piperidin-4-yl, N-(ethoxy-carbonyl)piperidin-4-yl, N-acetyl-4-ethyl-piperidin-4-yl, N-(n-propyl-carbonyl)-piperidin-4-yl, N-(2-methoxy-ethyl-carbonyl)-piperidin-4-yl, N-(oxetan-3-yl-carbonyl)-piperidin-4-yl, N-(oxetan-3-yl-methyl-carbonyl)-piperidin-4-yl, N-(2,2,2-trifluoro-ethyl-carbonyl)-piperidin-4-yl, N-(tetrahydropyran-4-yl-carbonyl)-piperidin-4-yl, N-(phenyl-carbonyl)-piperidin-4-yl, N-(tetrahydropyran-4-yl-sulfonyl)-piperidin-4-yl, N-(benzyl-oxy-carbonyl)piperidin-4-yl, N-(methoxy-methyl-carbonyl)-4-isopropyl-piperidin-4-yl, N-(1,4-dioxan-2-yl-carbonyl)piperidin-4-yl].

19) Another embodiment relates to compounds according to embodiment 16), wherein said substituent of A/at least one of said substituents of A is 1,2,4-oxadiazol-3-yl, wherein said oxadiazolyl group is mono-substituted, wherein the substituent is independently selected from $L^3$-$CY^3$, wherein $L^3$-represents a bond (i.e. the $CY^3$ is directly attached to the rest of the molecule); and $CY^3$ independently represents piperidin-4-yl which is unsubstituted, or mono- or di-substituted, wherein one substituent is attached to the nitrogen atom of said piperidine ring, wherein the substituent is —(C═O)—$R^{CO}$, wherein $R^{CO}$ represents $C_{1-3}$-alkyl optionally mono-substituted, wherein the substituent represents $C_{1-3}$-alkoxy or hydroxy (especially such $C_{1-3}$-alkyl is methyl, ethyl, n-propyl, isopropyl, tert-butyl, hydroxy-methyl, methoxy-methyl, or 2-methoxy-ethyl; in particular said —(C═O)—$R^{CO}$ is acetyl);

$C_{1-3}$-fluoroalkyl (especially 2,2,2-trifluoro-ethyl);

$C_{1-3}$-alkoxy (especially methoxy);

$C_{3-6}$-cycloalkyl-$(CH_2)_n$—, wherein optionally one or two carbon ring atom(s) is/are replaced by one or two oxygen ring atom(s); wherein n represents the integer 0, or 1 (especially such $C_{3-5}$-cycloalkyl-$(CH_2)_n$— represents cyclopropyl, cyclopentyl, oxetan-3-yl, oxetan-3-yl-methyl, 1,4-dioxan-2-yl, or tetrahydropyran-4-yl); or

[especially such —(C═O)—$R^{CO}$ represents acetyl, ethyl-carbonyl, n-propyl-carbonyl, isopropyl-carbonyl, tert-butyl-carbonyl, hydroxymethyl-carbonyl, 2,2,2-trifluoro-ethyl-carbonyl, methoxy-methyl-carbonyl, 2-methoxy-ethyl-carbonyl, methoxy-carbonyl, ethoxy-carbonyl, 2-methoxy-ethoxy-carbonyl, cyclopropyl-carbonyl, cyclopentyl-carbonyl, oxetan-3-yl-carbonyl, oxetan-3-yl-methyl-carbonyl, tetrahydropyran-4-yl-carbonyl, methoxy-methyl-carbonyl, or 1,4-dioxan-2-yl-carbonyl]

and/or one substitutent is attached to a carbon atom of the piperidine ring, wherein said substituent is $C_{1-3}$-alkyl (especially methyl), halogen (especially fluorine), hydroxy, or $C_{1-3}$-alkoxy (especially methoxy).

20) Another embodiment relates to compounds according to any one of embodiments 1) to 4), wherein said substituent of A/at least one of said substituents of A independently is —C≡C—$R^{T1}$; or

—C≡C—C(OH)($R^{T2}$)($R^{T3}$);

wherein said groups are as defined in embodiment 1).

21) Another embodiment relates to compounds according to embodiment 20), wherein said substituent of A/at least one of said substituents of A is —C≡C—$R^{T1}$, wherein $R^{T1}$ represents $C_{1-4}$-alkyl (notably methyl, ethyl, isopropyl, or isobutyl), wherein said $C_{1-4}$-alkyl independently is mono-substituted with hydroxy;

[especially such $C_{1-4}$-alkyl represents hydroxy-methyl, 1-hydroxy-ethyl, 2-hydroxy-ethyl, 1-hydroxy-2-methyl-propyl, or 1-hydroxy-1-methyl-ethyl];

$C_{1-3}$-alkoxy (especially methoxy);

—S(═O)$_2$—$R^{SOT}$, wherein $R^{SOT}$ represents $C_{1-3}$-alkyl, $C_{1-3}$-alkyl-amino, or $C_{3-5}$-cycloalkyl (especially such —S(═O)$_2$—$R^{SOT}$ represents methyl-sulfonyl, methyl-amino-sulfonyl or cyclopropyl-sulfonyl);

$C_{4-6}$-heterocyclyl containing one or two ring heteroatom(s) independently selected from nitrogen and oxygen (notably oxazolidinyl, imidazolidinyl, or pyrrolidinyl; especially oxazolidin-3-yl, imidazolidin-3-yl, or pyrrolidin-1-yl); wherein said $C_{4-6}$-heterocyclyl is mono-substituted with oxo; or di-substituted with oxo and one $C_{1-3}$-alkyl (especially methyl); (especially such $C_{4-6}$-heterocyclyl represents oxazolidin-2-on-3-yl, imidazolidin-2-on-3-yl, 1-methyl-imidazolidin-2-on-3-yl, or pyrrolidin-2-on-1-yl);

$C_{1-4}$-alkyl (notably methyl, ethyl, isopropyl, or isobutyl) which is independently di-substituted, wherein one substituent is hydroxy, and a second substituent is trifluoromethyl (especially 1-hydroxy-1-trifluoromethyl-ethyl);

$C_{3-6}$-cycloalkyl (especially cyclopropyl) which is mono-substituted (especially at the point of attachment of the $C_{3-6}$-cycloalkyl to the rest of the molecule) with hydroxy;

amino-sulfonyl which is optionally di-substituted with methyl;

phenyl which is mono-substituted with halogen (especially 4-fluoro-phenyl);

pyridinyl (especially pyridine-2-yl);

pyrimidinyl which is mono-substituted with $C_{1-3}$-alkyl (especially 6-methyl-pyrimidin-4-yl);

oxazolidinonyl (especially oxazolidin-2-on-3-yl);

[in particular such $C_{3-6}$-cycloalkyl represents 1-hydroxy-cyclopropyl, 1-hydroxy-cyclobutyl, 1-hydroxy-cyclopenty, 1-(amino-sulfonyl)-cyclopropyl, 1-(dimethyl-amino-sulfonyl)-cyclopropyl, 1-(6-methyl-pyrimidin-4-yl)-cyclopropyl, 1-(pyridine-2-yl)-cyclopropyl, 1-(4-fluoro-phenyl)-cyclopropyl, 1-(pyridine-2-yl)-cyclopropyl, or 1-(oxazolidin-2-on-3-yl)-cyclopropyl];

$C_{4-6}$-heterocyclyl containing one ring heteroatom independently selected from nitrogen and oxygen (notably azetidinyl, pyrrolidinyl, piperidinyl, tetrahydropyranyl; especially azetidin-3-yl, piperidin-4-yl, pyrrolidin-3-yl, pyrrolidin-2-yl, pyrrolidine-1-yl, or tetrahydropyran-4-yl); wherein said $C_{4-6}$-heterocyclyl is mono-, di-, or tri-substituted (especially mono- or di-substituted), wherein the substituent(s) is(are) independently selected from $C_{1-3}$-alkyl (especially methyl), hydroxy, oxo, $C_{1-3}$-alkyl-carbonyl (especially acetyl), $C_{1-3}$-alkoxy-carbonyl (especially tert-butoxy-carbonyl), $C_{1-3}$-alkyl-sulfonyl (especially methyl-sulfonyl), and $C_{1-3}$-alkyl-amino-sulfonyl (especially methyl-amino-sulfonyl);

[in particular such $C_{4-6}$-heterocyclyl represents N-(isopropyl-carbonyl)-3-hydroxy-azetidin-3-yl, N-(tert-butoxy-carbonyl)-3-hydroxy-azetidin-3-yl, N-methyl-3-hydroxy-pyrrolidin-2-one-3-yl, N-acetyl-2-methyl-pyrrolidin-2-yl, 3-hydroxy-N-(tert-butoxy-carbonyl)-pyrrolidin-3-yl, 2-oxo-pyrrolidine-1-yl, N-acetyl-piperidin-4-yl, N-acetyl-4-methyl-piperidin-4-yl, N-(methyl-amino-sulfonyl)-4-methyl-piperidin-4-yl, N-acetyl-4-hydroxy-piperidin-4-yl, N-(methyl-sulfonyl)-piperidin-4-yl, N-(tert-butoxy-carbonyl)piperidin-4-yl, 3-hydroxy-2-oxo-1-methyl-pyrrolidin-2-yl, or 4-hydroxy-tetrahydropyran-4-yl);

indolyl (especially indol-2-yl);

3-hydroxy-1-methyl-1,3-dihydro-indol-2-on-3-yl; or

[in particular such —C≡C—$R^{T1}$ represents 3-hydroxy-3-trifluoromethyl-but-1-yn-1-yl, 3-hydroxy-prop-1-yn-1-yl, 4-hydroxy-but-1-yn-1-yl, 3-hydroxy-but-1-yn-1-yl, 3-hydroxy-3-methyl-but-1-yn-1-yl, 3-hydroxy-4-methyl-pent-1-yn-1-yl, (1-hydroxy-cyclopropyl)-ethynyl, (1-hydroxy-cyclobutyl)-ethynyl, (1-hydroxy-cyclopentyl)-ethynyl, (8-hydroxy-5,6,7,8-tetrahydroquinolin-8-yl)-ethynyl, (7-hydroxy-6,7-dihydro-5H-cyclopenta[b]pyridin-7-yl)-ethynyl, (4-hydroxy-tetrahydropyran-4-yl)-ethynyl, (1-(isopropyl-carbonyl)-3-hydroxy-azetidin-3-yl)-ethynyl, (1-(tert-butoxy-carbonyl)-3-hydroxy-azetidin-3-yl)-ethynyl, (N-acetyl-4-hydroxy-piperidin-(3-hydroxy-N-(tert-butoxy-carbonyl)-pyrrolidin-3-yl)-ethynyl, (3-hydroxy-1-methyl-1,3-dihydro-indol-2-on-3-yl)-ethynyl, or (3-hydroxy-2-oxo-1-methyl-pyrrolidin-3-yl)-ethynyl]

—C≡C—C(OH)($R^{T2}$)($R^{T3}$) is as defined in embodiment 1).

22) Another embodiment relates to compounds according to embodiment 20), wherein said substituent of A/at least one of said substituents of A is —C≡C—C(OH)($R^{T2}$)($R^{T3}$), wherein $R^{T2}$ represents hydrogen or $C_{1-3}$-alkyl (notably methyl or ethyl; especially methyl);

$R^{T3}$ represents 6-membered heteroaryl containing one or two ring nitrogen atoms (especially pyridinyl, pyrazinyl, or pyrimidinyl; especially pyridin-2-yl, pyrimidin-2-yl, pyrazin-2-yl, or pyrimidin-4-yl; in particular pyrimidin-4-yl), wherein said 6-membered heteroaryl is independently unsubstituted, mono- or di-substituted; wherein the substituent(s), if any, is(are) independently selected from $C_{1-3}$-alkyl (especially methyl), $C_{1-3}$-cycloalkyl (especially cyclopropyl), $C_{1-3}$-fluoroalkyl (notably $C_1$-fluoroalkyl; especially difluoromethyl or trifluoromethyl), and $C_{1-3}$-alkoxy (especially methoxy);

[in particular such 6-membered heteroaryl is pyridin-2-yl, 6-methoxy-pyridin-2-yl, 6-methyl-pyridin-2-yl, pyrimidin-2-yl, 2-methoxy-pyrimidin-4-yl, 6-methoxy-pyrimidin-4-yl, pyrimidin-4-yl, 2-methyl-pyrimidin-4-yl, 6-methyl-pyrimidin-4-yl, 2,6-dimethyl-pyrimidin-4-yl, 2,6-dimethoxy-pyrimidin-4-yl, 2-methyl-6-methoxy-pyrimidin-4-yl, 2-methoxy-6-methyl-pyrimidin-4-yl, 5-methyl-pyrazin-2-yl, 6-cyclopropyl-pyrimidin-4-yl, 6-difluoromethyl-pyrimidin-4-yl, 2-trifluoromethyl-pyrimidin-4-yl, or 6-trifluoromethyl-pyrimidin-4-yl]

[in particular such —C≡C—C(OH)($R^{T2}$)($R^{T3}$) represents 3-hydroxy-3-(pyrimidin-2-yl)-but-1-yn-1-yl, 3-hydroxy-3-(6-methyl-pyrimidin-4-yl)-but-1-yn-1-yl, 3-hydroxy-3-(2-methoxy-pyrimidin-4-yl)-but-1-yn-1-yl, 3-hydroxy-3-(2-methoxy-6-methyl-pyrimidin-4-yl)-but-1-yn-1-yl, 3-hydroxy-3-(6-methoxy-pyrimidin-4-yl)-but-1-yn-1-yl, 3-hydroxy-3-(2,6-dimethoxy-pyrimidin-4-yl)-but-1-yn-1-yl, 3-hydroxy-3-(2-methyl-pyrimidin-4-yl)-but-1-yn-1-yl, 3-hydroxy-3-(6-methoxy-2-methyl-pyrimidin-4-yl)-but-1-yn-1-yl, 3-hydroxy-3-(pyridin-2-yl)-pent-1-yn-1-yl, 3-hydroxy-3-(6-methoxy-pyridin-2-yl)-but-1-yn-1-yl, 3-hydroxy-3-(6-methyl-pyridin-2-yl)-but-1-yn-1-yl, 3-hydroxy-3-(6-methyl-pyridin-2-yl)-pent-1-yn-1-yl, 3-hydroxy-3-(2,6-dimethyl-pyrimidin-4-yl)-but-1-yn-1-yl, 3-hydroxy-3-(6-methoxy-pyridin-2-yl)-pent-1-yn-1-yl, 3-hydroxy-3-(6-cyclopropyl-pyrimidin-4-yl)-but-1-yn-1-yl, 3-hydroxy-3-(6-difluoromethyl-pyrimidin-4-yl)-but-1-yn-1-yl, 3-hydroxy-3-(2-trifluoromethyl-pyrimidin-4-yl)-but-1-yn-1-yl, or 3-hydroxy-3-(6-trifluoromethyl-pyrimidin-4-yl)-but-1-yn-1-yl]

23) Another embodiment relates to compounds according to any one of embodiments 1) to 22), wherein B represents phenyl, which is mono-, di- or tri-substituted, wherein a first substituent is attached in para-position with respect to the point of attachment of B to the rest of molecule, wherein said substituent is selected from $C_{1-5}$-alkyl (notably methyl, ethyl, n-propyl, isopropyl, n-butyl, isobutyl, tert-butyl, 1-ethyl-propyl, 2,2-dimethyl-propyl, 1,1-dimethyl-propyl; especially methyl, ethyl, or isopropyl; in particular isopropyl);

$C_{1-3}$-alkoxy-$C_{1-4}$-alkyl (especially 3-methoxy-propyl);

$C_{1-2}$-fluoroalkyl (especially trifluoromethyl or 2,2,2-trifluoro-ethyl);

$C_{3-5}$-cycloalkyl (especially cyclopropyl or cyclobutyl) which independently is unsubstituted or mono-substituted (notably at the point of attachment of said $C_{3-5}$-cycloalkyl to the rest of the molecule) with $C_{1-3}$-alkyl (especially methyl) or $C_{1-3}$-fluoroalkyl (especially trifluoromethyl); and $C_1$-fluoroalkoxy (especially trifluoromethoxy);

and the remaining substituent(s) of B (wherein especially said remaining substituent(s) is/are attached in meta-position with respect to the point of attachment of B to the rest of molecule), if present, independently is/are selected from halogen (notably fluorine or chlorine; especially fluorine).

[in particular such group B represents 4-methyl-phenyl, 4-ethyl-phenyl, 4-propyl-phenyl, 4-isopropyl-phenyl, 4-butyl-phenyl, 4-isobutyl-phenyl, 4-tert-butyl-phenyl, 4-(1-ethyl-propyl)-phenyl, 4-(1,1-dimethyl-propyl)-phenyl, 4-(2,2-dimethyl-propyl)-phenyl, 3-chloro-4-isopropyl-phenyl, 3-fluoro-4-isopropyl-phenyl, 3,5-difluoro-4-isopropyl-phenyl, 4-cyclopropyl-phenyl, 4-trifluoromethyl-phenyl, 4-(2,2,2-trifluoro-ethyl)-phenyl, 4-trifluoromethoxy-phenyl, 4-(1-methyl-cyclopropyl)-phenyl, 4-cyclobutyl-phenyl, 4-(3-methoxy-propyl)-phenyl, or 4-(1-trifluoromethyl-cyclopropyl)-phenyl]

24) Another embodiment relates to compounds according to any one of embodiments 1) to 22), wherein B represents phenyl, which is mono-, di- or tri-substituted, wherein a first substituent is attached in para-position with respect to the point of attachment of B to the rest of molecule, wherein said substituent is selected from $C_{2-4}$-alkyl (notably n-propyl, isopropyl, n-butyl, isobutyl, tert-butyl; in particular isopropyl);

trifluoromethyl or 2,2,2-trifluoro-ethyl;

$C_{3-5}$-cycloalkyl (especially cyclopropyl or cyclobutyl) which independently is unsubstituted or mono-substituted (notably at the point of attachment of said $C_{3-5}$-cycloalkyl to the rest of the molecule) with $C_{1-3}$-alkyl (especially methyl) or $C_{1-3}$-fluoroalkyl (especially trifluoromethyl); and $C_1$-fluoroalkoxy (especially trifluoromethoxy);

and the remaining substituent(s) of B (wherein especially said remaining substituent(s) is/are attached in meta-position with respect to the point of attachment of B to the rest of molecule), if present, independently is/are selected from halogen (notably fluorine or chlorine; especially fluorine).

[in particular such group B represents 4-propyl-phenyl, 4-isopropyl-phenyl, 4-butyl-phenyl, 4-isobutyl-phenyl, 4-tert-butyl-phenyl, 3-chloro-4-isopropyl-phenyl, 3-fluoro-4-isopropyl-phenyl, 3,5-difluoro-4-isopropyl-phenyl, 4-cyclopropyl-phenyl, 4-trifluoromethyl-phenyl, 4-trifluoromethoxy-phenyl, 4-(2,2,2-trifluoro-ethyl)-phenyl, 4-(1-methyl-cyclopropyl)-phenyl, 4-cyclobutyl-phenyl, or 4-(1-trifluoromethyl-cyclopropyl)-phenyl]

25) Another embodiment relates to compounds according to any one of embodiments 1) to 22), wherein B represents phenyl, which is mono-substituted, wherein the substituent is attached in para-position with respect to the point of attachment of B to the rest of molecule, wherein said substituent is selected from isopropyl (preferred), trifluoromethyl, trifluoromethoxy, trifluoromethyl, cyclopropyl, cyclobutyl, 1-methyl-cyclopropyl, and 1-trifluoromethyl-cyclopropyl.

[in particular such group B represents 4-isopropyl-phenyl, 4-cyclopropyl-phenyl, 4-trifluoromethyl-phenyl, 4-trifluoromethoxy-phenyl, 4-(1-methyl-cyclopropyl)-phenyl, 4-cyclobutyl-phenyl, or 4-(1-trifluoromethyl-cyclopropyl)-phenyl]

26) Another embodiment relates to compounds according to any one of embodiments 1) to 25), wherein $R^1$ represents $C_{1-3}$-alkyl (notably methyl or ethyl; especially methyl);

27) Another embodiment relates to compounds according to any one of embodiments 1) to 26), wherein $R^2$ represents $C_{1-4}$-alkyl (especially methyl (preferred), ethyl, n-propyl, isopropyl, tert-butyl or isobutyl), $C_{3-5}$-cycloalkyl (especially cyclopropyl or cyclobutyl), $C_{3-5}$-cycloalkyl-$C_{1-3}$-alkyl (especially cyclopropyl-methyl), or $C_{1-3}$-fluoroalkyl (especially 2,2-difluoro-ethyl, or 2-fluoroethyl).

28) Another embodiment relates to compounds according to any one of embodiments 1) to 26), wherein $R^2$ represents methyl (preferred), ethyl, n-propyl, isopropyl, cyclopropyl, or cyclobutyl.

29) Another embodiment relates to compounds according to embodiment 1), wherein A represents pyridin-3-yl, wherein said pyridin-3-yl is mono-substituted in meta-position with respect to the point of attachment of said pyridin-3-yl to the rest of the molecule, wherein the substituent is 5-(hydroxy-methyl)-1,2,4-oxadiazol-3-yl, 5-(1-hydroxy-1-methyl-ethyl)-1,2,4-oxadiazol-3-yl, 5-(2-hydroxy-2-methyl-propyl)-1,2,4-oxadiazol-3-yl, or 5-(2-hydroxy-1,1-dimethyl-ethyl)-1,2,4-oxadiazol-3-yl;

B represents 4-propyl-phenyl, 4-isopropyl-phenyl, 4-isobutyl-phenyl, 4-tert-butyl-phenyl, 3-fluoro-4-isopropyl-phenyl, 3,5-difluoro-4-isopropyl-phenyl, 4-cyclopropyl-phenyl, 4-trifluoromethyl-phenyl, 4-trifluoromethoxy-phenyl, 4-(2,2,2-trifluoro-ethyl)-phenyl, 4-cyclobutyl-phenyl, or 4-(1-trifluoromethyl-cyclopropyl)-phenyl;

$R^1$ represents methyl; and $R^2$ represents methyl.

30) Another embodiment relates to compounds according to embodiment 1), wherein A represents pyridin-3-yl, wherein said pyridin-3-yl is mono-substituted in meta-position with respect to the point of attachment of said pyridin-3-yl to the rest of the molecule, wherein the substituent is 1,2,4-oxadiazol-3-yl, wherein said oxadiazolyl group is mono-substituted, wherein the substituent is piperidin-4-yl which is unsubstituted, or mono- or di-substituted, wherein one substituent is attached to the nitrogen atom of said piperidine ring, wherein the substituent is acetyl, ethyl-carbonyl, n-propyl-carbonyl, isopropyl-carbonyl, tert-butyl-carbonyl, hydroxymethyl-carbonyl, 2,2,2-trifluoro-ethyl-carbonyl, methoxy-methyl-carbonyl, 2-methoxy-ethyl-carbonyl, methoxy-carbonyl, ethoxy-carbonyl, 2-methoxy-ethoxy-carbonyl, cyclopropyl-carbonyl, cyclopentyl-carbonyl, oxetan-3-yl-carbonyl, oxetan-3-yl-methyl-carbonyl, tetrahydropyran-4-yl-carbonyl, methoxy-methyl-carbonyl, or 1,4-dioxan-2-yl-carbonyl;

and/or one substituent is attached to a carbon atom of the piperidine ring, wherein said substituent is $C_{1-3}$-alkyl (especially methyl), halogen (especially fluorine), hydroxy, or $C_{1-3}$-alkoxy (especially methoxy).

B represents 4-propyl-phenyl, 4-isopropyl-phenyl, 4-isobutyl-phenyl, 4-tert-butyl-phenyl, 3-fluoro-4-isopropyl-phenyl, 3,5-difluoro-4-isopropyl-phenyl, 4-cyclopropyl-phenyl, 4-trifluoromethyl-phenyl, 4-trifluoromethoxy-phenyl, 4-(2,2,2-trifluoro-ethyl)-phenyl, 4-cyclobutyl-phenyl, or 4-(1-trifluoromethyl-cyclopropyl)-phenyl;

$R^1$ represents methyl; and $R^2$ represents methyl.

31) Another embodiment relates to compounds according to embodiment 1), wherein A represents pyridin-3-yl, wherein said pyridin-3-yl is mono-substituted in meta-position with respect to the point of attachment of said pyridin-3-yl to the rest of the molecule, wherein the substituent is 3-hydroxy-3-(pyrimidin-2-yl)-but-1-yn-1-yl, 3-hydroxy-3-(6-methyl-pyrimidin-4-yl)-but-1-yn-1-yl, 3-hydroxy-3-(2-methoxy-pyrimidin-4-yl)-but-1-yn-1-yl, 3-hydroxy-3-(2-methoxy-6-methyl-pyrimidin-4-yl)-but-1-yn-1-yl, 3-hydroxy-3-(6-methoxy-pyrimidin-4-yl)-but-1-yn-1-yl, 3-hydroxy-3-(2,6-dimethoxy-pyrimidin-4-yl)-but-1-yn-1-yl, 3-hydroxy-3-(2-methyl-pyrimidin-4-yl)-but-1-yn-1-yl, 3-hydroxy-3-(6-methoxy-2-methyl-pyrimidin-4-yl)-but-1-yn-1-yl, 3-hydroxy-3-(2,6-dimethyl-pyrimidin-4-yl)-but-1-yn-1-yl, 3-hydroxy-3-(6-cyclopropyl-pyrimidin-4-yl)-but-1-yn-1-yl, 3-hydroxy-3-(6-difluoromethyl-pyrimidin-4-yl)-but-1-yn-1-yl, 3-hydroxy-3-(2-trifluoromethyl-pyrimidin-4-yl)-but-1-yn-1-yl, or 3-hydroxy-3-(6-trifluoromethyl-pyrimidin-4-yl)-but-1-yn-1-yl]

B represents 4-propyl-phenyl, 4-isopropyl-phenyl, 4-isobutyl-phenyl, 4-tert-butyl-phenyl, 3-fluoro-4-isopropyl-phenyl, 3,5-difluoro-4-isopropyl-phenyl, 4-cyclopropyl-phenyl, 4-trifluoromethyl-phenyl, 4-trifluoromethoxy-phenyl, 4-(2,2,2-trifluoro-ethyl)-phenyl, 4-cyclobutyl-phenyl, or 4-(1-trifluoromethyl-cyclopropyl)-phenyl;

$R^1$ represents methyl; and $R^2$ represents methyl.

32) Another embodiment relates to compounds according to any one of embodiments 1) to 31), which are also compounds of Formula (II) (i.e. the asymmetric carbon atom to which A and B are attached has the absolute configuration depicted in Formula (II))

Formula (II)

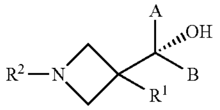

33) Another embodiment relates to a compound according to embodiment 1) selected from a group consisting of (3-Fluoro-1-methyl-azetidin-3-yl)-(5-pyrrolidin-1-yl-pyridin-3-yl)-(4-trifluoromethoxy-phenyl)-methanol;

3-[Hydroxy-(5-pyrrolidin-1-yl-pyridin-3-yl)-(4-trifluoromethoxy-phenyl)-methyl]-1-methyl-azetidine-3-carbonitrile;

(R)-(1-Ethyl-3-methyl-azetidin-3-yl)-(5-pyrrolidin-1-yl-pyridin-3-yl)-(4-trifluoromethoxy-phenyl)-methanol;

(R)-(3-Methyl-1-propyl-azetidin-3-yl)-(5-pyrrolidin-1-yl-pyridin-3-yl)-(4-trifluoromethoxy-phenyl)-methanol;

(R)-(1-Isopropyl-3-methyl-azetidin-3-yl)-(5-pyrrolidin-1-yl-pyridin-3-yl)-(4-trifluoromethoxy-phenyl)-methanol;

(R)-(1-Cyclopropylmethyl-3-methyl-azetidin-3-yl)-(5-pyrrolidin-1-yl-pyridin-3-yl)-(4-trifluoromethoxy-phenyl)-methanol;

(R)-(1-Cyclobutyl-3-methyl-azetidin-3-yl)-(5-pyrrolidin-1-yl-pyridin-3-yl)-(4-trifluoromethoxy-phenyl)-methanol;

(R)-(1-Isobutyl-3-methyl-azetidin-3-yl)-(5-pyrrolidin-1-yl-pyridin-3-yl)-(4-trifluoromethoxy-phenyl)-methanol;

(R)-(1-Cyclopropyl-3-methyl-azetidin-3-yl)-(5-pyrrolidin-1-yl-pyridin-3-yl)-(4-trifluoromethoxy-phenyl)-methanol;

(R)[1-(2-Fluoro-ethyl)-3-methyl-azetidin-3-yl]-(5-pyrrolidin-1-yl-pyridin-3-yl)-(4-trifluoromethoxy-phenyl)-methanol;

(R)[1-(2,2-Difluoro-ethyl)-3-methyl-azetidin-3-yl]-(5-pyrrolidin-1-yl-pyridin-3-yl)-(4-trifluoromethoxy-phenyl)-methanol;

(R)-(1-tert-Butyl-3-methyl-azetidin-3-yl)-(5-pyrrolidin-1-yl-pyridin-3-yl)-(4-trifluoromethoxy-phenyl)-methanol;

(1,3-Dimethyl-azetidin-3-yl)-(4-isopropyl-phenyl)[5-(3-methoxy-prop-1-ynyl)-pyridin-3-yl]-methanol 3-{5-[(R)-(1,3-Dimethyl-azetidin-3-yl)-hydroxy-(4-isopropyl-phenyl)-methyl]-pyridin-3-yl}-prop-1-yn-1-ol;

4-{5-[(R)-(1,3-Dimethyl-azetidin-3-yl)-hydroxy-(4-isopropyl-phenyl)-methyl]-pyridin-3-yl}-2-methyl-but-3-yn-2-ol;

(R)-4-{5-[(R)-(1,3-Dimethyl-azetidin-3-yl)-hydroxy-(4-isopropyl-phenyl)-methyl]-pyridin-3-yl}-but-3-yn-2-ol;

(S)-4-{5-[(R)-(1,3-Dimethyl-azetidin-3-yl)-hydroxy-(4-isopropyl-phenyl)-methyl]-pyridin-3-yl}-but-3-yn-2-ol;

1-{5-[(R)-(1,3-Dimethyl-azetidin-3-yl)-hydroxy-(4-isopropyl-phenyl)-methyl]-pyridin-3-ylethynyl}-cyclopentanol;

1-{5-[(R)-(1,3-Dimethyl-azetidin-3-yl)-hydroxy-(4-isopropyl-phenyl)-methyl]-pyridin-3-ylethynyl}-cyclopropanol;

3-{5-[(R)-(1,3-Dimethyl-azetidin-3-yl)-hydroxy-(4-isopropyl-phenyl)-methyl]-pyridin-3-ylethynyl}-3-hydroxy-azetidine-1-carboxylic acid tert-butyl ester;

1-{5-[(R)-(1,3-Dimethyl-azetidin-3-yl)-hydroxy-(4-isopropyl-phenyl)-methyl]-pyridin-3-ylethynyl}-cyclobutanol;

4-{5-[(R)-(1,3-Dimethyl-azetidin-3-yl)-hydroxy-(4-isopropyl-phenyl)-methyl]-pyridin-3-yl}-but-3-yn-1-ol;

(R)-(1,3-Dimethyl-azetidin-3-yl)-(4-isopropyl-phenyl)-[5-(1-methyl-1H-pyrazol-4-ylethynyl)-pyridin-3-yl]-methanol;

3-{5-[(R)-(1,3-Dimethyl-azetidin-3-yl)-hydroxy-(4-isopropyl-phenyl)-methyl]-pyridin-3-yl}-1-phenyl-prop-2-yn-1-ol;

4-{5-[(R)-(1,3-Dimethyl-azetidin-3-yl)-hydroxy-(4-isopropyl-phenyl)-methyl]-pyridin-3-yl}-2-phenyl-but-3-yn-2-ol;

1-{5-[(R)-(1,3-Dimethyl-azetidin-3-yl)-hydroxy-(4-isopropyl-phenyl)-methyl]-pyridin-3-yl}-4-methyl-pent-1-yn-3-ol;

4-{5-[(R)-(1,3-Dimethyl-azetidin-3-yl)-hydroxy-(4-isopropyl-phenyl)-methyl]-pyridin-3-ylethynyl}-tetrahydro-pyran-4-ol;

3-{5-[(R)-(1,3-Dimethyl-azetidin-3-yl)-hydroxy-(4-isopropyl-phenyl)-methyl]-pyridin-3-yl}-1-(tetrahydro-pyran-4-yl)-prop-2-yn-1-ol;

3-{5-[(R)-(1,3-Dimethyl-azetidin-3-yl)-hydroxy-(4-isopropyl-phenyl)-methyl]-pyridin-3-yl}-1-(1,3-dimethyl-1H-pyrazol-4-yl)-prop-2-yn-1-ol;

(R)-(1,3-Dimethyl-azetidin-3-yl)-(4-isopropyl-phenyl)-[5-(tetrahydro-pyran-4-ylethynyl)-pyridin-3-yl]-methanol;

3-{5-[(R)-(1,3-Dimethyl-azetidin-3-yl)-hydroxy-(4-isopropyl-phenyl)-methyl]-pyridin-3-yl}-1-(2-methyl-thiazol-4-yl)-prop-2-yn-1-ol;

4-{5-[(R)-(1,3-Dimethyl-azetidin-3-yl)-hydroxy-(4-isopropyl-phenyl)-methyl]-pyridin-3-yl}-2-(3-fluoro-phenyl)-but-3-yn-2-ol;

4-{5-[(R)-(1,3-Dimethyl-azetidin-3-yl)-hydroxy-(4-isopropyl-phenyl)-methyl]-pyridin-3-yl}-2-(4-methoxy-phenyl)-but-3-yn-2-ol;

4-{5-[(R)-(1,3-Dimethyl-azetidin-3-yl)-hydroxy-(4-isopropyl-phenyl)-methyl]-pyridin-3-yl}-2-(2-methoxy-phenyl)-but-3-yn-2-ol;

4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(2-methyl-thiazol-4-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(6-methoxy-pyridin-2-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-pyrimidin-2-yl-but-3-yn-2-ol;

4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-but-3-yn-2-ol;

3-{5-[(R)-(1,3-Dimethyl-azetidin-3-yl)-hydroxy-(4-isopropyl-phenyl)-methyl]-pyridin-3-yl}-1-(1,5-dimethyl-1H-pyrazol-3-yl)-prop-2-yn-1-ol;

8-{5-[(R)-(1,3-Dimethyl-azetidin-3-yl)-hydroxy-(4-isopropyl-phenyl)-methyl]-pyridin-3-ylethynyl}-5,6,7,8-tetrahydro-quinolin-8-ol;

7-{5-[(R)-(1,3-Dimethyl-azetidin-3-yl)-hydroxy-(4-isopropyl-phenyl)-methyl]-pyridin-3-ylethynyl}-6,7-dihydro-5H-[1]pyrindin-7-ol;

1-{5-[(R)-(1,3-Dimethyl-azetidin-3-yl)-hydroxy-(4-isopropyl-phenyl)-methyl]-pyridin-3-yl}-3-pyridin-2-yl-pent-1-yn-3-ol;

1-{5-[(R)-(1,3-Dimethyl-azetidin-3-yl)-hydroxy-(4-isopropyl-phenyl)-methyl]-pyridin-3-yl}-3-(6-methoxy-pyridin-2-yl)-pent-1-yn-3-ol;

1-(3-{5-[(R)-(1,3-Dimethyl-azetidin-3-yl)-hydroxy-(4-isopropyl-phenyl)-methyl]-pyridin-3-ylethynyl}-3-hydroxy-azetidin-1-yl)-2-methyl-propan-1-one;

(R)-(1,3-Dimethyl-azetidin-3-yl)-[5-(1H-indol-2-ylethynyl)-pyridin-3-yl]-(4-isopropyl-phenyl)-methanol;

(1,3-Dimethyl-azetidin-3-yl)-(4-isopropyl-phenyl)-[5-(3-methoxy-propyl)-pyridin-3-yl]-methanol;

3-{5-[(R)-(1,3-Dimethyl-azetidin-3-yl)-hydroxy-(4-isopropyl-phenyl)-methyl]-pyridin-3-yl}-propan-1-ol;

4-{5-[(R)-(1,3-Dimethyl-azetidin-3-yl)-hydroxy-(4-isopropyl-phenyl)-methyl]-pyridin-3-yl}-2-methyl-butan-2-ol;

(S)-4-{5-[(R)-(1,3-Dimethyl-azetidin-3-yl)-hydroxy-(4-isopropyl-phenyl)-methyl]-pyridin-3-yl}-butan-2-ol;

(R)-4-{5-[(R)-(1,3-Dimethyl-azetidin-3-yl)-hydroxy-(4-isopropyl-phenyl)-methyl]-pyridin-3-yl}-butan-2-ol;

1-(2-{5-[(R)-(1,3-Dimethyl-azetidin-3-yl)-hydroxy-(4-isopropyl-phenyl)-methyl]-pyridin-3-yl}-ethyl)-cyclopentanol;

1-(2-{5-[(R)-(1,3-Dimethyl-azetidin-3-yl)-hydroxy-(4-isopropyl-phenyl)-methyl]-pyridin-3-yl}-ethyl)-cyclopropanol;

3-(2-{5-[(R)-(1,3-Dimethyl-azetidin-3-yl)-hydroxy-(4-isopropyl-phenyl)-methyl]-pyridin-3-yl}-ethyl)-3-hydroxy-azetidine-1-carboxylic acid tert-butyl ester;

1-(2-{5-[(R)-(1,3-Dimethyl-azetidin-3-yl)-hydroxy-(4-isopropyl-phenyl)-methyl]-pyridin-3-yl}-ethyl)-cyclobutanol;

4-{5-[(R)-(1,3-Dimethyl-azetidin-3-yl)-hydroxy-(4-isopropyl-phenyl)-methyl]-pyridin-3-yl}-butan-1-ol;

(R)-(1,3-Dimethyl-azetidin-3-yl)-(4-isopropyl-phenyl)-{5-[2-(1-methyl-1H-pyrazol-4-yl)-ethyl]-pyridin-3-yl}methanol;

3-{5-[(R)-(1,3-Dimethyl-azetidin-3-yl)-hydroxy-(4-isopropyl-phenyl)-methyl]-pyridin-3-yl}-1-phenyl-propan-1-ol;

4-{5-[(R)-(1,3-Dimethyl-azetidin-3-yl)-hydroxy-(4-isopropyl-phenyl)-methyl]-pyridin-3-yl}-2-phenyl-butan-2-ol;

1-{5-[(R)-(1,3-Dimethyl-azetidin-3-yl)-hydroxy-(4-isopropyl-phenyl)-methyl]-pyridin-3-yl}-4-methyl-pentan-3-ol;

4-(2-{5-[(R)-(1,3-Dimethyl-azetidin-3-yl)-hydroxy-(4-isopropyl-phenyl)-methyl]-pyridin-3-yl}-ethyl)-tetrahydro-pyran-4-ol;

3-{5-[(R)-(1,3-Dimethyl-azetidin-3-yl)-hydroxy-(4-isopropyl-phenyl)-methyl]-pyridin-3-yl}-1-(tetrahydro-pyran-4-yl)-propan-1-ol;

3-{5-[(R)-(1,3-Dimethyl-azetidin-3-yl)-hydroxy-(4-isopropyl-phenyl)-methyl]-pyridin-3-yl}-1-(1,3-dimethyl-1H-pyrazol-4-yl)-propan-1-ol;

(R)-(1,3-Dimethyl-azetidin-3-yl)-(4-isopropyl-phenyl)-{5-[2-(tetrahydro-pyran-4-yl)-ethyl]-pyridin-3-yl}-methanol;

3-{5-[(R)-(1,3-Dimethyl-azetidin-3-yl)-hydroxy-(4-isopropyl-phenyl)-methyl]-pyridin-3-yl}-1-(2-methyl-thiazol-4-yl)-propan-1-ol;

4-{5-[(R)-(1,3-Dimethyl-azetidin-3-yl)-hydroxy-(4-isopropyl-phenyl)-methyl]-pyridin-3-yl}-2-(3-fluoro-phenyl)-butan-2-ol;

4-{5-[(R)-(1,3-Dimethyl-azetidin-3-yl)-hydroxy-(4-isopropyl-phenyl)-methyl]-pyridin-3-yl}-2-(4-methoxy-phenyl)-butan-2-ol;

4-{5-[(R)-(1,3-Dimethyl-azetidin-3-yl)-hydroxy-(4-isopropyl-phenyl)-methyl]-pyridin-3-yl}-2-(2-methoxy-phenyl)-butan-2-ol;

4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-butan-2-ol;

4-{5-[(R)-(1,3-Dimethyl-azetidin-3-yl)-hydroxy-(4-isopropyl-phenyl)-methyl]-pyridin-3-yl}-2-(2-methyl-thiazol-4-yl)-butan-2-ol;

4-{5-[(R)-(1,3-Dimethyl-azetidin-3-yl)-hydroxy-(4-isopropyl-phenyl)-methyl]-pyridin-3-yl}-2-(6-methoxy-pyridin-2-yl)-butan-2-ol;

4-{5-[(R)-(1,3-Dimethyl-azetidin-3-yl)-hydroxy-(4-isopropyl-phenyl)-methyl]-pyridin-3-yl}-2-pyrimidin-2-yl-butan-2-ol;

4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-butan-2-ol;

4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-butan-2-ol;

3-{5-[(R)-(1,3-Dimethyl-azetidin-3-yl)-hydroxy-(4-isopropyl-phenyl)-methyl]-pyridin-3-yl}-1-(1,5-dimethyl-1H-pyrazol-3-yl)-propan-1-ol;

8-(2-{5-[(R)-(1,3-Dimethyl-azetidin-3-yl)-hydroxy-(4-isopropyl-phenyl)-methyl]-pyridin-3-yl}-ethyl)-5,6,7,8-tetrahydro-quinolin-8-ol;

7-(2-{5-[(R)-(1,3-Dimethyl-azetidin-3-yl)-hydroxy-(4-isopropyl-phenyl)-methyl]-pyridin-3-yl}-ethyl)-6,7-dihydro-5H-[1]pyrindin-7-ol;

1-{5-[(R)-(1,3-Dimethyl-azetidin-3-yl)-hydroxy-(4-isopropyl-phenyl)-methyl]-pyridin-3-yl}-3-pyridin-2-yl-pentan-3-ol;

1-{5-[(R)-(1,3-Dimethyl-azetidin-3-yl)-hydroxy-(4-isopropyl-phenyl)-methyl]-pyridin-3-yl}-3-(6-methoxy-pyridin-2-yl)-pentan-3-ol;

(R)-(1,3-Dimethyl-azetidin-3-yl)-{5-[2-(1H-indol-2-yl)-ethyl]-pyridin-3-yl}-(4-isopropyl-phenyl)-methanol;

(R)-(4-Cyclopropyl-phenyl)-(1,3-dimethyl-azetidin-3-yl)-{5-[3-(tetrahydro-pyran-4-yl)-[1,2,4]oxadiazol-5-yl]-pyridin-3-yl}-methanol;

(R)-(4-Cyclopropyl-phenyl)-(1,3-dimethyl-azetidin-3-yl)-{5-[3-(2-methoxy-1,1-dimethyl-ethyl)-[1,2,4]oxadiazol-5-yl]-pyridin-3-yl}-methanol;

(R)-[5-(3-Cyclobutoxymethyl-[1,2,4]oxadiazol-5-yl)-pyridin-3-yl]-(4-cyclopropyl-phenyl)-(1,3-dimethyl-azetidin-3-yl)-methanol;

(R)-(1,3-Dimethyl-azetidin-3-yl)-(4-propyl-phenyl)-{5-[3-(tetrahydro-pyran-4-yloxymethyl)-[1,2,4]oxadiazol-5-yl]-pyridin-3-yl}-methanol;

(R)-(1,3-Dimethyl-azetidin-3-yl)-(4-propyl-phenyl)-{5-[3-(tetrahydro-pyran-4-yl)-[1,2,4]oxadiazol-5-yl]-pyridin-3-yl}-methanol;

(R)-[5-(3-Cyclobutoxymethyl-[1,2,4]oxadiazol-5-yl)-pyridin-3-yl]-(1,3-dimethyl-azetidin-3-yl)-(4-propyl-phenyl)-methanol;

(R)-(1,3-Dimethyl-azetidin-3-yl)-(4-isopropyl-phenyl)-{5-[3-(tetrahydro-pyran-4-yl)-[1,2,4]oxadiazol-5-yl]-pyridin-3-yl}-methanol;

(R)-(1,3-Dimethyl-azetidin-3-yl)-(4-isopropyl-phenyl)-[5-(3-morpholin-4-ylmethyl-[1,2,4]oxadiazol-5-yl)-pyridin-3-yl]-methanol;

(R)-(1,3-Dimethyl-azetidin-3-yl)-{5-[3-(2,6-dimethyl-morpholin-4-ylmethyl)-[1,2,4]oxadiazol-5-yl]-pyridin-3-yl}-(4-isopropyl-phenyl)-methanol;

(R)-(1,3-Dimethyl-azetidin-3-yl)-(4-isopropyl-phenyl)-{5-[3-(4-methyl-tetrahydro-pyran-4-yl)-[1,2,4]oxadiazol-5-yl]-pyridin-3-yl}-methanol;

(R)-(1,3-Dimethyl-azetidin-3-yl)-(4-isopropyl-phenyl)-{5-[(1S,2S,4R)-3-(7-oxa-bicyclo[2.2.1]hept-2-yl)-[1,2,4]oxadiazol-5-yl]-pyridin-3-yl}-methanol;

(R)-(1,3-Dimethyl-azetidin-3-yl)-(4-isopropyl-phenyl)-{5-[3-(tetrahydro-pyran-4-yloxymethyl)-[1,2,4]oxadiazol-5-yl]-pyridin-3-yl}-methanol;

(R)-(1,3-Dimethyl-azetidin-3-yl)-(4-isopropyl-phenyl)-[5-(3-morpholin-4-yl-[1,2,4]oxadiazol-5-yl)-pyridin-3-yl]-methanol;

(R)-(4-Cyclopropyl-phenyl)-(1,3-dimethyl-azetidin-3-yl)-{5-[3-(4-methoxy-tetrahydro-pyran-4-yl)-[1,2,4]oxadiazol-5-yl]-pyridin-3-yl}-methanol;

(R)-(4-Cyclopropyl-phenyl)-(1,3-dimethyl-azetidin-3-yl)-{5-[3-(3-hydroxymethyl-bicyclo[1.1.1]pent-1-yl)-[1,2,4]oxadiazol-5-yl]-pyridin-3-yl}-methanol;

(R)-(1,3-Dimethyl-azetidin-3-yl)-{5-[3-(3-hydroxymethyl-bicyclo[1.1.1]pent-1-yl)-[1,2,4]oxadiazol-5-yl]-pyridin-3-yl}-(4-isopropyl-phenyl)-methanol;
2-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-2-methyl-propan-1-ol;
2-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-propan-2-ol;
(R)-(1,3-Dimethyl-azetidin-3-yl)-(4-isopropyl-phenyl)-{5-[3-(1-methoxy-1-methyl-ethyl)-[1,2,4]oxadiazol-5-yl]-pyridin-3-yl}-methanol;
(R)-(1,3-Dimethyl-azetidin-3-yl)-(4-isopropyl-phenyl)-{5-[3-(1-methoxy-cyclobutyl)-[1,2,4]oxadiazol-5-yl]-pyridin-3-yl}-methanol;
1-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-2-methyl-propan-2-ol;
(R)-(1,3-Dimethyl-azetidin-3-yl)-(4-isopropyl-phenyl)-[5-(5-methanesulfonylmethyl-[1,2,4]oxadiazol-3-yl)-pyridin-3-yl]-methanol;
(R)-(1,3-Dimethyl-azetidin-3-yl)-(4-isopropyl-phenyl)-{5-[5-(2-methoxy-ethyl)-[1,2,4]oxadiazol-3-yl]-pyridin-3-yl}-methanol;
(R)-(1,3-Dimethyl-azetidin-3-yl)-(4-isopropyl-phenyl)-[5-(5-methoxymethyl-[1,2,4]oxadiazol-3-yl)-pyridin-3-yl]-methanol;
(R)-(1,3-Dimethyl-azetidin-3-yl)-(4-isopropyl-phenyl)-{5-[5-(tetrahydro-furan-3-yl)-[1,2,4]oxadiazol-3-yl]-pyridin-3-yl}-methanol;
(R)-(1,3-Dimethyl-azetidin-3-yl)-(4-isopropyl-phenyl)-{5-[5-(tetrahydro-pyran-4-yl)-[1,2,4]oxadiazol-3-yl]-pyridin-3-yl}-methanol;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclohexanol;
(R)-[5-(5-tert-Butoxymethyl-[1,2,4]oxadiazol-3-yl)-pyridin-3-yl]-(1,3-dimethyl-azetidin-3-yl)-(4-isopropyl-phenyl)-methanol;
(R)-(1,3-Dimethyl-azetidin-3-yl)-(4-isopropyl-phenyl)-{5-[5-(tetrahydro-pyran-4-ylmethyl)-[1,2,4]oxadiazol-3-yl]-pyridin-3-yl}-methanol;
4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclohexanol;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclohexanol;
(R)-(1,3-Dimethyl-azetidin-3-yl)-(4-isopropyl-phenyl)-{5-[5-(1-methoxy-cyclobutyl)-[1,2,4]oxadiazol-3-yl]-pyridin-3-yl}-methanol;
(R)-(1,3-Dimethyl-azetidin-3-yl)-(4-isopropyl-phenyl)-{5-[5-(6-oxa-spiro[2.5]oct-1-yl)-[1,2,4]oxadiazol-3-yl]-pyridin-3-yl}-methanol;
(R)-(1,3-Dimethyl-azetidin-3-yl)-(4-isopropyl-phenyl)-{5-[5-(tetrahydro-pyran-3-yl)-[1,2,4]oxadiazol-3-yl]-pyridin-3-yl}-methanol;
(R)-(1,3-Dimethyl-azetidin-3-yl)-(4-isopropyl-phenyl)-(5-{5-[1-(tetrahydro-furan-2-yl)methyl]-[1,2,4]oxadiazol-3-yl}-pyridin-3-yl)-methanol;
(R)-2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1,1-trifluoro-propan-2-ol;
(R)-(1,3-Dimethyl-azetidin-3-yl)-(4-isopropyl-phenyl)-{5-[5-(1-methoxy-1-methyl-ethyl)-[1,2,4]oxadiazol-3-yl]-pyridin-3-yl}-methanol;
(R)-{5-[5((R)-Cyclohexyl-hydroxy-methyl)-[1,2,4]oxadiazol-3-yl]-pyridin-3-yl}-(1,3-dimethyl-azetidin-3-yl)-(4-isopropyl-phenyl)-methanol;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclopropanol;
2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-propan-2-ol;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclopentanol;
3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclobutanol;
(R)-(1,3-Dimethyl-azetidin-3-yl)-{5-[5-(4-fluoro-tetrahydro-pyran-4-yl)-[1,2,4]oxadiazol-3-yl]-pyridin-3-yl}-(4-isopropyl-phenyl)-methanol;
(R)-(1,3-Dimethyl-azetidin-3-yl)-{5-[5((2R,4R,6S)-2,6-dimethyl-tetrahydro-pyran-4-yl)-[1,2,4]oxadiazol-3-yl]-pyridin-3-yl}-(4-isopropyl-phenyl)-methanol;
(R)-(1,3-Dimethyl-azetidin-3-yl)-(4-isopropyl-phenyl)-{5-[5-(tetrahydro-pyran-4-yloxymethyl)-[1,2,4]oxadiazol-3-yl]-pyridin-3-yl}-methanol;
(R)-(1,3-Dimethyl-azetidin-3-yl)-(4-isopropyl-phenyl)-(5-{5-[1-methyl-1-(tetrahydro-pyran-4-yl)-ethyl]-[1,2,4]oxadiazol-3-yl}-pyridin-3-yl)-methanol;
(R)-(1,3-Dimethyl-azetidin-3-yl)-(4-isopropyl-phenyl)-(5-{5-[2-(tetrahydro-pyran-4-yl)-ethyl]-[1,2,4]oxadiazol-3-yl}-pyridin-3-yl)-methanol;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclobutanol;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-2-methyl-propan-2-ol;
(R)-(1,3-Dimethyl-azetidin-3-yl)-(4-isopropyl-phenyl)-{5-[5-(7-oxa-bicyclo[2.2.1]hept-2-yl)-[1,2,4]oxadiazol-3-yl]-pyridin-3-yl}-methanol;
(R)-(1,3-Dimethyl-azetidin-3-yl)-(4-isopropyl-phenyl)-{5-[5-(4-methyl-tetrahydro-pyran-4-yloxymethyl)-[1,2,4]oxadiazol-3-yl]-pyridin-3-yl}-methanol;
(R)-(1,3-Dimethyl-azetidin-3-yl)-(4-isopropyl-phenyl)-[5-(5-oxetan-3-yl-[1,2,4]oxadiazol-3-yl)-pyridin-3-yl]-methanol;
(R)-(1,3-Dimethyl-azetidin-3-yl)-(4-isopropyl-phenyl)-{5-[5-(2-methoxy-1,1-dimethyl-ethyl)-[1,2,4]oxadiazol-3-yl]-pyridin-3-yl}-methanol;
2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-2-methyl-propan-1-ol;
(R)-(1,3-Dimethyl-azetidin-3-yl)-(4-isopropyl-phenyl)-{5-[5-(2-methoxy-2-methyl-propyl)-[1,2,4]oxadiazol-3-yl]-pyridin-3-yl}-methanol;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclobutanol;
(R)-(1,3-Dimethyl-azetidin-3-yl)-(4-isopropyl-phenyl)-{5-[5-(1-methoxymethyl-cyclopropylmethyl)-[1,2,4]oxadiazol-3-yl]-pyridin-3-yl}-methanol;
(R)-(1,3-Dimethyl-azetidin-3-yl)-(4-isopropyl-phenyl)-{5-[5-(2-pyrazol-1-yl-ethyl)-[1,2,4]oxadiazol-3-yl]-4-pyridin-3-yl}-methanol;
(R)—N-(2-(3-(5-((1,3-dimethylazetidin-3-yl)(hydroxy)(4-isopropylphenyl)methyl)pyridin-3-yl)-1,2,4-oxadiazol-5-yl)ethyl)acetamide-2,2,2-$d_3$;

(R)—N-(1-(3-(5-((1,3-dimethylazetidin-3-yl)(hydroxy)(4-isopropylphenyl)methyl)pyridin-3-yl)-1,2,4-oxadiazol-5-yl)-2-methylpropan-2-yl)acetamide-2,2,2-$d_3$;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2-hydroxy-ethanone;

(R)-1-(4-(3-(5-((1,3-dimethylazetidin-3-yl)(hydroxy)(4-isopropylphenyl)methyl)pyridin-3-yl)-1,2,4-oxadiazol-5-yl) piperidin-1-yl)ethan-1-one-2,2,2-d3;

N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-ethyl]-2-hydroxy-N-methyl-acetamide;

(R)—N-(2-(3-(5-((1,3-dimethylazetidin-3-yl)(hydroxy)(4-isopropylphenyl)methyl)pyridin-3-yl)-1,2,4-oxadiazol-5-yl)ethyl)-N-methylacetamide-$d_3$;

(1,3-Dimethyl-azetidin-3-yl)-(6-methoxy-pyridin-3-yl)-(4-trifluoromethoxy-phenyl)-methanol;

(1,3-Dimethyl-azetidin-3-yl)-(6-phenoxy-pyridin-3-yl)-(4-trifluoromethoxy-phenyl)-methanol;

(1,3-Dimethyl-azetidin-3-yl)-(6-ethoxy-pyridin-3-yl)-(4-trifluoromethoxy-phenyl)-methanol;

(1,3-Dimethyl-azetidin-3-yl)-(5-methyl-pyridin-3-yl)-(4-trifluoromethoxy-phenyl)-methanol;

(1,3-Dimethyl-azetidin-3-yl)-(4-propyl-phenyl)-(5-pyrrolidin-1-yl-pyridin-3-yl)-methanol;

(1,3-Dimethyl-azetidin-3-yl)-(4-methoxy-phenyl)-(5-pyrrolidin-1-yl-pyridin-3-yl)-methanol;

(1,3-Dimethyl-azetidin-3-yl)-(4-ethyl-phenyl)-(5-pyrrolidin-1-yl-pyridin-3-yl)-methanol;

(1,3-Dimethyl-azetidin-3-yl)-phenyl-(5-pyrrolidin-1-yl-pyridin-3-yl)-methanol;

(4-Cyclobutyl-phenyl)-(1,3-dimethyl-azetidin-3-yl)-(5-pyrrolidin-1-yl-pyridin-3-yl)-methanol;

(4-Cyclobutoxy-phenyl)-(1,3-dimethyl-azetidin-3-yl)-(5-pyrrolidin-1-yl-pyridin-3-yl)-methanol;

(1,3-Dimethyl-azetidin-3-yl)-(4-ethoxy-phenyl)-(5-pyrrolidin-1-yl-pyridin-3-yl)-methanol;

(4-tert-Butyl-phenyl)-(1,3-dimethyl-azetidin-3-yl)-(5-pyrrolidin-1-yl-pyridin-3-yl)-methanol;

(1,3-Dimethyl-azetidin-3-yl)-(4-isopropoxy-phenyl)-(5-pyrrolidin-1-yl-pyridin-3-yl)-methanol;

(1,3-Dimethyl-azetidin-3-yl)-(5-pyrrolidin-1-yl-pyridin-3-yl)-[4-(1-trifluoromethyl-cyclopropyl)-phenyl]-methanol;

(1,3-Dimethyl-azetidin-3-yl)-[4-(1-methyl-cyclopropyl)-phenyl]-(5-pyrrolidin-1-yl-pyridin-3-yl)-methanol;

(4-Cyclopropoxy-phenyl)-(1,3-dimethyl-azetidin-3-yl)-(5-pyrrolidin-1-yl-pyridin-3-yl)-methanol;

(S)-[2-(3,3-Difluoro-pyrrolidin-1-yl)-pyridin-4-yl]-(1,3-dimethyl-azetidin-3-yl)-(4-isopropyl-phenyl)-methanol;

(S)-[2-((3R,4S)-3,4-Difluoro-pyrrolidin-1-yl)-pyridin-4-yl]-(1,3-dimethyl-azetidin-3-yl)-(4-isopropyl-phenyl)-methanol;

(S)-(1,3-Dimethyl-azetidin-3-yl)-(2-isobutoxy-pyridin-4-yl)-(4-isopropyl-phenyl)-methanol;

4-{4-[(3)-(1,3-Dimethyl-azetidin-3-yl)-hydroxy-(4-isopropyl-phenyl)-methyl]-pyridin-2-yl}-2-methyl-butan-2-ol;

(R)-[6-(3,3-Difluoro-pyrrolidin-1-yl)-pyridazin-4-yl]-(1,3-dimethyl-azetidin-3-yl)-(4-isopropyl-phenyl)-methanol;

(S)-5-tert-Butyl-3-{5-[(R)-(1,3-dimethyl-azetidin-3-yl)-hydroxy-(4-isopropyl-phenyl)-methyl]-pyridin-3-yl}-oxazolidin-2-one;

(R)-1-{5-[(R)-(1,3-Dimethyl-azetidin-3-yl)-hydroxy-(4-isopropyl-phenyl)-methyl]-pyridin-3-yl}-pyrrolidin-3-ol;

(S)-1-{5-[(R)-(1,3-Dimethyl-azetidin-3-yl)-hydroxy-(4-isopropyl-phenyl)-methyl]-pyridin-3-yl}-pyrrolidin-3-ol;

(R)-(1,3-Dimethyl-azetidin-3-yl)-[5-((S)-3-hydroxymethyl-pyrrolidin-1-yl)-pyridin-3-yl]-(4-isopropyl-phenyl)-methanol;

(R)-(1,3-Dimethyl-azetidin-3-yl)-(4-isopropyl-phenyl)-(5-pyrrolidin-1-yl-pyridin-3-yl)-methanol;

(S)-1-{5-[(R)-(1,3-Dimethyl-azetidin-3-yl)-hydroxy-(4-isopropyl-phenyl)-methyl]-pyridin-3-yl}-3-methyl-pyrrolidin-3-ol;

3-Cyclopropyl-1-{5-[(R)-(1,3-dimethyl-azetidin-3-yl)-hydroxy-(4-isopropyl-phenyl)-methyl]-pyridin-3-yl}-pyrrolidin-3-ol;

2-((S)-1-{5-[(R)-(1,3-Dimethyl-azetidin-3-yl)-hydroxy-(4-isopropyl-phenyl)-methyl]-pyridin-3-yl}-pyrrolidin-3-yl)-propan-2-ol;

(R)-(1,3-Dimethyl-azetidin-3-yl)-(4-isopropyl-phenyl)-(5-morpholin-4-yl-pyridin-3-yl)-methanol;

(R)-(1,3-Dimethyl-azetidin-3-yl)-(4-isopropyl-phenyl)-(3,4,5,6-tetrahydro-2H-[1,3]-bipyridinyl-5'-yl)-methanol;

(R)-[5-(7-Aza-bicyclo[2.2.1]hept-7-yl)-pyridin-3-yl]-(1,3-dimethyl-azetidin-3-yl)-(4-isopropyl-phenyl)-methanol;

(R)-(1,3-Dimethyl-azetidin-3-yl)-(4-isopropyl-phenyl)-[5-((S)-2-methyl-pyrrolidin-1-yl)-pyridin-3-yl]-methanol;

1-{5-[(R)-(1,3-Dimethyl-azetidin-3-yl)-hydroxy-(4-isopropyl-phenyl)-methyl]-pyridin-3-yl}-3-trifluoromethyl-pyrrolidin-3-ol;

(R)-[5-(3,3-Difluoro-pyrrolidin-1-yl)-pyridin-3-yl]-(1,3-dimethyl-azetidin-3-yl)-(4-isopropyl-phenyl)-methanol;

5'-[(R)-(1,3-Dimethyl-azetidin-3-yl)-hydroxy-(4-isopropyl-phenyl)-methyl]-3,4,5,6-tetrahydro-2H-[1,3]-bipyridinyl-4-ol;

5'-[(R)-(1,3-Dimethyl-azetidin-3-yl)-hydroxy-(4-isopropyl-phenyl)-methyl]-3,4,5,6-tetrahydro-2H-[1,3]-bipyridinyl-3-ol:

(R)-{5-[(2-Benzyloxy-ethyl)-methyl-amino]-pyridin-3-yl}-(1,3-dimethyl-azetidin-3-yl)-(4-isopropyl-phenyl)-methanol;

(R)-(1,3-Dimethyl-azetidin-3-yl)-[4-(1-methyl-cyclopropyl)-phenyl]-(5-pyrrolidin-1-yl-pyridin-3-yl)-methanol;

(R)-[5-((3R,4S)-3,4-Difluoro-pyrrolidin-1-yl)-pyridin-3-yl]-(1,3-dimethyl-azetidin-3-yl)-[4-(1-trifluoromethyl-cyclopropyl)-phenyl]-methanol;

2-[(S)-1-(5-{(R)-(1,3-Dimethyl-azetidin-3-yl)-hydroxy-[4-(1-trifluoromethyl-cyclopropyl)-phenyl]-methyl}-pyridin-3-yl)-pyrrolidin-3-yl]-propan-2-ol;

(R)-(1,3-Dimethyl-azetidin-3-yl)-(5-pyrrolidin-1-yl-pyridin-3-yl)-[4-(1-trifluoromethyl-cyclopropyl)-phenyl]-methanol;

(R)-(4-tert-Butyl-phenyl)-(1,3-dimethyl-azetidin-3-yl)-(3,4,5,6-tetrahydro-2H-[1,3]-bipyridinyl-5'-yl)-methanol;

(R)-(1,3-Dimethyl-azetidin-3-yl)-(5-pyrrolidin-1-yl-pyridin-3-yl)-(4-trifluoromethoxy-phenyl)-methanol;

(R)-{5-[5-(1-Cyclopropanesulfonyl-piperidin-4-yl)-[1,2,4]oxadiazol-3-yl]-pyridin-3-yl}-(1,3-dimethyl-azetidin-3-yl)-(4-isopropyl-phenyl)-methanol;

2-({5-[(R)-(1,3-Dimethyl-azetidin-3-yl)-hydroxy-(4-isopropyl-phenyl)-methyl]-pyridin-3-yl}-methyl-amino)-ethanol;

(R)-1-((S)-1-{5-[(R)-(1,3-Dimethyl-azetidin-3-yl)-hydroxy-(4-isopropyl-phenyl)-methyl]-pyridin-3-yl}-pyrrolidin-3-yl)-ethanol;

3-{5-[(R)-(1,3-Dimethyl-azetidin-3-yl)-hydroxy-(4-isopropyl-phenyl)-methyl]-pyridin-3-yl}-oxazolidin-2-one;

3-{5-[(R)-(1,3-Dimethyl-azetidin-3-yl)-hydroxy-(4-isopropyl-phenyl)-methyl]-pyridin-3-yl}-5-phenyl-oxazolidin-2-one;

5-Benzyl-3-{5-[(R)-(1,3-dimethyl-azetidin-3-yl)-hydroxy-(4-isopropyl-phenyl)-methyl]-pyridin-3-yl}-oxazolidin-2-one;

3-{5-[(R)-(1,3-Dimethyl-azetidin-3-yl)-hydroxy-(4-isopropyl-phenyl)-methyl]-pyridin-3-yl}-5-isopropyl-oxazolidin-2-one;

6-{5-[(R)-(1,3-Dimethyl-azetidin-3-yl)-hydroxy-(4-isopropyl-phenyl)-methyl]-pyridin-3-yl}-4-oxa-6-aza-spiro[2.4]heptan-5-one;

3-{5-[(R)-(1,3-Dimethyl-azetidin-3-yl)-hydroxy-(4-isopropyl-phenyl)-methyl]-pyridin-3-yl}-1-oxa-3-aza-spiro[4.4]nonan-2-one;

3-{5-[(R)-(1,3-Dimethyl-azetidin-3-yl)-hydroxy-(4-isopropyl-phenyl)-methyl]-pyridin-3-yl}-5-(tetrahydro-pyran-4-yl)-oxazolidin-2-one;

3-{5-[(R)-(1,3-Dimethyl-azetidin-3-yl)-hydroxy-(4-isopropyl-phenyl)-methyl]-pyridin-3-yl}-5,5-dimethyl-oxazolidin-2-one;

3-{5-[(R)-(1,3-Dimethyl-azetidin-3-yl)-hydroxy-(4-isopropyl-phenyl)-methyl]-pyridin-3-yl}-8,8-difluoro-1-oxa-3-aza-spiro[4.5]decan-2-one;

9-{5-[(R)-(1,3-Dimethyl-azetidin-3-yl)-hydroxy-(4-isopropyl-phenyl)-methyl]-pyridin-3-yl}-7-oxa-9-aza-dispiro[3.1.4.1]undecan-8-one;

2-Cyclopropyl-7-{5-[(R)-(1,3-dimethyl-azetidin-3-yl)-hydroxy-(4-isopropyl-phenyl)-methyl]-pyridin-3-yl}-5-oxa-7-aza-spiro[3.4]octan-6-one;

7-{5-[(R)-(1,3-Dimethyl-azetidin-3-yl)-hydroxy-(4-isopropyl-phenyl)-methyl]-pyridin-3-yl}-2,2-dimethyl-5-oxa-7-aza-spiro[3.4]octan-6-one;

1-{5-[(R)-(1,3-Dimethyl-azetidin-3-yl)-hydroxy-(4-isopropyl-phenyl)-methyl]-pyridin-3-yl}-4-phenyl-pyrrolidin-2-one;

1-{5-[(R)-(1,3-Dimethyl-azetidin-3-yl)-hydroxy-(4-isopropyl-phenyl)-methyl]-pyridin-3-yl}-pyrrolidin-2-one;

1-{5-[(R)-(1,3-Dimethyl-azetidin-3-yl)-hydroxy-(4-isopropyl-phenyl)-methyl]-pyridin-3-yl}-4-isopropyl-pyrrolidin-2-one;

1-{5-[(R)-(1,3-Dimethyl-azetidin-3-yl)-hydroxy-(4-isopropyl-phenyl)-methyl]-pyridin-3-yl}-3-isopropyl-pyrrolidin-2-one;

1-{5-[(R)-(1,3-Dimethyl-azetidin-3-yl)-hydroxy-(4-isopropyl-phenyl)-methyl]-pyridin-3-yl}-4,4-dimethyl-pyrrolidin-2-one;

5-(5-((R)-(1,3-Dimethyl-azetidin-3-yl)(hydroxy)(4-isopropyl-phenyl)methyl)pyridin-3-yl)hexahydro-4H-furo[2,3-c]pyrrol-4-one;

2-{5-[(R)-(1,3-Dimethyl-azetidin-3-yl)-hydroxy-(4-isopropyl-phenyl)-methyl]-pyridin-3-yl}-2-aza-spiro[4.4]nonan-3-one;

6-{5-[(R)-(1,3-Dimethyl-azetidin-3-yl)-hydroxy-(4-isopropyl-phenyl)-methyl]-pyridin-3-yl}-6-aza-spiro[3.4]octan-5-one;

2-{5-[(R)-(1,3-Dimethyl-azetidin-3-yl)-hydroxy-(4-isopropyl-phenyl)-methyl]-pyridin-3-yl}-8-oxa-2-aza-spiro[4.5]decan-3-one;

1-{5-[(R)-(1,3-Dimethyl-azetidin-3-yl)-hydroxy-(4-isopropyl-phenyl)-methyl]-pyridin-3-yl}-3-(tetrahydro-pyran-4-yl)-pyrrolidin-2-one;

2-{5-[(R)-(1,3-Dimethyl-azetidin-3-yl)-hydroxy-(4-isopropyl-phenyl)-methyl]-pyridin-3-yl}-2-aza-spiro[4.5]decan-1-one;

2-{5-[(R)-(1,3-Dimethyl-azetidin-3-yl)-hydroxy-(4-isopropyl-phenyl)-methyl]-pyridin-3-yl}-8-oxa-2-aza-spiro[4.5]decan-1-one;

(S)-1-{5-[(R)-(1,3-Dimethyl-azetidin-3-yl)-hydroxy-(4-isopropyl-phenyl)-methyl]-pyridin-3-yl}-4-isobutyl-pyrrolidin-2-one;

4-Cyclopropyl-1-{5-[(R)-(1,3-dimethyl-azetidin-3-yl)-hydroxy-(4-isopropyl-phenyl)-methyl]-pyridin-3-yl}-pyrrolidin-2-one;

1-{5-[(R)-(1,3-Dimethyl-azetidin-3-yl)-hydroxy-(4-isopropyl-phenyl)-methyl]-pyridin-3-yl}-4-trifluoromethyl-pyrrolidin-2-one;

1-{5-[(R)-(1,3-Dimethyl-azetidin-3-yl)-hydroxy-(4-isopropyl-phenyl)-methyl]-pyridin-3-yl}-3-(2-methoxy-ethyl)-pyrrolidin-2-one;

1-{5-[(R)-(1,3-Dimethyl-azetidin-3-yl)-hydroxy-(4-isopropyl-phenyl)-methyl]-pyridin-3-yl}-4-(2-methoxy-ethyl)-pyrrolidin-2-one;

1-{5-[(R)-(1,3-Dimethyl-azetidin-3-yl)-hydroxy-(4-isopropyl-phenyl)-methyl]-pyridazin-3-yl}-pyrrolidin-2-one;

(1,3-Dimethyl-azetidin-3-yl)-(4-isopropyl-phenyl)-[5-((R)-3-isopropyl-pyrrolidin-1-yl)-pyridin-3-yl]-methanol;

(R)-(1,3-Dimethyl-azetidin-3-yl)-[5-((2R,6S)-2,6-dimethyl-morpholin-4-yl)-pyridin-3-yl]-(4-isopropyl-phenyl)-methanol;

(R)-(1,3-Dimethyl-azetidin-3-yl)-(4-isopropyl-phenyl)-[5-(6-oxa-3-aza-bicyclo[3.1.1]hept-3-yl)-pyridin-3-yl]-methanol;

(R)-[5-((3R,4S)-3,4-Difluoro-pyrrolidin-1-yl)-pyridin-3-yl]-(1,3-dimethyl-azetidin-3-yl)-(4-isopropyl-phenyl)-methanol;

(R)-[5-((3S,4S)-3,4-Difluoro-pyrrolidin-1-yl)-pyridin-3-yl]-(1,3-dimethyl-azetidin-3-yl)-(4-isopropyl-phenyl)-methanol;

(R)-(1,3-Dimethyl-azetidin-3-yl)-[5-((2S,6S)-2,6-dimethyl-morpholin-4-yl)-pyridin-3-yl]-(4-isopropyl-phenyl)-methanol;

(R)-(1,3-Dimethyl-azetidin-3-yl)-[5-(2R,6R)-2,6-dimethyl-morpholin-4-yl)-pyridin-3-yl]-(4-isopropyl-phenyl)-methanol;

(R)-(1,3-Dimethyl-azetidin-3-yl)-(4-isopropyl-phenyl)-{5-[3-(3-methyl-[1,2,4]oxadiazol-5-yl)-pyrrolidin-1-yl]-pyridin-3-yl}-methanol;

(R)-(1,3-Dimethyl-azetidin-3-yl)-(4-isopropyl-phenyl)-{5-[3-(4-methyl-thiazol-2-yl)-pyrrolidin-1-yl]-pyridin-3-yl}-methanol;

(R)-(1,3-Dimethyl-azetidin-3-yl)-(4-isopropyl-phenyl)-[5-(3-phenyl-pyrrolidin-1-yl)-pyridin-3-yl]-methanol;

(R)-(1,3-Dimethyl-azetidin-3-yl)-[5-(3,3-dimethyl-pyrrolidin-1-yl)-pyridin-3-yl]-(4-isopropyl-phenyl)-methanol;

(R)-(1,3-Dimethyl-azetidin-3-yl)-(4-isopropyl-phenyl)-[(1S,4S)-5-(2-oxa-5-aza-bicyclo[2.2.1]hept-5-yl)-pyridin-3-yl]-methanol;

(R)-(1,3-Dimethyl-azetidin-3-yl)-(4-isopropyl-phenyl)-[5-(2,2,6,6-tetrafluoro-morpholin-4-yl)-pyridin-3-yl]-methanol;

(R)-(1,3-Dimethyl-azetidin-3-yl)-(4-isopropyl-phenyl)-[5-(R)-2-methoxymethyl-morpholin-4-yl)-pyridin-3-yl]-methanol;

(R)-(1,3-Dimethyl-azetidin-3-yl)-(4-isopropyl-phenyl)-[5-(3)-2-methoxymethyl-morpholin-4-yl)-pyridin-3-yl]-methanol;

(R)-(1,3-Dimethyl-azetidin-3-yl)-(4-isopropyl-phenyl)-[5-(3-trifluoromethyl-pyrrolidin-1-yl)-pyridin-3-yl]-methanol;

(R)-(1,3-Dimethyl-azetidin-3-yl)-(4-isopropyl-phenyl)-[(1R,4R)-5-(2-oxa-5-aza-bicyclo[2.2.1]hept-5-yl)-pyridin-3-yl]-methanol;

(R)-(1,3-Dimethyl-azetidin-3-yl)-(4-isopropyl-phenyl)-[(1S,5R)-5-(8-oxa-3-aza-bicyclo[3.2.1]oct-3-yl)-pyridin-3-yl]-methanol;
(R)-(1,3-Dimethyl-azetidin-3-yl)-[(1S,4S)-5-(2-oxa-5-aza-bicyclo[2.2.1]hept-5-yl)-pyridin-3-yl]-[4-(1-trifluoromethyl-cyclopropyl)-phenyl]-methanol;
(R)-(1,3-Dimethyl-azetidin-3-yl)-(4-ethyl-phenyl)-(5-pyrrolidin-1-yl-pyridin-3-yl)-methanol;
(R)-(1,3-Dimethyl-azetidin-3-yl)-(4-ethyl-phenyl)-[5-(6-oxa-3-aza-bicyclo[3.1.1]hept-3-yl)-pyridin-3-yl]-methanol;
(R)-(1,3-Dimethyl-azetidin-3-yl)-(4-ethyl-phenyl)-[(1S,4S)-5-(2-oxa-5-aza-bicyclo[2.2.1]hept-5-yl)-pyridin-3-yl]-methanol;
(R)-(5-Benzyloxy-pyridin-3-yl)-(1,3-dimethyl-azetidin-3-yl)-(4-isopropyl-phenyl)-methanol;
(1,3-Dimethyl-azetidin-3-yl)-(4-isopropyl-phenyl)-[5-(2-pyridin-2-yl-ethoxy)-pyridin-3-yl]-methanol;
(1,3-Dimethyl-azetidin-3-yl)-(4-isopropyl-phenyl)-[5-(2-methoxy-ethoxy)-pyridin-3-yl]-methanol;
(1,3-Dimethyl-azetidin-3-yl)-(4-isopropyl-phenyl)-[5-(oxetan-3-ylmethoxy)-pyridin-3-yl]-methanol;
3-{5-[(R)-(1,3-Dimethyl-azetidin-3-yl)-hydroxy-(4-isopropyl-phenyl)-methyl]-pyridin-3-yloxy}-propan-1-ol;
(R)-(1,3-Dimethyl-azetidin-3-yl)-(5-isopropoxy-pyridin-3-yl)-(4-isopropyl-phenyl)-methanol;
(R)-(5-Cyclohexyloxy-pyridin-3-yl)-(1,3-dimethyl-azetidin-3-yl)-(4-isopropyl-phenyl)-methanol;
1-{5-[(R)-(1,3-Dimethyl-azetidin-3-yl)-hydroxy-(4-isopropyl-phenyl)-methyl]-pyridin-3-yloxy}-2-methyl-propan-2-ol;
(R)-(1,3-Dimethyl-azetidin-3-yl)-(4-isopropyl-phenyl)-[5-(3-methoxy-cyclopentyloxy)-pyridin-3-yl]-methanol;
(R)-[5-(3-Cyclopropyl-[1,2,4]oxadiazol-5-ylmethoxy)-pyridin-3-yl]-(1,3-dimethyl-azetidin-3-yl)-(4-isopropyl-phenyl)-methanol;
(R)-(1,3-Dimethyl-azetidin-3-yl)-{5-[2-(3,5-dimethyl-[1,2,4]triazol-1-yl)-ethoxy]-pyridin-3-yl}-(4-isopropyl-phenyl)-methanol;
4-{5-[(R)-(1,3-Dimethyl-azetidin-3-yl)-hydroxy-(4-isopropyl-phenyl)-methyl]-pyridin-3-yloxy}-2-methyl-butan-2-ol;
(R)-(1,3-Dimethyl-azetidin-3-yl)-(4-isopropyl-phenyl)-(5-methoxy-pyridin-3-yl)-methanol;
(R)-[5-(2-Benzyloxy-ethoxy)-pyridin-3-yl]-(1,3-dimethyl-azetidin-3-yl)-(4-isopropyl-phenyl)-methanol;
(R)-(1,3-Dimethyl-azetidin-3-yl)-(4-isopropyl-phenyl)-[5-(tetrahydro-pyran-4-yloxy)-pyridin-3-yl]-methanol; 2-{5-[(R)-(1,3-Dimethyl-azetidin-3-yl)-hydroxy-(4-isopropyl-phenyl)-methyl]-pyridin-3-yloxy}-ethanol;
4-{5-[(R)-(1,3-Dimethyl-azetidin-3-yl)-hydroxy-(4-isopropyl-phenyl)-methyl]-pyridin-3-yloxy}-cyclohexanol;
4-{5-[(R)-(1,3-Dimethyl-azetidin-3-yl)-hydroxy-(4-isopropyl-phenyl)-methyl]-pyridin-3-yloxy}-1-methyl-cyclohexanol;
(1,3-Dimethyl-azetidin-3-yl)-(2-phenoxy-pyrimidin-5-yl)-(4-trifluoromethoxy-phenyl)-methanol;
(6-Benzyloxy-pyridin-3-yl)-(1,3-dimethyl-azetidin-3-yl)-(4-trifluoromethoxy-phenyl)-methanol;
(1,3-Dimethyl-azetidin-3-yl)-(5-pyrazol-1-yl-pyridin-3-yl)-(4-trifluoromethoxy-phenyl)-methanol;
(1,3-Dimethyl-azetidin-3-yl)-(6-fluoro-5-pyrrolidin-1-yl-pyridin-3-yl)-(4-trifluoromethoxy-phenyl)-methanol;
5-[(1,3-Dimethyl-azetidin-3-yl)-hydroxy-(4-trifluoromethoxy-phenyl)-methyl]-3-pyrrolidin-1-yl-pyridine-2-carbonitrile;
(1,3-Dimethyl-azetidin-3-yl)-[6-(tetrahydro-pyran-4-yloxy)-pyridin-3-yl]-(4-trifluoromethoxy-phenyl)-methanol;
(1,3-Dimethyl-azetidin-3-yl)-[6-(oxetan-3-ylmethoxy)-pyridin-3-yl]-(4-trifluoromethoxy-phenyl)-methanol;
(1,3-Dimethyl-azetidin-3-yl)-(4-isopropyl-phenyl)-[5-(4-methyl-thiazol-2-yl)-pyridin-3-yl]-methanol;
(1,3-Dimethyl-azetidin-3-yl)-(4-isopropyl-phenyl)-[5-(5-methyl-thiazol-2-yl)-pyridin-3-yl]-methanol;
(1,3-Dimethyl-azetidin-3-yl)-(4-isopropyl-phenyl)-(2-methoxy-pyrimidin-5-yl)-methanol;
(S)-(1,3-Dimethyl-azetidin-3-yl)-(4-isopropyl-phenyl)-(2-pyrrolidin-1-yl-pyridin-4-yl)-methanol;
(1,3-Dimethyl-azetidin-3-yl)-[2-((R)-2-hydroxymethyl-pyrrolidin-1-yl)-pyridin-4-yl]-(4-isopropyl-phenyl)-methanol;
(1,3-Dimethyl-azetidin-3-yl)-(4-isopropyl-phenyl)-(3,4,5,6-tetrahydro-2H-[1,2']bipyridinyl-4'-yl)-methanol;
(1,3-Dimethyl-azetidin-3-yl)-(4-isopropyl-phenyl)-(2-morpholin-4-yl-pyridin-4-yl)-methanol;
(S)-(1,3-Dimethyl-azetidin-3-yl)-(2-ethyl-pyridin-4-yl)-(4-isopropyl-phenyl)-methanol;
(S)-(1,3-Dimethyl-azetidin-3-yl)-(4-isopropyl-phenyl)-[2-(tetrahydro-pyran-4-ylmethoxy)-pyridin-4-yl]-methanol;
(S)-(1,3-Dimethyl-azetidin-3-yl)-(4-isopropyl-phenyl)-[2-(2-methoxy-ethoxy)-pyridin-4-yl]-methanol;
(S)-(2-Cyclopentyl-pyridin-4-yl)-(1,3-dimethyl-azetidin-3-yl)-(4-isopropyl-phenyl)-methanol;
(R)-(1,3-Dimethyl-azetidin-3-yl)-(5-pyrrolidin-1-yl-pyridin-3-yl)-(4-trifluoromethyl-phenyl)-methanol;
(R)-(1,3-Dimethyl-azetidin-3-yl)-[5-((R)-3-hydroxymethyl-3-methyl-pyrrolidin-1-yl)-pyridin-3-yl]-(4-isopropyl-phenyl)-methanol;
(R)-(1,3-Dimethyl-azetidin-3-yl)-[5-((3)-3-fluoro-pyrrolidin-1-yl)-pyridin-3-yl]-(4-isopropyl-phenyl)-methanol;
(R)-(1,3-Dimethyl-azetidin-3-yl)-(4-isopropyl-phenyl)-{5-[4-(tetrahydro-pyran-4-yl)-[1,2,3]triazol-1-yl]-pyridin-3-yl}-methanol;
(1,3-Dimethyl-azetidin-3-yl)-(4-isopropyl-phenyl)-(5-methyl-pyridin-3-yl)-methanol;
(1,3-Dimethyl-azetidin-3-yl)-(5-isopropenyl-pyridin-3-yl)-(4-isopropyl-phenyl)-methanol;
(5-Cyclopropyl-pyridin-3-yl)-(1,3-dimethyl-azetidin-3-yl)-(4-isopropyl-phenyl)-methanol;
(5-Cyclopent-1-enyl-pyridin-3-yl)-(1,3-dimethyl-azetidin-3-yl)-(4-isopropyl-phenyl)-methanol;
3-{5-[(1,3-Dimethyl-azetidin-3-yl)-hydroxy-(4-isopropyl-phenyl)-methyl]-pyridin-3-yl}-cyclopent-2-enol;
(1,3-Dimethyl-azetidin-3-yl)-(4-isopropyl-phenyl)-(5-isopropyl-pyridin-3-yl)-methanol;
(5-Cyclopentyl-pyridin-3-yl)-(1,3-dimethyl-azetidin-3-yl)-(4-isopropyl-phenyl)-methanol;
3-{5-[(1,3-Dimethyl-azetidin-3-yl)-hydroxy-(4-isopropyl-phenyl)-methyl]-pyridin-3-yl}-cyclopentanol;
(R)-(1,3-Dimethyl-azetidin-3-yl)-(4-isopropyl-phenyl)-pyridin-3-yl-methanol;
3-{5-[(R)-(1,3-Dimethyl-azetidin-3-yl)-hydroxy-(4-isopropyl-phenyl)-methyl]-pyridin-3-yl}-cyclopent-2-enone;
3-{5-[(R)-(1,3-Dimethyl-azetidin-3-yl)-hydroxy-(4-isopropyl-phenyl)-methyl]-pyridin-3-yl}-1-methyl-cyclopent-2-enol;
(3S)-3-(5-((R)-(1,3-dimethylazetidin-3-yl)(hydroxy)(4-isopropylphenyl)methyl)pyridin-3-yl)-1-methylcyclopentan-1-ol;
(3R)-3-(5-((R)-(1,3-dimethylazetidin-3-yl)(hydroxy)(4-isopropylphenyl)methyl)pyridin-3-yl)-1-methylcyclopentan-1-ol;

3-{5-[(R)-(1,3-Dimethyl-azetidin-3-yl)-hydroxy-(4-isopropyl-phenyl)-methyl]-pyridin-3-yl}-1-ethyl-cyclopentanol;
3-{5-[(R)-(1,3-Dimethyl-azetidin-3-yl)-hydroxy-(4-isopropyl-phenyl)-methyl]-pyridin-3-yl}-1-isopropyl-cyclopentanol;
(R)-(1,3-Dimethyl-azetidin-3-yl)-(4-isopropyl-phenyl)-[5-(4-methyl-oxazol-2-yl)-pyridin-3-yl]-methanol;
(R)-(1,3-Dimethyl-azetidin-3-yl)-(5-ethyl-pyridin-3-yl)-(4-isopropyl-phenyl)-methanol;
(R)-(1,3-Dimethyl-azetidin-3-yl)-(4-isopropyl-phenyl)-(5-methyl-pyridin-3-yl)-methanol;
(R)-[5-(4,5-Di hydro-furan-3-yl)-pyridin-3-yl]-(1,3-dimethyl-azetidin-3-yl)-(4-isopropyl-phenyl)-methanol;
(R)-(1,3-Dimethyl-azetidin-3-yl)-(4-isopropyl-phenyl)-[5-(tetrahydro-furan-3-yl)-pyridin-3-yl]-methanol;
3-{5-[(R)-(1,3-Dimethyl-azetidin-3-yl)-hydroxy-(4-isopropyl-phenyl)-methyl]-pyridin-3-yl}-but-3-en-1-ol;
N-Cyclopentyl-5-[(R)-(1,3-dimethyl-azetidin-3-yl)-hydroxy-(4-isopropyl-phenyl)-methyl]-nicotinamide;
{5-[(R)-(1,3-Dimethyl-azetidin-3-yl)-hydroxy-(4-isopropyl-phenyl)-methyl]-pyridin-3-yl}-pyrrolidin-1-yl-methanone;
5-[(R)-(1,3-Dimethyl-azetidin-3-yl)-hydroxy-(4-isopropyl-phenyl)-methyl]-N-(tetrahydro-pyran-4-yl)-nicotinamide;
(1,3-Dimethyl-azetidin-3-yl)-[4-(3-methoxy-propyl)-phenyl]-(5-pyrrolidin-1-yl-pyridin-3-yl)-methanol;
(R)-(4-Cyclopropyl-phenyl)-(1,3-dimethyl-azetidin-3-yl)-(5-pyrrolidin-1-yl-pyridin-3-yl)-methanol;
(R)-(1,3-Dimethyl-azetidin-3-yl)-(5-pyrrolidin-1-yl-pyridin-3-yl)-p-tolyl-methanol;
5-[(R)-(1,3-Dimethyl-azetidin-3-yl)-hydroxy-(4-isopropyl-phenyl)-methyl]-3',4',5',6'-tetrahydro-2'H-[3,4]bipyridinyl-1'-carboxylic acid tert-butyl ester;
3-{5-[(R)-(1,3-Dimethyl-azetidin-3-yl)-hydroxy-(4-isopropyl-phenyl)-methyl]-pyridin-3-yl}-pyrrolidine-1-carboxylic acid tert-butyl ester;
(R)-(1,3-Dimethyl-azetidin-3-yl)-(4-isopropyl-phenyl)-[5-(tetrahydro-pyran-4-yl)-pyridin-3-yl]-methanol;
(R)-(1,3-Dimethyl-azetidin-3-yl)-(4-isopropyl-phenyl)-(3',4',5',6'-tetrahydro-2'H-[2',1'; 4',3"]terpyridin-5"-yl)-methanol;
(R)-(1,3-Dimethyl-azetidin-3-yl)-(4-isopropyl-phenyl)-(1'-phenyl-1'1,2',3',4',5',6'-hexahydro-[3,4]bipyridinyl-5-yl)-methanol;
(R)-(1,3-Dimethyl-azetidin-3-yl)-(4-isopropyl-phenyl)-[1'-(toluene-4-sulfonyl)-1',2',3',4',5',6'-hexahydro-[3,4]bipyridinyl-5-yl]-methanol;
(R)-(1,3-Dimethyl-azetidin-3-yl)-(4-isopropyl-phenyl)-[5-(tetrahydro-furan-2-yl)-pyridin-3-yl]-methanol;
(R)-(1,3-Dimethyl-azetidin-3-yl)-(4-isopropyl-phenyl)-[5-(5-methyl-tetrahydro-furan-2-yl)-pyridin-3-yl]-methanol;
(R)-(1,3-Dimethyl-azetidin-3-yl)-[5-(5,5-dimethyl-tetrahydro-furan-2-yl)-pyridin-3-yl]-(4-isopropyl-phenyl)-methanol;
3-{5-[(R)-(1,3-Dimethyl-azetidin-3-yl)-hydroxy-(4-isopropyl-phenyl)-methyl]-pyridin-3-yl}-2,2-difluoro-propan-1-ol;
(R)-(1,3-Dimethyl-azetidin-3-yl)-(4-isopropyl-phenyl)-[5-(5-methyl-oxazol-2-yl)-pyridin-3-yl]-methanol;
(R)-(1,3-Dimethyl-azetidin-3-yl)-(4-isopropyl-phenyl)-{5-[5-(tetrahydro-pyran-4-yl)-oxazol-2-yl]-pyridin-3-yl}-methanol;
(R)-(1,3-Dimethyl-azetidin-3-yl)-[5-(4-fluoro-phenoxymethyl)-pyridin-3-yl]-(4-isopropyl-phenyl)-methanol;
Isopropyl-carbamic acid 5-[(R)-(1,3-dimethyl-azetidin-3-yl)-hydroxy-(4-isopropyl-phenyl)-methyl]-pyridin-3-ylmethyl ester;
(R)-[5-(2-Benzyloxy-ethyl)-pyridin-3-yl]-(1,3-dimethyl-azetidin-3-yl)-(4-isopropyl-phenyl)-methanol;
4-{5-[(R)-(1,3-Dimethyl-azetidin-3-yl)-hydroxy-(4-isopropyl-phenyl)-methyl]-pyridin-3-yl}-1-methyl-cyclohexanol; 2-(2-{5-[(R)-(1,3-Dimethyl-azetidin-3-yl)-hydroxy-(4-isopropyl-phenyl)-methyl]-pyridin-3-yl}-cyclopropyl)-propan-2-ol;
(S)-(1,3-Dimethyl-azetidin-3-yl)-(4-isopropyl-phenyl)-{2-[5-(tetrahydro-pyran-4-yl)-[1,2,4]oxadiazol-3-yl]-pyridin-4-yl}-methanol;
(1,3-Dimethyl-azetidin-3-yl)-(4-isopropyl-phenyl)-(2-pyrrolidin-1-yl-pyrimidin-5-yl)-methanol; and
(1,3-Dimethyl-azetidin-3-yl)-(4-isopropyl-phenyl)-(6-pyrrolidin-1-yl-pyrazin-2-yl)-methanol.

34) Another embodiment relates to a compound according to embodiment 1) selected from a group consisting of
(R)—N-(1-(3-(5-((1,3-dimethylazetidin-3-yl)(hydroxy)(4-isopropylphenyl)methyl)pyridin-3-yl)-1,2,4-oxadiazol-5-yl)cyclopropyl)acetamide-2,2,2-d3;
(R)—N-(1-(3-(5-((1,3-dimethylazetidin-3-yl)(hydroxy)(4-isopropylphenyl)methyl)pyridin-3-yl)-1,2,4-oxadiazol-5-yl)cyclopropyl)-N-methylacetamide-d3;
(R)—N-((3-(5-((1,3-dimethylazetidin-3-yl)(hydroxy)(4-isopropylphenyl)methyl)pyridin-3-yl)-1,2,4-oxadiazol-5-yl)methyl)-N-methylacetamide-d3;
N-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl methyl)-2-hydroxy-acetamide;
(R)—N-((3-(5-((1,3-dimethylazetidin-3-yl)(hydroxy)(4-isopropylphenyl)methyl)pyridin-3-yl)-1,2,4-oxadiazol-5-yl)methyl)acetamide-2,2,2-d3;
1-(3-{5-[(R)-Hydroxy-(1-isopropyl-3-methyl-azetidin-3-yl)-(4-isopropyl-phenyl)-methyl]-pyridin-3-yl}-[1,2,4]oxadiazol-5-yl)-2-methyl-propan-2-ol;
1-(3-{5-[(R)-(1-Ethyl-3-methyl-azetidin-3-yl)-hydroxy-(4-isopropyl-phenyl)-methyl]-pyridin-3-yl}-[1,2,4]oxadiazol-5-yl)-2-methyl-propan-2-ol;
2-(3-{5-[(R)-Hydroxy-(1-isopropyl-3-methyl-azetidin-3-yl)-(4-isopropyl-phenyl)-methyl]-pyridin-3-yl}-[1,2,4]oxadiazol-5-yl)-propan-2-ol;
2-(3-{5-[(R)-(1-Ethyl-3-methyl-azetidin-3-yl)-hydroxy-(4-isopropyl-phenyl)-methyl]-pyridin-3-yl}-[1,2,4]oxadiazol-5-yl)-propan-2-ol;
4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidine-1-carboxylic acid benzyl ester;
1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-ethanone;
(R)-1-(3-(3-(5-((1,3-dimethylazetidin-3-yl)(hydroxy)(4-isopropylphenyl)methyl)pyridin-3-yl)-1,2,4-oxadiazol-5-yl)azetidin-1-yl)ethan-1-one-2,2,2-d3;
(R)-1-(3-(3-(5-((1,3-dimethylazetidin-3-yl)(hydroxy)(4-isopropylphenyl)methyl)pyridin-3-yl)-1,2,4-oxadiazol-5-yl)-3-methylazetidin-1-yl)ethan-1-one-2,2,2-d3;
(R)-1-(3-(3-(5-((1,3-dimethylazetidin-3-yl)(hydroxy)(4-isopropylphenyl)methyl)pyridin-3-yl)-1,2,4-oxadiazol-5-yl)-3-fluoroazetidin-1-yl)ethan-1-one-2,2,2-d3;
(R)-(1,3-Dimethyl-azetidin-3-yl)-(4-isopropyl-phenyl)-{5-[5-(1-methyl-1-morpholin-4-yl-ethyl)-[1,2,4]oxadiazol-3-yl]-pyridin-3-yl}-methanol;
4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-piperidin-2-one;

1-[(3)-3-(3-{5-[(R)-(1,3-Dimethyl-azetidin-3-yl)-hydroxy-(4-isopropyl-phenyl)-methyl]-pyridin-3-yl}[1,2,4]oxadiazol-5-yl)-pyrrolidin-1-yl]-ethanone;

1-[(R)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-1-yl]-ethanone;

N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-ethyl]-acetamide;

1-Benzyl-3-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-pyrrolidin-2-one;

3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,3-dimethyl-pyrrolidin-2-one;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-isobutyl-pyrrolidin-2-one;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-furan-2-ylmethyl-pyrrolidin-2-one;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-phenyl-pyrrolidin-2-one;

1-Benzyl-4-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-pyrrolidin-2-one;

5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-phenyl-pyrrolidin-2-one;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-2-one;

(S)-5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-2-one;

(R)-5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-2-one;

(S)-6-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-azetidin-2-one;

(S)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-azetidin-2-one;

(S)-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,4-dimethyl-pyrrolidin-2-one;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,4-dimethyl-pyrrolidin-2-one;

(R) or (S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,4-dimethyl-pyrrolidin-2-one;

(R)-(1,3-Dimethyl-azetidin-3-yl)-(4-isopropyl-phenyl)-[5-(5-piperidin-4-yl-[1,2,4]oxadiazol-3-yl)-pyridin-3-yl]-methanol;

(R)-(1,3-Dimethyl-azetidin-3-yl)-(4-isopropyl-phenyl)-{5-[5-(4-methyl-piperidin-4-yl)-[1,2,4]oxadiazol-3-yl]-pyridin-3-yl}-methanol;

(R)-(1,3-Dimethyl-azetidin-3-yl)-{5-[5-(4-fluoro-piperidin-4-yl)-[1,2,4]oxadiazol-3-yl]-pyridin-3-yl}-(4-isopropyl-phenyl)-methanol;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-butan-1-one;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2,2-dimethyl-propan-1-one;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2-methoxy-ethanone;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-3-methoxy-propan-1-one;

Cyclopropyl-[4-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-piperidin-1-yl]-methanone;

Cyclopentyl-[4-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-piperidin-1-yl]-methanone;

[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-(tetrahydro-pyran-4-yl)-methanone;

[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-phenyl-methanone;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-carboxylic acid methyl ester;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-carboxylic acid ethyl ester;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-carboxylic acid 2-methoxy-ethyl ester;

(R)-(1,3-Dimethyl-azetidin-3-yl)-(4-isopropyl-phenyl)-{5-[5-(1-methanesulfonyl-piperidin-4-yl)-[1,2,4]oxadiazol-3-yl]-pyridin-3-yl}-methanol;

(R)-(1,3-Dimethyl-azetidin-3-yl)-(4-isopropyl-phenyl)-(5-{5-[1-(propane-2-sulfonyl)-piperidin-4-yl]-[1,2,4]oxadiazol-3-yl}-pyridin-3-yl)-methanol;

(R)-(1,3-Dimethyl-azetidin-3-yl)-(4-isopropyl-phenyl)-(5-{5-[1-(propane-1-sulfonyl)-piperidin-4-yl]-[1,2,4]oxadiazol-3-yl}-pyridin-3-yl)-methanol;

(R)-(1,3-Dimethyl-azetidin-3-yl)-(4-isopropyl-phenyl)-(5-{5-[1-(2-methoxy-ethanesulfonyl)-piperidin-4-yl]-[1,2,4]oxadiazol-3-yl}-pyridin-3-yl)-methanol;

2-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-sulfonyl]-ethanol;

(R)-{5-[5-(1-Cyclopentanesulfonyl-piperidin-4-yl)-[1,2,4]oxadiazol-3-yl]-pyridin-3-yl}-(1,3-dimethyl-azetidin-3-yl)-(4-isopropyl-phenyl)-methanol;

(R)-(1,3-Dimethyl-azetidin-3-yl)-(4-isopropyl-phenyl)-(5-{5-[1-(tetrahydro-pyran-4-sulfonyl)-piperidin-4-yl]-[1,2,4]oxadiazol-3-yl}-pyridin-3-yl)-methanol;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-sulfonic acid methylamide;

(R)-(1,3-Dimethyl-azetidin-3-yl)-(4-isopropyl-phenyl)-{5-[5-(1-methylamino-cyclopropyl)-[1,2,4]oxadiazol-3-yl]-pyridin-3-yl}-methanol;

[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclopropyl]-methyl-carbamic acid ethyl ester;

N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclopropyl]-N-methyl-methanesulfonamide;

(R)-(1,3-Dimethyl-azetidin-3-yl)-[6-(2,2-dimethyl-cyclopentyloxy)-pyridazin-4-yl]-(4-isopropyl-phenyl)-methanol;

(R)-[6-(3,3-Difluoro-cyclopentyloxy)-pyridazin-4-yl]-(1,3-dimethyl-azetidin-3-yl)-(4-isopropyl-phenyl)-methanol;

2-(2-{5-[(R)-(1,3-Dimethyl-azetidin-3-yl)-hydroxy-(4-isopropyl-phenyl)-methyl]-pyridazin-3-yloxy}-phenyl)-ethanol;

2-(4-{5-[(R)-(1,3-Dimethyl-azetidin-3-yl)-hydroxy-(4-isopropyl-phenyl)-methyl]-pyridazin-3-yloxy}-phenyl)-ethanol;

(R)-[6-(Chroman-6-yloxy)-pyridazin-4-yl]-(1,3-dimethyl-azetidin-3-yl)-(4-isopropyl-phenyl)-methanol;

6-{5-[(R)-(1,3-Dimethyl-azetidin-3-yl)-hydroxy-(4-isopropyl-phenyl)-methyl]-pyridazin-3-yloxy}-3H-benzooxazol-2-one;

1-{5-[(R)-(1,3-Dimethyl-azetidin-3-yl)-hydroxy-(4-isopropyl-phenyl)-methyl]-pyridin-3-yl}-3-(6-methyl-pyrimidin-4-yl)-pent-1-yn-3-ol;

(S)-4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-but-3-yn-2-ol;

(R)-(1,3-Dimethyl-azetidin-3-yl)-{5-[1-(4-fluoro-phenyl)-cyclopropylethynyl]-pyridin-3-yl}-(4-isopropyl-phenyl)-methanol;

(S)-4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-but-3-yn-2-ol;

3-{5-[(R)-(1,3-Dimethyl-azetidin-3-yl)-hydroxy-(4-isopropyl-phenyl)-methyl]-pyridin-3-ylethynyl}-3-hydroxy-pyrrolidine-1-carboxylic acid tert-butyl ester;

4-{5-[(R)-(1,3-Dimethyl-azetidin-3-yl)-hydroxy-(4-isopropyl-phenyl)-methyl]-pyridin-3-ylethynyl}-piperidine-1-carboxylic acid tert-butyl ester;

1-{5-[(R)-(1,3-Dimethyl-azetidin-3-yl)-hydroxy-(4-isopropyl-phenyl)-methyl]-pyridin-3-yl}-3-(6-methyl-pyrimidin-4-yl)-pentan-3-ol;

2-(2-{5-[(R)-(1,3-Dimethyl-azetidin-3-yl)-hydroxy-(4-isopropyl-phenyl)-methyl]-pyridin-3-yl}-ethyl)-benzoic acid methyl ester;

(R)-(1,3-Dimethyl-azetidin-3-yl)-{5-[2-(2-hydroxymethyl-phenyl)-ethyl]-pyridin-3-yl}-(4-isopropyl-phenyl)-methanol;

4-{5-[(R)-(1,3-Dimethyl-azetidin-3-yl)-hydroxy-(4-isopropyl-phenyl)-methyl]-pyridin-3-yl}-2-(6-methoxy-pyrimidin-4-yl)-butan-2-ol;

3-(2-{5-[(R)-(1,3-Dimethyl-azetidin-3-yl)-hydroxy-(4-isopropyl-phenyl)-methyl]-pyridin-3-yl}-ethyl)-3-hydroxy-pyrrolidine-1-carboxylic acid tert-butyl ester;

(R)-(1,3-Dimethyl-azetidin-3-yl)-(4-isopropyl-phenyl)-{5-[2-(1H-pyrrolo[2,3-b]pyridin-2-yl)-ethyl]-pyridin-3-yl}-methanol;

4-(2-{5-[(R)-(1,3-Dimethyl-azetidin-3-yl)-hydroxy-(4-isopropyl-phenyl)-methyl]-pyridin-3-yl}-ethyl)-piperidine-1-carboxylic acid tert-butyl ester;

4-{5-[(R)-(1,3-Dimethyl-azetidin-3-yl)-hydroxy-(4-isopropyl-phenyl)-methyl]-pyridin-3-yl}-2-pyridin-2-yl-butan-2-ol;

1-Cyclopropyl-3-{5-[(R)-(1,3-dimethyl-azetidin-3-yl)-hydroxy-(4-isopropyl-phenyl)-methyl]-pyridin-3-yl}-1-pyridin-2-yl-propan-1-ol;

4-{5-[(R)-(1,3-Dimethyl-azetidin-3-yl)-hydroxy-(4-isopropyl-phenyl)-methyl]-pyridin-3-yl}-2-(5-methyl-pyridin-3-yl)-butan-2-ol;

8-(2-{5-[(R)-(1,3-Dimethyl-azetidin-3-yl)-hydroxy-(4-isopropyl-phenyl)-methyl]-pyridazin-3-yl}-ethyl)-5,6,7,8-tetrahydro-quinolin-8-ol;

4-{5-[(R)-(1,3-Dimethyl-azetidin-3-yl)-hydroxy-(4-isopropyl-phenyl)-methyl]-pyridazin-3-yl}-2-(6-methoxy-pyridin-2-yl)-butan-2-ol;

4-{5-[(R)-(1,3-Dimethyl-azetidin-3-yl)-hydroxy-(4-isopropyl-phenyl)-methyl]-pyridazin-3-yl}-2-(6-methyl-pyridin-2-yl)-butan-2-ol;

(1,3-Dimethyl-azetidin-3-yl)-(4-isopropyl-phenyl)-(6-pyrrolidin-1-yl-pyridin-2-yl)-methanol;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-fluoro-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-methyl-piperidin-1-yl]-ethanone;

4-{5-[(R)-(1,3-Dimethyl-azetidin-3-yl)-hydroxy-(4-isopropyl-phenyl)-methyl]-pyridin-3-yloxy}-cyclohexanone;

4-{5-[(R)-(1,3-Dimethyl-azetidin-3-yl)-hydroxy-(4-isopropyl-phenyl)-methyl]-pyridin-3-yl}-cyclohexanol;

(R)-(5-Cyclopentyloxymethyl-pyridin-3-yl)-(1,3-dimethyl-azetidin-3-yl)-(4-isopropyl-phenyl)-methanol;

1-(4-{5-[(R)-(1,3-Dimethyl-azetidin-3-yl)-hydroxy-(4-isopropyl-phenyl)-methyl]-pyridin-3-ylmethoxy}-piperidin-1-yl)-ethanone;

(R)-(1,3-Dimethyl-azetidin-3-yl)-(4-isopropyl-phenyl)-[6-(tetrahydro-pyran-4-yl)-pyridazin-4-yl]-methanol;

4-{5-[(R)-(1,3-Dimethyl-azetidin-3-yl)-hydroxy-(4-isopropyl-phenyl)-methyl]-pyridazin-3-yl}-2-phenyl-butan-2-ol;

(R)-(1,3-Dimethyl-azetidin-3-yl)-(4-isopropyl-phenyl)-{6-[(S)-(tetrahydro-furan-3-yl)oxy]-pyridazin-4-yl}-methanol;

(R)-(1,3-Dimethyl-azetidin-3-yl)-(4-isopropyl-phenyl)-{6-[(R)-(tetrahydro-furan-3-yl)oxy]-pyridazin-4-yl}-methanol;

1-{5-[(R)-(1,3-Dimethyl-azetidin-3-yl)-hydroxy-(4-isopropyl-phenyl)-methyl]-pyridazin-3-yl}-4-methyl-pyrrolidin-2-one;

1-{5-[(R)-(1,3-Dimethyl-azetidin-3-yl)-hydroxy-(4-isopropyl-phenyl)-methyl]-pyridazin-3-yl}-3-isopropyl-pyrrolidin-2-one;

1-{5-[(R)-(1,3-Dimethyl-azetidin-3-yl)-hydroxy-(4-isopropyl-phenyl)-methyl]-pyridazin-3-yl}-3,3-dimethyl-pyrrolidin-2-one;

1-{5-[(R)-(1,3-Dimethyl-azetidin-3-yl)-hydroxy-(4-isopropyl-phenyl)-methyl]-pyridazin-3-yl}-4,4-dimethyl-pyrrolidin-2-one;

5-{5-[(R)-(1,3-Dimethyl-azetidin-3-yl)-hydroxy-(4-isopropyl-phenyl)-methyl]-pyridazin-3-yl}-5-aza-spiro[2.4]heptan-6-one;

1-{5-[(R)-(1,3-Dimethyl-azetidin-3-yl)-hydroxy-(4-isopropyl-phenyl)-methyl]-pyridazin-3-yl}-4-trifluoromethyl-pyrrolidin-2-one;

4-Cyclopropyl-1-{5-[(R)-(1,3-dimethyl-azetidin-3-yl)-hydroxy-(4-isopropyl-phenyl)-methyl]-pyridazin-3-yl}-pyrrolidin-2-one;

2-{5-[(R)-(1,3-Dimethyl-azetidin-3-yl)-hydroxy-(4-isopropyl-phenyl)-methyl]-pyridazin-3-yl}-8-oxa-2-aza-spiro[4.5]decan-3-one;

3-{5-[(R)-(1,3-Dimethyl-azetidin-3-yl)-hydroxy-(4-isopropyl-phenyl)-methyl]-pyridazin-3-yl}-1-oxa-3-aza-spiro[4.5]decan-2-one;

1-{5-[(R)-(1,3-Dimethyl-azetidin-3-yl)-hydroxy-(4-isopropyl-phenyl)-methyl]-pyridazin-3-yl}-4-pyridin-2-yl-pyrrolidin-2-one;

1-{5-[(R)-(1,3-Dimethyl-azetidin-3-yl)-hydroxy-(4-isopropyl-phenyl)-methyl]-pyridazin-3-yl}-3-(2-methoxy-ethyl)-pyrrolidin-2-one;

1-{5-[(R)-(1,3-Dimethyl-azetidin-3-yl)-hydroxy-(4-isopropyl-phenyl)-methyl]-pyridazin-3-yl}-4-phenyl-pyrrolidin-2-one;

2-{5-[(R)-(1,3-Dimethyl-azetidin-3-yl)-hydroxy-(4-isopropyl-phenyl)-methyl]-pyridazin-3-yl}-2,3-dihydro-isoindol-1-one;

2-(3-{5-[(3)-(3-Fluoro-1-methyl-azetidin-3-yl)-hydroxy-(4-isopropyl-phenyl)-methyl]-pyridin-3-yl}-[1,2,4]oxadiazol-5-yl)-propan-2-ol;

2-(3-{5-[(3)-(1-Cyclopropyl-3-fluoro-azetidin-3-yl)-hydroxy-(4-isopropyl-phenyl)-methyl]-pyridin-3-yl}-[1,2,4]oxadiazol-5-yl)-propan-2-ol;

1-[4-(3-{5-[(3)-(3-Fluoro-1-methyl-azetidin-3-yl)-hydroxy-(4-isopropyl-phenyl)-methyl]-pyridin-3-yl}-[1,2,4]oxadiazol-5-yl)-piperidin-1-yl]-ethanone;

1-[4-(3-{5-[(3)-(1-Cyclopropyl-3-fluoro-azetidin-3-yl)-hydroxy-(4-isopropyl-phenyl)-methyl]-pyridin-3-yl}-[1,2,4]oxadiazol-5-yl)-piperidin-1-yl]-ethanone;

2-(3-{5-[(R)-(1-Cyclopropyl-3-methyl-azetidin-3-yl)-hydroxy-(4-isopropyl-phenyl)-methyl]-pyridin-3-yl}-[1,2,4]oxadiazol-5-yl)-propan-2-ol;

1-[4-(3-{5-[(R)-(1-Cyclopropyl-3-methyl-azetidin-3-yl)-hydroxy-(4-isopropyl-phenyl)-methyl]-pyridin-3-yl}-[1,2,4]oxadiazol-5-yl)-piperidin-1-yl]-ethanone;

(R)-(1-Cyclopropyl-3-methyl-azetidin-3-yl)-(4-isopropyl-phenyl)-{5-[5-(tetrahydro-pyran-4-yl)-[1,2,4]oxadiazol-3-yl]-pyridin-3-yl}-methanol;

trans-4-(3-{5-[(R)-(1-Cyclopropyl-3-methyl-azetidin-3-yl)-hydroxy-(4-isopropyl-phenyl)-methyl]-pyridin-3-yl}-[1,2,4]oxadiazol-5-yl)-cyclohexanol;

(R)-(1-Cyclopropyl-3-methyl-azetidin-3-yl)-(4-isopropyl-phenyl)-[5-(5-oxetan-3-yl-[1,2,4]oxadiazol-3-yl)-pyridin-3-yl]-methanol;

1-[(R)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidin-1-yl]-ethanone;

1-[3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-ethanone;

1-[3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-3-hydroxy-piperidin-1-yl]-ethanone;

1-[3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-3-methyl-piperidin-1-yl]-ethanone;

1-[3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-4-hydroxy-piperidin-1-yl]-ethanone;

N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclopropyl]-acetamide;

Tetrahydro-pyran-4-carboxylic acid [1-(3-{5-[(R)-(1,3-dimethyl-azetidin-3-yl)-hydroxy-(4-isopropyl-phenyl)-methyl]-pyridin-3-yl}-[1,2,4]oxadiazol-5-ylmethyl)-cyclopropyl]-amide;

N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclopropyl]-2-methoxy-acetamide;

N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclopropyl]-N-methyl-acetamide;

N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-propionamide;

N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-2-methoxy-acetamide;

Tetrahydro-pyran-4-carboxylic acid [2-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-amide;

N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-isobutyramide;

Cyclopropanecarboxylic acid [2-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-amide;

1-[cis-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-2-methyl-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-hydroxy-piperidin-1-yl]-2-methyl-propan-1-one;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-hydroxy-piperidin-1-yl]-propan-1-one;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-methoxy-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-3,3,3-trifluoro-propan-1-one;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2-oxetan-3-yl-ethanone;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-ethyl-piperidin-1-yl]-ethanone;

[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-oxetan-3-yl-methanone;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-isopropyl-piperidin-1-yl]-2-methoxy-ethanone;

1-[cis-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-3-methyl-piperidin-1-yl]-ethanone;

5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-piperidin-2-one;

5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-5-methyl-piperidin-2-one;

5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-methyl-pyrrolidin-2-one;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-3,3-dimethyl-pyrrolidine-2,5-dione;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-imidazolidine-2,4-dione;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidin-2-one;

3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-imidazolidine-2,4-dione;

3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-1-methyl-imidazolidine-2,4-dione;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-3-methyl-imidazolidine-2,4-dione;

3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-oxazolidin-2-one;

1-Cyclopropyl-3-(3-{5-[(R)-(1,3-dimethyl-azetidin-3-yl)-hydroxy-(4-isopropyl-phenyl)-methyl]-pyridin-3-yl}-[1,2,4]oxadiazol-5-ylmethyl)-imidazolidin-2-one;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidine-2,5-dione;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-3-methyl-imidazolidin-2-one;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-imidazolidin-2-one;

2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-propane-1,2-diol;

(R)-(1,3-Dimethyl-azetidin-3-yl)-(4-isopropyl-phenyl)-[5-(5-pyridin-3-yl-[1,2,4]oxadiazol-3-yl)-pyridin-3-yl]-methanol;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-piperidin-1-yl]-ethanone;

(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-acetonitrile;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-hydroxy-piperidin-1-yl]-ethanone;

3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-propionitrile;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-3-methoxy-piperidin-1-yl]-ethanone;

1-[(R)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-ethanone;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-tetrahydro-pyran-4-ol;

(R)-(1,3-Dimethyl-azetidin-3-yl)-{5-[5-(3-hydroxymethyl-bicyclo[1.1.1]pent-1-yl)-[1,2,4]oxadiazol-3-yl]-pyridin-3-yl}-(4-isopropyl-phenyl)-methanol;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-piperidine-2,6-dione;

2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-2,2-difluoro-ethanol;

(R)-(1,3-Dimethyl-azetidin-3-yl)-(4-isopropyl-phenyl)-{5-[5-(3-methoxy-phenyl)-[1,2,4]oxadiazol-3-yl]-pyridin-3-yl}-methanol;

(R)-(1,3-Dimethyl-azetidin-3-yl)-[5-(5-isopropyl-[1,2,4]oxadiazol-3-yl)-pyridin-3-yl]-(4-isopropyl-phenyl)-methanol;

(R)-(1,3-Dimethyl-azetidin-3-yl)-(4-isopropyl-phenyl)-{5-[5-(6-methyl-pyrimidin-4-yl)-[1,2,4]oxadiazol-3-yl]-pyridin-3-yl}-methanol;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-pyrrolidin-2-one;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-pyrrolidin-2-one;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-ethyl-pyrrolidin-2-one;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-ethyl-pyrrolidin-2-one;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-ethyl-pyrrolidin-2-one;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-ethyl-pyrrolidin-2-one;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-isopropyl-pyrrolidin-2-one;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-isopropyl-pyrrolidin-2-one;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-isopropyl-pyrrolidin-2-one;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-isopropyl-pyrrolidin-2-one;

1-[(3)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidin-1-yl]-ethanone;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one;

(R)-(1,3-Dimethyl-azetidin-3-yl)-(4-isopropyl-phenyl)-[5-(5-methyl-[1,2,4]oxadiazol-3-yl)-pyridin-3-yl]-methanol;

(R)-{5-[5-(1,1-Difluoro-ethyl)-[1,2,4]oxadiazol-3-yl]-pyridin-3-yl}-(1,3-dimethyl-azetidin-3-yl)-(4-isopropyl-phenyl)-methanol;

4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-tetrahydro-pyran-4-ol;

(R)-[5-(3-tert-Butoxymethyl-[1,2,4]oxadiazol-5-yl)-pyridin-3-yl]-4-(1,3-dimethyl-azetidin-3-yl)-(4-isopropyl-phenyl)-methanol;

(R)-(1,3-Dimethyl-azetidin-3-yl)-[5-(3-hydroxymethyl-[1,2,4]oxadiazol-5-yl)-pyridin-3-yl]-(4-isopropyl-phenyl)-methanol;

1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperazin-1-yl]-ethanone;

1-[3-(5-{5-[(R)-(1,3-Dimethyl-azetidin-3-yl)-hydroxy-(4-isopropyl-phenyl)-methyl]-pyridin-3-yl}-[1,2,4]oxadiazol-3-ylmethyl)-azetidin-1-yl]-ethanone;

4-(5-{5-[(R)-(1,3-Dimethyl-azetidin-3-yl)-hydroxy-(4-isopropyl-phenyl)-methyl]-pyridin-3-yl}-[1,2,4]oxadiazol-3-ylmethyl)-tetrahydro-pyran-4-ol;

[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-[1,4]dioxan-2-yl-methanone;

1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-2-methoxy-ethanone;

(R)-(1,3-Dimethyl-azetidin-3-yl)-(4-isopropyl-phenyl)-{5-[3-(1-methanesulfonyl-piperidin-4-yl)-[1,2,4]oxadiazol-5-yl]-pyridin-3-yl}-methanol;

(R)-(1,3-Dimethyl-azetidin-3-yl)-(4-isopropyl-phenyl)-(5-{3-[1-(2-methoxy-ethanesulfonyl)-piperidin-4-yl]-[1,2,4]oxadiazol-5-yl}-pyridin-3-yl)-methanol;

1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-2-hydroxy-ethanone;

(R)-(1,3-Dimethyl-azetidin-3-yl)-(4-isopropyl-phenyl)-(5-[1,2,4]oxadiazol-3-yl-pyridin-3-yl)-methanol;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-ethanone;

2-(3-{5-[(R)-(4-Bromo-phenyl)-(1,3-dimethyl-azetidin-3-yl)-hydroxy-methyl]-pyridin-3-yl}-[1,2,4]oxadiazol-5-yl)-propan-2-ol;

2-(3-{5-[(R)-(1,3-Dimethyl-azetidin-3-yl)-hydroxy-naphthalen-2-yl-methyl]-pyridin-3-yl}-[1,2,4]oxadiazol-5-yl)-propan-2-ol;

2-[3-(5-{(R)-(1,3-Dimethyl-azetidin-3-yl)-hydroxy-[4-(1-trifluoromethyl-cyclopropyl)-phenyl]-methyl}-pyridin-3-yl)-[1,2,4]oxadiazol-5-yl]-propan-2-ol;

2-[3-(5-{(R)-(1,3-Dimethyl-azetidin-3-yl)-hydroxy-[4-(2,2,2-trifluoro-1,1-dimethyl-ethyl)-phenyl]-methyl}-pyridin-3-yl)-[1,2,4]oxadiazol-5-yl]-propan-2-ol;

2-(3-{5-[(R)-(1,3-Dimethyl-azetidin-3-yl)-hydroxy-(4-isopropoxy-phenyl)-methyl]-pyridin-3-yl}-[1,2,4]oxadiazol-5-yl)-propan-2-ol;

2-[3-(5-{(R)-(1,3-Dimethyl-azetidin-3-yl)-hydroxy-[4-(1,2,2,2-tetrafluoro-1-trifluoromethyl-ethyl)-phenyl]-methyl}-pyridin-3-yl)-[1,2,4]oxadiazol-5-yl]-propan-2-ol;

(R)-2-(3-(5-((1,3-dimethylazetidin-3-yl)(hydroxy)(4-(pentafluoro-X6-sulfaneyl)phenyl)methyl)pyridin-3-yl)-1,2,4-oxadiazol-5-yl)propan-2-ol;

2-(3-{5-[(R)-(1,3-Dimethyl-azetidin-3-yl)-(3-fluoro-4-isopropyl-phenyl)-hydroxy-methyl]-pyridin-3-yl}-[1,2,4]oxadiazol-5-yl)-propan-2-ol;

2-(3-{5-[(R)-(4-tert-Butyl-phenyl)-(1,3-dimethyl-azetidin-3-yl)-hydroxy-methyl]-pyridin-3-yl}-[1,2,4]oxadiazol-5-yl)-propan-2-ol;

2-(3-{5-[(R)-Benzo[b]thiophen-5-yl-(1,3-dimethyl-azetidin-3-yl)-hydroxy-methyl]-pyridin-3-yl}-[1,2,4]oxadiazol-5-yl)-propan-2-ol;

2-(3-{5-[(R)-(1,3-Dimethyl-azetidin-3-yl)-hydroxy-(4-pentafluoroethyl-phenyl)-methyl]-pyridin-3-yl}-[1,2,4]oxadiazol-5-yl)-propan-2-ol;

2-[3-(5-{(R)-(1,3-Dimethyl-azetidin-3-yl)-hydroxy-[4-(1-methyl-cyclopropyl)-phenyl]-methyl}-pyridin-3-yl)-[1,2,4]oxadiazol-5-yl]-propan-2-ol;

2-(3-{5-[(R)-(1,3-Dimethyl-azetidin-3-yl)-hydroxy-(4-isopropyl-3-methyl-phenyl)-methyl]-pyridin-3-yl}-[1,2,4]oxadiazol-5-yl)-propan-2-ol;

2-(3-{5-[(R)-(1,3-Dimethyl-azetidin-3-yl)-hydroxy-(4-trifluoromethoxy-phenyl)-methyl]-pyridin-3-yl}-[1,2,4]oxadiazol-5-yl)-propan-2-ol;

1-[4-(3-{5-[(R)-(4-Bromo-phenyl)-(1,3-dimethyl-azetidin-3-yl)-hydroxy-methyl]-pyridin-3-yl}-[1,2,4]oxadiazol-5-yl)-piperidin-1-yl]-ethanone;

2-[3-(5-{(R)-(1,3-Dimethyl-azetidin-3-yl)-[4-(1-fluoro-1-methyl-ethyl)-phenyl]-hydroxy-methyl}-pyridin-3-yl)-[1,2,4]oxadiazol-5-yl]-propan-2-ol;

2-(3-{5-[(R)-[4-(1,1-Difluoro-ethyl)-phenyl]-(1,3-dimethyl-azetidin-3-yl)-hydroxy-methyl]-pyridin-3-yl}-[1,2,4]oxadiazol-5-yl)-propan-2-ol;

2-(3-{5-[(R)-(4-Bicyclo[1.1.1]pent-1-yl-phenyl)-(1,3-dimethyl-azetidin-3-yl)-hydroxy-methyl]-pyridin-3-yl}-[1,2,4]oxadiazol-5-yl)-propan-2-ol;

(R)-(1,3-Dimethyl-azetidin-3-yl)-{5-[5-(tetrahydro-pyran-4-yl)-[1,2,4]oxadiazol-3-yl]-pyridin-3-yl}-[4-(2,2,2-trifluoro-ethyl)-phenyl]-methanol;

2-[3-(5-{(R)-(1,3-Dimethyl-azetidin-3-yl)-[4-(1,1-dimethyl-propyl)-phenyl]-hydroxy-methyl}-pyridin-3-yl)-[1,2,4]oxadiazol-5-yl]-propan-2-ol;

1-[4-(3-{5-[(R)-(1,3-Dimethyl-azetidin-3-yl)-(3-fluoro-4-isopropyl-phenyl)-hydroxy-methyl]-pyridin-3-yl}-[1,2,4]oxadiazol-5-yl)-piperidin-1-yl]-ethanone;

1-{4-[3-(5-{(R)-(1,3-Dimethyl-azetidin-3-yl)-hydroxy-[4-(1-trifluoromethyl-cyclopropyl)-phenyl]-methyl}-pyridin-3-yl)-[1,2,4]oxadiazol-5-yl]-piperidin-1-yl}-ethanone;

1-[4-(3-{5-[(R)-(1,3-Dimethyl-azetidin-3-yl)-hydroxy-(4-trifluoromethoxy-phenyl)-methyl]-pyridin-3-yl}-[1,2,4]oxadiazol-5-yl)-piperidin-1-yl]-ethanone;

1-[4-(3-{5-[(R)-(1,3-Dimethyl-azetidin-3-yl)-hydroxy-(4-isopropoxy-phenyl)-methyl]-pyridin-3-yl}-[1,2,4]oxadiazol-5-yl)-piperidin-1-yl]-ethanone;

2-(3-{5-[(R)-(3-Chloro-4-isopropyl-phenyl)-(1,3-dimethyl-azetidin-3-yl)-hydroxy-methyl]-pyridin-3-yl}-[1,2,4]oxadiazol-5-yl)-propan-2-ol;

2-(3-{5-[(R)-(4-Cyclobutyl-phenyl)-(1,3-dimethyl-azetidin-3-yl)-hydroxy-methyl]-pyridin-3-yl}-[1,2,4]oxadiazol-5-yl)-propan-2-ol;

1-[4-(3-{5-[(R)-(4-Cyclobutyl-phenyl)-(1,3-dimethyl-azetidin-3-yl)-hydroxy-methyl]-pyridin-3-yl}-[1,2,4]oxadiazol-5-yl)-piperidin-1-yl]-ethanone;

1-[4-(3-{5-[(R)-(3,5-Difluoro-4-isopropyl-phenyl)-(1,3-dimethyl-azetidin-3-yl)-hydroxy-methyl]-pyridin-3-yl}-[1,2,4]oxadiazol-5-yl)-piperidin-1-yl]-ethanone;

2-(3-{5-[(R)-(3,5-Difluoro-4-isopropyl-phenyl)-(1,3-dimethyl-azetidin-3-yl)-hydroxy-methyl]-pyridin-3-yl}-[1,2,4]oxadiazol-5-yl)-propan-2-ol;

1-[4-(3-{5-[(R)-(4-Cyclobutoxy-phenyl)-(1,3-dimethyl-azetidin-3-yl)-hydroxy-methyl]-pyridin-3-yl}-[1,2,4]oxadiazol-5-yl)-piperidin-1-yl]-ethanone;

2-[3-(5-{(1,3-Dimethyl-azetidin-3-yl)-[4-(1-ethyl-propyl)-phenyl]-hydroxy-methyl}-pyridin-3-yl)-[1,2,4]oxadiazol-5-yl]-propan-2-ol;

1-{4-[3-(5-{(1,3-Dimethyl-azetidin-3-yl)-[4-(1-ethyl-propyl)-phenyl]-hydroxy-methyl}-pyridin-3-yl)-[1,2,4]oxadiazol-5-yl]-piperidin-1-yl}-ethanone;

2-[3-(5-{(1,3-Dimethyl-azetidin-3-yl)-[4-(2,2-dimethyl-propyl)-phenyl]-hydroxy-methyl}-pyridin-3-yl)-[1,2,4]oxadiazol-5-yl]-propan-2-ol;

1-{4-[3-(5-{(1,3-Dimethyl-azetidin-3-yl)-[4-(2,2-dimethyl-propyl)-phenyl]-hydroxy-methyl}-pyridin-3-yl)-[1,2,4]oxadiazol-5-yl]-piperidin-1-yl}-ethanone;

1-{4-[3-(5-{(1,3-Dimethyl-azetidin-3-yl)-hydroxy-[4-(1-methyl-cyclopropyl)-phenyl]-methyl}-pyridin-3-yl)-[1,2,4]oxadiazol-5-yl]-piperidin-1-yl}-ethanone;

2-(3-{5-[(R)-(1,3-Dimethyl-azetidin-3-yl)-hydroxy-(4-propyl-phenyl)-methyl]-pyridin-3-yl}-[1,2,4]oxadiazol-5-yl)-propan-2-ol;

2-(3-{5-[(R)-(4-Cyclopropyl-phenyl)-(1,3-dimethyl-azetidin-3-yl)-hydroxy-methyl]-pyridin-3-yl}-[1,2,4]oxadiazol-5-yl)-propan-2-ol;

2-(3-{5-[(R)-(1,3-Dimethyl-azetidin-3-yl)-(4-ethyl-phenyl)-hydroxy-methyl]-pyridin-3-yl}-[1,2,4]oxadiazol-5-yl)-propan-2-ol;

2-(3-{5-[(R)-(4-Butyl-phenyl)-(1,3-dimethyl-azetidin-3-yl)-hydroxy-methyl]-pyridin-3-yl}-[1,2,4]oxadiazol-5-yl)-propan-2-ol;

2-(3-{5-[(R)-(1,3-Dimethyl-azetidin-3-yl)-hydroxy-(4-trifluoromethyl-phenyl)-methyl]-pyridin-3-yl}-[1,2,4]oxadiazol-5-yl)-propan-2-ol;

2-[3-(5-{(R)-(1,3-Dimethyl-azetidin-3-yl)-hydroxy-[4-(2,2,2-trifluoro-ethyl)-phenyl]-methyl}-pyridin-3-yl)-[1,2,4]oxadiazol-5-yl]-propan-2-ol;

2-(3-{5-[(R)-(1,3-Dimethyl-azetidin-3-yl)-hydroxy-(4-isobutyl-phenyl)-methyl]-pyridin-3-yl}-[1,2,4]oxadiazol-5-yl)-propan-2-ol;

2-(3-{5-[(R)-(4-Cyclobutoxy-phenyl)-(1,3-dimethyl-azetidin-3-yl)-hydroxy-methyl]-pyridin-3-yl}-[1,2,4]oxadiazol-5-yl)-propan-2-ol;

2-(3-{5-[(R)-(1,3-Dimethyl-azetidin-3-yl)-hydroxy-(4-isopropenyl-phenyl)-methyl]-pyridin-3-yl}-[1,2,4]oxadiazol-5-yl)-propan-2-ol;

1-{4-[3-(5-{(R)-(1,3-Dimethyl-azetidin-3-yl)-hydroxy-[4-(2,2,2-trifluoro-ethyl)-phenyl]-methyl}-pyridin-3-yl)-[1,2,4]oxadiazol-5-yl]-piperidin-1-yl}-ethanone;

1-[4-(3-{5-[(R)-(1,3-Dimethyl-azetidin-3-yl)-hydroxy-(4-propyl-phenyl)-methyl]-pyridin-3-yl}-[1,2,4]oxadiazol-5-yl)-piperidin-1-yl]-ethanone;

1-[4-(3-{5-[(R)-Hydroxy-(1-isopropyl-3-methyl-azetidin-3-yl)-(4-isopropyl-phenyl)-methyl]-pyridin-3-yl}-[1,2,4]oxadiazol-5-yl)-piperidin-1-yl]-ethanone;

1-[4-(3-{5-[(R)-[1-(2,2-Difluoro-ethyl)-3-methyl-azetidin-3yl]-hydroxy-(4-isopropyl-phenyl)-methyl]-pyridin-3-yl}-[1,2,4]oxadiazol-5-yl)-piperidin-1-yl]-ethanone;

1-[4-(3-{5-[(R)-Hydroxy-[1-(2-hydroxy-ethyl)-3-methyl-azetidin-3-yl]-(4-isopropyl-phenyl)-methyl]-pyridin-3-yl}-[1,2,4]oxadiazol-5-yl)-piperidin-1-yl]-ethanone;

1-[4-(3-{5-[(R)-(1-Cyclopropylmethyl-3-methyl-azetidin-3-yl)-hydroxy-(4-isopropyl-phenyl)-methyl]-pyridin-3-yl}-[1,2,4]oxadiazol-5-yl)-piperidin-1-yl]-ethanone;

1-{4-[3-(5-{(R)-Hydroxy-(4-isopropyl-phenyl)-[1-(2-methoxy-ethyl)-3-methyl-azetidin-3-yl]-methyl}-pyridin-3-yl)-[1,2,4]oxadiazol-5-yl]-piperidin-1-yl}-ethanone;

1-{4-[3-(5-{(R)-Hydroxy-(4-isopropyl-phenyl)-[3-methyl-1-(3,3,3-trifluoro-propyl)-azetidin-3-yl]-methyl}-pyridin-3-yl)-[1,2,4]oxadiazol-5-yl]-piperidin-1-yl}-ethanone;

1-[4-(3-{5-[(R)-Hydroxy-(4-isopropyl-phenyl)-(3-methyl-1-propyl-azetidin-3-yl)-methyl]-pyridin-3-yl}-[1,2,4]oxadiazol-5-yl)-piperidin-1-yl]-ethanone;

1-[4-(3-{5-[(R)-(1-Ethyl-3-methyl-azetidin-3-yl)-hydroxy-(4-isopropyl-phenyl)-methyl]-pyridin-3-yl}-[1,2,4]oxadiazol-5-yl)piperidin-1-yl]-ethanone;

1-(4-{5-[(R)-(1,3-Dimethyl-azetidin-3-yl)-hydroxy-(4-isopropyl-phenyl)-methyl]-pyridin-3-ylethynyl}-piperidin-1-yl)-ethanone;

4-{5-[(R)-(1,3-Dimethyl-azetidin-3-yl)-hydroxy-(4-isopropyl-phenyl)-methyl]-pyridin-3-yl}-1,1,1-trifluoro-2-methyl-but-3-yn-2-ol;

Cyclopropanecarboxylic acid (3-{5-[(R)-(1,3-dimethyl-azetidin-3-yl)-hydroxy-(4-isopropyl-phenyl)-methyl]-pyridin-3-yl}-1,1-dimethyl-prop-2-ynyl)-amide;

N-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-isobutyramide;

N-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-2-methoxy-acetamide;

3-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-oxazolidin-2-one;

1-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-pyrrolidin-2-one;

1-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-3-methyl-imidazolidin-2-one;

1-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-imidazolidin-2-one;

3-(1-{5-[(R)-(1,3-Dimethyl-azetidin-3-yl)-hydroxy-(4-isopropyl-phenyl)-methyl]-pyridin-3-ylethynyl}-cyclopropyl)-oxazolidin-2-one; 1-((R)-2-{5-[(R)-(1,3-Dimethyl-azetidin-3-yl)-hydroxy-(4-isopropyl-phenyl)-methyl]-pyridin-3-ylethynyl}-2-methyl-pyrrolidin-1-yl)-ethanone;

1-(4-{5-[(R)-(1,3-Dimethyl-azetidin-3-yl)-hydroxy-(4-isopropyl-phenyl)-methyl]-pyridin-3-ylethynyl}-4-hydroxy-piperidin-1-yl)-ethanone;

1-[4-(3-{5-[(R)-(1,3-Dimethyl-azetidin-3-yl)-hydroxy-(4-isopropyl-phenyl)-methyl]-pyridin-3-yl}-1-hydroxy-1-methyl-prop-2-ynyl)-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}-1-hydroxy-prop-2-ynyl)-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}-prop-2-ynyl)-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}-1-hydroxy-prop-2-ynyl)-4-methyl-piperidin-1-yl]-ethanone;

1-(4-{5-[(R)-(1,3-Dimethyl-azetidin-3-yl)-hydroxy-(4-isopropyl-phenyl)-methyl]-pyridin-3-ylethynyl}-4-methyl-piperidin-1-yl)-ethanone;

(R)-(1,3-Dimethyl-azetidin-3-yl)-(4-isopropyl-phenyl)-[5-(1-methanesulfonyl-piperidin-4-ylethynyl)-pyridin-3-yl]-methanol;

4-{5-[(R)-(1,3-Dimethyl-azetidin-3-yl)-hydroxy-(4-isopropyl-phenyl)-methyl]-pyridin-3-ylethynyl}-4-methyl-piperidine-1-sulfonic acid methylamide;

(R)-(1,3-Dimethyl-azetidin-3-yl)-(4-isopropyl-phenyl)-[5-(3-methanesulfonyl-3-methyl-but-1-ynyl)-pyridin-3-yl]-methanol;

1-{5-[(R)-(1,3-Dimethyl-azetidin-3-yl)-hydroxy-(4-isopropyl-phenyl)-methyl]-pyridin-3-ylethynyl}-cyclopropane-sulfonic acid dimethylamide;

1-{5-[(R)-(1,3-Dimethyl-azetidin-3-yl)-hydroxy-(4-isopropyl-phenyl)-methyl]-pyridin-3-ylethynyl}-cyclopropane-sulfonic acid amide;

(R)-[5-(3-Cyclopropanesulfonyl-3-methyl-but-1-ynyl)-pyridin-3-yl]-(1,3-dimethyl-azetidin-3-yl)-(4-isopropyl-phenyl)-methanol;

(R)-3-{5-[(R)-(1,3-Dimethyl-azetidin-3-yl)-hydroxy-(4-isopropyl-phenyl)-methyl]-pyridin-3-ylethynyl}-3-hydroxy-1-methyl-pyrrolidin-2-one;

(S)-3-{5-[(R)-(1,3-Dimethyl-azetidin-3-yl)-hydroxy-(4-isopropyl-phenyl)-methyl]-pyridin-3-ylethynyl}-3-hydroxy-1-methyl-pyrrolidin-2-one;

4-{5-[(R)-(1,3-Dimethyl-azetidin-3-yl)-hydroxy-(4-isopropyl-phenyl)-methyl]-pyridin-3-ylethynyl}-3,4-dihydro-2H-pyrano[3,2-b]pyridin-4-ol;

3-{5-[(R)-(1,3-Dimethyl-azetidin-3-yl)-hydroxy-(4-isopropyl-phenyl)-methyl]-pyridin-3-ylethynyl}-3-hydroxy-1-methyl-1,3-dihydro-indol-2-one;

4-{5-[(R)-(1,3-Dimethyl-azetidin-3-yl)-hydroxy-(4-isopropyl-phenyl)-methyl]-pyridin-3-yl}-2-(1H-indazol-3-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(1-methyl-1H-indazol-3-yl)-but-3-yn-2-ol;

2-(1-Cyclopropyl-1H-pyrazol-3-yl)-4-{5-[(R)-(1,3-dimethyl-azetidin-3-yl)-hydroxy-(4-isopropyl-phenyl)-methyl]-pyridin-3-yl}-but-3-yn-2-ol;

4-{5-[(R)-(1,3-Dimethyl-azetidin-3-yl)-hydroxy-(4-isopropyl-phenyl)-methyl]-pyridin-3-yl}-2-(2-methyl-pyrimidin-4-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(5-methyl-pyrazin-2-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(2-methyl-thiazol-5-yl)-but-3-yn-2-ol;

2-(6-Cyclopropyl-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(6-methoxy-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(6-methoxy-pyrimidin-4-yl)-but-3-yn-2-ol;

N-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-acetamide;

(S)-4-{5-[(R)-(1,3-Dimethyl-azetidin-3-yl)-hydroxy-(4-isopropyl-phenyl)-methyl]-pyridin-3-yl}-2-(6-methoxy-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(6-methoxy-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(2-methoxy-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(2-methoxy-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(2-methoxy-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(2-methoxy-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(2,6-dimethyl-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(2,6-dimethyl-pyrimidin-4-yl)-but-3-yn-2-ol;

(R)-(8)-2-(2,6-Dimethoxy-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol;

(S)-2-(2,6-Dimethoxy-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol;

(R)-2-(2,6-Dimethoxy-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(2-methoxy-6-methyl-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(2-methoxy-6-methyl-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(6-methoxy-2-methyl-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(6-methoxy-2-methyl-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(6-methoxy-2-methyl-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(6-methoxy-2-methyl-pyrimidin-4-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(6-trifluoromethyl-pyrimidin-4-yl)-but-3-yn-2-ol;

2-(6-Difluoromethyl-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol;

(R)-(1,3-Dimethyl-azetidin-3-yl)-(4-isopropyl-phenyl)-[5-(1-pyridin-2-yl-cyclopropylethynyl)-pyridin-3-yl]-methanol;

(R)-(1,3-Dimethyl-azetidin-3-yl)-(4-isopropyl-phenyl)-{5-[1-(6-methyl-pyrimidin-4-yl)-cyclopropylethynyl]-pyridin-3-yl}-methanol;

1-[4-(2-{5-[(R)-(1,3-Dimethyl-azetidin-3-yl)-hydroxy-(4-isopropyl-phenyl)-methyl]-pyridin-3-yl}-ethyl)-piperidin-1-yl]-ethanone;

4-{5-[(R)-(1,3-Dimethyl-azetidin-3-yl)-hydroxy-(4-isopropyl-phenyl)-methyl]-pyridin-3-yl}-1,1,1-trifluoro-2-methyl-butan-2-ol;

3-(3-{5-[(R)-(1,3-Dimethyl-azetidin-3-yl)-hydroxy-(4-isopropyl-phenyl)-methyl]-pyridin-3-yl}-1,1-dimethyl-propyl)-oxazolidin-2-one;

1-(3-{5-[(R)-(1,3-Dimethyl-azetidin-3-yl)-hydroxy-(4-isopropyl-phenyl)-methyl]-pyridin-3-yl}-1,1-dimethyl-propyl)-pyrrolidin-2-one;

1-(3-{5-[(R)-(1,3-Dimethyl-azetidin-3-yl)-hydroxy-(4-isopropyl-phenyl)-methyl]-pyridin-3-yl}-1,1-dimethyl-propyl)-3-methyl-imidazolidin-2-one;

1-(3-{5-[(R)-(1,3-Dimethyl-azetidin-3-yl)-hydroxy-(4-isopropyl-phenyl)-methyl]-pyridin-3-yl}-1,1-dimethyl-propyl)-imidazolidin-2-one;

1-[(S)-2-(2-{5-[(R)-(1,3-Dimethyl-azetidin-3-yl)-hydroxy-(4-isopropyl-phenyl)-methyl]-pyridin-3-yl}-ethyl)-2-methyl-pyrrolidin-1-yl]-ethanone;

4-{5-[(R)-(1,3-Dimethyl-azetidin-3-yl)-hydroxy-(4-isopropyl-phenyl)-methyl]-pyridin-3-yl}-2-(1H-indazol-3-yl)-butan-2-ol;

2-(1-Cyclopropyl-1H-pyrazol-3-yl)-4-{5-[(R)-(1,3-dimethyl-azetidin-3-yl)-hydroxy-(4-isopropyl-phenyl)-methyl]-pyridin-3-yl}-butan-2-ol;

4-{5-[(R)-(1,3-Dimethyl-azetidin-3-yl)-hydroxy-(4-isopropyl-phenyl)-methyl]-pyridin-3-yl}-2-(2-methyl-pyrimidin-4-yl)-butan-2-ol;

4-{5-[(R)-(1,3-Dimethyl-azetidin-3-yl)-hydroxy-(4-isopropyl-phenyl)-methyl]-pyridin-3-yl}-2-(5-methyl-pyrazin-2-yl)-butan-2-ol;

4-{5-[(R)-(1,3-Dimethyl-azetidin-3-yl)-hydroxy-(4-isopropyl-phenyl)-methyl]-pyridin-3-yl}-2-(2-methyl-thiazol-5-yl)-butan-2-ol;

4-{5-[(R)-(1,3-Dimethyl-azetidin-3-yl)-hydroxy-(4-isopropyl-phenyl)-methyl]-pyridin-3-yl}-2-(3-methyl-isoxazol-5-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(1-methyl-1H-imidazol-2-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(5-methyl-thiophen-2-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(1-methyl-1H-pyrrol-2-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(2-trifluoromethyl-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(2-trifluoromethyl-pyrimidin-4-yl)-but-3-yn-2-ol;

(S)-(R)-4-{5-[(R)-(1,3-Dimethyl-azetidin-3-yl)-hydroxy-(4-isopropyl-phenyl)-methyl]-pyridin-3-yl}-2-(2-trifluoromethyl-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(2-trifluoromethyl-pyrimidin-4-yl)-but-3-yn-2-ol;

4-(5-{(R)-(1,3-Dimethyl-azetidin-3-yl)-hydroxy-[4-(1-trifluoromethyl-cyclopropyl)-phenyl]-methyl}-pyridin-3-yl)-2-(6-methyl-pyridin-2-yl)-but-3-yn-2-ol;

4-(5-{(R)-(1,3-Dimethyl-azetidin-3-yl)-hydroxy-[4-(1-methyl-cyclopropyl)-phenyl]-methyl}-pyridin-3-yl)-2-(6-methyl-pyridin-2-yl)-but-3-yn-2-ol;

4-{5-[(R)-(1,3-Dimethyl-azetidin-3-yl)-hydroxy-(4-trifluoromethyl-phenyl)-methyl]-pyridin-3-yl}-2-(6-methyl-pyridin-2-yl)-but-3-yn-2-ol;

4-{5-[(R)-(1,3-Dimethyl-azetidin-3-yl)-(4-ethyl-phenyl)-hydroxy-methyl]-pyridin-3-yl}-2-(6-methyl-pyridin-2-yl)-but-3-yn-2-ol;

4-{5-[(R)-(4-tert-Butyl-phenyl)-(1,3-dimethyl-azetidin-3-yl)-hydroxy-methyl]-pyridin-3-yl}-2-(6-methyl-pyridin-2-yl)-but-3-yn-2-ol;

4-{5-[(R)-(3-Ethyl-1-methyl-azetidin-3-yl)-hydroxy-(4-trifluoromethoxy-phenyl)-methyl]-pyridin-3-yl}-2-(6-methyl-pyridin-2-yl)-but-3-yn-2-ol;

4-(5-{(R)-(1,3-Dimethyl-azetidin-3-yl)-hydroxy-[4-(2,2,2-trifluoro-ethyl)-phenyl]-methyl}-pyridin-3-yl)-2-(6-methyl-pyridin-2-yl)-but-3-yn-2-ol;

4-{5-[(S)-(3-Fluoro-1-methyl-azetidin-3-yl)-hydroxy-(4-isopropyl-phenyl)-methyl]-pyridin-3-yl}-2-(6-methyl-pyridin-2-yl)-but-3-yn-2-ol;

1-(4-{5-[(R)-(1,3-Dimethyl-azetidin-3-yl)-hydroxy-(4-isopropyl-phenyl)-methyl]-pyridazin-3-ylethynyl}-piperidin-1-yl)-ethanone;

N-(3-{5-[(R)-(1,3-Dimethyl-azetidin-3-yl)-hydroxy-(4-isopropyl-phenyl)-methyl]-pyridazin-3-yl}-1,1-dimethyl-prop-2-ynyl)-acetamide;

1-(3-{5-[(R)-(1,3-Dimethyl-azetidin-3-yl)-hydroxy-(4-isopropyl-phenyl)-methyl]-pyridazin-3-yl}-1,1-dimethyl-prop-2-ynyl)-pyrrolidin-2-one;

4-{5-[(R)-Hydroxy-(1-isopropyl-3-methyl-azetidin-3-yl)-(4-isopropyl-phenyl)-methyl]-pyridin-3-yl}-2-(6-methyl-pyridin-2-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(6-methyl-pyridin-2-yl)-but-3-yn-2-ol;

4-{5-[(R)-Hydroxy-[1-(2-hydroxy-ethyl)-3-methyl-azetidin-3-yl]-(4-isopropyl-phenyl)-methyl]-pyridin-3-yl}-2-(6-methyl-pyridin-2-yl)-but-3-yn-2-ol;

4-{5-[(R)-[1-(2,2-Difluoro-ethyl)-3-methyl-azetidin-3-yl]-hydroxy-(4-isopropyl-phenyl)-methyl]-pyridin-3-yl}-2-(6-methyl-pyridin-2-yl)-but-3-yn-2-ol;

1-(4-{5-[(R)-(1,3-Dimethyl-azetidin-3-yl)-hydroxy-(4-isopropyl-phenyl)-methyl]-pyridin-3-yloxymethyl}-piperidin-1-yl)-ethanone;

4-{5-[(R)-(1-Cyclopropyl-3-methyl-azetidin-3-yl)-hydroxy-(4-isopropyl-phenyl)-methyl]-pyridin-3-yl}-2-(6-methyl-pyridin-2-yl)-but-3-yn-2-ol;

1-{5-[(R)-(1,3-Dimethyl-azetidin-3-yl)-hydroxy-(4-isopropyl-phenyl)-methyl]-pyridin-3-yl}-4-(2-isopropyl-pyrimidin-4-yl)-pyrrolidin-2-one;

1-{5-[(R)-(1,3-Dimethyl-azetidin-3-yl)-hydroxy-(4-isopropyl-phenyl)-methyl]-pyridin-3-yl}-4-(2-methyl-thiazol-5-yl)-pyrrolidin-2-one;

1-{5-[(R)-(1,3-Dimethyl-azetidin-3-yl)-hydroxy-(4-isopropyl-phenyl)-methyl]-pyridin-3-yl}-4-(6-methyl-pyridin-3-yl)-pyrrolidin-2-one;

1-{5-[(R)-(1,3-Dimethyl-azetidin-3-yl)-hydroxy-(4-isopropyl-phenyl)-methyl]-pyridin-3-yl}-4-(6-isopropyl-pyridin-2-yl)-pyrrolidin-2-one;

1-{5-[(R)-(1,3-Dimethyl-azetidin-3-yl)-hydroxy-(4-isopropyl-phenyl)-methyl]-pyridin-3-yl}-4-(6-trifluoromethyl-pyridin-3-yl)-pyrrolidin-2-one;

1-{5-[(R)-(1,3-Dimethyl-azetidin-3-yl)-hydroxy-(4-isopropyl-phenyl)-methyl]-pyridin-3-yl}-4-(1-methyl-1H-pyrazol-4-yl)-pyrrolidin-2-one;

1-{5-[(R)-(1,3-Dimethyl-azetidin-3-yl)-hydroxy-(4-isopropyl-phenyl)-methyl]-pyridin-3-yl}-4-(1,3-dimethyl-1H-pyrazol-4-yl)-pyrrolidin-2-one;

4-(1-Difluoromethyl-1H-pyrazol-4-yl)-1-{5-[(R)-(1,3-dimethyl-azetidin-3-yl)-hydroxy-(4-isopropyl-phenyl)-methyl]-pyridin-3-yl}-pyrrolidin-2-one;

1-{5-[(R)-(1,3-Dimethyl-azetidin-3-yl)-hydroxy-(4-isopropyl-phenyl)-methyl]-pyridin-3-yl}-4-(2-methyl-2H-[1,2,3]triazol-4-yl)-pyrrolidin-2-one;

4-(1-Acetyl-piperidin-4-yl)-1-{5-[(R)-(1,3-dimethyl-azetidin-3-yl)-hydroxy-(4-isopropyl-phenyl)-methyl]-pyridazin-3-yl}-pyrrolidin-2-one;

5-{5-[(R)-(1,3-Dimethyl-azetidin-3-yl)-hydroxy-(4-isopropyl-phenyl)-methyl]-pyridazin-3-yl}-hexahydro-furo[2,3-c]pyrrol-4-one;

1-{5-[(R)-(1,3-Dimethyl-azetidin-3-yl)-hydroxy-(4-isopropyl-phenyl)-methyl]-pyridazin-3-yl}-4-(6-isopropyl-pyridin-2-yl)-pyrrolidin-2-one;

1-(2-{5-[(R)-(1,3-Dimethyl-azetidin-3-yl)-hydroxy-(4-isopropyl-phenyl)-methyl]-pyridin-3-yl}-7,8-dihydro-5H-pyrido[4,3-d]pyrimidin-6-yl)-ethanone;

1-(2-{5-[(R)-(1,3-Dimethyl-azetidin-3-yl)-hydroxy-(4-isopropyl-phenyl)-methyl]-pyridin-3-yl}-7,8-dihydro-5H-[1,6]naphthyridin-6-yl)-ethanone;

1-[4-(2-{5-[(R)-(1,3-Dimethyl-azetidin-3-yl)-hydroxy-(4-isopropyl-phenyl)-methyl]-pyridin-3-yl}-pyrimidin-5-yl)-piperidin-1-yl]-ethanone; and 1-[4-(2-{5-[(R)-(1,3-Dimethyl-azetidin-3-yl)-hydroxy-(4-isopropyl-phenyl)-methyl]-pyridin-3-yl}-pyrimidin-4-yl)-piperidin-1-yl]-ethanone.

35) Another embodiment relates to a compound according to embodiment 1) selected from a group consisting of (R)-2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1,1-trifluoro-propan-2-ol;

2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-propan-2-ol;

2-(3-{5-[(S)-(1-Cyclopropyl-3-fluoro-azetidin-3-yl)-hydroxy-(4-isopropyl-phenyl)-methyl]-pyridin-3-yl}-[1,2,4]oxadiazol-5-yl)-propan-2-ol; and 2-(3-{5-[(R)-(4-Butyl-phenyl)-(1,3-dimethyl-azetidin-3-yl)-hydroxy-methyl]-pyridin-3-yl}-[1,2,4]oxadiazol-5-yl)-propan-2-ol.

36) Another embodiment relates to a compound according to embodiment 1) selected from a group consisting of 4-{5-[(R)-Hydroxy-[1-(2-hydroxy-ethyl)-3-methyl-azetidin-3-yl]-(4-isopropyl-phenyl)-methyl]-pyridin-3-yl}-2-(6-methyl-pyridin-2-yl)-but-3-yn-2-ol;

4-{5-[(R)-(1,3-Dimethyl-azetidin-3-yl)-hydroxy-(4-trifluoromethyl-phenyl)-methyl]-pyridin-3-yl}-2-(6-methyl-pyridin-2-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-but-3-yn-2-ol; and 4-{5-[(R)-(1,3-Dimethyl-azetidin-3-yl)-(4-ethyl-phenyl)-hydroxy-methyl]-pyridin-3-yl}-2-(6-methyl-pyridin-2-yl)-but-3-yn-2-ol.

37) Another embodiment relates to a compound according to embodiment 1) selected from a group consisting of 1-[4-(3-{5-[(R)-(1-Cyclopropyl-3-methyl-azetidin-3-yl)-hydroxy-(4-isopropyl-phenyl)-methyl]-pyridin-3-yl}-[1,2,4]oxadiazol-5-yl)-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-ethanone;

1-[4-(3-{5-[(R)-(1,3-Dimethyl-azetidin-3-yl)-hydroxy-(4-propyl-phenyl)-methyl]-pyridin-3-yl}-[1,2,4]oxadiazol-5-yl)-piperidin-1-yl]-ethanone; and 1-[4-(3-{5-[(R)-Hydroxy-(1-isopropyl-3-methyl-azetidin-3-yl)-(4-isopropyl-phenyl)-methyl]-pyridin-3-yl}-[1,2,4]oxadiazol-5-yl)-piperidin-1-yl]-ethanone.

38) Another aspect of the present invention relates to compounds of embodiment 1), which are also compounds of formula (Ip), wherein Formula (Ip)

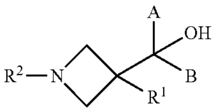

A represents a 6-membered heteroaryl containing from one to three ring nitrogen atom(s) (notably one or two ring nitrogen atoms; especially one or two ring nitrogen atoms in meta-position(s) and/or para-position of A with respect to the point of attachment of A to the rest of the molecule), wherein said 6-membered heteroaryl is independently unsubstituted, mono-, di- or tri-substituted (notably mono- or di-substituted in meta- and/or para-position of A with respect to the point of attachment of A to the rest of the molecule), wherein the substituent(s), if any, is(are) independently selected from

- halogen (especially fluorine);
- cyano;
- $C_{1-4}$-alkyl (notably methyl, ethyl, propyl, or isopropyl; especially methyl, ethyl, or propyl) which is unsubstituted or mono-substituted with
  - $C_{1-3}$-alkoxy (especially methoxy);
  - fluoro-phenoxy (especially 4-fluoro-phenoxy);
  - benzyl-oxy;
  - $C_{3-6}$-cycloalkyl which is optionally fused with a pyridine ring (notably at positions 2 and 3 adjacent to the nitrogen atom of said pyridine ring), wherein said $C_{3-6}$-cycloalkyl is unsubstituted or mono-substituted with hydroxy (notably at the point of attachment of the $C_{3-6}$-cycloalkyl to the $C_{1-4}$-alkyl);
  - pyrazolyl (notably pyrazol-4-yl) which is unsubstituted or mono-substituted with $C_{1-3}$-alkyl (especially methyl);
  - tetrahydropyranyl (notably tetrahydropyran-4-yl) which is unsubstituted or mono-substituted with hydroxy (especially 4-hydroxy-tetrahydropyran-4-yl);
  - indolyl (especially indol-2-yl);
  - N—($C_{1-3}$-alkyl)-amino-carbonyl-oxy; or
  - 1-($C_{1-4}$-alkyl-oxy-carbonyl)-3-hydroxyazetidin-3-yl;
- [in particular such $C_{1-4}$-alkyl which is unsubstituted or mono-substituted as defined above is methyl, ethyl, isopropyl, 2-(1-hydroxy-cyclopropyl)-ethyl, 2-(1-hydroxy-cyclobutyl)-ethyl, 2-(1-hydroxy-cyclopentyl)-ethyl, 3-methoxy-propyl, 4-fluoro-phenoxy-methyl, benzyl-oxy-methyl, N-(isopropyl)-amino-carbonyl-oxy-methyl, 2-(1-(tert-butoxy-carbonyl)-3-hydroxyazetidin-3-yl)-ethyl, 2-(1-methyl-pyrazol-4-yl)-ethyl, 2-(tetrahydropyran-4-yl)-ethyl, 2-(4-hydroxy-tetrahydropyran-4-yl)-ethyl, 2-(indol-2-yl)-ethyl, 2-(8-hydroxy-5,6,7,8-tetrahydroquinolin-8-yl)-ethyl, or 2-(7-hydroxy-6,7-dihydro-5H-cyclopenta[b]pyridin-7-yl)-ethyl]
- $C_{3-5}$-alkenyl which is unsubstituted (especially isopropenyl) or mono-substituted with hydroxy (especially 4-hydroxy-but-1-en-2-yl);

tetrahydropyranyl (especially tetrahydropyran-4-yl);

hydroxy-$C_{1-6}$-alkyl which is optionally further substituted with one or more fluorine atoms (especially 3-hydroxy-propyl, 4-hydroxy-butyl, 3-hydroxy-butyl, 3-hydroxy-3-methyl-butyl, 3-hydroxy-4-methyl-pentyl, or 2,2-difluoro-3-hydroxy-prop-1-yl);

$C_{3-5}$-alkyl (especially n-propyl, n-butyl, or n-pentyl) which is substituted with hydroxy and $R^{A1}$ (notably both substituents at position 3 with respect to the point of attachment of said $C_{3-5}$-alkyl to the rest of the molecule), wherein $R^{A1}$ represents tetrahydropyranyl (especially tetrahydropyran-4-yl);

phenyl which is unsubstituted or mono-substituted with fluorine (especially 3-fluoro-phenyl) or $C_{1-3}$-alkoxy (especially 2-methoxy-phenyl or 4-methoxy-phenyl); or 5- or 6-membered heteroaryl containing one or two ring heteroatom(s) being independently selected from nitrogen or sulfur (notably thiazolyl, pyrazolyl, pyridinyl, or pyrimidinyl; especially thiazol-4-yl, pyrazol-3-yl, pyrazol-4-yl, pyridin-2-yl, pyrimidin-2-yl, or pyrimidin-4-yl), wherein said 5- or 6-membered heteroaryl is independently unsubstituted, mono- or di-substituted, and wherein the substituent(s), if any, is(are) independently selected from $C_{1-3}$-alkyl (especially methyl) or $C_{1-3}$-alkoxy (especially methoxy);

[in particular such $C_{3-5}$-alkyl which is substituted as defined above is 3-hydroxy-3-(tetrahydropyran-4-yl)-propyl, 3-hydroxy-3-phenyl-propyl, 3-hydroxy-3-phenyl-butyl, 3-hydroxy-3-(m-fluoro-phenyl)-butyl, 3-hydroxy-3-(o-methoxy-phenyl)-butyl, 3-hydroxy-3-(p-methoxy-phenyl)-butyl, 3-hydroxy-3-(1,5-dimethyl-pyrazol-3-yl)-butyl, 3-hydroxy-3-(1-methyl-pyrazol-3-yl)-butyl, 3-hydroxy-3-(1,5-dimethyl-pyrazol-3-yl)-propyl, 3-hydroxy-3-(2-methyl-thiazol-4-yl)-butyl, 3-hydroxy-3-(6-methoxy-pyridin-2-yl)-butyl, 3-hydroxy-3-(pyrimidin-2-yl)-butyl, 3-hydroxy-3-(6-methoxy-pyrimidin-4-yl)-butyl, 3-hydroxy-3-(1,3-dimethyl-pyrazol-4-yl)-propyl, 3-hydroxy-3-(2-methyl-thiazol-4-yl)-propyl, 3-hydroxy-3-(pyridin-2-yl)-pentyl, or 3-hydroxy-3-(6-methoxy-pyridin-2-yl)-pentyl]

$C_{3-6}$-cycloalkyl which is unsubstituted, mono-, or di-substituted with $C_{1-3}$-alkyl (especially methyl, ethyl, isopropyl), hydroxy or hydroxy-$C_{1-3}$-alkyl (especially 1-hydroxy-1-methyl-ethyl), wherein optionally one ring carbon atom of said $C_{3-6}$-cycloalkyl is replaced by an oxygen atom;

[in particular such $C_{3-6}$-cycloalkyl which is unsubstituted, mono-, or di-substituted as defined above is cyclopropyl, cyclopentyl, 3-hydroxy-cyclopentyl, 3-hydroxy-3-methyl-cyclopentyl, 3-hydroxy-3-ethyl-cyclopentyl, 3-hydroxy-3-isopropyl-cyclopentyl, 2-(2-hydroxy-isopropyl)-cyclopropyl, 4-hydroxy-4-methyl-cyclohextyl, tetrahydrofuran-3-yl, tetrahydrofuran-2-yl, tetrahydropyran-4-yl, 5-methyl-tetrahydrofuran-2-yl, or 5,5-dimethyl-tetrahydrofuran-2-yl]

$C_{4-6}$-cycloalkenyl (notably cyclopentenyl; especially cyclopent-1-en-1-yl) which is unsubstituted, mono-, or di-substituted with $C_{1-3}$-alkyl, oxo (i.e. =O), or hydroxy, wherein optionally one ring carbon atom of said $C_{4-6}$-cycloalkenyl is replaced by an oxygen atom;

[in particular such $C_{4-6}$-cycloalkenyl which is unsubstituted, mono-, or di-substituted as defined above is 3-oxo-cyclopent-1-en-1-yl, 3-hydroxy-3-methyl-cyclopent-1-en-1-yl, 2,3-dihydro-furan-3-yl, or 5-methyl-furan-2-yl]

—O—$R^O$, wherein $R^O$ represents $C_{1-4}$-alkyl (especially methyl, ethyl, isopropyl, sec-butyl, or isobutyl);

hydroxy-$C_{1-6}$-alkyl (especially 2-hydroxy-ethyl, 3-hydroxy-propyl, 2-hydroxy-2-methyl-propyl, or 3-hydroxy-3-methyl-butyl);

$C_{1-3}$-alkoxy-$C_{2-3}$-alkyl (especially 2-methoxy-ethyl);

$C_{3-6}$-cycloalkyl (especially cyclopentyl or cyclohexyl) which is unsubstituted, mono-, or di-substituted with $C_{1-3}$-alkyl (especially methyl), hydroxy or $C_{1-3}$-alkoxy (especially methoxy);

tetrahydropyranyl (especially tetrahydropyran-4-yl);

tetrahydropyranyl-$C_{1-3}$-alkyl (especially tetrahydropyran-4-yl-methyl);

oxetanyl-$C_{1-3}$-alkyl (especially oxetan-3-yl-methyl);

phenyl;

benzyl;

benzyl-oxy-$C_{1-3}$-alkyl (especially 2-(benzyl-oxy)-ethyl);

pyridinyl-$C_{1-3}$-alkyl (especially 2-(pyridin-2-yl)-ethyl);

(3-cyclopropyl-1,2,4-oxadiazol-5-yl)-methyl; or 2-(3,5-dimethyl-1,2,4-triazol-1-yl)-ethyl;

[in particular such —O—$R^O$ is methoxy, ethoxy, isopropoxy, isobutoxy, sec-butoxy, phenoxy, benzyloxy, 2-(benzyloxy)-ethoxy, 2-methoxy-ethoxy, oxetan-3-yl-methoxy, 3-hydroxy-propoxy, cyclohexyl-oxy, 4-hydroxy-cyclohexyl-oxy, 4-methyl-4-hydroxy-cyclohexyl-oxy, 2-hydroxy-2-methyl-propoxy, 2-hydroxy-ethoxy, 3-hydroxy-3-methyl-butoxy, tetrahydropyran-4-yl-oxy, tetrahydropyran-4-yl-methoxy, 3-methoxy-cyclopentyl-oxy, (3-cyclopropyl-1,2,4-oxadiazol-5-yl)-methoxy, or 2-(3,5-dimethyl-1,2,4-triazol-1-yl)-ethoxy]

—C≡C—$R^{T1}$, wherein $R^{T1}$ represents hydroxy-$C_{1-4}$-alkyl (especially hydroxy-methyl, 1-hydroxy-ethyl, 2-hydroxy-ethyl, 1-hydroxy-2-methyl-propyl, or 1-hydroxy-1-methyl-ethyl);

$C_{1-3}$-alkoxy-$C_{1-3}$-alkyl (especially methoxy-methyl);

$C_{3-6}$-cycloalkyl which is mono-substituted with hydroxy (notably at the point of attachment of the $C_{3-6}$-cycloalkyl to the rest of the molecule; especially 1-hydroxy-cyclopropyl, 1-hydroxy-cyclobutyl, or 1-hydroxy-cyclopentyl);

$C_{3-6}$-cycloalkyl (notably cyclopentyl or cyclohexyl) fused with a pyridine ring (notably at positions 2 and 3 of the pyridine ring), wherein said $C_{3-6}$-cycloalkyl is mono-substituted with hydroxy (notably at position 1 of the $C_{3-6}$-cycloalkyl ring) (especially 8-hydroxy-5,6,7,8-tetrahydroquinolin-8-yl or 7-hydroxy-6,7-dihydro-5H-cyclopenta[b]pyridin-7-yl);

pyrazolyl (notably pyrazol-4-yl) which is mono-substituted with methyl (especially 1-methyl-pyrazol-4-yl);

tetrahydropyranyl (especially tetrahydropyran-4-yl) which is unsubstituted or mono-substituted with hydroxy (especially 4-hydroxy-tetrahydro-pyran-4-yl);

indolyl (notably indol-2-yl); or hydroxy-azetidinyl (notably 3-hydroxy-azetidin-3-yl) which is N-substituted with $C_{1-4}$-alkoxy-carbonyl (especially isopropyl-carbonyl or tert-butoxy-carbonyl);

[in particular such —C≡C—$R^{T1}$ is 3-hydroxy-prop-1-yn-1-yl, 4-hydroxy-but-1-yn-1-yl, 3-hydroxy-but-1-yn-1-yl, 3-hydroxy-3-methyl-but-1-yn-1-yl, 3-hydroxy-4-methyl-pent-1-yn-1-yl, 3-methoxy-prop-1-yn-1-yl, (1-hydroxy-cyclopropyl)-ethynyl, (1-hydroxy-cyclobutyl)-ethynyl, (1-hydroxy-cyclopentyl)-ethynyl, (8-hydroxy-5,6,7,8-tetrahydroquinolin-8-yl)-ethynyl, (7-hydroxy-6,7-dihydro-5H-cyclopenta[b]pyridin-7-yl)-ethynyl, (1-methyl-pyrazol-4-yl)-ethynyl, (tetrahydropyran-4-yl)-ethynyl, (4-hydroxy-tetrahydropyran-4-yl)-ethynyl, indol-2-yl-ethynyl, (1-(isopropyl-carbonyl)-3-hydroxy-azetidin-3-yl)-ethynyl, or (1-(tert-butoxy-carbonyl)-3-hydroxy-azetidin-3-yl)-ethynyl]

—C≡C—C(OH)($R^{T2}$)($R^{T3}$), wherein $R^{T2}$ represents hydrogen or $C_{1-3}$-alkyl (especially methyl or ethyl);

$R^{T3}$ represents phenyl which is unsubstituted or mono-substituted, wherein the substituent(s), if any, is(are) independently selected from $C_{1-3}$-alkoxy (notably methoxy) or halogen (notably fluorine);

[in particular such phenyl which is unsubstituted or mono-substituted is 3-fluoro-phenyl, 4-methoxy-phenyl, or 2-methoxy-phenyl]

5- to 6-membered heteroaryl containing one or two ring heteroatom(s) being independently selected from nitrogen or sulfur (notably thiazolyl, pyrazolyl, pyridinyl, or pyrimidinyl; especially thiazol-4-yl, pyrazol-3-yl, pyrazol-4-yl, pyridin-2-yl, pyrimidin-2-yl, or pyrimidin-4-yl), wherein said 5- or 6-membered heteroaryl is independently unsubstituted, mono- or di-substituted, and wherein the substituent(s), if any, is(are) independently selected from $C_{1-3}$-alkyl (especially methyl) and $C_{1-3}$-alkoxy (especially methoxy); or

[in particular such 5- to 6-membered heteroaryl is 1-methyl-pyrazol-3-yl, 1,3-dimethyl-pyrazol-4-yl, 1,5-dimethyl-pyrazol-3-yl, 2-methyl-thiazol-4-yl, pyridin-2-yl, 6-methoxy-pyridin-2-yl, pyrimidin-2-yl, pyrimidin-4-yl, or 1,5-dimethyl-pyrazol-3-yl]

tetrahydropyranyl (especially tetrahydropyran-4-yl);

[in particular such —C≡C—C(OH)($R^{T2}$)($R^{T3}$) is 3-hydroxy-3-(tetrahydropyran-4-yl)-prop-1-yn-1-yl, 3-hydroxy-3-phenyl-prop-1-yn-1-yl, 3-hydroxy-3-(2-methyl-thiazol-4-yl)-prop-1-yn-1-yl, 3-hydroxy-3-(1,3-dimethyl-pyrazol-4-yl)-prop-1-yn-1-yl, 3-hydroxy-3-phenyl-but-1-yn-1-yl, 3-hydroxy-3-(1-methyl-pyrazol-3-yl)-but-1-yn-1-yl, 3-hydroxy-3-(1,5-dimethyl-pyrazol-3-yl)-but-1-yn-1-yl, 3-hydroxy-3-(1-methyl-pyrazol-3-yl)-but-1-yn-1-yl, 3-hydroxy-3-(pyrimidin-2-yl)-but-1-yn-1-yl, 3-hydroxy-3-(1-methyl-pyrazol-3-yl)-but-1-yn-1-yl, 3-hydroxy-3-(3-fluoro-phenyl)-but-1-yn-1-yl, 3-hydroxy-3-(6-methyl-pyrimidin-4-yl)-but-1-yn-1-yl, 3-hydroxy-3-(pyridin-2-yl)-pent-1-yn-1-yl, 3-hydroxy-3-(6-methoxy-pyridin-2-yl)-but-1-yn-1-yl, 3-hydroxy-3-(6-methoxy-pyridin-2-yl)-pent-1-yn-1-yl, 3-hydroxy-3-(4-methoxy-phenyl)-but-1-yn-1-yl, or 3-hydroxy-3-(2-methoxy-phenyl)-but-1-yn-1-yl]

—$NR^{N1}R^{N2}$ wherein $R^{N1}$ represents $C_{1-3}$-alkyl (especially methyl);

$R^{N2}$ represents hydroxy-$C_{1-3}$-alkyl (especially 2-hydroxy-ethyl) or 2-(benzyl-oxy)-$C_{1-3}$-alkyl (especially 2-(benzyl-oxy)-ethyl);

or $R^{N1}$ and $R^{N2}$ form, together with the nitrogen to which they are attached, a heterocyclic ring of 4 to 6 members (notably 5 to 6 members), wherein the members needed to complete said heterocyclic ring are each independently selected from —$CH_2$—, —O—, —(C═O)—, —$CHR^X$— and —$C(R^Y)_2$—; wherein said heterocyclic ring does not contain more than one member independently selected from the group consisting of —O— and —(C═O)—; wherein said heterocyclic ring does not contain more than two members selected from the group consisting of —$CHR^X$—; and wherein said heterocyclic ring does not contain more than two members selected from the group consisting of —$C(R^Y)_2$—; wherein $R^X$ independently represents fluorine, methyl, isopropyl, isobutyl, tert-butyl, hydroxy, trifluoromethyl, hydroxy-methyl, 1-hydroxy-ethyl, 1-hydroxy-1-methyl-ethyl, cyclopropyl, 2-methoxy-ethyl, 4-methyl-thiazol-2-yl, phenyl, benzyl, tetrahydropyran-4-yl, 1,2,4-oxadiazolyl, 3-methyl-1,2,4-oxadiazol-5-yl, pyridin-2-yl, or 1-methoxy-methyl; and wherein $R^Y$ independently represents fluorine, hydroxy, cyclopropyl, methyl, hydroxy-methyl, or trifluoromethyl [notably such —$NR^{N1}R^{N2}$ is pyrrolidinyl; 2-pyrrolidonyl; oxazolidinonyl (especially 1,3-oxazolidin-2-on-3-yl); piperidinyl; or morpholinyl, optionally independently substituted with one or two substituents independently selected from a group consisting of $R^X$ and $R^Y$];

[in particular such —$NR^{N1}R^{N2}$ is pyrrolidin-1-yl, 3-fluoro-pyrrolidin-1-yl, 3,3-difluoro-pyrrolidin-1-yl, 3,4-difluoro-pyrrolidin-1-yl, 3-isopropyl-pyrrolidin-1-yl, 3,3-dimethyl-pyrrolidin-1-yl, 3-hydroxy-pyrrolidin-1-yl, 2-methyl-pyrrolidin-1-yl, 3-hydroxy-3-methyl-pyrrolidin-1-yl, 3-(hydroxy-methyl)-pyrrolidin-1-yl, 2-(hydroxy-methyl)-pyrrolidin-1-yl, 3-(1-hydroxy-ethyl)-pyrrolidin-1-yl, 3-hydroxy-3-cyclopropyl-pyrrolidin-1-yl, 3-hydroxy-3-trifluoromethyl-pyrrolidin-1-yl, 3-trifluoromethyl-pyrrolidin-1-yl, 3-(1-hydroxy-1-methyl-ethyl)-pyrrolidin-1-yl, 3-(1-hydroxy-ethyl)-pyrrolidin-1-yl, 3-(hydroxy-methyl)-3-methyl-pyrrolidin-1-yl, 1,3-oxazolidin-2-on-3-yl, 5-(tert-butyl)-1,3-oxazolidin-2-on-3-yl, 5-phenyl-1,3-oxazolidin-2-on-3-yl, 5-benzyl-1,3-oxazolidin-2-on-3-yl, 5-isopropyl-1,3-oxazolidin-2-on-3-yl, 5-(tetrahydropyran-4-yl)-1,3-oxazolidin-2-on-3-yl, 5,5-dimethyl-1,3-oxazolidin-2-on-3-yl, morpholin-4-yl, piperidin-1-yl, 4-hydroxy-piperidin-1-yl, 3-hydroxy-piperidin-1-yl, 3-(tetrahydropyran-4-yl)-pyrrolid-2-on-1-yl, N-methyl-N-(2-(benzyl-oxy)-ethyl)-amino, N-methyl-N-(2-hydroxy-ethyl)-amino, pyrrolid-2-on-1-yl, 4-phenyl-pyrrolid-2-on-1-yl, 4-isopropyl-pyrrolid-2-on-1-yl, 3-isopropyl-pyrrolid-2-on-1-yl, 4,4-dimethyl-pyrrolid-2-on-1-yl, 3-(piperidin-4-yl)-pyrrolid-2-on-1-yl, 4-isobutyl-pyrrolid-2-on-1-yl, 4-cyclopropyl-pyrrolid-2-on-1-yl, 4-trifluoromethyl-pyrrolid-2-on-1-yl, 3-(2-methoxy-ethyl)-pyrrolid-2-on-1-yl, 4-(2-methoxy-ethyl)-pyrrolid-2-on-1-yl, 2,2,6,6-tetrafluoro-morpholin-4-yl, 2,6-dimethyl-morpholin-4-yl, 2-(methoxy-methyl)-morpholin-4-yl, 3-(3-methyl-1,2,4-oxadiazol-5-yl)-pyrrolidin-1-yl, 3-(4-methyl-thiazol-2-yl)-pyrrolidin-1-yl, or 3-(phenyl)-pyrrolidin-1-yl]

—(C═O)—N($R^{N3}$)($R^{N4}$), wherein $R^{N3}$ represents hydrogen; and $R^{N4}$ represents $C_{3-6}$-cycloalkyl (especially cyclopentyl) or tetrahydropyranyl (especially tetrahydro-pyran-4-yl); or $R^{N3}$ and $R^{N4}$ form, together with the nitrogen to which they are attached, pyrrolidinyl;

[in particular such —(C═O)—N($R^{N3}$)($R^{N4}$) is N-cyclopentyl-amino-carbonyl, N-(tetrahydropyran-4-yl)-amino-carbonyl, or pyrrolidinyl-carbonyl]

piperidin-4-yl or pyrrolidin-3-yl which independently are mono-substituted at the nitrogen ring atom, wherein the substituent is selected from $C_{1-4}$-alkoxy-carbonyl (especially tert-butoxy-carbonyl), pyridinyl (especially pyridin-2-yl), phenyl and (4-methylphenyl)-sulfonyl;

[in particular such piperidin-4-yl or pyrrolidin-3-yl are N-(tert-butoxy-carbonyl)piperidin-4-yl, N-(tert-butoxy-carbonyl)-pyrrolidin-3-yl, N-(pyridin-2-yl)-piperidin-4-yl, N-(phenyl)-piperidin-4-yl, or N-((4-methylphenyl)-sulfonyl)-piperidin-4-yl]

5-membered heteroaryl containing from one to three (notably two or three; especially three) ring heteroatom(s) independently selected from nitrogen, oxygen and sulfur (notably pyrazolyl, triazolyl, oxazolyl, thiazolyl, oxadiazolyl; especially pyrazol-1-yl, 1,2,3-triazol-1-yl, oxazol-2-yl, thiazol-2-yl, 1,2,4-oxadiazol-5-yl or 1,2,4-oxadiazol-3-yl); wherein said 5-membered heteroaryl is independently unsubstituted, mono-, di-, or tri-substituted (notably mono-substituted; especially mono-substituted in position 3 with respect to the point of attachment of said 5-membered heteroaryl to A), wherein the substituent(s), if any, is(are) independently selected from $C_{1-4}$-alkyl which is unsubstituted or mono-substituted with hydroxy or $C_{1-4}$-alkoxy (especially methoxy and tert-butoxy);

[in particular such $C_{1-4}$-alkyl which is unsubstituted or mono-substituted as defined above is methyl, 1-hydroxy-1-methyl-ethyl, 2-hydroxy-2-methyl-propyl, 2-hydroxy-1,1-dimethyl-ethyl, methoxy-methyl, 2-methoxy-ethyl, 1-methoxy-1-methyl-ethyl, 2-methoxy-2-methyl-propyl, 2-methoxy-1,1-dimethyl-ethyl, tert-butoxy-methyl; preferably such $C_{1-4}$-alkyl group is 1-hydroxy-1-methyl-ethyl, 2-hydroxy-2-methyl-propyl, or 2-hydroxy-1,1-dimethyl-ethyl]

amino-$C_{1-4}$-alkyl (especially 2-amino-ethyl or 2-amino-2,2-dimethyl-ethyl), wherein the amino group is mono- or di-substituted (especially mono-substituted) with $C_{1-3}$-alkyl (especially methyl), $C_{1-3}$-alkyl-carbonyl including deuterated $C_{1-3}$-alkyl-carbonyl (especially acetyl or acetyl-2,2,2-$d_3$), or hydroxy-$C_{1-3}$-alkyl-carbonyl (especially hydroxy-methyl-carbonyl);

[in particular such amino-$C_{1-4}$-alkyl is N-acetyl-2-amino-ethyl, N-(acetyl-2,2,2-$d_3$)-2-amino-ethyl, N-acetyl-2-amino-2,2-dimethyl-ethyl, N-(acetyl-2,2,2-$d_3$)-2-amino-2,2-dimethyl-ethyl, N-methyl-N-(hydroxy-methyl-carbonyl)-2-amino-ethyl, N-methyl-N-acetyl-2-amino-ethyl, or N-methyl-N-(acetyl-2,2,2-$d_3$)-2-amino-ethyl]

$C_{3-6}$-cycloalkyl-$L^2$-, wherein

-$L^2$- represents a bond (i.e. the $C_{3-6}$-cycloalkyl is directly attached to the rest of the molecule), oxygen, $C_{1-3}$-alkylene (especially —$CH_2$—, —$CH_2$—$CH_2$—, or —$C(CH_3)_2$—), hydroxy-$C_{1-2}$-alkylene (especially —CH(OH)—) or oxy-$C_{1-2}$-alkylene (especially —O—$CH_2$—) (wherein the $C_{3-6}$-cycloalkyl is attached to the oxygen atom of said oxy-$C_{1-2}$-alkylene);

$C_{3-6}$-cycloalkyl is unsubstituted, mono-, or di-substituted with fluorine, $C_{1-3}$-alkyl (especially methyl), $C_{1-3}$-alkoxy (especially methoxy), hydroxy, hydroxy-$C_{1-3}$-alkyl, or $C_{1-3}$-alkoxy-$C_{1-3}$-alkyl; wherein optionally one ring carbon atom of said $C_{3-6}$-cycloalkyl is replaced by an oxygen atom;

[in particular such $C_{3-6}$-cycloalkyl-$L^2$- is oxetan-3-yl, cyclobutoxy-methyl, 1-hydroxy-cyclopropyl, 1-hydroxy-cyclobutyl, 3-hydroxy-cyclobutyl, 1-hydroxy-cyclopentyl, 3-hydroxy-3-methyl-cyclopentyl, 1-hydroxy-cyclohexyl, 4-hydroxy-cyclohexyl, (1-hydroxy-cyclohexyl)-methyl, (1-hydroxy-cyclobutyl)-methyl, 1-hydroxy-1-cyclohexylmethyl, 1-methoxy-cyclobutyl, 1-methoxy-cyclopentyl, 1-(1-(methoxy-methyl)-cyclopropyl)-methyl, tetrahydrofuran-2-yl-methyl, tetrahydrofuran-2-yl, tetrahydrofuran-3-yl, tetrahydropyran-3-yl, tetrahydropyran-4-yl, 4-methyl-tetrahydropyran-4-yl, 2,6-dimethyl-tetrahydropyran-4-yl, 4-methoxy-tetrahydropyran-4-yl, 4-fluoro-tetrahydropyran-4-yl, tetrahydropyran-4-yl-methyl, 2-(tetrahydropyran-4-yl)-ethyl, 1-(tetrahydropyran-4-yl)-1-methyl-ethyl, tetrahydropyran-4-yl-oxy-methyl, or (4-methyl-tetrahydropyran-4-yl)-oxy-methyl]

piperidin-4-yl which is N-substituted with $C_{1-3}$-alkyl-carbonyl (especially acetyl), (hydroxy-$C_{1-3}$-alkyl)-carbonyl (especially hydroxymethyl-carbonyl), or $C_{3-5}$-cycloalkyl-sulfonyl;

[in particular such piperidin-4-yl is N-acetyl-piperidin-4-yl, N-(hydroxymethyl-carbonyl)piperidin-4-yl, or N-(cyclopropyl-sulfonyl)-piperidin-4-yl]

morpholinyl-$L^3$- (notably (morpholin-4-yl)-$L^3$-), wherein -$L^3$- represents a bond (i.e. the morpholinyl is directly attached to the rest of the molecule) or $C_{1-2}$-alkylene; wherein said morpholinyl is unsubstituted or di-substituted with methyl;

[in particular such morpholinyl-$L^3$- is morpholin-4-yl, morpholin-4-yl-methyl, or (2,6-dimethyl-morpholin-4-yl)-methyl]

pyrazolyl-$C_{1-3}$-alkyl (especially 2-(pyrazol-1-yl)-ethyl);

$C_{1-3}$-alkyl-sulfonyl-$C_{1-3}$-alkyl (especially methyl-sulfonyl-methyl);

2,2,2-trifluoro-1-hydroxy-1-methyl-ethyl;

3-hydroxymethyl-bicyclo[1.1.1]pent-1-yl;

7-oxa-bicyclo[2.2.1]hept-2-yl; and 6-oxa-spiro[2.5]oct-1-yl;

5-oxo-4-oxa-6-azaspiro[2.4]hept-6-yl, 2,2-dimethyl-6-oxo-5-oxa-7-azaspiro[3.4]oct-7-yl, 2-cyclopropyl-6- oxo-5-oxa-7-azaspiro[3.4]oct-7-yl, 2-oxo-1-oxa-3-azaspiro[4.4]non-3-yl, 8,8-difluoro-2-oxo-1-oxa-3-azaspiro[4.5]dec-3-yl, or 8-oxo-7-oxa-9-azadispiro[3.1.4.1]undec-9-yl;

7-aza-bicyclo[2.2.1]hept-7-yl, 2-oxa-5-aza-bicyclo[2.2.1]hept-5-yl, 6-oxa-3-aza-bicyclo[3.1.1]hept-3-yl, or 8-oxa-3-azabicyclo[3.2.1]oct-3-yl;

5-oxo-6-azaspiro[3.4]oct-6-yl, 3-oxo-2-azaspiro[4.4]non-2-yl, 1-oxo-2-azaspiro[4.5]dec-2-yl, 1-oxo-8-oxa-2-azaspiro[4.5]dec-2-yl, 3-oxo-8-oxa-2-azaspiro[4.5]dec-2-yl, or 4-oxo-hexahydro-5H-furo[2,3-c]pyrrol-5-yl;

3-(7-hydroxy-6,7-dihydro-5H-cyclopenta[b]pyridin-7-yl)propyl or 3-(8-hydroxy-5,6,7,8-tetrahydroquinolin-8-yl)propyl); and 2-(6,7-dihydro-5H-[1]pyridin-7-ol)-ethyl or 2-(8-hydroxy-5,6,7,8-tetrahydro-quinolin-8-yl)-ethyl;

B represents phenyl, which is unsubstituted, mono-, di- or tri-substituted (especially mono-substituted in para-position with respect to the point of attachment of B to the rest of molecule), wherein the substituent(s), if any, is(are) independently selected from $C_{1-5}$-alkyl (especially methyl, ethyl, n-propyl, isopropyl, or tert-butyl; in particular isopropyl);

$C_{1-3}$-alkoxy (especially methoxy, ethoxy, or isopropoxy);

$C_{1-3}$-alkoxy-$C_{1-4}$-alkyl (especially 3-methoxy-propyl);

$C_{1-3}$-fluoroalkyl (especially trifluoromethyl);

$C_{3-5}$-cycloalkyl (especially cyclopropyl or cyclobutyl) which independently is unsubstituted or mono-substituted (notably at the point of attachment of said $C_{3-5}$-cycloalkyl to the rest of the molecule) with $C_{1-3}$-alkyl (especially methyl) or $C_{1-3}$-fluoroalkyl (especially trifluoromethyl);

$C_{3-5}$-cycloalkoxy (especially cyclopropoxy or cyclobutoxy); and $C_{1-3}$-fluoroalkoxy (especially trifluoromethoxy);

[in particular such B is phenyl, 4-methyl-phenyl, 4-ethyl-phenyl, 4-propyl-phenyl, 4-isopropyl-phenyl, 4-tert-butyl-phenyl, 4-cyclopropyl-phenyl, 4-methoxy-phenyl, 4-ethoxy-phenyl, 4-isopropoxy-phenyl, 4-trifluoromethyl-phenyl, 4-(1-methyl-cyclopropyl)-phenyl, 4-cyclobutyl-phenyl, 4-cyclopropoxy-phenyl, 4-cyclobutoxy-phenyl, 4-(trifluoromethoxy)-phenyl, 4-(3-methoxy-propyl)-phenyl, or 4-(1-trifluoromethyl-cyclopropyl)-phenyl]

$R^1$ represents $C_{1-3}$-alkyl (especially methyl), cyano, or halogen (especially fluorine);

$R^2$ represents $C_{1-4}$-alkyl (especially methyl, ethyl, n-propyl, isopropyl, tert-butyl or isobutyl), $C_{3-5}$-cycloalkyl (especially cyclopropyl or cyclobutyl), $C_{3-5}$-cycloalkyl-$C_{1-3}$-alkyl (especially cyclopropyl-methyl), or $C_{1-3}$-fluoroalkyl (especially 2,2-difluoroethyl or 2-fluoroethyl).

39) A further embodiment relates to compounds of Formula (Ip) according to embodiment 38), wherein the characteristics of any one of embodiments 2) to 32) apply mutatis mutandis.

40) One embodiment of the present invention relates to compounds according to embodiment 38), wherein A represents pyridinyl, pyrimidinyl, pyrazinyl, or pyridazinyl (notably pyridin-3-yl, pyridin-4-yl, pyrimidin-5-yl, pyrazin-2-yl, or pyridazin-4-yl; especially pyridin-3-yl), wherein A is independently unsubstituted, mono-, di- or tri-substituted (notably mono- or di-substituted in meta- and/or para-position of A with respect to the point of attachment of A to the rest of the molecule; especially mono-substituted in meta-position of A with respect to the point of attachment of A to the rest of the molecule), wherein the substituent(s), if any, is(are) as defined in embodiment 38).

41) Another embodiment of the present invention relates to compounds according to embodiment 38), wherein A represents pyridin-3-yl or pyridin-4-yl, wherein A is independently unsubstituted, mono-, di- or tri-substituted (notably mono- or di-substituted in meta- and/or para-position of A with respect to the point of attachment of A to the rest of the molecule; especially mono-substituted in meta-position of A with respect to the point of attachment of A to the rest of the molecule), wherein the substituent(s), if any, is(are) as defined in embodiment 38).

42) Another embodiment of the present invention relates to compounds according to embodiment 38), wherein A is unsubstituted;

mono-substituted (especially in meta-position of A with respect to the point of attachment of A to the rest of the molecule), wherein the substituent is as defined in embodiment 38).

di-substituted, wherein a first substituent is (notably in meta-position of A with respect to the point of attachment of A to the rest of the molecule) selected from the substituents defined in embodiment 38) (notably excluding halogen (especially fluorine) or cyano); and a second substituent is (notably in para-position of A with respect to the point of attachment of A to the rest of the molecule) selected from halogen (especially fluorine) and cyano.

[In a sub-embodiment of embodiment 4), A is pyridin-3-yl]

43) Another embodiment of the present invention relates to compounds according to any one of embodiments 40) to 42), wherein A is mono-substituted in meta-position of A with respect to the point of attachment of A to the rest of the molecule, wherein the substituent of A is 5-membered heteroaryl containing from one to three (notably two or three; especially three) ring heteroatom(s) independently selected from nitrogen, oxygen and sulfur (notably pyrazolyl, triazolyl, oxazolyl, thiazolyl, oxadiazolyl; especially pyrazol-1-yl, 1,2,3-triazol-1-yl, oxazol-2-yl, thiazol-2-yl, 1,2,4-oxadiazol-5-yl or 1,2,4-oxadiazol-3-yl; preferably 1,2,4-oxadiazol-5-yl or 1,2,4-oxadiazol-3-yl); wherein said 5-membered heteroaryl is independently unsubstituted, mono-, di-, or tri-substituted (notably mono-substituted; especially mono-substituted in position 3 with respect to the point of attachment of said 5-membered heteroaryl to A), wherein the substituent(s), if any, is(are) independently selected from $C_{1-4}$-alkyl which is unsubstituted or mono-substituted with hydroxy or $C_{1-4}$-alkoxy (especially methoxy and tert-butoxy);

[in particular such $C_{1-4}$-alkyl which is unsubstituted or mono-substituted as defined above is methyl, 1-hydroxy-1-methyl-ethyl, 2-hydroxy-2-methyl-propyl, 2-hydroxy-1,1-dimethyl-ethyl, methoxy-methyl, 2-methoxy-ethyl, 1-methoxy-1-methyl-ethyl, 2-methoxy-2-methyl-propyl, 2-methoxy-1,1-dimethyl-ethyl, tert-butoxy-methyl; preferably such $C_{1-4}$-alkyl group is 1-hydroxy-1-methyl-ethyl, 2-hydroxy-2-methyl-propyl, or 2-hydroxy-1,1-dimethyl-ethyl]

amino-$C_{1-4}$-alkyl (especially 2-amino-ethyl or 2-amino-2,2-dimethyl-ethyl), wherein the amino group is mono- or di-substituted (especially mono-substituted) with $C_{1-3}$-alkyl (especially methyl), $C_{1-3}$-alkyl-carbonyl including deuterated $C_{1-3}$-alkyl-carbonyl (especially acetyl or acetyl-2,2,2-$d_3$) or hydroxy-$C_{1-3}$-alkyl-carbonyl (especially hydroxy-methyl-carbonyl);

[in particular such amino-$C_{1-4}$-alkyl is N-acetyl-2-amino-ethyl, N-(acetyl-2,2,2-$d_3$)-2-amino-ethyl, N-acetyl-2-amino-2,2-dimethyl-ethyl, N-(acetyl-2,2,2-$d_3$)-2-amino-2,2-dimethyl-ethyl, N-methyl-N-(hydroxy-methyl-carbonyl)-2-amino-ethyl, N-methyl-N-acetyl-2-amino-ethyl, or N-methyl-N-(acetyl-2,2,2-$d_3$)-2-amino-ethyl]

$C_{3-6}$-cycloalkyl-$L^2$-, wherein

-$L^2$- represents a bond (i.e. the $C_{3-6}$-cycloalkyl is directly attached to the rest of the molecule), oxygen, $C_{1-3}$-alkylene (especially —$CH_2$—, —$CH_2$—$CH_2$—, or —$C(CH_3)_2$—), hydroxy-$C_{1-2}$-alkylene (especially —CH(OH)—) or oxy-$C_{1-2}$-alkylene (especially —O—$CH_2$—) (wherein the $C_{3-6}$-cycloalkyl is attached to the oxygen atom of said oxy-$C_{1-2}$-alkylene); and the $C_{3-6}$-cycloalkyl is unsubstituted, mono-, or di-substituted with fluorine, $C_{1-3}$-alkyl (especially methyl), $C_{1-3}$-alkoxy (especially methoxy), hydroxy, hydroxy-$C_{1-3}$-alkyl, or $C_{1-3}$-alkoxy-$C_{1-3}$-alkyl; wherein optionally one ring carbon atom of said $C_{3-6}$-cycloalkyl is replaced by an oxygen atom;

[in particular such $C_{3-6}$-cycloalkyl-$L^2$- is oxetan-3-yl, cyclobutoxy-methyl, 1-hydroxy-cyclopropyl, 1-hydroxy-cyclobutyl, 3-hydroxy-cyclobutyl, 1-hydroxy-cyclopentyl, 3-hydroxy-3-methyl-cyclopentyl, 1-hydroxy-cyclohexyl, 4-hydroxy-cyclohexyl, (1-hydroxy-cyclohexyl)-methyl, (1-hydroxy-cyclobutyl)-methyl, 1-hydroxy-1-cyclohexylmethyl, 1-methoxy-cyclobutyl, 1-methoxy-cyclopentyl, 1-(1-(methoxy-methyl)-cyclopropyl)-methyl, tetrahydrofuran-2-yl-methyl, tetrahydrofuran-2-yl, tetrahydrofuran-3-yl, tetrahydropyran-3-yl, tetrahydropyran-4-yl, 4-methyl-tetrahydropyran-4-yl, 2,6-dimethyl-tetrahydropyran-4-yl, 4-methoxy-tetrahydropyran-4-yl, 4-fluoro-tetrahydropyran-4-yl, tetrahydropyran-4-yl-methyl, 2-(tetrahydropyran-4-yl)-ethyl, 1-(tetrahydropyran-4-yl)-1-methyl-ethyl, tetrahydropyran-4-yl-oxy-methyl, or (4-methyl-tetrahydropyran-4-yl)-oxy-methyl]

piperidin-4-yl which is N-substituted with $C_{1-3}$-alkyl-carbonyl (especially acetyl), (hydroxy-$C_{1-3}$-alkyl)-carbonyl (especially hydroxymethyl-carbonyl), or $C_{3-6}$-cycloalkyl-sulfonyl;

[in particular such piperidin-4-yl is N-acetyl-piperidin-4-yl, N-(hydroxymethyl-carbonyl)piperidin-4-yl, or N-(cyclopropyl-sulfonyl)piperidin-4-yl]

morpholinyl-$L^3$- (notably (morpholin-4-yl)-$L^3$-), wherein -$L^3$- represents a bond (i.e. the morpholinyl is directly attached to the rest of the molecule) or $C_{1-2}$-alkylene; wherein said morpholinyl is unsubstituted or di-substituted with methyl;

[in particular such morpholinyl-$L^3$- is morpholin-4-yl, morpholin-4-yl-methyl, or (2,6-dimethyl-morpholin-4-yl)-methyl]

pyrazolyl-$C_{1-3}$-alkyl (especially 2-(pyrazol-1-yl)-ethyl);

$C_{1-3}$-alkyl-sulfonyl-$C_{1-3}$-alkyl (especially methyl-sulfonyl-methyl);

2,2,2-trifluoro-1-hydroxy-1-methyl-ethyl;

3-hydroxymethyl-bicyclo[1.1.1]pent-1-yl;

7-oxa-bicyclo[2.2.1]hept-2-yl; and 6-oxa-spiro[2.5]oct-1-yl.

44) Another embodiment of the present invention relates to compounds according to any one of embodiments 40) to 42), wherein A is mono-substituted in meta-position of A with respect to the point of attachment of A to the rest of the molecule, wherein the substituent of A is 5-membered heteroaryl containing from one to three (notably two or three; especially three) ring heteroatom(s) independently selected from nitrogen, oxygen and sulfur (notably pyrazolyl, triazolyl, oxazolyl, thiazolyl, oxadiazolyl; especially pyrazol-1-yl, 1,2,3-triazol-1-yl, oxazol-2-yl, thiazol-2-yl, 1,2,4-oxadiazol-5-yl or 1,2,4-oxadiazol-3-yl; most preferably 1,2,4-oxadiazol-5-yl or 1,2,4-oxadiazol-3-yl); wherein said 5-membered heteroaryl is independently unsubstituted, mono-, di-, or tri-substituted (notably mono-substituted; especially mono-substituted in position 3 with respect to the point of attachment of said 5-membered heteroaryl to A), wherein the substituent(s), if any, is(are) independently selected from amino-$C_{1-4}$-alkyl (especially 2-amino-ethyl or 2-amino-2,2-dimethyl-ethyl), wherein the amino group is mono- or di-substituted (especially mono-substituted) with $C_{1-3}$-alkyl (especially methyl), $C_{1-3}$-alkyl-carbonyl including deuterated $C_{1-3}$-alkyl-carbonyl (especially acetyl or acetyl-2,2,2-$d_3$), or hydroxy-$C_{1-3}$-alkyl-carbonyl (especially hydroxy-methyl-carbonyl);

[in particular such amino-$C_{1-4}$-alkyl is N-acetyl-2-amino-ethyl, N-(acetyl-2,2,2-$d_3$)-2-amino-ethyl, N-acetyl-2-amino-2,2-dimethyl-ethyl, N-(acetyl-2,2,2-$d_3$)-2-amino-2,2-dimethyl-ethyl, N-methyl-N-(hydroxy-methyl-carbonyl)-2-amino-ethyl, N-methyl-N-acetyl-2-amino-ethyl, or N-methyl-N-(acetyl-2,2,2-$d_3$)-2-amino-ethyl]

piperidin-4-yl which is N-substituted with $C_{1-3}$-alkyl-carbonyl (especially acetyl), (hydroxy-$C_{1-3}$-alkyl)-carbonyl (especially hydroxymethyl-carbonyl), or $C_{3-5}$-cycloalkyl-sulfonyl.

[in particular such piperidin-4-yl is N-acetyl-piperidin-4-yl, N-(hydroxymethyl-carbonyl)piperidin-4-yl, or N-(cyclopropyl-sulfonyl)-piperidin-4-yl]

45) Another embodiment of the present invention relates to compounds according to any one of embodiments 40) to 42), wherein A is mono-substituted in meta-position of A with respect to the point of attachment of A to the rest of the molecule, wherein the substituent is 1,2,4-oxadiazol-3-yl which is mono-substituted, wherein the substituent is independently selected from amino-$C_{1-4}$-alkyl (especially 2-amino-ethyl or 2-amino-2,2-dimethyl-ethyl), wherein the amino group is mono-substituted with $C_{1-3}$-alkyl-carbonyl including deuterated $C_{1-3}$-alkyl-carbonyl (especially acetyl or acetyl-2,2,2-$d_3$);

di-substituted, wherein a first substituent is $C_{1-3}$-alkyl (especially methyl) and a second substituent is $C_{1-3}$-alkyl-carbonyl (especially acetyl) or $C_{1-3}$-alkyl-carbonyl including deuterated $C_{1-3}$-alkyl-carbonyl (especially acetyl or acetyl-2,2,2-$d_3$); or di-substituted, wherein a first substituent is $C_{1-3}$-alkyl (especially methyl) and a second substituent is hydroxy-$C_{1-3}$-alkyl-carbonyl (especially hydroxy-methyl-carbonyl);

[in particular such amino-$C_{1-4}$-alkyl is N-acetyl-2-amino-ethyl, N-(acetyl-2,2,2-$d_3$)-2-amino-ethyl, N-acetyl-2-amino-2,2-dimethyl-ethyl, N-(acetyl-2,2, 2-$d_3$)-2-amino-2,2-dimethyl-ethyl, N-methyl-N-(hydroxy-methyl-carbonyl)-2-amino-ethyl, N-methyl-N-acetyl-2-amino-ethyl, or N-methyl-N-(acetyl-2,2,2-$d_3$)-2-amino-ethyl]

piperidin-4-yl which is N-substituted with $C_{1-3}$-alkyl-carbonyl (especially acetyl), (hydroxy-$C_{1-3}$-alkyl)-carbonyl (especially hydroxymethyl-carbonyl), or $C_{3-5}$-cycloalkyl-sulfonyl.

[in particular such piperidin-4-yl is N-acetyl-piperidin-4-yl, N-(hydroxymethyl-carbonyl)piperidin-4-yl, or N-(cyclopropyl-sulfonyl)-piperidin-4-yl]

46) Another embodiment of the present invention relates to compounds according to any one of embodiments 40) or 42), wherein A represents pyridinyl (especially pyridin-3-yl) which is mono-substituted in meta-position with respect to the point of attachment of A to the rest of the molecule, wherein the substituent is oxadiazolyl (especially 1,2,4-oxadiazol-3-yl) which is mono-substituted, wherein the substituent is $C_{1-4}$-alkyl which is unsubstituted or mono-substituted with hydroxy or $C_{1-4}$-alkoxy (especially such $C_{1-4}$-alkyl is 1-hydroxy-1-methyl-ethyl, 2-hydroxy-2-methyl-propyl, or 2-hydroxy-1,1-dimethyl-ethyl).

47) Another embodiment of the present invention relates to compounds according to any one of embodiments 40) to 42), wherein A is mono-substituted in meta-position of A with respect to the point of attachment of A to the rest of the molecule, wherein the substituent of A is —C≡C—$R^{T1}$, wherein $R^{T1}$ represents hydroxy-$C_{1-4}$-alkyl (especially hydroxy-methyl, 1-hydroxy-ethyl, 2-hydroxy-ethyl, 1-hydroxy-2-methyl-propyl, or 1-hydroxy-1-methyl-ethyl);

$C_{1-3}$-alkoxy-$C_{1-3}$-alkyl (especially methoxy-methyl);

$C_{3-6}$-cycloalkyl which is mono-substituted with hydroxy (notably at the point of attachment of the $C_{3-6}$-cycloalkyl to the rest of the molecule; especially 1-hydroxy-cyclopropyl, 1-hydroxy-cyclobutyl, or 1-hydroxy-cyclopentyl);

$C_{3-6}$-cycloalkyl (notably cyclopentyl or cyclohexyl) fused with a pyridine ring (notably at positions 2 and 3 of the pyridine ring), wherein said $C_{3-6}$-cycloalkyl is mono-substituted with hydroxy (notably at position 1 of the $C_{3-6}$-cycloalkyl ring) (especially 8-hydroxy-5,6,7,8-tetrahydroquinolin-8-yl or 7-hydroxy-6,7-dihydro-5H-cyclopenta[b]pyridin-7-yl);

pyrazolyl (notably pyrazol-4-yl) which is mono-substituted with methyl (especially 1-methyl-pyrazol-4-yl);

tetrahydropyranyl (especially tetrahydropyran-4-yl) which is unsubstituted or mono-substituted with hydroxy (especially 4-hydroxy-tetrahydropyran-4-yl);

indolyl (notably indol-2-yl); or hydroxy-azetidinyl (notably 3-hydroxy-azetidin-3-yl) which is N-substituted with $C_{1-4}$-alkoxy-carbonyl (especially isopropyl-carbonyl or tert-butoxy-carbonyl);

[in particular such —C≡C—$R^{T1}$ is 3-hydroxy-prop-1-yn-1-yl, 4-hydroxy-but-1-yn-1-yl, 3-hydroxy-but-1-yn-1-yl, 3-hydroxy-3-methyl-but-1-yn-1-yl, 3-hydroxy-4-methyl-pent-1-yn-1-yl, 3-methoxy-prop-1-yn-1-yl, (1-hydroxy-cyclopropyl)-ethynyl, (1-hydroxy-cyclobutyl)-ethynyl, (1-hydroxy-cyclopentyl)-ethynyl, (8-hydroxy-5,6,7,8-tetrahydroquinolin-8-yl)-ethynyl, (7-hydroxy-6,7-dihydro-5H-cyclopenta[b]pyridin-7-yl)-ethynyl, (1-methyl-pyrazol-4-yl)-ethynyl, (tetrahydropyran-4-yl)-ethynyl, (4-hydroxy-tetrahydropyran-4-yl)-ethynyl, indol-2-yl-ethynyl, (1-(isopropyl-carbonyl)-3-hydroxy-azetidin-3-yl)-ethynyl, or (1-(tert-butoxy-carbonyl)-3-hydroxy-azetidin-3-yl)-ethynyl]

—C≡C—C(OH)($R^{T2}$)($R^{T3}$), wherein $R^{T2}$ represents hydrogen or $C_{1-3}$-alkyl (especially methyl or ethyl);

$R^{T3}$ represents phenyl which is unsubstituted or mono-substituted, wherein the substituent, if any, is selected from $C_{1-3}$-alkoxy (notably methoxy) or halogen (notably fluorine);

[in particular such group is 3-fluoro-phenyl, 4-methoxy-phenyl, or 2-methoxy-phenyl]

5- to 6-membered heteroaryl containing one or two ring heteroatom(s) being independently selected from nitrogen or sulfur (notably thiazolyl, pyrazolyl, pyridinyl, or pyrimidinyl; especially thiazol-4-yl, pyrazol-3-yl, pyrazol-4-yl, pyridin-2-yl, pyrimidin-2-yl, or pyrimidin-4-yl), wherein said 5- or 6-membered heteroaryl is independently unsubstituted, mono- or di-substituted, and wherein the substituent(s), if any, is(are) independently selected from $C_{1-3}$-alkyl (especially methyl) and $C_{1-3}$-alkoxy (especially methoxy); or

[in particular such 5- to 6-membered heteroaryl group is 1-methyl-pyrazol-3-yl, 1,3-dimethyl-pyrazol-4-yl, 1,5-dimethyl-pyrazol-3-yl, 2-methyl-thiazol-4-yl, pyridin-2-yl, 6-methoxy-pyridin-2-yl, pyrimidin-2-yl, pyrimidin-4-yl, or 1,5-dimethyl-pyrazol-3-yl]

tetrahydropyranyl (especially tetrahydropyran-4-yl);

[in particular such —C≡C—C(OH)($R^{T2}$)($R^{T3}$) is 3-hydroxy-3-(tetrahydropyran-4-yl)-prop-1-yn-1-yl, 3-hydroxy-3-phenyl-prop-1-yn-1-yl, 3-hydroxy-3-(2-methyl-thiazol-4-yl)-prop-1-yn-1-yl, 3-hydroxy-3-(1,3-dimethyl-pyrazol-4-yl)-prop-1-yn-1-yl, 3-hydroxy-3-phenyl-but-1-yn-1-yl, 3-hydroxy-3-(1-methyl-pyrazol-3-yl)-but-1-yn-1-yl, 3-hydroxy-3-(1,5-dimethyl-pyrazol-3-yl)-but-1-yn-1-yl, 3-hydroxy-3-(1-methyl-pyrazol-3-yl)-but-1-yn-1-yl, 3-hydroxy-3-(pyrimidin-2-yl)-but-1-yn-1-yl, 3-hydroxy-3-(1-methyl-pyrazol-3-yl)-but-1-yn-1-yl, 3-hydroxy-3-(3-fluoro-phenyl)-but-1-yn-1-yl, 3-hydroxy-3-(6-methyl-pyrimidin-4-yl)-but-1-yn-1-yl, 3-hydroxy-3-(pyridin-2-yl)-pent-1-yn-1-yl, 3-hydroxy-3-(6-methoxy-pyridin-2-yl)-but-1-yn-1-yl, 3-hydroxy-3-(6-methoxy-pyridin-2-yl)-pent-1-yn-1-yl, 3-hydroxy-3-(4-methoxy-phenyl)-but-1-yn-1-yl, or 3-hydroxy-3-(2-methoxy-phenyl)-but-1-yn-1-yl]

48) Another embodiment of the present invention relates to compounds according to any one of embodiments 38) to 42), wherein A is mono-substituted in meta-position of A with respect to the point of attachment of A to the rest of the molecule, wherein the substituent of A is as defined in embodiment 42) or 46).

49) Another embodiment of the present invention relates to compounds according to any one of embodiments 38) to 48), wherein B represents phenyl, which is mono-substituted in para-position with respect to the point of attachment of B to the rest of molecule, wherein the substituent is selected from $C_{1-5}$-alkyl (especially ethyl, n-propyl, isopropyl, or tert-butyl; in particular isopropyl).

[in particular such B is 4-ethyl-phenyl, 4-propyl-phenyl, 4-isopropyl-phenyl, 4-tert-butyl-phenyl; in particular 4-isopropyl-phenyl]

50) Another embodiment of the present invention relates to compounds according to any one of embodiments 38) to 49), wherein $R^1$ represents $C_{1-3}$-alkyl (especially methyl).

51) Another embodiment of the present invention relates to compounds according to any one of embodiments 38) to 50), wherein $R^2$ represents $C_{1-4}$-alkyl (especially methyl, ethyl, n-propyl, isopropyl, tert-butyl or isobutyl).

52) Another embodiment of the present invention relates to compounds according to embodiment 38), wherein A represents pyridinyl (especially pyridin-3-yl) which is mono-substituted in meta-position with respect to the point of attachment of A to the rest of the molecule, wherein the substituent is oxadiazolyl (especially 1,2,4-oxadiazol-3-yl) which is mono-substituted, wherein the substituent is $C_{1-4}$-alkyl which is unsubstituted or mono-substituted with hydroxy or $C_{1-4}$-alkoxy (especially such $C_{1-4}$-alkyl which is unsubstituted or mono-substituted is 1-hydroxy-1-methyl-ethyl, 2-hydroxy-2-methyl-propyl, or 2-hydroxy-1,1-dimethyl-ethyl);

B represents phenyl which is mono-substituted in para-position with respect to the point of attachment of B to the rest of molecule, wherein the substituent is $C_{1-5}$-alkyl (especially isopropyl);

$R^1$ represents $C_{1-3}$-alkyl (especially methyl); and $R^2$ represents $C_{1-4}$-alkyl (especially methyl).

53) Another embodiment relates to compounds according to any one of embodiments 38) to 52), which are also compounds of Formula (IIp) (i.e. the asymmetric carbon atom to which A and B are attached has the absolute configuration depicted in Formula (IIp))

Formula (IIp)

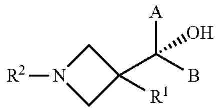

It is understood that for A being pyridin-3-yl, pyrimidin-5-yl, pyrazin-2-yl, or pyridazin-4-yl (especially pyridin-3-yl), the asymmetric carbon atom to which A and B are attached, as depicted in Formula (IIp), has absolute configuration (R). In the case where A represents pyridin-4-yl, the asymmetric carbon atom to which A and B are attached, as depicted in Formula (II), has absolute configuration (S).

Based on the dependencies of the different embodiments 1) to 37) as disclosed hereinabove, the following embodiments are thus possible and intended, and herewith specifically disclosed in individualized form:

2+1,3+1, 4+1, 11+1, 11+2+1, 11+3+1, 11+4+1, 12+11+1, 12+11+2+1, 12+11+3+1, 12+11+4+1, 13+11+1, 13+11+2+1, 13+11+3+1, 13+11+4+1, 14+11+1, 14+11+2+1, 14+11+3+1, 14+11+4+1, 15+11+1, 15+11+2+1, 15+11+3+1, 15+11+4+1, 16+1, 16+2+1, 16+3+1, 16+4+1, 17+16+1, 17+16+2+1, 17+16+3+1, 17+16+4+1, 18+16+1, 18+16+2+1, 18+16+3+1, 18+16+4+1, 19+16+1, 19+16+2+1, 19+16+3+1, 19+16+4+1, 20+1, 20+2+1, 20+3+1, 20+4+1, 21+20+1, 21+20+2+1, 21+20+3+1, 21+20+4+1, 22+20+1, 22+20+2+1, 22+20+3+1, 22+20+4+1, 23+1, 23+2+1, 23+3+1, 23+4+1, 23+5, 23+6, 23+7, 23+8, 23+9, 23+10, 23+11+1, 23+11+2+1, 23+11+3+1, 23+11+4+1, 23+12+11+1, 23+12+11+2+1, 23+12+11+3+1, 23+12+11+4+1, 23+13+11+1, 23+13+11+2+1, 23+13+11+3+1, 23+13+11+4+1, 23+14+11+1, 23+14+11+2+1, 23+14+11+3+1, 23+14+11+4+1, 23+15+11+1, 23+15+11+2+1, 23+15+11+3+1, 23+15+11+4+1, 23+16+1, 23+16+2+1, 23+16+3+1, 23+16+4+1, 23+17+16+1, 23+17+16+2+1, 23+17+16+3+1, 23+17+16+4+1, 23+18+16+1, 23+18+16+2+1, 23+18+16+3+1, 23+18+16+4+1, 23+19+16+1, 23+19+16+2+1, 23+19+16+3+1, 23+19+16+4+1, 23+20+1, 23+20+2+1, 23+20+3+1, 23+20+4+1, 23+21+20+1, 23+21+20+2+1, 23+21+20+3+1, 23+21+20+4+1, 23+22+20+1, 23+22+20+2+1, 23+22+20+3+1, 23+22+20+4+1, 26+1, 26+2+1, 26+3+1, 26+4+1, 26+5, 26+6, 26+7, 26+8, 26+9, 26+10, 26+11+1, 26+11+2+1, 26+11+3+1, 26+11+4+1, 26+12+11+1, 26+12+11+2+1, 26+12+11+3+1, 26+12+11+4+1, 26+13+11+1, 26+13+11+2+1, 26+13+11+3+1, 26+13+11+4+1, 26+14+11+1, 26+14+11+2+1, 26+14+11+3+1, 26+14+11+4+1, 26+15+11+1, 26+15+11+2+1, 26+15+11+3+1, 26+15+11+4+1, 26+16+1, 26+16+2+1, 26+16+3+1, 26+16+4+1, 26+17+16+1, 26+17+16+2+1, 26+17+16+3+1, 26+17+16+4+1, 26+18+16+1, 26+18+16+2+1, 26+18+16+3+1, 26+18+16+4+1, 26+19+16+1, 26+19+16+2+1, 26+19+16+3+1, 26+19+16+4+1, 26+20+1, 26+20+2+1, 26+20+3+1, 26+20+4+1, 26+21+20+1, 26+21+20+2+1, 26+21+20+3+1, 26+21+20+4+1, 26+22+20+1, 26+22+20+2+1, 26+22+20+3+1, 26+22+20+4+1, 26+23+1, 26+23+2+1,26+23+3+1,26+23+4+1,26+23+5,26+23+6,26+23+7,26+23+8,26+23+9,26+23+10,26+23+11+1,26+23+11+2+1, 26+23+11+3+1,26+23+11+4+1,26+23+12+11+1,26+23+12+11+2+1, 26+23+12+11+3+1, 26+23+12+11+4+1, 26+23+13+11+1, 26+23+13+11+2+1, 26+23+13+11+3+1, 26+23+13+11+4+1, 26+23+14+11+1, 26+23+14+11+2+1, 26+23+14+11+3+1, 26+23+14+11+4+1, 26+23+15+11+1,26+23+15+11+2+1,26+23+15+11+3+1, 26+23+15+11+4+1,26+23+16+1,26+23+16+2+1, 26+23+16+3+1,26+23+16+4+1,26+23+17+16+1,26+23+17+16+2+1, 26+23+17+16+3+1, 26+23+17+16+4+1, 26+23+18+16+1, 26+23+18+16+2+1, 26+23+18+16+3+1, 26+23+18+16+4+1, 26+23+19+16+1, 26+23+19+16+2+1, 26+23+19+16+3+1, 26+23+19+16+4+1, 26+23+20+1, 26+23+20+2+1, 26+23+20+3+1, 26+23+20+4+1, 26+23+21+20+1, 26+23+21+20+2+1, 26+23+21+20+3+1, 26+23+21+20+4+1, 26+23+22+20+1, 26+23+22+20+2+1, 26+23+22+20+3+1, 26+23+22+20+4+1, 26+24, 26+25, 28+1, 28+2+1,28+3+1,28+4+1, 28+5,28+6,28+7, 28+8,28+9, 28+10,28+11+1,28+11+2+1,28+11+3+1, 28+11+4+1, 28+12+11+1, 28+12+11+2+1, 28+12+11+3+1, 28+12+11+4+1, 28+13+11+1, 28+13+11+2+1, 28+13+11+3+1, 28+13+11+4+1, 28+14+11+1, 28+14+11+2+1, 28+14+11+3+1, 28+14+11+4+1, 28+15+11+1, 28+15+11+2+1, 28+15+11+3+1, 28+15+11+4+1, 28+16+1, 28+16+2+1, 28+16+3+1, 28+16+4+1, 28+17+16+1, 28+17+16+2+1, 28+17+16+3+1, 28+17+16+4+1, 28+18+16+1, 28+18+16+2+1, 28+18+16+3+1, 28+18+16+4+1, 28+19+16+1, 28+19+16+2+1, 28+19+16+3+1, 28+19+16+4+1, 28+20+1, 28+20+2+1, 28+20+3+1, 28+20+4+1, 28+21+20+1, 28+21+20+2+1, 28+21+20+3+1, 28+21+20+4+1, 28+22+20+1, 28+22+20+2+1, 28+22+20+3+1,28+22+20+4+1,28+23+1,28+23+2+1, 28+23+3+1,28+23+4+1,28+23+5,28+23+6,28+23+7, 28+23+8, 28+23+9, 28+23+10, 28+23+11+1, 28+23+11+2+1, 28+23+11+3+1, 28+23+11+4+1, 28+23+12+11+1, 28+23+12+11+2+1, 28+23+12+11+3+1, 28+23+12+11+4+1, 28+23+13+11+1, 28+23+13+11+2+1, 28+23+13+11+3+1, 28+23+13+11+4+1, 28+23+14+

11+1, 28+23+14+11+2+1, 28+23+14+11+3+1, 28+23+14+11+4+1, 28+23+15+11+1, 28+23+15+11+2+1, 28+23+15+11+3+1, 28+23+15+11+4+1, 28+23+16+1, 28+23+16+2+1, 28+23+16+3+1, 28+23+16+4+1, 28+23+17+16+1, 28+23+17+16+2+1, 28+23+17+16+3+1, 28+23+17+16+4+1, 28+23+18+16+1, 28+23+18+16+2+1, 28+23+18+16+3+1, 28+23+18+16+4+1, 28+23+19+16+1, 28+23+19+16+2+1, 28+23+19+16+3+1, 28+23+19+16+4+1, 28+23+20+1, 28+23+20+2+1, 28+23+20+3+1, 28+23+20+4+1, 28+23+21+20+1, 28+23+21+20+2+1, 28+23+21+20+3+1, 28+23+21+20+4+1, 28+23+22+20+1, 28+23+22+20+2+1, 28+23+22+20+3+1, 28+23+22+20+4+1, 28+24, 28+25, 28+26+1, 28+26+2+1,28+26+3+1,28+26+4+1,28+26+5,28+26+6,28+26+7,28+26+8,28+26+9,28+26+10, 28+26+11+1,28+26+11+2+1, 28+26+11+3+1,28+26+11+4+1,28+26+12+11+1,28+26+12+11+2+1,28+26+12+11+3+1, 28+26+12+11+4+1, 28+26+13+11+1, 28+26+13+11+2+1, 28+26+13+11+3+1, 28+26+13+11+4+1, 28+26+14+11+1, 28+26+14+11+2+1, 28+26+14+11+3+1, 28+26+14+11+4+1, 28+26+15+11+1,28+26+15+11+2+1,28+26+15+11+3+1, 28+26+15+11+4+1,28+26+16+1,28+26+16+2+1, 28+26+16+3+1,28+26+16+4+1,28+26+17+16+1,28+26+17+16+2+1, 28+26+17+16+3+1, 28+26+17+16+4+1,28+26+18+16+1, 28+26+18+16+2+1, 28+26+18+16+3+1, 28+26+18+16+4+1, 28+26+19+16+1, 28+26+19+16+2+1, 28+26+19+16+3+1, 28+26+19+16+4+1, 28+26+20+1, 28+26+20+2+1, 28+26+20+3+1, 28+26+20+4+1, 28+26+21+20+1, 28+26+21+20+2+1, 28+26+21+20+3+1, 28+26+21+20+4+1, 28+26+22+20+1, 28+26+22+20+2+1, 28+26+22+20+3+1, 28+26+22+20+4+1, 28+26+23+1, 28+26+23+2+1, 28+26+23+3+1, 28+26+23+4+1, 28+26+23+5, 28+26+23+6, 28+26+23+7, 28+26+23+8, 28+26+23+9,28+26+23+10,28+26+23+11+1,28+26+23+11+2+1,28+26+23+11+3+1, 28+26+23+11+4+1,28+26+23+12+11+1, 28+26+23+12+11+2+1, 28+26+23+12+11+3+1, 28+26+23+12+11+4+1, 28+26+23+13+11+1, 28+26+23+13+11+2+1, 28+26+23+13+11+3+1, 28+26+23+13+11+4+1, 28+26+23+14+11+1, 28+26+23+14+11+2+1, 28+26+23+14+11+3+1, 28+26+23+14+11+4+1, 28+26+23+15+11+1, 28+26+23+15+11+2+1, 28+26+23+15+11+3+1, 28+26+23+15+11+4+1, 28+26+23+16+1, 28+26+23+16+2+1, 28+26+23+16+3+1, 28+26+23+16+4+1, 28+26+23+17+16+1, 28+26+23+17+16+2+1, 28+26+23+17+16+3+1, 28+26+23+17+16+4+1, 28+26+23+18+16+1, 28+26+23+18+16+2+1, 28+26+23+18+16+3+1, 28+26+23+18+16+4+1, 28+26+23+19+16+1, 28+26+23+19+16+2+1, 28+26+23+19+16+3+1, 28+26+23+19+16+4+1, 28+26+23+20+1, 28+26+23+20+2+1, 28+26+23+20+3+1, 28+26+23+20+4+1, 28+26+23+21+20+1, 28+26+23+21+20+2+1, 28+26+23+21+20+3+1, 28+26+23+21+20+4+1, 28+26+23+22+20+1, 28+26+23+22+20+2+1, 28+26+23+22+20+3+1, 28+26+23+22+20+4+1, or 28+26+24, 28+26+25.

The invention relates to compounds of the Formula (I) as defined in embodiment 1), or to such compounds further limited by the characteristics of any one of embodiments 2) to 53), under consideration of their respective dependencies; to pharmaceutically acceptable salts thereof; and to the use of such compounds as medicaments especially in the treatment of diseases or disorders where CCR6 receptors are involved as described hereinbelow.

The present invention also includes isotopically labelled, especially $^{2}H$ (deuterium) labelled compounds of Formula (I), which compounds are identical to the compounds of Formula (I) except that one or more atoms have each been replaced by an atom having the same atomic number but an atomic mass different from the atomic mass usually found in nature. Isotopically labelled, especially $^{2}H$ (deuterium) labelled compounds of Formula (I) and salts thereof are within the scope of the present invention. Substitution of hydrogen with the heavier isotope $^{2}H$ (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

Where the plural form is used for compounds, salts, pharmaceutical compositions, diseases and the like, this is intended to mean also a single compound, salt, pharmaceutical composition, disease or the like.

Any reference to compounds of Formula (I) according to embodiments 1) to 53) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quére´ (Eds.), RSC Publishing, 2012.

Definitions provided herein are intended to apply uniformly to the compounds of Formula (I), as defined in any one of embodiments 1) to 53), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The compounds of Formula (I) may encompass compounds with one or more asymmetric centers, such as one or more asymmetric carbon atoms, which may be present in (R)- as well as (S)-configuration. The compounds of Formula (I) may further encompass compounds with one or more double bonds which are allowed to be present in Z- as well as E-configuration and/or compounds with substituents at a ring system which are allowed to be present, relative to each other, in cis- as well as trans-configuration. The compounds of Formula (I) may thus be present as mixtures of stereoisomers or preferably in stereoisomerically enriched form, especially as essentially pure stereoisomers. Mixtures of stereoisomers may be separated in a manner known to a person skilled in the art.

In case a particular compound (or generic structure) is designated as (R)- or (S)-enantiomer, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center. In analogy, cis- or trans-designations are to be understood as referring to the respective stereoisomer in enriched, especially essentially pure, form. Likewise, in case a particular compound (or generic structure) is designated as Z- or E-stereoisomer (or in case a specific double bond in a compound is designated as being in Z- or E-configuration), such designation is to be understood as referring to the respective compound (or generic structure) in enriched, especially essentially pure, stereoisomeric form (or to the compound that is in enriched, especially essentially pure, form with regard to the respective configuration of the double bond).

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

The compounds of Formula (I) according to embodiments 1) to 53) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I), or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" (or alternatively the term "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

The compounds of Formula (I) as defined hereinabove are useful for the prevention or treatment of various diseases, conditions or disorders ameliorated by modulating CCR6 receptors. Such diseases, conditions or disorders where CCR6 receptors are involved may be defined as inflammatory and/or autoimmune diseases, conditions or disorders; and cancer.

The compounds of Formula (I) as defined hereinabove are useful for the prevention or treatment of of various diseases, conditions or disorders ameliorated by modulating CCR6 receptors. Such diseases, conditions or disorders where CCR6 receptors are involved may be defined as including rheumatoid arthritis; ankylosing spondylitis; spondyloarthritis; psoriasis; psoriatic arthritis; inflammatory skin disorders such as rosacea; Crohn's disease; ulcerative colitis; inflammatory bowel disease; irritable bowel disease; dry eye disease; multiple sclerosis; systemic lupus erythematosus; Sjögren's disease; autoimmune hepatitis; Primary Sclerosing Cholangitis; Posterior uveitis; allergic conjunctivitis; allergic disease in the gastrointestinal tract; type I diabetes and endometriosis; diseases of the ocular surface in which elevated levels of IL-17A have been recorded such as meibomian gland dysfunction; GVHD; graft-versus host disease; autoimmune keratitis; filamentary keratitis; dry eye syndrome with rheumatic arthritis; dry eye syndrome without systemic disease; Stevens-Johnson syndrome; psoriasis including plaque psoriasis, guttate psoriasis, inverse psoriasis, pustular psoriasis, erythrodermic psoriasis; autoimmune keratitis; filamentary keratitis; autoimmune uveitis; allergic conjunctivitis; asthma; allergic disease of the gastrointestinal tract; T1D; endometriosis; meibomian gland dysfunction; graft-versus host disease; juvenile arthritis; juvenile rheumatoid arthritis; systemic onset rheumatoid arthritis; pauciarticular rheumatoid arthritis; pauciarticular juvenile rheumatoid arthritis; polyarticular rheumatoid arthritis; enteropathic arthritis; juvenile Reiter's Syndrome; ankylosing spondylitis; juvenile ankylosing spondylitis; SEA Syndrome; reactive arthritis (reactive arthropathy); psoriatic arthropathy; juvenile enteropathic arthritis; polymyalgia rheumatica; enteropathic spondylitis; juvenile idiopathic arthritis (JIA); juvenile psoriatic arthritis; juvenile rheumatoid arthritis; systemic onset juvenile rheumatoid arthritis; acute pancreatitis; chronic pancreatitis; giant cell arteritis; and secondary osteoarthritis from inflammatory diseases.

Further, such diseases, conditions or disorders where CCR6 receptors are involved may be defined as including cancer such as skin cancer e.g. melanoma (superficial spreading, nodular, lentigo maligna and acral lentiginous melanoma); advanced melanoma; metastatic melanoma; Merkel cell carcinoma; Kaposi sarcoma; basal cell carcinoma; squamous cell carcinoma; and pre-cancerous skin lesions such as actinic keratosis; lung cancer including small cell lung cancer and non-small (SCLC, NSCLC) such as squamous and non-squamous NSCLC; pleuropulmonary blastoma and tracheobronchial tumors; bladder cancer including urinary bladder cancer; urothelial cell carcinoma; mesothelioma; renal carcinomas including renal cell carcinoma (RCC) such as clear cell RCC; papillary RCC; chromophobe RCC; non-clear cell RCC; unclassified RCC; metastatic renal cell carcinoma; metastatic renal clear cell carcinoma; renal parenchymal carcinoma; gastro-intestinal cancers including colorectal cancer; metastatic colorectal cancer; familial adenomatous polyposis (FAP); rectum carcinoma; colon carcinoma; colorectal adenoma; colorectal adenocarcinoma; colorectal cancer liver metastases; hereditary non-polyposis colorectal cancer; esophageal cancer; gastric cancer; advanced gastric cancer; gallbladder cancer;

cholangiocarcinoma; hepatocellular carcinoma; pancreatic cancer such as pancreatic adenocarcinoma or pancreatic ductal (adeno)carcinoma; pancreatic neuroendocrine tumors; endometrial cancer; ovarian cancer; prostate cancer including castrate-resistant prostate cancer; brain tumors including brain metastases, malignant gliomas, glioblastoma multiforme, medulloblastoma, meningiomas, astrocytoma; peripheral neuroectodermal tumors; oligoastrocytic tumors; oligodendrogliomas; ependymal tumors; anaplastic astrocytoma; pilocytic astrocytoma; craniopharyngioma; spinal cord tumors; brain stem glioma; central nervous system atypical teratoid/rhabdoid tumor; medulloblastoma; central nervous system germ cell tumors; craniopharyngioma; ependymoma; neuroblastoma; head and neck cancer such as esthesioneuroblastoma; cervical cancer; advanced cervical cancer; breast cancer including normal-like, basal-like, claudin-low, HER2 positive, luminal-A, luminal-B and triple negative breast carcinoma; pregnancy breast cancer and male breast cancer; oral tumors; nasopharyngeal tumors; heart tumors; thoracic cancer; lymphomas such as Hodgkin lymphoma, non-Hodgkin lymphoma, Burkitt lymphoma; primary intra-ocular B-Cell lymphoma; diffuse large B-cell lymphoma; primary mediastinal large B-cell lymphoma; mucosa-associated lymphoid tissue (MALT) lymphoma; gastric MALT lymphoma; cutaneous T-cell lymphoma; primary central nervous system lymphoma; Sézary syndrome and Waldenström macroglobulinemia; leukemia such as acute lymphoblastic leukemia; acute myeloid leukemia; chronic lymphocytic leukemia; chronic myelogenous leukemia; hairy cell leukemia; chronic myeloid leukemia; adult T-cell leukemia; carcinomas; adenocarcinomas; thyroid carcinoma including papillary thyroid carcinoma and medullary thyroid carcinoma choriocarcinoma; sarcomas including Ewing's sarcoma; bone cancer such as osteosarcoma; high-grade osteosarcoma; rhabdomyosarcoma; Ewing sarcoma; malignant fibrous histiocytoma of the bone; chordoma; soft tissue sarcoma; myeloma; multiple myelomas; labial carcinoma; larynx carcinoma; hypopharynx carcinoma; tongue carcinoma; salivary gland carcinoma; cervix carcinoma; uterine corpus carcinoma; endometrium carcinoma; chorion carcinoma; testis carcinoma; urinary carcinoma; bronchial carcinoma; basalioma; teratoma; retinoblastoma; choroid melanoma; seminoma; chondrosarcoma; myosarcoma; liposarcoma; fibrosarcoma; plasmacytoma; hepatocarcinoma; advanced liver cancer; gastrointestinal stromal tumors; neuroendocrine tumors; bile duct cancer; appendix cancer; gastrointestinal carcinoid tumor; carcinoid tumor; islet cell tumor; small intestine cancer; stomach cancer; adrenocortical carcinoma; parathyroid cancer; paraganglioma; pheochromocytoma; pituitary tumor; penile cancer; renal pelvis and ureter cancer; testicular cancer; urethral cancer; Wilms tumor; extracranial germ cell tumor; extragonadal germ cell tumor; fallopian tube cancer; gestational trophoblastic tumor; primary peritoneal cancer; vaginal cancer; vulvar cancer; hypopharyngeal cancer; laryngeal cancer; papillomatosis cancer; lip and oral cavity cancer; metastatic squamous neck cancer; mouth cancer; nasopharyngeal cancer; oropharyngeal cancer; paranasal sinus and nasal cavity and paranasal sinus cancer; parathyroid cancer; pharyngeal cancer; throat cancer; chronic myeloproliferative neoplasm; Langerhans cell histiocytosis; plasma cell neoplasm; myelodysplastic syndromes; myeloproliferative neoplasm; midline tract carcinoma; virally induced tumors; and diseases involving CCR6 and/or CCL20 mediated metastasis, chemotaxis, cell adhesion, trans-endothelial migration, cell proliferation and/or survival.

Notably, such diseases, conditions or disorders, where CCR6 receptors are involved refer to rheumatoid arthritis; ankylosing spondylitis; spondyloarthritis; psoriasis; psoriatic arthritis; inflammatory skin disorders e.g. rosacea; Crohn's disease; ulcerative colitis; irritable bowel disease; inflammatory bowel disease; dry eye disease; multiple sclerosis; systemic lupus erythematosus; Sjögren's disease; autoimmune hepatitis; Primary Sclerosing Cholangitis; psoriasis including plaque psoriasis, guttate psoriasis, inverse psoriasis, pustular psoriasis, erythrodermic psoriasis; autoimmune keratitis; filamentary keratitis; autoimmune uveitis; allergic conjunctivitis; asthma; allergic disease of the gastrointestinal tract; type 1 diabetes (T1D); endometriosis; meibomian gland dysfunction; graft-versus host disease; lymphoma including T cell lymphoma and primary mediastinal B-cell lymphoma; brain cancer including glioma and glioblastoma; breast cancer including triple negative breast cancer; colorectal cancer; hepatocarcinoma; renal cell carcinoma; lung cancer including non-small cell lung cancer and small cell lung cancer; gastric cancer; melanoma including Merkel cell carcinoma, cutaneous squamous cell carcinoma and malignant melanoma; bladder cancer; head and neck cancer including squamous cell head and neck carcinoma; Hodgkin's lymphoma; cervical cancer; endometrial cancer; colon cancer; gastrointestinal stromal tumors; pancreatic cancer; prostatic cancer; leukemia including acute myeloid leukemia; ovarian cancer; oesophageal carcinomas; mesothelioma; neuroblastoma; sarcoma e.g. high-grade osteosarcoma; astrocytoma; myeloma; urothelial cancer including locally advanced and metastatic urothelial cancer; MSI-H or dMMR cancer; rectal cancer; laryngeal cancer; salivary adenocarcinoma; multiple myeloma; cholangiocarcinoma; oral squamous cell carcinoma; thyroid cancer; and esophagogastric junction cancer.

Especially, such diseases, conditions or disorders, where CCR6 receptors are involved are selected from

- inflammatory/autoimmune diseases, conditions or disorders such as psoriasis; psoriatic arthritis; rheumatoid arthritis; ankylosing spondylitis; spondyloarthritis; inflammatory skin disorders e.g. rosacea; Crohn's disease; ulcerative colitis; irritable bowel disease; dry eye disease; multiple sclerosis; systemic lupus erythematosus; Sjögren's disease; autoimmune hepatitis; and Primary Sclerosing Cholangitis; In particular, psoriasis or psoriatic arthritis; and/or
- cancer such as lymphoma (e.g. T cell lymphoma); brain cancer (e.g. glioma or glioblastoma); breast cancer; colorectal cancer; hepatocarcinomas; renal cell carcinoma; lung cancer; and gastric cancer.

For avoidance of any doubt, if compounds are described as useful for the prevention or treatment of certain diseases, conditions or disorders, such compounds are likewise suitable for use in the preparation of a medicament for the prevention or treatment of said diseases.

The present invention also relates to a method for the prevention or treatment of diseases, conditions or disorders, mentioned hereinabove and/or hereinbelow comprising administering to a subject a pharmaceutically active amount of a compound as described hereinabove or/and hereinbelow either alone or in combination with other pharmacologically active compounds and/or therapies.

The meaning of the term "prevention" may also be understood as "prophylaxis".

Preparation of Compounds of Formula (I)

A further aspect of the invention is a process for the preparation of compounds of Formula (I). Compounds according to Formula (I) of the present invention can be prepared from commercially available or well-known starting materials according to the methods described in the experimental part; by analogous methods; or according to the general sequence of reactions outlined below. Optimum reaction conditions may vary with the particular reactants or solvents used, but such conditions can be determined by a person skilled in the art by routine optimisation procedures. In the schemes below, the generic groups A, B, $R^1$ and $R^2$ are as defined for the compounds of Formula (I); the number of carbon atoms "n" is 1. X represents a halogen atom, notably chlorine or bromine. The meaning of the generic group R' is derivable from the compounds of Formula (I) and/or the exemplified embodiments. Other abbreviations used herein are explicitly defined, or are as defined in the experimental section. In some instances, the functional groups described may be incompatible with the assembly illustrated in the schemes and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into salts, especially pharmaceutically acceptable salts thereof in a manner known per se.

General Preparation Routes:

Compounds of Formula (I) can be prepared starting from an intermediate of Formula (A1), which is reacted with N,O-dimethylhydroxylamine hydrochloride under standard conditions (e.g. HATU, DIPEA, DMF) to give the Weinreb amide derivative of Formula (A2) (Scheme A). Upon reaction with a compound of Formula (A3) wherein X is iodine or bromine, in presence of n-butyl lithium or n-hexyl lithium in THF at a temperature around −78° C., the ketone derivative of Formula (A4) is produced, which can be further reacted with a compound of Formula (A5) wherein X is a halogen atom, preferably bromine, similarly using n-butyl lithium or n-hexyl lithium in THF at a temperature around −78° C., to provide the tertiary alcohol intermediate of Formula (A6). A chiral separation by HPLC over a chiral stationary phase can be performed at this stage to yield enantiomerically pure intermediates of Formula (A6). Cleavage of the protecting group under standard conditions such as treatment with HCl in dioxane in the case of a Boc protecting group, or treatment with Pd/C (50% water) in EtOH or EA under hydrogen atmosphere in case of a Cbz protecting group, provides the free NH derivative of Formula (A7). A reductive amination step can be performed with an aldehyde of Formula (A8) or a ketone of Formula (A9) under standard conditions such as using $NaBH(OAc)_3$ or $NaBH_3CN$ as reductive agent, in presence of a base such as DIPEA or TEA, or in presence of an acid such as acetic acid, in a solvent such as DCM, MeOH, THF or dioxane, or a mixture thereof, and at a temperature around RT to provide compounds of Formula (I). Alternatively, the intermediate of Formula (A7) can be coupled to a reactant of Formula (A10) wherein X is iodine or bromine, in presence of a base such as TEA, DIPEA or $Cs_2CO_3$, in a solvent such as MeOH, THF or DMF, and stirring at a temperature from 0° C. to 70° C. Furthermore, the compounds of Formula (I) wherein $R^2$ is cyclopropyl can be prepared by coupling with (1-ethoxycyclopropoxy)trimethysilane, using $NaBH(OAc)_3$ in presence AcOH in EtOH and at RT. For the compounds of Formula (I) wherein $R^2$ is tert-butyl, specific conditions were used that are fully described in the experimental part (Example 12).

Scheme A

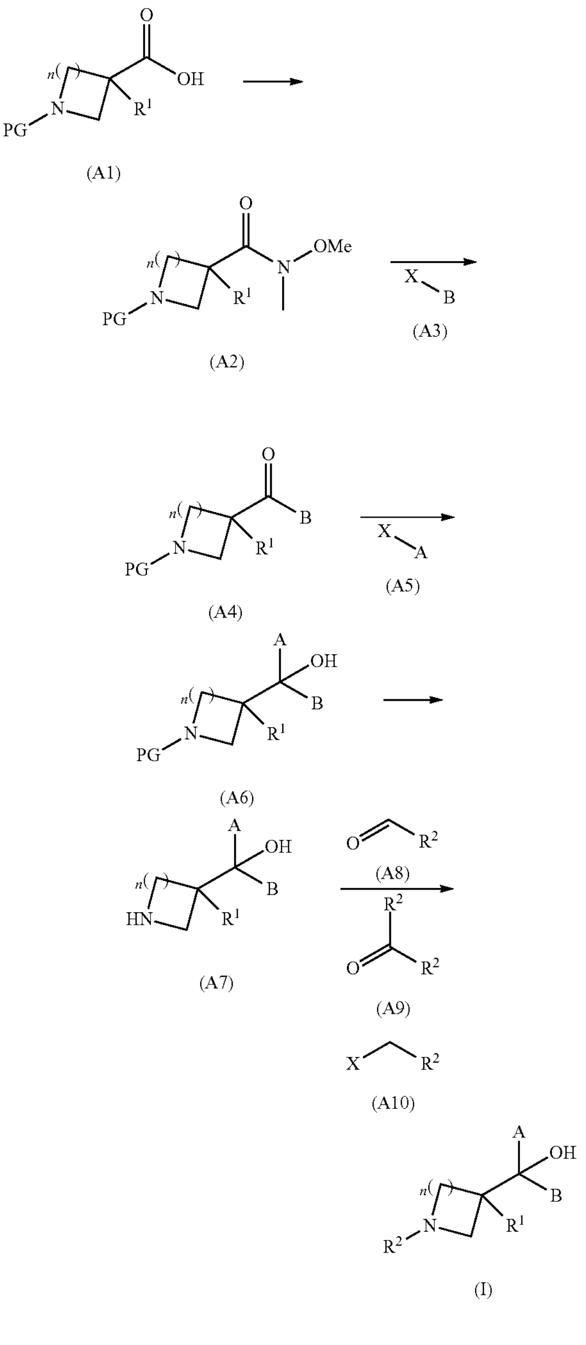

Alternatively, the compounds of Formula (I) can be prepared following the route described in Scheme B. The protecting group in intermediate (A4) can be removed and the free NH of the resulting intermediate (B1) can be reacted with an aldehyde of structure (A8), a ketone of structure (A9), a reactant of Formula (A10), or (1-ethoxycyclopropoxy)trimethysilane, as previously described. The resulting intermediate of Formula (B2) can be reacted with a compound of Formula (A5) wherein X is a halogen atom, preferably bromine, using conditions described in Scheme A to provide compounds of Formula (I), or using a iPrMgCl—LiCl-mediated halogen-metal exchange protocol in presence of LiCl in THF and heating at around 60° C.

Scheme B

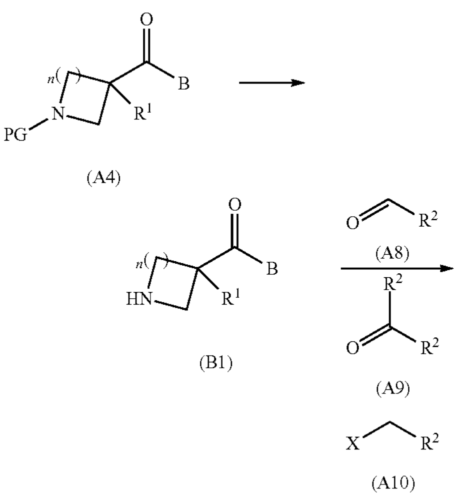

(A4)

(B1)

(A8)

(A9)

(A10)

-continued

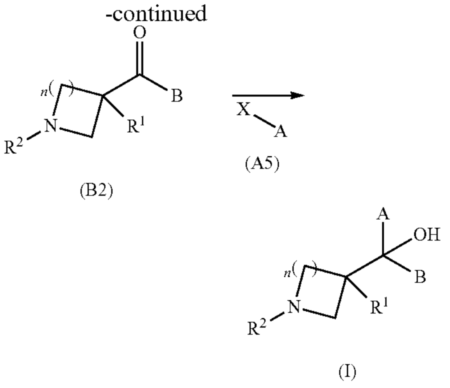

(B2)

(A5)

(I)

Alternatively, the compounds of Formula (I) can be prepared using the same synthetic strategies as those described in Schemes A and B, with the difference of performing the addition of the compound of Formula (A5) prior to the addition of the compound of Formula (A3) in the synthetic sequence (Scheme C), and using the same conditions as those reported previously.

Scheme C

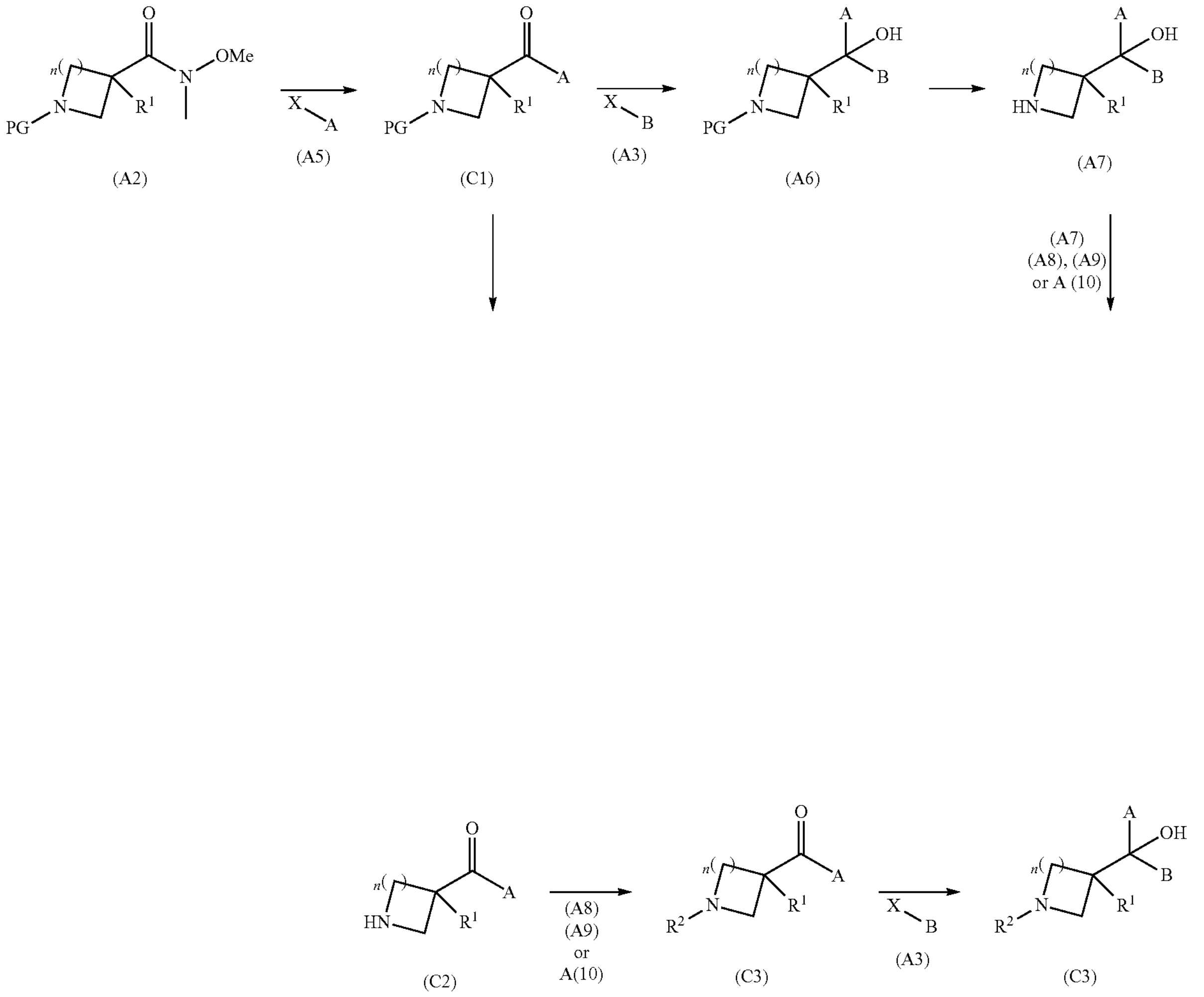

(A2)

(A5)

(C1)

(A3)

(A6)

(A7)

(C2)

(C3)

(A3)

(C3)

The intermediates of Formula (D1) (see Scheme D) wherein C and/or D are/is a nitrogen atom and R is a protecting group, or wherein C and/or D are/is a nitrogen atom and R is $R^2$, can be prepared starting from the appropriate compound of Formula (A5) wherein A contains a cyano group in meta position to the halogen atom X, X being iodine or bromine, following the route described in Scheme A for the synthesis of intermediates of Formula (A6), or of Formula (I), respectively. Alternatively, an intermediate of Formula (D1) can be prepared starting from a compound of Formula (A5) wherein A contains a bromine atom in meta position to the halogen atom X, X being iodine or bromine, and using the same conditions as described above. The bromine atom may be further transformed into a cyano group using zinc cyanide, in presence of zinc and $Pd_2(dba)_3$, using a ligand such as 1,1'-bis(diphenylphosphino)ferrocene, in a solvent such as DMF and heating at around 150° C. An intermediate of Formula (D1) can be transformed into a hydroxyamidine derivative of Formula (D2) by reaction with hydroxylamine hydrochloride in a solvent such as EtOH or DMSO, in presence of a base such as TEA or $K_2CO_3$, and at a temperature between 80° C. and 100° C. The resulting hydroxyamidine intermediate (D2) can be further reacted with a carboxylic acid of Formula (D3) to form an oxadiazole-containing derivative of Formula (D4) if R is a protecting group, or a compound of Formula (I) if R is $R^2$, using a coupling agent such as HATU, PyBOP, EDC combined with HOBt, CDI, in presence of a base such as DIPEA or $K_3PO_4$, optionally in presence of molecular sieves 3A, in a solvent such as dioxane, DMSO or DMF, and heating at a temperature between 80° C. and 100° C. Alternatively, the formation of the oxadiazole ring can be performed in two steps (i) coupling with the carboxylic acid partner of Formula (D3) as described before at RT and (ii) heating at a temperature between 80° C. and 100° C. in presence of molecular sieves 3A. Moreover, a compound of Formula (D2) can be reacted with trimethyl orthoformate, in presence of boron trifluoride and TEA, in a solvent such as DMA, and heating at around 50° C. to provide a compound of Formula (D4) wherein R' is hydrogen. The intermediate of Formula (D4) can be further transformed into a compound of Formula (I) following the two-step protocol described in Scheme A.

Scheme D

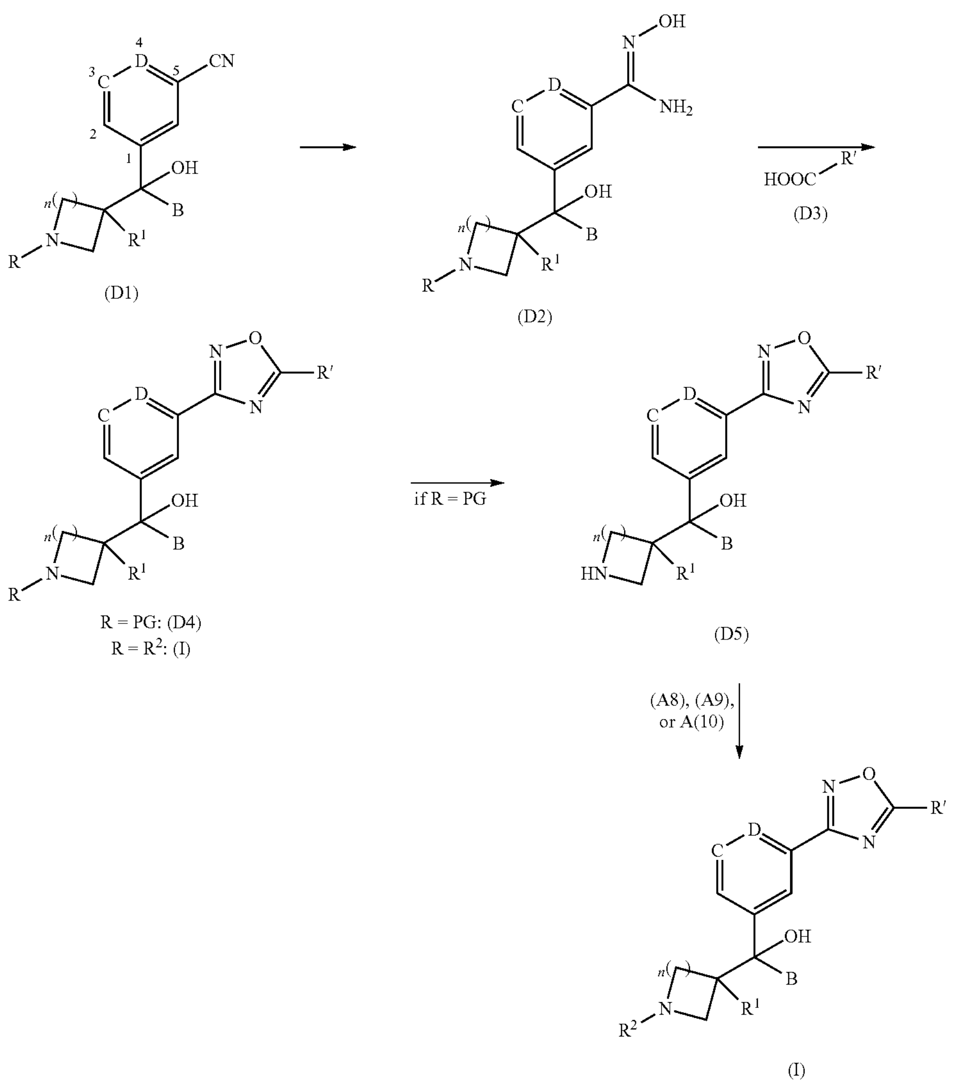

The intermediates of Formula (E1) (see Scheme E) wherein C and/or D are/is a nitrogen atom and R is a protecting group, or wherein C and/or D are/is a nitrogen atom and R is $R^2$, can be prepared starting from the appropriate compound of Formula (A5) wherein A contains a protected acid function such as a tert-butyl carboxylic acid moiety in meta position to the halogen atom X, following the route described in Scheme A for the synthesis of intermediates of Formula (A6), or compounds of Formula (I), respectively. An intermediate of Formula (E1) can be transformed into an intermediate of Formula (E3) wherein R is a protecting group, or into a compound of Formula (I) wherein R is $R^2$, by reaction with a hydroxyamidine derivative of Formula (E2) using conditions described in Scheme (D). Hydroxyamidine derivatives of Formula (E2), if not commercially available, can be prepared using the same protocol as described in Scheme (D).

Scheme E

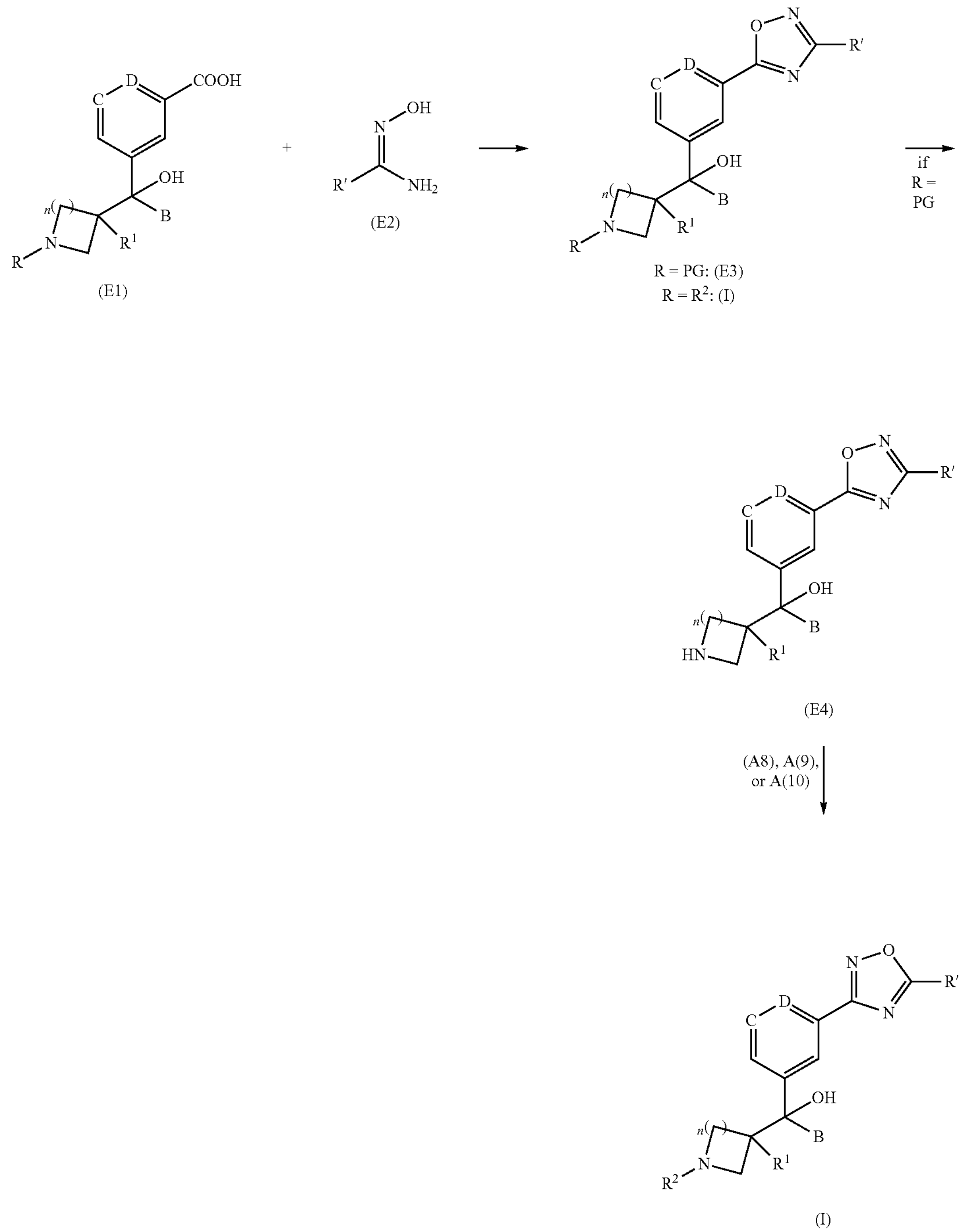

(E1)
(E2)
R = PG: (E3)
R = $R^2$: (I)
(E4)
(I)

Furthermore, the intermediates of Formula (D4) and (E3) wherein R is $R^2$ and R' contains a protected amine function can be transformed into compounds of formula (I) following a two-step protocol. Firstly, the amine protecting group can be cleaved using standard conditions such as treatment with HCl in dioxane in the case of a Boc protecting group. The resulting amine-containing intermediate can be subsequently engaged in a coupling reaction, with an acid chloride reactant, in presence of a base such as DIPEA, in a suitable solvent such as THF; or with an acid-containing reactant of formula (D3), using HATU as coupling agent, in presence of a base such as DBU, in a suitable solvent such as DMF; or with a sulfonyl chloride reactant, in presence of a base such as DIPEA, in a suitable solvent such as DCM. In case diacylation was observed during the coupling reaction, subsequent treatment with $K_2CO_3$ in MeOH can provide the desired compound of formula (I).

The intermediates of Formula (F1) (see Scheme F) wherein X is a chlorine atom, C is CH, and D is nitrogen; or wherein X is a chlorine atom, C and D are nitrogen atoms; or wherein X is a bromine atom, C is a nitrogen atom, and D is CH; can be prepared following the route described in Scheme B using the appropriate derivative of Formula (A5).

Compounds of Formula (I) can be prepared by reacting an intermediate of Formula (F1) wherein X is a bromine atom, C is a nitrogen atom, and D is CH; or wherein X is a chlorine atom, and C and D are nitrogen atoms; with an NH-containing reagent of Formula (F2), using standard conditions for a Buchwald type reaction, using a palladium catalyst such as $Pd_2(dba)_3$, in presence of a ligand such as Xantphos, RuPhos, or BINAP, in presence of a base such as NaOtBu, in toluene, and heating at a temperature around 100° C. Alternatively, the coupling reaction can be performed using a copper catalyst such as CuI, in presence of a ligand such as L-proline, in presence of a base such as $K_2CO_3$, in a solvent such as DMSO and heating at a temperature around 100° C.

Furthermore, compounds of Formula (I) can be prepared by reacting an intermediate of Formula (F1), wherein X is a chlorine atom, and C and D are nitrogen atoms; or wherein X is a chlorine atom, C is CH, and D is a nitrogen atom; with an NH-containing reagent of Formula (F2), using standard conditions for an aromatic nucleophilic substitution type reaction, optionally in presence of a base such as DIPEA, and heating at a temperature between 100° C. and 150° C. in a solvent such as n-butanol, NMP, or dioxane.

An intermediate of Formula (F1) wherein X is a bromine atom, C is a nitrogen atom, and D is CH; or wherein X is a chlorine atom, and C and D are nitrogen atoms; can be further reacted with an amide-containing reagent of Formula (F3), or with a carbamate-containing reagent of Formula (F4), using a copper catalyst such as CuI, in presence of a ligand such as N,N-dimethylenediamine, in presence of a base such as $K_2CO_3$, in a solvent such as dioxane, and heating at a temperature around 110° C.

In addition, an intermediate of Formula (F1) wherein X is a chlorine atom, C is CH, and D is nitrogen; or wherein X is a bromine atom, C is nitrogen, and D is CH; or wherein X is a bromine atom, and C and D are CH can be reacted with an alkyne-containing reagent of Formula (F5), using standard conditions for a Sonogashira type reaction, using a palladium catalyst such as $Pd(PPh_3)_4$, $Pd(OAc)_2$, or $PdCl_2(PPh_3)_2$, optionally combined with a copper catalyst such as CuI, optionally in presence of a ligand such as $PPh_3$, in presence of a base such as piperidine, $Et_2NH$, or $K_3PO_4$, in a solvent such as THF, DMF, or DMSO/toluene mixture, and heating at a temperature between 60° C. and 80° C. The alkyne (F5) reagents are either commercially available or accessible via multistep synthesis as described in the experimental part.

The resulting alkyne-containing compound of Formula (I) can be further transformed by hydrogenation of the alkyne functionality into an alkane chain using Pd/C (50% water) in EtOH or MeOH and under a hydrogen atmosphere.

Furthermore, an intermediate of Formula (F1) wherein X is a chlorine atom, C is CH, and D is nitrogen; or wherein X is a bromine atom, C is nitrogen, and D is CH; or wherein X is a bromine atom, and C and D are CH can be reacted with an boronic acid or boronate ester reagent of Formula (F6) using standard conditions for a Suzuki type reaction, using a palladium catalyst such as $Pd(PPh_3)_4$, $Pd(dppf)_2Cl_2$ or $PdCl_2(PPh_3)_2$, in presence of a base such as $Na_2CO_3$ or $K_3PO_4$, in a solvent such as MeCN/water, DME/water or dioxane/water mixture, and heating at a temperature around 80° C.

An intermediate of Formula (F1) wherein X is bromine can be converted by Miyaura borylation using standard conditions to the corresponding boronic acid or ester of Formula (F10) and subsequently treated with a reagent of Formula (F9) in a Suzuki type reaction as described previously.

In addition, an intermediate of Formula (F1) wherein X is a chlorine atom, C is CH, and D is nitrogen; or wherein X is a bromine atom, C is nitrogen, and D is CH can be reacted with a alkyl zinc reagent of Formula (F7) using standard conditions for a Negishi type reaction, using a palladium catalyst such as $Pd(dppf)_2Cl_2$, in a solvent such as toluene, and heating at a temperature around 70° C.

Furthermore, compounds of Formula (I) can be prepared by reacting an intermediate of Formula (F1) wherein X is a chlorine atom, C is CH, and D is a nitrogen atom, with an alcohol reagent of Formula (F8), using standard conditions for an aromatic nucleophilic substitution type reaction, in presence of a base such as NaH, and heating at a temperature between 100° C. and 110° C., optionally in a solvent such as dioxane.

It will be understood by one skilled in the art that the steps described in Scheme (F) can be performed with the protected azetidine ring (n=1) prior to the introduction of the $R^2$ group, and following the two-step protocol from the intermediate (A6) described in Scheme (A) to yield compounds of Formula (I).

Scheme F
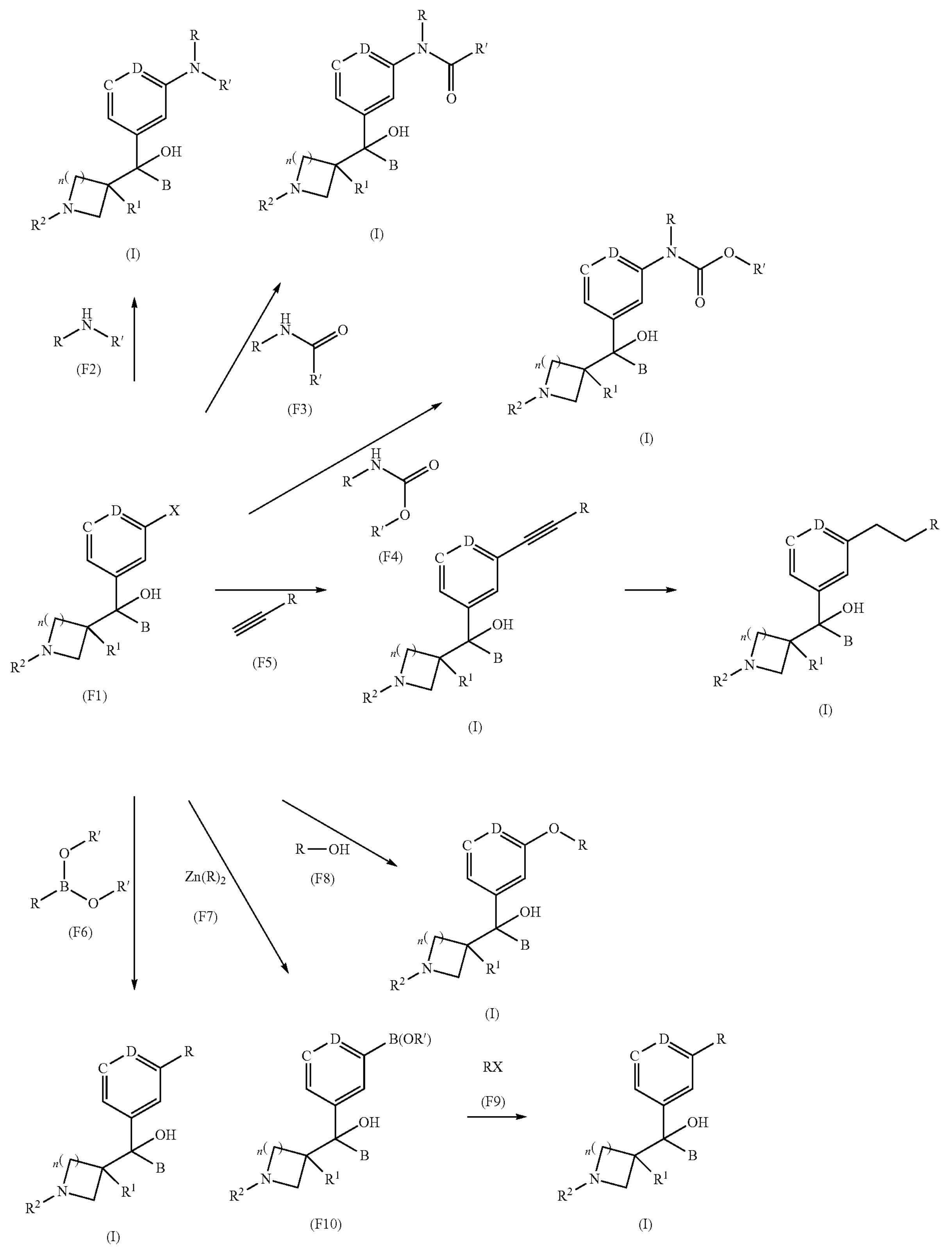

The intermediates of Formula (G1) (see Scheme G) wherein C is CH, and D is a nitrogen atom; or wherein C is a nitrogen atom, and D is CH can be prepared following the route described in Scheme B using the appropriate derivative of Formula (A5) that contains a protected phenol group in the form of a benzyloxy or methyloxy functionality. Deprotection using Pd/C in EtOH under hydrogen atmosphere, or 2-diethylamino-ethanethiol and KOtBu in DMF, respectively, provides the intermediates of Formula (G1). Such intermediates of Formula (G1) can be transformed into compounds of Formula (I) by performing a Mitsunobu type reaction with a hydroxy-containing derivative of Formula (G2), using conditions such as cyanomethyltributylphosphorane in toluene and heating at a temperature around 110° C. It will be understood by one skilled in the art that the Mitsunobu reaction can be performed with the protected azetidine ring (n=1) prior to the introduction of the $R^2$ group, and following the synthetic sequence from the intermediate (A6) described in Scheme (A) to yield compounds of Formula (I).

Scheme G

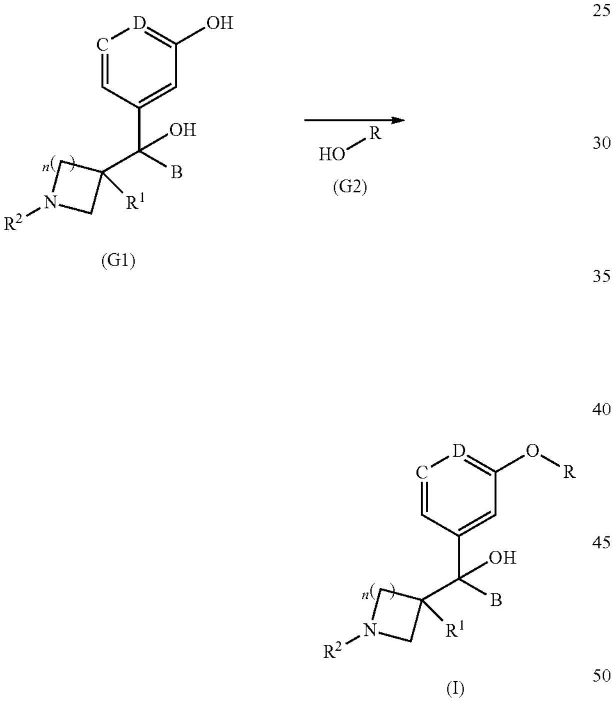

(G1) (G2) (I)

The intermediates of Formula (A5) (see Scheme H) wherein C is CH, and D is a nitrogen atom; or wherein C is a nitrogen atom, and D is CH can be prepared via a two-step procedure: (i) treatment of an appropriate nitrile of Formula (H1) with hydroxylamine hydrochloride in a solvent such as EtOH or DMSO, in presence of a base such as $K_2CO_3$ or TEA, and at a temperature between 80° C. and 100° C. and (ii) subsequent treatment of the resulting hydroxyamidine derivative of Formula (H2) with a carboxylic acid of Formula (D3) using a coupling agent such as HATU, PyBOP, EDC combined with HOBt, or CDI in possible presence of a base such as DIPEA or $K_3PO_4$, in a solvent such as dioxane, DMF or DMSO, and heating at a temperature between 80° C. and 100° C.

Scheme H

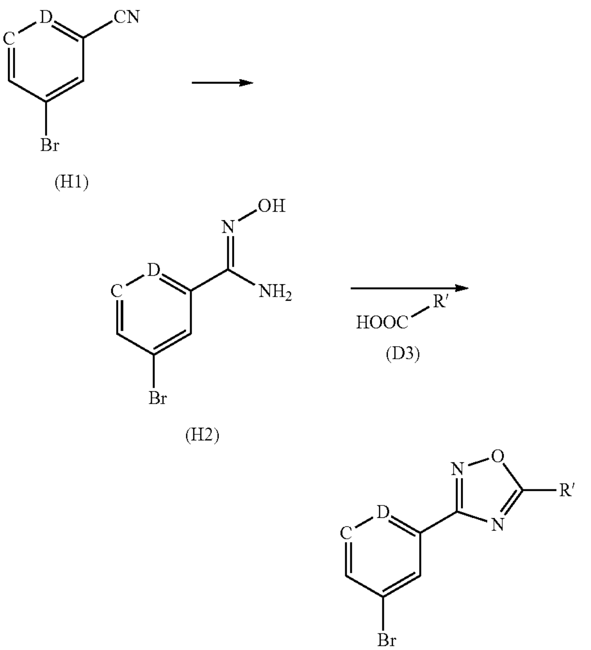

(H1) (H2) (D3) (A5)

The intermediates of Formula (J1) (see Scheme J) can be prepared following the route described in Scheme A using the appropriate derivative of Formula (A3) that contains a bromo-phenyl group. Such intermediates of Formula (J1) can be transformed into compounds of Formula (I) wherein R represents an appropriate $C_{1-5}$-alkyl, $C_{1-4}$-fluoroalkyl, or $C_{2-4}$-alkenyl group by Suzuki cross coupling with boron species of Formula (J2) wherein R represents an appropriate $C_{1-5}$-alkyl, $C_{1-3}$-alkoxy-$C_{1-4}$-alkyl, $C_{1-4}$-fluoroalkyl, $C_{2-4}$-alkenyl group and BX represents $BF_3K$, Bpin or $B(OH)_2$ in the presence of a suitable palladium catalyst such as cataCXium®A Pd G3 and a suitable base such as $Cs_2CO_3$ and heating in a suitable solvent such as a mixture of toluene and water at temperatures around 100° C.

Alternatively, intermediates of Formula (J1) can be transformed into intermediate of Formula (J3) by Miyaura borylation using standard conditions such as treatment with bis(pinacolato)diboron in the presence of a suitable palladium catalyst such as $Pd(dppf)Cl_2$.DCM and a suitable base such as KOAc and heating in a suitable solvent such as dioxane at temperatures around 80° C.

Such intermediates of Formula (J3) can be transformed into compounds of Formula (I) wherein R represents a trifluoromethyl group by copper catalyzed perfluoroalkylation with a trifluoromethylation reagent of Formula (J4) such as $(phen)CuCF_3$ in the optional presence of a suitable base such as KF and heating in a suitable solvent such as DMF at temperatures around 50° C.

Alternatively, intermediates of Formula (J3) can be transformed into compounds of Formula (I) wherein R represents a $C_{1-3}$-alkoxy or $C_{3-5}$-cycloalkoxy group via a two-step procedure: (i) treatment with an aq. solution of hydrogen peroxide in the presence of NaOH in a solvent such as THF at temperatures between 0° C. and RT and (ii) subsequent treatment of the resulting phenol intermediate of Formula (J5) with an appropriate $C_{1-3}$-alkyl or $C_{3-5}$-cycloalkyl halide of formula (J6) in the presence of suitable base such as $K_2CO_3$ and heating in a suitable solvent such as DMF at temperatures around 100° C.

Scheme J

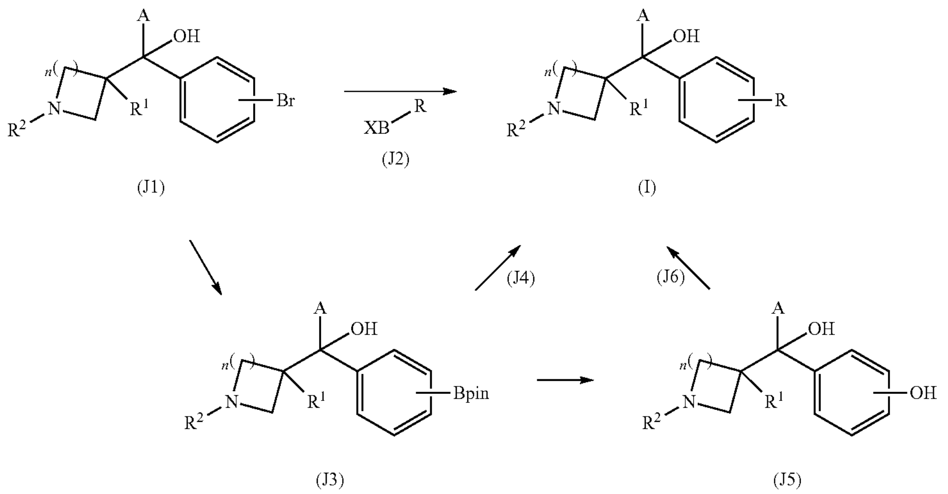

Reactants of Formula (A3), (A5), (A8), (A9), (D3), (E2), (F2) to (F9), (G2), (J2), (J4) and (J6) are either commercially available or can be synthesized according to published protocols.

Whenever the compounds of Formula (I) are obtained in the form of mixtures of enantiomers, the enantiomers can be separated using methods known to one skilled in the art: e.g. by formation and separation of diastereomeric salts or by HPLC over a chiral stationary phase. Enantiomeric separation may be performed at the stage of intermediate (A6) or with compounds of Formula (I).

EXPERIMENTAL SECTION

Abbreviations (as Used Herein and in the Description Above)

Ac acetyl
aq. aqueous
BINAP (2,2'-bis(diphenylphosphino)-1,1'-binaphthyl)
Boc tert-butyloxycarbonyl
BSA Bovine serum albumin
Brine saturated aqueous NaCl solution
Bu butyl
cataCXium®A Pd G3 mesylate[(di(1-adamantyl)-n-butylphosphine)-2-(2'-amino-1,1'-biphenyl)]palladium (II)
Cbz benzyloxycarbonyl
CC column chromatography on silica gel
CDI 1,1'-carbonyldiimidazole
CV column volume
dba dibenzylideneacetone
DCM dichloromethane
DBU 1,8-diazabicyclo[5.4.0]undec-7-ene
DIPEA N-ethyldiisopropylamine
DMA N,N-Dimethylacetamide
DME 1,2-dimethoxyethane
DMAP 4-dimethylaminophenol
DMEM Dulbecco's modified eagle media
DMF dimethylformamide
DMP Dess Martin periodinane
DMSO dimethylsulfoxide
dppf 1,1'-bis(diphenylphosphino)ferrocene
EA ethyl acetate
EDC 1-ethyl-3-(3-dimethylaminopropyl)carbodiimide
eq Equivalent
Et ethyl
FCS fetal calf serum
FLIPR Fluorescent imaging plate reader
Fluo-8-AM acetyloxymethyl 2-[N-[2-(acetyloxymethoxy)-2-oxoethyl]-4-[3-(acetyloxymethoxy)-6-oxoxanthen-9-yl]-2-[2-[2-[bis[2-(acetyloxymethoxy)-2-oxoethyl]amino]phenoxy]ethoxy]anilino]acetate
h hour(s)
HATU 2-(7-Aza-1H-benzotriazole-1-yl)-1,1,3,3-tetramethyluronium
HEK Human embryonic kidney
Hep heptanes
HOBt hydroxybenzotriazole
HV high vacuo
HPLC high performance liquid chromatography
LC liquid chromatography
LiHMDS lithium-bis(trimethylsilyl)amide
M molarity [mol $L^{-1}$]
Me methyl
MS mass spectrometry
min minute(s)
MTBE methyl tert-butyl ether
NMP N-methyl-2-pyrrolidone
NMR nuclear magnetic resonance spectroscopy
org. organic
Pd/C palladium on carbon
PG protecting group
Ph phenyl
phen phenanthroline
pin pinacol
Prep preparative
PyBOP (benzotriazol-1-yloxy)tripyrrolidinophosphonium hexafluorophosphate rpm rotations per minute
RT room temperature
RuPhos 2-dicyclohexylphosphino-2',6'-diisopropoxybiphenyl
sat. saturated
t tert
TBAF tetrabutylammoniumfluorid
TEA triethylamine
TFA trifluoroacetic acid
THF tetrahydrofuran
TLC Thin layer chromatography
$t_R$ retention time
UPLC Ultra performance liquid chromatography
Xantphos 4,5-bis(diphenylphosphino)-9,9-dimethylxanthene I. Chemistry The following Examples illustrate the preparation of compounds of the invention but do not at all limit the scope thereof.

General: All temperatures are stated in degrees Celsius (° C.). Unless otherwise indicated, the reactions take place at RT under an argon atmosphere and are run in a flame dried round-bottomed flask or sealable tube equipped with a magnetic stir bar.

Characterization Methods Used:

The LC-MS retention times have been obtained using the following elution conditions:

I) LC-MS (A):

Zorbax RRHD SB-Aq, 1.8 □m, 2.1×50 mm column thermostated at 40° C. The two elution solvents were as follows: solvent A=water+0.04% TFA; solvent B=MeCN. The eluent flow rate was 0.8 mL/min and the characteristics of the eluting mixture proportion in function of the time t from start of the elution are summarized in the table below (a linear gradient being used between two consecutive time points):

| t (min) | 0 | 1.2 | 1.9 | 2.1 |
|---|---|---|---|---|
| Solvent A (%) | 95 | 5 | 5 | 95 |
| Solvent B (%) | 5 | 95 | 95 | 5 |

II) LC-MS (B):

Acquity UPLC CSH C18 1.7 um, 2.1×50 mm from Waters thermostated at 60° C. The two elution solvents were as follows: solvent A=water+0.05% HCOOH; solvent B=MeCN+0.045% HCOOH. The eluent flow rate was 1 mL/min and the characteristics of the eluting mixture proportion in function of the time t from start of the elution are summarized in the table below (a linear gradient being used between two consecutive time points):

| t (min) | 0 | 2.0 | 2.1 |
|---|---|---|---|
| Solvent A (%) | 98 | 2 | 98 |
| Solvent B (%) | 2 | 98 | 2 |

The chiral SFC or HPLC retention times have been obtained using the following elution conditions:

I) Chiral SFC (A):

CHIRALCEL OD-H, 5 □m, 4.6×250 mm column thermostated at 40° C. was used. The two elution solvents were as follows: solvent A=$CO_2$; solvent B=MeOH. The eluent flow rate was 4 mL/min, the duration of the run was 5 min and the isocratic solvent proportion was 92% (A)/8% (B).

II) Chiral SFC (B):

CHIRALCEL OZ-H, 5 □m, 4.6×250 mm column thermostated at 40° C. was used. The two elution solvents were as follows: solvent A=$CO_2$; solvent B=MeOH+0.1% DEA. The eluent flow rate was 4 mL/min, the duration of the run was 4 min and the isocratic solvent proportion was 85% (A)/15% (B).

III) Chiral SFC (C):

CHIRALPAK AD-H, 5 □m, 4.6×250 mm column thermostated at 40° C. was used. The two elution solvents were as follows: solvent A=$CO_2$; solvent B=EtOH. The eluent flow rate was 4 mL/min, the duration of the run was 3 min and the isocratic solvent proportion was 80% (A)/20% (B).

IV) Chiral SFC (D):

CHIRALPAK IB, 5 □m, 4.6×250 mm column thermostated at 40° C. was used. The two elution solvents were as follows: solvent A=$CO_2$; solvent B=EtOH. The eluent flow rate was 4 mL/min, the duration of the run was 5 min and the isocratic solvent proportion was 85% (A)/15% (B).

V) Chiral SFC (E):

CHIRALPAK IC, 5 □m, 4.6×250 mm column thermostated at 40° C. was used. The two elution solvents were as follows: solvent A=$CO_2$; solvent B=MeOH+0.1% DEA. The eluent flow rate was 4 mL/min, the duration of the run was 5 min and the isocratic solvent proportion was 60% (A)/40% (B).

VI) Chiral SFC (F):

CHIRALPAK IB, 5 □m, 4.6×250 mm column thermostated at 40° C. was used. The two elution solvents were as follows: solvent A=$CO_2$; solvent B=MeOH. The eluent flow rate was 4 mL/min, the duration of the run was 4 min and the isocratic solvent proportion was 90% (A)/10% (B).

VII) Chiral SFC (G):

CHIRALPAK AD-H, 5 □m, 4.6×250 mm column thermostated at 40° C. was used. The two elution solvents were as follows: solvent A=$CO_2$; solvent B=EtOH. The eluent flow rate was 4 mL/min, the duration of the run was 4 min and the isocratic solvent proportion was 75% (A)/25% (B).

VIII) Chiral SFC (H):

CHIRALCEL OZ-H, 5 □m, 4.6×250 mm column thermostated at 40° C. was used. The two elution solvents were as follows: solvent A=$CO_2$; solvent B=MeOH+0.1% DEA. The eluent flow rate was 4 mL/min, the duration of the run was 5 min and the isocratic solvent proportion was 85% (A)/15% (B).

IX) Chiral SFC (I):

CHIRALCEL OD-H, 5 □m, 4.6×250 mm column thermostated at 40° C. was used. The two elution solvents were as follows: solvent A=$CO_2$; solvent B=MeOH. The eluent flow rate was 4 mL/min, the duration of the run was 3.5 min and the isocratic solvent proportion was 90% (A)/10% (B).

X) Chiral SFC (J):

CHIRALPAK AD-H, 5 □m, 4.6×250 mm column thermostated at 40° C. was used. The two elution solvents were as follows: solvent A=$CO_2$; solvent B=MeCN/EtOH 1/1+0.1% DEA. The eluent flow rate was 4 mL/min, the duration of the run was 5 min and the isocratic solvent proportion was 75% (A)/25% (B).

XI) Chiral SFC (K):

CHIRALPAK AS-H, 5 □m, 4.6×250 mm column thermostated at 40° C. was used. The two elution solvents were as follows: solvent A=$CO_2$; solvent B=MeCN/EtOH+0.1% DEA. The eluent flow rate was 4 mL/min, the duration of the run was 3 min and the isocratic solvent proportion was 70% (A)/30% (B).

XII) Chiral SFC (L):

CHIRALCEL OD-H, 5 □m, 4.6×250 mm column thermostated at 40° C. was used. The two elution solvents were as follows: solvent A=$CO_2$; solvent B=MeOH+0.1% DEA. The eluent flow rate was 4 mL/min, the duration of the run was 5 min and the isocratic solvent proportion was 85% (A)/15% (B).

XIII) Chiral SFC (M):

CHIRALPAK AD-H, 5 □m, 4.6×250 mm column thermostated at 40° C. was used. The two elution solvents were as follows: solvent A=$CO_2$; solvent B=EtOH+1% DEA. The eluent flow rate was 4 mL/min, the duration of the run was 3 min and the isocratic solvent proportion was 75% (A)/25% (B).

XIV) Chiral SFC (N):

REGIS (R,R) Whelk-O1, 5 □m, 4.6×250 mm column thermostated at 40° C. The two elution solvents were as follows: solvent A=$CO_2$; solvent B=DCM/MeOH 1/1+0.1% DEA. The eluent flow rate was 4 mL/min, the duration of the run was 5 min and the isocratic solvent proportion was 70% (A)/30% (B).

XV) Chiral SFC(O):

CHIRALPAK ID, 5 □m, 4.6×250 mm column thermostated at 40° C. The two elution solvents were as follows: solvent A=$CO_2$; solvent B=MeCN/EtOH 1/1+0.1% DEA. The eluent flow rate was 4 mL/min, the duration of the run was 5 min and the isocratic solvent proportion was 65% (A)/35% (B).

XVI) Chiral SFC (P):

CHIRALPAK IB, 5 □m, 4.6×250 mm column thermostated at 40° C. was used. The two elution solvents were as follows: solvent A=$CO_2$; solvent B=MeOH+0.1% DEA. The eluent flow rate was 4 mL/min, the duration of the run was 5 min and the isocratic solvent proportion was 90% (A)/10% (B).

XVII) Chiral SFC (Q):

CHIRALPAK IB, 5 □m, 4.6×250 mm column thermostated at 40° C. was used. The two elution solvents were as follows: solvent A=$CO_2$; solvent B=MeOH. The eluent flow rate was 4 mL/min, the duration of the run was 2.50 min and the isocratic solvent proportion was 80% (A)/20% (B).

XVIII) Chiral SFC (R):

CHIRALPAK IH, 5 □m, 4.6×250 mm column thermostated at 40° C. was used. The two elution solvents were as follows: solvent A=$CO_2$; solvent B=MeCN+EtOH 1/1. The eluent flow rate was 4 mL/min, the duration of the run was 5 min and the isocratic solvent proportion was 85% (A)/15% (B).

XIX) Chiral HPLC (S):

CHIRALPAK AY-H, 5 □m, 4.6×250 mm column thermostated at 25° C. was used. The two elution solvents were as follows: solvent A=Hept; solvent B=2-Propanol. The eluent flow rate was 1 mL/min, the duration of the run was 15 min and the isocratic solvent proportion was 80% (A)/20% (B).

XX) Chiral SFC (T):

CHIRALPAK IH, 5 □m, 4.6×250 mm column thermostated at 40° C. was used. The two elution solvents were as follows: solvent A=$CO_2$; solvent B=Hept+EtOH 1/1. The eluent flow rate was 4 mL/min, the duration of the run was 5 min and the isocratic solvent proportion was 85% (A)/15% (B).

XXI) Chiral SFC (U):

CHIRALCEL OD-H, 5 □m, 4.6×250 mm column thermostated at 40° C. was used. The two elution solvents were as follows: solvent A=$CO_2$; solvent B=EtOH. The eluent flow rate was 4 mL/min, the duration of the run was 2.5 min and the isocratic solvent proportion was 80% (A)/20% (B).

XXII) Chiral SFC (V):

CHIRALPAK AD-H, 5 □m, 4.6×250 mm column thermostated at 40° C. was used. The two elution solvents were as follows: solvent A=002; solvent B=EtOH. The eluent flow rate was 4 mL/min, the duration of the run was 5 min and the isocratic solvent proportion was 85% (A)/15% (B).

XXIII) Chiral SFC (W):

CHIRALPAK AD-H, 5 □m, 4.6×250 mm column thermostated at 40° C. was used. The two elution solvents were as follows: solvent A=$CO_2$; solvent B=EtOH. The eluent flow rate was 4 mL/min, the duration of the run was 3.5 min and the isocratic solvent proportion was 90% (A)/10% (B).

XXIV) Chiral HPLC (X):

CHIRALCEL OD-H, 5 □m, 4.6×250 mm column thermostated at 25° C. was used. The two elution solvents were as follows: solvent A=Heptane; solvent B=EtOH. The eluent flow rate was 0.8 mL/min, the duration of the run was 20 min and the isocratic solvent proportion was 80% (A)/20% (B).

XXV) Chiral HPLC (Y):

CHIRALPAK IG, 5 □m, 4.6×250 mm column thermostated at 25° C. was used. The two elution solvents were as follows: solvent A=Hept+0.05% DEA; solvent B=MeOH/EtOH 1/1+0.05% DEA. The eluent flow rate was 1 mL/min, the duration of the run was 15 min and the isocratic solvent proportion was 30% (A)/70% (B).

XXVI) Chiral SFC (Z):

CHIRALCEL OD-H, 5 □m, 4.6×250 mm column thermostated at 40° C. was used. The two elution solvents were as follows: solvent A=$CO_2$; solvent B=MeOH. The eluent flow rate was 4 mL/min, the duration of the run was 2.5 min and the isocratic solvent proportion was 75% (A)/25% (B).

XXVII) Chiral SFC (AA):

A (R,R) Whelk-O1, 5 □m, 4.6×250 mm column thermostated at 40° C. was used. The two elution solvents were as follows: solvent A=$CO_2$; solvent B=MeCN/iPrOH 1/1. The eluent flow rate was 4 mL/min, the duration of the run was 3.5 min and the isocratic solvent proportion was 80% (A)/20% (B).

XXVIII) Chiral SFC (AB):

A Chiralpak AD-H, 5 □m, 4.6×250 mm column thermostated at 40° C. was used. The two elution solvents were as follows: solvent A=$CO_2$; solvent B=MeOH. The eluent flow rate was 4 mL/min, the duration of the run was 3.5 min and the isocratic solvent proportion was 85% (A)/15% (B).

XXIX) Chiral SFC (AC):

A Chiralpak IB, 5 □m, 4.6×250 mm column thermostated at 40° C. was used. The two elution solvents were as follows: solvent A=$CO_2$; solvent B=MeCN/EtOH 1/1. The eluent flow rate was 4 mL/min, the duration of the run was 5 min and the isocratic solvent proportion was 70% (A)/30% (B).

XXX) Chiral SFC (AD):

A Chiralpak IG, 5 □m, 4.6×250 mm column thermostated at 40° C. was used. The two elution solvents were as follows: solvent A=$CO_2$; solvent B=EtOH. The eluent flow rate was 4 mL/min, the duration of the run was 3 min and the isocratic solvent proportion was 85% (A)/15% (B).

XXXI) Chiral SFC (AE):

CHIRALCEL OD-H, 5 □m, 4.6×250 mm column thermostated at 40° C. was used. The two elution solvents were as follows: solvent A=$CO_2$; solvent B=MeOH. The eluent flow rate was 4 mL/min, the duration of the run was 5.0 min and the isocratic solvent proportion was 90% (A)/10% (B).

XXXII) Chiral SFC (AF):

CHIRALCEL OD-H, 5 □m, 4.6×250 mm column thermostated at 40° C. was used. The two elution solvents were as follows: solvent A=$CO_2$; solvent B=MeOH. The eluent flow rate was 4 mL/min, the duration of the run was 5.0 min and the isocratic solvent proportion was 80% (A)/20% (B).

XXXIII) Chiral SFC (AG):

CHIRALPAK AD-H, 5 □m, 4.6×250 mm column thermostated at 40° C. was used. The two elution solvents were as follows: solvent A=$CO_2$; solvent B=EtOH. The eluent flow rate was 5 mL/min, the duration of the run was 3.5 min and the isocratic solvent proportion was 95% (A)/5% (B).

XXXIV) Chiral HPLC (AH):

CHIRALPAK AY-H, 5 □m, 4.6×250 mm column thermostated at 25° C. was used. The two elution solvents were as follows: solvent A=$CO_2$; solvent B=EtOH. The eluent flow rate was 1 mL/min, the duration of the run was 5 min and the isocratic solvent proportion was 90% (A)/10% (B).

XXXV) Chiral SFC (Al):

CHIRALPAK IC, 5 □m, 4.6×250 mm column thermostated at 40° C. was used. The two elution solvents were as follows: solvent A=$CO_2$; solvent B=EtOH. The eluent flow rate was 4 mL/min, the duration of the run was 5 min and the isocratic solvent proportion was 90% (A)/10% (B).

XXXVI) Chiral SFC (AJ):

CHIRALPAK IC, 5 □m, 4.6×250 mm column thermostated at 40° C. was used. The two elution solvents were as follows: solvent A=$CO_2$; solvent B=ACN/EtOH 1/1. The eluent flow rate was 4 mL/min, the duration of the run was 3.5 min and the isocratic solvent proportion was 90% (A)/10% (B).

XXXVII) Chiral HPLC (AK):

CHIRALPAK AY-H, 5 □m, 4.6×250 mm column thermostated at 25° C. was used. The two elution solvents were as follows: solvent A=Hept; solvent B=EtOH. The eluent flow rate was 0.8 mL/min, the duration of the run was 10 min and the isocratic solvent proportion was 75% (A)/25% (B).

XXXVIII) Chiral HPLC (AL):

CHIRALPAK IC, 5 □m, 4.6×250 mm column thermostated at 25° C. was used. The two elution solvents were as follows: solvent A=Hept; solvent B=EtOH. The eluent flow rate was 0.8 mL/min, the duration of the run was 20 min and the isocratic solvent proportion was 95% (A)/5% (B).

(XXXIX) Chiral SFC (AM):

CHIRALCEL OZ-H, 5 □m, 4.6×250 mm column thermostated at 40° C. was used. The two elution solvents were as follows: solvent A=$CO_2$; solvent B=MeOH. The eluent flow rate was 4 mL/min, the duration of the run was 4 min and the isocratic solvent proportion was 70% (A)/30% (B).

(XL) Chiral SFC (AN):

CHIRALPAK AD-H, 5 □m, 4.6×250 mm column thermostated at 40° C. was used. The two elution solvents were as follows: solvent A=$CO_2$; solvent B=EtOH+1% DEA. The eluent flow rate was 4 mL/min, the duration of the run was 3 min and the isocratic solvent proportion was 85% (A)/15% (B).

(XLI) Chiral SFC (AO):

A REGIS (R,R) Whelk O1, 5 □m, 4.6×250 mm column thermostated at 40° C. was used. The two elution solvents were as follows: solvent A=$CO_2$; solvent B=MeCN/iPrOH 1/1. The eluent flow rate was 4 mL/min, the duration of the run was 5 min and the isocratic solvent proportion was 80% (A)/20% (B).

(XLII) Chiral SFC (AP):

CHIRALPAK OD-H, 5 □m, 4.6×250 mm column thermostated at 40° C. was used. The two elution solvents were as follows: solvent A=$CO_2$; solvent B=MeOH+0.1% DEA. The eluent flow rate was 4 mL/min, the duration of the run was 5 min and the isocratic solvent proportion was 90% (A)/10% (B).

(XLIII) Chiral SFC (AQ):

CHIRALPAK IC, 5 □m, 4.6×250 mm column thermostated at 40° C. was used. The two elution solvents were as follows: solvent A=$CO_2$; solvent B=MeOH. The eluent flow rate was 4 mL/min, the duration of the run was 3.5 min and the isocratic solvent proportion was 80% (A)/20% (B).

(XLIV) Chiral SFC (AR):

A CHIRALPAK IB, 5 □m, 4.6×250 mm column thermostated at 40° C. was used. The two elution solvents were as follows: solvent A=$CO_2$; solvent B=MeCN/MeOH 1/1. The eluent flow rate was 4 mL/min, the duration of the run was 3.5 min and the isocratic solvent proportion was 80% (A)/20% (B).

(XLV) Chiral HPLC (AS):

CHIRALPAK IE, 5 □m, 4.6×250 mm column thermostated at 25° C. was used. The two elution solvents were as follows: solvent A=Hept; solvent B=EtOH. The eluent flow rate was 0.8 mL/min, the duration of the run was 15 min and the isocratic solvent proportion was 10% (A)/90% (B).

(XLVI) Chiral HPLC (AT):

CHIRALCEL OZ-H, 5 □m, 4.6×250 mm column thermostated at 25° C. was used. The two elution solvents were as follows: solvent A=Hept; solvent B=EtOH. The eluent flow rate was 0.8 mL/min, the duration of the run was 20 min and the isocratic solvent proportion was 10% (A)/90% (B).

(XLVII) Chiral HPLC (AU):

CHIRALPAK AD-H, 5 □m, 4.6×250 mm column thermostated at 25° C. was used. The two elution solvents were as follows: solvent A=Hept; solvent B=EtOH. The eluent flow rate was 0.8 mL/min, the duration of the run was 20 min and the isocratic solvent proportion was 80% (A)/20% (B).

(XLVIII) Chiral SFC (AV):

A CHIRALPAK IB, 5 □m, 4.6×250 mm column thermostated at 40° C. was used. The two elution solvents were as follows: solvent A=$CO_2$; solvent B=MeCN/MeOH 1/1. The eluent flow rate was 4 mL/min, the duration of the run was 5 min and the isocratic solvent proportion was 85% (A)/15% (B).

(XLIX) Chiral SFC (AW):

A CHIRALPAK IB, 5 □m, 4.6×250 mm column thermostated at 40° C. was used. The two elution solvents were as follows: solvent A=$CO_2$; solvent B=MeCN/MeOH 1/1. The eluent flow rate was 4 mL/min, the duration of the run was 5 min and the isocratic solvent proportion was 75% (A)/25% (B).

(L) Chiral SFC (AX):

A CHIRALPAK IE, 5 □m, 4.6×250 mm column thermostated at 40° C. was used. The two elution solvents were as follows: solvent A=$CO_2$; solvent B=EtOH. The eluent flow rate was 4 mL/min, the duration of the run was 5 min and the isocratic solvent proportion was 60% (A)/40% (B).

(LI) Chiral SFC (AY):

A REGIS (R,R) Whelk O1, 5 □m, 4.6×250 mm column thermostated at 40° C. was used. The two elution solvents were as follows: solvent A=$CO_2$; solvent B=MeCN/EtOH 1/1. The eluent flow rate was 4 mL/min, the duration of the run was 5 min and the isocratic solvent proportion was 85% (A)/15% (B).

(LII) Chiral SFC (AZ):

A CHIRALPAK IB, 5 □m, 4.6×250 mm column thermostated at 40° C. was used. The two elution solvents were as follows: solvent A=$CO_2$; solvent B=EtOH. The eluent flow rate was 4 mL/min, the duration of the run was 5 min and the isocratic solvent proportion was 70% (A)/30% (B).

Compound purity and identity was further confirmed by NMR spectroscopy (Bruker Avance II 400 MHz Ultrashield™ or Bruker Ascend™ 500 equipped with a 5 mm DCH cryoprobe), 1H (400 MHz or 500 MHz). The chemical shifts are reported in parts per million (ppm) relative to tetramethylsilane (TMS), and multiplicities are given as s (singlet), d (doublet), t (triplet), or m (multiplet).

Preparative LC-MS Methods Used:

The purifications by preparative LC-MS have been performed using the conditions described hereafter.

I) Prep LC-MS (I):

A X-Bridge column (Waters C18, 10 μm OBD, 50×150 mm) was used. The two elution solvents were as follows: solvent A=MeCN; solvent B=water+0.5% $NH_4OH$ (25%). The eluent flow rate and the characteristics of the eluting mixture proportion in function of the time t from start of the elution are summarized in the tables below (a linear gradient being used between two consecutive time points):

| t (min) | 0 | 0.3 | 0.8 | 7.5 | 7.7 | 9.5 | 10 | 11.5 | 12 |
|---|---|---|---|---|---|---|---|---|---|
| Flow (mL/min) | 75 | 75 | 150 | 150 | 150 | 150 | 150 | 150 | 75 |
| Solvent A (%) | 40 | 40 | 40 | 67 | 95 | 95 | 40 | 40 | 40 |
| Solvent B (%) | 60 | 60 | 60 | 33 | 5 | 5 | 60 | 60 | 60 |

II) Prep LC-MS (II):

A X-Bridge column (Waters C18, 10 μm OBD, 50×150 mm) was used. The two elution solvents were as follows: solvent A=water+0.5% $NH_4OH$ (25%); solvent B=MeCN. The characteristics of the eluting mixture proportion in function of the time t from start of the elution are summarized in the tables below (a linear gradient being used between two consecutive time points):

| t (min) | 0 | 0.3 | 0.8 | 8 | 8.1 | 10.1 | 10.5 | 12.0 | 12.5 |
|---|---|---|---|---|---|---|---|---|---|
| Flow (mL/min) | 75 | 75 | 150 | 150 | 150 | 150 | 150 | 150 | 75 |
| Solvent A (%) | 50 | 50 | 50 | 15 | 5 | 5 | 50 | 50 | 50 |
| Solvent B (%) | 50 | 50 | 50 | 85 | 95 | 95 | 50 | 50 | 50 |

III) Prep LC-MS (III):

A Zorbax column (SB-AQ, 7 μm OBD, 50×150 mm) was used. The two elution solvents were as follows: solvent A=water+0.5% formic acid; solvent B=MeCN. The characteristics of the eluting mixture proportion in function of the time t from start of the elution are summarized in the tables below (a linear gradient being used between two consecutive time points):

| t (min) | 0 | 0.3 | 0.8 | 6 | 6.1 | 8.1 | 8.5 | 10.0 | 10.5 |
|---|---|---|---|---|---|---|---|---|---|
| Flow (mL/min) | 75 | 75 | 150 | 150 | 150 | 150 | 150 | 150 | 75 |
| Solvent A (%) | 60 | 60 | 60 | 40 | 5 | 5 | 60 | 60 | 60 |
| Solvent B (%) | 40 | 40 | 40 | 60 | 95 | 95 | 40 | 40 | 40 |

IV) Prep LC-MS (IV):

A X-Bridge column (Waters C18, 10 μm OBD, 50×150 mm) was used. The two elution solvents were as follows: solvent A=MeCN; solvent B=water+0.5% $NH_4OH$ (25%). The eluent flow rate and the characteristics of the eluting mixture proportion in function of the time t from start of the elution are summarized in the tables below (a linear gradient being used between two consecutive time points):

| t (min) | 0 | 0.3 | 0.8 | 7.0 | 7.5 | 10 | 10.5 | 12 | 12.5 |
|---|---|---|---|---|---|---|---|---|---|
| Flow (mL/min) | 75 | 75 | 150 | 150 | 150 | 150 | 150 | 150 | 75 |
| Solvent A (%) | 40 | 40 | 40 | 85 | 95 | 95 | 40 | 40 | 40 |
| Solvent B (%) | 60 | 60 | 60 | 15 | 5 | 5 | 60 | 60 | 60 |

V) Prep LC-MS (V):

A X-Bridge column (Waters C18, 10 μm OBD, 30×75 mm) was used. The two elution solvents were as follows: solvent A=water+0.5% $NH_4OH$ (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 90 | 90 | 5 | 5 | 90 | 90 |
| Solvent B (%) | 10 | 10 | 95 | 95 | 10 | 10 |

VI) Prep LC-MS (VI):

A X-Bridge column (Waters C18, 10 μm OBD, 30×75 mm) was used. The two elution solvents were as follows: solvent A=water+0.5% $NH_4OH$ (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 80 | 80 | 5 | 5 | 80 | 80 |
| Solvent B (%) | 20 | 20 | 95 | 95 | 20 | 20 |

VII) Prep LC-MS (VII):

X-Bridge column (Waters C18, 10 μm OBD, 30×75 mm) was used. The two elution solvents were as follows: solvent A=water+0.5% $NH_4OH$ (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 3.5 | 6.0 | 6.2 | 6.6 |
|---|---|---|---|---|---|---|
| Solvent A (%) | 70 | 70 | 5 | 5 | 70 | 70 |
| Solvent B (%) | 30 | 30 | 95 | 95 | 30 | 30 |

VIII) Prep LC-MS (VIM):

X-Bridge column (Waters C18, 10 μm OBD, 30×75 mm) was used. The two elution solvents were as follows: solvent A=water+0.5% $NH_4OH$ (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 3.5 | 6.0 | 6.2 | 6.6 |
|---|---|---|---|---|---|---|
| Solvent A (%) | 50 | 50 | 5 | 5 | 50 | 50 |
| Solvent B (%) | 50 | 50 | 95 | 95 | 50 | 50 |

IX) Prep LC-MS (IX):

An Agilent column (Zorbax SB-Aq, 5 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 3 | 4.0 | 6.0 | 6.2 | 6.6 |
|---|---|---|---|---|---|---|---|
| Solvent A (%) | 95 | 95 | 50 | 5 | 5 | 95 | 95 |
| Solvent B (%) | 5 | 5 | 50 | 95 | 95 | 5 | 5 |

X) Prep LC-MS (X):

A X-Bridge column (Waters C18, 10 μm OBD, 50×150 mm) was used. The two elution solvents were as follows: solvent A=MeCN; solvent B=water+0.5% $NH_4OH$ (25%). The eluent flow rate and the characteristics of the eluting mixture proportion in function of the time t from start of the elution are summarized in the tables below (a linear gradient being used between two consecutive time points):

| t (min) | 0 | 0.3 | 0.8 | 8.0 | 8.1 | 10.1 | 10.5 | 12 | 12.5 |
|---|---|---|---|---|---|---|---|---|---|
| Flow (mL/min) | 75 | 75 | 150 | 150 | 150 | 150 | 150 | 150 | 75 |
| Solvent A (%) | 50 | 50 | 50 | 75 | 95 | 95 | 50 | 50 | 50 |
| Solvent B (%) | 50 | 50 | 50 | 25 | 5 | 5 | 50 | 50 | 50 |

XI) Prep LC-MS (XI):

A X-Bridge column (Waters C18, 10 μm OBD, 50×150 mm) was used. The two elution solvents were as follows: solvent A=MeCN; solvent B=water+0.5% $NH_4OH$ (25%). The eluent flow rate and the characteristics of the eluting mixture proportion in function of the time t from start of the elution are summarized in the tables below (a linear gradient being used between two consecutive time points):

| t (min) | 0 | 0.3 | 0.8 | 10.0 | 15.0 | 15.5 | 17 | 17.5 |
|---|---|---|---|---|---|---|---|---|
| Flow (mL/min) | 75 | 75 | 150 | 150 | 150 | 150 | 150 | 75 |
| Solvent A (%) | 30 | 30 | 30 | 95 | 95 | 30 | 30 | 30 |
| Solvent B (%) | 70 | 70 | 70 | 5 | 5 | 70 | 70 | 70 |

XII) Prep LC-MS (XII):

A Zorbax SB-Aq column (Agilent, 5 μm, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 3.5 | 6.0 | 6.2 | 6.6 |
|---|---|---|---|---|---|---|
| Solvent A (%) | 70 | 70 | 5 | 5 | 70 | 70 |
| Solvent B (%) | 30 | 30 | 95 | 95 | 30 | 30 |

XIII) Prep LC-MS (XIII):

A X-Bridge column (Waters C18, 10 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 3 | 4.0 | 6.0 | 6.2 | 6.6 |
|---|---|---|---|---|---|---|---|
| Solvent A (%) | 95 | 95 | 50 | 5 | 5 | 95 | 95 |
| Solvent B (%) | 5 | 5 | 50 | 95 | 95 | 5 | 5 |

XIV) Prep LC-MS (XIV):

An Agilent column (Zorbax SB-Aq, 5 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 90 | 90 | 5 | 5 | 90 | 90 |
| Solvent B (%) | 10 | 10 | 95 | 95 | 10 | 10 |

XV) Prep LC-MS (XV):

A X-Bridge column (Waters C18, 10 μm OBD, 30×75 mm) was used. The two elution solvents were as follows: solvent A=water+0.5% $NH_4OH$ (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 3 | 4.0 | 6.0 | 6.2 | 6.6 |
|---|---|---|---|---|---|---|---|
| Solvent A (%) | 95 | 95 | 50 | 5 | 5 | 95 | 95 |
| Solvent B (%) | 5 | 5 | 50 | 95 | 95 | 5 | 5 |

XVI) Prep LC-MS (XVI):

A X-Bridge column (Waters C18, 10 μm OBD, 50×150 mm) was used. The two elution solvents were as follows: solvent A=MeCN; solvent B=water+0.5% $NH_4OH$ (25%). The eluent flow rate and the characteristics of the eluting mixture proportion in function of the time t from start of the elution are summarized in the tables below (a linear gradient being used between two consecutive time points):

| t (min) | 0 | 0.3 | 0.8 | 7.0 | 7.2 | 9.0 | 9.5 | 11 | 11.5 |
|---|---|---|---|---|---|---|---|---|---|
| Flow (mL/min) | 75 | 75 | 150 | 150 | 150 | 150 | 150 | 150 | 75 |
| Solvent A (%) | 35 | 35 | 35 | 65 | 95 | 95 | 35 | 35 | 35 |
| Solvent B (%) | 65 | 65 | 65 | 35 | 5 | 5 | 65 | 65 | 65 |

XVII) Prep LC-MS (XVII):

A Zorbax column (SB-AQ, 7 μm OBD, 50×150 mm) was used. The two elution solvents were as follows: solvent A=water+0.5% formic acid; solvent B=MeCN. The characteristics of the eluting mixture proportion in function of the time t from start of the elution are summarized in the tables below (a linear gradient being used between two consecutive time points):

| t (min) | 0 | 0.3 | 0.8 | 7.5 | 7.7 | 9.5 | 10 | 11.5 | 12 |
|---|---|---|---|---|---|---|---|---|---|
| Flow (mL/min) | 75 | 75 | 150 | 150 | 150 | 150 | 150 | 150 | 75 |
| Solvent A (%) | 60 | 60 | 60 | 33 | 5 | 5 | 60 | 60 | 60 |
| Solvent B (%) | 40 | 40 | 40 | 67 | 95 | 95 | 40 | 40 | 40 |

XVIII) Prep LC-MS (XVIII):

A X-Bridge column (Waters C18, 10 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 90 | 90 | 5 | 5 | 90 | 90 |
| Solvent B (%) | 10 | 10 | 95 | 95 | 10 | 10 |

XIX) Prep LC-MS (XIX):

A X-Bridge column (Waters C18, 10 μm OBD, 50×150 mm) was used. The two elution solvents were as follows: solvent A=MeCN; solvent B=water+0.5% formic acid. The characteristics of the eluting mixture proportion in function of the time t from start of the elution are summarized in the tables below (a linear gradient being used between two consecutive time points):

| t (min) | 0 | 0.3 | 0.8 | 9 | 9.2 | 11 | 11.5 | 13 | 13.5 |
|---|---|---|---|---|---|---|---|---|---|
| Flow (mL/min) | 75 | 75 | 150 | 150 | 150 | 150 | 150 | 150 | 75 |
| Solvent A (%) | 40 | 40 | 40 | 72 | 95 | 95 | 40 | 40 | 40 |
| Solvent B (%) | 60 | 60 | 60 | 28 | 5 | 5 | 60 | 60 | 60 |

XX) Prep LC-MS (XX):

An Agilent column (Zorbax SB-Aq, 5 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 80 | 80 | 5 | 5 | 80 | 80 |
| Solvent B (%) | 20 | 20 | 95 | 95 | 20 | 20 |

XXI) Prep LC-MS (XXI):

A X-Bridge column (Waters C18, 10 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 1.0 | 3.5 | 4.0 | 6.0 | 6.2 | 6.6 |
|---|---|---|---|---|---|---|---|
| Solvent A (%) | 100 | 100 | 80 | 5 | 5 | 100 | 100 |
| Solvent B (%) | 0 | 0 | 20 | 95 | 95 | 0 | 0 |

XXII) Prep LC-MS (XXII):

An Agilent column (Zorbax SB-Aq, 5 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 3.0 | 6.0 | 6.2 | 6.6 |
|---|---|---|---|---|---|---|
| Solvent A (%) | 50 | 50 | 5 | 5 | 50 | 50 |
| Solvent B (%) | 50 | 50 | 95 | 95 | 50 | 50 |

XXIII) Prep LC-MS (XXIII):

An Agilent column (Zorbax SB-Aq, 5 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 1.0 | 3.5 | 4.0 | 6.0 | 6.2 | 6.6 |
|---|---|---|---|---|---|---|---|
| Solvent A (%) | 100 | 100 | 80 | 5 | 5 | 100 | 100 |
| Solvent B (%) | 0 | 0 | 20 | 95 | 95 | 0 | 0 |

XXIV) Prep LC-MS (XXIV):

A Zorbax column (SB-AQ, 7 μm OBD, 50×150 mm) was used. The two elution solvents were as follows: solvent A=water+0.5% formic acid; solvent B=MeCN. The characteristics of the eluting mixture proportion in function of the time t from start of the elution are summarized in the tables below (a linear gradient being used between two consecutive time points):

| t (min) | 0 | 0.3 | 0.8 | 6 | 6.1 | 8.1 | 8.5 | 10.0 | 10.5 |
|---|---|---|---|---|---|---|---|---|---|
| Flow (mL/min) | 75 | 75 | 150 | 150 | 150 | 150 | 150 | 150 | 75 |
| Solvent A (%) | 60 | 60 | 60 | 50 | 5 | 5 | 60 | 60 | 60 |
| Solvent B (%) | 40 | 40 | 40 | 50 | 95 | 95 | 40 | 40 | 40 |

XXV) Prep LC-MS (XXV):

A X-Bridge column (Waters C18, 10 μm OBD, 50×150 mm) was used. The two elution solvents were as follows: solvent A=water+0.5% $NH_4OH$ (25%); solvent B=MeCN. The characteristics of the eluting mixture proportion in function of the time t from start of the elution are summarized in the tables below (a linear gradient being used between two consecutive time points):

| t (min) | 0 | 0.3 | 0.8 | 8 | 8.1 | 10.1 | 10.5 | 12.0 | 12.5 |
|---|---|---|---|---|---|---|---|---|---|
| Flow (mL/min) | 75 | 75 | 150 | 150 | 150 | 150 | 150 | 150 | 75 |
| Solvent A (%) | 45 | 45 | 45 | 30 | 5 | 5 | 45 | 45 | 45 |
| Solvent B (%) | 55 | 55 | 55 | 70 | 95 | 95 | 55 | 55 | 55 |

XXVI) Prep LC-MS (XXVI):

A Zorbax column (SB-AQ, 7 μm OBD, 50×150 mm) was used. The two elution solvents were as follows: solvent A=MeCN; solvent B=water+0.5% formic acid. The characteristics of the eluting mixture proportion in function of the time t from start of the elution are summarized in the tables below (a linear gradient being used between two consecutive time points):

| t (min) | 0 | 0.3 | 0.8 | 8 | 8.1 | 10.1 | 10.5 | 12.0 | 12.5 |
|---|---|---|---|---|---|---|---|---|---|
| Flow (mL/min) | 75 | 75 | 150 | 150 | 150 | 150 | 150 | 150 | 75 |
| Solvent A (%) | 40 | 40 | 40 | 65 | 95 | 95 | 40 | 40 | 40 |
| Solvent B (%) | 60 | 60 | 60 | 35 | 5 | 5 | 60 | 60 | 60 |

XXVII) Prep LC-MS (XXVII):

A X-Bridge column (Waters C18, 10 μm OBD, 50×150 mm) was used. The two elution solvents were as follows: solvent A=water+0.5% $NH_4OH$ (25%); solvent B=MeCN. The characteristics of the eluting mixture proportion in function of the time t from start of the elution are summarized in the tables below (a linear gradient being used between two consecutive time points):

| t (min) | 0 | 0.3 | 0.8 | 8 | 8.1 | 10.1 | 10.5 | 12.0 | 12.5 |
|---|---|---|---|---|---|---|---|---|---|
| Flow (mL/min) | 75 | 75 | 150 | 150 | 150 | 150 | 150 | 150 | 75 |
| Solvent A (%) | 60 | 60 | 60 | 25 | 5 | 5 | 60 | 60 | 60 |
| Solvent B (%) | 40 | 40 | 40 | 75 | 95 | 95 | 40 | 40 | 40 |

XXVIII) Prep LC-MS (XXVIII)

A X-Bridge column (Waters C18, 10 μm OBD, 50×150 mm) was used. The two elution solvents were as follows: solvent A=water+0.5% formic acid; solvent B=MeCN. The eluent flow rate and the characteristics of the eluting mixture proportion in function of the time t from start of the elution are summarized in the tables below (a linear gradient being used between two consecutive time points):

| t (min) | 0 | 0.3 | 0.8 | 7.0 | 7.5 | 10.0 | 10.5 | 12.0 | 12.5 |
|---|---|---|---|---|---|---|---|---|---|
| Flow (mL/min) | 75 | 75 | 150 | 150 | 150 | 150 | 150 | 150 | 75 |
| Solvent A (%) | 70 | 70 | 70 | 20 | 5 | 5 | 70 | 70 | 70 |
| Solvent B (%) | 30 | 30 | 30 | 80 | 95 | 95 | 30 | 30 | 30 |

XXIX) Prep LC-MS (XXIX):

A X-Bridge column (Waters C18, 10 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 80 | 80 | 5 | 5 | 80 | 80 |
| Solvent B (%) | 20 | 20 | 95 | 95 | 20 | 20 |

XXX) Prep LC-MS (XXX):

A X-Bridge column (Waters C18, 10 μm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 70 | 70 | 5 | 5 | 70 | 70 |
| Solvent B (%) | 30 | 30 | 95 | 95 | 30 | 30 |

XXXI) Prep LC-MS (XXXI)

A X-Bridge column (Waters C18, 10 μm OBD, 50×150 mm) was used. The two elution solvents were as follows: solvent A=water+0.5% $NH_4OH$ (25%); solvent B=MeCN. The characteristics of the eluting mixture proportion in function of the time t from start of the elution are summarized in the tables below (a linear gradient being used between two consecutive time points):

| t (min) | 0 | 0.3 | 0.8 | 11.0 | 15.0 | 15.5 | 17.0 | 17.5 |
|---|---|---|---|---|---|---|---|---|
| Flow (mL/min) | 75 | 75 | 150 | 150 | 150 | 150 | 150 | 75 |
| Solvent A (%) | 80 | 80 | 80 | 5 | 5 | 80 | 80 | 80 |
| Solvent B (%) | 20 | 20 | 20 | 95 | 95 | 20 | 20 | 20 |

XXXII) Prep LC-MS (XXXII):

A X-Bridge column (Waters C18, 10 μm OBD, 30×75 mm) was used. The two elution solvents were as follows: solvent A=water+0.5% $NH_4OH$ (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 1.0 | 3.5 | 4.0 | 6.0 | 6.2 | 6.6 |
|---|---|---|---|---|---|---|---|
| Solvent A (%) | 100 | 100 | 80 | 5 | 5 | 100 | 100 |
| Solvent B (%) | 0 | 0 | 20 | 95 | 95 | 0 | 0 |

XXXIII) Prep LC-MS (XXXIII):

acidic large scale (Zorbax 50×150 mm, 7 um), 90% Water_150 ml_to 75%_8 min_RT_0,49

A Zorbax column (SB-AQ, 7 μm OBD, 50×150 mm) was used. The two elution solvents were as follows: solvent A=MeCN; solvent B=water+0.5% formic acid. The characteristics of the eluting mixture proportion in function of the time t from start of the elution are summarized in the tables below (a linear gradient being used between two consecutive time points):

| t (min) | 0 | 0.3 | 0.8 | 8 | 8.1 | 10.1 | 10.5 | 12.0 | 12.5 |
|---|---|---|---|---|---|---|---|---|---|
| Flow (mL/min) | 75 | 75 | 150 | 150 | 150 | 150 | 150 | 150 | 75 |
| Solvent A (%) | 10 | 10 | 10 | 25 | 95 | 95 | 10 | 10 | 10 |
| Solvent B (%) | 90 | 90 | 90 | 75 | 5 | 5 | 90 | 90 | 90 |

XXXIV) Prep LC-MS (XXXIV):

A Zorbax column (SB-AQ, 7 μm OBD, 50×150 mm) was used. The two elution solvents were as follows: solvent A=MeCN; solvent B=water+0.5% formic acid. The characteristics of the eluting mixture proportion in function of the time t from start of the elution are summarized in the tables below (a linear gradient being used between two consecutive time points):

| t (min) | 0 | 0.3 | 0.8 | 8 | 8.1 | 10.1 | 10.5 | 12.0 | 12.5 |
|---|---|---|---|---|---|---|---|---|---|
| Flow (mL/min) | 75 | 75 | 150 | 150 | 150 | 150 | 150 | 150 | 75 |
| Solvent A (%) | 20 | 20 | 20 | 35 | 95 | 95 | 20 | 20 | 20 |
| Solvent B (%) | 80 | 80 | 80 | 65 | 5 | 5 | 80 | 80 | 80 |

XXXV) Prep LC-MS (XXXV):

A Zorbax column (SB-AQ, 7 μm OBD, 50×150 mm) was used. The two elution solvents were as follows: solvent A=water+0.5% formic acid (25%); solvent B=MeCN. The characteristics of the eluting mixture proportion in function of the time t from start of the elution are summarized in the tables below (a linear gradient being used between two consecutive time points):

| t (min) | 0 | 0.3 | 0.8 | 8 | 8.1 | 10.1 | 10.5 | 12.0 | 12.5 |
|---|---|---|---|---|---|---|---|---|---|
| Flow (mL/min) | 75 | 75 | 150 | 150 | 150 | 150 | 150 | 150 | 75 |
| Solvent A (%) | 60 | 60 | 60 | 25 | 5 | 5 | 60 | 60 | 60 |
| Solvent B (%) | 40 | 40 | 40 | 75 | 95 | 95 | 40 | 40 | 40 |

XXXVI) Prep LC-MS (XXXVI):

A Zorbax column (SB-AQ, 7 µm OBD, 50×150 mm) was used. The two elution solvents were as follows: solvent A=water+0.5% formic acid (25%); solvent B=MeCN. The characteristics of the eluting mixture proportion in function of the time t from start of the elution are summarized in the tables below (a linear gradient being used between two consecutive time points):

| t (min) | 0 | 0.3 | 0.8 | 8 | 8.1 | 10.1 | 10.5 | 12.0 | 12.5 |
|---|---|---|---|---|---|---|---|---|---|
| Flow (mL/min) | 75 | 75 | 150 | 150 | 150 | 150 | 150 | 150 | 75 |
| Solvent A (%) | 80 | 80 | 80 | 50 | 5 | 5 | 80 | 80 | 80 |
| Solvent B (%) | 20 | 20 | 20 | 50 | 95 | 95 | 20 | 20 | 20 |

XXXVII) Prep LC-MS (XXXVII):

A X-Bridge column (Waters C18, 10 µm OBD, 50×150 mm) was used. The two elution solvents were as follows: solvent A=water+0.5% $NH_4OH$ (25%); solvent B=MeCN. The characteristics of the eluting mixture proportion in function of the time t from start of the elution are summarized in the tables below (a linear gradient being used between two consecutive time points):

| t (min) | 0 | 0.3 | 0.8 | 6 | 6.1 | 8.1 | 8.5 | 10.0 | 10.5 |
|---|---|---|---|---|---|---|---|---|---|
| Flow (mL/min) | 75 | 75 | 150 | 150 | 150 | 150 | 150 | 150 | 75 |
| Solvent A (%) | 60 | 60 | 60 | 50 | 5 | 5 | 60 | 60 | 60 |
| Solvent B (%) | 40 | 40 | 40 | 50 | 95 | 95 | 40 | 40 | 40 |

Preparative Chiral HPLC and SFC Methods Used:

The purifications by preparative chiral HPLC or SFC have been performed using the conditions described hereafter.

I) Prep Chiral SFC (I):

A ChiralCel OD-H column (5□m, 30×250 mm) thermostated at 40° C. was used. The elution solvent was $CO_2$/MeOH 92/8, the run lasted for 6.50 min and at a flow rate of 160 mL/min.

II) Prep Chiral SFC (10:

A ChiralCel OZ-H column (5□m, 30×250 mm) thermostated at 40° C. was used. The elution solvent was $CO_2$/MeOH+0.1% DEA 85/15, the run lasted for 5.50 min and at a flow rate of 160 mL/min.

III) Prep Chiral SFC (III):

A ChiralPak AD-H column (5□m, 30×250 mm) thermostated at 40° C. was used. The elution solvent was $CO_2$/EtOH 80/20, the run lasted for 5 min and at a flow rate of 160 mL/min.

IV) Prep Chiral SFC (IV):

A ChiralPak IB (5□m, 30×250 mm) column thermostated at 40° C. was used. The elution solvent was $CO_2$/EtOH 85/15, run for 3.90 min and at a flow rate of 160 mL/min.

V) Prep Chiral SFC (V):

A ChiralPak IC (5□m, 30×250 mm) column thermostated at 40° C. was used. The elution solvent was $CO_2$/MeOH+0.1% DEA 60/40, run for 5 min and at a flow rate of 160 mL/min.

VI) Prep Chiral SFC (VI):

A ChiralPak IB (5□m, 30×250 mm) column thermostated at 40° C. was used. The elution solvent was $CO_2$/MeOH 90/10, run for 4 min and at a flow rate of 160 mL/min.

VII) Prep Chiral SFC (VII):

A ChiralPak AD-H (5□m, 30×250 mm) column thermostated at 40° C. was used. The elution solvent was $CO_2$/EtOH 75/25, run for 5 min and at a flow rate of 160 mL/min.

VIII) Prep Chiral SFC (VIII):

A ChiralCel OD-H (5□m, 30×250 mm) column thermostated at 40° C. was used. The elution solvent was $CO_2$/MeOH 90/10, run for 6 min and at a flow rate of 160 mL/min.

IX) Prep Chiral SFC (IX):

A ChiralPak AD-H (5□m, 30×250 mm) column thermostated at 40° C. was used. The elution solvent was $CO_2$/50% MeCN-50% EtOH−0.1% DEA 75/25, run for 5.5 min and at a flow rate of 160 mL/min.

X) Prep Chiral SFC (X):

A ChiralPak AS-H (5□m, 30×250 mm) column thermostated at 40° C. was used. The elution solvent was $CO_2$/50% MeCN-50% EtOH−0.1% DEA 72/28, run for 4.5 min and at a flow rate of 160 mL/min.

XI) Prep Chiral SFC (XI):

A ChiralPak AS-H (5□m, 30×250 mm) column thermostated at 40° C. was used. The elution solvent was $CO_2$/50% MeCN-50% EtOH−0.1% DEA 70/30, run for 4 min and at a flow rate of 160 mL/min.

XII) Prep Chiral SFC (XII):

A ChiralPak OD-H (5□m, 30×250 mm) column thermostated at 40° C. was used. The elution solvent was $CO_2$/MeOH+0.1% DEA 85/15, run for 9.30 min and at a flow rate of 160 mL/min.

XIII) Prep Chiral SFC (XIII):

A ChiralPak AD-H (5□m, 30×250 mm) column thermostated at 40° C. was used. The elution solvent was $CO_2$/EtOH+0.1% DEA 75/25, run for 4 min and at a flow rate of 160 mL/min.

XIV) Prep Chiral SFC (XIV):

A (R,R) Whelk (5□m, 30×250 mm) column thermostated at 40° C. was used. The elution solvent was $CO_2$/50% DCM-50% MeOH−0.1% DEA 70/30, run for 7.9 min and at a flow rate of 160 mL/min.

XV) Prep Chiral SFC (XV):

A ChiralPak ID (5□m, 30×250 mm) column thermostated at 40° C. was used. The elution solvent was $CO_2$/50% MeCN-50% EtOH−0.1% DEA 65/35, run for 4.75 min and at a flow rate of 160 mL/min.

XVI) Prep Chiral SFC (XVI):

A ChiralPak IB (5□m, 30×250 mm) column thermostated at 40° C. was used. The elution solvent was $CO_2$/MeOH+0.1% DEA 90/10, run for 4.50 min and at a flow rate of 160 mL/min.

XVII) Prep Chiral SFC (XVII):

A ChiralPak IB (5□m, 30×250 mm) column thermostated at 40° C. was used. The elution solvent was $CO_2$/MeOH 80/20, run for 4 min and at a flow rate of 160 mL/min.

XVIII) Prep Chiral SFC (XVIII):

A ChiralPak IH (5□m, 30×250 mm) column thermostated at 40° C. was used. The elution solvent was $CO_2$/50% MeCN-50% EtOH 85/15, run for 6 min and at a flow rate of 160 mL/min.

XIX) Prep Chiral SFC (XIX):

A ChiralPak AD-H (5□m, 30×250 mm) column thermostated at 40° C. was used. The elution solvent was $CO_2$/EtOH 85/15, run for 5 min and at a flow rate of 160 mL/min.

XX) Prep Chiral SFC (XX):

A ChiralPak AD-H (5□m, 30×250 mm) column thermostated at 40° C. was used. The elution solvent was $CO_2$/EtOH 90/10, run for 4.8 min and at a flow rate of 160 mL/min.

XXI) Prep chiral HPLC (XXI):

A ChiralPak AY-H (5□m, 30×250 mm) column thermostated at 25° C. was used. The elution solvent was Hept/2-Propanol 80/20, run for 12 min and at a flow rate of 38 mL/min.

XXII) Prep Chiral SFC (XXII):

A ChiralPak IH (5□m, 30×250 mm) column thermostated at 40° C. was used. The elution solvent was $CO_2$/50% Hept-50% EtOH 85/15, run for 3.5 min and at a flow rate of 160 mL/min.

XXIII) Prep Chiral SFC (XXIII):

A ChiralCel OD-H column (5□m, 30×250 mm) thermostated at 40° C. was used. The elution solvent was $CO_2$/EtOH 80/20, the run lasted for 3.50 min and at a flow rate of 160 mL/min.

XXIV) Prep Chiral SFC (XXIV):

A ChiralCel OD-H (5□m, 30×250 mm) column thermostated at 40° C. was used. The elution solvent was $CO_2$/MeOH 85/15, run for 6 min and at a flow rate of 160 mL/min.

XXV) Prep Chiral SFC (XXV)

A Chiralpak AD-H (5□m, 30×250 mm) column thermostated at 40° C. was used. The elution solvent was $CO_2$/EtOH 95/5, run for 5.5 min and at a flow rate of 160 mL/min.

XXVI) Prep chiral HPLC (XXVI):

A ChiralPak IG (5□m, 20×250 mm) column thermostated at 25° C. was used. The elution solvent was Hept/50% MeOH-50% EtOH–0.1% DEA 30/70, run for 14 min and at a flow rate of 20 mL/min.

XXVII) Prep Chiral SFC (XXVII):

A ChiralCel OD-H (5□m, 30×250 mm) column thermostated at 40° C. was used. The elution solvent was $CO_2$/MeOH 75/25, run for 4 min and at a flow rate of 160 mL/min.

XXVIII) Prep Chiral SFC (XXVIII):

A (R,R) Whelk-O1 (5□m, 30×250 mm) column thermostated at 40° C. was used. The elution solvent was $CO_2$/50% iPrOH-50% MeCN 80/20, run for 4 min and at a flow rate of 160 mL/min.

XXIX) Prep Chiral SFC (XXIX):

A Chiralpak AD-H (5□m, 30×250 mm) column thermostated at 40° C. was used. The elution solvent was $CO_2$/MeOH 85/15, run for 4 min and at a flow rate of 160 mL/min.

XXX) Prep Chiral SFC (XXX):

A Chiralpak IB (5□m, 30×250 mm) column thermostated at 40° C. was used. The elution solvent was $CO_2$/MeOH 70/30, run for 6 min and at a flow rate of 160 mL/min.

XXXI) Prep Chiral SFC (XXXI):

A ChiralPak IB (5□m, 30×250 mm) column thermostated at 40° C. was used. The elution solvent was $CO_2$/MeOH 90/10, run for 3.5 min and at a flow rate of 160 mL/min.

XXXII) Prep Chiral SFC (XXXII):

A ChiralPak ID (5□m, 30×250 mm) column thermostated at 40° C. was used. The elution solvent was $CO_2$/EtOH–0.1% DEA 60/40, run for 6 min and at a flow rate of 160 mL/min.)

(XXIII) Prep Chiral SFC (XXXIII):

A ChiralPak IC (5□m, 30×250 mm) column thermostated at 40° C. was used. The elution solvent was $CO_2$EtOH–0.1% DEA 60/40, run for 6 min and at a flow rate of 160 mL/min.

XXXIV) Prep Chiral SFC (XXXIV):

A ChiralPak IH (5□m, 30×250 mm) column thermostated at 40° C. was used. The elution solvent was $CO_2$/EtOH 55/45, run for 3.5 min and at a flow rate of 160 mL/min.

XXXV) Prep Chiral SFC (XXXV):

A ChiralPak IG (5□m, 30×250 mm) column thermostated at 40° C. was used. The elution solvent was $CO_2$/EtOH 85/15, run for 6 min and at a flow rate of 160 mL/min.

XXXVI) Prep Chiral SFC (XXXVI):

A ChiralPak IC (5□m, 30×250 mm) column thermostated at 40° C. was used. The elution solvent was $CO_2$/EtOH 75/25, run for 3.5 min and at a flow rate of 160 mL/min.

XXXVII) Prep Chiral SFC (XXXVII):

A Chiralpak AY-H (5□m, 30×250 mm) column thermostated at 40° C. was used. The elution solvent was $CO_2$/EtOH 90/10, run for 3.4 min and at a flow rate of 160 mL/min.

XXXVIII) Prep Chiral SFC (XXXVIII):

A ChiralPak IC (5□m, 30×250 mm) column thermostated at 40° C. was used. The elution solvent was $CO_2$/EtOH 90/10, run for 2.5 min and at a flow rate of 160 mL/min.

XXXIX) Prep Chiral SFC (XXXIX):

A ChiralPak IC (5□m, 30×250 mm) column thermostated at 40° C. was used. The elution solvent was $CO_2$/ACN:EtOH 1:1 90/10, run for 4.4 min and at a flow rate of 160 mL/min.

XL) Prep chiral HPLC (XL):

A ChiralPak AY-H (5□m, 30×250 mm) column thermostated at 40° C. was used. The elution solvent was Hep/EtOH 75/25, run for 11 min and at a flow rate of 38 mL/min.

XLI) Prep chiral HPLC (XLI):

A ChiralPak IC (5□m, 20×250 mm) column thermostated at 40° C. was used. The elution solvent was heptane/EtOH 95/5, run for 11.6 min and at a flow rate of 16 mL/min.

XLII) Prep Chiral SFC (XLII):

A ChiralPak AD-H (5□m, 30×250 mm) column thermostated at 40° C. was used. The elution solvent was $CO_2$/EtOH 90/10, run for 5.0 min and at a flow rate of 160 mL/min.

XLIII) Prep chiral HPLC (XLIII):

A ChiralCel OJ-H column (5□m, 20×250 mm) thermostated at 40° C. was used. The elution solvent was Hept/EtOH 80/20, the run lasted for 10.5 min and at a flow rate of 16 mL/min.

XLIV) Prep Chiral SFC (XLIV):

A ChiralCel OJ-H column (5□m, 30×250 mm) thermostated at 40° C. was used. The elution solvent was $CO_2$/MeOH 90/10, the run lasted for 4 min and at a flow rate of 16 mL/min.

XLV) Prep Chiral SFC (XLV):

A ChiralCel OZ-H column (5□m, 30×250 mm) thermostated at 40° C. was used. The elution solvent was $CO_2$/MeOH 70/30, the run lasted for 4 min and at a flow rate of 160 mL/min.

XLVI) Prep Chiral SFC (XLVI):

A ChiralPak AD-H (5□m, 30×250 mm) column thermostated at 40° C. was used. The elution solvent was $CO_2$/EtOH–0.1% DEA 85/15, run for 5.0 min and at a flow rate of 160 mL/min.

XLVII) Prep Chiral SFC (XLVII):

A Chiralpak IB (5□m, 30×250 mm) column thermostated at 40° C. was used. The elution solvent was $CO_2$/(MeCN:EtOH 1:1) 70/30, run for 6 min and at a flow rate of 160 mL/min.

XLVIII) Prep Chiral SFC (XLVIII):

A Regis (R,R)-Whelk O1 (5□m, 30×250 mm) column thermostated at 40° C. was used. The elution solvent was $CO_2$/(MeCN:iPrOH 1:1) 80/20, run for 5 min and at a flow rate of 160 mL/min.

XLIX) Prep Chiral SFC (XLIX):

A ChiralPak OD-H (5□m, 30×250 mm) column thermostated at 40° C. was used. The elution solvent was $CO_2$/MeOH–0.1% DEA 90/10, run for 9.0 min and at a flow rate of 160 mL/min.

L) Prep Chiral SFC (L):

A ChiralPak IC (5□m, 30×250 mm) column thermostated at 40° C. was used. The elution solvent was $CO_2$/MeOH 80/20, run for 4 min and at a flow rate of 160 mL/min.

LI) Prep Chiral SFC (LI):

A Chiralpak IB (5□m, 30×250 mm) column thermostated at 40° C. was used. The elution solvent was $CO_2$/(MeCN:MeOH 1:1) 80/20, run for 6 min and at a flow rate of 160 mL/min.

LII) Prep chiral HPLC (LII):

A ChiralPak IE (5□m, 30×250 mm) column thermostated at 25° C. was used. The elution solvent was Hept/EtOH 10/90, run for 12.0 min and at a flow rate of 34 mL/min.

LIII) Prep chiral HPLC (LIII):

A Chiralcel OZ-H (5□m, 30×250 mm) column thermostated at 25° C. was used. The elution solvent was Hept/EtOH 10/90, run for 14.0 min and at a flow rate of 34 mL/min.

LIV) Prep chiral HPLC (LIV):

A Chiralpak AD-H (5□m, 30×250 mm) column thermostated at 25° C. was used. The elution solvent was Hept/EtOH 80/20, run for 10.0 min and at a flow rate of 34 mL/min.

LV) Prep Chiral SFC (LV):

A Chiralpak IB (5□m, 30×250 mm) column thermostated at 40° C. was used. The elution solvent was $CO_2$/(MeCN:MeOH 1:1) 85/15, run for 6 min and at a flow rate of 160 mL/min.

LVI) Prep Chiral SFC (LVI):

A Chiralpak IB (5□m, 30×250 mm) column thermostated at 40° C. was used. The elution solvent was $CO_2$/(MeCN:MeOH 1:1) 75/25, run for 7 min and at a flow rate of 160 mL/min.

LVII) Prep Chiral SFC (LVII):

A Chiralpak IE (5□m, 30×250 mm) column thermostated at 40° C. was used. The elution solvent was $CO_2$/EtOH 60/40, run for 5 min and at a flow rate of 160 mL/min.

LVIII) Prep Chiral SFC (LVIII):

A Regis (R,R)-Whelk O1 (5□m, 30×250 mm) column thermostated at 40° C. was used. The elution solvent was $CO_2$/(MeCN:EtOH 1:1) 85/15, run for 8 min and at a flow rate of 160 mL/min.

LIX) Prep Chiral SFC (LIX):

A Chiralpak IB (5□m, 30×250 mm) column thermostated at 40° C. was used. The elution solvent was $CO_2$/EtOH 70/30, run for 6 min and at a flow rate of 160 mL/min.

Preparation of Intermediate Examples of Formula (A3), (A4), (A5), (A6), (A7), (B2), (C1), (C3), (D1), (D2), (D3), (D4), (D5), (E1), (E2), (F1), (F3), (F4), (F5), (G1), (J3) and (J5)

Example A3.1: 5-Bromo-1,3-difluoro-2-isopropylbenzene

A3.1.1: 2-(4-Bromo-2,6-difluoro-phenyl)-propan-2-ol

To a solution of 4-bromo-2,6-difluorobenzoic acid methyl ester (1 eq) in THF (6.4 mL/mmol) was added at 0° C., a 3M solution of methylmagnesium bromide in $Et_2O$ (3 eq). The ice bath was removed, and the reaction mixture was stirred for 1.5 h at RT. It was quenched with a half sat. solution of $NH_4Cl$ and extracted with EA. The combined org. phases were dried over $MgSO_4$ and concentrated in vacuo. The crude was purified by CC using Sfär prepacked cartridges from Biotage and eluting with Hept/EA to afford the title compound as colorless liquid. $^1$H NMR (500 MHz, DMSO) δ: 7.34 (m, 2H), 5.32 (s, 1H), 1.56 (t, J=2.0 Hz, 6H).

A3.1.2: 5-Bromo-1,3-difluoro-2-isopropylbenzene

To a solution of 2-(4-bromo-2,6-difluoro-phenyl)-propan-2-ol (1 eq) and triethylsilane (1.1 eq) in DCM (7.8 mL/mmol) was added at 0° C., TFA (11 eq). The ice bath was removed, and the reaction mixture was stirred for 3 h at RT. It was quenched with a half sat. solution of $NaHCO_3$ and extracted with DCM. The combined org. phases were dried over $MgSO_4$ and concentrated in vacuo. The crude was purified by CC using Sfär prepacked cartridges from Biotage and eluting with pentane/EA to afford the title compound as colorless liquid. $^1$H NMR (500 MHz, DMSO) δ: 7.40 (m, 2H), 3.22-3.31 (m, 1H), 1.27 (d, J=7.1 Hz, 6H).

Example A4.1: 3-Methyl-3-(4-trifluoromethoxy-benzoyl)-azetidine-1-carboxylic acid tert-butyl ester

A4.1.1. 3-(Methoxy-methyl-carbamoyl)-3-methyl-azetidine-1-carboxylic acid tert-butyl ester To a pale yellow solution of 1-Boc-3-methylazetidine-3-carboxylic acid (20 g) in DCM (500 mL) were added N,O-dimethylhydroxylamine hydrochloride (8.97 g) and DIPEA (54 mL). The mixture was then cooled at 0° C. and propylphosphonic anhydride solution in EA (50% w/w, 68 mL) was slowly added. The resulting pale yellow solution was stirred 18 h at RT and quenched with aq. sat. $NaHCO_3$ solution. The org. layer was washed with citric acid (10%) and water. The combined org. layers were dried ($MgSO_4$), filtered off and evaporated to dryness to afford 24.1 g of the title compound as yellowish resin which was used without further purification. LC-MS (A): $t_R$=0.78 min; $[M+H]^+$: 259.32.

A4.1.2. 3-Methyl-3-(4-trifluoromethoxy-benzoyl)-azetidine-1-carboxylic acid tert-butyl ester To a solution of 1-bromo-4-(trifluoromethoxy)benzene (12.2 mL) in anhydrous THF (150 mL) under argon cooled down to −78° C. was added n-BuLi (2.5M in hexane, 29.7 mL) dropwise over 45 min so that the internal temperature did not rise above −70° C. The resulting mixture was stirred at −78° C. for 20 min. A solution of Example A4.1.1 (16 g) in anhydrous THF (50 mL) was added dropwise keeping the internal temperature below −70° C. The resulting dark yellow solution was allowed to warm up to RT and was stirred overnight. The reaction mixture was quenched with water and extracted with DCM. The org. layers were washed with brine, dried ($MgSO_4$), filtered off and evaporated to dryness. The resulting crude material was purified by CC (Biotage, SNAP 340 g, solvent A: Hep; solvent B: EA; gradient in % B: 10 over 2 CV, to 30 over 3 CV, 30 over 2 CV) to afford 18 g of the title compound as yellow foam. LC-MS (A): $t_R$=1.07 min; $[M-Me+H]^+$: 345.11.

Example A4.2 to Example A4.11 were synthesized starting from the appropriate Weinreb amide of Formula (A2) and bromo derivative of Formula (A3) and following the procedure described in Example A4.1. LC-MS data of Example A4.2 to Example A4.11 are listed in the table below. The LC-MS conditions used were LC-MS (A).

| Example N° | Name | $t_R$ | [M + H]$^+$ |
|---|---|---|---|
| A4.2 | 3-(4-Isopropyl-benzoyl)-3-methyl-azetidine-1-carboxylic acid tert-butyl ester | 1.09 | 318.26 |
| A4.3 | 3-(4-tert-Butyl-benzoyl)-3-methyl-azetidine-1-carboxylic acid tert-butyl ester | 1.12 | 332.28 |
| A4.4 | 3-(4-Ethyl-benzoyl)-3-methyl-azetidine-1-carboxylic acid tert-butyl ester | 1.03 | 418.04 [M-Me+H$^+$] |
| A4.5 | 3-Methyl-3-(4-trifluoromethyl-benzoyl)-azetidine-1-carboxylic acid tert-butyl ester | 1.07 | 344.16 |
| A4.6 | 3-Methyl-3-[4-(1-methyl-cyclopropyl)-benzoyl]-azetidine-1-carboxylic acid tert-butyl ester | 1.1 | 330.28 |
| A4.7 | 3-Methyl-3-[4-(1-trifluoromethyl-cyclopropyl)-benzoyl]-azetidine-1-carboxylic acid tert-butyl ester | 1.1 | 384.28 |
| A4.8 | 3-(4-Bromo-benzoyl)-3-methyl-azetidine-1-carboxylic acid tert-butyl ester | 1.04 | 353.9 |
| A4.9 | 3-Methyl-3-(4-propyl-benzoyl)-azetidine-1-carboxylic acid tert-butyl ester | 1.08 | 318.24 |
| A4.10 | 3-(4-Cyclopropyl-benzoyl)-3-methyl-azetidine-1-carboxylic acid tert-butyl ester | 1.06 | 316.18 |
| A4.11 | 3-Fluoro-3-(4-trifluoromethoxy-benzoyl)-azetidine-1-carboxylic acid tert-butyl ester | 1.09 | 363.94 |

Example A4.12: 3-Cyano-3-(4-trifluoromethoxy-benzoyl)-azetidine-1-carboxylic acid tert-butyl ester To a solution of 3-cyano-3-(methoxy-methyl-carbamoyl)-azetidine-1-carboxylic acid tert-butyl ester (1.4 g) in anhydrous THF (40 mL) under argon cooled down to 0° C. was added 4-(trifluoromethoxy)phenylmagnesium bromide (0.5M in THF, 20.8 mL) dropwise. The resulting mixture was stirred at 0° C. for 30 min, allowed to warm up to RT and stirred overnight. The reaction mixture was quenched with sat. aq. $NH_4Cl$, stirred for 15 min and extracted with EA/water. The aq. layer was back extracted twice with EA. The org. layers were dried ($MgSO_4$), filtered off and evaporated to dryness. The resulting crude material was purified by CC (Biotage, SNAP 100 g, solvent A: Hep; solvent B: EA; gradient in % B: 0 over 3 CV, 0 to 10 over 5 CV, 10 over 10 CV) to afford 1.2 g of the title compound as yellow solid. LC-MS (A): $t_R$=1.06 min; [M+H]$^+$: 371.15.

Example A4.13: 3-Fluoro-3-(4-isopropyl-benzoyl)-azetidine-1-carboxylic acid tert-butyl ester To a solution of 1-[(tert-butoxy)carbonyl]-3-fluoroazetidine-3-carboxylic acid (500 mg) in DCM (16 mL) were added N,O-dimethylhydroxylamine hydrochloride (221 mg), DIPEA (1.36 mL) and propylphosphonic anhydride solution in DCM (50% w/w, 1.64 mL). The resulting mixture was stirred 40 min at RT. Then it was diluted with DCM and washed once with aq. sat. $NaHCO_3$ solution. The org. layer was washed with citric acid (10%) and brine. The aq. layers were back extracted with twice DCM. The combined org. layers were dried ($MgSO_4$), filtered off, evaporated and dried at HV to afford 630 mg of the title compound as yellow oil. LC-MS (A): $t_R$=0.62 min; [M+H]$^+$: 263.13.

Example A4.14 to A4.18, A4.20, A4.22 to A.4.33 were synthesized starting from the appropriate Weinreb amide of Formula (A2) and the appropriate bromo derivative of Formula (A3) and following the procedure described in Example A4.1. LC-MS data of Example A4.14 to A4.18, A4.20, and A4.22 to A4.33 are listed in the table below. The LC-MS conditions used were LC-MS (A).

| Example N° | Name | $t_R$ | [M + H]$^+$ |
|---|---|---|---|
| A4.14 | 3-Methyl-3-(naphthalene-2-carbonyl)-azetidine-1-carboxylic acid tert-butyl ester | 1.08 | 311.04 |
| A4.15 | 3-Methyl-3-[4-(1-trifluoromethyl-cyclopropyl)-benzoyl]-azetidine-1-carboxylic acid tert-butyl ester | 1.12 | 383.97 |
| A4.16 | 3-Methyl-3-[4-(2,2,2-trifluoro-1,1-dlmethyl-ethyl)-benzoyl]-azetidine-1-carboxylic acid tert-butyl ester | 1.13 | 385.87 |
| A4.17 | 3-(4-isopropoxy-benzoyl)-3-methyl-azetidine-1-carboxylic acid tert-butyl ester | 1.06 | 334.15 |
| A4.18 | 3-Methyl-3-[4-(1,2,2,2-tetrafluoro-1-trifluoromethyl-ethyl)-benzoyl]-azetidine-1-carboxylic acid tert-butyl ester | 1.16 | 443.90 |
| A4.20 | 3-(3-Fluoro-4-isopropyl-benzoyl)-3-methyl-azetidine-1-carboxylic acid tert-butyl ester2 | 1.13 | 336.13 |
| A4.22 | 3-Methyl-3-(4-pentafluoroethyl-benzoyl)-azetidine-1-carboxylic acid tert-butyl ester | 1.14 | 394.04 |
| A4.23 | 3-(4-Isopropyl-3-methyl-benzoyl)-3-methyl-azetidine-1-carboxylic acid tert-butyl ester | 1.13 | 332.10 |
| A4.24 | 3-[4-(1-Fluoro-1-methyl-ethyl)-benzoyl]-3-methyl-azetidine-1-carboxylic acid tert-butyl ester | 1.08 | 336.10 |
| A4.25 | 3-[4-(1,1-Dlfluoro-ethyl)-benzoyl]-3-methyl-azetidine-1-carboxylic acid tert-butyl ester | 1.06 | 340.05 |
| A4.26 | 3-(4-Bicyclo[1.1.1]pent-1-yl-benzoyl)-3-methyl-azetidine-1-carboxylic acid tert-butyl ester | 1.15 | 342.09 |
| A4.27 | 3-[4-(1,1-Dimethyl-propyl)-benzoyl]-3-methyl-azetidine-1-carboxylic acid tert-butyl ester | 1.18 | 346.16 |
| A4.28 | 3-(3-Chloro-4-isopropyl-benzoyl)-3-methyl-azetidine-1-carboxylic acid tert-butyl ester | 1.15 | 352.08 |

-continued

| Example N° | Name | $t_R$ | $[M + H]^+$ |
|---|---|---|---|
| A4.29 | 3-(4-Cyclobutyl-benzoyl)-3-methyl-azetidine-1-carboxylic acid tert-butyl ester | 1.13 | 330.12 |
| A4.30 | 3-(3,5-Difluoro-4-isopropyl-benzoyl)-3-methyl-azetidine-1-carboxylic acid tert-butyl ester | 1.14 | 353.79 |
| A4.31 | 3-(4-Cyclobutoxy-benzoyl)-3-methyl-azetidine-1-carboxylic acid tert-butyl ester | 1.09 | 346.12 |
| A4.32 | 3-[4-(1-Ethyl-propyl)-benzoyl]-3-methyl-azetidine-1-carboxylic acid tert-butyl ester | 1.16 | 331.13 |
| A4.33 | 3-[4-(2,2-Dimethyl-propyl)-benzoyl]-3-methyl-azetidine-1-carboxylic acid tert-butyl ester | 1.17 | 346.16 |

Example A4.19: 3-methyl-3-(4-(pentafluoro-λ6-sulfaneyl)benzoyl)azetidine-1-carboxylic acid tert-butyl ester

A4.19.1: 3-Formyl-3-methyl-azetidine-1-carboxylic acid tert-butyl ester

To a solution of Example A4.1.1 (1 eq) in THF (6.7 mL/mmol) was added dropwise at −78° C., a 1M solution of diisobutylaluminium hydride in DCM (1.2 eq). The reaction mixture was stirred for 30 min at −78° C., quenched with MeOH and partitioned between a sat. solution of potassium sodium tartrate tetrahydrate and DCM. The org. phase was dried over $MgSO_4$ and concentrated in vacuo to provide the crude title compound as yellowish oil. $^1H$ NMR (400 MHz, DMSO) δ: 9.69 (s, 1H), 4.04 (d, J=8.1 Hz, 2H), 3.59 (d, J=8.2 Hz, 2H), 1.39 (s, 9H), 1.35 (s, 3H)

A4.19.2: 3-(Hydroxy(4-(pentafluoro-λ6-sulfaneyl)phenyl)methyl)-3-methylazetidine-1-carboxylic acid tert-butyl ester To a solution of 4-bromophenylsulphur pentafluoride (1.5 eq) in anhydrous $Et_2O$ (7.5 mL/mmol) under argon and cooled to −78° C., was added dropwise a 1.6M solution of tBuLi (1.1 eq). The reaction mixture was stirred for 5 min and a solution of 3-formyl-3-methyl-azetidine-1-carboxylic acid tert-butyl ester (1 eq) in anhydrous THF (2 mL/mmol) was added dropwise. The resulting dark yellow solution was stirred for 45 min at −78° C., the dry ice bath was removed, and the reaction mixture was additionally stirred for 45 min. It was quenched with water and extracted with EA. The org. phase was washed with brine, dried over $MgSO_4$ and concentrated in vacuo. The crude was purified by CC using Sfär prepacked cartridges from Biotage and eluting with Hept/EA to afford the title compound as white solid. LC-MS (A): $t_R$=1.03 min; $[M+H]^+$: 403.91

A4.19.3: 3-Methyl-3-(4-(pentafluoro-λ6-sulfaneyl)benzoyl)azetidine-1-carboxylic acid tert-butyl ester To a solution of 3-(hydroxy(4-(pentafluoro-λ6-sulfaneyl)phenyl)methyl)-3-methylazetidine-1-carboxylic acid tert-butyl ester (1 eq) in DCM (3.5 mL/mmol) was added at RT, DMP (1.2 eq). The reaction mixture was stirred for 15 min at RT, diluted with DCM, quenched with water and filtered. The filtrate was washed with a sat. solution of $NaHCO_3$ and the org. phase was dried over $MgSO_4$ and concentrated in vacuo. The crude was purified by CC using Sfär prepacked cartridges from Biotage and eluting with Hept/EA to afford the title compound as colorless sticky oil. LC-MS (A): $t_R$=1.12 min; $[M+H]^+$: 401.73

Example A4.21: 3-(Benzo[b]thiophene-5-carbonyl)-3-methyl-azetidine-1-carboxylic acid tert-butyl ester The title compound was synthesized starting from the appropriate Weinreb amide of Formula (A2) and the appropriate bromo derivative of Formula (A3) and following the procedure described in Example A4.1. It was isolated from the resulting mixture of 3-(benzo[b]thiophene-2-carbonyl)-3-methyl-azetidine-1-carboxylic acid tert-butyl ester and 3-(benzo[b]thiophene-5-carbonyl)-3-methyl-azetidine-1-carboxylic acid tert-butyl ester by Prep chiral SFC (111). LC-MS (A): $t_R$=1.07 min; $[M+H]^+$: 332.04.

Example A4.34 3-Ethyl-3-(4-trifluoromethoxy-benzoyl)-azetidine-1-carboxylic acid tert-butyl ester

A4.34.1 3-Ethyl-azetidine-1,3-dicarboxylic acid 1-tert-butyl ester 3-ethyl ester To a solution of ethyl 1-Boc-azetidine-3-carboxylate (993 mg) and iodoethane (0.338 mL) in THF (10 mL) was added potassium bis(trimethylsilyl)amide (1.55 mL) as a solution in toluene (10 mL) at −78° C. The reaction was stirred overnight and allowed to slowly warm up to RT. The reaction was quenched by the addition of aqueous aq. sat. $NH_4Cl$ (20 mL) and diluted with water (20 mL) and EA (20 mL). The phases were separated and the aqueous phase was extracted with EA (3×, 30 mL). The combined organic phases were washed with brine, dried over $MgSO_4$ and concentrated in vacuo. The product was obtained as 677 mg yellow oil. LC-MS (A) $t_R$=0.88 min; $[M+H]^+$: 257.16

A4.34.2 3-Ethyl-azetidine-1,3-dicarboxylic acid mono-tert-butyl ester

To the solution of A4.34.1 (676 mg) in water (3.72 mL) and dioxane (3.72 mL) was added lithium hydroxide monohydrate (780 mg) and the mixture was heated to 70° C. (bath temperature) for 3 h. The reaction was diluted in water (ca. 20 mL) and EA (ca. 20 mL) and acidified (ca. pH=4) with aqueous HCl (2 M). The phases were separated, the aqueous phase was extracted with EA (3×, 15 mL), the combined organic phases were washed with brine, dried over $MgSO_4$ and concentrated in vacuo to give the pure product as 555 mg yellowish solid. LC-MS (A) $t_R$=0.65 min, $[M+H]^+$: 229.13

A4.34.3 3-Ethyl-3-(methoxy-methyl-carbamoyl)-azetidine-1-carboxylic acid tert-butyl ester To a suspension of A4.34.2 (550 mg), N,O-dimethylhydroxylamine hydrochloride (468 mg) and DMAP (2.93 mg) in DCM (9 mL) was added N-(3-dimethylaminopropyl)-N'-ethylcarbodiimide hydrochloride (929 mg) and triethylamine (1.35 mL). The mixture was stirred at RT for 2 h. The reaction was diluted with water (10 mL) and and EA (10 mL) and the pH was adjusted to 1. The phases were separated and the aqueous phase was extracted with EA (3×, 10 mL). The combined organic phases were washed with brine, dried over $MgSO_4$ and concentrated in vacuo to yield the product as 570 mg yellowish oil. LC-MS (A) $t_R$=0.77 min; $[M+H]^+$: 272.17

A4.34.4 3-Ethyl-3-(4-trifluoromethoxy-benzoyl)-azetidine-1-carboxylic acid tert-butyl ester The title compound was synthesized from Example A4.34.3 and following the procedure described in Example A4.1 step A4.1.2. LC-MS (A): $t_R$=0.99 min; $[M+H]^+$: 373.15.

Example A4.35 3-Methyl-3-[4-(2,2,2-trifluoro-ethyl)-benzoyl]-azetidine-1-carboxylic acid tert-butyl ester A flask was charged with A4.8 (647 mg), $CsCO_3$ (1803 mg), $H_2O$ (782 μL) and toluene (9.13 mL). The suspension was degassed with argon in ultrasonic bath for 5 min, then t 4,4,5,5-Tetramethyl-2-(2,2,2-trifluoroethyl)-1,3,2-dioxaborolane (486 μL) and cataCXium A Pd G3 (140 mg) were added under argon. The flask was 3× evacuated and back-filled with argon. The resulting suspension was stirred at 100° C. under argon overnight. The reaction mixture was allowed to cool down, filtrated, the filter was washed with EA, the filtrate was evaporated to dryness and purified by CC (Biotage, 25 g sphere duo, A: Hept, B: EA, gradient (in % B): 10 for 3 CV, 10 to 30 over 1 CV, 30 for 3 CV, 30 to 50 over 2 CV, 50 for 1 CV) to give 569 mg brown solid. LC-MS (A) $t_R$=1.06 min; $[M+H]^+$: 358.06

Example A5.1: 2-[3-(5-Bromo-pyridin-3-yl)-[1,2,4]oxadiazol-5-yl]-propan-2-ol

H2.1: 5-Bromo-N-hydroxy-nicotinamidine

To a solution of 5-bromonicotinonitrile (2 g) in DMF (10 mL) were sequentially added hydroxylamine hydrochloride (1.14 g) and TEA (3.05 mL). The reaction mixture was heated to 85° C. for 1 h, cooled to RT and quenched with water (20 mL). The resulting precipitate was filtered off and dried at 65° C. under vacuo to afford 2.1 g of the title compound as white solid. LC-MS (A): $t_R$=0.36 min; $[M+H]^+$: 215.98.

A5.1: 2-[3-(5-Bromo-pyridin-3-yl)-[1,2,4]oxadiazol-5-yl]-propan-2-ol

To a solution of CDI (11.6 g) in DMF (35 mL) under argon, was added dropwise at RT a solution of 2-hydroxy-isobutiric acid (7.23 g) in DMF (15 mL). After stirring for 30 min, a suspension of intermediate H2.1 (10 g) in DMF (50 mL) was added slowly at RT. The mixture was heated to 90° C., stirred for 18 h and cooled to RT. It was quenched with dropwise addition of water (100 mL) at 0° C. and aged for 30 min at 0° C. The resulting precipitate was filtered and dried at 65° C. under vacuo to afford 9.1 g of the title compound as white solid. LC-MS (A): $t_R$=0.77 min; $[M+H]^+$: 283.98.

Example A5.2: 1-{4-[3-(5-Bromo-pyridin-3-yl)-[1,2,4]oxadiazol-5-yl]-piperidin-1-yl}-ethanone The title compound was synthesized following the procedure described in Example A5.1 except that 2-hydroxy-isobutiric acid was replaced by 1-acetyl-4-piperidinecarboxylic acid in the second step. LC-MS (A): $t_R$=0.84 min; $[M+H]^+$: 350.91.

Examples A6.1 to A6.25

Intermediate A6.1.1 to A6.30.1 were synthesized starting from the appropriate precursor of Formula (A4) and the appropriate bromo derivative of Formula (A5) and following the procedure described in Example A7.1 step A7.1.1 except that nBuLi was replaced by HexLi. Prep LC-MS conditions and LC-MS data are listed in the table below. The LC-MS conditions used were LC-MS (A).

| Example No | Name | $t_R$ | $[M + H]^+$ | Prep LC-MS | Precursor A4 | Precursor A5 |
|---|---|---|---|---|---|---|
| A6.1.1 | 3-(Hydroxy-{5-[5-(1-hydroxy-1-methyl-ethyl)-[1,2,4]oxadiazol-3-yl]-pyridin-3-yl}-naphthalen-2-yl-methyl)-3-methyl-azetidine-1-carboxylic acid tert-butyl ester | 1.01 | 531.08 | XXXI | A4.14 | A5.1 |
| A6.2.1 | 3-{Hydroxy-{5-[5-(1-hydroxy-1-methyl-ethyl)-[1,2,4]oxadiazol-3-yl]-pyridin-3-yl}-[4-(1-trifluoromethyl-cyclopropyl)-phenyl]-methyl}-3-methyl-azetidine-1-carboxylic acid tert-butyl ester | 1.05 | 589.08 | VI | A4.15 | A5.1 |
| A6.3.1 | 3-{Hydroxy-{5-[5-(1-hydroxy-1-methyl-ethyl)-[1,2,4]oxadiazol-3-yl]-pyridin-3-yl}-[4-(2,2,2-trifluoro-1,1-dimethyl-ethyl)-phenyl]-methyl}-3-methyl-azetidine-1-carboxylic acid tert-butyl ester | 1.05 | 590.97 | VII | A4.16 | A5.1 |
| A6.4.1 | 3-[Hydroxy-{5-[5-(1-hydroxy-1-methyl-ethyl)-[1,2,4]oxadiazol-3-yl]-pyridin-3-yl}-(4-isopropoxy-phenyl)-methyl]-3-methyl-azetidine-1-carboxylic acid tert-butyl ester | 0.98 | 539.15 | VI | A4.17 | A5.1 |
| A6.5.1 | 3-((3-Fluoro-4-isopropyl-phenyl)-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | 1.05 | 541.05 | XXXI | A4.20 | A5.1 |
| A6.6.1 | 3-((4-tert-Butyl-phenyl)-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | 1.05 | 537.00 | VII | A4.3 | A5.1 |

-continued

| Example No | Name | $t_R$ | $[M + H]^+$ | Prep LC-MS | Precursor A4 | Precursor A5 |
|---|---|---|---|---|---|---|
| A6.7.1 | 3-(Benzo[b]thiophen-5-yl-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | 0.99 | 537.04 | VI | A4.21 | A5.1 |
| A6.8.1 | 3-[Hydroxy-{5-[5-(1-hydroxy-1-methyl-ethyl)-[1,2,4]oxadiazol-3-yl]-pyridin-3-yl}-(4-pentafluoroethyl-phenyl)-methyl]-3-methyl-azetidine-1-carboxylic acid tert-butyl ester | 1.06 | 599.07 | XX | A4.22 | A5.1 |
| A6.9.1 | 3-{Hydroxy-{5-[5-(1-hydroxy-1-methyl-ethyl)-[1,2,4]oxadiazol-3-yl]-pyridin-3-yl}-[4-(1-methyl-cyclopropyl)-phenyl]-methyl}-3-methyl-azetidine-1-carboxylic acid tert-butyl ester | 1.04 | 535.10 | VII | A4.6 | A5.1 |
| A6.10.1 | 3-[Hydroxy-{5-[5-(1-hydroxy-1-methyl-ethyl)-[1,2,4]oxadiazol-3-yl]-pyridin-3-yl}-(4-isopropyl-3-methyl-phenyl)-methyl]-3-methyl-azetidine-1-carboxylic acid tert-butyl ester | 1.06 | 537.13 | VII | A4.23 | A5.1 |
| A6.11.1 | 3-[Hydroxy-{5-[5-(1-hydroxy-1-methyl-ethyl)-[1,2,4]oxadiazol-3-yl]-pyridin-3-yl}-(4-trifluoromethoxy-phenyl)-methyl]-3-methyl-azetidine-1-carboxylic acid tert-butyl ester | 1.02 | 565.09 | VI + XXIX | A4.1 | A5.1 |
| A6.12.1 | 3-([4-(1-Fluoro-1-methyl-ethyl)-phenyl]-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | 1.00 | 541.13 | VI | A4.24 | A5.1 |
| A6.13.1 | 3-([4-(1,1-Difluoro-ethyl)-phenyl]-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | 0.99 | 545.96 | VI | A4.25 | A5.1 |
| A6.14.1 | 3-((4-Bicyclo[1.1.1]pent-1-yl-phenyl)-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | 1.08 | 547.19 | VII | A4.26 | A5.1 |
| A6.15.1 | 3-([4-(1,1-Dimethyl-propyl)-phenyl]-hydroxy-{5-[5-(1-hydroxy-1-methyl-ethyl)-[1,2,4]oxadiazol-3-yl]-pyridin-3-yl}-methyl)-3-methyl-azetldine-1-carboxylic acid tert-butyl ester | 1.10 | 551.23 | VII | A4.27 | A5.1 |
| A6.16.1 | 3-[{5-[5-(1-Acetyl-piperidin-4-yl)-[1,2,4]oxadiazol-3-yl]-pyridin-3-yl}-(3-fluoro-4-isopropyl-phenyl)-hydroxy-methyl]-3-methyl-azetidine-1-carboxylic acid tert-butyl ester | 1.09 | 608.10 | VI | A4.20 | A5.2 |
| A6.17.1 | 3-{{5-[5-(1-Acetyl-piperidin-4-yl)-[1,2,4]oxadiazol-3-yl]-pyridin-3-yl}-hydroxy-[4-(1-trifluoromethyl-cyclopropyl)-phenyl]-methyl}-3-methyl-azetidine-1-carboxylic acid tert-butyl ester | 1.09 | 656.23 | VI | A4.15 | A5.2 |
| A6.18.1 | 3-[{5-[5-(1-Acetyl-piperidin-4-yl)-[1,2,4]oxadiazol-3-yl]-pyridin-3-yl}-hydroxy-(4-trifluoromethoxy-phenyl)-methyl]-3-methyl-azetidine-1-carboxylic acid tert-butyl ester | 1.06 | 632.20 | VI | A4.1 | A5.2 |
| A6.19.1 | 3-[{5-[5-(1-Acetyl-piperidin-4-yl)-[1,2,4]oxadiazol-3-yl]-pyridin-3-yl}-hydroxy-(4-isopropoxy-phenyl)-methyl]-3-methyl-azetidine-1-carboxylic acid tert-butyl ester | 1.03 | 606.25 | VI | A4.17 | A5.2 |
| A6.20.1 | 3-((3-Chloro-4-isopropyl-phenyl)-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | 1.07 | 557.15 | VII | A4.28 | A5.1 |
| A6.21.1 | 3-((4-Cyclobutyl-phenyl)-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | 1.05 | 535.11 | VII | A4.29 | A5.1 |
| A6.22.1 | 3-[{5-[5-(1-Acetyl-piperidin-4-yl)-[1,2,4]oxadiazol-3-yl]-pyridin-3-yl}-(4-cyclobutyl-phenyl)-hydroxy-methyl]-3-methyl-azetidine-1-carboxylic acid tert-butyl ester | 1.10 | 602.16 | VI | A4.29 | A5.2 |

-continued

| Example No | Name | $t_R$ | $[M + H]^+$ | Prep LC-MS | Precursor A4 | Precursor A5 |
|---|---|---|---|---|---|---|
| A6.23.1 | 3-[{5-[5-(1-Acetyl-piperidin-4-yl)-[1,2,4]oxadiazol-3-yl]-pyridin-3-yl}-(3,5-difluoro-4-isopropyl-phenyl)-hydroxy-methyl]-3-methyl-azetidine-1-carboxylic acid tert-butyl ester | 1.11 | 626.11 | VI | A4.30 | A5.2 |
| A6.24.1 | 3-((3,5-Difluoro-4-isopropyl-phenyl)-hydroxy-{5-[5-(1-hydroxy-1-methyl-ethyl)-[1,2,4]oxadiazol-3-yl]-pyridin-3-yl}-methyl)-3-methyl-azetldine-1-carboxylic acid tert-butyl ester | 1.06 | 559.09 | VII | A4.30 | A5.1 |
| A6.25.1 | 3-[{5-[5-(1-Acetyl-piperidin-4-yl)-[1,2,4]oxadiazol-3-yl]-pyridin-3-yl}-(4-cyclobutoxy-phenyl)-hydroxy-methyl]-3-methyl-azetidine-1-carboxylic acid tert-butyl ester | 1.05 | 618.39 | VI | A4.31 | A5.2 |
| A6.26.1 | 3-([4-(1-Ethyl-propyl)-phenyl]-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | 1.10 | 551.15 | VII | A4.32 | A5.1 |
| A6.27.1 | 3-{{5-[5-(1-Acetyl-piperidin-4-yl)-[1,2,4]oxadiazol-3-yl]-pyridin-3-yl}-[4-(1-ethyl-propyl)-phenyl]-hydroxy-methyl}-3-methyl-azetidine-1-carboxylic acid tert-butyl ester | 1.16 | 618.30 | VII | A4.32 | A5.2 |
| A6.28.1 | 3-([4-(2,2-Dimethyl-propyl)-phenyl]-hydroxy-{5-[5-(1-hydroxy-1-methyl-ethyl)-[1,2,4]oxadiazol-3-yl]-pyridin-3-yl}-methyl)-3-methyl-azetldine-1-carboxylic acid tert-butyl ester | 1.10 | 551.12 | VII | A4.33 | A5.1 |
| A6.29.1 | 3-{{5-[5-(1-Acetyl-piperidin-4-yl)-[1,2,4]oxadiazol-3-yl]-pyridin-3-yl}-[4-(2,2-dimethyl-propyl)-phenyl]-hydroxy-methyl}-3-methyl-azetidine-1-carboxylic acid tert-butyl ester | 1.15 | 618.23 | VII | A4.33 | A5.2 |
| A6.30.1 | 3-{{5-[5-(1-Acetyl-piperidin-4-yl)-[1,2,4]oxadiazol-3-yl]-pyridin-3-yl}-hydroxy-[4-(1-methyl-cyclopropyl)-phenyl]-methyl}-3-methyl-azetidine-1-carboxylic acid tert-butyl ester | 1.08 | 602.18 | VI | A4.6 | A5.2 |

Example A6.1.1 to A6.25.1 were purified by Prep chiral SFC or HPLC to afford the title compound of Formula (A6) as pure enantiomer. The Prep chiral SFC or HPLC conditions and chiral SFC or HPLC data are listed in the table below

| Example N° | Name | Chiral HPLC/ SFC | $t_R$ | Prep chiral SFC or HPLC | Precursor |
|---|---|---|---|---|---|
| A6.1 | 3-((R)-Hydroxy-5-[5-(1-hydroxy-1-methyl-ethyl)-[1,2,4]oxadiazol-3-yl]-pyridin-3-yl}-naphthalen-2-yl-methyl)-3-methyl-azetidine-1-carboxylic acid tert-butyl ester | AC | 2.076 | XLVII | A6.1.1 |
| A6.2 | 3-{(R)-Hydroxy-{5-[5-(1-hydroxy-1-methyl-ethyl)-[1,2,4]oxadiazol-3-yl]-pyridin-3-yl}-[4-(1-trifluoromethyl-cyclopropyl)-phenyl]-methyl}-3-methyl-azetidine-1-carboxylic acid tert-butyl ester | I | 3.088 | VIII | A6.2.1 |
| A6.3 | 3-{(R)-Hydroxy-{5-[5-(1-hydroxy-1-methyl-ethyl)-[1,2,4]oxadiazol-3-yl]-pyridin-3-yl}-[4-(2,2,2-trifluoro-1,1-dimethyl-ethyl)-phenyl]-methyl}-3-methyl-azetidine-1-carboxylic acid tert-butyl ester | F | 2.55 | VI | A6.3.1 |
| A6.4 | 3-[(R)-Hydroxy-{5-[5-(1-hydroxy-1-methyl-ethyl)-[1,2,4]oxadiazol-3-yl]-pyridin-3-yl}-(4-isopropoxy-phenyl)-methyl]-3-methyl-azetidine-1-carboxylic acid tert-butyl ester | AM | 2.00 | XLV | A6.4.1 |
| A6.5 | 3-((R)-(3-Fluoro-4-isopropyl-phenyl)-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | AN | 1.884 | XLVI | A6.5.1 |

-continued

| Example N° | Name | Chiral HPLC/ SFC | $t_R$ | Prep chiral SFC or HPLC | Precursor |
|---|---|---|---|---|---|
| A6.6 | 3-((R)-(4-tert-Butyl-phenyl)-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | C | 1.47 | III | A6.6.1 |
| A6.7 | 3-((R)-Benzo[b]thiophen-5-yl-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | AC | 2.33 | XLVII | A6.7.1 |
| A6.8 | 3-[(R)-Hydroxy-{5-[5-(1-hydroxy-1-methyl-ethyl)-[1,2,4]oxadiazol-3-yl]-pyridin-3-yl}-(4-pentafluoroethyl-phenyl)-methyl]-3-methyl-azetidine-1-carboxylic acid tert-butyl ester | AO | 2.02 | XLVIII | A6.8.1 |
| A6.9 | 3-{(R)-Hydroxy-{5-[5-(1-hydroxy-1-methyl-ethyl)-[1,2,4]oxadiazol-3-yl]-pyridin-3-yl}-[4-(1-methyl-cyclopropyl)-phenyl]-methyl}-3-methyl-azetidine-1-carboxylic acid tert-butyl ester | AV | 3.05 | LV | A6.9.1 |
| A6.10 | 3-[(R)-Hydroxy-{5-[5-(1-hydroxy-1-methyl-ethyl)-[1,2,4]oxadiazol-3-yl]-pyridin-3-yl}-(4-isopropyl-3-methyl-phenyl)-methyl]-3-methyl-azetidine-1-carboxylic acid tert-butyl ester | AP | 3.40 | XLIX | A6.10.1 |
| A6.11 | 3-[(R)-Hydroxy-{5-[5-(1-hydroxy-1-methyl-ethyl)-[1,2,4]oxadiazol-3-yl]-pyridin-3-yl}-(4-trifluoromethoxy-phenyl)-methyl]-3-methyl-azetidine-1-carboxylic acid tert-butyl ester | V | 1.36 | XIX | A6.11.1 |
| A6.12 | 3-((R)-[4-(1-Fluoro-1-methyl-ethyl)-phenyl]-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | C | 1.39 | III | A6.12.1 |
| A6.13 | 3-((R)-[4-(1,1-Difluoro-ethyl)-phenyl]-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | AQ | 2.25 | L | A6.13.1 |
| A6.14 | 3-((R)-(4-Bicyclo[1.1.1 ] pent-1-yl-phenyl)-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | AR | 1.959 | LI | A6.14.1 |
| A6.15 | 3-((R)-[4-(1,1-Dimethyl-propyl)-phenyl]-hyd roxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | AV | 2.45 | LV | A6.15.1 |
| A6.16 | 3-[(R)-{5-[5-(1-Acetyl-piperidin-4-yl)-[1,2,4]oxadiazol-3-yl]-pyridin-3-yl}-(3-fluoro-4-isopropyl-phenyl)-hydroxy-methyl]-3-methyl-azetidine-1-carboxylic acid tert-butyl ester | AS | 9.894 | LII | A6.16.1 |
| A6.17 | 3-{(R)-{5-[5-(1-Acetyl-piperidin-4-yl)-[1,2,4]oxadiazol-3-yl]-pyridin-3-yl}-hydroxy-[4-(1-trifluoromethyl-cyclopropyl)-phenyl]-methyl}-3-methyl-azetidine-1-carboxylic acid tert-butyl ester | AS | 9.387 | LI | A6.17.1 |
| A6.18 | 3-[(R)-{5-[5-(1-Acetyl-piperidin-4-yl)-[1,2,4]oxadiazol-3-yl]-pyridin-3-yl}-hydroxy-(4-trifluoromethoxy-phenyl)-methyl]-3-methyl-azetidine-1-carboxylic acid tert-butyl ester | AS | 8.907 | LII | A6.18.1 |
| A6.19 | 3-[(R)-{5-[5-(1-Acetyl-piperidin-4-yl)-[1,2,4]oxadiazol-3-yl]-pyridin-3-yl}-hydroxy-(4-isopropoxy-phenyl)-methyl]-3-methyl-azetidine-1-carboxylic acid tert-butyl ester | AT | 7.62 | LII | A6.19.1 |
| A6.20 | 3-((R)-(3-Chloro-4-isopropyl-phenyl)-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | AU | 4.807 | LIV | A6.20.1 |
| A6.21 | 3-((R)-(4-Cyclobutyl-phenyl)-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | AV | 3.68 | LV | A6.21.1 |
| A6.22 | 3-[(R)-{5-[5-(1-Acetyl-piperidin-4-yl)-[1,2,4]oxadiazol-3-yl]-pyridin-3-yl}-(4-cyclobutyl-phenyl)-hydroxy-methyl]-3-methyl-azetidine-1-carboxylic acid tert-butyl ester | AW | 3.06 | LVI | A6.22.1 |
| A6.23 | 3-[(R)-{5-[5-(1-Acetyl-piperidin-4-yl)-[1,2,4]oxadiazol-3-yl]-pyridin-3-yl}-(3,5-difluoro-4-isopropyl-phenyl)-hydroxy-methyl]-3-methyl-azetidine-1-carboxylic acid tert-butyl ester | AX | 2.94 | LVII | A6.23.1 |

-continued

| Example N° | Name | Chiral HPLC/ SFC | $t_R$ | Prep chiral SFC or HPLC | Precursor |
|---|---|---|---|---|---|
| A6.24 | 3-((R)-(3,5-Difluoro-4-isopropyl-phenyl)-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester | AY | 3.15 | LVIII | A6.24.1 |
| A6.25 | 3-[(R)-{5-[5-(1-Acetyl-piperidin-4-yl)-[1,2,4]oxadiazol-3-yl]-pyridin-3-yl}-(4-cyclobutoxy-phenyl)-hydroxy-methyl]-3-methyl-azetidine-1-carboxylic acid tert-butyl ester | AZ | 2.785 | LIX | A6.25.1 |

Example A6.26 to Example A6.28 were synthesized following the procedure described in Example A7.1 step A7.1.1 using the ketone precursor and 3,5-dibromopyridine. The ketone precursor, LC-MS (A) data, prep LC-MS method, chiral preparative and analytical SFC data are listed in the table below.

| Example N° | Name | Ketone precursor | $t_R$ | $[M + H]^+$ | Prep LC-MS | Chiral prep SFC | Chiral analytical LC-MS |
|---|---|---|---|---|---|---|---|
| A6.26 | 3-[(R)-(5-Bromo-pyridin-3-yl)-hydroxy-(4-trifluoromethoxy-phenyl)-methyl]-3-ethyl-azetidine-1-carboxylic acid tert-butyl ester | A4.34 | 1.12 | 530.92 | (VII) | (XLIV) | 1.77 (AE) |
| A6.27 | 3-{(R)-(5-Bromo-pyridin-3-yl)-hydroxy-[4-(2,2,2-trifluoro-ethyl)-phenyl]-methyl}-3-methyl-azetidine-1-carboxylic acid tert-butyl ester | A4.35 | 1.07 | 515.02 | (VII) | (XIX) | 1.70 (V) |
| A6.28 | 3-[(S)-(5-Bromo-pyridin-3-yl)-hydroxy-(4-isopropyl-phenyl)-methyl]-3-fluoro-azetidine-1-carboxylic acid tert-butyl ester | A4.13 | 1.14 | 478.96 | (VII) then (XII) | (XXIII) | 1.60 (AF) |

Example A6.29 3-[(R)-(5-Bromo-pyridin-3-yl)-hydroxy-(4-trifluoromethyl-phenyl)-methyl]-3-methyl-azetidine-1-carboxylic acid tert-butyl ester was synthesized following the procedure described Example A7.1 step A7.1.1 using A4.5 and 3,5-dibromopyridine, purified by prep LC-MS (XXV) and chiral separation conditions (XLII). LC-MS (A) $t_R$=1.07 min; $[M+H]^+$: 501.13; chiral SFC (W) $t_R$=1.792 min.

Example A7.1: (R)-(3-Methyl-azetidin-3-yl)-(5-pyrrolidin-1-yl-pyridin-3-yl)-(4-trifluoromethoxy-phenyl)-methanol, hydrochloride salt

A7.1.1. 3-[Hydroxy-(5-pyrrolidin-1-yl-pyridin-3-yl)-(4-trifluoromethoxy-phenyl)-methyl]-3-methyl-azetidine-1-carboxylic acid tert-butyl ester To a solution of Example A4.1 (15 g) and 3-bromo-5-pyrrolidinopyridine (12.6 g) in anhydrous THF (150 mL) under argon cooled down to −78° C. was added n-BuLi (2.5M in hexane, 20.04 mL) dropwise over 20 min so that the internal temperature did not rise above −65° C. The resulting dark yellow solution was stirred at −78° C. for 1 h30 and allowed to warm up to RT. The reaction mixture was quenched with water and extracted with DCM. The org. layers were dried ($MgSO_4$), filtered off and evaporated to dryness. The resulting crude material was taken up in MeCN/MeOH (9/1 v/v) and filtrated off. The solution was purified by Prep LC-MS (IV) to afford 6.67 g of the title compound as yellow solid. LC-MS (A): $t_R$=0.9 min; $[M+H]^+$: 508.31.

A7.1.2 3-[(R)-Hydroxy-(5-pyrrolidin-1-yl-pyridin-3-yl)-(4-trifluoromethoxy-phenyl)-methyl]-3-methyl-azetidine-1-carboxylic acid tert-butyl ester Example A7.1.1 (6.67 g) was purified by Prep chiral SFC (II) to afford the title compound as pure enantiomer (3.35 g) as yellow solid. LC-MS (A): $t_R$=0.89 min; $[M+H]^+$: 508.31. Chiral SFC (A): $t_R$=2.8 min. The absolute configuration of the compound of Example A7.1.2 was determined to be (R)- by obtaining a suitable crystal of one of the two separated enantiomers (solvent: methylcyclohexane) and performing single crystal X-ray diffraction experiment.

A7.1.3. (R)-(3-Methyl-azetidin-3-yl)-(5-pyrrolidin-1-yl-pyridin-3-yl)-(4-trifluoromethoxy-phenyl)-methanol, hydrochloride salt A pale-yellow solution of Example A7.1.2 (3.25 g) in HCl in dioxane (4M, 15 mL) was stirred 1 h at RT. The crude was evaporated to dryness to give the title compound as yellow solid. LC-MS (A): $t_R$=0.60 min; $[M+H]^+$: 408.33.

Example A7.2 and Example A7.3 were synthesized starting from the appropriate Example of Formula (A4) and following the procedure described in Example A7.1 but omitting the chiral separation step A7.1.2. LC-MS data of Example A7.2 and Example A7.3 are listed in the table below. The LC-MS conditions used were LC-MS (A).

| Example N° | Name | $t_R$ | [M + H]+ |
|---|---|---|---|
| A7.2 | 3-[Hydroxy-(5-pyrrolidin-1-yl-pyridin-3-yl)-(4-trifluoromethoxy-phenyl)-methyl]-azetidine-3-carbonitrile, hydrochloride salt | 0.62 | 419.27 |
| A7.3 | (3-Fluoro-azetidin-3-yl)-(5-pyrrolidin-1-yl-pyridin-3-yl)-(4-trifluoromethoxy-phenyl)-methanol, hydrochloride salt | 0.61 | 412.20 |

Example A7.4 to Example A7.33 were synthesized starting from the appropriate precursor of Formula (A6) and following the procedure described in Example A7.1 step A7.1.3 except that the reaction mixture was stirred for 18 h at RT. LC-MS data of Example A7.4 to Example A7.33 are listed in the table below. The LC-MS conditions used were LC-MS (A).

| Example N° | Name | $t_R$ | [M + H]+ | Precursor A6 |
|---|---|---|---|---|
| A7.4 | 2-(3-{5-[(R)-Hydroxy-(3-methyl-azetidin-3-yl)-naphthalen-2-yl-methyl]-pyridin-3-yl}-[1,2,4]oxadiazol-5-yl)-propan-2-ol, hydrochloride salt | 0.65 | 431.08 | A6.1 |
| A7.5 | 2-[3-(5-{(R)-Hydroxy-(3-methyl-azetidin-3-yl)-[4-(1-trifluoromethyl-cyclopropyl)-phenyl]-methyl}-pyridin-3-yl)-[1,2,4]oxadiazol-5-yl]-propan-2-ol, hydrochloride salt | 0.71 | 489.03 | A6.2 |
| A7.6 | 2-[3-(5-{(R)-Hydroxy-(3-methyl-azetidin-3-yl)-[4-(2,2,2-trifluoro-1,1-dimethyl-ethyl)-phenyl]-methyl}-pyridin-3-yl)-[1,2,4]oxadiazol-5-yl]-propan-2-ol, hydrochloride salt | 0.70 | 490.95 | A6.3 |
| A7.7 | 2-(3-{5-[(R)-Hydroxy-(4-isopropoxy-phenyl)-(3-methyl-azetidin-3-yl)-methyl]-pyridin-3-yl}-[1,2,4]oxadiazol-5-yl)-propan-2-ol, hydrochloride salt | 0.66 | 439.19 | A6.4 |
| A7.8 | 2-(3-{5-[(R)-(3-Fluoro-4-isopropyl-phenyl)-hydroxy-(3-methyl-azetidin-3-yl)-methyl]-pyridin-3-yl}-[1,2,4]oxadiazol-5-yl)-propan-2-ol, hydrochloride salt | 0.68 | 441.11 | A6.5 |
| A7.9 | 2-(3-{5-[(R)-(4-tert-Butyl-phenyl)-hydroxy-(3-methyl-azetidin-3-yl)-methyl]-pyridin-3-yl}-[1,2,4]oxadiazol-5-yl)-propan-2-ol, hydrochloride salt | 0.71 | 437.04 | A6.6 |
| A7.10 | 2-(3-{5-[(R)-Benzo[b]thiophen-5-yl-hydroxy-(3-methyl-azetidin-3-yl)-methyl]-pyridin-3-yl}-[1,2,4]oxadiazol-5-yl)-propan-2-ol, hydrochloride salt | 0.63 | 437.08 | A6.7 |
| A7.11 | 2-(3-{5-[(R)-Hydroxy-(3-methyl-azetidin-3-yl)-(4-pentafluoroethyl-phenyl)-methyl]-pyridin-3-yl}-[1,2,4]oxadiazol-5-yl)-propan-2-ol, hydrochloride salt | 0.70 | 499.03 | A6.8 |
| A7.12 | 2-[3-(5-{(R)-Hydroxy-(3-methyl-azetidin-3-yl)-[4-(1-methyl-cyclopropyl)-phenyl]-methyl}-pyridin-3-yl)-[1,2,4]oxadiazol-5-yl]-propan-2-ol, hydrochloride salt | 0.68 | 435.17 | A6.9 |
| A7.13 | 2-(3-{5-[(R)-Hydroxy-(4-isopropyl-3-methyl-phenyl)-(3-methyl-azetidin-3-yl)-methyl]-pyridin-3-yl}-[1,2,4]oxadiazol-5-yl)-propan-2-ol, hydrochloride salt | 0.69 | 437.13 | A6.10 |
| A7.14 | 2-(3-{5-[(R)-Hydroxy-(3-methyl-azetidin-3-yl)-(4-trifluoromethoxy-phenyl)-methyl]-pyridin-3-yl}-[1,2,4]oxadiazol-5-yl)-propan-2-ol, hydrochloride salt | 0.66 | 464.97 | A6.11 |
| A7.15 | 2-(3-{5-[(R)-[4-(1-Fluoro-1-methyl-ethyl)-phenyl]-hydroxy-(3-methyl-azetidin-3-yl)-methyl]-pyridin-3-yl}-[1,2,4]oxadiazol-5-yl)-propan-2-ol, hydrochloride salt | 0.64 | 441.15 | A6.12 |
| A7.16 | 2-(3-{5-[(R)-[4-(1,1-Difluoro-ethyl)-phenyl]-hydroxy-(3-methyl-azetidin-3-yl)-methyl]-pyridin-3-yl}-[1,2,4]oxadiazol-5-yl)-propan-2-ol, hydrochloride salt | 0.64 | 445.15 | A6.13 |
| A7.17 | 2-(3-{5-[(R)-(4-Bicyclo[1.1.1]pent-1-yl-phenyl)-hydroxy-(3-methyl-azetidin-3-yl)-methyl]-pyridin-3-yl}-[1,2,4]oxadiazol-5-yl)-propan-2-ol, hydrochloride salt | 0.72 | 447.18 | A6.14 |
| A7.18 | 2-(3-{5-[(R)-[4-(1,1-Dimethyl-propyl)-phenyl]-hydroxy-(3-methyl-azetidin-3-yl)-methyl]-pyridin-3-yl}-[1,2,4]oxadiazol-5-yl)-propan-2-ol, hydrochloride salt | 0.76 | 451.22 | A6.15 |
| A7.19 | 1-[4-(3-{5-[(R)-(3-Fluoro-4-isopropyl-phenyl)-hydroxy-(3-methyl-azetidin-3-yl)-methyl]-pyridin-3-yl}-[1,2,4]oxadiazol-5-yl)-piperidin-1-yl]-ethanone, hydrochloride salt | 0.73 | 508.08 | A6.16 |

-continued

| Example N° | Name | $t_R$ | [M + H]+ | Precursor A6 |
|---|---|---|---|---|
| A7.20 | 1-{4-[3-(5-{(R)-Hydroxy-(3-methyl-azetidin-3-yl)-[4-(1-trifluoromethyl-cyclopropyl)-phenyl]-methyl}-pyridin-3-yl)-[1,2,4]oxadiazol-5-yl]-piperidin-1-yl}-ethanone, hydrochloride salt | 0.74 | 556.07 | A6.17 |
| A7.21 | 1-[4-(3-{5-[(R)-Hydroxy-(3-methyl-azetidin-3-yl)-(4-trifluoromethoxy-phenyl)-methyl]-pyridin-3-yl}-[1,2,4]oxadiazol-5-yl)-piperidin-1-yl]-ethanone, hydrochloride salt | 0.71 | 532.03 | A6.18 |
| A7.22 | 1-[4-(3-{5-[(R)-Hydroxy-(4-isopropoxy-phenyl)-(3-methyl-azetidin-3-yl)-methyl]-pyridin-3-yl}-[1,2,4]oxadiazol-5-yl)-piperidin-1-yl]-ethanone, hydrochloride salt | 0.69 | 506.12 | A6.19 |
| A7.23 | 2-(3-{5-[(R)-(3-Chloro-4-isopropyl-phenyl)-hydroxy-(3-methyl-azetidin-3-yl)-methyl]-pyridin-3-yl}-[1,2,4]oxadiazol-5-yl)-propan-2-ol, hydrochloride salt | 0.73 | 457.15 | A6.20 |
| A7.24 | 2-(3-{5-[(R)-(4-Cyclobutyl-phenyl)-hydroxy-(3-methyl-azetidin-3-yl)-methyl]-pyridin-3-yl}-[1,2,4]oxadiazol-5-yl)-propan-2-ol, hydrochloride salt | 0.71 | 435.10 | A6.21 |
| A7.25 | 1-[4-(3-{5-[(R)-(4-Cyclobutyl-phenyl)-hydroxy-(3-methyl-azetidin-3-yl)-methyl]-pyridin-3-yl}-[1,2,4]oxadiazol-5-yl)-piperidin-1-yl]-ethanone, hydrochloride salt | 0.74 | 502.21 | A6.22 |
| A7.26 | 1-[4-(3-{5-[(R)-(3,5-Difluoro-4-isopropyl-phenyl)-hydroxy-(3-methyl-azetidin-3-yl)-methyl]-pyridin-3-yl}-[1,2,4]oxadiazol-5-yl)-piperidin-1-yl]-ethanone, hydrochloride salt | 0.74 | 526.08 | A6.23 |
| A7.27 | 2-(3-{5-[(R)-(3,5-Difluoro-4-isopropyl-phenyl)-hydroxy-(3-methyl-azetidin-3-yl)-methyl]-pyridin-3-yl}-[1,2,4]oxadiazol-5-yl)-propan-2-ol, hydrochloride salt | 0.72 | 459.17 | A6.24 |
| A7.28 | 1-[4-(3-{5-[(R)-(4-Cyclobutoxy-phenyl)-hydroxy-(3-methyl-azetidin-3-yl)-methyl]-pyridin-3-yl}-[1,2,4]oxadiazol-5-yl)-piperidin-1-yl]-ethanone, hydrochloride salt | 0.72 | 518.17 | A6.25 |
| A7.29 | 2-(3-{5-[[4-(1-Ethyl-propyl)-phenyl]-hydroxy-(3-methyl-azetidin-3-yl)-methyl]-pyridin-3-yl}-[1,2,4]oxadiazol-5-yl)-propan-2-ol, hydrochloride salt | 0.77 | 451.25 | A6.26.1 |
| A7.30 | 1-[4-(3-{5-[[4-(1-Ethyl-propyl)-phenyl]-hydroxy-(3-methyl-azetidin-3-yl)-methyl]-pyridin-3-yl}-[1,2,4]oxadiazol-5-yl)-piperidin-1-yl]-ethanone, hydrochloride salt | 0.80 | 518.23 | A6.27.1 |
| A7.31 | 2-(3-{5-[[4-(2,2-Dimethyl-propyl)-phenyl]-hydroxy-(3-methyl-azetidin-3-yl)-methyl]-pyridin-3-yl}-[1,2,4]oxadiazol-5-yl)-propan-2-ol, hydrochloride salt | 0.76 | 451.25 | A6.28.1 |
| A7.32 | 1-[4-(3-{5-[[4-(2,2-Dimethyl-propyl)-phenyl]-hydroxy-(3-methyl-azetidin-3-yl)-methyl]-pyridin-3-yl}-[1,2,4]oxadiazol-5-yl)-piperidin-1-yl]-ethanone, hydrochloride salt | 0.77 | 518.13 | A6.29.1 |
| A7.33 | 1-{4-[3-(5-{Hydroxy-(3-methyl-azetidin-3-yl)-[4-(1-methyl-cyclopropyl)-phenyl]-methyl}-pyridin-3-yl)-[1,2,4]oxadiazol-5-yl]-piperidin-1-yl}-ethanone, hydrochloride salt | 0.72 | 502.13 | A6.30.1 |

Example A7.34 (RS)-4-{5-[(R)-Hydroxy-(4-isopropyl-phenyl)-(3-methyl-azetidin-3-yl)-methyl]-pyridin-3-yl}-2-(6-methyl-pyridin-2-yl)-but-3-yn-2-ol

A7.34. 1-[(R)-Hydroxy-{5-[(RS)-3-hydroxy-3-(6-methyl-pyridin-2-yl)-but-1-ynyl]-pyridin-3-yl}-(4-isopropyl-phenyl)-methyl]-3-methyl-azetidine-1-carboxylic acid tert-butyl ester The title compound was synthesized starting from F1.11 using Example F5.27, and following the procedure described in Example 15, where the amount of $Pd(PPh_3)_4$ was adjusted to 0.1 eq and the base was changed to pyrrolidine (3.5 eq). Purified with prep LC-MS method (V). LC-MS (A) $t_R$=0.89; [M+H]$^+$: 556.24

A734.2 (RS)-4-{5-[(R)-Hydroxy-(4-isopropyl-phenyl)-(3-methyl-azetidin-3-yl)-methyl]-pyridin-3-yl}-2-(6-methyl-pyridin-2-yl)-but-3-yn-2-ol To a solution of A7.34.1 (250 mg) in dioxane (2 mL) was added HCl 4M in dioxane (473 μL) dropwise at RT. The resulting suspension was stirred for 23 h before neutralized basified to pH=10 by the dropwise addition of NaOH 1M, diluted with water and DCM, extracted using a phase separator and was re-extracted 2× with DCM. The org layer was concentrated in vacuo and dried in HV to give 191 mg yellowish solid. LC-MS (A) $t_R$=0.61 min; [M+H]$^+$: 465.22

Example A7.35 to Example A7.37 were synthesized from the protected amine listed in the table below following the procedure in Example 309 step 309.2. The LC-MS date can be found in the table below. The method used was LC-MS (A).

| Example N° | Name | $t_R$ | [M + H]+ | Precursor |
|---|---|---|---|---|
| A7.35 | (S)-(5-bromopyridin-3-yl)(3-ethylazetidin-3-yl)(4-(trifluoromethoxy)phenyl)methanol, hydrochloride salt | 0.75 | 431.01 | A6.26 |
| A7.36 | (R)-(5-bromopyridin-3-yl)(3-methylazetidin-3-yl)(4-(2,2,2-trifluoroethyl)phenyl)methanol, hydrochloride salt | 0.71 | 415.01 | A6.27 |

-continued

| Example N° | Name | $t_R$ | [M + H]$^+$ | Precursor |
|---|---|---|---|---|
| A7.37 | (S)-(5-bromopyridin-3-yl)(3-fluoroazetidin-3-yl)(4-isopropylphenyl)methanol, hydrochloride salt | 0.72 | 380.95 | A6.28 |

Example A7.38: (R)-(5-Bromo-pyridin-3-yl)-(3-methyl-azetidin-3-yl)-(4-trifluoromethyl-phenyl)-methanol The title compound was synthesized following the procedure described in Example 309 step 309.2 using Example A6.29. Instead of evaporation the reaction mixture was cooled with an ice-bath and slowly basified to pH=8 with aq. sat. $NaHCO_3$ and extracted with 3×DCM. The combined org. layers were dried over $MgSO_4$, filtrated off, evaporated and dried at HV to give 1.59 g light yellow foam. LC-MS (A) $t_R$=0.71 min; [M+H]$^+$: 403.17

Example B2.1: (1,3-Dimethyl-azetidin-3-yl)-(4-trifluoromethoxy-phenyl)-methanone

B2.1.1. (3-Methyl-azetidin-3-yl)-(4-trifluoromethoxy-phenyl)-methanone; as hydrochloric salt A pale yellow solution of Example A4.1.2 (2 g) in HCl in dioxane (4M, 10 mL) was stirred for 30 min at RT. The crude was evaporated to dryness and used in the next step without further purification. LC-MS (A): $t_R$=0.66 min; [M+H]$^+$: 260.29.

B2.1.2. (1,3-Dimethyl-azetidin-3-yl)-(4-trifluoromethoxy-phenyl)-methanone

To a light yellow solution of Example B2.1.1 (1.5 g) in MeOH (35 mL) was added AcOH (3.5 mL), followed successively by formaldehyde (37% in water, 2.27 mL) and $NaBH(OAc)_3$ (2.22 g). The resulting solution was stirred for 30 min at RT and evaporated in vacuo. The residue was diluted with water and the resulting mixture was basified with aq. sat. $NaHCO_3$ solution. and extracted with DCM. The org. layers were dried ($MgSO_4$), filtered off and evaporated to dryness. The resulting crude material was purified by CC (Biotage, SNAP 50 g, solvent A: DCM; solvent B: MeOH; gradient in % B: 0 over 3 CV, 0 to 3 over 5 CV, 3 over 5 CV) to afford 950 mg of the title compound as yellow sticky glue. LC-MS (A): $t_R$=0.67 min; [M+H]$^+$: 274.02

Example B2.2 and Example B2.3 were synthesized following the procedure described in Example B2.1, but using THF instead of MeOH as solvent in the reductive amination step for the synthesis of Example B2.3. LC-MS data of Example B2.2 and Example B2.3 are listed in the table below. The LC-MS conditions used were LC-MS (A).

| Example N° | Name | $t_R$ | [M + H]$^+$ |
|---|---|---|---|
| B2.2 | (1,3-Dimethyl-azetidin-3-yl)-(4-isopropyl-phenyl)-methanone | 0.67 | 232.33 |
| B2.3 | (4-tert-Butyl-phenyl)-(1,3-dimethyl-azetidin-3-yl)-methanone | 0.72 | 246.38 |

Example C1.1: 3-Methyl-3-(5-pyrrolidin-1-yl-pyridine-3-carbonyl)-azetidine-1-carboxylic acid tert-butyl ester The title compound was synthesized starting from 3-bromo-5-pyrrolidinopyridine and Example A4.1.1, following the synthesis procedure described in Example A7.1 step A7.1.1, and was purified by Prep LC-MS (I). LC-MS (A): $t_R$=0.79 min; $[M+H]^+$: 346.24

C1.2: 3-(5-Ethoxy-pyridine-3-carbonyl)-3-methyl-azetidine-1-carboxylic acid tert-butyl ester The title compound was synthesized starting from 3-bromo-5-ethoxypyridine and Example A4.1.1, following the synthesis procedure described in Example A7.1 step A7.1.1, and was purified by CC (Biotage, SNAP 50 g, solvent A: Hep; solvent B: EA; gradient in % B: 0 over 2 CV, 0 to 30 over 3 CV, 30 over 5 CV). LC-MS (A): $t_R$=0.94 min; $[M+H]^+$: 321.19.

Example C3.1: (1,3-Dimethyl-azetidin-3-yl)-(5-pyrrolidin-1-yl-pyridin-3-yl)-methanone C3.1.1. (3-Methyl-azetidin-3-yl)-(5-pyrrolidin-1-yl-pyridin-3-yl)-methanone, hydrochloride salt A yellowish solution of Example C1.1 (1.45 g) in HCl in dioxane (4M, 10 mL) was stirred at RT for 45 min and evaporated in vacuo to afford the title compound (1.2 g) as yellow solid. LC-MS (A): $t_R$=0.44 min; $[M+H]^+$: 246.34.

C3.1.2. (1,3-Dimethyl-azetidin-3-yl)-(5-pyrrolidin-1-yl-pyridin-3-yl)-methanone

The title compound (170 mg, yellow resin) was prepared starting from Example C3.1.1 (1.12 g), and following the procedure described in Example B2.1 step B2.1.2. The crude material was purified by Prep LC-MS (XXIII). LC-MS (A): $t_R$=1.09 min; $[M+H]^+$: 422.40.

Example D1.1: 5-[(R)-(1,3-Dimethyl-azetidin-3-yl)-hydroxy-(4-isopropyl-phenyl)-methyl]-nicotinonitrile D1.1.1. 3-[(5-Bromo-pyridin-3-yl)-hydroxy-(4-isopropyl-phenyl)-methyl]-3-methyl-azetidine-1-carboxylic acid tert-butyl ester The title compound was synthesized starting from Example A4.2 and 3,5-dibromopyridine, following the synthesis procedure described in Example A7.1 step A7.1.1, and was purified by CC (Biotage, SNAP 100 g, solvent A: Hep; solvent B: EA; gradient in % B: 0 over 3 CV, 0 to 60 over 15 CV). LC-MS (A): $t_R$=1.12 min; $[M+H]^+$: 475.22.

D1.1.2. 3-[(5-Cyano-pyridin-3-yl)-hydroxy-(4-isopropyl-phenyl)-methyl]-3-methyl-azetidine-1-carboxylic acid tert-butyl ester To a solution of Example D1.1.1 (11 g) in anhydrous DMF (113 mL) under argon atmosphere were sequentially added zinc (powder, 268 mg), zinc cyanide (4.44 g), $Pd_2(dba)_3$ (1.48 g) and 1,1'-bis(diphenylphosphino)ferrocene (7.37 g). The reaction mixture was refluxed for 20 h, cooled down to RT, quenched with water and extracted with EA. The combined org. layers were dried over $Na_2SO_4$, filtered off and evaporated to dryness. The crude was purified by CC (Biotage, SNAP 100 g, solvent A: Hep; solvent B: EA; gradient in % B: 10 over 4.4 CV, 10 to 22 over 2 CV, 22 over 4 CV, 22 to 40 over 1 CV, 40 over 5.3 CV) and by Prep LC-MS (XIX) to afford the title product as white solid (5.8 g). LC-MS (A): $t_R$=1.09 min; $[M+H]^+$: 422.40.

D1.1.3. 3-[(R)-(5-Cyano-pyridin-3-yl)-hydroxy-(4-isopropyl-phenyl)-methyl]-3-methyl-azetidine-1-carboxylic acid tert-butyl ester Example D1.1.2 (4.5 g) was purified by Prep chiral SFC (VIII) to afford the title compound as pure enantiomer (1.85 g).

Chiral SFC (I): $t_R$=2.53 min.

D1.1.4. 5-[(R)-Hydroxy-(4-isopropyl-phenyl)-(3-methyl-azetidin-3-yl)-methyl]-nicotinonitrile, hydrochloride salt Example D1.1.3 (1.5 g) was dissolved in EA (15 mL) and HCl in dioxane (4M, 8.9 mL) was added. The reaction mixture was stirred overnight at RT, concentrated in vacuo and dried under HV. The residue was directly used in the next step without further purification. LC-MS (A): $t_R$=0.69 min; $[M+H]^+$: 321.99.

D1.1.5. 5-[(R)-(1,3-Dimethyl-azetidin-3-yl)-hydroxy-(4-isopropyl-phenyl)-methyl]-nicotinonitrile To a solution of Example D1.1.4 (1.27 g) in dioxane (26 mL) were added TEA (1.49 mL) and formaldehyde (37% in water, 0.93 mL), followed by $NaBH(OAc)_3$ (1.17 g). The reaction mixture was stirred at RT until completion of the reaction, filtered off, and the filtrate was purified by Prep LC-MS (XVI) to afford the title product as white powder (970 mg). LC-MS (A): $t_R$=0.70 min; $[M+H]^+$: 336.13.

Example D1.2: 3—{(R)-(5-Cyano-pyridin-3-yl)-hydroxy-[4-(2,2,2-trifluoro-ethyl)-phenyl]-methyl}-3-methyl-azetidine-1-carboxylic acid tert-butyl ester The title compound was synthesized starting from Example D1.3 and 4,4,5,5-tetramethyl-2-(2,2,2-trifluoro-ethyl)-1,3,2-dioxaborolane, following the synthesis procedure described in Example 572, and was purified by Prep LC-MS (XXIX). LC-MS (A): $t_R$=1.03 min; $[M+H]^+$: 462.15.

Example D1.3: 3-[(R)-(4-Bromo-phenyl)-(5-cyano-pyridin-3-yl)-hydroxy-methyl]-3-methyl-azetidine-1-carboxylic acid tert-butyl ester D1.3.1: 3-[(4-Bromo-phenyl)-(5-cyano-pyridin-3-yl)-hydroxy-methyl]-3-methyl-azetidine-1-carboxylic acid tert-butyl ester The title compound was synthesized starting from Example A4.8 and 5-bromonicotinonitrile, following the synthesis procedure described in Example A7.1 step A7.1.1 except that nBuLi was replaced by HexLi, and was purified by Prep LC-MS (XXVIII). LC-MS (A): $t_R$=1.02 min; $[M+H]^+$: 459.87.

D1.3.2: 3-[(R)-(4-Bromo-phenyl)-(5-cyano-pyridin-3-yl)-hydroxy-methyl]-3-methyl-azetidine-1-carboxylic acid tert-butyl ester Example D1.3.1 was purified by Prep chiral SFC (XXVII) to afford the title compound as pure enantiomer. Chiral SFC (Z): $t_R$=1.72 min.

Example D1.4: 3-{(5-Cyano-pyridin-3-yl)-hydroxy-[4-(1,2,2,2-tetrafluoro-1-trifluoromethyl-ethyl)-phenyl]-methyl}-3-methyl-azetidine-1-carboxylic acid tert-butyl ester The title compound was synthesized starting from Example A4.18 and 5-bromonicotinonitrile, following the synthesis procedure described in Example A7.1 step A7.1.1 except that nBuLi was replaced by HexLi, and was purified by CC (Biotage, SNAP, solvent A: Hep; solvent B: EA; gradient in % B: 10 over 3 CV, 10 to 50 over 13 CV). LC-MS (A): $t_R$=1.11 min; $[M+H]^+$: 547.88.

Example D1.5: 3-((5-cyanopyridin-3-yl)(hydroxy)(4-(pentafluoro-λ6-sulfaneyl)phenyl)methyl)-3-methylazetidine-1-carboxylic acid tert-butyl ester The title compound was synthesized starting from Example A4.19 and 5-bromonicotinonitrile, following the synthesis procedure described in Example A7.1 step A7.1.1 except that nBuLi was replaced by HexLi, and was purified by CC (Biotage, Sfär, solvent A: Hep; solvent B: EA; gradient in % B: 12 over 1 CV, 12 to 100 over 10 CV). LC-MS (A): $t_R$=1.05 min; $[M+H]^+$: 505.86.

Example D2.1: 5-[(R)-(1,3-Dimethyl-azetidin-3-yl)-hydroxy-(4-isopropyl-phenyl)-methyl]-N-hydroxy-nicotinamidine To a solution of Example D1.1 (970 mg) in EtOH (19 mL) were sequentially added $K_2CO_3$ (1.60 g) and hydroxylamine hydrochloride (609 mg). The reaction mixture was refluxed for 45 min, cooled down to RT, and filtered off. The resulting solution was evaporated in vacuo to afford 1.12 g of the title compound as off-white solid. LC-MS (A): $t_R$=0.53 min; $[M+H]^+$: 369.25.

Example D2.2: 3-[(R)-Hydroxy-[5-(N-hydroxycarbamimidoyl)-pyridin-3-yl]-(4-isopropyl-phenyl)-methyl]-3-methyl-azetidine-1-carboxylic acid tert-butyl ester The title compound was obtained starting from Example D1.1.3 and following the procedure described in Example D2.1, but stirring the reaction mixture at RT. LC-MS (A): $t_R$=0.81 min; $[M+H]^+$: 455.03.

Example D2.3: 3—{(R)-(4-Bromo-phenyl)-hydroxy-[5-(N-hydroxycarbamimidoyl)-pyridin-3-yl]-methyl}-3-methyl-azetidine-1-carboxylic acid tert-butyl ester The title compound was obtained starting from Example D1.3 and following the procedure described in Example D2.1. LC-MS (A): $t_R$=0.74 min; $[M+H]^+$: 492.95.

Example D2.4: 3-{Hydroxy-[5-(N-hydroxycarbamimidoyl)-pyridin-3-yl]-[4-(1,2,2,2-tetrafluoro-1-trifluoromethyl-ethyl)-phenyl]-methyl}-3-methyl-azetidine-1-carboxylic acid tert-butyl ester The title compound was obtained starting from Example D1.4 and following the procedure described in Example D2.1. LC-MS (A): $t_R$=0.87 min; $[M+H]^+$: 580.89.

Example D2.5: 3-(hydroxy(5-(N'-hydroxycarbamimidoyl)pyridin-3-yl)(4-(pentafluoro-λ6-sulfaneyl)phenyl)methyl)-3-methylazetidine-1-carboxylic acid tert-butyl ester The title compound was obtained starting from Example D1.5 and following the procedure described in Example D2.1. LC-MS (A): $t_R$=0.81 min; $[M+H]^+$: 538.93.

Example D2.6: 3—{(R)-Hydroxy-[5-(N-hydroxy-carbamimidoyl)-pyridin-3-yl]-[4-(2,2,2-trifluoro-ethyl)-phenyl]-methyl}-3-methyl-azetidine-1-carboxylic acid tert-butyl ester The title compound was obtained starting from Example D1.2 and following the procedure described in Example D2.1. LC-MS (A): $t_R$=0.79 min; $[M+H]^+$: 495.03.

Example D3.1: 1-(acetamido-2,2,2-d3)cyclopropane-1-carboxylic acid

D3.1.1 1-tert-Butoxycarbonylamino-cyclopropanecarboxylic acid benzyl ester

To a solution of Boc-1-aminocyclopropane-1-carboxylic acid (100 mg) in DCM (2 mL) were added DCC (155 mg) and DMAP (31 mg) followed by benzyl alcohol (51.5 μL). The resulting solution was stirred overnight at RT. The resulting mixture was filtrated then basified with aq. sat. $NaHCO_3$ solution and extracted with DCM. The org. layers were dried ($MgSO_4$), filtered off and evaporated to dryness. LC-MS (A): $t_R$=0.94 min; $[M+H]^+$: 291.93.

D3.1.2 1-Amino-cyclopropanecarboxylic acid benzyl ester, hydrochloride salt

A solution of Example D3.1.1 (145 mg) in HCl in dioxane (4M, 2 mL) was stirred 30 min at RT. The crude was evaporated to dryness and used in the next step without further purification. LC-MS (A): $t_R$=0.51 min; $[M+H]^+$: 192.25.

D3.1.3 Benzyl 1-(acetamido-2,2,2-d3)cyclopropane-1-carboxylate

To a solution of Example D3.1.2 (113 mg) in DCM (2 mL) were added DIPEA (257 μL), HOBt (81.1 mg) and EDC·HCl (115 mg) followed by acetic acid-2,2,2-d3 (43 μL). The resulting solution was stirred overnight at RT. Crude was basified with aq. sat. $NaHCO_3$ solution and extracted with DCM over phase separator. The resulting solution was evaporated to dryness. LC-MS (A): $t_R$=0.66 min; $[M+H]^+$: 237.1.

D3.1.4
1-(acetamido-2,2,2-d3)cyclopropane-1-carboxylic acid

To a solution of Example D3.1.3 (117 mg) in EA (2 mL) was added Pd/C (10% w/w, 50% water, 41.3 mg). The resulting solution was stirred under $H_2$ atmosphere was at RT for 5 h, filtered over a glass paper fiber filter and the filtrate was concentrated in vacuo and dried under HV. LC-MS (A): $t_R$=0.41 min.

Example D3.2: 1—(N-methylacetamido-2,2,2-d3) cyclopropane-1-carboxylic acid

D3.2.1 1-(tert-Butoxycarbonyl-methyl-amino)-cyclopropanecarboxylic acid benzyl ester To a solution of 1-((tert-Butoxycarbonyl)(methy)amino) cyclopropanecarboxylic acid (100 mg) in DMF (1 mL) were added $K_2CO_3$ (62.3 mg) followed by benzyl bromide (54.6 μL). The resulting solution was stirred overnight at RT. The resulting mixture was extracted with water and DCM. The org. layers were dried ($MgSO_4$), filtered off and evaporated to dryness. LC-MS (A): $t_R$=1.02 min; $[M+H]^+$: 305.93.

D3.2.2 1—(N-methylacetamido-2,2,2-d3)cyclopropane-1-carboxylic acid

The title compound was synthesized starting from Example D3.2.1 following the three-step procedure described in Example D3.1 steps D3.1.2 to D3.1.4. LC-MS (A): $t_R$=0.4 min; $[M+H]^+$: 161.15.

Example D3.3 to Example D3.8 and Example D3.12 were synthesized starting from the appropriate commercial amine and acid reagents following the procedure described in Example D3.2. LC-MS data of Example D3.3 to Example D3.8 and Example D3.12 are listed in the table below. The LC-MS conditions used were LC-MS (A).

| Example N° | Name | $t_R$ | $[M + H]^+$ |
|---|---|---|---|
| D3.3 | N-(acetyl-d3)-N-methylglycine | 0.27 | 135.42 |
| D3.4 | (2-Hydroxy-acetylamino)-acetic acid | No UV trace | — |
| D3.5 | (acetyl-d3)glycine | No UV trace | — |
| D3.6 | 1-(acetyl-d3)azetidine-3-carboxylic acid | 0.31 | 146.94 |
| D3.7 | 1-(acetyl-d3)-3-methylazetidine-3-carboxylic acid | 0.38 | 161.16 |
| D3.8 | 1-(acetyl-d3)-3-fluoroazetidine-3-carboxylic acid | 0.23 | 164.84 |
| D3.12 | 1-(Acetyl-methyl-amino)-cyclopropanecarboxylic acid | 0.4 | 158.16 |

Example D3.9:
(S)-1-Acetyl-pyrrolidine-3-carboxylic acid

D3.9.1 (S)-Pyrrolidine-1,3-dicarboxylic acid 3-benzyl ester 1-tert-butyl ester

The title compound (275 mg) was synthesized starting from (S)-1-N-Boc-beta-proline (200 mg) following the procedure described in Example D3.2 steps D3.2.1. LC-MS (A): $t_R$=0.99 min; $[M+H]^+$: 305.84.

D3.9.2 (S)-Pyrrolidine-3-carboxylic acid benzyl ester

A solution of Example Da 9.1 (275 mg) in HCl in dioxane (4M, 3 mL) was stirred 2 h at RT. The crude was evaporated to dryness and used in the next step without further purification. LC-MS (A): $t_R$=0.52 min; $[M+H]^+$: 206.19.

D3.9.3 (S)-1-Acetyl-pyrrolidine-3-carboxylic acid benzyl ester

To a solution of Example D3.9.2 (185 mg) in THF (3 mL) were added DIPEA (308 μL) and acetyl chloride (64.7 μL), mixture was stirred 2 h at RT. The crude was evaporated to dryness and placed under HV. LC-MS (A): $t_R$=0.76 min; $[M+H]^+$: 248.13.

D3.9.4 (S)-1-Acetyl-pyrrolidine-3-carboxylic acid

The title compound (141.6 mg) was synthesized starting from Example D3.9.3 (223 mg) following the procedure described in Example D3.1 step D3.1.4. LC-MS (A): $t_R$=0.36 min; $[M+H]^+$: 158.17.

Example D3.10 and Example D3.11 were synthesized starting from the appropriate commercially available acid following the procedure described in Example D3.9. LC-MS data of Example D3.10 and Example D3.11 are listed in the table below. The LC-MS conditions used were LC-MS (A).

| Example N° | Name | $t_R$ | [M + H]$^+$ |
|---|---|---|---|
| D3.10 | (R)-1-Acetyl-pyrrolidine-3-carboxylic acid | 0.35 | 158.15 |
| D3.11 | 2-Acetylamino-2-methyl-propionic acid | 0.31 | 146.23 |

Example D3.13: 1-Acetyl-4-hydroxy-piperidine-4-carboxylic acid

D3.13.1 4-Hydroxy-piperidine-4-carboxylic acid, hydrochloride salt

N-Boc-4-hydroxy-4-piperidinecarboxylic acid (124 mg) was treated with a solution of HCl in dioxane (4 M, 1.25 mL) and stirred at RT for 2.5 h. The mixture was concentrated and dried under HV to give the desired product as a white solid (87 mg). LC-MS (A): $t_R$=0.17 min; [M+H]$^+$: 146.09.

D3.13.2 1-Acetyl-4-hydroxy-piperidine-4-carboxylic acid

To a mixture of Example D3.13.1 (87 mg) and 4-dimethylaminopyridine (59 mg) in THF (0.5 mL) was added acetic anhydride (55 mg) and $NEt_3$ (0.20 mL). The mixture was heated at 60° C. for 90 min. After cooling to RT, the reaction was treated with aq. HCl (1 M) and extracted with EA/MeOH (9:1) five times. The combined organic layers were dried over $MgSO_4$, filtered, concentrated and dried under HV to give the title compound as a white solid (87 mg). LC-MS (A): $t_R$=0.47 min; [M+MeCN+H]$^+$: 230.19.

Example D3.14: 1-Acetyl-3-methoxy-piperidine-4-carboxylic acid

D3.14.1 3-Methoxy-piperidine-4-carboxylic acid

1-[(tert-butoxy)carbonyl]-3-methoxypiperidine-4-carboxylic acid (200 mg) was treated with a solution of HCl in dioxane (4 M, 2 mL) and stirred for 30 min. The reaction mixture was concentrated under vacuo to give the desired product as a slightly yellow solid (193 mg). LC-MS (A): $t_R$=0.19 min; [M+H]$^+$: 160.12.

D3.14.2 1-Acetyl-3-methoxy-piperidine-4-carboxylic acid

To a mixture of Example D3.14.1 (193 mg) and $Et_3N$ (0.16 mL) in DCM (2.5 mL) was added acetic anhydride (0.11 mL). The reaction was stirred at RT for 2 h, then concentrated under vacuo. The crude was recrystallized from hot EtOH to give the title compound as white crystals (61 mg). LC-MS (A): $t_R$=0.38 min; [M+H]$^+$: 202.32.

Example D3.15: (R)- or (S)-1-Methyl-5-oxo-pyrrolidine-3-carboxylic acid

D3.15.1 (R)- or (S)-1-Methyl-5-oxo-pyrrolidine-3-carboxylic acid ethyl ester A mixture of rac-1-methyl-5-oxopyrrolidine-3-carboxylic acid (500 mg), $H_2SO_4$ (0.5 mL) in EtOH (5 mL) was stirred at RT for 1 h. The solvent was evaporated and the residue was purified by prep LC-MS (XXXIII) to give the racemic mixture. To obtain the enantiomeric pure compound the racemate was subjected to prep chiral SFC (XXXV). The second eluting product was isolated to give the title compound. LC-MS (A): $t_R$=0.50 min; [M+H]$^+$: 172.06. Chiral SFC (AD): $t_R$=2.23 min.

D3.15.2 (R)- or (S)-1-Methyl-5-oxo-pyrrolidine-3-carboxylic acid

To a solution of Example D3.15.1 (34 mg) in THF (1 mL) was added a solution of LiOH in $H_2O$ (0.8 mL). The mixture was stirred at RT for 16 h, extracted with DCM and EA. The combined organic layers were concentrated and the residue was used in the next step without further purification. LC-MS (A): $t_R$=0.32 min; [M+H]$^+$: 144.12.

Example D3.16: rac-1-Ethyl-5-oxo-pyrrolidine-3-carboxylic acid

Example D3.16 was synthesized from rac-1-Ethyl-5-oxo-pyrrolidine-3-carboxylic acid methyl ester through saponification, which is described for Example D3.15, without chiral separation. LC-MS (A): $t_R$=0.38 min; [M+H]$^+$: 158.10.

Example D3.17: (S)- or (R)-1-Isopropyl-5-oxo-pyrrolidine-3-carboxylic acid

Example D3.17 was synthesized from rac-5-oxo-1-(propan-2-yl)pyrrolidine-3-carboxylic acid, analogously to the 2-step procedure described for Example D3.15. The racemic ester in step 1 was purified by prep LC-MS (XV+XXXIV), the enantiomers were separated by prep chiral SFC (XXXVI). The ester of the title compound was the first eluting enantiomer. LC-MS (A): $t_R$=0.44 min; [M+H]': 171.99.

Example D3.18: (R)- or (S)-1-Isopropyl-5-oxo-pyrrolidine-3-carboxylic acid

Example D3.18 was synthesized from rac-5-oxo-1-(propan-2-yl)pyrrolidine-3-carboxylic acid, analogously to the 2-step procedure described for D3.15. The racemic ester in step 1 was purified by prep LC-MS (XV+XXXIV), the enantiomers were separated by prep chiral SFC (XXXVI). The ester of the title compound was the second eluting enantiomer. LC-MS (A): $t_R$=0.44 min; [M+H]$^+$: 172.00.

Example D3.19: ((S)-1-Acetyl-pyrrolidin-3-yl)-acetic acid

D3.19.1 (S)-Pyrrolidin-3-yl-acetic acid, hydrochloride salt (S)-(1-Boc-pyrrolidin-3-yl)-acetic acid (325 mg) was treated with a solution of HCl in dioxane (4 M, 3.5 mL) and stirred at RT for 1 h. The reaction was diluted with EA and stirred for 30 min. The suspension was filtered and washed with EA to give the desired compound as a white solid (182 mg). LC-MS (A): $t_R$=0.22 min; [M+H]': 130.07.

D3.19.2 ((S)-1-Acetyl-pyrrolidin-3-yl)-acetic acid

To a suspension of Example D3.19.1 (60 mg) in THF (2 mL) was added acetyl chloride (30 mg) and $NEt_3$ (0.10 mL). The resulting mixture was stirred at RT for 30 min. The reaction was filtered, the residue was washed with EA/dioxane (3:1) and the combined filtrates were purified by prep LC-MS (IX) to give the title compound as a white solid (27 mg). LC-MS (A): $t_R$=0.42 min; $[M+H]^+$: 172.02.

Example D4.1: 3—((R)-(4-Bromo-phenyl)-hydroxy-{5-[5-(1-hydroxy-1-methyl-ethyl)-[1,2,4]oxadiazol-3-yl]-pyridin-3-yl}-methyl)-3-methyl-azetidine-1-carboxylic acid tert-butyl ester The title compound was synthesized starting from Example D2.3 and 2-hydroxyisobutiric acid, following the procedure described in Example 134, and was purified by CC (Biotage, Sfär, solvent A: Hep; solvent B: EA; gradient in % B: 18 over 1 CV, 18 to 100 over 6 CV). LC-MS (A): $t_R$=0.99 min; [M+H]': 558.98.

Example D4.2: 3—{(R)-Hydroxy-{5-[5-(1-hydroxy-1-methyl-ethyl)-[1,2,4]oxadiazol-3-yl]-pyridin-3-yl}-[4-(1,2,2,2-tetrafluoro-1-trifluoromethyl-ethyl)-phenyl]-methyl}-3-methyl-azetidine-1-carboxylic acid tert-butyl ester D4.2.1 3-{Hydroxy-(5-{5-(1-hydroxy-1-methyl-ethyl)-[1,2,4]oxadiazol-3-yl}-pyridin-3-yl}-[4-(1,2,2,2-tetrafluoro-1-trifluoromethyl-ethyl)-phenyl]-methyl)-3-methyl-azetidine-1-carboxylic acid tert-butyl ester The title compound was synthesized starting from Example D2.4 and 2-hydroxyisobutiric acid, following the procedure described in Example 134, and was purified by Prep LC-MS (XI). LC-MS (A): $t_R$=1.09 min; $[M+H]^+$: 649.04.

D4.2.2 3—{(R)-Hydroxy-{5-[5-(1-hydroxy-1-methyl-ethyl)-[1,2,4]oxadiazol-3-yl]-pyridin-3-yl}-[4-(1,2,2,2-tetrafluoro-1-trifluoromethyl-ethyl)-phenyl]-methyl}-3-methyl-azetidine-1-carboxylic acid tert-butyl ester Example D4.2.1 was purified by Prep chiral SFC (XXVIII) to afford the title compound as pure enantiomer. Chiral SFC (AA): $t_R$=1.79 min.

Example D4.3: (R)-3-(hydroxy(5-(5-(2-hydroxypropan-2-yl)-1,2,4-oxadiazol-3-yl)pyridin-3-yl)(4-(pentafluoro-λ6-sulfaneyl)phenyl)methyl)-3-methylazetidine-1-carboxylic acid tert-butyl ester D4.3.1 3-(hydroxy(5-(5-(2-hydroxypropan-2-yl)-1,2,4-oxadiazol-3-yl)pyridin-3-yl)(4-(pentafluoro-λ6-sulfaneyl)phenyl)methyl)-3-methylazetidine-1-carboxylic acid tert-butyl ester The title compound was synthesized starting from Example D2.5 and 2-hydroxyisobutiric acid, following the procedure described in Example 134, and was purified by Prep LC-MS (VI). LC-MS (A): $t_R$=1.03 min; $[M+H]^+$: 607.04.

D4.3.2 (R)-3-(hydroxy(5-(5-(2-hydroxypropan-2-yl)-1,2,4-oxadiazol-3-yl)-pyridin-3-yl)(4-(pentafluoro-λ6-sulfaneyl)phenyl)methyl)-3-methylazetidine-1-carboxylic acid tert-butyl ester Example D4.3.1 was purified by Prep chiral SFC (XXIX) to afford the title compound as pure enantiomer. Chiral SFC (AB): $t_R$=1.14 min.

Example D4.4: 3-[(R)-{5-[5-(1-Acetyl-piperidin-4-yl)-[1,2,4]oxadiazol-3-yl]-pyridin-3-yl}-(4-bromo-phenyl)-hydroxy-methyl]-3-methyl-azetidine-1-carboxylic acid tert-butyl ester The title compound was synthesized starting from Example D2.3 and 1-acetyl-4-piperidinecarboxylic acid, following the procedure described in Example 134, and was purified by CC (Biotage, SNAP, solvent A: DCM; solvent B: MeOH; gradient in % B: 1 over 1 CV, 1 to 5 over 10 CV5 over 3 CV). LC-MS (A): $t_R$=1.03 min; [M+H]+: 627.99.

Example D4.5: 3—{(R)-Hydroxy-{5-[5-(tetrahydro-pyran-4-yl)-[1,2,4]oxadiazol-3-yl]-pyridin-3-yl}-[4-(2,2,2-trifluoro-ethyl)-phenyl]-methyl}-3-methyl-azetidine-1-carboxylic acid tert-butyl ester The title compound was synthesized starting from Example D2.6 and tetrahydropyran-4-carboxylic acid, following the procedure described in Example 134, and was purified by Prep LC-MS (XXX). LC-MS (A): $t_R$=1.07 min; $[M+H]^+$: 589.18.

Example D5.1: 2-(3-{5-[(R)-(4-Bromo-phenyl)-hydroxy-(3-methyl-azetidin-3-yl)-methyl]-pyridin-3-yl}-[1,2,4]oxadiazol-5-yl)-propan-2-ol, hydrochloride salt The title compound was obtained starting from Example D4.1 and following the procedure described in Example A7.1 step A7.1.3 except that the reaction mixture was stirred for 18 h at RT. LC-MS (A): $t_R$=0.62 min; $[M+H]^+$: 458.95.

Example D5.2: 2-[3-(5-{(R)-Hydroxy-(3-methyl-azetidin-3-yl)-[4-(1,2,2,2-tetrafluoro-1-trifluoromethyl-ethyl)-phenyl]-methyl}-pyridin-3-yl)-[1,2,4]oxadiazol-5-yl]-propan-2-ol, hydrochloride salt The title compound was obtained starting from Example D4.2 and following the procedure described in Example A7.1 step A7.1.3 except that the reaction mixture was stirred for 18 h at RT. LC-MS (A): $t_R$=0.74 min; $[M+H]^+$: 548.97.

Example D5.3: (R)-2-(3-(5-(hydroxy(3-methylazetidin-3-yl)(4-(pentafluoro-λ6-sulfaneyl)phenyl)methyl)pyridin-3-yl)-1,2,4-oxadiazol-5-yl)propan-2-ol, hydrochloride salt The title compound was obtained starting from Example D4.3 and following the procedure described in Example A7.1 step A7.1.3 except that the reaction mixture was stirred for 18 h at RT. LC-MS (A): $t_R$=0.69 min; $[M+H]^+$: 506.93.

Example D5.4: 1-[4-(3-{5-[(R)-(4-Bromo-phenyl)-hydroxy-(3-methyl-azetidin-3-yl)-methyl]-pyridin-3-yl}-[1,2,4]oxadiazol-5-yl)-piperidin-1-yl]-ethanone, hydrochloride salt The title compound was obtained starting from Example D4.4 and following the procedure described in Example A7.1 step A7.1.3 except that the reaction mixture was stirred for 18 h at RT. LC-MS (A): $t_R$=0.66 min; $[M+H]^+$: 525.84.

Example D5.5: (R)-(3-Methyl-azetidin-3-yl)-{5-[5-(tetrahydro-pyran-4-yl)-[1,2,4]oxadiazol-3-yl]-pyridin-3-yl}-[4-(2,2,2-trifluoro-ethyl)-phenyl]-methanol, hydrochloride salt The title compound was obtained starting from Example D4.5 and following the procedure described in Example A7.1 step A7.1.3 except that the reaction mixture was stirred for 18 h at RT. LC-MS (A): $t_R$=0.70 min; $[M+H]^+$: 489.12.

Example E1.1: 5-[(R)-(1-tert-Butoxycarbonyl-3-methyl-azetidin-3-yl)-hydroxy-(4-isopropyl-phenyl)-methyl]-nicotinic acid

E1.1.1. 5-[(1-tert-Butoxycarbonyl-3-methyl-azetidin-3-yl)-hydroxy-(4-isopropyl-phenyl)-methyl]-nicotinic acid tert-butyl ester The title compound was synthesized starting from Example A4.2 and tert-butyl 5-bromonicotinate, following the synthesis procedure described in Example A4.1 step A4.1.2, and purified twice by CC (Biotage, SNAP 330 g, solvent A: Hep; solvent B: EA; gradient in % B: 0 over 2 min, 0 to 10 over 3 min, 10 over 5 min, 10 to 100 over 25 min, 100 over 5 min) followed by Prep LC-MS (II). LC-MS (A): $t_R$=1.14 min; $[M+H]^+$: 497.26.

E1.1.2. 5-[(R)-(1-tert-Butoxycarbonyl-3-methyl-azetidin-3-yl)-hydroxy-(4-isopropyl-phenyl)-methyl]-nicotinic acid tert-butyl ester Example E1.1.1 (14.8 g) was purified by Prep chiral SFC (I) to afford the title compound as pure enantiomer (5.97 g) as beige solid. LC-MS (A): $t_R$=1.14 min; $[M+H]^+$: 497.26. Chiral SFC (A): $t_R$=2.795 min.

E1.1.3. (R)-5-(hydroxy(4-isopropylphenyl)(3-methylazetidin-3-yl)methyl)nicotinic acid, hydrochloride salt A solution of Example E1.1.2 (5.97 g) in HCl in dioxane (4M, 120 mL) was stirred at RT until completion of the reaction. The mixture was concentrated to dryness and dried under HV. The resulting white solid (5 g) was directly used in the next step without further purification. LC-MS (A): $t_R$=0.58 min; $[M+H]^+$: 341.17.

E1.1.4. 5-[(R)-(1-tert-Butoxycarbonyl-3-methyl-azetidin-3-yl)-hydroxy-(4-isopropyl-phenyl)-methyl]-nicotinic acid To a suspension of Example E1.1.3 (5 g) and di-tert-butyl dicarbonate (3.23 g) in THF (60 mL) was added dropwise TEA (3.4 mL). The reaction mixture was stirred at RT for 1 h and concentrated in vacuo. The residue was purified by Prep LC-MS (III) to afford the desired compound as white solid (4 g). LC-MS (A): $t_R$=0.92 min; $[M+H]^+$: 441.2.

Example E1.2 to Example E1.3 were synthesized starting from the appropriate compound of Formula (A4) and following the four-step procedure described in Example E1.1. LC-MS data of Example E1.2 to Example E1.3 are listed in the table below. The LC-MS conditions used were LC-MS (A). The preparative and chiral SFC methods used in the second step, and the preparative LC-MS methods used in the last step are indicated in the table below.

| Example N° | Name | $t_R$ | $[M + H]^+$ | Prep chiral SFC | $t_R$ (Chiral SFC) | Prep LC-MS |
|---|---|---|---|---|---|---|
| E1.2 | 5-[(R)-(1-tert-Butoxycarbonyl-3-methyl-azetidin-3-yl)-(4-cyclopropyl-phenyl)-hydroxy-methyl]-nicotinic acid | 0.88 | 439.25 | (IV) | 2.01 (D) | (XIV) |
| E1.3 | 5-[(R)-(1-tert-Butoxycarbonyl-3-methyl-azetidin-3-yl)-hydroxy-(4-propyl-phenyl)-methyl]-nicotinic acid | 0.92 | 441.26 | (VI) | 1.80 (F) | (III) |

Example E2.1: N-Hydroxy-tetrahydro-pyran-4-carboxamidine

To a solution of 4-cyanotetrahydro-4H-pyran (389 mg) in EtOH (9 mL) and water (2 mL) were sequentially added $K_2CO_3$ (726 mg) and hydroxylamine hydrochloride (730 mg). The reaction mixture was refluxed for 20 h, cooled down to RT, and filtered off. The solid was further washed with EtOH and the resulting solution was concentrated in vacuo. EA was added to the residue and the resulting mixture was concentrated and dried under HV to afford the title compound as yellow solid (494 mg). LC-MS (A): $t_R$=0.21 min; $[M+H]^+$: 145.27.

Example E2.2 to Example E2.13 were synthesized starting from the appropriate cyano derivative and following the procedure described in Example E2.1. LC-MS data of Example E2.2 to Example E2.13 are listed in the table below. The LC-MS conditions used were LC-MS (A).

| Example N° | Name | $t_R$ | $[M + H]^+$ |
|---|---|---|---|
| E2.2 | N-Hydroxy-3-methoxy-2,2-dimethyl-propionamidine | 0.30 | 147.25 |
| E2.3 | N-Hydroxy-4-methoxy-tetrahydro-pyran-4-carboxamidine | 0.25 | 175.39 |
| E2.4 | N-Hydroxy-3-hydroxymethyl-bicyclo[1.1.1]pentane-1-carboxamidine | 0.22 | 157.15 |
| E2.5 | N-Hydroxy-2-morpholin-4-yl-acetamidine | 0.20 | 160.22 |
| E2.6 | 2-(2,6-Dimethyl-morpholin-4-yl)-N-hydroxy-acetamidine | 0.26 | 188.40 |
| E2.7 | N-Hydroxy-4-methyl-tetrahydro-pyran-4-carboxamidine | 0.24 | 159.26 |
| E2.8 | (1S,2S,4R)-N-Hydroxy-7-oxa-bicyclo[2.2.1]heptane-2-carboxamidine | 0.26 | 157.24 |
| E2.9 | 3,N-Dihydroxy-2,2-dimethyl-propionamidine | 0.20 | 133.23 |

-continued

| Example N° | Name | $t_R$ | [M + H]$^+$ |
|---|---|---|---|
| E2.10 | 2,N-Dihydroxy-2-methyl-propionamidine | 0.19 | 119.25 |
| E2.11 | N-Hydroxy-2-methoxy-2-methyl-propionamidine | 0.21 | 133.23 |
| E2.12 | N-Hydroxy-1-methoxy-cyclobutanecarboxamidine | 0.26 | 145.15 |
| E2.13 | 3,N-Dihydroxy-3-methyl-butyramidine | 0.20 | 133.26 |

Example E2.14: 4—(N-Hydroxycarbamimidoyl)-piperidine-1-carboxylic acid benzyl ester To a solution of 1-N-Cbz-4-cyanopiperidine (100 mg) in EtOH (4 mL) were added hydroxylamine hydrochloride (42.2 mg) and DIPEA (110 μL), mixture was stirred 41 h at 80° C. Reaction mixture was evaporated to dryness, resulting crude was extracted with EA and water, organic phase was washed with brine. The combined org. layers were dried ($MgSO_4$), filtrated off, evaporated and dried under HV to give 104 mg of the title compound as a pale yellow resin. LC-MS (A): $t_R$=0.59 min; [M+H]$^+$: 278.17.

Example E2.15: (E)-1-acetyl-N'-hydroxypiperidine-4-carboximidamide

To a solution of 1-acetylpiperidine-4-carbonitrile (955 mg) in DMSO (5 mL) were added hydroxylamine hydrochloride (621 mg) and Et3N (1.66 mL), the resulting mixture was stirred 10 h at 90° C. and filtrated. Filtrate was lyophilisated, resulting oil was stripped in MeCN, resulting precipitate was filtered and washed with MeCN. The title compound was obtained as 620 mg of an off-white solid. LC-MS (A): $t_R$=0.24 min; [M+H]$^+$: 186.28.

Example E2.16: 4, N-Dihydroxy-tetrahydro-pyran-4-carboxamidine

To a solution of 4-hydroxy-4-carbonitrile (200 mg) in EtOH (8 mL) were added hydroxylamine hydrochloride (315 mg) and $K_2CO_3$ (826 mg). The mixture was stirred at 80° C. for 40 h, cooled to RT, filtered, concentrated and dried under HV to give the title compound as a pale sticky solid (231 mg). LC-MS (A): $t_R$=0.19 min; [M+H]$^+$: 161.07.

Example E2.17 to Example E2.20 were synthesized according to the procedure described for Example E2.16 from the corresponding nitriles. If necessary, purification was performed with prep LC-MS. Retention times and observed masses of the products, as well as purification methods (if applicable) are given in the table below.

| Example N° | Name | $t_R$ | [M + H]$^+$ | prep LC-MS Method |
|---|---|---|---|---|
| E2.17 | 2-tert-Butoxy-N-hydroxy-acetamidine | 0.33 | 147.20 | — |
| E2.18 | 4-Acetyl-N-hydroxy-piperazine-1-carboxamidine | 0.21 | 187.35 | (XXXII) |
| E2.19 | 4-(N-Hydroxycarbamimidoyl)-piperidine-1-carboxylic acid tert-butyl ester | 0.51 | 244.28 | — |
| E2.20 | N-Hydroxy-2-(4-hydroxy-tetrahydro-pyran-4-yl)-acetamidine | 0.20 | 175.34 | — |

Example E2.21: 1-[2-(tert-Butyl-diphenyl-silanyloxy)-acetyl]-N-hydroxy-piperidine-4-carboxamidine E2.21.1 Piperidine-4-carbonitrile, hydrochloride Salt N-Boc-piperidine-4-carbonitrile (600 mg) was treated with a solution of HCl in dioxane (4 M, 7.2 mL) and stirred at RT for 2 h. The reaction mixture was concentrated and dried under HV to give the desired product as a pale solid (455 mg). LC-MS (A): $t_R$=0.20 min; $[M+H]^+$: 111.17.

E2.21.2 (cert-Butyl-diphenyl-silanyloxy)-acetic acid

To a solution of glycolic acid (2.00 g), N,N-dimethyl-4-aminopyridine (318 mg) and $NEt_3$ (10.9 mL) in THF (100 mL) was added tert-butyl(chloro)diphenylsilane (7.6 mL) dropwise at 0° C. The mixture was allowed to warm to RT and was stirred for 16 h. The reaction mixture was acidified with aq. HCl (1M) until pH 1 was reached. The solution was extracted with $Et_2O$ (3 times) and the combined organic layers were dried over $MgSO_4$, filtered and concentrated under vacuo to give a colorless oil, which was purified by CC (CombiFlash, RediSep 330 g, gradient of n-Heptane/EA 100:0 to 70:30 over 25 min at 200 mL/min) to yield the desired product as a colorless oil (7.05 g). LC-MS (A): $t_R$=1.05 min; product mass was not observed; $^1$H-NMR (500 MHz, DMSO-d6): δ=12.56 (br s, 1H), 7.67-7.63 (m, 4H), 7.51-7.41 (m, 6H), 4.19 (s, 2H), 1.02 (s, 9H) ppm.

E2.21.3 1[-2-(tert-Butyl-diphenyl-silanyloxy)-acetyl]-piperidine-4-carbonitrile

To a suspension of Example E2.21.1 (455 mg), Example E2.21.2 (1.27 g) and HATU (1.89 g) in THF (8.5 mL) was added DIPEA (1.59 mL). The reaction was stirred at RT for 4 h. Then it was diluted with EA, washed with aq. HCl (1 M), sat. aq. $NaHCO_3$, water and brine, dried over $Na_2SO_4$, filtered and concentrated under vacuo. The residue was purified by CC (CombiFlash, RediSep 220 g, gradient of n-Heptane/EA 100:0 to 0:100 over 30 min at 150 mL/min) to give the desired product as a colorless oil (968 mg). LC-MS (A): $t_R$=1.09 min; $[M+H]^+$: 407.27.

E2.21.4 1-[2-(tert-Butyl-diphenyl-silanyloxy)-acetyl]-N-hydroxy-piperidine-4-carboxamidine To a solution of Example E2.21.3 (968 mg) in EtOH (8 mL) were added hydrodxylamine hydrochloride (501 mg) and $K_2CO_3$ (1.32 g). The reaction mixture was stirred at 80° C. for 16 h. The reaction mixture was concentrated under vacuo to give a yellow oil, which was purified by prep LC-MS (XIV) to give the title compound as a white solid (79 mg). LC-MS (A): $t_R$=0.83 min; $[M+H]^+$: 440.32.

Example E2.22: 2-(1-Acetyl-azetidin-3-yl)-N-hydroxy-acetamidine

E2.22.1 Azetidin-3-yl-acetonitrile, hydrochloride Salt

3-Cyanomethyl-azetidine-1-carboxylic acid tert-butyl ester (500 mg) was treated with a solution of HCl in dioxane (4 M, 6.1 mL). The mixture was stirred for 1 h, concentrated and dried under HV to give the desired product as a yellow viscous oil (474 mg). $^1$H-NMR (500 MHz, DMSO-d6): δ=9.18 (br s, 2H) 4.06-3.98 (m, 2H), 3.75-3.67 (m, 2H), 3.10 (hept, J=7.6 Hz, 1H), 2.93 (d, J=7.0 Hz, 2H) ppm.

E2.22.2 (1-Acetyl-azetidin-3-yl)-acetonitrile

A mixture of Example E2.22.1 (231 mg) and $K_2CO_3$ in THF (5 mL) was cooled to 0° C. before acetyl chloride (138 mg) was added dropwise. The reaction was allowed to warm to RT and was stirred for 1 h. The mixture was filtered, the residue was washed with THF, suspended in MeOH, sonicated and filtered. The filtrate was concentrated under vacuo to give the desired product as an orange sticky solid (226 mg). It was used for the next step without further purification. LC-MS (A): $t_R$=0.36 min; $[M+H]^+$: 139.14.

E2.22.3 2-(1-Acetyl-azetidin-3-yl)-N-hydroxy-acetamidine

The title compound was synthesized from Example E2.22.2 according to the procedure described for Example E2.16. A yellow sticky solid was obtained. LC-MS (A): $t_R$=0.21 min; $[M+H]^+$: 171.87.

Example F1.1: (5-Bromo-pyridin-3-yl)-(1,3-dimethyl-azetidin-3-yl)-(4-isopropyl-phenyl)-methanol F1.1.1. (5-Bromo-pyridin-3-yl)-(4-isopropyl-phenyl)-(3-methyl-azetidin-3-yl)-methanol A pale yellow solution of Example D1.1.1 (2.15 g) in HCl in dioxane (4M, 10 mL) was stirred for 2 h at RT. The reaction mixture was cooled at 0° C., slowly basified with aq. sat. $NaHCO_3$ solution and extracted with DCM. The org. phases were dried ($MgSO_4$), filtrated off and evaporated to dryness to give the title compound (1.76 g). LC-MS (A): $t_R$=0.74 min; $[M+H]^+$: 375.19.

F1.1.2. (5-Bromo-pyridin-3-yl)-(1,3-dimethyl-azetidin-3-yl)-(4-isopropyl-phenyl)-methanol To a light yellow solution of Example F1.1.1 (1.75 g) in THF (40 mL), AcOH (0.4 mL) was added at RT, followed successively by formaldehyde (37% in water, 0.695 mL) and $NaBH(OAc)_3$ (1.53 g). The resulting solution was stirred for 1 h10 at RT, was basified with aq. sat. $NaHCO_3$ solution, diluted with water, and extracted with EA. The org. layers were dried ($MgSO_4$), filtered off, and evaporated to dryness to afford 1.91 g of the title compound as beige solid. LC-MS (A): $t_R$=0.76 min; $[M+H]^+$: 389.22.

Example F1.2: (R)-(5-Bromo-pyridin-3-yl)-(1,3-dimethyl-azetidin-3-yl)-(4-isopropyl-phenyl)-methanol F1.2.1. 3-[(R)-(5-Bromo-pyridin-3-yl)-hydroxy-(4-isopropyl-phenyl)-methyl]-3-methyl-azetidine-1-carboxylic acid tert-butyl ester The title compound was obtained by chiral separation of Example D1.1.1 using Prep chiral SFC (111). LC-MS (A): $t_R$=1.12 min; $[M+H]^+$: 475.20; Chiral SFC (C): 1.4 min.

F1.2.2. (R)-(5-Bromo-pyridin-3-yl)-(4-isopropyl-phenyl)-(3-methyl-azetidin-3-yl)-methanol, dihydrochloride salt A pale yellow solution of Example F1.2.1 (3.7 g) in HCl in dioxane (4M, 27 mL) was stirred 2 h at RT and evaporated to dryness to give the title compound (3.98 g) as white solid. LC-MS (A): $t_R$=0.73 min; $[M+H]^+$: 375.13

F1.2.3. (R)-(5-Bromo-pyridin-3-yl)-(1,3-dimethyl-azetidin-3-yl)-(4-isopropyl-phenyl)-methanol The title compound was synthesized starting from Example F1.2.2 and following the synthesis procedure described in Example F1.1 step F1.1.2, additional equivalents of formaldehyde and $NaBH(OAc)_3$ were added until completion of the reaction. LC-MS (A): $t_R$=0.74 min; $[M+H]^+$: 389.18.

Example F1.3: (2-Chloro-pyridin-4-yl)-(1,3-dimethyl-azetidin-3-yl)-(4-isopropyl-phenyl)-methanol F1.3.1. 3-[(2-Chloro-pyridin-4-yl)-hydroxy-(4-isopropyl-phenyl)-methyl]-3-methyl-azetidine-1-carboxylic acid tert-butyl ester The title compound (516 mg, colorless foam) was synthesized starting from Example A4.2 (415 mg) and 4-bromo-2-chloropyridine (200 μL), and following the procedure described in Example A7.1 step A7.1.1. The crude material was purified by CC (Biotage, SNAP 40 g, solvent A: Hep; solvent B: EA; gradient in % B: 0 to 50 over 20 min). LC-MS (A): $t_R$=1.12 min; $[M+H]^+$: 431.31.

F1.3.2. (2-Chloro-pyridin-4-yl)-(4-isopropyl-phenyl)-(3-methyl-azetidin-3-yl)-methanol, hydrochloride salt A solution of Example F1.3.1 (644 mg) in HCl in dioxane (4M, 5 mL) and MeOH (2.5 mL) was stirred at RT for 15 min and evaporated in vacuo. The resulting residue was triturated in $Et_2O$ and the solvent was evaporated in vacuo to afford the title compound (650 mg) as yellow foam. LC-MS (A): $t_R$=0.72 min; $[M+H]^+$: 331.27.

F1.3.3. (2-Chloro-pyridin-4-yl)-(1,3-dimethyl-azetidin-3-yl)-(4-isopropyl-phenyl)-methanol The title compound (483 mg, beige foam) was synthesized starting from Example F1.3.2 (650 mg), and following the procedure described in Example F1.1 step F1.1.2. LC-MS (A): $t_R$=0.75 min; $[M+H]^+$: 345.27.

Example F1.4: 3—[(S)-(2-Chloro-pyridin-4-yl)-hydroxy-(4-isopropyl-phenyl)-methyl]-3-methyl-azetidine-1-carboxylic acid tert-butyl ester The title compound was obtained by chiral separation of Example F1.3.1 using Prep Chiral SFC (XVII). LC-MS (A): $t_R$=1.12 min; $[M+H]^+$: 431.36; Chiral SFC (Q): 1.31 min.

Example F1.5: (S)-(2-Chloro-pyridin-4-yl)-(1,3-dimethyl-azetidin-3-yl)-(4-isopropyl-phenyl)-methanol The title compound (852 mg, white solid) was synthesized starting from Example F1.4 (1.1 g), and following the procedure described in Example F1.3 step F1.3.2 and F1.3.3. The crude material was purified by Prep LC-MS (XIII). LC-MS (A): $t_R$=0.74 min; $[M+H]^+$: 345.16.

Example F1.6: (R)-(6-Chloro-pyridazin-4-yl)-(1,3-dimethyl-azetidin-3-yl)-(4-isopropyl-phenyl)-methanol F1.6.1. 3-[(6-Chloro-pyridazin-4-yl)-hydroxy-(4-isopropyl-phenyl)-methyl]-3-methyl-azetidine-1-carboxylic acid tert-butyl ester The title compound (4.34 g, brown solid) was synthesized starting from Example A4.2 (8.5 g) and 5-bromo-3-chloropyridazine (6 g), and following the procedure described in Example A7.1 step A7.1.1, however using toluene instead of THF as solvent. The crude material was purified by CC (Biotage, SNAP 330 g, solvent A: Hep; solvent B: EA; gradient in % B: 0 to 50 over 40 min). LC-MS (A): $t_R$=1.06 min; $[M+H]^+$: 432.22.

F1.6.2. 3—[R-(6-Chloro-pyridazin-4-yl)-hydroxy-(4-isopropyl-phenyl)-methyl]-3-methyl-azetidine-1-carboxylic acid tert-butyl ester The title compound was obtained by chiral separation of Example F1.6.1 using Prep Chiral SFC (XVIII). LC-MS (A): $t_R$=1.05 min; $[M+H]^+$: 432.22; Chiral SFC (R): 1.26 min.

F1.6.3. (R)-(6-Chloro-pyridazin-4-yl)-(4-isopropyl-phenyl)-(3-methyl-azetidin-3-yl)-methanol, hydrochloric salt A solution of Example F1.6.2 (377 mg) in HCl in dioxane (4M, 7 mL) was stirred at RT for 2 h and evaporated in vacuo. The crude material was evaporated to dryness to give 351 mg of the title compound as yellow solid. LC-MS (A): $t_R$=0.67 min; $[M+H]^+$: 332.13.

F1.6.4. (R)-(6-Chloro-pyridazin-4-yl)-(1,3-dimethyl-azetidin-3-yl)-(4-isopropyl-phenyl)-methanol The title compound (215 mg, beige foam) was synthesized starting from Example F1.6.3, and following the procedure described in Example F1.1 step F1.1.2, however additional equivalents of formaldehyde and $NaBH(OAc)_3$ were added until completion of the reaction. LC-MS (A): $t_R$=0.67 min; $[M+H]^+$: 346.10.

Example F1.7 to Example F1.10 were synthesized starting from appropriate compound of Formula (A4) and 3,5-dibromopyridine, following the four-step procedure described in Example F1.6. Chiral Prep SFC conditions used in step 2, Prep LC-MS conditions used in step 4 and LC-MS data of Example F1.7 to Example F1.10 are listed in the table below. The LC-MS conditions used were LC-MS (A).

| Example N° | Name | $t_R$ | $[M + H]^+$ | (A4) | Prep LC-MS step 4 | Chiral Prep SFC step 2 |
|---|---|---|---|---|---|---|
| F1.7 | (R)-(5-Bromo-pyridin-3-yl)-(1,3-dimethyl-azetidin-3-yl)-[4-(1-methyl-cyclopropyl)-phenyl]-methanol | 0.77 | 401.13 | A4.6 | none | (III) |

-continued

| Example N° | Name | $t_R$ | $[M + H]^+$ | (A4) | Prep LC-MS step 4 | Chiral Prep SFC step 2 |
|---|---|---|---|---|---|---|
| F1.8 | (R)-(5-Bromo-pyridin-3-yl)-(1,3-dimethyl-azetidin-3-yl)-[4-(1-trifluoromethyl-cyclopropyl)-phenyl]-methanol | 0.79 | 455.16 | A4.7 | none | (XX) |
| F1.9 | (R)-(5-Bromo-pyridin-3-yl)-(4-tert-butyl-phenyl)-(1,3-dimethyl-azetidin-3-yl)-methanol | 0.8 | 403.23 | A4.3 | (VII) | (XIX) |
| F1.10 | (R)-(5-Bromo-pyridin-3-yl)-(1,3-dimethyl-azetidin-3-yl)-(4-ethyl-phenyl)-methanol | 0.72 | 377.19 | A4.4 | none | (XIX) |

Example F1.11: 3-[(R)-(5-Bromo-pyridin-3-yl)-hydroxy-(4-isopropyl-phenyl)-methyl]-3-methyl-azetidine-1-carboxylic acid tert-butyl ester Example D1.1.1 (9 g) was purified by Prep chiral SFC (Ill) to afford the title compound as pure enantiomer (4.31 g). Chiral SFC (C): $t_R$=1.377 min. LC-MS (A): $t_R$=1.12 min; $[M+H]^+$: 475.20.

Example F1.12 to Example F1.14 were synthesized starting from appropriate compound of Formula (A7) following the procedure described in Example D1.1 step D1.1.5. The LC-MS data are listed in the table below. The LC-MS conditions used were LC-MS (A).

| Example N° | Name | $t_R$ | $[M + H]^+$ | (A7) |
|---|---|---|---|---|
| F1.12 | (R)-(5-Bromo-pyridin-3-yl)-(1,3-dimethyl-azetidin-3-yl)-[4-(2,2,2-trifluoro-ethyl)-phenyl]-methanol | 0.71 | 428.93 | A7.36 |
| F1.13 | (R)-(5-Bromo-pyridin-3-yl)-(3-ethyl-1-methyl-azetidin-3-yl)-(4-trifluoromethoxy-phenyl)-methanol | 0.76 | 447.02 | A7.35 |
| F1.14 | (S)-(5-Bromo-pyridin-3-yl)-(3-fluoro-1-methyl-azetidin-3-yl)-(4-isopropyl-phenyl)-methanol | 0.74 | 393.03 | A7.37 |

Example F1.15 (R)-(5-Bromo-pyridin-3-yl)-(1,3-dimethyl-azetidin-3-yl)-(4-trifluoromethyl-phenyl)-methanol was synthesized starting from Example A7.38 following the procedure described in Example D1.1 step D1.1.5 and purified by prep LC-MS (VI). LC-MS (A) $t_R$=0.72 min; $[M+H]^+$: 415.22.

Example F3.1 (for synthesis, see F4.10): 4-(2-Methoxy-ethyl)-pyrrolidin-2-one

Example F3.2: 4-(2-Isopropyl-pyrimidin-4-yl)-pyrrolidin-2-one

F3.2.1. (E)-3-(2-Isopropyl-pyrimidin-4-yl)-acrylic acid ethyl ester

To an ice-cold suspension of NaH (60% in mineral oil, 250 mg) in DMF (5.5 L) was added triethyl phosphonoacetate (0.36 mL) and the resulting mixture was stirred for 30 min at 0° C. A solution of 2-isopropyl-4-pyrimidinecarbaldehyde (250 mg) in DMF (0.5 mL) was added and the resulting suspension was stirred for 1 h30 at RT. The reaction mixture was quenched and diluted with water and extracted with EA (3×). The combined org. layers were washed with brine, dried ($MgSO_4$), filtered off and evaporated to dryness. The resulting crude material (417 mg) was used without further purification. LC-MS (A): $t_R$=0.89 min; $[M+H]^+$: 221.11.

F3.2.2. 3-(2-Isopropyl-pyrimidin-4-yl)-4-nitro-butyric acid ethyl ester

To a solution of Example F.3.2.1 (232 mg) in nitromethane (0.2 mL) was added tetramethylguanidine (25 mg) at 0° C. and the reaction mixture was allowed to reach RT. After stirring for 27 h, the reaction mixture was diluted with EA and water, and extracted with EA. The combined org. layers were washed with brine, dried ($MgSO_4$), filtered off and evaporated to dryness. The resulting crude material was purified by CC (Biotage, SNAP 10 g, solvent A: DCM; solvent B: DCM/MeOH 8/2; gradient in % B: 0 over 3 CV, 0 to 25 over 8 CV, 25 for 2 CV, 25 to 50 over 3 CV, 50 for 2 CV) to afford 65 mg of the title compound as yellow oil. LC-MS (A): $t_R$=0.88 min; $[M+H]^+$: 282.1.

F3.2.3. 4-(2-Isopropyl-pyrimidin-4-yl)-pyrrolidin-2-one

To a flask charged with Pd/C (30 mg) were added a solution of Example F3.2.2 (65 mg) in EtOH (0.5 mL) and ammonium formate (94 mg) at RT under argon and the resulting suspension was stirred at 80° C. for 1 h30. The reaction mixture was allowed to cool down, filtrated through a syringe filter, and the filtrate evaporated to dryness. The resulting crude material was purified by CC (Biotage, SNAP 10 g, solvent A: DCM; solvent B: DCM/MeOH 8/2; gradient in % B: 0 over 3 CV, 0 to 25 over 7 CV, 25 for 2 CV) to afford 16 mg of the title compound as colorless oil. LC-MS (A): $t_R$=0.52 min; $[M+H]^+$: 206.17.

Example F3.3: 4-(2-Methyl-thiazol-5-yl)-pyrrolidin-2-one

F3.3.1. (E)-3-(2-Methyl-thiazol-5-yl)-acrylic acid octyl ester

To a solution of 5-bromo-2-methylthiazole (250 mg) in DMF (7.5 mL) were added successively n-octyl acrylate (388 mg), DABCO (6.6 mg), $K_2CO_3$ (194 mg), $Pd(OAc)_2$ (6.4 mg). The resulting brown suspension was stirred at 120° C. for 21 h. After cooling to RT, the reaction mixture was diluted with water, and extracted with DCM (3×), and the filtrate evaporated to dryness. The resulting crude material was purified by CC (Biotage, SNAP 10 g, solvent A: EA; solvent B: Hept; gradient in % B: 0 over 3 CV, 0 to 15 over 3 CV, 15 to 30 over 3 CV, 30 over 3 CV) to afford 57 mg of the title compound as orange resin. LC-MS (A): $t_R$=1.22 min; $[M+H]^+$: 282.16.

F3.3.2. 3-(2-Methyl-thiazol-5-yl)-4-nitro-butyric acid octyl ester

The title compound (27 mg, orange resin) was synthesized starting from Example F3.3.1, and following the procedure described in Example F3.2 step 2, however running the reaction under higher dilution (1.5 mL nitromethane). LC-MS (A): $t_R$=1.12 min; $[M+H]^+$: 343.05.

F3.3.3. 4-(2-Methyl-thiazol-5-yl)-pyrrolidin-2-one

The title compound (6 mg, beige solid) was synthesized starting from Example F3.3.2, and following the procedure described in Example F3.2 step 3. Further addition of 3 eq ammonium formate and 0.03 eq Pd/C were required to advance the reaction conversion. LC-MS (A): $t_R$=0.4 min; $[M+H]^+$: 183.14.

Example F3.4 to Example F3.10 were synthesized starting from the appropriate heteroaryl bromide derivative, following the three-step procedure described in Example F3.3, omitting the addition of ammonium formate and Pd/C in step 3. If the cyclization was sluggish, 10 eq of TEA was added. The purification (CC, Biotage, (solumn size) SNAP solvent A: DCM, solvent B: DCM/MeOH 8/2), gradients in % B and the LC-MS (A) data can be found in the table below.

| Example N° | Name | $t_R$ | $[M + H]^+$ | Purification |
|---|---|---|---|---|
| F3.4 | 4-(6-Methyl-pyridin-3-yl)-pyrrolidin-2-one | 0.24 | 177.24 | (25 g) 0 for 3CV, 0 to 15 over 5CV, 15 for 5CV, 15 to 30 over 5CV |
| F3.5 | 4-(6-Isopropyl-pyridin-2-yl)-pyrrolidin-2-one | 0.37 | 205.18 | (25 g) 25 for 3CV, 25 to 50 over 3CV, 50 for 1CV |
| F3.6 | 4-(6-Trifluoromethyl-pyridin-3-yl)-pyrrolidin-2-one | 0.6 | 231.05 | (25 g) 25 for 6CV |
| F3.7 | 4-(1-Methyl-1H-pyrazol-4-yl)-pyrrolidin-2-one | 0.43 | 166.05 | (10 g) 0 for 3CV, 0 to 15 over 5CV, 15 for 5CV, 100 for 5CV |
| F3.8 | 4-(1,3-Dimethyl-1H-pyrazol-4-yl)-pyrrolidin-2-one | 0.43 | 180.25 | (10 g) 15 for 3CV, 15 to 30 in 5CV, 30 for 5CV |
| F3.9 | 4-(1-Difluoromethyl-1H-pyrazol-4-yl)-pyrrolidin-2-one | 0.48 | 202.13 | (10 g) 0 to 15 over 3CV, 15 for 5CV, 15 to 30 over 5CV |
| F3.10 | 4-(2-Methyl-2H-[1,2,3]triazol-4-yl)-pyrrolidin-2-one | 0.41 | 167.06 | — |

Example F4.1: 5-Benzyl-oxazolidin-2-one

1-Amino-3-phenylpropan-2-ol (150 mg) and CDI (268 mg) were dissolved in THF (30 mL). The resulting mixture was stirred for 16 h30 at RT and evaporated to dryness. The resulting crude material was purified by CC (Biotage, SNAP 10 g, solvent A: Hep; solvent B: EA; gradient in % B: 50 over 4 CV, 50 to 100 over 5 CV, 100 over 1 CV) to afford 57 mg of the title compound as yellow solid. LC-MS (A): $t_R$=0.65 min; $[M+H]^+$: 178.40.

Example F4.2: 5-Isopropyl-oxazolidin-2-one

To a solution of 1-amino-3-methyl-2-butanol hydrochloride (150 mg) and DIPEA (69.9 μL) in THF (3 mL) cooled at 0° C. was added a solution of bis(trichloromethyl)carbonate (101 mg) in THF (2 mL) and the resulting suspension was stirred for 40 min at 0° C. The reaction mixture was diluted with EA, washed with aq. sat. $NaHCO_3$ solution, water and brine. The org. layers were dried ($MgSO_4$), filtrated off and evaporate to dryness. The resulting crude material was purified by CC (Biotage, SNAP 10 g, solvent A: Hep; solvent B: EA; gradient in % B: 0 over 2 CV, 0 to 100 over 10 CV, 100 over 2 CV) to afford 16 mg of the title compound as yellow solid. LC-MS (A): $t_R$=0.49 min; $[M+H]^+$: 130.30.

Example F4.3 to Example F4.5 were synthesized starting from the appropriate amine and carbonate reagents, following the procedure described in Example F4.2 and using solvents and bases listed in the table below. Prep LC-MS conditions and LC-MS data of Example F4.3 to Example F4.5 are listed in the table below. The LC-MS conditions used were LC-MS (A).

| Example N° | Name | $t_R$ | $[M + H]^+$ | Solvent Base |
|---|---|---|---|---|
| F4.3 | 4-Oxa-6-aza-spiro[2.4]heptan-5-one | 0.36 | 114.15 | THF DIPEA |
| F4.4 | 5-(Tetrahydro-pyran-4-yl)-oxazolidin-2-one | 0.42 | 172.14 | DCM TEA |
| F4.5 | 5-tert-Butyl-oxazolidin-2-one | 0.58 | 144.28 | THF DIPEA |

Example F4.6: 8,8-Difluoro-1-oxa-3-aza-spiro[4.5]decan-2-one

F4.6.1. 4,4-Difluoro-1-trimethylsilanyloxy-cyclohexanecarbonitrile

To an ice-cold solution of 4,4-difluorocyclohexanone (5 g) in DCM (100 mL) were added TMSCN (5.71 mL) followed by ZnI (119 mg). The reaction mixture was stirred for 2 h30 at 0° C., was quenched with $Na_2CO_3$ solution (10%) and extracted with DCM. The org. layers were dried ($MgSO_4$), filtrated off and evaporated to dryness to give 8.26 g of yellow oil.

F4.6.2. 1-Aminomethyl-4,4-difluoro-cyclohexanol, hydrochloride salt

To an ice-cold solution of $LiAlH_4$ in THF (1M, 53.1 mL) in $Et_2O$ (28 mL) was added dropwise a solution of Example F4.6.1 (8.26 g) in $Et_2O$ (14 mL). The reaction mixture was stirred for 45 min at RT, cooled down to 0° C. and ice-cold water (4.25 mL) followed by NaOH (1M, 4.25 mL) were added. The resulting mixture was stirred for 30 min, diluted with $Et_2O$, filtered off and evaporated to dryness. The residue was dissolved in $Et_2O$ (67 mL) and HCl in dioxane (4M, 34 mL) was added dropwise at 0° C. The mixture was stirred for 1 h at 0° C. and filtered off. The resulting precipitate was dried under HV to give 5.5 g of the title compound as white solid. LC-MS (A): $t_R$=0.27 min; $[M+H]^+$:207.27.

F4.6.3. 8,8-Difluoro-1-oxa-3-aza-spiro[4.5]decan-2-one

A solution of Example F4.6.2 (250 mg) and TEA (174 μL) in DCM (7 mL) was stirred for 15 min at RT. Carbonic acid di-2-pyridyl ester (274 mg) was added and the mixture was stirred overnight at RT, diluted with water and extracted with DCM. The org. layers were dried ($MgSO_4$), filtrated off, and evaporated to dryness. The resulting crude material was purified by CC (Biotage, SNAP 10 g, solvent A: DCM; solvent B: MeOH; gradient in % B: 3 over 5 CV, 3 to 5 over 2 CV, 5 over 2 CV) to afford 208 mg of the title compound as white solid. LC-MS (A): $t_R$=0.57 min; $[M+H]^+$: 192.36.

Example F4.7 to Example F4.9 were synthesized starting from the appropriate ketone derivative, and following the three-step procedure described in Example F4.6. LC-MS data of Example F4.7 to Example F4.9 are listed in the table below. The LC-MS conditions used were LC-MS (A).

| Example N° | Name | $t_R$ | $[M + H]^+$ |
|---|---|---|---|
| F4.7 | 7-Oxa-9-aza-dispiro[3.1.4.1 ]undecan-8-one | 0.71 | 168.17 |
| F4.8 | 2-Cyclopropyl-5-oxa-7-aza-spiro[3.4]octan-6-one | 0.69 | 168.21 |
| F4.9 | 2,2-Dimethyl-5-oxa-7-aza-spiro[3.4]octan-6-one | 0.65 | 156.25 |

Example F4.10: 4-(2-Methoxy-ethyl)-pyrrolidin-2-one

F4.10.1. (E)-5-Methoxy-pent-2-enoic acid ethyl ester

To an ice-cold suspension of NaH (60% in mineral oil, 440 mg) in THF (24 mL) was added triethyl phosphonoacetate (2.26 mL) and the resulting mixture was stirred for 20 min at 0° C. A solution of 3-methoxy-propionaldehyde (1 g) in THF (14 mL) was added dropwise over 15 min and the resulting solution was stirred for 1 h15 at 0° C. The reaction mixture was diluted with $Et_2O$ and water and extracted with $Et_2O$. The org. phases were washed with brine, dried ($MgSO_4$), filtered off and evaporated to dryness. The resulting crude material was purified by CC (Biotage, SNAP 50 g, solvent A: Hep; solvent B: EA; gradient in % B: 0 over 1 CV, 0 to 10 over 2 CV, 10 over 2 CV, 10 to 30 over 2 CV, 30 over 1 CV, 30 to 50 over 1 CV, 50 to 70 over 1 CV) to afford 1.02 g of the title compound as colourless oil. LC-MS (A): $t_R$=0.72 min; $[M+H]^+$: 159.18.

F4.10.2. 5-Methoxy-3-nitromethyl-pentanoic acid ethyl ester

To an ice-cold solution of Example F4.10.1 (564 mg) and nitromethane (274 μL) was added DBU (426 μL). The reaction mixture was stirred for 17 h at RT, cooled down to 0° C., quenched with water and extracted with DCM. The org. layers were washed with aq. HCl solution (1M) and brine, dried ($MgSO_4$), filtrated off and evaporated to dryness to give 377 mg of the title compound as yellow oil. LC-MS (A): $t_R$=0.79 min; $[M+H]^+$: 220.22.

F4.10.3. 4-(2-Methoxy-ethyl)-pyrrolidin-2-one

To a solution of Example F4.10.2 (50 mg) and TEA (31.7 μL) in EtOH (0.5 mL) was added $Pd(OH)_2/C$ (20%, 8.01 mg) and the resulting mixture was stirred for 23 h at RT under hydrogen atmosphere. The reaction mixture was filtered off and evaporated to dryness. The resulting crude material was dissolved in EtOH (1 mL) and stirred for 22 h at 40° C. then for 7 days at RT. The reaction mixture was evaporated to dryness to give 24 mg of the title compound as yellow oil. LC-MS (A): $t_R$=0.41 min; $[M+H]^+$: 144.21.

Example F5.1: 1-(Tetrahydro-pyran-4-yl)-prop-2-yn-1-ol

F5.1.1. 1-(Tetrahydro-pyran-4-yl)-3-trimethylsilanyl-prop-2-yn-1-ol

To an ice-cold solution of trimethylsilylacetylene (637 μL) in THF (10 mL) was added dropwise n-BuLi in hexane (2.5M, 2 mL). The resulting mixture was stirred for 1 h at 0° C. and a solution of 4-formyltetrahydropyran (500 mg) in THF (2 mL) was added. The reaction mixture was stirred for 30 min at 0° C. and for 1 h at RT. Water was added and the mixture was extracted with $Et_2O$. The org. layer was evaporated to dryness to give 875 mg of the title compound as white solid. LC-MS (A): $t_R$=0.83 min; $[M+H]^+$: 213.33.

F5.1.2. 1-(Tetrahydro-pyran-4-yl)-prop-2-yn-1-ol

To a solution of Example F5.1.1 (875 mg) in MeOH (30 mL) was added $K_2CO_3$ (1.14 g). The resulting mixture was stirred overnight at RT, concentrated, diluted with $Et_2O$, and washed successively with 1M HCl solution, 1M $NaHCO_3$ solution and brine. The org. phases were dried ($MgSO_4$), filtrated off and evaporated to dryness to afford 384 mg of the title compound as white solid. $^1$H-NMR (DMSO): 5.36 (d, 1H); 4.00 (m, 1H); 3.86 (m, 2H); 3.28 (d, 1H); 3.25 (m, 2H); 1.63 (m, 3H); 1.29 (m, 2H).

Example F5.2 to Example F5.17

Example F5.2 to Example F5.17 were synthesized starting from the appropriate ketone or aldehyde, and following the procedure described in Example F5.1. Prep LC-MS conditions and LC-MS data of Example F5.2 to Example F5.17 are listed in the tables below. The LC-MS conditions used were LC-MS (A).

| Example N° | Name | $t_R$ | $[M + H]^+$ | Prep LC-MS |
|---|---|---|---|---|
| F5.2 | 1-(1,3-Dimethyl-1H-pyrazol-4-yl)-prop-2-yn-1-ol | 0.44 | 151.18 | none |
| F5.3 | 1-(2-Methyl-thiazol-4-yl)-prop-2-yn-1-ol | 0.45 | 154.11 | (IX) |
| F5.4 | 2-(3-Fluoro-phenyl)-but-3-yn-2-ol | 0.75 | $[M + MeCN + H]^+$ = 206.08 | none |
| F5.7 | 2-(1-Methyl-1H-pyrazol-3-yl)-but-3-yn-2-ol | 0.43 | 151.18 | none |
| F5.8 | 2-(2-Methyl-thiazol-4-yl)-but-3-yn-2-ol | 0.5 | 168.08 | none |
| F5.9 | 2-(6-Methoxy-pyridin-2-yl)-but-3-yn-2-ol | 0.69 | 178.25 | none |
| F5.10 | 2-Pyrimidin-2-yl-but-3-yn-2-ol | 0.39 | 149.18 | none |
| F5.11 | 2-(1,5-Dimethyl-1H-pyrazol-3-yl)-but-3-y n-2-ol | 0.5 | 165.1 | none |
| F5.12 | 2-(6-Methyl-pyrimidin-4-yl)-but-3-yn-2-ol | 0.49 | 163.1 | none |
| F5.13 | 1-(1,5-Dimethyl-1H-pyrazol-3-yl)-prop-2-yn-1-ol | 0.45 | 151.18 | (IX) |
| F5.14 | 8-Ethynyl-5,6,7,8-tetrahydro-quinolin-8-ol | 0.41 | 174.13 | (XV) |
| F5.15 | 7-Ethynyl-6,7-dihydro-5H-[1]pyrindin-7-ol | 0.42 | 160.08 | (XV) |
| F5.16 | 3-Pyridin-2-yl-pent-1-yn-3-ol | 0.4 | 162.1 | (XV) |
| F5.17 | 3-(6-Methoxy-pyridin-2-yl)-pent-1-yn-3-ol | 0.79 | 192.21 | (XV) |

| Example N° | Name | $t_R$ | H-NMR ($CDCl_3$) | Prep LC-MS |
|---|---|---|---|---|
| F5.5 | 2-(4-Methoxy-phenyl)-but-3-yn-2-ol | 0.73 | 7.61 (d, 2H); 6.91 (d, 2H); 3.84 (s, 3H); 2.69 (s, 1H); 2.34 (s, 1H); 1.80 (s, 3H) | none |
| F5.6 | 2-(2-Methoxy-phenyl)-but-3-yn-2-ol | 0.76 | 7.57 (d, 1H); 7.32 (t, 1H); 7.00 (m, 2H); 4.58 (s, 1H); 3.97 (s, 1H); 2.59 (s, 1H); 1.92 (s, 3H) | none |

Example F5.18: 1-(3-Ethynyl-3-hydroxy-azetidin-1-yl)-2-methyl-propan-1-one

To a solution of 3-ethynyl-3-hydroxyazetidine trifluoroacetate (100 mg) and TEA (132 μL) in DCM (2 mL) was added dropwise isobutyryl chloride (48.1 μL) at RT. The resulting mixture was stirred for 25 min at RT, diluted with water and basified with aq. sat. $NaHCO_3$ solution. The org. layers were dried ($MgSO_4$), filtrated off and evaporated to dryness.

The residue was purified by CC (Biotage SNAP 10 g, solvent A: DCM; solvent B: MeOH; gradient in % B: 3 over 2 CV, 3 to 5 over 2 CV, 5 over 3 CV) to afford 37 mg of the title compound as yellow oil. LC-MS (A): $t_R$=0.48 min; $[M+H]^+$: 168.05.

Example F5.19: 3-(6-Methyl-pyrimidin-4-yl)-pent-1-yn-3-ol

F5.19.1 6-Methyl-pyrimidine-4-carboxylic acid methoxy-methyl-amide

To a solution of 6-methylpyrimidine-4-carboxylic acid (500 mg) in DCM (50 mL) were added N,O-dimethylhydroxylamine hydrochloride (342 mg), DIPEA (2.06 mL) and propylphosphonic anhydride solution in DCM (50% w/w, 2.54 mL). The resulting mixture was stirred 2 h at RT and quenched with aq. sat. $NaHCO_3$ solution. The org. layer was washed with citric acid (10%) and water. The combined org. layers were dried ($MgSO_4$), filtered off and evaporated to dryness to afford 453 mg of the title compound as brown oil which was used without further purification. LC-MS (A): $t_R$=0.48 min; $[M+H]^+$: 182.22.

F5.19.2 1-(6-Methyl-pyrimidin-4-yl)-propan-1-one

To a yellow solution of Example F5.19.1 (445 mg) cooled at −78° C. under argon was added ethylmagnesium bromide in THF (1M, 4.91 mL) and the resulting suspension was stirred 1 h. The resulting crude was quenched with aq. sat. $NH_4Cl$ solution, diluted with water and extracted with DCM. The combined org. layers were dried ($MgSO_4$), filtrated off and evaporated to dryness. The residue was purified by CC (Biotage, snap10 g, solvent A: Hep; solvent B: EA; gradient in % B: 30 over 3 CV, 30 to 70 over 6 CV, 70 over 2 CV to afford 77 mg of the title compound as yellow solid. LC-MS (A): $t_R$=0.63 min; $[M+H]^+$: 151.16.

F5.19.3 3-(6-Methyl-pyrimidin-4-yl)-pent-1-yn-3-ol

The title compound (45 mg, yellow oil) was synthesized from Example F5.19.2 (73 mg) and trimethylsilylacetylene (74.4 μL) and following the two-step procedure described in Example F5.1. LC-MS (A): $t_R$=0.56 min; $[M+H]^+$: 177.27.

Example F5.20 to Example F5.30 were synthesized starting from the appropriate commercially available ketone or aldehyde reagent, and following the two-step procedure described in Example F5.1. Prep LC-MS and Chiral Prep (SFC & HPLC) conditions, Chiral HPLC & SFC and LC-MS data are listed in the table below. The LC-MS conditions used were LC-MS (A).

| Example N° | Name | LC-MS $t_R$ | $[M + H]^+$ | Prep LC-MS | Chiral Prep | Chiral HPLC// SFC $t_R$ (method) |
|---|---|---|---|---|---|---|
| F5.20 | (S)-2-(6-Methyl-pyrimidin-4-yl)-but-3-yn-2-ol | 0.49 | 163.08 | — | XXI | 7.0 (S) |
| F5.21 | (R)-2-(6-Methyl-pyrimidin-4-yl)-but-3-yn-2-ol | 0.49 | 163.08 | — | XXI | 8.7 (S) |
| F5.22 | (S)- or (R)-2-(1,5-Dimethyl-1H-pyrazol-3-yl)-but-3-yn-2-ol | 0.5 | 165.12 | — | XXII | 1.56 (T) |
| F5.23 | (R)- or (S)-2-(1,5-Dimethyl-1H-pyrazol-3-yl)-but-3-yn-2-ol | 0.5 | 165.11 | — | XXII | 1.94 (T) |
| F5.24 | (S)- or (R)-2-(1-Methyl-1H-pyrazol-3-yl)-but-3-yn-2-ol | 0.43 | 151.2 | (IX) | XXIII | 1.17 (U) |
| F5.25 | (R)- or (S)-2-(1-Methyl-1H-pyrazol-3-yl)-but-3-yn-2-ol | 0.43 | 151.13 | (IX) | XXIII | 1.67 (U) |
| F5.26 | 2-(6-Methoxy-pyrimidin-4-yl)-but-3-yn-2-ol | 0.53 | 179.26 | — | — | — |
| F5.27 | 2-(6-Methyl-pyridin-2-yl)-but-3-yn-2-ol | 0.36 | 162.09 | | — | — |
| F5.28 | 2-Pyridin-2-yl-but-3-yn-2-ol | 0.33 | 148.17 | — | — | — |
| F5.29 | 1-Cyclopropyl-1-pyridin-2-yl-prop-2-yn-1-ol | 0.42 | 174.13 | (XV) | — | — |
| F5.30 | 2-(5-Methyl-pyridin-3-yl)-but-3-yn-2-ol | 0.36 | 162.08 | — | — | — |

The absolute configuration for the Example F5.20 was assessed by single crystal X-ray diffraction (suitable crystal obtained through diffusion of heptane into a solution of the compound in EA) and proved to be in absolute (S)-configuration. Consequently, the absolute configuration for the Example F5.21 was assigned (R).

Example F5.31 to Example F5.42 were synthesized using the commercially available ketone following the procedure described in Example F5.1. CC (Biotage) gradients and column size, if CC was made, and LC-MS data are listed in the table below. The LC-MS conditions used were LC-MS (A).

| Example N° | Name | $t_R$ | [M + H]$^+$ | solvents (column size, SNAP) CC gradient (in % B) |
|---|---|---|---|---|
| F5.31 | 1-(4-Ethynyl-4-hydroxy-piperidin-1-yl)-ethanone | 0.42 | 168.09 | A: DCM B: DCM/MeOH 8/2 (10 g) 15 for 3CV, 15 to 50 over 5CV, 50 for 2CV |
| F5.32 | rac-1-[4-(1-Hydroxy-1-methyl-prop-2-ynyl)-piperidin-1-yl]-ethanone | 0.52 | 196.23 | A: DCM B: DCM/MeOH (10 g) 15 for 2CV, 15 to 25 over 2CV, 25 for 2CV, 25 to 50 over 2CV, 50 for 2CV |
| F5.33 | rac-1-[4-(1-Hydroxy-prop-2-ynyl)-piperidin-1-yl]-ethanone | 0.49 | 182.21 | A: DCM B: DCM/MeOH (10 g) 15 for 3CV, 15 to 25 over 3CV, 25 for 2CV |
| F5.34 | rac-4-(1-Hydroxy-prop-2-ynyl)-4-methyl-piperidine-1-carboxylic acid tert-butyl ester | 0.86 | 254.15 | A: DCM B: DCM/MeOH (10 g) 30 for 2CV, 30 to 50 over 2CV, 50 for 30V |
| F5.35 | rac-4-Ethynyl-3,4-dihydro-2H-pyrano[3,2-b]pyridin-4-ol | 0.43 | 176.24 | — |
| F5.36 | rac-3-Ethynyl-3-hydroxy-1-methyl-1,3-dihydro-indol-2-one | 0.63 | 188.17 | A: DCM B: DCM/MeOH (10 g) 0 for 3CV, 0 to 15 over 5CV, 15 for 5CV, 15 to 30 over 5CV, 30 for 5CV |
| F5.37 | rac-2-(1H-lndazol-3-yl)-but-3-yn-2-ol | 0.62 | 187.26 | A: DCM B: DCM/MeOH (10 g) 30 for 2CV, 30 to 50 over 2CV, 50 for 3CV, 50 to 100 over 3CV, 100 for 5CV |
| F5.38 | rac-2-(1-Methyl-1H-indazol-3-yl)-but-3-yn-2-ol | 0.70 | 201.18 | A: DCM B: DCM/MeOH (10 g) 30 for 2CV, 30 to 50 over 2CV, 50 for 3CV, 50 to 100 over 3CV, 100 for 5CV |
| F5.39 | rac-2-(2-Methyl-pyrimidin-4-yl)-but-3-yn-2-ol | 0.48 | 163.06 | A: DCM B: DCM/MeOH (10 g) 15 for 4CV, 15 to 25 over 2CV, 25 for 2CV |
| F5.40 | rac-2-(5-Methyl-pyrazin-2-yl)-but-3-yn-2-ol | 0.49 | 163.11 | A: DCM B: DCM/MeOH (10 g) 15 for 3CV, 15 to 25 over 4CV, 25 for 2CV |
| F5.41 | rac-2-(2-Methyl-thiazol-5-yl)-but-3-yn-2-ol | 0.53 | 168.04 | A: DCM B: DCM/MeOH (10 g) 15 for 4CV, 15 to 50 over 60V, 50 for 2CV |

Example F5.42 rac-2-(6-Cyclopropyl-pyrimidin-4-yl)-but-3-yn-2-ol

F5.42.1 1-(6-Cyclopropyl-pyrimidin-4-yl)-ethanone

A vial was charged with Bis(triphenylphosphine)palladium(II) dichloride (34.2 mg), 4-bromo-6-cyclopropylpyrimidine (100 mg), toluene (200 μmL) and tributyl(1-ethoxyvinyl)tin (216 μL) at RT, sealed and shaken at 95° C. overnight. After evaporation to dryness the residue was taken up in dioxane (900 μL) and HCl 2N (169 μL) to be stirred for 6 h at RT. The reaction mixture was diluted with EA and washed 2× with water and 1× with brine. Afterwards the aq. layers were re-extracted with 2× EA. The combined org. layers were dried over $MgSO_4$, filtrated off, evaporated and purified by CC (Biotage, 10 g snap, solvent A: heptane, solvent B: EA, gradient (in % B): 10 for 3 CV, 10 to 100 over 10 CV, 100 for 2 CV) to give 82 mg light yellow oil. LC-MS (A) $t_R$=0.69 min; [M-FH]' 163.10.

F5.42.2 rac-2-(6-Cyclopropyl-pyrimidin-4-yl)-but-3-yn-2-ol

The title compound was synthesized starting from Example F5.42.1 following the two-step procedure described in Example F5.1, EA was used instead of $Et_2O$ for extraction. Furthermore, instead of quenching in step 2 the work-up was skipped and the mixture was filtered and evaporated to dryness and the crude purified by CC (Biotage, 10 g, gradients: A:DCM B: DCM/MeOH 0 for 2 CV, 0 to 25 for 6 CV, 25 for 2 CV, 25 to 50 over 3 CV, 50 for 2 CV. LC-MS (A) $t_R$=0.59 min; $[M+H]^+$ 189.20.

Example F5.43 to Example F5.53 were synthesized using the appropriate ketone following the procedure described in Example F5.1. CC (Biotage) gradients and column size, if CC was made, and LC-MS data are listed in the table below. The LC-MS conditions used were LC-MS (A). For chiral separated compounds the prep LC-MS and chiral separation method is listed in the table below. The ketones are listed in the table below unless commercially available.

| Example N° | Name | $t_R$ | $[M + H]^+$ | solvents (column size, SNAP) CC gradient (in % B) | Prep LC-MS | Chiral Separation | Chiral $t_R$ (analytic Method) | Ketone |
|---|---|---|---|---|---|---|---|---|
| F5.43 | (R)- or (S)-2-(6-Methoxy-pyrimidin-4-yl)-but-3-yn-2-ol | 0.53 | 179.20 | A: DCM B: DCM/MeOH (10 g) 30 for 2CV, 30 to 50 over 2CV, 50 for 3CV | (V) | (XXV) | 2.50 (AJ) | F5.K1 |
| F5.44 | (S)- or (R)-2-(6-Methoxy-pyrimidin-4-yl)-but-3-yn-2-ol | 0.53 | 179.21 | A: DCM B: DCM/MeOH (10 g) 30 for 2CV, 30 to 50 over 2CV, 50 for 3CV | (V) | (XXV) | 3.17 (AJ) | F5.K1 |
| F5.45 | (R)- or (S)-2-(2-Methoxy-pyrimidin-4-yl)-but-3-yn-2-ol | 0.55 | 179.21 | A: DCM B: DCM/MeOH (10 g) 0 to 30 over 3CV, 30 for 5CV, 30 to 5 over 4CV | (V) | (XXXVII) | 1.38 (AH) | F5.K2 |
| F5.46 | (S)- or (R)-2-(2-Methoxy-pyrimidin-4-yl)-but-3-yn-2-ol | 0.55 | 179.21 | A: DCM B: DCM/MeOH (10 g) 0 to 30 over 3CV, 30 for 5CV, 30 to 5 over 4CV | (V) | (XXXVII) | 1.66 (AH) | F5.K2 |
| F5.47 | (R)- or (S)-2-(2,6-Dimethyl-pyrimidin-4-yl)-but-3-yn-2-ol | 0.46 | 177.26 | A: DCM B: DCM/MeOH (25 g) 0 to 30 over 3CV, 30 for 5CV, 30 to 50 in 5CV | (V) | (XXIX) | 1.39 (AI) | F5.K3 |
| F5.48 | (S)- or (R)-2-(2,6-Dimethyl-pyrimidin-4-yl)-but-3-yn-2-ol | 0.46 | 177.25 | A: DCM B: DCM/MeOH (25 g) 0 to 30 over 3CV, 30 for 5CV, 30 to 50 in 5CV | (V) | (XXIX) | 1.72 (AI) | F5.K3 |
| F5.49 | (R)- or (S)-2-(2,6-Dimethoxy-pyrimidin-4-yl)-but-3-yn-2-ol | 0.68 | 209.13 | A: Hp B:EA (10 g) 10 for 3CV, 10 to 30 over 2CV, 30 for 3CV Then 10 for 3CV, 10 to 30 over 6CV, 30 for 2CV | (XVI) | (XXXIX) | 1.60 (AG) | F5.K4 |
| F5.50 | (S)- or (R)-2-(2,6-Dimethoxy-pyrimidin-4-yl)-but-3-yn-2-ol | 0.68 | 209.12 | A: Hp B:EA (10 g) 10 for 3CV, 10 to 30 over 2CV, 30 for 3CV Then 10 for 3CV, 10 to 30 over 6CV, 30 for 2CV | (XVI) | (XXXIX) | 2.38 (AG) | F5.K4 |
| F5.51 | (S)- or (R)-2-(2-Methoxy-6-methyl-pyrimidin-4-yl)-but-3-yn-2-ol | 0.62 | 193.19 | — | (XVI) | ( )) | 7.36 (AK) | F5.K5 |
| F5.52 | (R)- or (S)-2-(6-Methoxy-2-methyl-pyrimidin-4-yl)-but-3-yn-2-ol | 0.52 | 193.20 | — | (XVI) | (XLI) | 8.4 (AL) | F5.K6 |
| F5.53 | (S)- or (R)-2-(6-Methoxy-2-methyl-pyrimidin-4-yl)-but-3-yn-2-ol | 0.52 | 193.19 | — | (XVI) | (XLI) | 9.93 (AL) | F5.K6 |

Precursors Ketones for Alkynes Examples F5.43 to F5.53

Example F5.K1
1-(6-Methoxy-pyrimidin-4-yl)-ethanone

F5.K1.1 6-Methoxy-pyrimidine-4-carboxylic acid methoxy-methyl-amide

The title compound was synthesized following the procedure described in Example F5.19.1, except the washing with citric acid (10%), which was left out, starting from 6-methoxypyrimidine-4-carboxylic acid. LC-MS (A) $t_R$=0.53 min, $[M+H]^+$: 198.16

F5.K1.2 1-(6-Methoxy-pyrimidin-4-yl)-ethanone

A solution of F5.K1.1 (600 mg) in THF abs. (10 mL) was 3× evacuated and backfilled with argon, then cooled to −78° C. Then a methylmagnesium bromide solution (230 μL, 3.0M in diethyl ether) was added dropwise under argon at −78° C. After stirring for 15 min at RT, the mixture was quenched with aq. sat. $NH_4Cl$, diluted with water and extracted with 3× DCM (phase separator). The combined org. layers were evaporated to dryness and purified by CC (Biotage, SNAP 25 g, solvent A: heptane, solvent B: EA 0 to 15 over 2 CV, 15 for 2 CV, 15 to 30 over 2 CV, 30 for 2 CV, 30 to 70 over 3 CV, 70 for 3 CV) to give 290 mg yellowish solid. LC-MS (A) $t_R$=0.62 min; $[M+H]^+$: 153.10.

Example F5.K2
1-(2-Methoxy-pyrimidin-4-yl)-ethanone

F5.K2.1 2-Methoxy-pyrimidine-4-carboxylic acid methoxy-methyl-amide

The title compound was synthesized following the procedure described in Example F5.K1, step F5.K1.1, using 2-methoxypyrimidine-4-carboxylic acid. LC-MS (A) $t_R$=0.53 min, $[M+H]^+$: 198.16

F5. K2.2 1-(2-Methoxy-pyrimidin-4-yl)-ethanone

The title compound was synthesized following the procedure described in Example F5.K1, step F5.K1.2, using F5.K2.1, purified by CC (Biotage, 25 g SNAP, solvent A: Hept, solvent B: EA, gradient (in % B): 0 to 15 over 2 CV, 15 for 2 CV, 15 to 30 over 2 CV, 30 for 2 CV, 30 to 70 over 3 CV, 70 for 3 CV). LC-MS (A) $t_R$=0.61 min, $[M+H]^+$: 153.12

Example F5.K3
1-(2,6-Dimethyl-pyrimidin-4-yl)-ethanone

F5. K3.1 2,6-Dimethyl-pyrimidine-4-carboxylic acid methoxy-methyl-amide

The title compound was synthesized following the procedure described in Example F5.K1, step F5.K1.1, starting from 2,6-dimethylpyrimidine-4-carboxylic acid. LC-MS (A) $t_R$=0.49 min, $[M+H]^+$: 196.19

F5. K3.2 1-(2,6-Dimethyl-pyrimidin-4-yl)-ethanone

The title compound was synthesized following the procedure described in Example F5.K1, step F5.K1.2, using F5.K3.1, purified by CC (Biotage, 10 g SNAP, solvent A. Hept, solvent B: EA, gradient (in % B): 15 for 3 CV, 15 to 30 over 5 CV, 30 for 5 CV. LC-MS (A) $t_R$=0.58 min, $[M+H]^+$: 151.15

Example F5.K4
1-(2-Chloro-6-methoxy-pyrimidin-4-yl)-ethanone

F5.K4.1
2-Chloro-6-methoxy-pyrimidine-4-carboxylic acid methyl ester

To a suspension of methyl 2,4-dichloropyrimidine-6-carboxylate (1000 mg) in MeOH abs. (20 ml) was added sodium methoxide solution 0.5M in MeOH (9.46 mL) slowly at 0° C. under argon. The resulting suspension was stirred at 0° C. under argon overnight, allowed to reach RT. AcOH was added to the reaction mixture and stirred for 10 min, then the mixture was evaporated to dryness. The residue was taken up in EA and washed with 1×aq. sat. $NaHCO_3$ and 1× brine. Afterwards the aq. layers were 2× re-extracted with EA. The combined org. layers were dried over $MgSO_4$, filtrated off, evaporated and dried at HV to 826 mg off-white solid. LC-MS (A) $t_R$=0.72; $[M+H]^+$: 203.09

F5.K4.2
2-chloro-6-methoxy-pyrimidine-4-carboxylic acid, as sodium salt

To solution of Example F5.K4.1 (803 mg) in MeOH (4 mL), THF (2 mL) and DCM (500 μL) was added NaOH 1N (3.96 mL) at RT and the solution was stirred for 3 h at RT. The reaction mixture was evaporated and dried at HV to give 865 mg beige solid. LC-MS (A) $t_R$=0.54 min, $[M+H]^+$: 189.09.

F5.K4.3
2-Chloro-6-methoxy-pyrimidine-4-carboxylic acid methoxy-methyl-amide

The title compound was synthesized following the procedure described in Example F5.K1, step F5.K1.1 using Example F5.K4.2. LC-MS (A) $t_R$=0.49 min, $[M+H]^+$: 196.19

F5. K4.4
1-(2-Chloro-6-methoxy-pyrimidin-4-yl)-ethanone

The title compound was synthesized following the procedure described in Example F5.K1, step F5.K1.2, using F5.K4.3. LC-MS (A) $t_R$=0.79 min, $[M+H]^+$: 187.13

Example F5.K5
1-(2-Methoxy-6-methyl-pyrimidin-4-yl)-ethanone

F5.K5.1
2-Methoxy-6-methyl-pyrimidine-4-carboxylic acid

Methyl 2-chloro-methylpyrimidine-4-carboxylate (5.0 g) was suspended in MeOH (67 mL) and NaOH 1N (67 mL) was added. The mixture was stirred for 1 h at RT, then MeOH was evaporated off. At 0° C. the mixture was acidified to pH=2 with HCl (25%). The crystals were filtrated, washed with water and heptane and dried at HV at 35° C. overnight to give 3.0 g beige crystals 1H NMR (400 MHz, DMSO) δ: 13.67-13.76 (m, 1H), 7.52 (s, 1H), 3.94 (s, 3H), 2.50 (s, 3H)

F5.K5.2

2-Methoxy-6-methyl-pyrimidine-4-carboxylic acid methoxy-methyl-amide

The title compound was synthesized following the procedure described in Example F5.K1, step F5.K1.1 using Example F5.K5.1. LC-MS (A) $t_R$=0.57 min, $[M+H]^+$: 212.13

F5.K5.3

1-(2-Methoxy-6-methyl-pyrimidin-4-yl)-ethanone

The title compound was synthesized following the procedure described in Example F5.K1, step F5.K1.2, using Example F5.K5.2. LC-MS (A) $t_R$=0.68 min, $[M+H]^+$: 167.06

Example F5.K6

1-(6-Methoxy-2-methyl-pyrimidin-4-yl)-ethanone

F5.K6.1

6-Methoxy-2-methyl-pyrimidine-4-carboxylic acid methyl ester

A flask was charged with Example F5.K4.1 (787 mg), $Pd(PPh_3)_4$ (227 mg) and THF abs. (60 mL) at RT under argon. To this solution trimethylaluminum solution 2M in toluene (3.89 mL) was added in one portion at RT. The resulting solution was stirred at 75° C. ET under argon over weekend. The mixture was poured slowly into 1M $NaH_2PO_4$ and extracted with 3×DCM. The combined org. layers were dried over $MgSO_4$, filtrated, evaporated and purified by CC (Biotage, 10 g snap, solvent A: heptane, B: EA, Gradient (in % B): 50 for 3 CV, 50 to 70 over 2 CV, 70 for 1 CV) to give 507 mg brown solid. LC-MS (A) $t_R$=0.62 min; $[M+H]^+$: 183.17

F5.K6.2

6-methoxy-2-methyl-pyrimidine-4-carboxylic acid, sodium salt

The title compound was synthesized following the procedure described in Example F5.K4, step F5.K4.2 using Example F5.K6.1. LC-MS (A) $t_R$=0.33 min, $[M+H]^+$: 169.01

F5.K6.3

6-Methoxy-2-methyl-pyrimidine-4-carboxylic acid methoxy-methyl-amide

The title compound was synthesized following the procedure described in Example F5.K1, step F5.K1.1 using Example F5.K6.2. LC-MS (A) $t_R$=0.56 min, $[M+H]^+$: 212.13

F5.K6.4

1-(6-Methoxy-2-methyl-pyrimidin-4-yl)-ethanone

The title compound was synthesized following the procedure described in Example F5.K1, step F5.K1.2, using F5.K6.3. LC-MS (A) $t_R$=0.64 min, $[M+H]^+$: 167.05

Example F5.54

1-(4-Ethynyl-piperidin-1-yl)-ethanone

To a suspension of the 4-ethynylpiperidine hydrochloride (125 mg) in EA (2.5 ml) and aq. sat. $NaHCO_3$ (2.5 ml) was added acetic anhydride (157 μL) at RT and the mixture was stirred for 1 h. Then the phases were separated. The aq. layer was extracted with 1×EA and the aq. layers were washed with 1× brine. The combined org. layers were dried over $MgSO_4$, filtrated off, evaporated and dried at HV to give 136 mg colourless oil. LC-MS (A) $t_R$=0.61 min; $[M+H]^+$: 152.16.

Example F5.55 1—((S)-2-Ethynyl-2-methyl-pyrrolidin-1-yl)-ethanone

The title compound was synthesized following the procedure described in Example F5.54 using (2S)-2-ethynyl-2-methylpyrrolidine hydrochloride as amine. LC-MS (A) $t_R$=0.59 min; $[M+H]^+$: 152.15.

Example F5.56

1-(4-Prop-2-ynyl-piperidin-1-yl)-ethanone

F5.56.1 4-Prop-2-ynyl-piperidine-1-carboxylic acid tert-butyl ester

To a suspension N-BOC-4-piperidineacetaldehyde (250 mg) in MeOH (5 mL) were added $K_2CO_3$ (456 mg) and dimethyl (diazomethyl)phosphonate (191 mg) at RT. The resulting suspension was stirred at RT under argon. After 1 h45 the mixture was diluted with DCM, filtrated over celite and evaporated to dryness. The crude was purified by CC (Biotage), 25 g SNAP, A: Hep, B: EA Gradient (% B) 0 for 3 CV, 0 to 15 over 3 CV, 15 for 3 CV, 15 to 30 over 3 CV, 30 for 3 CV to give 158 mg colorless resin. LC-MS (A) $t_R$=0.99 min; $[M+H]^+$: 224.12.

F5.56.2 4-(prop-2-yn-1-yl)piperidine, hydrochloride Salt

A colorless solution of Example F5.56.1 (155 mg) in 4M HCl in dioxane (1.5 mL) was stirred at RT for 2 h30. Then the reaction mixture was evaporated to dryness to give 130 mg off-white solid. $^1$H-NMR (400 MHz, $CDCl_3$) δ: 9.58-9.80 (m, 1H), 9.31-9.46 (m, 1H), 3.47-3.60 (m, 2H), 2.81-2.96 (m, 2H), 2.16-2.34 (m, 2H), 1.97-2.12 (m, 3H), 1.74-1.90 (m, 4H)

F5.56.3 1-(4-Prop-2-ynyl-piperidin-1-yl)-ethanone

The title compound was synthesized following the procedure described in Example F5.54 using F5.56.2 as amine. LC-MS (A) $t_R$=0.69 min; $[M+H]^+$: 166.10.

Example F5.57 rac-1-[4-(1-Hydroxy-prop-2-ynyl)-4-methyl-piperidin-1-yl]-ethanone F5.57.1 rac-1-(4-Methyl-piperidin-4-yl)-prop-2-yn-1-ol, hydrochloride salt The title compound was synthesized following the procedure described in Example F5.56, step 2 using F5.34 as Boc-protected amine. $^1$H-NMR (400 MHz, MeOD) δ: 1.16 (s, 3H), 1.64 (d, J=15.4 Hz, 1H), 1.69-1.74 (m, 1H), 1.88-1.98 (m, 2H), 2.94 (d, J=1.4 Hz, 1H), 3.11-3.19 (m, 2H), 3.30 (m, 2H), 4.14 (d, J=1.3 Hz, 1H)

F5.57.2 rac-1-[4-(1-Hydroxy-prop-2-ynyl)-4-methyl-piperidin-1-yl]-ethanone

The title compound was synthesized following the procedure described in Example F5.54 using F5.57.1 as amine. LC-MS (A) $t_R$=0.56 min; [M+H]$^+$: 196.20.

Example F5.58

1-(4-Ethynyl-4-methyl-piperidin-1-yl)-ethanone

F5.58.1 4-Ethynyl-4-methyl-piperidine, hydrochloride salt

The title compound was synthesized following the procedure described in Example F5.56, step 2 using tert-butyl 4-ethynyl-4-methylpiperdidine-1-carboxylate. LC-MS (A) $t_R$=0.39 min; [M+H]$^+$: 124.21

F5.58.2

1-(4-Ethynyl-4-methyl-piperidin-1-yl)-ethanone

The title compound was synthesized following the procedure described in Example F5.54 using F5.58.1 as amine. LC-MS (A) $t_R$=0.71 min; [M+H]$^+$: 166.11.

Example F5.59 rac-1,1,1-Trifluoro-2-methyl-but-3-yn-2-ol

To a solution of ethyl magnesium bromide solution 0.5M in THF (863 µl) at 0° C. was added 1,1,1-trifluoroacetone (399 µl). After stirring for 1 h, the mixture was quenched with HCl 1N, diluted with water and extracted with 3× diethyl ether. The combined org. layers were dried over $MgSO_4$, filtrated off and evaporated to dryness to afford 520 mg yellowish resin. 1H NMR (500 MHz, $CDCl_3$) δ: 2.63 (s, 1H), 1.67 (m, 4H).

Example F5.60 to F5.62 were synthesized following the procedure described in Example F5.18 using 2-methyl-3-butyn-2-amine and the appropriate commercially available acid chloride. The CC (Biotage, SNAP, 10 g, solvent A: heptane, solvent B: EA) gradients can be found in the table below, if a CC was necessary. The LC-MS conditions used were LC-MS (A).

| Example N° | Name | $t_R$ | [M + H]$^+$ | CC gradient (in % B) |
|---|---|---|---|---|
| F5.60 | Cyclopropanecarboxylic acid (1,1-dimethyl-prop-2-ynyl)-amide | 0.60 | 152.14 | 30 for 3CV, 30 to 50 over 3CV, 50 for 2CV |
| F5.61 | N-(1,1-Dimethyl-prop-2-ynyl)-isobutyramide | 0.62 | 154.17 | 30 for 4CV, 30 to 50 over 2CV, 50 for 2CV |
| F5.62 | N-(1,1-Dimethyl-prop-2-ynyl)-2-methoxy-acetamide | 0.54 | 156.17 | — |

Example F5.63

3-(1,1-Dimethyl-prop-2-ynyl)-oxazolidin-2-one

F5.63.1 (1,1-Dimethyl-prop-2-ynyl)-carbamic acid 2-chloro-ethyl ester $K_2CO_3$ was added to a solution 2-methyl-3-butyn-2-amine (250 mg) in MeCN (10 ml) at 0° C. Then a solution of 2-chloroethyl chloroformate (336 µL) in MeCN (5 ml) was added dropwise within 5 min at 0° C. The resulting white susp was stirred at 0° C. and allowed to warm up to RT for 2 h. The reaction mixture was evaporated and the residue was extracted with EA/water. The org. layer was washed one with brine. The aq. layers were back extracted with twice EA. The combined org. layers were dried over $MgSO_4$, filtrated off and evaporated to dryness to give 594 mg of a colorless oil.

LC-MS (A) $t_R$=0.75 min; [M+H]$^+$: 190.13

F5.63.2

3-(1,1-Dimethyl-prop-2-ynyl)-oxazolidin-2-one

To a solution of Example F5.63.1 in THF (12 ml) and treated with NaH (60% dispersion in mineral oil, 357 mg) at RT for 1 h. The reaction mixture was quenched with HCl 1N (approx. 1 ml), diluted with water and with 3× EA. The org. phases were washed with 1× brine, combined, dried over $MgSO_4$, filtrated off and evaporated to dryness. The crude was purified by CC (Biotage, 10 g snap, solvent A: Heptane, solvent B: EA, gradient in % B: 10 for 3 CV, 10 to 30 over 2 CV, 30 for 3 CV, 30 to 50 over 1 CV, 50 for 1 CV) to give 528 mg pale grey oil. LC-MS (A) $t_R$=0.58 min; [M+H]$^+$: 154.12

Example F5.64

1-(1,1-Dimethyl-prop-2-ynyl)-pyrrolidin-2-one

F5.64.1

4-Chloro-N-(1,1-dimethyl-prop-2-ynyl)-butyramide

The title compound was synthesized following the procedure described in Example F5.63.1 using 2-methyl-3-butyn-2-amine. LC-MS (A) $t_R$=0.69 min; [M+H]$^+$: 188.20.

F5.64.2

1-(1,1-Dimethyl-prop-2-ynyl)-pyrrolidin-2-one

The title compound was synthesized following the procedure described in Example F5.63.2 using the Example F5.64.1, while the purification by CC was omitted. LC-MS (A) $t_R$=0.62 min; [M+H]$^+$: 152.13

Example F5.65

1-(1,1-Dimethyl-prop-2-ynyl)-imidazolidin-2-one

Example F5.65.1 1-(2-Chloro-ethyl)-3-(1,1-dimethyl-prop-2-ynyl)-urea

The title compound was synthesized using the procedure described in F5.55.1 using 2-methyl-3-butyn-2-amine and purified by CC (Biotage, 10 g SNAP, A: DCM, B: DCM/MeOH 8/2, Gradient (in % B): 0 for 3 CV, 0 to 15 over 6 CV, 15 for 1 CV). LC-MS (A) $t_R$=0.63 min; [M+H]$^+$:189.18.

F5.65.2

1-(1,1-Dimethyl-prop-2-ynyl)-imidazolidin-2-one

The title compound was synthesized following the procedure described in Example F5.63.2 using Example F5.65.1, while the purification by CC was omitted. LC-MS (A) $t_R$=0.56 min; [M+H]$^+$: 153.13

Example F5.66 1-(1,1-Dimethyl-prop-2-ynyl)-3-methyl-imidazolidin-2-one

Example F5.65 (70 mg) was dissolved in THF abs. (1 mL) and cooled to 0° C., then NaH (60% dispersion in mineral oil, 22.1 mg) was added under argon and the susp was stirred for 5 min at 0° C. under argon, then iodomethane(28.9 μL) was added and the susp was stirred at 0° C. under argon, for 1 h30. The reaction mixture was quenched with aq. sat. $NH_4Cl$, diluted with water and extracted with 3×DCM (phase separator). The combined org. layers were evaporated and dried at HV. 75 mg yellow oil. LC-MS (A) $t_R$=0.64 min; $[M+H]^+$:167.08

Example F5.67 3-(1-Ethynyl-cyclopropyl)-oxazolidin-2-one

F5.67.1 (1-Ethynyl-cyclopropyl)-carbamic acid 2-chloro-ethyl ester

The title compound was synthesized following the procedure described in Example F5.63, step 1 using 1-ethynyl-cyclopropylamine hydrochloride as amine. LC-MS (A) $t_R$=0.68 min; $[M+H]^+$: 188.13

F5.67.2 3-(1-Ethynyl-cyclopropyl)-oxazolidin-2-one

The title compound was synthesized following the procedure described in Example F5.66, step 2 using Example F5.69.1. The used gradient (in % B) is: 0 for 3 CV, 0 to 10 over 8 CV, 10 for 3 CV, 10 to 100 over 10 CV, 100 for 2 CV LC-MS (A) $t_R$=0.53 min; $[M+H]^+$: 152.09

Example F5.68 2-(1-Ethynyl-cyclopropyl)-pyridine

F5.68.1 (1-Pyridin-2-yl-cyclopropyl)-methanol

A suspension of the 1-(pyridine-2-yl)cyclopropanecarboxylic acid (300 mg) in diethyl ether abs. (3.6 mL) was cooled to 0° C. under argon, then $LiAlH_4$ 1 M in THF (2.14 mL) was added slowly. The resulting suspension was stirred at RT under argon overnight. The reaction mixture was quenched by adding 89 μL water, 89 μL NaOH (15%) and 267 μL water. The mixture was stirred for 20 min, then filtrated off and evaporated to dryness. 218 mg yellow oil. LC-MS (A) $t_R$=0.21 min; $[M+H]^+$: 150.14

F5.68.2 1-Pyridin-2-yl-cyclopropanecarbaldehyde

To a solution of F5.68.1 (100 mg) and DIPEA (950 μL) in DCM (2 mL) was added a solution of sulfur trioxide pyridine complex 45% (308 mg) in DMSO (2 mL) at 0° C. dropwise. The resulting solution was stirred for 30 min at 0° C. After 2 h the reaction mixture was quenched with 5 ml cold water. The two layers were separated (phase separator) and the aq. layer was extracted twice with DCM. The combined org. layers were evaporated to dryness. 273 mg orange liquid. LC-MS (A) $t_R$=0.28 min; $[M+H]^+$: 148.18

F5.68.3 2-(1-Ethynyl-cyclopropyl)-pyridine

The title compound was synthesized following the procedure described in Example F5.56, step 1 using F5.68.2 aldehyde. Filtration over plug of celite with DCM/MeOH 9 was carried out instead of CC. LC-MS (A) $t_R$=0.47 min; $[M+H]^+$: 144.20.

Example F5.69 4-(1-Ethynyl-cyclopropyl)-6-methyl-pyrimidine

F5.69.1 (6-Methyl-pyrimidin-4-yl)-acetic acid methyl ester

To a solution of methyl 2-(6-chloropyrimidin-4-yl)acetate (600 mg) and bis(tri-tert-butylphosphine)palladium(0) (82.2 mg) in THF abs. (10 mL) was added dropwise at 0° C. a dimethylzinc solution (345 μL, 2.0 M in toluene) under argon. The reaction mixture was further stirred at RT overnight. The reaction mixture was quenched with water, extracted 3× with DCM and purified by CC (Biotage, 25 g SNAP, solvent A: DCM, solvent B: DCM/MeOH 8/2, gradient (in % B) 0 for 3 CV, 0 to 15 over 5 CV, 15 for 5 CV) to give 485 mg orange resin. LC-MS (A) $t_R$=0.52 min; $[M+H]^+$: 167.04

F5.69.2 1-(6-Methyl-pyrimidin-4-yl)-cyclopropanecarboxylic acid methyl ester

To a solution of F5.69.1 (485 mg) in DMF abs. (20 mL) was added at 0° C. NaH (60% dispersion in mineral oil) (70 mg) and the mixture stirred at 0° C. for 10 min. Subsequently, 1,2-dibromoethane (267 μL) was added and the mixture stirred for additional 5 min. Again, NaH (60% dispersion in mineral oil) (70 mg) was added and stirring continued at 0° C. for 4 h. The reaction was quenched by the addition of $NH_4Cl$ aq. sat. and extracted with DCM 3×, dried over $MgSO_4$, concentrated in vacuo, and purified by CC (Biotage, 25 g SNAP, solvent A: DCM, solvent B: DCM/MeOH 8/2, gradient (in % B): 0 for 3 CV, 0 to 15 over 10 CV, 15 for 5 CV) to give 280 mg yellowish resin. LC-MS (A) $t_R$=0.64 min, $[M+H]^+$: 193.13

F5.69.2 3 [1-(6-Methyl-pyrimidin-4-yl)-cyclopropyl]-methanol

A lithium borohydride solution (10.4 mL, 2.0 M in THF) was added dropwise at RT under argon to a solution of F5.69.2 (180 mg) in MeOH abs. (3.5 mL) and stirred overnight. The mixture was cooled to 0° C. and carefully quenched by the dropwise addition of HCl 2N to adjust the pH to 7, and the aq. phase was extracted with DCM 3×. The combined org. phases were evaporated to dryness and the crude purified by CC (Biotage, 10 g SNAP, solvent A: DCM, solvent B: DCM/MeOH 8/2, gradient (% B) 0 for 3 CV, 0 to 15 over 5 CV, 15 for 5 CV) to give 68 mg yellowish resin. LC-MS (A) $t_R$=0.42 min; $[M+H]^+$: 165.09

F5.69.3 1-(6-Methyl-pyrimidin-4-yl)-cyclopropanecarbaldehyde

To solution of F5.69.2 (48 mg) in DCM abs. (2.5 mL) were added molecular sieves (3A) and Dess-Martin periodinane (248 mg) at RT under argon. The resulting suspension was stirred at RT for 30 min. The mixture was filtrated over silica, evaporated and purified by CC (Biotage, 10 g SNAP, solvent A: DCM, solvent B: DCM/MeOH 8/2, gradient (% B): 0 for 3 CV, 0 to 15 over 5 CV, 15 for 5 CV to give 110 mg yellowish wax. LC-MS (A) $t_R$=0.54 min, $[M+H]^+$:163.12

F5.69.4 4-(1-Ethynyl-cyclopropyl)-6-methyl-pyrimidine

The title compound was synthesized following the procedure described in Example F5.56.1 using F5.69.3 as aldehyde. CC (Biotage), 10 g SNAP, A: DCM, B: DCM/MeOH 8/2 0 for 3 CV, 0 to 15 over 5 CV, 15 for 5 CV, 15 to 50 over 3 CV, 50 for 5 CV. LC-MS (A) $t_R$=0.74 min; $[M+H]^+$: 159.15.

Example F5.70
4-Ethynyl-1-methanesulfonyl-piperidine

To a suspension of the 4-ethynylpiperidine hydrochloride (70 mg) and TEA (324 μL) in DCM (1.5 mL) was added slowly methanesulfonyl chloride (54.7 μL) at 0° C. and the suspension was stirred under argon overnight. The reaction mixture was quenched with water and the phases were separated with a phase separator. The aq. layer was 1× re-extracted with DCM. The combined org. layers were evaporated to dryness and purified by CC (Biotage, 10 g SNAP, solvent A: heptane, solvent B: EA; 30 for 3 CV, 30 to 50 over 2 CV, 50 for 1 CV) to give 68 mg white powder. $^1$H-NMR (500 MHz, CDCl3) δ: 3.41 (m, 2H), 3.23 (m, 2H), 2.81 (s, 3H), 2.69 (m, 1H), 2.17 (d, J=2.5 Hz, 1H), 1.95 (m, 2H), 1.82 (m, 2H).

Example F5.71
4-Ethynyl-4-methyl-piperidine-1-sulfonic acid methylamide

The title compound was synthesized following the procedure described in Example F5.70 using F5.58.1. CC (Biotage, 10 g SNAP, solvent A: heptane, solvent B: EA; 30 for 3 CV, 30 to 50 over 3 CV, 50 for 2 CV). LC-MS (A) $t_R$=0.76 min; $[M+H]^+$: 217.11.

Example F5.72 4
(2-Methyl-but-3-yne-2-sulfonyl)-cyclopropane

To a suspension of sodium cyclopropanesulfinate (150 mg), CuCl (9.08 mg), 3-chloro-3-methyl-1-butyne in DMF (500 μL) was stirred at 40° C. overnight. The mixture was allowed to cool to RT, diluted with EA/water and extracted with EA. The combined org. layers were washed with brine, dried over $MgSO_4$, filtrated off, evaporated to dryness. The crude was purified by CC (Biotage, 10 g snap, solvent A: Hp, solvent B: EA, Gradient (in % B): 30 for 3 CV, 30 to 100 over 10 CV, 100 for 2 CV) to give 57 mg pale yellow oil. LC-MS (A) $t_R$=0.85 min; $[M+H]^+$: 214.09

Example F5.73 rac-2-(1-Cyclopropyl-1H-pyrazol-3-yl)-but-3-yn-2-ol

F5.73.1
1-(1-Cyclopropyl-1H-pyrazol-3-yl)-ethanone

A mixture of 1-(1H-pyrazol-3-yl)ethan-1-one (200 mg), cyclopropylboronic acid (306 mg), 2,2'-bipyridyl (550 mg), $Na_2CO_3$ (185 mg), copper(II) acetate (313 mg) and toluene (16 mL) was stirred at 100° C. under argon overnight.

The reaction mixture was diluted with water and extracted with 3×DCM. The org. layers were washed with 1× brine, combined, dried over $MgSO_4$, filtrated off, evaporated. The crude was purified by CC (Biotage, 25 g snap, solvent A: heptane, solvent B: EA, Gradient (in % B): 0 for 3 CV, 0 to 30 over 7 CV, 30 for 2 CV), followed by a second CC (Biotage, 10 g snap, solvent A: heptane, solvent B: EA, gradient (in % B): 10 for 3 CV, 10 to 30 over 4 CV, 30 for 2 CV) to give 50 mg pale yellow oil. LC-MS (A) $t_R$=0.64 min, $[M+H]^+$: 151.16

F5.73.2 rac-2-(1-Cyclopropyl-1H-pyrazol-3-yl)-but-3-yn-2-ol

To a solution of ethynyl magnesium bromide (918 μL, 0.5M in THF) at 0° C. was added dropwise a solution of F5.73.1 (46 mg) in THF (800 μL) under argon and reaction mixture stirred at 50° C. overnight. The mixture was allowed to cool down to RT, quenched with aq. sat. $NH_4Cl$, diluted with water and extracted with 3×DCM. The combined org. layers were dried over $MgSO_4$, filtrated off, evaporated and purified by CC (Biotage, 10 g snap, solvent A: heptane, B: EA, Gradient (in % B): 30 for 3 CV, 30 to 50 for 2 CV, 50 for 2 CV, 50 to 70 over 2 CV, 70 for 2 CV) to give 22 mg pale yellow oil. LC-MS (A) $t_R$=0.57 min; $[M+H]^+$: 177.24

Example F5.74 rac-2-(6-Trifluoromethyl-pyrimidin-4-yl)-but-3-yn-2-ol

F5.74.1 6-Trifluoromethyl-pyrimidine-4-carboxylic acid methoxy-methyl-amide

The title compound was synthesized following the procedure described Example F5.K1 step 1 using 6-trifluoromethyl)pyrimidine-4-carboxylic acid. LC-MS (A) $t_R$=0.70 min, $[M+H]^+$: 235.97

F5.74.2 1-(6-Trifluoromethyl-pyrimidin-4-yl)-3-triisopropylsilanyl-propynone

To a solution of the Weinreb amide F5.74.1 (452 mg) in THF abs. (9 mL) and (triisopropylsilyl)acetylene (578 μL) in a heated-out flask was added LiHMDS 1M (2.5 mL) dropwise at −78° C. under argon. The resulting solution was stirred at −78° C. under argon for 45 min, before it was allowed to warm up to RT, to be quenched with aq. sat. $NaHCO_3$ and extracted with 3× EA. Afterwards the org. layers were washed with 1× brine, combined, dried over $MgSO_4$, filtrated off, evaporated and dried at HV to give 712 mg dark brown oil. LC-MS (A) $t_R$=1.29 min, $[M+H]^+$: 357.01.

F5.74.3 rac-2-(6-Trifluoromethyl-pyrimidin-4-yl)-4-triisopropylsilanyl-but-3-yn-2-ol To a solution of F5.74.2 (723 mg) in THF abs. (7 mL) was added dropwise methylmagnesium bromide solution (810 μL, 3.0M in diethyl ether) at 0° C. under argon. The resulting solution was stirred at 0° C. under argon for 1 h30. The reaction mixture was quenched with aq. sat. $NH_4Cl$ at 0° C., diluted with water and extracted with 3×DCM. The combined org. layers were dried over $MgSO_4$, filtrated off, purified by CC (Biotage, 25 g sphere, A: Hp, B: EA, 10 for 3 CV, 10 to 30 over 3 CV, 30 for 2 CV) to give 507 mg brown oil. LC-MS (A) $t_R$=1.24 min, $[M+H]^+$: 373.10

F5.74.4 rac-2-(6-Trifluoromethyl-pyrimidin-4-yl)-but-3-yn-2-ol

To a solution of the F5.74.3 (499 mg) in THF abs. (5 mL) was added TBAF (1.47 mL) at 0° C. After stirring for 30 min at 0° C. under argon the reaction mixture was quenched and diluted with aq. sat. $NH_4Cl$ and extracted with 2×DCM. Afterwards the aq. layers were washed with 1×aq. sat. $NH_4Cl$ and 1× brine. The combined org. layers were dried over $MgSO_4$, filtrated, evaporated and purified by Prep LC-MS (XVI, then IX) to give 99 mg pale brown oil. LC-MS (A) $t_R$=0.70 min, $[M+H]^+$: 217.07

Example F5.75 rac-2-(6-Difluoromethyl-pyrimidin-4-yl)-but-3-yn-2-ol

F5.75.1 6-Difluoromethyl-pyrimidine-4-carboxylic acid methoxy-methyl-amide

The title compound was synthesized following the procedure described Example F5.$K_1$ step F5.$K_1$.1 using 6-(difluoromethyl)pyrimidine-4-carboxylic acid. LC-MS (A) $t_R$=0.58 min, $[M+H]^+$: 218.09.

F5.75.2 1-(6-Difluoromethyl-pyrimidin-4-yl)-3-triisopropylsilanyl-propynone

The title compound was synthesized following the procedure described Example F5.75 step F5.75.2 using F5.75.1. LC-MS (A) $t_R$=1.24 min, $[M+H]^+$: 339.10.

F5.75.3 rac-2-(6-Difluoromethyl-pyrimidin-4-yl)-4-triisopropylsilanyl-but-3-yn-2-ol The title compound was synthesized following the procedure described Example F5.75 step F5.75.3 using F5.75.2. The compound was purified by CC (Biotage, 25 g SPHERE, 10 for 4 CV, 10 to 30 over 2 CV, 30 for 1 CV) LC-MS (A) $t_R$=1.17 min, $[M+H]^+$: 355.06.

F5.75.4 rac-2-(6-Difluoromethyl-pyrimidin-4-yl)-but-3-yn-2-ol

The title compound was synthesized following the procedure described Example F5.75 step F5.75.4 starting from Example F5.75.3. The compound was purified by CC (Biotage, 25 g SPHERE, A: heptane, B: EA), gradient (in % B): 10 for 3 CV, 10 to 30 over 3 CV, 30 for 3 CV). LC-MS (A) $t_R$=0.57 min, $[M+H]^+$: 199.16.

Example F5.76 (R)- or (S)-2-(2-Trifluoromethyl-pyrimidin-4-yl)-but-3-yn-2-ol

F5.76.1 N-methoxy-N-methyl-2-(trifluoromethyl) pyrimidine-4-carboxamide

The title compound was synthesized following the procedure described Example F5.K1 step F5.K1.1 using 2-(trifluoromethyl)pyrimidine-4-carboxylic acid. LC-MS (A) $t_R$=0.72 min, $[M+H]^+$: 235.82.

F5.76.2 1-(2-Trifluoromethyl-pyrimidin-4-yl)-3-triisopropylsilanyl-propynone

The title compound was synthesized following the procedure described Example F5.75 step F5.75.2 starting from Example F5.76.1. LC-MS (A) $t_R$=1.25 min, $[M+H]^+$: 357.75.

F5.76.3 rac-2-(2-Trifluoromethyl-pyrimidin-4-yl)-4-triisopropylsilanyl-but-3-yn-2-ol The title compound was synthesized following the procedure described Example F5.75 step F5.75.3 using F5.76.2. The compound was purified by CC (Biotage, 25 g SPHERE, 0 for 2 CV, 0 to 10 over 3 CV, 10 for 3 CV, 10 to 30 over 3 CV) L-C-MS (A): $t_R$=1.20 min, $[M+H]^+$: 373.10.

F5.76.4 (R)- or (S)-2-(2-Trifluoromethyl-pyrimidin-4-yl)-but-3-yn-2-ol

The title compound was synthesized following the procedure described Example F5.75 step F5.75.4 using F5.76.3. The compound was purified by Chiral prep (XLIII)/Analytical (X): 7.0 min. LC-MS (A): $t_R$=0.72 min. $^1$H-NMR (400 MHz, MeOD) δ: 9.00 (d, J=5.2 Hz, 1H), 8.04 (d, J=5.2 Hz, 1H), 3.07 (s, 1H), 1.83 (s, 3H).

Example F5.77 (S)- or (R)-2-(2-Trifluoromethyl-pyrimidin-4-yl)-but-3-yn-2-ol

The title compound was synthesized following the procedure described Example F5.75 step F5.75.4 using F5.76.3. The compound was purified by Chiral prep (XLIII)/Analytical (X): 8.9 min. LC-MS (A): $t_R$=0.72 min. $^1$H-NMR (400 MHz, MeOD) δ: 9.00 (d, J=5.2 Hz, 1H), 8.04 (d, J=5.2 Hz, 1H), 3.07 (s, 1H), 1.83 (s, 3H).

Example F5.78 2-(3-Methyl-isoxazol-5-yl)-but-3-yn-2-ol

A heated-out flask was charged with a solution of trimethylsilylacetylene (361 μL) in THF abs. (4 mL) and cooled to 0° C., then n-BuLi 2.5 M in hexanes (11.14 mL) was added slowly under argon. The solution was stirred for 1 h at 0° C. under argon, then a solution of 1-(3-methyl-5-isoxazolyl)ethanone (250 mg) in THF abs. (5 mL) was added slowly at 0° C. under argon. The resulting solution was further stirred at 0° C. under argon for 45 min. The reaction mixture was quenched by dropwise addition of MeOH (5 mL), allowed to warm up to RT, then $K_2CO_3$ (262 mg) was added. The resulting suspension was stirred at RT for 20 min, before filtrated off, evaporated to dryness and purified by CC (Biotage, 10 g Snap, A: Hep, B: EA, gradient (in % B): 30 for 3 CV, 30 to 50 over 2 CV, 50 for 2 CV) to give 200 mg yellow oil. LC-MS (A): $t_R$=0.57 min, $[M+H]^+$: 152.14.

Example F5.79 to Example F5.81 were synthesized following the procedure described in Example F5.78. The LC-MS data and the CC gradients (in % B) are listed in the table below. The LC-MS conditions used were LC-MS (A).

| Example N° | Name | $t_R$ | $[M+H]^+$ | CC conditions Column, solvent A/B gradient (in % B) |
|---|---|---|---|---|
| F5.79 | rac-2-(1-Methyl-1H-imidazol-2-yl)-but-3-yn-2-ol | 0.29 | 151.16 | 25 g SPHERE, DCM/MeOH 8:2 25 for 3CV, 25 to 50 over 3CV, 50 for 1CV |
| F5.80 | rac-2-(5-Methyl-thiophen-2-yl)-but-3-yn-2-ol | 0.77 | 149.12 | 25 g SPHERE, Hep/EA 10 for 3CV, 10 to 30 over 2CV, 30 for 1CV |

-continued

| Example N° | Name | $t_R$ | [M + H]$^+$ | CC conditions Column, solvent A/B gradient (in % B) |
|---|---|---|---|---|
| F5.81 | rac-2-(1-Methyl-1H-pyrrol-2-yl)-but-3-yn-2-ol | 0.65 | 150.24 | — |

Example G1.1: 5-[(1,3-Dimethyl-azetidin-3-yl)-hydroxy-(4-isopropyl-phenyl)-methyl]-pyridin-3-ol

G1.1.1. 3-[Hydroxy-(4-isopropyl-phenyl)-(5-methoxy-pyridin-3-yl)-methyl]-3-methyl-azetidine-1-carboxylic acid tert-butyl ester A flask was charged with 3-bromo-5-methoxypyridine (5.35 g), THF (20 mL) and iPrMgCl·LiCl (1.3M in THF, 24 mL) under argon at RT and the resulting brown solution was stirred at 60° C. for 30 min. A solution of Example A4.2 (3.98 g) in THF (20 mL) was added dropwise and the resulting mixture was stirred at RT for 3 h15, quenched with aq. sat. $NH_4Cl$ solution and water, and extracted with DCM. The org. layers were evaporated in vacuo to afford 6.45 g of dark-orange resin. LC-MS (A): $t_R$=0.90 min; [M+H]$^+$: 427.33.

G1.1.2. (4-Isopropyl-phenyl)-(5-methoxy-pyridin-3-yl)-(3-methyl-azetidin-3-yl)-methanol A solution of Example G1.1.1 (6.45 g) in HCl in dioxane (4M, 30 mL) was stirred for 40 min, diluted with water and extracted with EA. The aq. layer was basified to pH12 with aq. NaOH solution (1M) and extracted with EA. The org. layers were dried ($MgSO_4$) and evaporated to dryness to give 5.4 g of the title compound as orange solid. LC-MS (A): $t_R$=0.59 min; [M+H]$^+$: 327.25.

G1.1.3. (1,3-Dimethyl-azetidin-3-yl)-(4-isopropyl-phenyl)-(5-methoxy-pyridin-3-yl)-methanol Example G1.1.3 was synthesized starting from Example G1.1.2 (5.4 g), and following the procedure described in Example B2.1 step B2.1.2. The resulting crude material was purified by CC (Biotage, SNAP 100 g, solvent A: DCM; solvent B: MeOH; gradient in % B: 0 over 3 CV, 0 to 3 over 5 CV, 3 over 5 CV, 3 to 6 over 5 CV, 6 to 10 over 3 CV, 10 over 5 CV, 10 to 20 over 2 CV, 20% over 5 CV) to afford 1.98 g of the title compound as orange solid. LC-MS (A): $t_R$=0.61 min; [M+H]$^+$: 341.25.

G1.1.4. 5-[(1,3-Dimethyl-azetidin-3-yl)-hydroxy-(4-isopropyl-phenyl)-methyl]-pyridin-3-ol To a solution of Example G1.1.3 (50 mg) in DMF (0.5 mL) were added 2-diethylamino-ethanethiol hydrochloride (31.2 mg) and KOtBu (43.4 mg) and the resulting mixture was stirred at reflux for 1 h. Aq. sat. $NaHCO_3$ solution was added dropwise at RT, the resulting mixture was diluted with water and extracted with EA. The org. layers were dried ($MgSO_4$) and evaporated to dryness. The resulting crude material was purified by CC (Biotage, SNAP 10 g, solvent A: MeOH; gradient in % A: 100 over 15 CV). The isolated fractions were evaporated off and the residue was dissolved in THF. The resulting mixture was filtrated off and the solvent was evaporated to dryness to afford 15 mg of the title compound as yellow resin. LC-MS (A): $t_R$=0.52 min; [M+H]$^+$: 327.25.

Example G1.2: 5-[(R)-(1,3-Dimethyl-azetidin-3-yl)-hydroxy-(4-isopropyl-phenyl)-methyl]-pyridin-3-ol

G1.2.1. 3[(5-Benzyloxy-pyridin-3-yl)-hydroxy-(4-isopropyl-phenyl)-methyl]-3-methyl-azetidine-1-carboxylic acid tert-butyl ester The title compound was synthesized starting from Example A4.2 (3.9 g) and 3-(benzyloxy)-5-bromopyridine (4.39 g), and following the procedure described in Example A7.1 step A7.1.1. The crude material was purified by Prep LC-MS (II) to afford 4.79 g of the title compound as white solid. LC-MS (A): $t_R$=1.01 min; [M+H]$^+$: 503.30.

G1.2.2. 3-[(R)-(5-Benzyloxy-pyridin-3-yl)-hydroxy-(4-isopropyl-phenyl)-methyl]-3-methyl-azetidine-1-carboxylic acid tert-butyl ester The title compound was obtained by chiral separation of Example G1.2.1 (4.79 g) by Prep chiral SFC (VII). LC-MS (A): $t_R$=1.01 min; [M+H]$^+$: 503.16; chiral SFC (G): 2.7 min.

G1.2.3. (R)-(5-Benzyloxy-pyridin-3-yl)-(4-isopropyl-phenyl)-(3-methyl-azetidin-3-yl)-methanol, hydrochloride salt A solution of Example G1.2.2 (1.99 g) in HCl in dioxane (4M, 15 mL) was stirred for 1 h and evaporated to dryness to give 2.05 g of the title compound as off-white solid. LC-MS (A): $t_R$=0.73 min; [M+H]$^+$: 403.12.

G1.2.4. (R)-(5-Benzyloxy-pyridin-3-yl)-(1,3-dim ethyl-azetidin-3-yl)-(4-isopropyl-phenyl)-methanol The title compound was synthesized starting from Example G1.2.3, and following the procedure described in Example B2.1 step B2.1.2. LC-MS (B): $t_R$=0.783 min; [M+H]$^+$: 417.4.

G1.2.5. 5-[(R)-(1,3-Dimethyl-azetidin-3-yl)-hydroxy-(4-isopropyl-phenyl)-methyl]-pyridin-3-ol A mixture of Example G1.2.4 (1.62 g) and Pd/C (10% w/w, 50% water, 206 mg) in EtOH (40 mL) was stirred at RT under hydrogen atmosphere for 2 h and filtered off over a celite plug. The resulting solution was evaporated to dryness to provide the title compound (1.04 g) as pale yellow solid. LC-MS (A): $t_R$=0.52 min; [M+H]$^+$: 327.16.

Example J3.1: 2-[3-(5-{(R)-(1,3-Dimethyl-azetidin-3-yl)-hydroxy-[4-(4,4,5,5-tetramethyl-[1,3,2]dioxaborolan-2-yl)-phenyl]-methyl}-pyridin-3-yl)-[1,2,4]oxadiazol-5-yl]-propan-2-ol A mixture of Example 532 (1 eq), bis(pinacolato)diboron (1.1 eq), Pd(dppf)$Cl_2$.DCM (0.03 eq) and KOAc (3 eq) in dioxane (5 mL/mmol) was flushed with argon, heated at 80° C. in a sealed vial and stirred for 18 h. It was filtered over Celite, the cake was washed with EA and the filtrate was concentrated in vacuo. The crude was purified by Prep LC-MS (XV) to afford the title compound as brown oil. LC-MS (A): $t_R$=0.70 min; $[M+H]^+$: 521.08

Example J5.1: 4—((R)-(1,3-Dimethyl-azetidin-3-yl)-hydroxy-{5-[5-(1-hydroxy-1-methyl-ethyl)-[1,2,4]oxadiazol-3-yl]-pyridin-3-yl}-methyl)-phenol To a solution of boronic ester intermediate (J3.1) (1 eq) in THF (31 mL/mmol) was added at 0° C., NaOH (2.5 eq) and a 30% aq. solution of hydrogen peroxide (2.5 eq). The mixture was stirred at RT for 1 h and quenched with a half sat. solution of $NH_4Cl$. It was acidified to pH 0 with 1M HCl and washed with EA. The aq. phase was basified to pH 10 with a 1M NaOH and extracted with EA/MeOH 99/1 then EA/MeOH 95/5. The combined org. phases were dried over $MgSO_4$ and concentrated in vacuo. The crude was purified by Prep LC-MS (XV) to afford the title compound as white solid. LC-MS (A): $t_R$=0.52 min; $[M+H]^+$: 411.08

Depending on the purification conditions, the title compounds/intermediates in Intermediate Examples of Formula (A3), (A4), (A5), (A6), (A7), (B2), (C1), (C3), (D1), (D2), (D3), (D4), (D5), (E1), (E2), (F1), (F3), (F4), (F5), (G1), (J3) and (J5) may be isolated as free bases or as salts such as formate salts, or hydrochloride salts, or sodium salts. Whenever isolating a title compound/intermediate as a salt, formate salt or hydrochloride salt or sodium salt is indicated at the end of the chemical name and can refer to a mono-, di- or tri-formate salt; or a mono-, di-, or tri-hydrochloride salt; or a mono-, or di-sodium salt.

Preparation of Examples of Formula (I)

Example 1: (3-Fluoro-1-methyl-azetidin-3-yl)-(5-pyrrolidin-1-yl-pyridin-3-yl)-(4-trifluoromethoxy-phenyl)-methanol To a light-yellow solution of Example A7.3 (45 mg) in DCM (1 mL) was added formaldehyde (26.2 μL, 37% in water) followed by $NaBH(OAc)_3$ (33.6 mg). The resulting solution was stirred for 30 min at RT and was basified with aq. sat. $NaHCO_3$ solution. The resulting mixture was extracted with DCM and the org. layers were dried ($MgSO_4$), filtered off and evaporated to dryness. The resulting crude material was purified by Prep LC-MS (VI) to afford 17 mg of the title compound as white solid. LC-MS (A): $t_R$=0.63 min; $[M+H]^+$: 426.21.

Example 2: 3-[Hydroxy-(5-pyrrolidin-1-yl-pyridin-3-yl)-(4-trifluoromethoxy-phenyl)-methyl]-1-methyl-azetidine-3-carbonitrile Example 2 was synthesized starting from Example A7.2 and following the procedure described in Example B2.1 step B2.1.2. The material was purified by Prep LC-MS (V). LC-MS (A): $t_R$=0.63 min; $[M+H]^+$: 433.15.

Example 3: (R)-(1-Ethyl-3-methyl-azetidin-3-yl)-(5-pyrrolidin-1-yl-pyridin-3-yl)-(4-trifluoromethoxy-phenyl)-methanol To a light-yellow solution of Example A7.1 (20 mg) in MeOH (0.5 mL), AcOH (0.05 mL) was added at RT, followed successively by acetaldehyde (15.2 μL) and $NaBH(OAc)_3$ (19.7 mg). The resulting solution was stirred 17 h at RT. Acetaldehyde (5 μL) and $NaBH(OAc)_3$ (9.85 mg) were added again and the reaction mixture was stirred for 4 days. The mixture was quenched with water, filtered off and evaporated to dryness. The resulting crude material was purified by Prep LC-MS (VII) to afford 6 mg of the title compound as white solid. LC-MS (A): $t_R$=0.64 min; $[M+H]^+$: 436.29.

Example 4 to Example 8 were synthesized starting from the appropriate aldehyde or ketone, following the procedure described in Example 3. LC-MS data of Example 4 to Example 9 are listed in the table below. The LC-MS conditions used were LC-MS (A).

| Example N° | Name | $t_R$ | $[M+H]^+$ |
|---|---|---|---|
| 4 | (R)-(3-Methyl-1-propyl-azetidin-3-yl)-(5-pyrrolidin-1-yl-pyridin-3-yl)-(4-trifluoromethoxy-phenyl)-methanol | 0.66 | 450.05 |
| 5 | (R)-(1-Isopropyl-3-methyl-azetidin-3-yl)-(5-pyrrolidin-1-yl-pyridin-3-yl)-(4-trifluoromethoxy-phenyl)-methanol | 0.65 | 450.04 |
| 6 | (R)-(1-Cyclopropylmethyl-3-methyl-azetidin-3-yl)-(5-pyrrolidin-1-yl-pyridin-3-yl)-(4-trifluoromethoxy-phenyl)-methanol | 0.67 | 462.27 |
| 7 | (R)-(1-Cyclobutyl-3-methyl-azetidin-3-yl)-(5-pyrrolidin-1-yl-pyridin-3-yl)-(4-trifluoromethoxy-phenyl)-methanol | 0.67 | 462.27 |
| 8 | (R)-(1-Isobutyl-3-methyl-azetidin-3-yl)-(5-pyrrolidin-1-yl-pyridin-3-yl)-(4-trifluoromethoxy-phenyl)-methanol | 0.69 | 464.3 |

Example 9: (R)-(1-Cyclopropyl-3-methyl-azetidin-3-yl)-(5-pyrrolidin-1-yl-pyridin-3-yl)-(4-trifluoromethoxy-phenyl)-methanol To a light yellow solution of Example A7.1 (20 mg) in EtOH (0.5 mL), AcOH (0.05 mL) was added at RT, followed successively by (1-ethoxycyclopropoxy)trimethylsilane (91.5 µL) and sodium cyanoborohydride (28.3 mg). The resulting solution was stirred for 17 h at RT. 1-Ethoxycyclopropoxy)trimethylsilane (45.7 µL) and sodium cyanoborohydride (14.1 mg) were added again and the reaction mixture was stirred for 4 days. The mixture was quenched with water and evaporated to dryness. The resulting crude material was purified by Prep LC-MS (VII) to afford 4 mg of the title compound as white solid. LC-MS (A): $t_R$=0.65 min; [M+H]$^+$: 448.28.

Example 10: (R)-[1-(2-Fluoro-ethyl)-3-methyl-azetidin-3-yl]-(5-pyrrolidin-1-yl-pyridin-3-yl)-(4-trifluoromethoxy-phenyl)-methanol To a light yellow solution of Example A7.1 (20 mg) in MeOH (0.5 mL), TEA (13.8 µL) was added, followed by 1-fluoro-2-iodo-ethane (17.4 µL). The reaction mixture was stirred at reflux for 22 h. 1-Fluoro-2-iodo-ethane (3.95 µL) and TEA (3.14 µL) were added and the mixture was stirred at reflux for 48 h. The resulting crude material was filtered off and purified by Prep LC-MS (V) to afford 5 mg of the title compound as white solid. LC-MS (A): $t_R$=0.63 min; [M+H]$^+$: 454.24.

Example 11: (R)-[1-(2,2-Difluoro-ethyl)-3-methyl-azetidin-3-yl]-(5-pyrrolidin-1-yl-pyridin-3-yl)-(4-trifluoromethoxy-phenyl)-methanol The title compound was synthesized starting from Example A7.1 and 1,1-difluoro-2-iodoethane, following the synthesis procedure described in Example 10. LC-MS (A): $t_R$=0.65 min; [M+H]$^+$: 472.2.

Example 12: (R)-(1-tert-Butyl-3-methyl-azetidin-3-yl)-(5-pyrrolidin-1-yl-pyridin-3-yl)-(4-trifluoromethoxy-phenyl)-methanol 12.1. (R)-(1-Isopropenyl-3-methyl-azetidin-3-yl)-(5-pyrrolidin-1-yl-pyridin-3-yl)-(4-trifluoromethoxy-phenyl)-methanol To a light yellow solution of Example A7.1 (20 mg) and acetone (19.9 µL) in water (0.5 mL) was added dropwise at 0° C. a solution of KCN (18.1 mg) in water (0.5 mL). The resulting mixture was stirred for 69 h at RT, was diluted with water and extracted with EA. The org. layers were washed with brine, dried ($MgSO_4$), filtrated off and evaporated to dryness to afford 80 mg of the title compound. LC-MS (A): $t_R$=0.62 min; [M+H]$^+$: 448.26.

12.2 (R)-(1-tert-Butyl-3-methyl-azetidin-3-yl)-(5-pyrrolidin-1-yl-pyridin-3-yl)-(4-trifluoromethoxy-phenyl)-methanol To a solution of Example 12.1 (77 mg) in THF (1.5 mL) was added dropwise methylmagnesium bromide (3M in diethyl ether, 573 µL) at 0° C. The resulting mixture was stirred for 10 min at 0° C. then at 60° C. overnight. The reaction mixture was cooled down, quenched by addition of aq. sat. $NH_4Cl$ solution, diluted with water and extracted with EA. The org. layers were washed with water and brine, dried ($MgSO_4$), filtrated off and evaporated to dryness. The resulting crude material was first purified by Prep LC-MS (VIII) then by Prep LC-MS (IX) to afford 9 mg of the title compound as white powder. LC-MS (A): $t_R$=0.65 min; [M+H]$^+$: 464.29.

Example 13: (1,3-Dimethyl-azetidin-3-yl)-(4-isopropyl-phenyl)-[5-(3-methoxy-prop-1-ynyl)-pyridin-3-yl]-methanol To a solution of Example F1.1 (100 mg) in DMSO (2 mL) and toluene (0.3 mL), methyl propargyl ether (33.5 mg) was added at RT followed by palladium(II) acetate (2.89 mg), triphenylphosphine (83.7 mg) and $K_3PO_4$ (65.4 mg). The resulting solution was stirred for 66 h at 80° C., was allowed to cool down, was diluted with MeOH and water, filtered off and purified by Prep LC-MS (VII) to afford 32 mg of the title compound as purple powder. LC-MS (A): $t_R$=0.75 min; [M+H]$^+$: 379.34.

Example 14: 3-{5-[(R)-(1,3-Dimethyl-azetidin-3-yl)-hydroxy-(4-isopropyl-phenyl)-methyl]-pyridin-3-yl}-prop-1-yn-1-ol Example 14 was synthesized starting from Example F1.2 and propargyl alcohol following the procedure described in Example 13. The crude material was purified by Prep LC-MS (VI). LC-MS (A): $t_R$=0.65 min; [M+H]$^+$: 365.25.

Example 15: 4-{5-[(R)-(1,3-Dimethyl-azetidin-3-yl)-hydroxy-(4-isopropyl-phenyl)-methyl]-pyridin-3-yl}-2-methyl-but-3-yn-2-ol To a solution of Example F1.2 (70 mg) in THF (2.5 mL) was added 2-methyl-3-butyn-2-ol (24 µL) followed by CuI (0.86 mg), tetrakis(triphenylphosphine)palladium(0) (83.2 mg) and piperidine (93 µL). The resulting reaction mixture was stirred for 2 h at 80° C., cooled down, diluted with MeOH and water, filtrated through a syringe filter and purified by Prep LC-MS (VI) then by Prep LC-MS (XIII) to afford 38 mg of the title compound as white powder. LC-MS (A): $t_R$=0.69 min; [M+H]$^+$: 393.33.

Example 16 to Example 46 were synthesized starting from Example F1.2 and the appropriate alkyne of Formula (F5), and following the procedure described in Example 15. The alkyne precursors of Formula (F5) are indicated in the table below unless commercially available. Prep LC-MS conditions and LC-MS data are listed in the table below. The LC-MS conditions used were LC-MS (A).

| Example N° | Name | $t_R$ | [M + H]$^+$ | (F5) | Prep LC-MS |
|---|---|---|---|---|---|
| 16 | (R)-4-5-[(R)-(1,3-Dimethyl-azetidin-3-yl)-hydroxy-(4-isopropyl-phenyl)-methyl]-pyridin-3-yl}-but-3-yn-2-ol | 0.66 | 379.3 | — | (V) then (XIII) |
| 17 | (S)-4-{5-[(R)-(1,3-Dimethyl-azetidin-3-yl)-hydroxy-(4-isopropyl-phenyl)-methyl]-pyridin-3-yl}-but-3-yn-2-ol | 0.67 | 379.27 | — | (V) then (XIII) |

-continued

| Example N° | Name | $t_R$ | [M + H]$^+$ | (F5) | Prep LC-MS |
|---|---|---|---|---|---|
| 18 | 1-{5-[(R)-(1,3-Dimethyl-azetidin-3-yl)-hydroxy-(4-isopropyl-phenyl)-methyl]-pyridin-3-ylethynyl}-cyclopentanol | 0.74 | 419.33 | — | (IX) |
| 19 | 1-{5-[(R)-(1,3-Dimethyl-azetidin-3-yl)-hydroxy-(4-isopropyl-phenyl)-methyl]-pyridin-3-ylethynyl}-cyclopropanol | 0.69 | 391.3 | — | (IX) |
| 20 | 3-{5-[(R)-(1,3-Dimethyl-azetidin-3-yl)-hydroxy-(4-isopropyl-phenyl)-methyl]-pyridin-3-ylethynyl}-3-hydroxy-azetidine-1-carboxylic acid tert-butyl ester | 0.78 | 506.32 | — | (IX) |
| 21 | 1-{5-[(R)-(1,3-Dimethyl-azetidin-3-yl)-hydroxy-(4-isopropyl-phenyl)-methyl]-pyridin-3-ylethynyl}-cyclobutanol | 0.71 | 405.14 | — | (IX) |
| 22 | 4-{5-[(R)-(1,3-Dimethyl-azetidin-3-yl)-hydroxy-(4-isopropyl-phenyl)-methyl]-pyridin-3-yl}-but-3-yn-1-ol | 0.64 | 379.29 | — | (IX) |
| 23 | (R)-(1,3-Dimethyl-azetidin-3-yl)-(4-isopropyl-phenyl)-[5-(1-methyl-1H-pyrazol-4-ylethynyl)-pyridin-3-yl]-methanol | 0.76 | 415.31 | — | (IX) then (VI) |
| 24 | 3-{5-[(R)-(1,3-Dimethyl-azetidin-3-yl)-hydroxy-(4-isopropyl-phenyl)-methyl]-pyridin-3-yl}-1-phenyl-prop-2-yn-1-ol | 0.78 | 441.25 | — | (IX) then (VI) |
| 25 | 4-{5-[(R)-(1,3-Dimethyl-azetidin-3-yl)-hydroxy-(4-isopropyl-phenyl)-methyl]-pyridin-3-yl}-2-phenyl-but-3-yn-2-ol | 0.81 | 455.26 | — | (XIV) |
| 26 | 1-{5-[(R)-(1,3-Dimethyl-azetidin-3-yl)-hydroxy-(4-isopropyl-phenyl)-methyl]-pyridin-3-yl}-4-methyl-pent-1-yn-3-ol | 0.75 | 407.26 | — | (VI) |
| 27 | 4-{5-[(R)-(1,3-Dimethyl-azetidin-3-yl)-hydroxy-(4-isopropyl-phenyl)-methyl]-pyridin-3-ylethynyl}-tetrahydro-pyran-4-ol | 0.67 | 435.24 | — | (V) |
| 28 | 3-{5-[(R)-(1,3-Dimethyl-azetidin-3-yl)-hydroxy-(4-isopropyl-phenyl)-methyl]-pyridin-3-yl}-1-(tetrahydro-pyran-4-yl)-prop-2-yn-1-ol | 0.69 | 449.13 | F5.1 | (IX) |
| 29 | 3-{5-[(R)-(1,3-Dimethyl-azetidin-3-yl)-hydroxy-(4-isopropyl-phenyl)-methyl]-pyridin-3-yl}-1-(1,3-dimethyl-1H-pyrazol-4-yl)-prop-2-yn-1-ol | 0.75 | 459.24 | F5.2 | (IX) |
| 30 | (R)-(1,3-Dimethyl-azetidin-3-yl)-(4-isopropyl-phenyl)-[5-(tetrahydro-pyran-4-ylethynyl)-pyridin-3-yl]-methanol | 0.77 | 419.2 | — | (V) |
| 31 | 3-{5-[(R)-(1,3-Dimethyl-azetidin-3-yl)-hydroxy-(4-isopropyl-phenyl)-methyl]-pyridin-3-yl}-1-(2-methyl-thiazol-4-yl)-prop-2-yn-1-ol | 0.71 | 462.18 | F5.3 | (IX) |
| 32 | 4-{5-[(R)-(1,3-Dimethyl-azetidin-3-yl)-hydroxy-(4-isopropyl-phenyl)-methyl]-pyridin-3-yl}-2-(3-fluoro-phenyl)-but-3-yn-2-ol | 0.82 | 473.19 | F5.4 | (VIII) then (XIV) |
| 33 | 4-{5-[(R)-(1,3-Dimethyl-azetidin-3-yl)-hydroxy-(4-isopropyl-phenyl)-methyl]-pyridin-3-yl}-2-(4-methoxy-phenyl)-but-3-yn-2-ol | 0.80 | 485.07 | F5.5 | (VIII) then (XIV) |
| 34 | 4-{5-[(R)-(1,3-Dimethyl-azetidin-3-yl)-hydroxy-(4-isopropyl-phenyl)-methyl]-pyridin-3-yl}-2-(2-methoxy-phenyl)-but-3-yn-2-ol | 0.81 | 485.17 | F5.6 | (VIII) then (XIV) |
| 35 | 4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-but-3-y n-2-ol | 0.68 | 459.11 | F5.7 | (XV) then (XIV) |
| 36 | 4-{5-[(R)-(1,3-Dimethyl-azetidin-3-yl)-hydroxy-(4-isopropyl-phenyl)-methyl]-pyridin-3-yl}-2-(2-methyl-thiazol-4-yl)-but-3-yn-2-ol | 0.72 | 476.05 | F5.8 | (VII) then (IX) |
| 37 | 4-{5-[(R)-(1,3-Dimethyl-azetidin-3-yl)-hydroxy-(4-isopropyl-phenyl)-methyl]-pyridin-3-yl}-2-(6-methoxy-pyridin-2-yl)-but-3-yn-2-ol | 0.81 | 486.17 | F5.9 | (XV) then (IX) |
| 38 | 4-{5-[(R)-(1,3-Dimethyl-azetidin-3-yl)-hydroxy-(4-isopropyl-phenyl)-methyl]-pyridin-3-yl}-2-pyrimidin-2-yl-but-3-yn-2-ol | 0.69 | 457.17 | F5.10 | (XV) then (IX) |
| 39 | 4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-but-3-yn-2-ol | 0.71 | 473.2 | F5.11 | (XV) then (IX) |
| 40 | 4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-but-3-yn-2-ol | 0.73 | 471.17 | F5.12 | (XV) then (IX) |
| 41 | 3-{5-[(R)-(1,3-Dimethyl-azetidin-3-yl)-hydroxy-(4-isopropyl-phenyl)-methyl]-pyridin-3-yl}-1-(1,5-dimethyl-1H-pyrazol-3-yl)-prop-2-yn-1-ol | 0.69 | 459.16 | F5.13 | (IX) |
| 42 | 8-{5-[(R)-(1,3-Dimethyl-azetidin-3-yl)-hydroxy-(4-isopropyl-phenyl)-methyl]-pyridin-3-ylethynyl}-5,6,7,8-tetrahydro-quinolin-8-ol | 0.65 | 481.85 | F5.14 | (IX) |

-continued

| Example N° | Name | $t_R$ | [M + H]$^+$ | (F5) | Prep LC-MS |
|---|---|---|---|---|---|
| 43 | 7-{5-[(R)-(1,3-Dimethyl-azetidin-3-yl)-hydroxy-(4-isopropyl-phenyl)-methyl]-pyridin-3-ylethynyl}-6,7-dihydro-5H-[1]pyrindin-7-ol | 0.7 | 468.14 | F5.15 | (IX) |
| 44 | 1-{5-[(R)-(1,3-Dimethyl-azetidin-3-yl)-hydroxy-(4-isopropyl-phenyl)-methyl]-pyridin-3-yl}-3-pyridin-2-yl-pent-1-yn-3-ol | 0.67 | 470.18 | F5.16 | (IX) |
| 45 | 1-{5-[(R)-(1,3-Dimethyl-azetidin-3-yl)-hydroxy-(4-isopropyl-phenyl)-methyl]-pyridin-3-yl}-3-(6-methoxy-pyridin-2-yl)-pent-1-yn-3-ol | 0.84 | 500.14 | F5.17 | (IX) |
| 46 | 1-(3-{5-[(R)-(1,3-Dimethyl-azetidin-3-yl)-hydroxy-(4-isopropyl-phenyl)-methyl]-pyridin-3-ylethynyl}-3-hydroxy-azetidin-1-yl)-2-methyl-propan-1-one | 0.69 | 476.17 | F5.18 | (IX) |

Example 47: (R)-(1,3-Dimethyl-azetidin-3-yl)-[5-(1H-indol-2-ylethynyl)-pyridin-3-yl]-(4-isopropyl-phenyl)-methanol

47.1. (R)-(1,3-Dimethyl-azetidin-3-yl)-(4-isopropyl-phenyl)-(5-trimethylsilanylethynyl-pyridin-3-yl)-methanol Example 47.1 was synthesized starting from Example F1.2 and trimethylsilylacetylene and following the procedure described in Example 15. The crude material was purified by Prep LC-MS (V). LC-MS (A): $t_R$=0.89 min; [M+H]$^+$: 407.22.

47.2. (R)-(1,3-Dimethyl-azetidin-3-yl)-(5-ethynyl-pyridin-3-yl)-(4-isopropyl-phenyl)-methanol To a solution of Example 47.1 (24 mg) in MeOH (0.5 mL) was added $K_2CO_3$ (8.16 mg). The resulting mixture was stirred for 2 h30 at RT, diluted with EA, washed with water and brine. The org. layers were dried ($MgSO_4$), filtrated off, and evaporated to dryness to afford 21 mg of the title compound as brown solid. LC-MS (A): $t_R$=0.73 min; [M+H]$^+$: 335.19.

47.3. (R)-(1,3-Dimethyl-azetidin-3-yl)-[5-(1H-indol-2-ylethynyl)-pyridin-3-yl]-(4-isopropyl-phenyl)-methanol The title compound was synthesized starting from Example 47.2 and 2-iodo-1H-indole, following the procedure described in Example 15. The crude material was purified by Prep LC-MS (VII). LC-MS (A): $t_R$=0.88 min; [M+H]$^+$: 449.82.

Example 48: (1,3-Dimethyl-azetidin-3-yl)-(4-isopropyl-phenyl)-[5-(3-methoxy-propyl)-pyridin-3-yl]-methanol A solution of Example 13 (29 mg) was dissolved in EtOH (2 mL), Pd/C (10% w/w, 50% water, 8.12 mg) was added and resulting mixture was stirred for 41 h under hydrogen. The reaction mixture was filtered off and evaporated to dryness to afford 21 mg of the title compound as brown resin. LC-MS (A): $t_R$=0.6 min; [M+H]$^+$: 383.36.

Example 49 to Example 81 were synthesized starting from the appropriate alkyne-containing Example and following the procedure described in Example 48. Precursor alkyne-containing Examples, Prep LC-MS conditions and LC-MS data are listed in the table below. The LC-MS conditions used were LC-MS (A).

| Example N° | Name | $t_R$ | [M + H]$^+$ | Prep LC-MS | Precursor Example |
|---|---|---|---|---|---|
| 49 | 3-{5-[(R)-(1,3-Dimethyl-azetidin-3-yl)-hydroxy-(4-isopropyl-phenyl)-methyl]-pyridin-3-yl}-propan-1-ol | 0.51 | 369.18 | none | 14 |
| 50 | 4-{5-[(R)-(1,3-Dimethyl-azetidin-3-yl)-hydroxy-(4-isopropyl-phenyl)-methyl]-pyridin-3-yl}-2-methyl-butan-2-ol | 0.56 | 397.37 | none | 15 |
| 51 | (S)-4-{5-[(R)-(1,3-Dimethyl-azetidin-3-yl)-hydroxy-(4-isopropyl-phenyl)-methyl]-pyridin-3-yl}-butan-2-ol | 0.54 | 383.35 | none | 16 |
| 52 | (R)-4-{5-[(R)-(1,3-Dimethyl-azetidin-3-yl)-hydroxy-(4-isopropyl-phenyl)-methyl]-pyridin-3-yl}-butan-2-ol | 0.54 | 383.36 | none | 17 |
| 53 | 1-(2-{5-[(R)-(1,3-Dimethyl-azetidin-3-yl)-hydroxy-(4-isopropyl-phenyl)-methyl]-pyridin-3-yl}-ethyl)-cyclopentanol | 0.62 | 423.1 | none | 18 |
| 54 | 1-(2-{5-[(R)-(1,3-Dimethyl-azetidin-3-yl)-hydroxy-(4-isopropyl-phenyl)-methyl]-pyridin-3-yl}-ethyl)-cyclopropanol | 0.56 | 395.16 | (IX) | 19 |
| 55 | 3-(2-{5-[(R)-(1,3-Dimethyl-azetidin-3-yl)-hydroxy-(4-isopropyl-phenyl)-methyl]-pyridin-3-yl}-ethyl)-3-hydroxy-azetidine-1-carboxylic acid tert-butyl ester | 0.65 | 510.38 | none | 20 |
| 56 | 1-(2-{5-[(R)-(1,3-Dimethyl-azetidin-3-yl)-hydroxy-(4-isopropyl-phenyl)-methyl]-pyridin-3-yl}-ethyl)-cyclobutanol | 0.59 | 409.37 | none | 21 |
| 57 | 4-{5-[(R)-(1,3-Dimethyl-azetidin-3-yl)-hydroxy-(4-isopropyl-phenyl)-methyl]-pyridin-3-yl}-butan-1-ol | 0.54 | 383.33 | none | 22 |
| 58 | (R)-(1,3-Dimethyl-azetidin-3-yl)-(4-isopropyl-phenyl)-{5-[2-(1-methyl-1H-pyrazol-4-yl)-ethyl]-pyridin-3-yl}-methanol | 0.59 | 419.32 | (IX) | 23 |
| 59 | 3-{5-[(R)-(1,3-Dimethyl-azetidin-3-yl)-hydroxy-(4-isopropyl-phenyl)-methyl]-pyridin-3-yl}-1-phenyl-propan-1-ol | 0.64 | 445.26 | (VI) | 24 |

-continued

| Example N° | Name | $t_R$ | [M + H]$^+$ | Prep LC-MS | Precursor Example |
|---|---|---|---|---|---|
| 60 | 4-{5-[(R)-(1,3-Dimethyl-azetidin-3-yl)-hydroxy-(4-isopropyl-phenyl)-methyl]-pyridin-3-yl}-2-phenyl-butan-2-ol | 0.66 | 459.26 | (VI) | 25 |
| 61 | 1-{5-[(R)-(1,3-Dimethyl-azetidin-3-yl)-hydroxy-(4-isopropyl-phenyl)-methyl]-pyridin-3-yl}-4-methyl-pentan-3-ol | 0.62 | 411.29 | (VI) | 26 |
| 62 | 4-(2-{5-[(R)-(1,3-Dimethyl-azetidin-3-yl)-hydroxy-(4-isopropyl-phenyl)-methyl]-pyridin-3-yl}-ethyl)-tetrahydro-pyran-4-ol | 0.54 | 439.26 | (V) | 27 |
| 63 | 3-{5-[(R)-(1,3-Dimethyl-azetidin-3-yl)-hydroxy-(4-isopropyl-phenyl)-methyl]-pyridin-3-yl}-1-(tetrahydro-pyran-4-yl)-propan-1-ol | 0.57 | 453.24 | (V) | 28 |
| 64 | 3-{5-[(R)-(1,3-Dimethyl-azetidin-3-yl)-hydroxy-(4-isopropyl-phenyl)-methyl]-pyridin-3-yl}-1-(1,3-dimethyl-1H-pyrazol-4-yl)-propan-1-ol | 0.55 | 463.25 | (V) | 29 |
| 65 | (R)-(1,3-Dimethyl-azetidin-3-yl)-(4-isopropyl-phenyl)-{5-[2-(tetrahydro-pyran-4-yl)-ethyl]-pyridin-3-yl}-methanol | 0.62 | 423.09 | (V) | 30 |
| 66 | 3-{5-[(R)-(1,3-Dimethyl-azetidin-3-yl)-hydroxy-(4-isopropyl-phenyl)-methyl]-pyridin-3-yl}-1-(2-methyl-thiazol-4-yl)-propan-1-ol | 0.58 | 465.97 | (V) | 31 |
| 67 | 4-{5-[(R)-(1,3-Dimethyl-azetidin-3-yl)-hydroxy-(4-isopropyl-phenyl)-methyl]-pyridin-3-yl}-2-(3-fluoro-phenyl)-butan-2-ol | 0.69 | 477.23 | none | 32 |
| 68 | 4-{5-[(R)-(1,3-Dimethyl-azetidin-3-yl)-hydroxy-(4-isopropyl-phenyl)-methyl]-pyridin-3-yl}-2-(4-methoxy-phenyl)-butan-2-ol | 0.66 | 489.05 | none | 33 |
| 69 | 4-{5-[(R)-(1,3-Dimethyl-azetidin-3-yl)-hydroxy-(4-isopropyl-phenyl)-methyl]-pyridin-3-yl}-2-(2-methoxy-phenyl)-butan-2-ol | 0.69 | 489.24 | none | 34 |
| 70 | 4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-butan-2-ol | 0.56 | 463.08 | none | 35 |
| 71 | 4-{5-[(R)-(1,3-Dimethyl-azetidin-3-yl)-hydroxy-(4-isopropyl-phenyl)-methyl]-pyridin-3-yl}-2-(2-methyl-thiazol-4-yl)-butan-2-ol | 0.60 | 480.08 | none | 36 |
| 72 | 4-{5-[(R)-(1,3-Dimethyl-azetidin-3-yl)-hydroxy-(4-isopropyl-phenyl)-methyl]-pyridin-3-yl}-2-(6-methoxy-pyridin-2-yl)-butan-2-ol | 0.68 | 490.2 | (IX) | 37 |
| 73 | 4-{5-[(R)-(1,3-Dimethyl-azetidin-3-yl)-hydroxy-(4-isopropyl-phenyl)-methyl]-pyridin-3-yl}-2-pyrimidin-2-yl-butan-2-ol | 0.59 | 461.19 | (IX) | 38 |
| 74 | 4-{5-[(R)-(1,3-Dimethyl-azetidin-3-yl)-hydroxy-(4-isopropyl-phenyl)-methyl]-pyridin-3-yl}-2-(1,5-di methyl-1H-pyrazol-3-yl)-butan-2-ol | 0.59 | 477.22 | none | 39 |
| 75 | 4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-butan-2-ol | 0.60 | 475.19 | none | 40 |
| 76 | 3-{5-[(R)-(1,3-Dimethyl-azetidin-3-yl)-hydroxy-(4-isopropyl-phenyl)-methyl]-pyridin-3-yl}-1-(1,5-dimethyl-1H-pyrazol-3-yl)-propan-1-ol | 0.57 | 463.20 | (V) | 41 |
| 77 | 8-(2-{5-[(R)-(1,3-Dimethyl-azetidin-3-yl)-hydroxy-(4-isopropyl-phenyl)-methyl]-pyridin-3-yl}-ethyl)-5,6,7,8-tetrahydro-quinolin-8-ol | 0.53 | 486.18 | (IX) | 42 |
| 78 | 7-(2-{5-[(R)-(1,3-Dimethyl-azetidin-3-yl)-hydroxy-(4-isopropyl-phenyl)-methyl]-pyridin-3-yl}-ethyl)-6,7-dihydro-5H-[1]pyrindin-7-ol | 0.55 | 472.17 | (IX) | 43 |
| 79 | 1-{5-[(R)-(1,3-Dimethyl-azetidin-3-yl)-hydroxy-(4-isopropyl-phenyl)-methyl]-pyridin-3-yl}-3-pyridin-2-yl-pentan-3-ol | 0.54 | 474.19 | (IX) | 44 |
| 80 | 1-{5-[(R)-(1,3-Dimethyl-azetidin-3-yl)-hydroxy-(4-isopropyl-phenyl)-methyl]-pyridin-3-yl}-3-(6-methoxy-pyridin-2-yl)-pentan-3-ol | 0.72 | 504.15 | (IX) | 45 |
| 81 | (R)-(1,3-Dimethyl-azetidin-3-yl)-{5-[2-(1H-indol-2-yl)-ethyl]-pyridin-3-yl}-(4-isopropyl-phenyl)-methanol | 0.71 | 453.94 | none | 46 |

Example 82: (R)-(4-Cyclopropyl-phenyl)-(1,3-dimethyl-azetidin-3-yl)-{5-[3-(tetrahydro-pyran-4-yl)-[1,2,4]oxadiazol-5-yl]-pyridin-3-yl}-methanol 82.1. 3—((R)-(4-Cyclopropyl-phenyl)-hydroxy-{5-[3-(tetra hydro-pyran-4-yl)-[1,2,4]oxadiazol-5-yl]-pyridin-3-yl}-methyl)-3-methyl-azetidine-1-carboxylic acid tert-butyl ester A vial was charged with Example E1.2 (50 mg), Example E2.1 (24.7 mg), and HOBt.$H_2O$ (23.4 mg). Dioxane (1.1 mL) and DIPEA (0.039 mL) were added followed by EDC. HCl (28.7 mg). The reaction mixture was heated at 90° C. until completion of the reaction. The reaction mixture was cooled down to RT and partitioned between DCM and sat. aq. $NaHCO_3$. The org. layer was filtered over a phase separator and concentrated in vacuo. The residue (105 mg) was purified by Prep LC-MS (XII) to afford the title product as a white solid (27.5 mg). LC-MS (A): $t_R$=1.09 min; $[M+H]^+$: 547.25.

82.2. (R)-(4-Cyclopropyl-phenyl)-(3-methyl-azetidin-3-yl)-{5-[3-(tetra hydro-pyran-4-yl)-[1,2,4]oxadiazol-5-yl]-pyridin-3-yl}-methanol, hydrochloride salt Example 82.1 (27.5 mg) was dissolved with HCl in dioxane (4M, 0.13 mL). The reaction mixture was stirred at RT until completion, was concentrated in vacuo, dried under HV and used without further purification. LC-MS (A): $t_R$=0.74 min; $[M+H]^+$: 447.33.

82.3. (R)-(4-Cyclopropyl-phenyl)-(1,3-dimethyl-azetidin-3-yl)-{5-[3-(tetrahydro-pyran-4-yl)-[1,2,4]oxadiazol-5-yl]-pyridin-3-yl}-methanol The title compound was prepared starting from Example 82.2, and following the procedure described in Example D1.1 step D1.1.5. LC-MS (B): $t_R$=0.68 min; $[M+H]^+$: 461.40.

Example 83 to Example 93 were synthesized starting from the appropriate compounds of Formula (E1) and (E2) and following the three-step procedure described in Example 82, and were purified by Prep LC-MS at the end of the sequence if needed. The precursors of Formula (E1) and (E2) are indicated in the table below unless commercially available. The Prep LC-MS methods and the LC-MS data are listed in the table below. The LC-MS conditions used were LC-MS (B) except for Example 92 where the LC-MS conditions used were LC-MS (A).

| Example N° | Name | $t_R$ | $[M+H]^+$ | (E1)/ (E2) | Prep LC-MS |
|---|---|---|---|---|---|
| 83 | (R)-(4-Cyclopropyl-phenyl)-(1,3-dimethyl-azetidin-3-yl)-{5-[3-(2-methoxy-1,1-dimethyl-ethyl)-[1,2,4]oxadiazol-5-yl]-pyridin-3-yl}-methanol | 0.780 | 463.3 | E1.2 E2.2 | none |
| 84 | (R)-[5-(3-Cyclobutoxymethyl-[1,2,4]oxadiazol-5-yl)-pyridin-3-yl]-(4-cyclopropyl-phenyl)-(1,3-dimethyl-azetidin-3-yl)-methanol | 0.786 | 461.3 | E1.2 — | (XIV) |
| 85 | (R)-(1,3-Dimethyl-azetidin-3-yl)-(4-propyl-phenyl)-{5-[3-(tetrahydro-pyran-4-yloxymethyl)-[1,2,4]oxadiazol-5-yl]-pyridin-3-yl}-methanol | 0.734 | 493.3 | E1.3 — | (IX) |
| 86 | (R)-(1,3-Dimethyl-azetidin-3-yl)-(4-propyl-phenyl)-{5-[3-(tetrahydro-pyran-4-yl)-[1,2,4]oxadiazol-5-yl]-pyridin-3-yl}-methanol | 0.743 | 463.3 | E1.3 — | none |
| 87 | (R)-[5-(3-Cyclobutoxymethyl-[1,2,4]oxadiazol-5-yl)-pyridin-3-yl]-(1,3-dimethyl-azetidin-3-yl)-(4-propyl-phenyl)-methanol | 0.840 | 463.3 | E1.3 — | none |
| 88 | (R)-(1,3-Dimethyl-azetidin-3-yl)-(4-isopropyl-phenyl)-{5-[3-(tetrahydro-pyran-4-yl)-[1,2,4]oxadiazol-5-yl]-pyridin-3-yl}-methanol | 0.718 | 463.4 | E1.1 — | (IX) |
| 89 | (R)-(1,3-Dimethyl-azetidin-3-yl)-(4-isopropyl-phenyl)-[5-(3-morpholin-4-ylmethyl-[1,2,4]oxadiazol-5-yl)-pyridin-3-yl]-methanol | 0.588 | 478.3 | E1.1 E2.5 | (VI) |
| 90 | (R)-(1,3-Dimethyl-azetidin-3-yl)-{5-[3-(2,6-dimethyl-morpholin-4-ylmethyl)-[1,2,4]oxadiazol-5-yl]-pyridin-3-yl}-(4-isopropyl-phenyl)-methanol | 0.669 | 506.4 | E1.1 E2.6 | (VI) |
| 91 | (R)-(1,3-Dimethyl-azetidin-3-yl)-(4-isopropyl-phenyl)-{5-[3-(4-methyl-tetrahydro-pyran-4-yl)-[1,2,4]oxadiazol-5-yl]-pyridin-3-yl}-methanol | 0.777 | 477.3 | E1.1 E2.7 | (IX) |
| 92 | (R)-(1,3-Dimethyl-azetidin-3-yl)-(4-isopropyl-phenyl)-{5-[(1S,2S,4R)-3-(7-oxa-bicyclo[2.2.1]hept-2-yl)-[1,2,4]oxadiazol-5-yl]-pyridin-3-yl}-methanol | 0.78 | 475.29 | E1.1 E2.8 | (IX) |
| 93 | (R)-(1,3-Dimethyl-azetidin-3-yl)-(4-isopropyl-phenyl)-{5-[3-(tetrahydro-pyran-4-yloxymethyl)-[1,2,4]oxadiazol-5-yl]-pyridin-3-yl}-methanol | 0.720 | 493.3 | E1.1 — | (IX) |

Example 94: (R)-(1,3-Dimethyl-azetidin-3-yl)-(4-isopropyl-phenyl)-[5-(3-morpholin-4-yl-[1,2,4]oxadiazol-5-yl)-pyridin-3-yl]-methanol 94.1. 3-[(R)-[5-(3-Amino-[1,2,4]oxadiazol-5-yl)-pyridin-3-yl]-hydroxy-(4-isopropyl-phenyl)-methyl]-3-methyl-azetidine-1-carboxylic acid tert-butyl ester The title compound was prepared starting from Example E1.1 and N-hydroxyguanidine sulfate and using the conditions described in Example 82 step 82.1. The material was purified by Prep LC-MS (VI). LC-MS (A): $t_R$=1.00 min; $[M+H]^+$: 480.39.

94.2. (R)-[5-(3-Chloro-[1,2,4]oxadiazol-5-yl)-pyridin-3-yl]-(4-isopropyl-phenyl)-(3-methyl-azetidin-3-yl)-methanol To an ice-cold solution of Example 94.1 (9 mg) in conc. HCl (37% fuming, 0.1 mL) was added a solution of sodium nitrite (1.31 mg) in water (0.05 mL). The reaction mixture was stirred at 0° C. for 1 h, diluted with water and quenched with solid $NaHCO_3$. The mixture was extracted with DCM and the combined org. layers were filtered over a phase separator, concentrated in vacuo and dried under HV to afford the title compound (7.5 mg) that was used without further purification. LC-MS (A): $t_R$=0.77 min; $[M+H]^+$: 399.28.

94.3. (R)-[5-(3-Chloro-[1,2,4]oxadiazol-5-yl)-pyridin-3-yl]-(1,3-dimethyl-azetidin-3-yl)-(4-isopropyl-phenyl)-methanol The title compound was synthesized starting from Example 94.3 and using the conditions described in Example F1.1 step F1.1.2. LC-MS (A): $t_R$=0.79 min; $[M+H]^+$: 413.3.

94.4. (R)-(1,3-Dimethyl-azetidin-3-yl)-(4-isopropyl-phenyl)-[5-(3-morpholin-4-yl-[1,2,4]oxadiazol-5-yl)-pyridin-3-yl]-methanol Example 94.3 (7.7 mg) was dissolved in EtOH (0.1 mL) and transferred in a sealed vial. Morpholine (33.2 µL) and DIPEA (64.4 µL) were added and the reaction mixture was heated at 90° C. for 4 h. The mixture was cooled down to RT, diluted in MeCN and purified by Prep LC-MS (IX) to afford the title compound as white solid (0.5 mg). LC-MS (A): $t_R$=0.76 min; $[M+H]^+$: 464.4.

Example 95: (R)-(4-Cyclopropyl-phenyl)-(1,3-dimethyl-azetidin-3-yl)-{5-[3-(4-methoxy-tetrahydro-pyran-4-yl)-[1,2,4]oxadiazol-5-yl]-pyridin-3-yl}-methanol 95.1. 3—((R)-(4-Cyclopropyl-phenyl)-hydroxy-{5-[3-(4-methoxy-tetrahydro-pyran-4-yl)-[1,2,4]oxadiazol-5-yl]-pyridin-3-yl}-methyl)-3-methyl-azetidine-1-carboxylic acid tert-butyl ester A sealed vial was charged with Example E1.2 (100 mg) and DMF (2.2 mL) was added, followed by DIPEA (0.12 mL) and PyBOP (182 mg). After stirring at RT for 15 min, Example E2.3 (79.4 mg) and $K_3PO_4$ (198 mg) were added. The reaction mixture was heated overnight at 100° C. The mixture was cooled down to RT, partitioned between DCM and water/sat. aq. $NaHCO_3$. The phases were separated, and the aq. layer was extracted twice with DCM. The org. layers were filtered over a phase separator and concentrated to dryness. The residue was purified by Prep LC-MS (XII) to afford the desired product as white solid (94.7 mg). LC-MS (A): $t_R$=1.08 min; $[M+H]^+$: 577.21.

95.2. (R)-(4-Cyclopropyl-phenyl)-{5-[3-(4-methoxy-tetra hydro-pyran-4-yl)-[1,2,4]oxadiazol-5-yl]-pyridin-3-yl}-(3-methyl-azetidin-3-yl)-methanol, hydrochloride salt Example 95.2 was prepared starting from Example 95.1 and following the procedure described in Example 82 step 82.2. LC-MS (A): $t_R$=0.72 min; $[M+H]^+$: 477.28.

95.3. (R)-(4-Cyclopropyl-phenyl)-(1,3-dimethyl-azetidin-3-yl)-{5-[3-(4-methoxy-tetrahydro-pyran-4-yl)-[1,2,4]oxadiazol-5-yl]-pyridin-3-yl}-methanol Example 95.3 was prepared starting from Example 95.2 and following the procedure described in Example D1.1 step D1.1.5. The material was purified by Prep LC-MS (IX). LC-MS (B): $t_R$=0.693 min; $[M+H]^+$: 491.3.

Example 96 to Example 102 were synthesized starting from the appropriate compounds of Formula (E1) and (E2) and following the three-step procedure described in Example 95, and were purified by Prep LC-MS at the end of the sequence if needed. The precursors of Formula (E1) and (E2) are indicated in the table below unless commercially available. The Prep LC-MS methods and the LC-MS data are listed in the table below. The LC-MS conditions used were LC-MS (B).

| Example N° | Name | $t_R$ | $[M+H]^+$ | (E1)/ (E2) | Prep LC-MS |
|---|---|---|---|---|---|
| 96 | (R)-(4-Cyclopropyl-phenyl)-(1,3-dimethyl-azetidin-3-yl)-{5-[3-(3-hydroxymethyl-bicyclo[1.1.1]pent-1-yl)-[1,2,4]oxadiazol-5-yl]-pyridin-3-yl}-methanol | 0.646 | 473.4 | E1.2 E2.4 | (IX) |
| 97 | (R)-(1,3-Dimethyl-azetidin-3-yl)-{5-[3-(3-hydroxymethyl-bicyclo[1.1.1] pent-1-yl)-[1,2,4]oxadiazol-5-yl]-pyridin-3-yl}-(4-isopropyl-phenyl)-methanol | 0.695 | 475.0 | E1.1 E2.4 | (IX) |
| 98 | 2-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-2-methyl-propan-1-ol | 0.709 | 451.3 | E1.1 E2.9 | (VI) |
| 99 | 2-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-propan-2-ol | 0.671 | 437.3 | E1.1 E2.10 | (V) |
| 100 | (R)-(1,3-Dimethyl-azetidin-3-yl)-(4-isopropyl-phenyl)-{5-[3-(1-methoxy-1-methyl-ethyl)-[1,2,4]oxadiazol-5-yl]-pyridin-3-yl}-methanol | 0.767 | 451.3 | E1.1 E2.11 | (VI) |

-continued

| Example N° | Name | $t_R$ | [M + H]$^+$ | (E1)/ (E2) | Prep LC-MS |
|---|---|---|---|---|---|
| 101 | (R)-(1,3-Dimethyl-azetidin-3-yl)-(4-isopropyl-phenyl)-{5-[3-(1-methoxy-cyclobutyl)-[1,2,4]oxadiazol-5-yl]-pyridin-3-yl}-methanol | 0.808 | 463.3 | E1.1 E2.12 | (VII) |
| 102 | 1-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-2-methyl-propan-2-ol | 0.684 | 451.3 | E1.1 E2.13 | (V) |

Example 103: (R)-(1,3-Dimethyl-azetidin-3-yl)-(4-isopropyl-phenyl)-[5-(5-methanesulfonylmethyl-[1,2,4]oxadiazol-3-yl)-pyridin-3-yl]-methanol A mixture of Example D2.1 (25.4 mg), 2-(methylsulfonyl)acetic acid (10.7 mg), PyBOP (53.9 mg), $K_3PO_4$ (29.8 mg) and DIPEA (18 μL) in DMF (0.8 mL) was heated at 85° C. for 16 h, cooled down to RT, and water (200 μL) was added. The resulting solution was purified by Prep LC-MS (IX) then (V) to afford the desired product. LC-MS (B): $t_R$=0.646 min; [M+H]$^+$: 471.3.

Example 104 to Example 133 were synthesized starting from Example D2.1 and the appropriate carboxylic acid of Formula (D3), and following the procedure described in Example 103. The Prep LC-MS methods used are indicated in the table below. LC-MS data of Example 104 to 133 are listed in the table below. The LC-MS conditions used were LC-MS (B).

| Example N° | Name | $t_R$ | [M + H]$^+$ | Prep LC-MS |
|---|---|---|---|---|
| 104 | (R)-(1,3-Dimethyl-azetidin-3-yl)-(4-isopropyl-phenyl)-{5-[5-(2-methoxy-ethyl)-[1,2,4]oxadiazol-3-yl]-pyridin-3-yl}-methanol | 0.702 | 437.4 | (IX) + (VI) |
| 105 | (R)-(1,3-Dimethyl-azetidin-3-yl)-(4-isopropyl-phenyl)-[5-(5-methoxymethyl-[1,2,4]oxadiazol-3-yl)-pyridin-3-yl]-methanol | 0.703 | 423.3 | (IX) + (VI) |
| 106 | (R)-(1,3-Dimethyl-azetidin-3-yl)-(4-isopropyl-phenyl)-{5-[5-(tetrahydro-furan-3-yl)-[1,2,4]oxadiazol-3-yl]-pyridin-3-yl}-methanol | 0.71 | 449.3 | (IX) + (VI) |
| 107 | (R)-(1,3-Dimethyl-azetidin-3-yl)-(4-isopropyl-phenyl)-{5-[5-(tetrahydro-pyran-4-yl)-[1,2,4]oxadiazol-3-yl]-pyridin-3-yl}-methanol | 0.731 | 463.3 | (IX) + (VI) |
| 108 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclohexanol | 0.806 | 477.3 | (IX) + (VII) |
| 109 | (R)-[5-(5-tert-Butoxymethyl-[1,2,4]oxadiazol-3-yl)-pyridin-3-yl]-(1,3-dimethyl-azetidin-3-yl)-(4-isopropyl-phenyl)-methanol | 0.841 | 465.3 | (XIV) + (VIII) |
| 110 | (R)-(1,3-Dimethyl-azetidin-3-yl)-(4-isopropyl-phenyl)-{5-[5-(tetrahydro-pyran-4-ylmethyl)-[1,2,4]oxadiazol-3-yl]-pyridin-3-yl}-methanol | 0.751 | 477.3 | (IX) + (VI) |
| 111 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclohexanol | 0.69 | 477.3 | (IX) + (VI) |
| 112 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclohexanol | 0.806 | 491.4 | (IX) + (VII) |
| 113 | (R)-(1,3-Dimethyl-azetidin-3-yl)-(4-isopropyl-phenyl)-{5-[5-(1-methoxy-cyclobutyl)-[1,2,4]oxadiazol-3-yl]-pyridin-3-yl}-methanol | 0.824 | 463.3 | (XIV) + (VIII) |
| 114 | (R)-(1,3-Dimethyl-azetidin-3-yl)-(4-isopropyl-phenyl)-{5-[5-(6-oxa-spiro[2.5]oct-1-yl)-[1,2,4]oxadiazol-3-yl]-pyridin-3-yl}-methanol | 0.779 | 489.4 | (XIV) + (VII) |
| 115 | (R)-(1,3-Dimethyl-azetidin-3-yl)-(4-isopropyl-phenyl)-{5-[5-(tetrahydro-pyran-3-yl)-[1,2,4]oxadiazol-3-yl]-pyridin-3-yl}-methanol | 0.759 | 463.3 | (IX) + (VII) |
| 116 | (R)-(1,3-Dimethyl-azetidin-3-yl)-(4-isopropyl-phenyl)-(5-{5-[1-(tetrahydro-furan-2-yl)methyl]-[1,2,4]oxadiazol-3-yl}-pyridin-3-yl)-methanol | 0.741 | 463.4 | (IX) + (VII) |
| 117 | (R)-2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1,1-trifluoro-propan-2-ol | 0.778 | 491.2 | (IX) + (VI) |
| 118 | (R)-(1,3-Dimethyl-azetidin-3-yl)-(4-isopropyl-phenyl)-{5-[5-(1-methoxy-1-methyl-ethyl)-[1,2,4]oxadiazol-3-yl]-pyridin-3-yl}-methanol | 0.785 | 451.3 | (IX) + (VII) |
| 119 | (R)-{5-[5-((R)-Cyclohexyl-hydroxy-methyl)-[1,2,4]oxadiazol-3-yl]-pyridin-3-yl}-(1,3-dimethyl-azetidin-3-yl)-(4-isopropyl-phenyl)-methanol | 0.847 | 491.5 | (XIV) + (VIII) |
| 120 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclopropanol | 0.675 | 435.2 | (IX) + (XV) |

-continued

| Example N° | Name | $t_R$ | [M + H]$^+$ | Prep LC-MS |
|---|---|---|---|---|
| 121 | 2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-propan-2-ol | 0.685 | 437.3 | (IX) + (VI) |
| 122 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclopentanol | 0.753 | 463.3 | (IX) + (VI) |
| 123 | 3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclobutanol | 0.652 | 449.4 | (IX) + (V) |
| 124 | (R)-(1,3-Dimethyl-azetidin-3-yl)-{5-[5-(4-fluoro-tetrahydro-pyran-4-yl)-[1,2,4]oxadiazol-3-yl]-pyridin-3-yl}-(4-isopropyl-phenyl)-methanol | 0.772 | 481.3 | (IX) + (VII) |
| 125 | (R)-(1,3-Dimethyl-azetidin-3-yl)-{5-[5-((2R,4R,6S)-2,6-dimethyl-tetrahydro-pyran-4-yl)-[1,2,4]oxadiazol-3-yl]-pyridin-3-yl}-(4-isopropyl-phenyl)-methanol | 0.827 | 491.3 | (XIV) + (VIII) |
| 126 | (R)-(1,3-Dimethyl-azetidin-3-yl)-(4-isopropyl-phenyl)-{5-[5-(tetrahydro-pyran-4-yloxymethyl)-[1,2,4]oxadiazol-3-yl]-pyridin-3-yl}-methanol | 0.728 | 493.3 | (IX) + (VI) |
| 127 | (R)-(1,3-Dimethyl-azetidin-3-yl)-(4-isopropyl-phenyl)-(5-{5-[1-methyl-1-(tetrahydro-pyran-4-yl)-ethyl]-[1,2,4]oxadiazol-3-yl}-pyridin-3-yl)-methanol | 0.84 | 505.4 | (XIV) + (V) |
| 128 | (R)-(1,3-Dimethyl-azetidin-3-yl)-(4-isopropyl-phenyl)-(5-{5-[2-(tetrahydro-pyran-4-yl)-ethyl]-[1,2,4]oxadiazol-3-yl}-pyridin-3-yl)-methanol | 0.792 | 491.3 | (XIV) + (VII) |
| 129 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclobutanol | 0.716 | 449.3 | (IX) + (VI) |
| 130 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-2-methyl-propan-2-ol | 0.69 | 451.3 | (IX) + (VI) |
| 131 | (R)-(1,3-Dimethyl-azetidin-3-yl)-(4-isopropyl-phenyl)-{5-[5-(7-oxa-bicyclo[2.2.1]hept-2-yl)-[1,2,4]oxadiazol-3-yl]-pyridin-3-yl}-methanol | 0.76 | 475.3 | (IX) + (VII) |
| 132 | (R)-(1,3-Dimethyl-azetidin-3-yl)-(4-isopropyl-phenyl)-{5-[5-(4-methyl-tetrahydro-pyran-4-yloxymethyl)-[1,2,4]oxadiazol-3-yl]-pyridin-3-yl}-methanol | 0.77 | 507.3 | (IX) + (VI) |
| 133 | (R)-(1,3-Dimethyl-azetidin-3-yl)-(4-isopropyl-phenyl)-[5-(5-oxetan-3-yl-[1,2,4]oxadiazol-3-yl)-pyridin-3-yl]-methanol | 0.667 | 435.3 | (IX) + (VII) |

Example 134: (R)-(1,3-Dimethyl-azetidin-3-yl)-(4-isopropyl-phenyl)-{5-[5-(2-methoxy-1,1-dimethyl-ethyl)-[1,2,4]oxadiazol-3-yl]-pyridin-3-yl}-methanol A mixture of Example D2.1 (40 mg), 3-methoxy-2,2-dimethylpropanoic acid (15.8 mg), PyBOP (86.8 mg), $K_3PO_4$(92.2 mg) and DIPEA (55.8 µL) in DMF (1 mL) was heated at 80° C. for 20 h, cooled down to RT, quenched with water and extracted with DCM. The combined organic layers were dried ($MgSO_4$), filtered off and concentrated in vacuo. The residue was purified by Prep LC-MS (XVIII) and (VIII) to afford 25 mg of the desired product. LC-MS (B): $t_R$=0.834 min; [M+H]$^+$: 465.3.

Example 135 to 138 were synthesized starting from Example D2.1 and the appropriate carboxylic acid of Formula (D3), and following the procedure described in Example 134. LC-MS data of Example 135 to 138 are listed in the table below. The LC-MS conditions used were LC-MS (B). The Prep LC-MS methods used are indicated in the table below.

| Example N° | Name | $t_R$ | [M + H]$^+$ | Prep LC-MS |
|---|---|---|---|---|
| 135 | 2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-2-methyl-propan-1-ol | 0.179 | 451.3 | (XII) + (VI) |
| 136 | (R)-(1,3-Dimethyl-azetidin-3-yl)-(4-isopropyl-phenyl)-{5-[5-(2-methoxy-2-methyl-propyl)-[1,2,4]oxadiazol-3-yl]-pyridin-3-yl}-methanol | 0.786 | 465.3 | (XVIII) + (VII) |
| 137 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclobutanol | 0.727 | 463.3 | (XIII) + (VI) + SFC(XIII) + (VI) |
| 138 | (R)-(1,3-Dimethyl-azetidin-3-yl)-(4-isopropyl-phenyl)-{5-[5-(1-methoxymethyl-cyclopropylmethyl)-[1,2,4]oxadiazol-3-yl]-pyridin-3-yl}-methanol | 0.801 | 477.3 | (XIII) |

Example 139: (R)-(1,3-Dimethyl-azetidin-3-yl)-(4-isopropyl-phenyl)-{5-[5-(2-pyrazol-1-yl-ethyl)-[1,2,4]oxadiazol-3-yl]-pyridin-3-yl}-methanol The title compound was obtained starting from Example D2.1 and 3-(1H-pyrazol-1-yl)propanoic acid, and following the procedure described in Example 82 step 82.1, but heating the reaction mixture at 100° C. The crude material was purified by Prep LC-MS (IX). LC-MS (A): $t_R$=0.75 min; $[M+H]^+$: 473.3.

Example 140: (R)—N-(2-(3-(5-((1,3-dimethylazetidin-3-yl)(hydroxy)(4-isopropylphenyl)methyl)pyridin-3-yl)-1,2,4-oxadiazol-5-yl)ethyl)acetamide-2,2,2-$d_3$ 140.1. 3-[(R)-{5-[5-(2-Benzyloxycarbonylamino-ethyl)-[1,2,4]oxadiazol-3-yl]-pyridin-3-yl}-hydroxy-(4-isopropyl-phenyl)-methyl]-3-methyl-azetidine-1-carboxylic acid tert-butyl ester The title compound was obtained starting from Example D2.2 and Cbz-beta-Alanine, and following the procedure described in Example 134. LC-MS (A): $t_R$=1.12 min; $[M+H]^+$: 642.18.

140.2. 3-[(R)-{5-[5-(2-Amino-ethyl)-[1,2,4]oxadiazol-3-yl]-pyridin-3-yl}-hydroxy-(4-isopropyl-phenyl)-methyl]-3-methyl-azetidine-1-carboxylic acid tert-butyl ester A mixture of Example 140.1 (76.4 mg) and Pd/C (9.88 mg) in EtOH (2 mL) under $H_2$ atmosphere was stirred at RT for 6 h, filtered over a glass paper fiber filter and the filtrate was concentrated in vacuo and dried under HV to afford 30.2 mg of the title compound. LC-MS (A): $t_R$=0.81 min; $[M+H]^+$: 508.01.

140.3. Cert-Butyl (R)-3-((5-(5-(2-(acetamido-2,2,2-d3)ethyl)-1,2,4-oxadiazol-3-yl)pyridin-3-yl)(hydroxy)(4-isopropylphenyl)methyl)-3-methylazetidine-1-carboxylate A mixture of Example 140.2 (30.2 mg), acetic acid-2,2,2-$d_3$ (99 atom % D, 10.2 μL), HOBt (9.65 mg), DIPEA (30.6 μL) and EDC·HCl (13.7 mg) in DCM (1 mL) was stirred overnight at RT, quenched with aq. sat. $NaHCO_3$ and extracted with DCM. The combined org. layers were dried ($MgSO_4$), filtered off and concentrated in vacuo to afford 32.9 mg of the title compound. LC-MS (A): $t_R$=0.99 min; $[M+H]^+$: 533.25.

140.4. (R)—N-(2-(3-(5-(hydroxy(4-isopropylphenyl)(3-methylazetidin-3-yl)methyl)pyridin-3-yl)-1,2,4-oxadiazol-5-yl)ethyl)acetamide-2,2,2-$d_3$, hydrochloride salt A solution of Example 140.3 (32.9 mg) in HCl in dioxane (4M, 2 mL) was stirred at RT for 30 min, concentrated in vacuo and dried under HV to afford 29.1 mg of the title compound. LC-MS (A): $t_R$=0.66 min; $[M+H]^+$: 453.06.

140.5. (R)—N-(2-(3-(5-((1,3-dimethylazetidin-3-yl)(hydroxy)(4-isopropylphenyl)methyl)pyridin-3-yl)-1,2,4-oxadiazol-5-yl)ethyl)acetamide-2,2,2-$d_3$ The title compound was obtained starting from Example 140.4, and following the procedure described in Example D1.1 step D1.1.5. The reaction mixture was filtered off and the filtrate was purified by Prep LC-MS (IX) and (V) to afford the desired compound (6.9 mg) as a white powder. LC-MS (B): $t_R$=0.617 min; $[M+H]^+$: 467.3.

Example 141 to Example 143 were synthesized starting from Example D2.2, and following the five-step procedure described in Example 140, using the appropriate carboxylic acid derivative of Formula (D3) in the first step. The Prep LC-MS methods and the LC-MS data are listed in the table below. The LC-MS conditions used were LC-MS (B).

| Example N° | Name | $t_R$ | $[M+H]^+$ | Prep LC-MS |
|---|---|---|---|---|
| 141 | (R)-N-(1-(3-(5-((1,3-dimethylazetidin-3-yl)(hydroxy)(4-isopropylphenyl)methyl)pyridin-3-yl)-1,2,4-oxadiazol-5-yl)-2-methylpropan-2-yl)acetamide-2,2,2-d3 | 0.696 | 495.4 | (IX) + (VI) |
| 142 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2-hydroxy-ethanone | 0.655 | 520.3 | (IX) + (VI) |
| 143 | (R)-1-(4-(3-(5-((1,3-dimethylazetidin-3-yl)(hydroxy)(4-isopropylphenyl)methyl)pyridin-3-yl)-1,2,4-oxadiazol-5-yl)piperidin-1-yl)eth an-1-one-2,2,2-d3 | 0.671 | 507.5 | (IX) + (VI) |

Example 144: N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-ethyl]-2-hydroxy-N-methyl-acetamide 144.1. 3-(tert-Butoxycarbonyl-methyl-amino)-propionic acid benzyl ester To a solution of 3-[(tert-butoxycarbonyl)(methyl)amino] propanoic acid (100 mg) in DMF (1 mL) were added benzyl bromide (58.4 µL) and $K_2CO_3$ (66.6 mg). The reaction mixture was stirred at RT for 2 h, quenched with water and extracted with EA. The org. layer was dried ($MgSO_4$), filtered off, concentrated in vacuo and dried under HV to afford 141 mg of the title compound. LC-MS (A): $t_R$=0.99 min; $[M+H]^+$: 294.1.

144.2. 3-Methylamino-propionic acid benzyl ester, hydrochloride salt

A solution of Example 144.1 (141 mg) in HCl in dioxane (4M, 3 mL) was stirred at RT for 30 min, concentrated in vacuo and dried under HV to afford 46.6 mg of the title compound. LC-MS (A): $t_R$=0.51 min; $[M+H]^+$: 194.21.

144.3. 3-[(2-Hydroxy-acetyl)-methyl-amino]-propionic acid benzyl ester

The title compound was obtained starting from Example 144.2 and glycolic acid, and following the procedure described in Example 140 step 140.3. LC-MS (A): $t_R$=0.67 min; $[M+H]^+$: 252.07.

144.4. 3-[(2-Hydroxy-acetyl)-methyl-amino]-propionic acid

A mixture of Example 144.3 (60.6 mg) and Pd/C (19.9 mg) in EA (1 mL) under $H_2$ atmosphere was stirred at RT for 3 h. Additional Pd/C was added and the reaction mixture was stirred overnight at RT, filtered over a glass paper fiber filter. The filtrate was concentrated in vacuo and dried under HV to afford 19.4 mg of the desired compound. LC-MS (A): $t_R$=0.26 min; $[M+H]^+$: 162.2.

144.5. 3-[(R)-Hydroxy-[5-(5-{2-[(2-hydroxy-acetyl)-methyl-amino]-ethyl}-[1,2,4]oxadiazol-3-yl)-pyridin-3-yl]-(4-isopropyl-phenyl)-methyl]-3-methyl-azetidine-1-carboxylic acid tert-butyl ester The title compound was obtained starting from Example D2.2 and Example 144.4, and following the procedure described in Example 134, but with a second addition of reagents after the night and an additional night of stirring. LC-MS (A): $t_R$=0.97 min; $[M+H]^+$: 580.01.

144.6. 2-Hydroxy-N[2-(3-{5-[(R)-hydroxy-(4-isopropyl-phenyl)-(3-methyl-azetidin-3-yl)-methyl]-pyridin-3-yl}-[1,2,4]oxadiazol-5-yl)-ethyl]-N-methyl-acetamide, hydrochloride salt A solution of Example 144.5 (68.4 mg) in HCl in dioxane (4M, 2 mL) was stirred at RT for 1 h, concentrated in vacuo and dried under HV to afford 60.9 mg of the title compound. LC-MS (A): $t_R$=0.65 min; $[M+H]^+$: 480.0.

144.7. N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-ethyl]-2-hydroxy-N-methyl-acetamide The title compound was obtained starting from Example 144.6, and following the procedure described in Example 82 step 82.3, with a direct filtration of the reaction mixture and purification by Prep LC-MS (IX) and (VI) to afford 6.2 mg of the desired compound. LC-MS (B): $t_R$=0.616 min; $[M+H]^+$: 494.4.

Example 145: (R)—N-(2-(3-(5-((1,3-dimethylazetidin-3-yl)(hydroxy)(4-isopropylphenyl)methyl)pyridin-3-yl)-1,2,4-oxadiazol-5-yl)-ethyl)-N-methylacetamide-$d_3$ The title compound was obtained starting from Example 144.2, and following the procedure described in Example 144 step 144.3 to 144.7, using acetic acid-2,2,2-$d_3$ instead of glycolic acid in step 144.3. The crude material was purified by Prep LC-MS (IX) and (VI). LC-MS (B): $t_R$=0.651 min; $[M+H]^+$: 481.3.

Example 146: (1,3-Dimethyl-azetidin-3-yl)-(6-methoxy-pyridin-3-yl)-(4-trifluoromethoxy-phenyl)-methanol 5-Bromo-2-methoxypyridine (110 µL) and iPrMgCl·LiCl (1.3M in THF, 704 µL) were dissolved in THF (0.5 mL) and the resulting solution was stirred for 2 h at 60° C. A solution of Example B2.1 (100 mg) in THF (0.5 mL) was added, the resulting mixture was stirred for 4 h at RT and was quenched with aq. sat. $NH_4Cl$, diluted with water and extracted with DCM. The org. layers were evaporated to dryness. The resulting crude material was purified by Prep LC-MS (VI) to afford 50 mg of the title compound as brown solid. LC-MS (A): $t_R$=0.74 min; $[M+H]^+$: 383.20.

Example 147 to Example 149 were synthesized starting from the appropriate commercially available bromo derivative and following the procedure described in Example 146. Prep LC-MS conditions and LC-MS data of Example 147 to Example 149 are listed in the table below. The LC-MS conditions used were LC-MS (A). An additional purification step was performed with Example 147 (Preparative TLC, 0.5 mm, 254 nm, eluent DCM/MeOH 95/5+0.1% TEA).

| Example N° | Name | $t_R$ | $[M+H]^+$ | Prep LC-MS |
|---|---|---|---|---|
| 147 | (1,3-Dimethyl-azetidin-3-yl)-(6-phenoxy-pyridin-3-yl)-(4-trifluoromethoxy-phenyl)-methanol | 0.82 | 445.2 | (VII) |
| 148 | (1,3-Dimethyl-azetidin-3-yl)-(6-ethoxy-pyridin-3-yl)-(4-trifluoromethoxy-phenyl)-methanol | 0.53 | 367.23 | (V) |
| 149 | (1,3-Dimethyl-azetidin-3-yl)-(5-methyl-pyridin-3-yl)-(4-trifluoromethoxy-phenyl)-methanol | 0.75 | 397.25 | (VII) |

Example 150: (1,3-Dimethyl-azetidin-3-yl)-(4-propyl-phenyl)-(5-pyrrolidin-1-yl-pyridin-3-yl)-methanol 150.1. 3-[(Hydroxy-(4-propyl-phenyl)-(5-pyrrolidin-1-yl-pyridin-3-yl)-methyl]-3-methyl-azetidine-1-carboxylic acid tert-butyl ester The title compound was synthesized starting from Example C1.1 and 1-bromo-4-propylbenzene, following the procedure described in Example 146. The resulting crude material was purified by Prep LC-MS (VII). LC-MS (A): $t_R$=0.92 min; $[M+H]^+$: 466.13.

150.2. (3-Methyl-azetidin-3-yl)-(4-propyl-phenyl)-(5-pyrrolidin-1-yl-pyridin-3-yl)-methanol A solution of Example 150.1 (11 mg) in MeOH (0.1 mL) and HCl in dioxane (4M, 0.5 mL) was stirred for 4 h, was basified with 1M NaOH solution, diluted with water and extracted with DCM. The org. layers were evaporated to dryness to give 14 mg of the title compound as white solid. LC-MS (A): $t_R$=0.62 min; $[M+H]^+$: 366.35.

150.3. (1,3-Dimethyl-azetidin-3-yl)-(4-propyl-phenyl)-(5-pyrrolidin-1-yl-pyridin-3-yl)-methanol The title compound was synthesized starting from Example 150.2 and following the procedure described in Example F1.1 step F1.1.2. LC-MS (A): $t_R$=0.62 min; $[M+H]^+$: 380.41.

Example 151 to Example 157 were synthesized starting from the appropriate commercially available bromo derivative and following the three-step procedure described in Example 150. Prep LC-MS conditions and LC-MS data of Example 151 to Example 157 are listed in the table below. The LC-MS conditions used were LC-MS (A).

| Example N° | Name | $t_R$ | [M + H]$^+$ | Prep LC-MS |
|---|---|---|---|---|
| 151 | (1,3-Dimethyl-azetidin-3-yl)-(4-methoxy-phenyl)-(5-pyrrolidin-1-yl-pyridin-3-yl)-methanol | 0.53 | 368.36 | (XIII) |
| 152 | (1,3-Dimethyl-azetidin-3-yl)-(4-ethyl-phenyl)-(5-pyrrolidin-1-yl-pyridin-3-yl)-methanol | 0.58 | 366.36 | (XIII) |
| 153 | (1,3-Dimethyl-azetidin-3-yl)-phenyl-(5-pyrrolidin-1-yl-pyridin-3-yl)-methanol | 0.50 | 338.06 | (XIII) |
| 154 | (4-Cyclobutyl-phenyl)-(1,3-dimethyl-azetidin-3-yl)-(5-pyrrolidin-1-yl-pyridin-3-yl)-methanol | 0.65 | 392.38 | (XIII) |
| 155 | (4-Cyclobutoxy-phenyl)-(1,3-dimethyl-azetidin-3-yl)-(5-pyrrolidin-1-yl-pyridin-3-yl)-methanol | 0.61 | 408.36 | (XIII) |
| 156 | (1,3-Dimethyl-azetidin-3-yl)-(4-ethoxy-phenyl)-(5-pyrrolidin-1-yl-pyridin-3-yl)-methanol | 0.55 | 382.33 | (XVIII) |
| 157 | (4-tert-Butyl-phenyl)-(1,3-dimethyl-azetidin-3-yl)-(5-pyrrolidin-1-yl-pyridin-3-yl)-methanol | 0.85 | 394.44 | (IX) |

Example 158 to Example 161 were synthesized starting from Example $C_3$.1 and the appropriate bromo derivative, following the procedure described in Example A4.1 step A4.1.2. Prep LC-MS conditions and LC-MS data of Example 158 to Example 161 are listed in the table below. The LC-MS conditions used were LC-MS (A).

| Example N° | Name | $t_R$ | [M + H]$^+$ | Prep LC-MS |
|---|---|---|---|---|
| 158 | (1,3-Dimethyl-azetidin-3-yl)-(4-isopropoxy-phenyl)-(5-pyrrolidin-1-yl-pyridin-3-yl)-methanol | 0.58 | 396.41 | (IX) |
| 159 | (1,3-Dimethyl-azetidin-3-yl)-(5-pyrrolidin-1-yl-pyridin-3-yl)-[4-(1-trifluoromethyl-cyclopropyl)-phenyl]-methanol | 0.65 | 446.31 | (IX) |
| 160 | (1,3-Dimethyl-azetidin-3-yl)-[4-(1-methyl-cyclopropyl)-phenyl]-(5-pyrrolidin-1-yl-pyridin-3-yl)-methanol | 0.63 | 392.42 | (IX) |
| 161 | (4-Cyclopropoxy-phenyl)-(1,3-dimethyl-azetidin-3-yl)-(5-pyrrolidin-1-yl-pyridin-3-yl)-methanol | 0.58 | 394.36 | (IX) |

Example 162: (S)-[2-(3,3-Difluoro-pyrrolidin-1-yl)-pyridin-4-yl]-(1,3-dimethyl-azetidin-3-yl)-(4-isopropyl-phenyl)-methanol 162.1. 3—[(S)-[2-(3,3-Difluoro-pyrrolidin-1-yl)-pyridin-4-yl]-hydroxy-(4-isopropyl-phenyl)-methyl]-3-methyl-azetidine-1-carboxylic acid tert-butyl ester Example F1.4 (35 mg) and 3,3-difluoropyrrolidine (18.3 mg) were suspended in toluene (1 mL), and BINAP (3.03 mg), $Pd_2(dba)_3$ (1.53 mg) and NaOtBu (24.1 mg) were added. The reaction mixture was stirred for 4 h at 100° C., cooled down to RT, filtered off and evaporated to dryness. The residue was purified by Prep LC-MS (XIV) to afford 33.5 mg of the title compound as white solid. LC-MS (A): $t_R$=0.89 min; $[M+H]^+$: 502.31.

162.2. (S)-[2-(3,3-Difluoro-pyrrolidin-1-yl)-pyridin-4-yl]-(4-isopropyl-phenyl)-(3-methyl-azetidin-3-yl)-methanol, hydrochloride salt Example 162.1 (32.5 mg) was dissolved in HCl in dioxane (4M, 0.5 mL) and the reaction mixture was stirred for 4 h at RT and evaporated to dryness to give 42.7 mg of the title compound as colorless oil which was used without purification. LC-MS (A): $t_R$=0.59 min; $[M+H]^+$: 402.00.

162.3. (S)-[2-(3,3-Difluoro-pyrrolidin-1-yl)-pyridin-4-yl]-(1,3-dimethyl-azetidin-3-yl)-(4-isopropyl-phenyl)-methanol The title compound was synthesized starting from Example 162.2, and following the procedure described in Example F1.1 step F1.1.2. The crude material was purified by Prep LC-MS (IX). LC-MS (A): $t_R$=0.61 min; $[M+H]^+$: 416.25.

Example 163: (S)-[2-((3R,4S)-3,4-Difluoro-pyrrolidin-1-yl)-pyridin-4-yl]-(1,3-dimethyl-azetidin-3-yl)-(4-isopropyl-phenyl)-methanol 163.1. 3—[(S)-[2-((3R,4S)-3,4-Difluoro-pyrrolidin-1-yl)-pyridin-4-yl]-hydroxy-(4-isopropyl-phenyl)-methyl]-3-methyl-azetidine-1-carboxylic acid tert-butyl ester Example F1.7 (40 mg), cis-3,4-difluoropyrrolidine hydrochloride (68.7 mg) and DIPEA (159 μL) were dissolved in NMP (2 mL) and the mixture was stirred for 22 h at 150° C. DIPEA (159 μL) and cis-3,4-difluoropyrrolidine hydrochloride (68.7 mg) were added, the mixture was further stirred for 2 h at 150° C., and the solvent was evaporated in vacuo. The residue was purified by Prep LC-MS (IX) to afford 11.7 mg of the title compound as beige solid. LC-MS (A): $t_R$=0.89 min; $[M+H]^+$: 502.32.

163.2. (S)-[2-((3R,4S)-3,4-Difluoro-pyrrolidin-1-yl)-pyridin-4-yl]-(4-isopropyl-phenyl)-(3-methyl-azetidin-3-yl)-methanol, hydrochloride salt Example 163.1 (11.7 mg) was dissolved in HCl in dioxane (4M, 0.2 mL) and the mixture was stirred for 1 h at RT and evaporated to dryness to give 13 mg of the title compound as colorless oil, which was used without further purification. LC-MS (A): $t_R$=0.58 min; $[M+H]^+$: 402.01.

163.3. (S)-[2-((3R,4S)-3,4-Difluoro-pyrrolidin-1-yl)-pyridin-4-yl]-(1,3-dimethyl-azetidin-3-yl)-(4-isopropyl-phenyl)-methanol The title compound was synthesized starting from Example 163.2 and following the procedure described in Example F1.1 step F1.1.2. The resulting crude material was purified by Prep LC-MS (IX). LC-MS (A): $t_R$=0.61 min; $[M+H]^+$: 416.25.

Example 164: (S)-(1,3-Dimethyl-azetidin-3-yl)-(2-isobutoxy-pyridin-4-yl)-(4-isopropyl-phenyl)-methanol 164.1. (S)-(2-Isobutoxy-pyridin-4-yl)-(4-isopropyl-phenyl)-(3-methyl-azetidin-3-yl)-methanol To a solution of Example F1.4 (40 mg) in 2-methyl-1-propanol (1 mL) was added NaH (60% in mineral oil, 26.7 mg) and the resulting mixture was stirred for 70 h at 110° C. After cooling down, the mixture was diluted with MeCN/water and purified by Prep LC-MS (XIV) to afford 25.3 mg of the title compound as white solid. LC-MS (A): $t_R$=0.82 min; $[M+H]^+$: 369.14.

164.2. (S)-(1,3-Dimethyl-azetidin-3-yl)-(2-isobutoxy-pyridin-4-yl)-(4-isopropyl-phenyl)-methanol The title compound was synthesized starting from Example 164.1 (25.3 mg) and following the procedure described in Example F1.1 step F1.1.2. The resulting crude material was purified by Prep LC-MS (VIII). LC-MS (A): $t_R$=0.84 min; $[M+H]^+$: 383.23.

Example 165: 4-{4-[(S)-(1,3-Dimethyl-azetidin-3-yl)-hydroxy-(4-isopropyl-phenyl)-methyl]-pyridin-2-yl}-2-methyl-butan-2-ol 165.1. 3—[(S)-Hydroxy-[2-(3-hydroxy-3-methyl-but-1-ynyl)-pyridin-4-yl]-(4-isopropyl-phenyl)-methyl]-3-methyl-azetidine-1-carboxylic acid tert-butyl ester Example F1.4 (40 mg) and 2-methyl-3-butyn-2-ol (13.8 μL) were dissolved in DMF (1 mL). CuI (0.884 mg), $PPh_3$ (5.13 mg), $Pd(PPh)_3Cl_2$ (3.29 mg), and $Et_2NH$ (150 μL) were added and the reaction mixture was stirred for 17 h at 60° C. After cooling down, DCM was added and the resulting mixture was washed with water and brine, dried ($MgSO_4$), filtered off and evaporated to dryness. The residue was purified by Prep LC-MS (XX) to afford 38.2 mg of the title compound as white solid. LC-MS (A): $t_R$=0.82 min; $[M+H]^+$: 479.32.

165.2. 3—[(S)-Hydroxy-[2-(3-hydroxy-3-methyl-butyl)-butyl)-4-yl]-(4-isopropyl-phenyl)-methyl]-3-methyl-azetidine-1-carboxylic acid tert-butyl ester The title compound was synthesized starting from Example 165.1, and following the procedure described in Example 48. LC-MS (A): $t_R$=0.85 min; $[M+H]^+$: 483.34.

165.3. 4-{4-[(S)-Hydroxy-(4-isopropyl-phenyl)-(3-methyl-azetidin-3-yl)-methyl]-pyridin-2-yl}-2-methyl-butan-2-ol, hydrochloride salt Example 165.2 (34.4 mg) was dissolved in HCl in dioxane (4M, 0.6 mL), the mixture was stirred for 1 h at RT and was evaporated to dryness to give the title compound (43.6 mg) as yellow oil. LC-MS (A): $t_R$=0.54 min; $[M+H]^+$: 383.24.

165.4. 4-{4-[(S)-(1,3-Dimethyl-azetidin-3-yl)-hydroxy-(4-isopropylphenyl)-methyl]-pyridin-2-yl}-2-methyl-butan-2-ol The title compound was synthesized starting from Example 165.3, and following the procedure described in Example F1.1 step F1.1.2. The crude material was purified by Prep LC-MS (XIV). LC-MS (A): $t_R$=0.55 min; $[M+H]^+$: 397.28.

Example 166: (R)-[6-(3,3-Difluoro-pyrrolidin-1-yl)-pyridazin-4-yl]-(1,3-dimethyl-azetidin-3-yl)-(4-isopropyl-phenyl)-methanol Example F1.6 (35 mg) was dissolved in dioxane (1 mL), and DIPEA (55.6 μL) and 3,3-difluoropyrrolidine (22 mg) were added. The reaction mixture was stirred for 48 h at 100° C. After cooling down, MeCN/water was added and the resulting material was first purified by Prep LC-MS (VI) then by Prep LC-MS (IX) to afford the title compound (5.1 mg) as white solid. LC-MS (A): $t_R$=0.65 min; $[M+H]^+$: 417.10.

Example 167: (S)-5-tert-Butyl-3-{5-[(R)-(1,3-dimethyl-azetidin-3-yl)-hydroxy-(4-isopropyl-phenyl)-methyl]-pyridin-3-yl}-oxazolidin-2-one 167.1. 5-tert-Butyl-3-{5-[(R)-(1,3-dimethyl-azetidin-3-yl)-hydroxy-(4-isopropyl-phenyl)-methyl]-pyridin-3-yl}-oxazolidin-2-one Example F1.2 (50 mg) and Example F4.5 (18.4 mg) were dissolved in dioxane (2.5 mL), $K_2CO_3$ (35.5 mg), N,N-dimethylethylenediamine (14 μL) and CuI (24.6 mg) were added and the reaction mixture was stirred for 44 h at 110° C. The reaction mixture was allowed to cool down to RT, was filtrated off and evaporated to dryness. The residue was purified by Prep LC-MS (VII) to afford 33 mg of the title compound as white solid. LC-MS (A): $t_R$=0.77 min; $[M+H]^+$: 452.31.

167.2. (S)-5-tert-Butyl-3-{5-[(R)-(1,3-dimethyl-azetidin-3-yl)-hydroxy-(4-isopropyl-phenyl)-methyl]-pyridin-3-yl}-oxazolidin-2-one The title compound (3 mg) was obtained by Prep chiral SFC (XIV) of Example 167.1 (20.9 mg) followed by Prep LC-MS (VI). The stereochemistry at the oxazolidinone ring was arbitrarily assigned. LC-MS (B): $t_R$=0.767 min; $[M+H]^+$: 452.5; Chiral SFC (N): 4.0 min.

Example 168: (R)-1-{5-[(R)-(1,3-Dimethyl-azetidin-3-yl)-hydroxy-(4-isopropyl-phenyl)-methyl]-pyridin-3-yl}-pyrrolidin-3-ol 168.1. (3R)-1-(5-((1,3-dimethylazetidin-3-yl)(hydroxy)(4-isopropylphenyl)methyl)pyridin-3-yl)pyrrolidin-3-ol The title compound was synthesized starting from Example F1.1 and (R)-3-pyrrolidinol, following the procedure described in Example 162 step 162.1. The crude material was purified by Prep LC-MS (V) to afford 40 mg of the title compound as white solid. LC-MS (A): $t_R$=0.54 min; $[M+H]^+$: 396.40.

168.2. (R)-1-{5-[(R)-(1,3-Dimethyl-azetidin-3-yl)-hydroxy-(4-isopropyl-phenyl)-methyl]-pyridin-3-yl}-pyrrolidin-3-ol The title compound was obtained by Prep chiral SFC (X) of Example 168.1. LC-MS (A): $t_R$=0.54 min; $[M+H]^+$: 396.41. Chiral SFC (K): $t_R$=1.3 min.

Example 169 and Example 170 were synthesized starting from Example F1.1 and the appropriate amine reagent, and following the two-step procedure described in Example 168. Chiral Prep SFC conditions, Chiral SFC and LC-MS data are listed in the table below. The LC-MS conditions used were LC-MS (B).

| Example N° | Name | LC-MS $t_R$ | [M + H]$^+$ | Chiral Prep SFC | Chiral SFC $t_R$ (method) |
|---|---|---|---|---|---|
| 169 | (S)-1-5-[(R)-(1,3-Dimethyl-azetidin-3-yl)-hydroxy-(4-isopropyl-phenyl)-methyl]-pyridin-3-yl}-pyrrolidin-3-ol | 0.411 | 396.4 | (XI) | 1.3 (K) |
| 170 | (R)-(1,3-Dimethyl-azetidin-3-yl)-[5-((S)-3-hydroxymethyl-pyrrolidin-1-yl)-pyridin-3-yl]-(4-isopropyl-phenyl)-methanol | 0.433 | 410.5 | (XII) | 3.3 (L) |

Example 171 to Example 188 were synthesized starting from the appropriate compound of Formula (F1) and amine reactant, and following the procedure described in Example 162 step 162.1. Prep LC-MS conditions, compounds of Formula (F1) and LC-MS data are listed in the table below. The LC-MS conditions used were LC-MS (B).

| Example N° | Name | $t_R$ | [M + H]$^+$ | Prep LC-MS | (F1) |
|---|---|---|---|---|---|
| 171 | (R)-(1,3-Dimethyl-azetidin-3-yl)-(4-isopropyl-phenyl)-(5-pyrrolidin-1-yl-pyridin-3-yl)-methanol | 0.508 | 380.4 | (V) | F1.2 |
| 172 | (S)-1-{5-[(R)-(1,3-Dimethyl-azetidin-3-yl)-hydroxy-(4-isopropyl-phenyl)-methyl]-pyridin-3-yl}-3-methyl-pyrrolidin-3-ol | 0.447 | 410.4 | (V) | F1.2 |
| 173 | 3-Cyclopropyl-1-{5-[(R)-(1,3-dimethyl-azetidin-3-yl)-hydroxy-(4-isopropyl-phenyl)-methyl]-pyridin-3-yl}-pyrrolidin-3-ol | 0.512 | 436.5 | (V) | F1.2 |
| 174 | 2-((S)-1-{5-[(R)-(1,3-Dimethyl-azetidin-3-yl)-hydroxy-(4-isopropyl-phenyl)-methyl]-pyridin-3-yl}-pyrrolidin-3-yl)-propan-2-ol | 0.504 | 438.2 | (V) | F1.2 |
| 175 | (R)-(1,3-Dimethyl-azetidin-3-yl)-(4-isopropyl-phenyl)-(5-morpholin-4-yl-pyridin-3-yl)-methanol | 0.492 | 396.4 | (V) | F1.2 |
| 176 | (R)-(1,3-Dimethyl-azetidin-3-yl)-(4-isopropyl-phenyl)-(3,4,5,6-tetrahydro-2H-[1,3']bipyridinyl-5'-yl)-methanol | 0.582 | 394.4 | (V) | F1.2 |
| 177 | (R)-[5-(7-Aza-bicyclo[2.2.1]hept-7-yl)-pyridin-3-yl]-(1,3-dimethyl-azetidin-3-yl)-(4-isopropyl-phenyl)-methanol | 0.612 | 406.4 | (V) | F1.2 |
| 178 | (R)-(1,3-Dimethyl-azetidin-3-yl)-(4-isopropyl-phenyl)-[5-((S)-2-methyl-pyrrolidin-1-yl)-pyridin-3-yl]-methanol | 0.549 | 394.4 | (V) | F1.2 |
| 179 | 1-{5-[(R)-(1,3-Dimethyl-azetidin-3-yl)-hydroxy-(4-isopropyl-phenyl)-methyl]-pyridin-3-yl}-3-trifluoromethyl-pyrrolidin-3-ol | 0.552 | 464.4 | (V) | F1.2 |
| 180 | (R)-[5-(3,3-Difluoro-pyrrolidin-1-yl)-pyridin-3-yl]-(1,3-dimethyl-azetidin-3-yl)-(4-isopropyl-phenyl)-methanol | 0.576 | 416.4 | (VII) | F1.2 |
| 181 | 5H[(R)-(1,3-Dimethyl-azetidin-3-yl)-hydroxy-(4-isopropyl-phenyl)-methyl]-3,4,5,6-tetrahydro-2H-[1,3']bipyridinyl-4-ol | 0.437 | 410.4 | (V) | F1.2 |
| 182 | 5'-[(R)-(1,3-Dimethyl-azetidin-3-yl)-hydroxy-(4-isopropyl-phenyl)-methyl]-3,4,5,6-tetrahydro-2H-[1,3']bipyridinyl-3-ol | 0.462 | 410.4 | (V) | F1.2 |
| 183 | (R)-{5-[(2-Benzyloxy-ethyl)-methyl-amino]-pyridin-3-yl}-(1,3-dimethyl-azetidin-3-yl)-(4-isopropyl-phenyl)-methanol | 0.624 | 474.5 | (IX) | F1.2 |
| 184 | (R)-(1,3-Dimethyl-azetidin-3-yl)-[4-(1-methyl-cyclopropyl)-phenyl]-(5-pyrrolidin-1-yl-pyridin-3-yl)-methanol | 0.522 | 392.4 | (V) | F1.3 |
| 185 | (R)-[5-((3R,4S)-3,4-Difluoro-pyrrolidin-1-yl)-pyridin-3-yl]-(1,3-dimethyl-azetidin-3-yl)-[4-(1-trifluoromethyl-cyclopropyl)-phenyl]-methanol | 0.582 | 482.4 | (V) | F1.4 |
| 186 | 2-[(S)-1-(5-{(R)-(1,3-Dimethyl-azetidin-3-yl)-hydroxy-[4-(1-trifluoromethyl-cyclopropyl)-phenyl]-methyl}-pyridin-3-yl)-pyrrolidin-3-yl]-propan-2-ol | 0.558 | 504.25 | (V) | F1.4 |
| 187 | (R)-(1,3-Dimethyl-azetidin-3-yl)-(5-pyrrolidin-1-yl-pyridin-3-yl)-[4-(1-trifluoromethyl-cyclopropyl)-phenyl]-methanol | 0.55 | 446.4 | (V) | F1.4 |
| 188 | (R)-(4-tert-Butyl-phenyl)-(1,3-dimethyl-azetidin-3-yl)-(3,4,5,6-tetrahydro-2H-[1,3']bipyridinyl-5'-yl)-methanol | 0.621 | 408.5 | (VII) | F1.9 |

Example 189: (R)-(1,3-Dimethyl-azetidin-3-yl)-(5-pyrrolidin-1-yl-pyridin-3-yl)-(4-trifluoromethoxy-phenyl)-methanol The title compound (192 mg, white powder) was synthesized starting from Example A7.1 (339 mg), and following the procedure described in Example F1.1 step F1.1.2. The crude material was purified by Prep LC-MS (VI). LC-MS (A): $t_R$=0.61 min; $[M+H]^+$: 422.30.

Example 190: (R)-{5-[5-(1-Cyclopropanesulfonyl-piperidin-4-yl)-[1,2,4]oxadiazol-3-yl]-pyridin-3-yl}-(1,3-dimethyl-azetidin-3-yl)-(4-isopropyl-phenyl)-methanol 190.1. 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-carboxylic acid tert-butyl ester The title compound (750 mg, white powder) was obtained starting from Example D2.1 (1.01 g) and N-Boc-isonipecotic acid (1.02 g), and following the procedure described in Example 134. The crude material was however purified by prep LC-MS (XXIV) and (XXV). LC-MS (A): $t_R$=0.88 min; $[M+H]^+$: 561.90.

190.2. (R)-(1,3-dimethylazetidin-3-yl)(4-isopropylphenyl)(5-(5-(piperidin-4-yl)-1,2,4-oxadiazol-3-yl)pyridin-3-yl)methanol, hydrochloride salt A solution of Example 190.1 (750 mg) in HCl in dioxane (4M, 15 mL) was stirred at RT for 2 h, concentrated in vacuo and dried under HV to afford 714 mg of the title compound. LC-MS (A): $t_R$=0.57 min; $[M+H]^+$: 462.12.

190.3. (R)-{5-[5-(1-Cyclopropanesulfonyl-piperidin-4-yl)-[1,2,4]oxadiazol-3-yl]-pyridin-3-yl}-(1,3-dimethyl-azetidin-3-yl)-(4-isopropyl-phenyl)-methanol A solution of Example 190.2 (29.8 mg) and DIPEA (38 μL) in DCM (1 mL) was stirred at −20° C. for 1 h. Cyclopropanesulfonyl chloride (5.7 μL) was added, the resulting mixture was stirred overnight at RT and evaporated in vacuo. The crude material was purified by Prep LC-MS (XIV) followed by Prep LC-MS (VI) to afford the title compound (12 mg) as white powder. LC-MS (A): $t_R$=0.80 min; $[M+H]^+$: 566.03.

Example 191: 2-({5-[(R)-(1,3-Dimethyl-azetidin-3-yl)-hydroxy-(4-isopropyl-phenyl)-methyl]-pyridin-3-yl}-methyl-amino)-ethanol Example 183 (25 mg) was dissolved in EtOH (1 mL), and TEA (13.4 μL) and Pd/C (10% w/w, 50% water, 2.55 mg) were added and the reaction mixture was stirred at RT under hydrogen for 18 h. The same amounts of TEA and Pd/C were added again and the mixture was further stirred at RT under hydrogen for 24 h. The mixture was filtered off and the same amount of Pd/C was added to the resulting solution. The mixture was stirred under hydrogen for 17 h. The same procedure was repeated 3 times and the mixture was finally filtered off and evaporated in vacuo. The residue was purified by Prep LC-MS (IX) to afford 4 mg of the title compound as white solid. LC-MS (B): $t_R$=0.396 min; $[M+H]^+$: 384.40.

Example 192: (R)-1-((S)-1-{5-[(R)-(1,3-Dimethyl-azetidin-3-yl)-hydroxy-(4-isopropyl-phenyl)-methyl]-pyridin-3-yl}-pyrrolidin-3-yl)-ethanol 192.1. (S)-1-Pyrrolidin-3-yl-ethanone, hydrochloride salt Tert-butyl-(3S)-3-acetylpyrrolidine-1-carboxylate (100 mg) was dissolved in HCl in dioxane (4M, 1 mL), the reaction mixture was stirred for 1 h30 at RT and evaporated to dryness to give 69 mg of the title compound as brown oil which was used without further purification. LC-MS (A): $t_R$=0.2 min; $[M+H]^+$: 114.24.

192.2. 1—((S)-1-{5-[(R)-(1,3-Dimethyl-azetidin-3-yl)-hydroxy-(4-isopropyl-phenyl)-methyl]-pyridin-3-yl}-pyrrolidin-3-yl)-ethanone The title compound was synthesized starting from Example F1.2 and Example 192.1, and following the procedure described in Example 162 step 162.1. The crude material was purified by Prep LC-MS (VI) to afford. LC-MS (A): $t_R$=0.6 min; $[M+H]^+$: 422.38.

192.3. (R)-1-((S)-1-{5-[(R)-(1,3-Dimethyl-azetidin-3-yl)-hydroxy-(4-isopropyl-phenyl)-methyl]-pyridin-3-yl}-pyrrolidin-3-yl)-ethanol Example 192.2 (41 mg) was dissolved in MeOH (0.5 mL) and $NaBH_4$ (3.86 mg) was added at 0° C. The reaction mixture was stirred for 3 h at 0° C. then for 70 h at RT. The reaction mixture was diluted with water, extracted with DCM, and the org. layers were evaporated to dryness. The residue was purified by Prep LC-MS (V) to afford the title compound as first eluting peak (11 mg) as white solid. The stereochemistry at the α-carbon to the secondary hydroxy group was arbitrarily assigned to (R). LC-MS (B): $t_R$=0.458 min; $[M+H]^+$:424.4.

Example 193 to Example 221 were synthesized from Example F1.2 and the appropriate compound of Formula (F3) or Formula (F4), following the procedure described in Example 167 step 167.1. Compounds of Formula (F3) or Formula (F4), unless commercially available, Prep LC-MS conditions and LC-MS data are listed in the table below. The LC-MS conditions used were LC-MS (B).

| Example N° | Name | $t_R$ | $[M+H]^+$ | Prep LC-MS | (F4) |
|---|---|---|---|---|---|
| 193 | 3-{5-[(R)-(1,3-Dimethyl-azetidin-3-yl)-hydroxy-(4-isopropyl-phenyl)-methyl]-pyridin-3-yl}-oxazolidin-2-one | 0.581 | 396.40 | (V) | — |
| 194 | 3-{5-[(R)-(1,3-Dimethyl-azetidin-3-yl)-hydroxy-(4-isopropyl-phenyl)-methyl]-pyridin-3-yl}-5-phenyl-oxazolidin-2-one | 0.765 | 472.4 | (VII) | — |

-continued

| Example N° | Name | $t_R$ | [M + H]$^+$ | Prep LC-MS | (F4) |
|---|---|---|---|---|---|
| 195 | 5-Benzyl-3-{5-[(R)-(1,3-dimethyl-azetidin-3-yl)-hydroxy-(4-isopropyl-phenyl)-methyl]-pyridin-3-yl}-oxazolidin-2-one | 0.776 | 486.4 | (VII) | F4.1 |
| 196 | 3-{5-[(R)-(1,3-Dimethyl-azetidin-3-yl)-hydroxy-(4-isopropyl-phenyl)-methyl]-pyridin-3-yl}-5-isopropyl-oxazolidin-2-one | 0.727 | 438.4 | (VI) | F4.2 |
| 197 | 6-{5-[(R)-(1,3-Dimethyl-azetidin-3-yl)-hydroxy-(4-isopropyl-phenyl)-methyl]-pyridin-3-yl}-4-oxa-6-aza-spiro[2.4]heptan-5-one | 0.672 | 422.4 | (VI) | F4.3 |
| 198 | 3-{5-[(R)-(1,3-Dimethyl-azetidin-3-yl)-hydroxy-(4-isopropyl-phenyl)-methyl]-pyridin-3-yl}-1-oxa-3-aza-spiro[4.4]nonan-2-one | 0.737 | 450.4 | (VI) | — |
| 199 | 3-{5-[(R)-(1,3-Dimethyl-azetidin-3-yl)-hydroxy-(4-isopropyl-phenyl)-methyl]-pyridin-3-yl}-5-(tetrahydro-pyran-4-yl)-oxazolidin-2-one | 0.651 | 480.4 | (V) then (IX) | F4.4 |
| 200 | 3-{5-[(R)-(1,3-Dimethyl-azetidin-3-yl)-hydroxy-(4-isopropyl-phenyl)-methyl]-pyridin-3-yl}-5,5-dimethyl-oxazolidin-2-one | 0.664 | 424.4 | (VI) | — |
| 201 | 3-{5-[(R)-(1,3-Dimethyl-azetidin-3-yl)-hydroxy-(4-isopropyl-phenyl)-methyl]-pyridin-3-yl}-8,8-difluoro-1-oxa-3-aza-spiro[4.5]decan-2-one | 0.756 | 500.4 | (VI) then (IX) | F4.6 |
| 202 | 9-{5-[(R)-(1,3-Dimethyl-azetidin-3-yl)-hydroxy-(4-isopropyl-phenyl)-methyl]-pyridin-3-yl}-7-oxa-9-aza-dispiro[3.1.4.1]undecan-8-one | 0.832 | 476.4 | (VII) | F4.7 |
| 203 | 2-Cyclopropyl-7-{5-[(R)-(1,3-dimethyl-azetidin-3-yl)-hydroxy-(4-isopropyl-phenyl)-methyl]-pyridin-3-yl}-5-oxa-7-aza-spiro[3.4]octan-6-one | 0.822 | 476.4 | (VII) then (IX) | F4.8 |
| 204 | 7-{5-[(R)-(1,3-Dimethyl-azetidin-3-yl)-hydroxy-(4-isopropyl-phenyl)-methyl]-pyridin-3-yl}-2,2-dimethyl-5-oxa-7-aza-spiro[3.4]octan-6-one | 0.807 | 464.4 | (VII) | F4.9 |
| 205 | 1-{5-[(R)-(1,3-Dimethyl-azetidin-3-yl)-hydroxy-(4-isopropyl-phenyl)-methyl]-pyridin-3-yl}-4-phenyl-pyrrolidin-2-one | 0.771 | 470.4 | (VII) | — |
| 206 | 1-{5-[(R)-(1,3-Dimethyl-azetidin-3-yl)-hydroxy-(4-isopropyl-phenyl)-methyl]-pyridin-3-yl}-pyrrolidin-2-one | 0.595 | 394.4 | (V) then (XIV) | — |
| 207 | 1-{5-[(R)-(1,3-Dimethyl-azetidin-3-yl)-hydroxy-(4-isopropyl-phenyl)-methyl]-pyridin-3-yl}-4-isopropyl-pyrrolidin-2-one | 0.749 | 436.5 | (VII) | — |
| 208 | 1-{5-[(R)-(1,3-Dimethyl-azetidin-3-yl)-hydroxy-(4-isopropyl-phenyl)-methyl]-pyridin-3-yl}-3-isopropyl-pyrrolidin-2-one | 0.749 | 436.5 | (VII) | — |
| 209 | 1-{5-[(R)-(1,3-Dimethyl-azetidin-3-yl)-hydroxy-(4-isopropyl-phenyl)-methyl]-pyridin-3-yl}-4,4-dimethyl-pyrrolidin-2-one | 0.689 | 422.5 | (VII) | — |
| 210 | 5-(5-((R)-(1,3-Dimethyl-azetidin-3-yl)(hydroxy)(4-isopropyl-phenyl)methyl)pyridin-3-yl)hexahydro-4H-furo[2,3-c]pyrrol-4-one (mixture of diastereomers) | 0.594 | 436.4 | (VII) | — |
| 211 | 2-{5-[(R)-(1,3-Dimethyl-azetidin-3-yl)-hydroxy-(4-isopropyl-phenyl)-methyl]-pyridin-3-yl}-2-aza-spiro[4.4]nonan-3-one | 0.758 | 448.5 | (VII) | — |
| 212 | 6-{5-[(R)-(1,3-Dimethyl-azetidin-3-yl)-hydroxy-(4-isopropyl-phenyl)-methyl]-pyridin-3-yl}-6-aza-spiro[3.4]octan-5-one | 0.721 | 434.4 | (VII) | — |
| 213 | 2-{5-[(R)-(1,3-Dimethyl-azetidin-3-yl)-hydroxy-(4-isopropyl-phenyl)-methyl]-pyridin-3-yl}-8-oxa-2-aza-spiro[4.5]decan-3-one | 0.614 | 464.4 | (VII) | — |
| 214 | 1-{5-[(R)-(1,3-Dimethyl-azetidin-3-yl)-hydroxy-(4-isopropyl-phenyl)-methyl]-pyridin-3-yl}-3-(tetrahydro-pyran-4-yl)-pyrrolidin-2-one | 0.66 | 478.5 | (VII) then (IX) | — |
| 215 | 2-{5-[(R)-(1,3-Dimethyl-azetidin-3-yl)-hydroxy-(4-isopropyl-phenyl)-methyl]-pyridin-3-yl}-2-aza-spiro[4.5]decan-1-one | 0.801 | 462.5 | (VII) then (XIV) | — |
| 216 | 2-{5-[(R)-(1,3-Dimethyl-azetidin-3-yl)-hydroxy-(4-isopropyl-phenyl)-methyl]-pyridin-3-yl}-8-oxa-2-aza-spiro[4.5]decan-1-one | 0.631 | 464.4 | ((VII) then (IX) | — |
| 217 | (S)-1-{5-[(R)-( 1,3-Dimethyl-azeti din-3-yl)-hydroxy-(4-isopropyl-phenyl)-methyl]-pyridin-3-yl}-4-isobutyl-pyrrolidin-2-one | 0.811 | 450.5 | ((VII) then (XIV) | — |
| 218 | 4-Cyclopropyl-1-{5-[(R)-(1,3-dimethyl-azetidin-3-yl)-hydroxy-(4-isopropyl-phenyl)-methyl]-pyridin-3-yl}-pyrrolidin-2-one | 0.72 | 434.4 | (VI) then (IX) | — |
| 219 | 1-{5-[(R)-(1,3-Dimethyl-azetidin-3-yl)-hydroxy-(4-isopropyl-phenyl)-methyl]-pyridin-3-yl}-4-trifluoromethyl-pyrrolidin-2-one | 0.703 | 462.4 | (VI) then (IX) | — |

-continued

| Example N° | Name | $t_R$ | [M + H]$^+$ | Prep LC-MS | (F4) |
|---|---|---|---|---|---|
| 220 | 1-{5-[(R)-(1,3-Dimethyl-azetidin-3-yl)-hydroxy-(4-isopropyl-phenyl)-methyl]-pyridin-3-yl}-3-(2-methoxy-ethyl)-pyrrolidin-2-one | 0.656 | 452.4 | (VI) then (IX) | — |
| 221 | 1-{5-[(R)-(1,3-Dimethyl-azetidin-3-yl)-hydroxy-(4-isopropyl-phenyl)-methyl]-pyridin-3-yl}-4-(2-methoxy-ethyl)-pyrrolidin-2-one | 0.646 | 452.5 | (VI) then (IX) | F3.1 = F4.10 |

Example 222: 1-{5-[(R)-(1,3-Dimethyl-azetidin-3-yl)-hydroxy-(4-isopropyl-phenyl)-methyl]-pyridazin-3-yl}-pyrrolidin-2-one The title compound was synthesized starting from Example F1.6 and 2-pyrrolidone, and following the procedure described in Example 167 step 167.1. The crude material was purified by Prep LC-MS (IX). LC-MS (A): $t_R$=0.68 min; [M+H]$^+$: 395.19.

Example 223: (1,3-Dimethyl-azetidin-3-yl)-(4-isopropyl-phenyl)-[5-((R)-3-isopropyl-pyrrolidin-1-yl)-pyridin-3-yl]-methanol

223.1. 3-Hydroxy-3-isopropenyl-pyrrolidine-1-carboxylic acid tert-butyl ester To a solution of N-Boc-3-pyrrolidinone (1 g) in THF (7 mL) was added at RT isopropenylmagnesium bromide in THF (0.5M, 11.7 mL). The resulting mixture was stirred for 15 min at 70° C., allowed to cool down to RT, poured into aq. sat. $NH_4Cl$ solution and extracted with EA. The org. layers were dried ($MgSO_4$), filtrated off and evaporated to dryness. The resulting crude material was purified by CC (Biotage, SNAP 50 g, solvent A: Hep; solvent B: EA; gradient in % B: 30 over 3 CV, 30 to 50 over 3 CV, 50 over 2 CV) to afford 249 mg of the title compound as yellow oil. LC-MS (A): $t_R$=0.78 min; [M+H]$^+$: 228.20

223.2. 3-Isopropyl-pyrrolidine-1-carboxylic acid tert-butyl ester

A mixture of Example 223.1 (243 mg) and Pd/C (10% w/w, 50% water, 113 mg) in MeOH (3.5 mL) was stirred for 1 h30 at RT under hydrogen atmosphere, filtrated off and evaporated to dryness. The resulting crude material was purified by CC (Biotage, SNAP 10 g, solvent A: Hep; solvent B: EA; gradient in % B: 10 over 2 CV, 10 to 50 over 10 CV, 50 over 2 CV) to afford 50 mg of the title compound as yellow oil. LC-MS (A): $t_R$=1.02 min; [M+H]$^+$: 214.36.

223.3. 3-Isopropyl-pyrrolidine, hydrochloride salt

A mixture of Example 223.2 (47 mg) in HCl in dioxane (4M, 0.5 mL) was stirred for 1 h at RT and evaporated to dryness under HV to give 38 mg of the title compound as brown solid. LC-MS (A): $t_R$=0.42 min; [M+H]$^+$: 114.28.

223.4. (1,3-Dimethyl-azetidin-3-yl)-(4-isopropyl-phenyl)-[5-((R)-3-isopropyl-pyrrolidin-1-yl)-pyridin-3-yl]-methanol Example F1.2 (50 mg) and Example 223.3 (20.2 mg) were dissolved in toluene (1 mL), XantPhos (3.83 mg), $Pd_2(dba)_3$ (6.06 mg) and NaOtBu (27.4 mg) were added and the resulting mixture was stirred for 18 h at 100° C. The reaction mixture was allowed to cool down to RT, filtrated off and evaporated to dryness. The residue was purified by Prep LC-MS (VII) then by Prep LC-MS (IX) to afford 6 mg of the title compound as white solid. LC-MS (B): $t_R$=0.665 min; [M+H]$^+$: 422.5.

Example 224 to Example 244 were synthesized from the appropriate amine reactant and compound of Formula (F1), and following the procedure described in Example 223 step 223.4. Compounds of Formula (F1), Prep LC-MS conditions and LC-MS data are listed in the table below. The LC-MS conditions used were LC-MS (B).

| Example N° | Name | $t_R$ | [M + H]$^+$ | Prep LC-MS | (F1) |
|---|---|---|---|---|---|
| 224 | (R)-(1,3-Dimethyl-azetidin-3-yl)-[5-((2R,6S)-2,6-dimethyl-morpholin-4-yl)-pyridin-3-yl]-(4-isopropyl-phenyl)-methanol | 0.577 | 424.4 | (VI) | F1.2 |
| 225 | (R)-(1,3-Dimethyl-azetidin-3-yl)-(4-isopropyl-phenyl)-[5-(6-oxa-3-aza-bicyclo[3.1.1]hept-3-yl)-pyridin-3-yl]-methanol | 0.439 | 408.4 | (V) | F1.2 |
| 226 | (R)-[5-((3R,4S)-3,4-Difluoro-pyrrolidin-1-yl)-pyridin-3-yl]-(1,3-dimethyl-azetidin-3-yl)-(4-isopropyl-phenyl)-methanol | 0.526 | 416.4 | (VII) | F1.2 |
| 227 | (R)-[5-((3S,4S)-3,4-Difluoro-pyrrolidin-1-yl)-pyridin-3-yl]-(1,3-dimethyl-azetidin-3-yl)-(4-isopropyl-phenyl)-methanol | 0.522 | 416.4 | (VII) | F1.2 |
| 228 | (R)-(1,3-Dimethyl-azetidin-3-yl)-[5-((2S,6S)-2,6-dimethyl-morpholin-4-yl)-pyridin-3-yl]-(4-isopropyl-phenyl)-methanol | 0.556 | 424.4 | (IX) then (V) | F1.2 |
| 229 | (R)-(1,3-Dimethyl-azetidin-3-yl)-[5-((2R,6R)-2,6-dimethyl-morpholin-4-yl)-pyridin-3-yl]-(4-isopropyl-phenyl)-methanol | 0.556 | 424.4 | (IX) then (V) | F1.2 |

-continued

| Example N° | Name | $t_R$ | [M + H]$^+$ | Prep LC-MS | (F1) |
|---|---|---|---|---|---|
| 230 | (R)-(1,3-Dimethyl-azetidin-3-yl)-(4-isopropyl-phenyl)-{5-[3-(3-methyl-[1,2,4]oxadiazol-5-yl)-pyrrolidin-1-yl]-pyridin-3-yl}-methanol | 0.531 | 462.4 | (IX) then (V) | F1.2 |
| 231 | (R)-(1,3-Dimethyl-azetidin-3-yl)-(4-isopropyl-phenyl)-{5-[3-(4-methyl-thiazol-2-yl)-pyrrolidin-1-yl]-pyridin-3-yl}-methanol | 0.589 | 477.4 | (IX) | F1.2 |
| 232 | (R)-(1,3-Dimethyl-azetidin-3-yl)-(4-isopropyl-phenyl)-[5-(3-phenyl-pyrrolidin-1-yl)-pyridin-3-yl]-methanol | 0.68 | 456.5 | (XIV) | F1.2 |
| 233 | (R)-(1,3-Dimethyl-azetidin-3-yl)-[5-(3,3-dimethyl-pyrrolidin-1-yl)-pyridin-3-yl]-(4-isopropyl-phenyl)-methanol | 0.6 | 408.5 | (XIV) | F1.2 |
| 234 | (R)-(1,3-Dimethyl-azetidin-3-yl)-(4-isopropyl-phenyl)-[(1S,4S)-5-(2-oxa-5-aza-bicyclo[2.2.1] hept-5-yl)-pyridin-3-yl]-methanol | 0.454 | 408.4 | (VI) | F1.2 |
| 235 | (R)-(1,3-Dimethyl-azetidin-3-yl)-(4-isopropyl-phenyl)-[5-(2,2,6,6-tetrafluoro-morpholin-4-yl)-pyridin-3-yl]-methanol | 0.752 | 468.4 | (XV) | F1.2 |
| 236 | (R)-(1,3-Dimethyl-azetidin-3-yl)-(4-isopropyl-phenyl)-[5-((R)-2-methoxymethyl-morpholin-4-yl)-pyridin-3-yl]-methanol | 0.527 | 440.5 | (VI) then (IX) | F1.2 |
| 237 | (R)-(1,3-Dimethyl-azetidin-3-yl)-(4-isopropyl-phenyl)-[5-((S)-2-methoxymethyl-morpholin-4-yl)-pyridin-3-yl]-methanol | 0.528 | 440.5 | (VI) then (IX) | F1.2 |
| 238 | (R)-(1,3-Dimethyl-azetidin-3-yl)-(4-isopropyl-phenyl)-[5-(3-trifluoromethyl-pyrrolidin-1-yl)-pyridin-3-yl]-methanol | 0.613 | 448 | (XV) then (IX) | F1.2 |
| 239 | (R)-(1,3-Dimethyl-azetidin-3-yl)-(4-isopropyl-phenyl)-[(1R,4R)-5-(2-oxa-5-aza-bicyclo[2.2.1]hept-5-yl)-pyridin-3-yl]-methanol | 0.451 | 408.4 | (VI) then (IX) | F1.2 |
| 240 | (R)-(1,3-Dimethyl-azetidin-3-yl)-(4-isopropyl-phenyl)-[(1S,5R)-5-(8-oxa-3-aza-bicyclo[3.2.1]oct-3-yl)-pyridin-3-yl]-methanol | 0.515 | 422.4 | (VI) then (IX) | F1.2 |
| 241 | (R)-(1,3-Dimethyl-azetidin-3-yl)-[(1S,4S)-5-(2-oxa-5-aza-bicyclo[2.2.1]hept-5-yl)-pyridin-3-yl]-[4-(1-trifluoromethyl-cyclopropyl)-phenyl]-methanol | 0.504 | 474.4 | (VI) | F1.8 |
| 242 | (R)-(1,3-Dimethyl-azetidin-3-yl)-(4-ethyl-phenyl)-(5-pyrrolidin-1-yl-pyridin-3-yl)-methanol | 0.462 | 366.4 | (VI) | F1.10 |
| 243 | (R)-(1,3-Dimethyl-azetidin-3-yl)-(4-ethyl-phenyl)-[5-(6-oxa-3-aza-bicyclo[3.1.1]hept-3-yl)-pyridin-3-yl]-methanol | 0.392 | 394.4 | (V) | F1.10 |
| 244 | (R)-(1,3-Dimethyl-azetidin-3-yl)-(4-ethyl-phenyl)-[(1S,4S)-5-(2-oxa-5-aza-bicyclo[2.2.1]hept-5-yl)-pyridin-3-yl]-methanol | 0.405 | 394.4 | (V) | F1.10 |

Example 245: (R)-(5-Benzyloxy-pyridin-3-yl)-(1,3-dimethyl-azetidin-3-yl)-(4-isopropyl-phenyl)-methanol The title compound was synthesized following the four-step procedure described in Example G1.2 step G1.2.1 to step G1.2.4. LC-MS (B): $t_R$=0.783 min; [M+H]$^+$: 417.40.

Example 246: (1,3-Dimethyl-azetidin-3-yl)-(4-isopropyl-phenyl)-[5-(2-pyridin-2-yl-ethoxy)-pyridin-3-yl]-methanol To a solution of Example G1.1 (30 mg) and 2-(2-hydroxyethyl)pyridine (19.3 μL) in toluene (1 mL) was added cyanomethyltributylphosphorane (44.4 mg). The reaction mixture was stirred for 23 h at 110° C. and evaporated to dryness. The residue was purified by Prep LC-MS (VI) then by Prep LC-MS (IX) to afford 8 mg of the title compound as off-white solid. LC-MS (B): $t_R$=0.532 min; [M-FH]': 432.40.

Example 247 to Example 259 were synthesized from the appropriate compounds of Formula (G1) and (G2), and following the procedure described in Example 246. Compounds of Formula (G1), Prep LC-MS conditions, and LC-MS data are listed in the table below. The LC-MS conditions used were LC-MS (B).

| Example N° | Name | $t_R$ | [M + H]$^+$ | Prep LC-MS | (G1) |
|---|---|---|---|---|---|
| 247 | (1,3-Dimethyl-azetidin-3-yl)-(4-isopropyl-phenyl)-[5-(2-methoxy-ethoxy)-pyridin-3-yl]-methanol | 0.606 | 385.2 | (VI) then (IX) | G1.1 |
| 248 | (1,3-Dimethyl-azetidin-3-yl)-(4-isopropyl-phenyl)-[5-(oxetan-3-ylmethoxy)-pyridin-3-yl]-methanol | 0.585 | 397.2 | (VI) then (IX) | G1.1 |
| 249 | 3-{5-[(R)-(1,3-Dimethyl-azetidin-3-yl)-hydroxy-(4-isopropyl-phenyl)-methyl]-pyridin-3-yloxy}-propan-1-ol | 0.546 | 385.4 | (XIII) | G1.2 |
| 250 | (R)-(1,3-Dimethyl-azetidin-3-yl)-(5-isopropoxy-pyridin-3-yl)-(4-isopropyl-phenyl)-methanol | 0.685 | 369.4 | (XIII) | G1.2 |

-continued

| Example N° | Name | $t_R$ | [M + H]$^+$ | Prep LC-MS | (G1) |
|---|---|---|---|---|---|
| 251 | (R)-(5-Cyclohexyloxy-pyridin-3-yl)-(1,3-dimethyl-azetidin-3-yl)-(4-isopropyl-phenyl)-methanol | 0.813 | 409.4 | (XIII) | G1.2 |
| 252 | 1-{5-[(R)-(1,3-Dimethyl-azetidin-3-yl)-hydroxy-(4-isopropyl-phenyl)-methyl]-pyridin-3-yloxy}-2-methyl-propan-2-ol | 0.386 | 399.3 | (XIII) | G1.2 |
| 253 | (R)-(1,3-Dimethyl-azetidin-3-yl)-(4-isopropyl-phenyl)-[5-(3-methoxy-cyclopentyloxy)-pyridin-3-yl]-methanol | 0.698 | 425.5 | (XIII) | G1.2 |
| 254 | (R)-[5-(3-Cyclopropyl-[1,2,4]oxadiazol-5-ylmethoxy)-pyridin-3-yl]-(1,3-dimethyl-azetidin-3-yl)-(4-isopropyl-phenyl)-methanol | 0.726 | 449.3 | (XIII) | G1.2 |
| 255 | (R)-(1,3-Dimethyl-azetidin-3-yl)-{5-[2-(3,5-dimethyl-[1,2,4]triazol-1-yl)-ethoxy]-pyridin-3-yl}-(4-isopropyl-phenyl)-methanol | 0.553 | 450.5 | (V) | G1.2 |
| 256 | 4-{5-[(R)-(1,3-Dimethyl-azetidin-3-yl)-hydroxy-(4-isopropyl-phenyl)-methyl]-pyridin-3-yloxy}-2-methyl-butan-2-ol | 0.622 | 413.4 | (XIII) | G1.2 |
| 257 | (R)-(1,3-Dimethyl-azetidin-3-yl)-(4-isopropyl-phenyl)-(5-methoxy-pyridin-3-yl)-methanol | 0.584 | 341.3 | (XIII) | G1.2 |
| 258 | (R)-[5-(2-Benzyloxy-ethoxy)-pyridin-3-yl]-(1,3-dimethyl-azetidin-3-yl)-(4-isopropyl-phenyl)-methanol | 0.792 | 461.5 | (VIII) | G1.2 |
| 259 | (R)-(1,3-Dimethyl-azetidin-3-yl)-(4-isopropyl-phenyl)-[5-(tetrahydro-pyran-4-yloxy)-pyridin-3-yl]-methanol | 0.630 | 411.2 | (IX) | G1.2 |

Example 260: 2-{5-[(R)-(1,3-Dimethyl-azetidin-3-yl)-hydroxy-(4-isopropyl-phenyl)-methyl]-pyridin-3-yloxy}-ethanol A mixture of Example 258 (9 mg) and $Pd(OH)_2/C$ (20%, 0.686 mg) in MeOH (0.5 mL) was stirred for 55 h at RT under hydrogen atmosphere, was filtered off and evaporated to dryness. The resulting crude material was redissolved in MeOH (0.5 mL), the same amount of $Pd(OH)_2/C$ was added, and the resulting mixture was stirred for 21 h at RT under hydrogen atmosphere, filtered off, evaporated to dryness and purified by Prep LC-MS (V) to afford 1 mg of the title compound as white solid. LC-MS (B): $t_R$=0.512 min; [M+H]$^+$: 371.40.

Example 261: 4-{5-[(R)-(1,3-Dimethyl-azetidin-3-yl)-hydroxy-(4-isopropyl-phenyl)-methyl]-pyridin-3-yloxy}-cyclohexanol 261.1. (R)-(1,3-Dimethyl-azetidin-3-yl)-[5-(1,4-dioxa-spiro[4.5]dec-8-yloxy)-pyridin-3-yl]-(4-isopropyl-phenyl)-methanol The title compound was synthesized from 1,4-dioxaspiro[4,5]decan-8-ol and Example G1.2, and following the procedure described in Example 246. The crude material was purified by Prep LC-MS (VI). LC-MS (A): $t_R$=0.69 min; [M+H]$^+$: 467.18.

261.2 4-{5-[(R)-(1,3-Dimethyl-azetidin-3-yl)-hydroxy-(4-isopropyl-phenyl)-methyl]-pyridin-3-yloxy}-cyclohexanone To an ice-cold solution of Example 261.1 (58 mg) in dioxane (0.6 mL) were added $H_2SO_4$ (0.12 mL) and water (0.12 mL). The resulting mixture was stirred for 4 h at 0° C., basified with aq. sat. $NaHCO_3$ solution, diluted with water and extracted with DCM. The org. phases were dried ($MgSO_4$), filtrated off and evaporated to dryness to give 31 mg of the title compound as white solid. LC-MS (A): $t_R$=0.65 min; [M+H]$^+$: 423.19.

261.3 4-{5-[(R)-(1,3-Dimethyl-azetidin-3-yl)-hydroxy-(4-isopropyl-phenyl)-methyl]-pyridin-3-yloxy}-cyclohexanol To an ice-cold solution of Example 261.2 (10 mg) in MeOH (0.3 mL) was added $NaBH_4$ (0.94 mg). The resulting mixture was stirred for 1 h at 0° C., quenched with water and extracted with DCM. The org. phases were dried ($MgSO_4$), filtrated off, evaporated to dryness and purified by Prep LC-MS (V) to give 5 mg of the title compound as white solid. LC-MS (A): $t_R$=0.61 min; [M+H]$^+$: 425.22.

Example 262: 4-{5-[(R)-(1,3-Dimethyl-azetidin-3-yl)-hydroxy-(4-isopropyl-phenyl)-methyl]-pyridin-3-yloxy}-1-methyl-cyclohexanol To a solution of Example 261.2 (16 mg) in THF (0.5 mL) was added dropwise methylmagnesium bromide in $Et_2O$ (3M, 44.3 μL). The resulting mixture was stirred for 1 h25 at RT, quenched with aq. sat. $NH_4Cl$ solution and extracted with DCM. The org. layers were dried ($MgSO_4$), filtrated off and evaporated to dryness. The resulting crude material was purified by Prep LC-MS (VI) to afford 7 mg of the title compound as white powder. LC-MS (A): $t_R$=0.63 min; [M+H]$^+$: 439.22.

Example 263 to Example 265 were synthesized starting from Example B2.1 and the appropriate bromoderivative of Formula (A5), and following the procedure described in Example A7.1 step A7.1.1. Prep LC-MS conditions and LC-MS data of Example 263 to Example 265 are listed in the table below. The LC-MS conditions used were LC-MS (A).

| Example N° | Name | $t_R$ | [M + H]+ | Prep LC-MS |
|---|---|---|---|---|
| 263 | (1,3-Dimethyl-azetidin-3-yl)-(2-phenoxy-pyrimidin-5-yl)-(4-trifluoromethoxy-phenyl)-methanol | 0.77 | 446.21 | (VI) |
| 264 | (6-Benzyloxy-pyridin-3-yl)-(1,3-dimethyl-azetidin-3-yl)-(4-trifluoromethoxy-phenyl)-methanol | 0.87 | 459.13 | (VIII) |
| 265 | (1,3-Dimethyl-azetidin-3-yl)-(5-pyrazol-1-yl-pyridin-3-yl)-(4-trifluoromethoxy-phenyl)-methanol | 0.73 | 419.19 | (VI) then (V) |

Example 266: (1,3-Dimethyl-azetidin-3-yl)-(6-fluoro-5-pyrrolidin-1-yl-pyridin-3-yl)-(4-trifluoromethoxy-phenyl)-methanol

266.1. 5-Bromo-2-fluoro-3-pyrrolidin-1-yl-pyridine

To an ice-cold solution of 3-amino-5-bromo-2-fluoro-pyridne (200 mg) in THF (4 mL) and MeOH (4 mL) was added $H_2SO_4$ (222 μL) in water (1.78 mL), followed by 2,5-dimethoxytetrahydrofuran (403 μL) and finally $NaBH_4$ portionwise (115 mg). The resulting mixture was stirred for 21 h at RT, diluted with water and basified with aq. sat. $NaHCO_3$ solution. The org. layer was washed with water and brine, dried ($MgSO_4$), filtrated off and evaporated to dryness. The residue was purified by CC (Biotage, SNAP 10 g, solvent A: Hep; solvent B: EA; gradient in % B: 0 over 1 CV, 0 to 10 over 6 CV, 10 over 2 CV), followed by Prep LC-MS (VII) to afford 31 mg of the title compound as white solid. LC-MS (A): $t_R$=0.99 min; [M+H]$^+$: 245.21.

266.2. (1,3-Dimethyl-azetidin-3-yl)-(6-fluoro-5-pyrrolidin-1-yl-pyridin-3-yl)-(4-trifluoromethoxy-phenyl)-methanol The title compound was synthesized starting from Example B2.1 (34 mg) and Example 266.1 (30.5 mg), and following the procedure described in Example A7.1 step A7.1.1. The crude material was purified by Prep LC-MS (VII) then by Prep LC-MS (XIV) to afford 4 mg of the title compound as white solid. LC-MS (B): $t_R$=0.803 min; [M+H]$^+$: 440.40.

Example 267: 5-[(1,3-Dimethyl-azetidin-3-yl)-hydroxy-(4-trifluoromethoxy-phenyl)-methyl]-3-pyrrolidin-1-yl-pyridine-2-carbonitrile

267.1. 5-Bromo-3-pyrrolidin-1-yl-pyridine-2-carbonitrile

To a solution of 5-bromo-3-fluoropicolinonitrile (186 mg) in THF (4.5 ml) was added DIPEA (317 μL) and pyrrolidine (77.6 μL). The resulting solution was stirred overnight at RT, diluted with EA and washed with water and brine. The org. phases were dried ($MgSO_4$), filtrated off and evaporated to dryness. The residue was purified by CC (Biotage, snap10 g, solvent A: Hep; solvent B: EA; gradient in % B: 10 over 2 CV, 10 to 30 over 3 CV, 30 over 2 CV) to afford 223 mg of the title compound as pale yellow solid. LC-MS (A): $t_R$=0.93 min; [M+H]$^+$: 252.19.

267.2. 5-[(1,3-Dimethyl-azetidin-3-yl)-hydroxy-(4-trifluoromethoxy-phenyl)-methyl]-3-pyrrolidin-1-yl-pyridine-2-carbonitrile The title compound was synthesized starting from Example B2.1 (50 mg) and Example 267.1 (46.1 mg), following the procedure described in Example A7.1 step A7.1.1. The crude material was purified by Prep LC-MS (VI) to afford 2 mg of the title compound as pale yellow solid. LC-MS (A): $t_R$=0.82 min; [M+H]$^+$: 447.26.

Example 268: (1,3-Dimethyl-azetidin-3-yl)-[6-(tetrahydro-pyran-4-yloxy)-pyridin-3-yl]-(4-trifluoromethoxy-phenyl)-methanol

268.1. 5-Bromo-2-(tetrahydro-pyran-4-yloxy)-pyridine

To a solution of 5-bromo-2-chloropyridine (250 mg) in THF (1.5 mL) was added KOtBu(152 mg) and tetrahydro-4-pyranol (132 μL) and the resulting solution was stirred under microwave conditions for 30 min at 120° C. The reaction mixture was diluted with EA and washed with water and brine. The org. phases were dried ($MgSO_4$), filtrated off and evaporated to dryness. The residue was purified by CC (Biotage, SNAP10 g, solvent A: Hep; solvent B: EA; gradient in % B: 5 over 2 CV, 5 to 10 over 2 CV, 10 over 2 CV) to afford 240 mg of the title compound as white solid. LC-MS (A): $t_R$=0.89 min; [M+H]$^+$: 260.16.

268.2. (1,3-Dimethyl-azetidin-3-yl)-[6-(tetrahydro-pyran-4-yloxy)-pyridin-3-yl]-(4-trifluoromethoxy-phenyl)-methanol The title compound was synthesized starting from Example B2.1 (50 mg) and Example 268.1 (104 mg), and following the procedure described in Example A7.1 step A7.1.1. The crude material was purified by Prep LC-MS (VI) then Prep LC-MS (IX) to afford 7 mg of the title compound as white solid. LC-MS (A): $t_R$=0.77 min; [M+H]$^+$: 453.14.

Example 269: (1,3-Dimethyl-azetidin-3-yl)-[6-(oxetan-3-ylmethoxy)-pyridin-3-yl]-(4-trifluoromethoxy-phenyl)-methanol The title compound (11 mg, white solid) was synthesized following the two-step procedure described in Example 268, using oxetan-3-yl-methanol instead of tetrahydro-4-pyranol. The crude material was purified by Prep LC-MS (VI) to afford 11 mg of the title compound as white solid. LC-MS (A): $t_R$=0.73 min; [M+H]$^+$: 439.16.

Example 270: (1,3-Dimethyl-azetidin-3-yl)-(4-isopropyl-phenyl)-[5-(4-methyl-thiazol-2-yl)-pyridin-3-yl]-methanol

270.1. 3-Bromo-5-(4-methyl-thiazol-2-yl)-pyridine

A suspension of 5-bromopyridine-3-carbothioamide (150 mg) and chloroacetone (66 μL) in EtOH (5 mL) was stirred for 5 days at 80° C. and evaporated to dryness. The resulting residue was purified by CC (Biotage, SNAP10 g, solvent A: Hep; solvent B: EA; gradient in % B: 10 over 2 CV, 10 to 30 over 2 CV, 30 over 2 CV) to afford 121 mg of the title compound as brown solid. LC-MS (A): $t_R$=0.89 min; $[M+H]^+$: 257.13.

270.2. (1,3-Dimethyl-azetidin-3-yl)-(4-isopropyl-phenyl)-[5-(4-methyl-thiazol-2-yl)-pyridin-3-yl]-methanol The title compound was synthesized starting from Example B2.2 (50 mg) and Example 270.1 (71.7 mg), and following the procedure described in Example A7.1 step A7.1.1. The crude material was purified by Prep LC-MS (VII) then Prep LC-MS (IX) to afford 5 mg of the title compound as white solid. LC-MS (A): $t_R$=0.79 min; $[M+H]^+$: 408.32.

Example 271: (1,3-Dimethyl-azetidin-3-yl)-(4-iso-propyl-phenyl)-[5-(5-methyl-thiazol-2-yl)-pyridin-3-yl]-methanol 271.1. 3-Bromo-5-(5-methyl-thiazol-2-yl)-pyridine A suspension of 5-bromopyridine-3-carbothioamide (150 mg) and 2-bromo-1,1-diethoxypropane (139 mg) in AcOH (1.5 mL) was stirred for 4 h at 120° C. and was evaporated to dryness. The resulting residue was taken up in aq. sat. $NaHCO_3$ solution. The org. layers were washed with water and brine, dried ($MgSO_4$), filtrated off and evaporated to dryness. The resulting crude material was purified by CC (Biotage, SNAP10 g, solvent A: Hep; solvent B: EA; gradient in % B: 10 over 2 CV, 10 to 30 over 2 CV, 30 over 2 CV) to afford 82 mg of the title compound as brown solid. LC-MS (A): $t_R$=0.92 min; $[M+H]^+$: 257.13.

271.2. (1,3-Dimethyl-azetidin-3-yl)-(4-isopropyl-phenyl)-[5-(5-methyl-thiazol-2-A-pyridin-3-yl]-methanol The title compound was synthesized starting from Example B2.2 (50 mg) and Example 271.1 (71.7 mg), and following the procedure described in Example A7.1 step A7.1.1. The crude material was purified by Prep LC-MS (VII) then Prep LC-MS (XIV) to afford 5 mg of the title compound as white solid. LC-MS (B): $t_R$=0.734 min; $[M+H]^+$: 408.4.

Example 272: (1,3-Dimethyl-azetidin-3-yl)-(4-iso-propyl-phenyl)-(2-methoxy-pyrimidin-5-yl)-methanol The title compound was synthesized starting from Example B2.2 (50 mg) and 5-bromo-2-methoxypyrimidine (41.7 mg), and following the procedure described in Example A7.1 step A7.1.1. The crude material was purified by Prep LC-MS (VI) then Prep LC-MS (IX) to afford 2 mg of the title compound as white solid. LC-MS (A): $t_R$=0.80 min; $[M+H]^+$: 342.19.

Example 273: (S)-(1,3-Dimethyl-azetidin-3-yl)-(4-isopropyl-phenyl)-(2-pyrrolidin-1-yl-pyridin-4-yl)-methanol 273.1. (1,3-Dimethyl-azetidin-3-yl)-(4-isopropyl-phenyl)-(2-pyrrolidin-1-yl-pyridin-4-yl)-methanol Example F1.5 (75 mg) and pyrrolidine (100 μL) were dissolved in Dioxane (1 mL) and the reaction mixture was stirred for 20 h at 110° C. Pyrrolidine (100 μL) was added and the mixture was stirred for 70 h at 110° C. The mixture was allowed to cool down, was diluted with MeCN and purified by Prep LC-MS (XIV). The solvent of collected fractions was evaporated and the resulting aq. layer was basified with 1M NaOH solution and extracted with EA. The org. layers were washed with brine, dried ($MgSO_4$), filtered off and evaporated to dryness. The residue was purified by Prep LC-MS (VII) to afford 17.7 mg of the title compound as yellow oil. LC-MS (B): $t_R$=0.58 min; $[M+H]^+$: 380.27.

273.2 (S)-(1,3-Dimethyl-azetidin-3-yl)-(4-isopropyl-phenyl)-(2-pyrrolidin-1-yl-pyridin-4-yl)-methanol The title compound (9 mg) was obtained by Prep chiral SFC (IX) of Example 273.1 (17.7 mg). LC-MS (A): $t_R$=0.58 min; $[M+H]^+$: 380.22; Chiral SFC (J): 2.8 min.

Example 274 to Example 276 were synthesized starting from the appropriate amine reagent of Formula (F2), and following the procedure described in Example 273 step 273.1, but using different solvents and bases listed in the table below. Prep LC-MS conditions and LC-MS data of Example 274 to Example 276 are listed in the table below. The LC-MS conditions used were LC-MS (A).

| Example N° | Name | $t_R$ | $[M+H]^+$ | Prep LC-MS | Solvent Base |
|---|---|---|---|---|---|
| 274 | (1,3-Dimethyl-azetidin-3-yl)-[2-((R)-2-hydroxymethyl-pyrrolidin-1-yl)-pyridin-4-yl]-(4-isopropyl-phenyl)-methanol | 0.56 | 410.33 | (XV) then (IX) | NMP DIPEA |
| 275 | (1,3-Dimethyl-azetidin-3-yl)-(4-isopropyl-phenyl)-(3,4,5,6-tetrahydro-2H-[1,2']bipyridinyl-4'-yl)-methanol | 0.64 | 394.32 | (XV) | n-Butanol DIPEA |
| 276 | (1,3-Dimethyl-azetidin-3-yl)-(4-isopropyl-phenyl)-(2-morpholin-4-yl-pyridin-4-yl)-methanol | 0.59 | 396.32 | (XV) | NMP none |

Example 277: (S)-(1,3-Dimethyl-azetidin-3-yl)-(4-isopropyl-phenyl)-[2-(tetrahydro-pyran-4-yl-methoxy)-pyridin-4-yl]-methanol Example F1.5 (35 mg) and tetrahydro-2H-pyran-4-yl-methanol (52 mg) were dissolved in dioxane (1 mL) and NaH (60% in mineral oil, 17.1 mg) was added. The reaction mixture was stirred for 7 h at 100° C. DMF (1 mL) was added and the mixture was stirred for 72 h at 130° C. After cooling down to RT, the mixture was diluted with MeCN/water and purified by Prep LC-MS (IX) to afford the title compound (4.5 mg) as white solid. LC-MS (A): $t_R$=0.78 min; $[M+H]^+$: 425.31.

Example 278: (S)-(1,3-Dimethyl-azetidin-3-yl)-(4-isopropyl-phenyl)-[2-(2-methoxy-ethoxy)-pyridin-4-yl]-methanol The title compound (7.4 mg, white solid) was prepared following the procedure described in Example 277, and using 2-methoxy-ethanol instead of tetrahydro-2H-pyran-4-yl-methanol. LC-MS (A): $t_R$=0.74 min; $[M+H]^+$: 385.14.

Example 279: (S)-(1,3-Dimethyl-azetidin-3-yl)-(2-ethyl-pyridin-4-yl)-(4-isopropyl-phenyl)-methanol To a solution of Example F1.5 (30 mg) in dioxane (0.5 mL) was added diethylzinc solution in toluene (15%, 104 μL) and $Pd(dppf)Cl_2$ (1.12 mg) and the mixture was stirred for 5 h30 at 70° C. Diethylzinc solution in toluene (15%, 104 μL) was added again and the mixture was further stirred for 6 h30 at 70° C. The reaction mixture was quenched by careful addition of water, diluted with MeOH and filtered off. The resulting crude material was purified by Prep LC-MS (V) then by Prep LC-MS (XIV) to afford 1.3 mg of the title compound as white solid. LC-MS (A): $t_R$=0.54 min; $[M+H]^+$: 339.25.

Example 280: (S)-(2-Cyclopentyl-pyridin-4-yl)-(1,3-dimethyl-azetidin-3-yl)-(4-isopropyl-phenyl)-methanol 280.1. (S)-(2-Cyclopent-1-enyl-pyridin-4-yl)-(1,3-dimethyl-azetidin-3-yl)-(4-isopropyl-phenyl)-methanol To a solution of Example F1.5 (50 mg) and cyclopentene-1-yl-boronic acid (16.1 mg) in MeCN (0.5 mL) were added $Na_2CO_3$ (1M, 0.5 mL) and $Pd(PPh)_3Cl_2$ (4.49 mg), and the mixture was stirred for 3 h30 at 80° C. The reaction mixture was cooled down to RT, diluted with MeOH, filtered off and purified by Prep LC-MS (V) to afford 30 mg of the title compound as white solid. LC-MS (A): $t_R$=0.63 min; $[M+H]^+$: 377.33.

280.2. (S)-(2-Cyclopentyl-pyridin-4-yl)-(1,3-dimethyl-azetidin-3-yl)-(4-isopropyl-phenyl)-methanol The title compound (23 mg, white solid) was synthetized starting from Example 280.1 (27 mg), and following the procedure described in Example 48. LC-MS (A): $t_R$=0.62 min; $[M+H]^+$: 379.35.

Example 281: (R)-(1,3-Dimethyl-azetidin-3-yl)-(5-pyrrolidin-1-yl-pyridin-3-yl)-(4-trifluoromethyl-phenyl)-methanol 281.1. 3-[Hydroxy-(5-pyrrolidin-1-yl-pyridin-3-yl)-(4-trifluoromethyl-phenyl)-methyl]-3-methyl-azetidine-1-carboxylic acid tert-butyl ester The title compound was synthesized starting from Example A4.5 (1.13 g) and 3-bromo-5-pyrrolidinopyridine (990 mg), and following the procedure described in Example A7.1 step A7.1.1. The crude material was purified by Prep LC-MS (IV) to afford 480 mg of the title compound as light yellow solid. LC-MS (A): $t_R$=0.89 min; $[M+H]^+$: 492.32.

281.2. 3-[(R)-Hydroxy-5-pyrrolidin-1-yl-pyridin-3-yl)-(4-trifluoromethyl-phenyl)-methyl]-3-methyl-azetidine-1-carboxylic acid tert-butyl ester The title compound was obtained by Prep chiral SFC (II) of Example 281.1. LC-MS (A): $t_R$=0.87 min; $[M+H]^+$: 492.29; Chiral SFC (H): 3.0 min.

281.3. (R)-(3-Methyl-azetidin-3-yl)-(5-pyrrolidin-1-yl-pyridin-3-yl)-(4-trifluoromethyl-phenyl)-methanol, hydrochloride salt A solution of Example 281.2 (215 mg) in HCl in dioxane (4M, 2 mL) was stirred for 1 h45. The mixture was evaporated to dryness to give 210 mg of the title compound as orange solid. LC-MS (A): $t_R$=0.60 min; $[M+H]^+$: 392.33.

281.4. ((R)-(1,3-Dimethyl-azetidin-3-yl)-(5-pyrrolidin-1-yl-pyridin-3-yl)-(4-trifluoromethyl-phenyl)-methanol The title compound was synthesized starting from Example 281.3 (50 mg), and following the procedure described in Example B2.1 step B2.1.2 (16 mg, colorless resin). LC-MS (B): $t_R$=0.488 min; $[M+H]^+$: 406.4.

Example 282: (R)-(1,3-Dimethyl-azetidin-3-yl)-[5-(R)-3-hydroxymethyl-3-methyl-pyrrolidin-1-yl)-pyridin-3-yl]-(4-isopropyl-phenyl)-methanol 282.1. (R)-3-Methyl-pyrrolidine-3-carboxylic acid methyl ester, hydrochloride salt To an ice-cold MeOH solution (20 mL) was added drop-wise $SOCl_2$ (1 mL), followed 30 min later by (R)-3-methyl-pyrrolidine-3-carboxylic acid (500 mg) and the resulting suspension was stirred for 65 h at RT. The reaction mixture was evaporated to dryness to afford 784 mg of the title compound as brown solid. LC-MS (A): $t_R$=0.31 min; $[M+H]^+$: 144.27.

282.2. (R)-3-Methyl-pyrrolidine-1,3-dicarboxylic acid 1-tert-butyl ester 3-methyl ester To a solution of Example 282.1 (768 mg) in DCM (30 mL) were successively added TEA (1.79 mL) and $Boc_2O$ (952 mg). The resulting mixture was stirred for 1 h10 at RT, diluted with water and extracted with DCM. The org. layers were dried ($MgSO_4$), filtrated off, and evaporated to dryness to afford 832 mg of the title compound as brown oil. LC-MS (A): $t_R$=0.87 min; $[M+H]^+$: 244.34.

282.3. (R)-3-Hydroxymethyl-3-methyl-pyrrolidine-1-carboxylic acid tert-butyl ester To an ice-cold solution of Example 282.2 (820 mg) in THF (30 mL) was $LiAlH_4$ in THF (2M, 1.01 mL). The resulting mixture was stirred for 1 h at 0° C., carefully quenched with ice-water then with aq. sat. $NaHCO_3$ solution, and extracted with EA. The org. layers were washed with water and brine, dried ($MgSO_4$), filtrated off, and evaporated to dryness to afford 716 mg of the title compound as yellow oil. LC-MS (A): $t_R$=0.72 min; $[M+H]^+$: 216.22.

282.4. ((R)-3-Methyl-pyrrolidin-3-yl)-methanol, hydrochloride salt

A solution of Example 282.4 (715 mg) in HCl in dioxane (4M, 7 mL) was stirred for 1 h50 at RT and evaporated to dryness to give 377 mg of the title compound as brown solid. LC-MS (A): $t_R$=0.2 min; $[M+H]^+$: 116.30.

282.5. (R)-(1,3-Dimethyl-azetidin-3-yl)-[5-((R)-3-hydroxymethyl-3-methyl-pyrrolidin-1-yl)-pyridin-3-yl]-(4-isopropyl-phenyl)-methanol To a solution of Example F1.2 (50 mg) and Example 282.4 (97.4 mg) in DMSO (1 mL), were added $K_2CO_3$ (54.1 mg), L-proline (16.3 mg) and CuI (13.2 mg) and the resulting mixture was stirred for 44 h at 100° C., cooled down to RT, filtrated off and evaporated to dryness. The residue was purified by Prep LC-MS (IX) then by Prep LC-MS (VI) to afford 14 mg of the title compound as white solid. LC-MS (B): $t_R$=0.475 min; $[M+H]^+$: 424.4.

Example 283: (R)-(1,3-Dimethyl-azetidin-3-yl)-[5-(S)-3-fluoro-pyrrolidin-1-yl)-pyridin-3-yl]-(4-isopropyl-phenyl)-methanol To a solution of Example F1.2 (50 mg) and (S)-(±)-3-fluoropyrrolidne hydrochloride (41.5 mg) in toluene (1 mL) was added RuPhos (6.29 mg), $Pd_2(dba)_3$ (6.05 mg) and NaOtBu (57.1 mg). The reaction mixture was stirred for 1 h at 110° C., cooled down to RT, diluted with water and extracted with DCM. The org. layers were dried ($MgSO_4$) and evaporated to dryness. The residue was purified by Prep LC-MS (VI) to afford 71 mg of the title compound as white solid. LC-MS (B): $t_R$=0.493 min; $[M+H]^+$: 398.40.

Example 284: (R)-(1,3-Dimethyl-azetidin-3-yl)-(4-isopropyl-phenyl)-{5-[4-(tetrahydro-pyran-4-yl)-[1,2,3]triazol-1-yl}-pyridin-3-yl]-methanol To a solution of Example F1.2 (50 mg) in EtOH (0.7 mL) were added 4-ethynyloxane (70.7 mg), sodium azide (16.9 mg), (±)-Sodium L-ascorbate (2.57 mg), N,N-dimethylethylenediamine (4.23 µL) and CuI (4.92 mg). The resulting mixture was stirred for 20 h20 at 90° C. 4-Ethynyloxane (70.7 mg) was added again and the mixture was stirred for 5 h30 at 90° C., diluted with water, MeOH and DMF, filtrated off and purified by Prep LC-MS (VI) to afford 1 mg of the title compound as white solid. LC-MS (B): $t_R$=0.66 min; $[M+H]^+$: 462.40.

Example 285 to Example 288 were synthesized starting from Example F1.1 and the appropriate boronic acid reagent of Formula (F6), following the procedure described in Example 280 step 280.1. Prep LC-MS conditions and LC-MS data are listed in the table below. The LC-MS conditions used were LC-MS (A).

| Example N° | Name | $t_R$ | [M + H]$^+$ | Prep LC-MS |
|---|---|---|---|---|
| 285 | (1,3-Dimethyl-azetidin-3-yl)-(4-isopropyl-phenyl)-(5-methyl-pyridin-3-yl)-methanol | 0.55 | 325.31 | (V) |
| 286 | (1,3-Dimethyl-azetidin-3-yl)-(5-isopropenyl-pyridin-3-yl)-(4-isopropyl-phenyl)-methanol | 0.66 | 351.31 | (VII) |
| 287 | (5-Cyclopropyl-pyridin-3-yl)-(1,3-dimethyl-azetidin-3-yl)-(4-isopropyl-phenyl)-methanol | 0.62 | 351.28 | (VII) |
| 288 | (5-Cyclopent-1-enyl-pyridin-3-yl)-(1,3-dimethyl-azetidin-3-yl)-(4-isopropyl-phenyl)-methanol | 0.71 | 377.36 | (VII) |

Example 289: 3-{5-[(1,3-Dimethyl-azetidin-3-yl)-hydroxy-(4-isopropyl-phenyl)-methyl]-pyridin-3-yl}-cyclopent-2-enol 289.1. 3-{5-[(1,3-Dimethyl-azetidin-3-yl)-hydroxy-(4-isopropyl-phenyl)-methyl]-pyridin-3-yl}-cyclopent-2-enone The title compound was synthesized starting from Example F1.1 (250 mg) and 3-(4,4,5,5-tetramethyl-1,3,2-dioxaborolan-2-yl)cyclopent-2-en-1-one (140 mg), following the procedure described in Example 280 step 280.1. The crude material was purified by Prep LC-MS (XIV) to afford 122 mg of the title compound as off-white powder. LC-MS (A): $t_R$=0.7 min; $[M+H]^+$: 391.32.

289.2 3-{5-[(1,3-Dimethyl-azetidin-3-yl)-hydroxy-(4-isopropyl-phenyl)-methyl]-pyridin-3-yl}-cyclopent-2-enol To an ice-cold suspension of Example 289.1 (122 mg) in THF (18 mL) and MeOH (1.8 mL) was added $NaBH_4$ (47.3 mg) portionwise and the resulting mixture was stirred for 19 h30 at RT. $NaBH_4$ (47.3 mg) was added and the mixture was stirred for 3 h30 at RT then for 45 h at 40° C. and for 6 h at 65° C. $NaBH_4$ (23.6 mg) was added and the mixture was stirred for 18 h at 65° C. The reaction mixture was allowed to cool down to RT, quenched with aq. sat. $NH_4Cl$ and extracted with EA. The org. layers were washed with aq. sat. $NH_4Cl$ and brine, dried ($MgSO_4$), filtrated off, and evaporated to dryness. The residue was purified by Prep LC-MS (IX) to afford 5 mg of the title compound as white solid. LC-MS (B): $t_R$=0.576 min; $[M+H]^+$: 393.40.

Example 290 to Example 293 were synthesized from the appropriate precursor, following the procedure described in Example 48 and using the solvents listed in the table below. Precursors and LC-MS data are listed in the table below. The LC-MS conditions used were LC-MS (B).

| Example N° | Name | $t_R$ | $[M+H]^+$ | Precursor | Solvent |
|---|---|---|---|---|---|
| 290 | (1,3-Dimethyl-azetidin-3-yl)-(4-isopropyl-phenyl)-(5-isopropyl-pyridin-3-yl)-methanol | 0.609 | 353.4 | 286 | MeOH |
| 291 | (5-Cyclopentyl-pyridin-3-yl)-(1,3-dimethyl-azetidin-3-yl)-(4-isopropyl-phenyl)-methanol | 0.691 | 379.4 | 288 | EtOH |
| 292 | 3-{5-[(1,3-Dimethyl-azetidin-3-yl)-hydroxy-(4-isopropyl-phenyl)-methyl]-pyridin-3-yl}-cyclopentanol | 0.509 | 395.4 | 289 | EtOH |
| 293 | (R)-(1,3-Dimethyl-azetidin-3-yl)-(4-isopropyl-phenyl)-pyridin-3-yl-methanol | 0.492 | 311.3 | F1.2 | EtOH |

Example 294: 3-{5-[(R)-(1,3-Dimethyl-azetidin-3-yl)-hydroxy-(4-isopropyl-phenyl)-methyl]-pyridin-3-yl}-cyclopent-2-enone The title compound (182 mg, off-white solid) was synthesized following the procedure described in Example 289 step 289.1, but starting from Example F1.2 (250 mg). The crude material was purified by Prep LC-MS (V) then by Prep LC-MS (IX). LC-MS (B): $t_R$=0.612 min; $[M+H]^+$: 391.32.

Example 295: 3-{5-[(R)-(1,3-Dimethyl-azetidin-3-yl)-hydroxy-(4-isopropyl-phenyl)-methyl]-pyridin-3-yl}-1-methyl-cyclopent-2-enol The title compound (18 mg, yellow powder) was synthesized starting from Example 294 (50 mg), and following the procedure described in Example 262. The crude material was purified by Prep LC-MS (V). LC-MS (B): $t_R$=0.614 min; $[M+H]^+$: 407.40.

Example 296: (3S)-3-(5-((R)-(1,3-dimethylazetidin-3-yl)(hydroxy)(4-isopropylphenyl)methyl)pyridin-3-yl)-1-methylcyclopentan-1-ol The title compound (mixture of two diastereomers, 8 mg, white powder) was synthesized starting from Example 295 (22 mg), and following the procedure described in Example 48. The crude material was purified by Prep LC-MS (VI). The chirality at carbon atom 3 of the cyclopentyl ring was arbitrarily assigned to (S). The chirality at carbon atom 1 of the cyclopentyl ring is undefined. LC-MS (B): $t_R$=0.531 min; $[M+H]^+$: 409.5.

Example 297: (3R)-3-(5-((R)-(1,3-dimethylazetidin-3-yl)(hydroxy)(4-isopropylphenyl)methyl)pyridin-3-yl)-1-methylcyclopentan-1-ol The title compound (mixture of two diastereomers, 5 mg, white powder) was isolated as second eluting compound from Prep LC-MS (VI) of Example 296. The chirality at carbon atom 3 of the cyclopentyl ring was arbitrarily assigned to (R). The chirality at carbon atom 1 of the cyclopentyl ring is undefined. LC-MS (B): $t_R$=0.558 min; $[M+H]^+$: 409.5.

Example 298: 3-{5-[(R)-(1,3-Dimethyl-azetidin-3-yl)-hydroxy-(4-isopropyl-phenyl)-methyl]-pyridin-3-yl}-1-ethyl-cyclopentanol 298.1. 3-{5-[(R)-(1,3-Dimethyl-azetidin-3-yl)-hydroxy-(4-isopropyl-phenyl)-methyl]-pyridin-3-yl}-1-ethyl-cyclopent-2-enol The title compound (as mixture of diastereomers, 10 mg, white powder) was synthesized starting from Example 294 (64 mg) and ethylmagnesium bromide solution in THF (1M, 513 µL), following the procedure described in Example 262. The crude material was purified by Prep LC-MS (VI). LC-MS (A): $t_R$=0.64 min; $[M+H]^+$: 421.34.

298.2 3-{5-[(R)-(1,3-Dimethyl-azetidin-3-yl)-hydroxy-(4-isopropyl-phenyl)-methyl]-pyridin-3-yl}-1-ethyl-cyclopentanol The title compound (10 mg, white powder) was synthesized from Example 298.1 (10 mg), and following the procedure described in Example 48. The crude material was purified by Prep LC-MS (VI). LC-MS (B): $t_R$=0.584 min; $[M+H]^+$: 423.50.

Example 299: 3-{5-[(R)-(1,3-Dimethyl-azetidin-3-yl)-hydroxy-(4-isopropyl-phenyl)-methyl]-pyridin-3-yl}-1-isopropyl-cyclopentanol The title compound was synthesized starting from isopropylmagnesiumbromide solution in THF, and following the two-step procedure described in Example 298. LC-MS (A): $t_R$=0.67 min; $[M+H]^+$: 437.40.

Example 300: (R)-(1,3-Dimethyl-azetidin-3-yl)-(4-isopropyl-phenyl)-[5-(4-methyl-oxazol-2-yl)-pyridin-3-yl]-methanol To a solution of 4-methyloxazole (25 mg) in THF (0.5 mL) cooled down to −78° C. was added dropwise n-BuLi in hexane (2.5M, 143 µL), followed by $ZnCl_2$ in 2-methyltetrahydrofuran (1.9M, 235 µL). The resulting solution was stirred for 50 min at RT. Example F1.2 (116 mg) and $Pd(PPh_3)_4$ (35.1 mg) were added and the mixture was stirred for 18 h at 60° C., cooled down to RT, diluted with EA and washed with water and brine. The org. layers were dried ($MgSO_4$), filtrated off and evaporated to dryness. The residue was purified by Prep LC-MS (VI) to afford 14 mg of the title compound as white powder. LC-MS (B): $t_R$=0.692 min; $[M+H]^+$: 392.40.

Example 301: (R)-(1,3-Dimethyl-azetidin-3-yl)-(5-ethyl-pyridin-3-yl)-(4-isopropyl-phenyl)-methanol The title compound (8 mg, brown solid) was synthesized starting from Example F1.2 (50 mg), following the procedure described in Example 279. The crude material was purified by Prep LC-MS (VI). LC-MS (A): $t_R$=0.58 min; $[M+H]^+$: 339.30.

Example 302: (R)-(1,3-Dimethyl-azetidin-3-yl)-(4-isopropyl-phenyl)-(5-methyl-pyridin-3-yl)-methanol The title compound (14 mg, white solid) was synthesized starting from Example F1.2 (50 mg) and methylboronic acid (8.72 mg), following the procedure described in Example 280 step 280.1. The crude material was purified by Prep LC-MS (VI) then by Prep LC-MS (XXI). LC-MS (A): $t_R$=0.54 min; $[M+H]^+$: 325.33.

Example 303: (R)-[5-(4,5-Dihydro-furan-3-yl)-pyridin-3-yl]-(1,3-dimethyl-azetidin-3-yl)-(4-isopropyl-phenyl)-methanol To a solution of Example F1.2 (50 mg) and 4,5-dihydro-furan-3-boronic acid pinacol ester (52.5 mg) in dioxane (1 mL) and water (0.25 mL) were added $K_3PO_4$ (81.8 mg) and [1,1'-bis(diphenylphosphino)ferrocene]dichloropalladium (II) complex with DCM (21 mg), and the resulting mixture was stirred for 1 h at 80° C. It was then allowed to cool down to RT, diluted with MeCN and water and filtrated off. The resulting solution was purified by Prep LC-MS (VI) then by Prep LC-MS (IX) to afford 25 mg of the title compound as white solid. LC-MS (B): $t_R$=0.604 min; $[M+H]^+$: 379.40.

Example 304: (R)-(1,3-Dimethyl-azetidin-3-yl)-(4-isopropyl-phenyl)-[5-(tetrahydro-furan-3-yl)-pyridin-3-yl]-methanol Example 303 (21 mg) was dissolved in EtOH with 1% toluene (10 mL) and the reaction was conducted in a HCube®-Pro equipped with a 10% (w/w) Pd/C cartridge (7 cm long) under a flow of 1.0 mL/min, a hydrogen pressure of 3 bar and a temperature of 30° C. After reaction completion, the solvent was evaporated and the residue was purified by Prep LC-MS (V) to afford 5.5 mg of the title compound as colorless solid. LC-MS (B): $t_R$=0.551 min; $[M+H]^+$: 381.40.

Example 305: 3-{5-[(R)-(1,3-Dimethyl-azetidin-3-yl)-hydroxy-(4-isopropyl-phenyl)-methyl]-pyridin-3-yl}-but-3-en-1-ol The title compound (35 mg, off-white solid) was synthesized starting from Example F1.2 (50 mg) and 3-buten-1-ol-3-boronic acid pinacol ester (50.9 mg), and following the procedure described in Example 303. The crude material was purified by Prep LC-MS (VI). LC-MS (B): $t_R$=0.561 min; $[M+H]^+$: 381.40.

Example 306: N-Cyclopentyl-5-[(R)-(1,3-dimethyl-azetidin-3-yl)-hydroxy-(4-isopropyl-phenyl)-methyl]-nicotinamide 306.1. 3-[(R)-(5-Cyclopentylcarbamoyl-pyridin-3-yl)-hydroxy-(4-isopropyl-phenyl)-methyl]-3-methyl-azetidine-1-carboxylic acid tert-butyl ester A mixture of Example E1.1 (50 mg), HATU (56.1 mg) and DIPEA (58.3 µL) in DCM (0.6 mL) was stirred at RT for 15 min and cyclopentylamine (14.7 µL) was added. The reaction mixture was stirred at RT for 2 h, quenched with aq. sat. $NaHCO_3$ and extracted with DCM. The combined organic extracts were dried ($MgSO_4$), filtered off and concentrated in vacuo. The crude was purified by Prep LC-MS (VII) to afford the title compound as white solid (45.5 mg). LC-MS (A): $t_R$=1.06 min; $[M+H]^+$: 508.43.

306.2. N-Cyclopentyl-5-[(R)-hydroxy-(4-isopropyl-phenyl)-(3-methyl-azetidin-3-yl)-methyl]-nicotinamide, hydrochloride salt A solution of Example 306.1 (43 mg) in HCl in dioxane (4M, 0.21 mL) was stirred at RT for 2 h30, concentrated in vacuo and dried under HV to afford 37.6 mg of the title compound. LC-MS (A): $t_R$=0.72 min; $[M+H]^+$: 408.26.

306.3. N-Cyclopentyl-5-[(R)-(1,3-dimethyl-azetidin-3-yl)-hydroxy-(4-isopropyl-phenyl)-methyl]-nicotinamide Example 306.3 was obtained starting from Example 306.2 (37.6 mg) and following the procedure described in Example D1.1 step D1.1.5, with a direct filtration of the reaction mixture through a syringe filter and purification by Prep LC-MS (IX) to afford the title product as a white solid (29.2 mg). LC-MS (B): $t_R$=0.701 min; $[M+H]^+$: 422.5.

Example 307 and Example 308 were synthesized starting from Example E1.1 and the appropriate amine reagent, and following the three-step procedure described in Example 306. The Prep LC-MS methods and the LC-MS data are listed in the table below. The LC-MS conditions used were LC-MS (B).

| Example N° | Name | $t_R$ | [M + H]$^+$ | Prep LC-MS |
|---|---|---|---|---|
| 307 | {5-[(R)-(1,3-Dimethyl-azetidin-3-yl)-hydroxy-(4-isopropyl-phenyl)-methyl]-pyridin-3-yl}-pyrrolidin-1-yl-methanone | 0.622 | 408.4 | (IX) |
| 308 | 5-[(R)-(1,3-Dimethyl-azetidin-3-yl)-hydroxy-(4-isopropyl-phenyl)-methyl]-N-(tetrahydro-pyran-4-yl)-nicotinamide | 0.591 | 438.4 | (IX) |

Example 309: (1,3-Dimethyl-azetidin-3-yl)-[4-(3-methoxy-propyl)-phenyl]-(5-pyrrolidin-1-yl-pyridin-3-yl)-methanol

309.1. 3-[(4-Bromo-phenyl)-hydroxy-(5-pyrrolidin-1-yl-pyridin-3-yl)-methyl]-3-methyl-azetidine-1-carboxylic acid tert-butyl ester The title compound (180 mg) was prepared starting from Example C1.1 (150 mg) and 1,4-dibromobenzene (73.8 μL), and following the procedure described in Example A4.1 step A4.1.2. LC-MS (A): $t_R$=0.88 min; $[M+H]^+$: 502.28.

309.2. (4-Bromo-phenyl)-(3-methyl-azetidin-3-yl)-(5-pyrrolidin-1-yl-pyridin-3-yl)-methanol, hydrochloride salt A solution of Example 309.1 (175 mg) in HCl in dioxane (4M, 5 mL) was stirred for 30 min at RT and evaporated to dryness to afford 170 mg of the title compound as yellow solid. LC-MS (A): $t_R$=0.57 min; $[M+H]^+$:402.03.

309.3. (4-Brom o-phenyl)-(1,3-dim ethyl-azetidin-3-yl)-(5-pyrrolidin-1-yl-pyridin-3-yl)-methanol The title compound (138 mg, beige solid) was synthesized starting from Example 309.2 (170 mg), and following the procedure described in Example B2.1 step B2.1.2. LC-MS (A): $t_R$=0.57 min; $[M+H]^+$: 416.29.

309.4. (1,3-Dimethyl-azetidin-3-yl)-[4-((E)-3-methoxy-propenyl)-phenyl]-(5-pyrrolidin-1-yl-pyridin-3-yl)-methanol The title compound (30 mg, white solid) was synthesized starting from Example 309.3 (50 mg) and trans-3-methoxy-1-propenylboronic acid pinacol ester (53.7 μL), following the procedure described in Example 303. The crude material was purified by Prep LC-MS (IX). LC-MS (A): $t_R$=0.57 min; $[M+H]^+$: 408.43.

309.5. (1,3-Dimethyl-azetidin-3-yl)-[4-(3-methoxy-propyl)-phenyl]-(5-pyrrolidin-1-yl-pyridin-3-yl)-methanol The title compound (11 mg, yellow solid) was synthesized starting from Example 309.4 (28 mg), and following the procedure described in Example 48. The crude material was purified by Prep LC-MS (XIV). LC-MS (B): $t_R$=0.445 min; $[M+H]^+$: 410.5.

Example 310 and Example 311 were synthesized starting from Example 309.3 and the appropriate boronic acid reagent, and following the procedure described in Example 303. Prep LC-MS conditions and LC-MS data are listed in the table below. The LC-MS conditions used were LC-MS (B).

| Example N° | Name | $t_R$ | [M + H]$^+$ | Prep LC-MS |
|---|---|---|---|---|
| 310 | (R)-(4-Cyclopropyl-phenyl)-(1,3-dimethyl-azetidin-3-yl)-(5-pyrrolidin-1-yl-pyridin-3-yl)-methanol | 0.468 | 378.2 | (VII) then (IX) |
| 311 | (R)-(1,3-Dimethyl-azetidin-3-yl)-(5-pyrrolidin-1-yl-pyridin-3-yl)-p-tolyl-methanol | 0.408 | 352.4 | (VI) then (IX) |

Example 312: 5-[(R)-(1,3-Dimethyl-azetidin-3-yl)-hydroxy-(4-isopropyl-phenyl)-methyl]-3',4',5',6'-tetrahydro-2'H-[3,4']bipyridinyl-1'-carboxylic acid tert-butyl ester 312.1. 5-[(R)-(1,3-Dimethyl-azetidin-3-yl)-hydroxy-(4-isopropyl-phenyl)-methyl]-3',6'-dihydro-2'H-[3,4']bipyridinyl-1'-carboxylic acid tert-butyl ester The title compound was synthesized starting from Example F1.2 (50 mg) and 3,6-dihydro-2H-pyridine-1-N-Boc-4-boronic acid, pinacol ester (81 mg), and following the procedure described in Example 303. The crude material was purified by Prep LC-MS (V) to give 33 mg of the title compound as white solid. LC-MS (A): $t_R$=0.76 min; $[M+H]^+$: 492.34.

312.2. 5-[(R)-(1,3-Dimethyl-azetidin-3-yl)-hydroxy-(4-isopropyl-phenyl)-methyl]-3',4',5',6'-tetrahydro-2'H-[3,4']bipyridinyl-1'-carboxylic acid tert-butyl ester The title compound was synthesized from Example 312.1 (30 mg) and following the procedure described in Example 48. The crude material was purified by Prep LC-MS (XV) to give 11 mg of the title compound as white solid. LC-MS (B): $t_R$=0.77 min; $[M+H]^+$: 494.50.

Example 313 and Example 314 were synthesized from Example F1.2 and the appropriate boronic ester following the two-step procedure described in Example 312. Prep LC-MS conditions and LC-MS data are listed in the table below. The LC-MS conditions used were LC-MS (B).

| Example N° | Name | $t_R$ | $[M+H]^+$ | Prep LC-MS |
|---|---|---|---|---|
| 313 | 3-{5-[(R)-(1,3-Dimethyl-azetidin-3-yl)-hydroxy-(4-isopropyl-phenyl)-methyl]-pyridin-3-yl}-pyrrolidine-1-carboxylic acid tert-butyl ester | 0.76 | 480.50 | (XV) |
| 314 | (R)-(1,3-Dimethyl-azetidin-3-yl)-(4-isopropyl-phenyl)-[5-(tetrahydro-pyran-4-yl)-pyridin-3-yl]-methanol | 0.556 | 395.40 | none |

Example 315: (R)-(1,3-Dimethyl-azetidin-3-yl)-(4-isopropyl-phenyl)-(3',4',5',6'-tetrahydro-2'H-[2,1'; 4',3"]terpyridin-5"-yl)-methanol 315.1. (R)-(3',6'-Dihydro-2'H-[2,1'; 4',3"]terpyridine-5"-yl)-(1,3-dimethyl-azetidin-3-yl)-(4-isopropyl-phenyl)-methanol The title compound was synthesized starting from Example F1.2 (43 mg) and 4-(4,4,5,5-tetramethyl-1,3,2-dioxaborolan-2-yl)-3,6-dihydro-2H-1,2'-bipyridine (32.6 mg), and following the procedure described in Example 303. The crude material was purified by Prep LC-MS (XIII) to afford 35 mg of the title compound as white powder. LC-MS (A): $t_R$=0.56 min; $[M+H]^+$: 469.21.

315.2. (R)-(1,3-Dimethyl-azetidin-3-yl)-(4-isopropyl-phenyl)-(3',4',5',6'-tetrahydro-2'H-[2,1'; 4',3"]terpyridin-5"-yl)-methanol The title compound was synthesized starting from Example 315.1 (33 mg), and following the procedure described in Example 48 but using MeOH as solvent. The crude material was purified by Prep LC-MS (XXI) to afford 6 mg of the title compound as white solid. LC-MS (B): $t_R$=0.466 min; $[M+H]^+$: 471.5.

Example 316 and Example 317 were synthesized starting from Example F1.2 and the appropriate boronic ester, and following the two-step procedure described in Example 315. Prep LC-MS conditions and LC-MS data are listed in the table below. The LC-MS conditions used were LC-MS (A).

| Example N° | Name | $t_R$ | $[M+H]^+$ | Prep LC-MS |
|---|---|---|---|---|
| 316 | (R)-(1,3-Dimethyl-azetidin-3-yl)-(4-isopropyl-phenyl)-(1 phenyl-1',2',3',4',5',6'-hexahydro-[3,4']bipyridinyl-5-yl)-methanol | 0.61 | 470.11 | (IX) then (VIII) |
| 317 | (R)-(1,3-Dimethyl-azetidin-3-yl)-(4-isopropyl-phenyl)-[1 (toluene-4-sulfonyl)-1',2',3',4',5',6'-hexahydro-[3,4']bipyridinyl-5-yl]-methanol | 0.76 | 547.9 | none |

Example 318: (R)-(1,3-Dimethyl-azetidin-3-yl)-(4-isopropyl-phenyl)-[5-(tetrahydro-furan-2-yl)-pyridin-3-yl]-methanol 318.1. 3—{(R)-Hydroxy-(4-isopropyl-phenyl)-[5-(tetrahydro-furan-2-yl)-pyridin-3-yl]-methyl}-3-methyl-azetidine-1-carboxylic acid tert-butyl ester To a vial equipped with a magnetic stirring bar, Example F1.11 (100 mg), [4,4'-bis(1,1-dimethylethyl)-2,2'-bipyridine-N1,N1']bis[3,5-difluoro-2-[5-(trifluoromethyl)-2-pyridinyl-N]phenyl-C]iridium(III) hexafluorophosphate (2.36 mg), $NiCl_2$ glyme (4.72 mg), 4,4'-di-tert-butyl-2,2'-dipyridyl (8.64 mg) and $Cs_2CO_3$ (208 mg) were added. The vial was placed under nitrogen and dry DMF (10 mL) was added followed by tetrahydro-2-furoic acid (60.6 μL). The solution was degassed for 15 min by sparging with nitrogen and was irradiated with a 34 W blue LED placed approximately 8 cm away from the vial. The reaction mixture was stirred for 17 h under irradiation, was diluted with aq. sat. $NaHCO_3$ and extracted with $Et_2O$ (3 times). The combined org. layers were washed with water and brine, dried ($MgSO_4$) and concentrated in vacuo. The residue was purified by CC (Biotage, SNAP 4 g, solvent A: Hep; solvent B: EA; gradient in % B: 0 over 1 min, 0 to 100 over 12 min, 100 over 8 min) and by Prep LC-MS (VII) to afford the title product as white solid (7.2 mg). LC-MS (A): $t_R$=0.90 min; $[M+H]^+$: 467.36.

318.2. (R)-(4-Isopropyl-phenyl)-(3-methyl-azetidin-3-yl)-[5-(tetrahydro-furan-2-yl)-pyridin-3-yl]-methanol, hydrochloride salt The title compound was obtained starting from Example 318.1, and following the protocol described in Example 309 step 309.2. LC-MS (A): $t_R$=0.59 min; $[M+H]^+$: 367.27.

318.3. (R)-(1,3-Dimethyl-azetidin-3-yl)-(4-isopropyl-phenyl)-[5-(tetrahydro-furan-2-yl)-pyridin-3-yl]-methanol The title compound was obtained starting from Example 318.2 (9.3 mg), and following the procedure described in Example F1.1 step F1.1.2. Prep LC-MS (XIV) afforded 2.4 mg of colorless oil. LC-MS (B): $t_R$=0.60 min; $[M+H]^+$: 381.4.

Example 319 to Example 320 were synthesized starting from Example F1.11 and the appropriate carboxylic acid, and following the three-step procedure described in Example 318. The Prep LC-MS methods and the LC-MS data are listed in the table below. The LC-MS conditions used were LC-MS (B).

| Example N° | Name | $t_R$ | [M + H]$^+$ | Prep LC-MS |
|---|---|---|---|---|
| 319 | (R)-(1,3-Dimethyl-azetidin-3-yl)-(4-isopropyl-phenyl)-[5-(5-methyl-tetrahydro-furan-2-yl)-pyridin-3-yl]-methanol | 0.647 | 395.4 | (V) |
| 320 | (R)-(1,3-Dimethyl-azetidin-3-yl)-[5-(5,5-dimethyl-tetrahydro-furan-2-yl)-pyridin-3-yl]-(4-isopropyl-phenyl)-methanol | 0.689 | 409.5 | (V) + (XIV) |

Example 321: 3-{5-[(R)-(1,3-Dimethyl-azetidin-3-yl)-hydroxy-(4-isopropyl-phenyl)-methyl]-pyridin-3-yl}-2,2-difluoro-propan-1-ol 321.1. 3-[(R)-[5-(2-Ethoxycarbonyl-2,2-difluoro-ethyl)-pyridin-3-yl]-hydroxy-(4-isopropyl-phenyl)-methyl]-3-methyl-azetidine-1-carboxylic acid tert-butyl ester To a vial equipped with a stirring bar were added (4,4'-di-tert-butyl-2,2'-bipyridine)bis[3,5-difluoro-2-[5-trifluoromethyl-2-pyridinyl-N)phenyl-C]iridium(III) hexafluorophosphate (2.36 mg), Example F1.11 (100 mg), ethyl 3-bromo-2,2-difluoropropionate (96.1 mg), tris(trimethylsilyl)silane (0.1 mL) and LiOH (10.3 mg). The vial was sealed, purged with nitrogen, and MeCN (1 mL) was added. To a separate vial were added nickel(11) chloride ethylene glycol dimethyl ether complex (2.36 mg) and 4,4'-di-tert-butyl-2,2'-dipyridyl (2.82 mg). The vial was sealed, purged with nitrogen, MeCN (1 mL) was added and after sonicating the resulting solution for 5 minutes, 0.1 mL were added to the first vial. The resulting mixture was degassed by sparging with nitrogen and irradiated in a photoreactor device (Penn PhD M2, 100% irradiation) at RT for 4 h. The mixture was purified by CC (Biotage, SNAP 12 g, solvent A: Hep; solvent B: EA; gradient in % B: 0 over 1 min, 0 to 100 over 12 min, 100 over 20 min) and by Prep LC-MS (XX) to afford the title compound as a beige solid (12.5 mg). LC-MS (A): $t_R$=1.01 min; $[M+H]^+$: 533.24.

321.2. 3-[(R)-[5-(2,2-Difluoro-3-hydroxy-propyl)-pyridin-3-yl]-hydroxy-(4-isopropyl-phenyl)-methyl]-3-methyl-azetidine-1-carboxylic acid tert-butyl ester To a suspension of $NaBH_4$ (0.66 mg) in EtOH (0.5 mL) was added dropwise a solution of Example 321.1 (12.5 mg) in EtOH (1 mL). The reaction mixture was stirred at RT for 3 h, concentrated in vacuo and aq. sat. $NH_4Cl$ was added. The mixture was extracted with EA and the org. layer was dried ($MgSO_4$), filtered off, and concentrated in vacuo to afford 10 mg as white solid. LC-MS (A): $t_R$=0.85 min; $[M+H]^+$: 491.27.

321.3. 2,2-Difluoro-3-{5-[(R)-hydroxy-(4-isopropyl-phenyl)-(3-methyl-azetidin-3-yl)-methyl]-pyridin-3-yl}-propan-1-ol, hydrochloride salt A solution of Example 321.2 (10 mg) in HCl in dioxane (4M, 0.2 mL) was stirred at RT for 1 h, and concentrated in vacuo to afford 11 mg of title compound as oil. LC-MS (A): $t_R$=0.57 min; $[M+H]^+$: 391.22.

321.4. 3-{5-[(R)-(1,3-Dimethyl-azetidin-3-yl)-hydroxy-(4-isopropyl-phenyl)-methyl]-pyridin-3-yl}-2,2-difluoro-propan-1-ol The title compound (1.2 mg, white solid) was obtained starting from Example 321.3 (11.1 mg), and following the procedure described in Example F1.1 step F1.1.2. The crude was purified by Prep LC-MS (IX). LC-MS (B): $t_R$=0.566 min; $[M+H]^+$: 405.4.

Example 322: (R)-(1,3-Dimethyl-azetidin-3-yl)-(4-isopropyl-phenyl)-[5-(5-methyl-oxazol-2-yl)-pyridin-3-yl]-methanol 322.1. 5-Bromo-N-prop-2-ynyl-nicotinamide To a solution of 5-bromopyridine-3-carboxylic acid (500 mg) in THF (12 mL) were added HATU (1.66 g), DIPEA (0.831 mL) and propargylamine (0.19 mL) at RT. The resulting mixture was stirred at 50° C. for 1 h40, cooled down to RT, diluted with EA and washed with water and brine. The org. layer was dried ($MgSO_4$), filtered off and concentrated in vacuo. The crude material was purified by CC (Biotage, SNAP 50 g, solvent A: Hep; solvent B: EA; gradient in % B: 50 over 4 CV, 50 to 70 over 2 CV, 70 over 2 CV) to afford the title compound as white solid (513 mg). LC-MS (A): $t_R$=0.65 min; $[M+H]^+$: 239.15.

322.2. 3-Bromo-5-(5-methylene-4,5-dihydro-oxazol-2-yl)-pyridine

To a white suspension of Example 322.1 (488 mg) in DCM (20 mL) was added $AuCl_3$ (61.9 mg). The resulting light yellow suspension was stirred at RT for 1 h30, diluted with DCM and washed with aq. sat. $NaHCO_3$. The aq. layer was extracted with DCM. The combined org. layers were dried ($MgSO_4$), filtered off, and concentrated in vacuo. The crude material was purified by CC (Biotage, SNAP 25 g, solvent A: Hep; solvent B: EA; gradient in % B: 10 over 3 CV, 10 to 30 over 2 CV, 30 over 2 CV) to afford the title compound as white solid (340 mg). LC-MS (A): $t_R$=0.82 min; $[M+H]^+$: 239.01.

322.3. 3-Bromo-5-(5-methyl-oxazol-2-yl)-pyridine

To a solution of Example 322.2 (340 mg) in toluene (14 mL) was added DBU (0.263 mL). The resulting mixture was heated at 80° C. for 2 h, cooled down to RT and quenched with aq. sat. $NH_4Cl$. The org. layer was washed with aq. sat. $NH_4Cl$, dried ($MgSO_4$), filtered off, and concentrated in vacuo to afford the title compound as yellow solid (222 mg). LC-MS (A): $t_R$=0.85 min; $[M+H]^+$: 241.16.

322.4. 3-{Hydroxy-(4-isopropyl-phenyl)-[5-(5-methyl-oxazol-2-yl)-pyridin-3-yl]-methyl}-3-methyl-azetidine-1-carboxylic acid tert-butyl ester The title compound was obtained starting from Example A4.2 (125 mg) and Example 322.3 (122 mg), and following the procedure described in Example A7.1 step A7.1.1. The crude material was purified by Prep LC-MS (VI) and (XII). The resulting material was dissolved in DCM and the solution was washed with aq. sat. $NaHCO_3$. The aq. layer was extracted twice with DCM and the combined org. extracts were dried ($MgSO_4$), filtered off, and concentrated in vacuo to afford the title compound as yellow solid (39 mg). LC-MS (A): $t_R$=1.13 min; $[M+H]^+$: 478.32.

322.5. 3—{(R)-Hydroxy-(4-isopropyl-phenyl)-[5-(5-methyl-oxazol-2-yl)-pyridin-3-yl]-methyl}-3-methyl-azetidine-1-carboxylic acid tert-butyl ester Example 322.4 (39 mg) was purified by Prep chiral SFC (XVI) to afford the title compound as pure enantiomer (14 mg). Chiral SFC (P): $t_R$=3.217 min. LC-MS (A): $t_R$=1.13 min; $[M+H]^+$: 478.33.

322.6. (R)-(4-Isopropyl-phenyl)-(3-methyl-azetidin-3-yl)-[5-(5-methyl-oxazol-2-yl)-pyridin-3-yl]-methanol A solution of Example 322.5 (13 mg) in HCl in dioxane (4M, 0.4 mL) was stirred at RT for 2 h, cooled down to 0° C., basified with aq. sat. $NaHCO_3$ and extracted with DCM. The combined org. extracts were dried ($MgSO_4$), filtered off, and concentrated in vacuo to afford 7 mg of the title compound as yellow solid. LC-MS (A): $t_R$=0.74 min; $[M+H]^+$: 378.35. 322.7. (R)-(1,3-Dimethyl-azetidin-3-yl)-(4-isopropyl-phenyl)-[5-(5-methyl-oxazol-2-yl)-pyridin-3-yl]-methanol The title compound (2 mg, white solid) was obtained starting from Example 322.6 (7 mg), and following the procedure described in Example F1.1 step F1.1.2. However, the reaction mixture was basified with aq. sat. $NaHCO_3$, filtered through a syringe filter and purified by Prep LC-MS (VI). LC-MS (B): $t_R$=0.69 min; $[M+H]^+$: 392.4.

Example 323: (R)-(1,3-Dimethyl-azetidin-3-yl)-(4-isopropyl-phenyl)-{5-[5-(tetrahydro-pyran-4-yl)-oxazol-2-yl]-pyridin-3-yl}-methanol

323.1. 3—((R)-Hydroxy-(4-isopropyl-phenyl)-{5-[2-oxo-2-(tetrahydro-pyran-4-yl)-ethylcarbamoyl]-pyridin-3-yl}-methyl)-3-methyl-azetidine-1-carboxylic acid tert-butyl ester To a solution of Example E1.1 (75 mg) and HATU (86.8 mg) in DCM (0.85 mL) was added DIPEA (87.4 μL). The resulting mixture was stirred at RT for 15 min and 2-amino-1-(oxan-4-yl)ethan-1-one hydrochloride (41.9 mg) was added. The reaction mixture was stirred at RT, quenched with aq. sat. $NaHCO_3$ and extracted with DCM. The org. layers were dried ($MgSO_4$), filtered off and concentrated in vacuo. The crude material was purified by CC (Biotage, SNAP 24 g, solvent A: DCM; solvent B: 9:1 DCM/MeOH; gradient in % B: 0 over 1 min, 0 to 10 over 3 min, 10 over 5 min, 10 to 100 over 20 min, 100 over 5 min) to afford the title compound as a white glass (99.8 mg). LC-MS (A): $t_R$=0.96 min; $[M+H]^+$: 566.26.

323.2. 3—((R)-Hydroxy-(4-isopropyl-phenyl)-{5-[5-(tetrahydro-pyran-4-yl)-oxazol-2-yl]-pyridin-3-yl}-methyl)-3-methyl-azetidine-1-carboxylic acid tert-butyl ester A solution of Example 323.1 (99.8 mg) in pyridine (0.466 mL) containing molecular sieves (3A powder, 170 mg) was treated with phosphorus(V) oxychloride (81.6 μL). The reaction mixture was stirred at RT for 5 h30, diluted with EA and poured into an ice-chilled solution of aq. sat. $NaHCO_3$. The two layers were separated and the aq. phase was extracted twice with EA. The combined org. layers were dried ($MgSO_4$), filtered off and concentrated in vacuo. The crude was purified by Prep LC-MS (XXII) to afford the title compound as beige solid (9.7 mg). LC-MS (A): $t_R$=1.16 min; $[M+H]^+$: 548.13.

323.3. (R)-(4-Isopropyl-phenyl)-(3-methyl-azetidin-3-yl)-{5-[5-(tetrahydro-pyran-4-yl)-oxazol-2-yl]-pyridin-311}-methanol, hydrochloride salt A solution of Example 323.2 (9.7 mg) in HCl (4M in dioxane, 0.1 mL) was stirred at RT for 2 h, concentrated in vacuo and dried under HV to afford the title compound (9.2 mg) as beige solid. LC-MS (A): $t_R$=0.76 min; $[M+H]^+$: 448.35.

323.4. (R)-(1,3-Dimethyl-azetidin-3-yl)-(4-isopropyl-phenyl)-{5-[5-(tetra hydro-pyran-4-yl)-oxazol-2-yl]-pyridin-3-yl}-methanol The title compound (3 mg, white solid) was obtained starting from Example 323.3 (9.2 mg), and following the procedure described in Example D1.1 step D1.1.5. However, the reaction mixture was filtered through a syringe filter and purified by Prep LC-MS (IX). LC-MS (B): $t_R$=0.712 min; $[M+H]^+$: 462.4.

Example 324: (R)-(1,3-Dimethyl-azetidin-3-yl)-[5-(4-fluoro-phenoxymethyl)-pyridin-3-yl]-(4-isopropyl-phenyl)-methanol

324.1. 3—{(R)-Hydroxy-(4-isopropyl-phenyl)-[5-(methoxy-methyl-carbamoyl)-pyridin-3-yl]-methyl}-3-methyl-azetidine-1-carboxylic acid tert-butyl ester To a suspension of Example E1.1 (500 mg) in DCM (6 mL) were added N,O-dimethylhydroxylamine hydrochloride (128 mg) and DIPEA (0.68 mL). The mixture was cooled down to 0° C. and propylphosphonic anhydride (50% w/w in EA, 0.88 mL) was slowly added. The resulting solution was stirred 1 h at RT and quenched with aq. sat. $NaHCO_3$ solution. The aq. layer was extracted twice with DCM and the combined org. layers were dried ($MgSO_4$), filtered off and evaporated to dryness to afford 596 mg of the title compound as white foam. LC-MS (A): $t_R$=0.98 min; $[M+H]^+$: 483.99.

324.2. 3-[(R)-(5-Formyl-pyridin-3-yl)-hydroxy-(4-isopropyl-phenyl)-methyl]-3-methyl-azetidine-1-carboxylic acid tert-butyl ester To an ice-cold solution of Example 324.1 (596 mg) in dry THF (6 mL) was added dropwise $LiAlH_4$ (2M in THF, 1.9 mL). The reaction mixture was stirred for 1 h at −78° C. and quenched by dropwise addition of aq. sat. $NH_4Cl$ solution. The mixture was allowed to warm to RT and EA was added. The solids were filtered off, washed with EA and water, and the filtrate was transferred in a separatory funnel. The layers were separated and the aq. phase was extracted twice with EA. The combined org. layers were dried ($MgSO_4$), filtered off and concentrated to dryness to afford the title compound as light yellow foam (494 mg). LC-MS (A): $t_R$=1.04 min; $[M+H]^+$: 425.19.

324.3. 3-[(R)-Hydroxy-(5-hydroxymethyl-pyridin-3-yl)-(4-isopropyl-phenyl)-methyl]-3-methyl-azetidine-1-carboxylic acid tert-butyl ester A solution of Example 324.2 (494 mg) in dry MeOH (5.8 mL) under nitrogen atmosphere was cooled down to 0° C. and treated with $NaBH_4$(53.9 mg). The reaction mixture was stirred at 0° C. for 5 min and at RT for 30 min, quenched with aq. sat. $NaHCO_3$ solution. and extracted with EA. The combined org. layers were dried ($MgSO_4$), filtered off, and concentrated in vacuo to afford 516.6 mg of the title compound as light yellow foam. LC-MS (A): $t_R$=0.79 min; $[M+H]^+$: 427.19.

324.4. 3-[(R)-[5-(4-Fluoro-phenoxymethyl)-pyridin-3-yl]-hydroxy-(4-isopropyl-phenyl)-methyl]-3-methyl-azetidine-1-carboxylic acid tert-butyl ester To an ice-chilled mixture of Example 324.3 (100 mg), 4-fluorophenol (58.4 mg) and triphenylphosphine polymer bound (3 mmol/g, 313 mg) in THF (1.2 mL) under nitrogen atmosphere was added diisopropyl azodicarboxylate (0.188 mL). The reaction mixture was stirred at RT for 17 h, filtered off, and concentrated. The resulting solution was filtered through a syringe filter and purified by Prep LC-MS (XX) to afford 11.5 mg of the title compound as white solid. LC-MS (A): $t_R$=1.01 min; $[M+H]^+$: 521.17.

324.5. (R)-[5-(4-Fluoro-phenoxymethyl)-pyridin-3-yl]-(4-isopropyl-phenyl)-(3-methyl-azetidin-3-yl)-methanol, hydrochloride salt A solution of Example 324.4 (11.5 mg) in HCl (4M in Dioxane, 0.1 mL) was stirred at RT for 1 h and concentrated in vacuo to afford the title compound (10.5 mg) as oil. LC-MS (A): $t_R$=0.74 min; $[M+H]^+$: 421.20.

324.6. (R)-(1,3-Dimethyl-azetidin-3-yl)-[5-(4-fluoro-phenoxymethyl)-pyridin-3-yl]-(4-isopropyl-phenyl)-methanol The title compound (4.5 mg, white solid) was obtained starting from Example 324.5 (10.9 mg), and following the procedure described in Example D1.1 step D1.1.5. The reaction mixture was however diluted with MeCN, filtered through a syringe filter and purified by Prep LC-MS (VI). LC-MS (B): $t_R$=0.782 min; $[M+H]^+$: 435.4.

Example 325: Isopropyl-carbamic acid 5-[(R)-(1,3-dimethyl-azetidin-3-yl)-hydroxy-(4-isopropyl-phenyl)-methyl]-pyridin-3-ylmethyl ester 325.1. 3-[(R)-Hydroxy-(5-isopropylcarbamoyloxymethyl-pyridin-3-yl)-(4-isopropyl-phenyl)-methyl]-3-methyl-azetidine-1-carboxylic acid tert-butyl ester To an ice-cold solution of Example 324.3 (100 mg) and 4-dimethylaminopyridine (63 mg) in DCM (1.2 mL) was added isopropyl isocyanate (51.7 μL). The reaction mixture was stirred at 45° C. for 17 h, cooled down to RT, quenched with aq. sat. $NaHCO_3$ solution and extracted with DCM. The combined org. extracts were dried ($MgSO_4$), filtered off, concentrated in vacuo and the residue was purified by Prep LC-MS (XIV) to afford 74 mg of the title compound as white solid. LC-MS (A): $t_R$=0.93 min; $[M+H]^+$: 512.22.

325.2. Isopropyl-carbamic acid 5-[(R)-hydroxy-(4-isopropyl-phenyl)-(3-methyl-azetidin-3-yl)-methyl]-pyridin-3-ylmethyl ester A solution of Example 325.1 (73.6 mg) in HCl (4M in Dioxane, 0.36 mL) was stirred at RT for 1 h, concentrated in vacuo and dried under HV to afford 70 mg of the title compound as oil. LC-MS (A): $t_R$=0.64 min; $[M+H]^+$: 412.22.

325.3. Isopropyl-carbamic acid 5-[(R)-(1,3-dimethyl-azetidin-3-yl)-hydroxy-(4-isopropyl-phenyl)-methyl]-pyridin-3-ylmethyl ester The title compound (47.2 mg, white solid) was obtained starting from Example 325.2 (69.7 mg), and following the procedure described in Example D1.1 step D1.1.5. The reaction mixture was however diluted with MeCN, filtered through a syringe filter and purified by Prep LC-MS (V). LC-MS (B): $t_R$=0.656 min; $[M+H]^+$: 426.4.

Example 326: (R)-[5-(2-Benzyloxy-ethyl)-pyridin-3-yl]-(1,3-dimethyl-azetidin-3-yl)-(4-isopropyl-phenyl)-methanol To a solution of Example F1.2 (50 mg) and potassium (2-benzyloxyethyl)trifluoroborate (32.6 mg) in toluene (1.5 mL) and water (0.5 mL) were added $Cs_2CO_3$ (126 mg), $Pd(OAc)_2$ (1.44 mg) and RuPhos (6.31 mg). The resulting mixture was stirred for 23 h at 95° C., allowed to cool down to RT, diluted with water and extracted with EA. The org. layers were dried ($MgSO_4$), filtrated off and evaporated to dryness. The crude material was purified by Prep LC-MS (VII) to give 30 mg of the title compound as white solid. LC-MS (B): $t_R$=0.728 min; $[M+H]^+$: 445.50.

Example 327: 4-{5-[(R)-(1,3-Dimethyl-azetidin-3-yl)-hydroxy-(4-isopropyl-phenyl)-methyl]-pyridin-3-yl}-1-methyl-cyclohexanol 327.1. (R)-(1,3-Dimethyl-azetidin-3-yl)-[5-(1,4-dioxa-spiro[4.5]dec-7-en-8-yl)-pyridin-3-yl]-(4-isopropyl-phenyl)-methanol The title compound (174 mg, white solid) was synthesized starting from Example F1.2 (400 mg) and 1,4-dioxa-spiro[4,5]dec-7-en-8-boronic acid pinacol ester (558 mg), and following the procedure described in Example 303. The crude material was however purified by CC (Biotage, SNAP 25 g, solvent A: DCM; solvent B: MeOH; gradient in % B: 0 over 2 CV, 0 to 5 over 5 CV, 5 over 2 CV, 5 to 10 over 3 CV; 10 over 2 CV, 10 to 20 over 2 CV, 20 over 2 CV, 100 over 5 CV and 100% MeOH+0.1% TEA over 10 CV). LC-MS (A): $t_R$=0.65 min; $[M+H]^+$: 449.1.

327.2. (R)-(1,3-Dimethyl-azetidin-3-yl)-[5-(1,4-dioxa-spiro[4.5]dec-8-yl)-pyridin-3-yl]-(4-isopropyl-phenyl)-methanol The title compound (116 mg, brown solid) was synthesized starting from Example 327.1 (172 mg), and following the procedure described in Example 48. LC-MS (A): $t_R$=0.62 min; $[M+H]^+$: 451.08.

327.3. 4-{5-[(R)-(1,3-Dimethyl-azetidin-3-yl)-hydroxy-(4-isopropyl-phenyl)-methyl]-pyridin-3-yl}-cyclohexanone To an ice-cold solution of Example 327.2 (89 mg) in dioxane (1 mL) were added water (0.2 mL) and $H_2SO_4$ (0.2 mL). The resulting solution was stirred for 3 h at 0° C., basified with aq. sat. $NaHCO_3$ solution, diluted with water and extracted with DCM. The org. layers were dried ($MgSO_4$), filtrated off, and evaporated to dryness to give 72 mg of the title compound as brown solid. LC-MS (A): $t_R$=0.58 min; $[M+H]^+$: 407.14.

327.4. 4-{5-[(R)-(1,3-Dimethyl-azetidin-3-yl)-hydroxy-(4-isopropyl-phenyl)-methyl]-pyridin-3-yl}-1-methyl-cyclohexanol The title compound (9 mg, white powder) was synthesized starting from Example 327.3 (30 mg), and following the procedure described in Example 262. The crude material was purified by Prep LC-MS (VII). LC-MS (B): $t_R$=0.591 min; $[M+H]^+$: 423.5.

Example 328: 2-(2-{5-[(R)-(1,3-Dimethyl-azetidin-3-yl)-hydroxy-(4-isopropyl-phenyl)-methyl]-pyridin-3-yl}-cyclopropyl)-propan-2-ol 328.1. 2-{5-[(R)-(1,3-Dimethyl-azetidin-3-yl)-hydroxy-(4-isopropyl-phenyl)-methyl}-pyridin-3-yl]-cyclopropanecarboxylic acid ethyl ester The title compound (10 mg, yellow solid) was synthesized starting from Example F1.2 (250 mg) and (2-(ethoxy-carbonyl)cyclopropyl)boronic acid pinacol ester, and following the procedure described in Example 280 step 280.1. The crude material was purified by Prep LC-MS (XV). LC-MS (A): $t_R$=0.69 min; $[M+H]^+$: 423.22.

328.2. 2-(2-{5-[(R)-(1,3-Dimethyl-azetidin-3-yl)-hydroxy-(4-isopropyl-phenyl)-methyl]-pyridin-3-yl}-cyclopropyl)-propan-2-ol The title compound (3.4 mg, white solid) was synthesized starting from Example 328.1 (10 mg), and following the procedure described in Example 262. The crude material was purified by Prep LC-MS (IX). LC-MS (B): $t_R$=0.566 min; $[M+H]^+$: 409.5.

Example 329: (S)-(1,3-Dimethyl-azetidin-3-yl)-(4-isopropyl-phenyl)-{2-[5-(tetrahydro-pyran-4-yl)-[1,2,4]oxadiazol-3-yl]-pyridin-4-yl}-methanol 329.1. 3-[(2-Cyano-pyridin-4-yl)-hydroxy-(4-isopropyl-phenyl)-methyl]-3-methyl-azetidine-1-carboxylic acid tert-butyl ester The title compound was synthesized starting from Example A4.2 and 4-bromopyridine-2-carbonitrile, and following the procedure described in Example A7.1 step A7.1.1. LC-MS (A): $t_R$=1.07 min; $[M+H]^+$: 422.31.

329.2. 4-[Hydroxy-(4-isopropyl-phenyl)-(3-methyl-azetidin-3-yl)-methyl]-pyridine-2-carbonitrile, hydrochloride salt A solution of Example 329.1 (4.5 g) in dioxane (25 mL) and HCl in dioxane (4M, 25 mL) was stirred for 2 h. The solution was lyophilized to give 3.8 g of the title compound as light brown solid. LC-MS (A): $t_R$=0.70 min; $[M+H]^+$: 322.00.

329.3. 4-[(1,3-Dimethyl-azetidin-3-yl)-hydroxy-(4-isopropyl-phenyl)-methyl]-pyridine-2-carbonitrile The title compound (1.92 g, off-white solid) was synthesized starting from Example 329.2, and following the procedure described in Example D1.1 step D1.1.5. The resulting crude material was purified by Prep LC-MS (XVI). LC-MS (A): $t_R$=0.72 min; $[M+H]^+$: 336.23.

329.4. 4—[(S)-(1,3-Dimethyl-azetidin-3-yl)-hydroxy-(4-isopropyl-phenyl)-methyl]-pyridine-2-carbonitrile The title compound (0.8 g, off-white powder) was obtained by chiral separation of Example 329.3 (1.92 g) using Prep chiral SFC (V) method. LC-MS (A): $t_R$=0.72 min; $[M+H]^+$: 336.12, Chiral SFC (E): 2.1 min.

329.5. 4—[(S)-(1,3-Dimethyl-azetidin-3-yl)-hydroxy-(4-isopropyl-phenyl)-methyl]-N-hydroxy-pyridine-2-carboxamidine The title compound (27 mg, beige solid) was synthesized starting from Example 329.4 (25 mg), and following the procedure described in Example E2.1. LC-MS (A): $t_R$=0.59 min; $[M+H]^+$: 369.18.

329.6. (S)-(1,3-Dimethyl-azetidin-3-yl)-(4-isopropyl-phenyl)-{2-[5-(tetrahydro-pyran-4-yl)-[1,2,4]oxadiazol-3-yl]-pyridin-4-yl}-methanol The title compound (6 mg, white solid) was synthesized starting from Example 329.5 (27 mg), and following the procedure described in Example 95 step 95.1. The crude material was purified by Prep LC-MS (IX). LC-MS (A): $t_R$=0.75 min; $[M+H]^+$: 463.29.

Example 330: (1,3-Dimethyl-azetidin-3-yl)-(4-isopropyl-phenyl)-(2-pyrrolidin-1-yl-pyrimidin-5-yl)-methanol 330.1. 3-[Hydroxy-(4-isopropyl-phenyl)-(2-pyrrolidin-1-yl-pyrimidin-5-yl)-methyl]-3-methyl-azetidine-1-carboxylic acid tert-butyl ester The title compound was synthesized starting from Example A4.2 and 5-bromo-2-(pyrrolidin-1-yl)pyrimidine, and following the procedure described in Example A4.1 step A4.1.2. LC-MS (A): $t_R$=0.97 min; $[M+H]^+$: 467.11.

330.2. (4-Isopropylphenyl)(3-methylazetidin-3-yl)(2-(pyrrolidin-1-yl)pyrimidin-5-yl)methanol, hydrochloride salt The title compound was synthesized starting from Example 330.1, and following the procedure described in Example 309. LC-MS (A): $t_R$=0.67 min; $[M+H]^+$: 367.18.

330.3. (1,3-Dimethyl-azetidin-3-yl)-(4-isopropyl-phenyl)-(2-pyrrolidin-1-yl-pyrimidin-5-yl)-methanol The title compound (54 mg, white powder) was synthesized starting from Example 330.2 (110 mg), and following the procedure described in Example D1.1 step D1.1.5. The crude material was purified by Prep LC-MS (IX) and Prep LC-MS (VII). LC-MS (A): $t_R$=0.69 min; $[M+H]^+$: 381.2.

Example 331: (1,3-Dimethyl-azetidin-3-yl)-(4-isopropyl-phenyl)-(6-pyrrolidin-1-yl-pyrazin-2-yl)-methanol 331.1. 2-Bromo-6-pyrrolidin-1-yl-pyrazine To a solution of 2,6-dibromopyrazine (500 mg) in MeOH (5 mL) was added pyrrolidine (0.52 mL). The reaction mixture was stirred at RT overnight, quenched with water and extracted with DCM. The organic layer was filtered over a phase separator and concentrated under reduced pressure. The resulting residue was purified Prep-LC-MS (V) affording the title compound (406 mg) as yellow solid. LC-MS (A): $t_R$=0.88 min; $[M+H]^+$: 228.1.

331.2. (1,3-Dimethyl-azetidin-3-yl)-(4-isopropyl-phenyl)-(6-pyrrolidin-1-yl-pyrazin-2-yl)-methanol The title compound was synthesized starting from Example A4.2 and Example 331.1, and following the procedure described in Example 330 steps 330.1 to 330.3. The crude material was purified twice by Prep LC-MS (IX). LC-MS (A): $t_R$=0.80 min; $[M+H]^+$: 381.22.

Depending on the purification conditions, the title compounds/intermediates in Example 1 to 331 may be isolated as free bases or as salts such as formate salts, or hydrochloride salts. Whenever isolating a title compound/intermediate as a salt, formate salt or hydrochloride salt is indicated at the end of the chemical name and can refer to a mono-, di- or tri-formate salt, or mono-, di-, or tri-hydrochloride salt.

Example 332: (R)—N-(1-(3-(5-((1,3-dimethylazetidin-3-yl)(hydroxy)(4-isopropylphenyl)methyl)pyridin-3-yl)-1,2,4-oxadiazol-5-yl)cyclopropypacetamide-2,2,2-d3

332.1 tert-butyl (R)-3-((5-(5-(1-(acetamido-2,2,2-d3)cyclopropyl)-1,2,4-oxadiazol-3-yl)pyridin-3-yl)(hydroxy)(4-isopropylphenyl)methyl)-3-methylazetidine-1-carboxylate The title compound (80.2 mg) was synthesized starting from Example D2.2 (64.5 mg) and Example D3.1 (22.8 mg), and following the procedure described in Example 134. Crude was extracted with water and DCM over phase separator, resulting solution was evaporated to dryness. LC-MS (A): $t_R$=0.98 min; $[M+H]^+$: 565.01.

332.2 (R)—N-(1-(3-(5-(hydroxy(4-isopropylphenyl)(3-methylazetidin-3-yl)methyl)pyridin-3-yl)-1,2,4-oxadiazol-5-yl)cyclopropyl)acetamide-2,2,2-d3, hydrochloride salt A solution of Example 332.1 (80.2 mg) in HCl in dioxane (4M, 4 mL) was stirred 1 h at RT. The crude was evaporated to dryness and used in the next step without further purification. LC-MS (A): $t_R$=0.67 min; $[M+H]^+$: 464.99.

332.3 (R)—N-(1-(3-(5-(1,3-dimethylazetidin-3-yl)(hydroxy)(4-isopropylphenyl)methyl)pyridin-3-yl)-1,2,4-oxadiazol-5-yl)cyclopropyl)acetamide-2,2,2-d3

The title compound (0.2 mg, white powder) was synthesized from Example 332.2 (66 mg), and following the procedure described in Example D1.1 step D.1.1.5. The crude was filtered off, and the filtrate was purified by Prep LC-MS (IX) and (V). LC-MS (A): $t_R$=0.69 min; $[M+H]^+$: 479.18.

Example 333 to Example 336 were synthesized starting from Example D2.2 and the appropriate acid of formula (D3), following the three-step procedure described in Example 332. The acid precursors of formula (D3) are indicated in the table below. Prep LC-MS conditions and LC-MS data are listed in the table below. The LC-MS conditions used were LC-MS (A).

| Example N° | Name | $t_R$ | $[M + H]^+$ | (D3) | Prep LC-MS |
|---|---|---|---|---|---|
| 333 | (R)-N-(1-(3-(5-((1,3-dimethylazetidin-3-yl)(hydroxy)(4-isopropylphenyl)methyl)pyridin-3-yl)-1,2,4-oxadiazol-5-yl)cyclopropyl)-N-methylacetamide-d3 | 0.75 | 493.19 | D3.2 | (IX) then (V) |
| 334 | (R)-N-((3-(5-((1,3-dimethylazetidin-3-yl)(hydroxy)(4-isopropylphenyl)methyl)pyridin-3-yl)-1,2,4-oxadiazol-5-yl)methyl)-N-methylacetamide-d3 | 0.7 | 467.19 | D3.3 | (IX) then (V) |
| 335 | N-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-2-hydroxy-acetamide | 0.63 | 465.84 | D3.4 | (IX) then (V) |
| 336 | (R)-N-((3-(5-((1,3-dimethylazetidin-3-yl)(hydroxy)(4-isopropylphenyl)methyl)pyridin-3-yl)-1,2,4-oxadiazol-5-yl)methyl)acetamide-2,2,2-d3 | 0.66 | 453.21 | D3.5 | (IX) then (V) |

Example 337: 1-(3-{5-[(R)-Hydroxy-(1-isopropyl-3-methyl-azetidin-3-yl)-(4-isopropyl-phenyl)-methyl]-pyridin-3-yl}-[1,2,4]oxadiazol-5-yl)-2-methyl-propan-2-ol 337.1 3-[(R)-Hydroxy-{5-[5-(2-hydroxy-2-methyl-propyl)-[1,2,4]oxadiazol-3-yl]-pyridin-3-yl}-(4-isopropyl-phenyl)-methyl]-3-methyl-azetidine-1-carboxylic acid tert-butyl ester The title compound was synthesized starting from Example D2.2 (1.023 g) and 3-hydroxy-3-methylbutanoic acid (348 mg) following the procedure described in Example 134. The crude material was purified by Prep LC-MS (XXVI) to afford 560 mg of a yellow solid. LC-MS (A): $t_R$=1.03 min; $[M+H]^+$: 537.29.

337.2 1-(3-{5-[(R)-Hydroxy-(4-isopropyl-phenyl)-(3-methyl-azetidin-3-yl)-methyl]-pyridin-3-yl}-[1,2,4]oxadiazol-5-yl)-2-methyl-propan-2-ol, hydrochloride salt A solution of Example 337.1 (560 mg) in HCl in dioxane (4M, 4 mL) and dioxane (4 mL) was stirred 1 h at RT. HCl in dioxane (4M, 4 mL) was added again and mixture further stirred over weekend. The crude was evaporated to dryness to give 450 mg of the title compound. LC-MS (A): $t_R$=0.7 min; $[M+H]^+$: 437.21.

337.3 1-(3-{5-[(R)-Hydroxy-(1-isopropyl-3-methyl-azetidin-3-yl)-(4-isopropyl-phenyl)-methyl]-pyridin-3-yl}-[1,2,4]oxadiazol-5-yl)-2-methyl-propan-2-ol To a solution of Example 337.2 (47.6 mg) in dioxane (2 mL) and EtOH (1 mL) were added $Et_3N$ (45.5 µL) and acetone (56.1 µL), followed by $NaBH(OAc)_3$ (35.7 mg). The reaction mixture was stirred at RT until completion of the reaction, filtered off, and the filtrate was purified by Prep LC-MS (IX) and (VI) to afford the title product as off-white solid (14 mg). LC-MS (A): $t_R$=0.76 min; $[M+H]^+$: 479.1.

Example 338: 1-(3-{5-[(R)-(1-Ethyl-3-methyl-azetidin-3-yl)-hydroxy-(4-isopropyl-phenyl)-methyl]-pyridin-3-yl}-[1,2,4]oxadiazol-5-yl)-2-methyl-propan-2-ol To a solution of Example 337.2 (47.6 mg) in dioxane (2 mL) and EtOH (1 mL) were added $Et_3N$ (45.5 µL) and acetaldehyde (43.1 µL), followed by $NaBH(OAc)_3$ (35.7 mg). The reaction mixture was stirred at RT until completion of the reaction, filtered off, and the filtrate was purified by Prep LC-MS (IX) and (VI) to afford the title product as off-white solid (16 mg). LC-MS (A): $t_R$=0.74 min; $[M+H]^+$: 465.07.

Example 339: 2-(3-{5-[(R)-Hydroxy-(1-isopropyl-3-methyl-azetidin-3-yl)-(4-isopropyl-phenyl)-methyl]-pyridin-3-yl}-[1,2,4]oxadiazol-5-yl)-propan-2-ol 339.1 3-[(R)-Hydroxy-{5-[5-(1-hydroxy-1-methyl-ethyl)-[1,2,4]oxadiazol-3-yl]-pyridin-3-yl}-(4-isopropyl-phenyl)-methyl]-3-methyl-azetidine-1-carboxylic acid tert-butyl ester The title compound was synthesized starting from Example D2.2 (1.02 g) and 2-hydroxy-2-methylpropanoic acid (291 mg) following the procedure described in Example 134. The crude material was purified by Prep LC-MS (XVII) to afford 580 mg of a yellow solid. LC-MS (A): $t_R$=1.03 min; $[M+H]^+$: 523.32.

339.2 2-(3-{5-[(R)-Hydroxy-(4-isopropyl-phenyl)-(3-methyl-azetidin-3-yl)-methyl]-pyridin-3-yl}-[1,2,4]oxadiazol-5-yl)-propan-2-ol The title compound was synthesized starting from Example 339.1 (580 mg) following the procedure described in Example 309 step 309.2. The crude was evaporated to dryness to give 510 mg of the title compound as white solid as hydrochloride salt. LC-MS (A): $t_R$=0.7 min; $[M+H]^+$: 423.21.

339.3 2-(3-{5-[(R)-Hydroxy-(1-isopropyl-phenyl)-(3-methyl-azetidin-3-yl)-(4-isopropyl-phenyl)-methyl]-pyridin-3-yl}-[1,2,4]oxadiazol-5-yl)-propan-2-ol The title compound was synthesized starting from Example 339.2 following the procedure described in Example 337 step 337.3. The crude material was purified by Prep LC-MS (IX) and (VI). LC-MS (A): $t_R$=0.76 min; $[M+H]^+$: 465.11.

Example 340: 2-(3-{5-[(R)-(1-Ethyl-3-methyl-azetidin-3-yl)-hydroxy-(4-isopropyl-phenyl)-methyl]-pyridin-3-yl}-[1,2,4]oxadiazol-5-yl)-propan-2-ol The title compound was synthesized starting from Example D2.2 and 2-hydroxy-2-methylpropanoic acid and following a three-step procedure composed of Example 339 step 339.1 and step 339.2 followed by Example 338. The crude material was purified by Prep LC-MS (IX) then (VI) and finally by Prep TLC (Dioxane-F2% Et3N 80%/EtOH20%). LC-MS (A): $t_R$=0.74 min; $[M+H]^+$: 451.11.

Example 341 and Example 342 were synthesized starting from Example E1.1 and the appropriate hydroxyamidine of formula (E2), and following the procedure described in Example 332. The hydroxyamidine precursors of formula (E2) are indicated in the table below. Prep LC-MS conditions and LC-MS data are listed in the table below. The LC-MS conditions used were LC-MS (A).

| Example N° | Name | $t_R$ | $[M+H]^+$ | (E2) | Prep LC-MS |
|---|---|---|---|---|---|
| 341 | 4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidine-1-carboxylic acid benzyl ester | 0.91 | 596.28 | E2.14 | (VIII) |
| 342 | 1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-ethanone | 0.74 | 504.24 | E2.15 | (IX) |

Example 343 to Example 364 were synthesized starting from Example D2.1 and the appropriate acid of formula (D3), and following the procedure described in Example 134. The acid precursors of formula (D3) are indicated in the table below unless commercially available. Prep LC-MS conditions and LC-MS data are listed in the table below. The LC-MS conditions used were LC-MS (A).

| Example N° | Name | $t_R$ | [M + H]$^+$ | (D3) | Prep LC-MS |
|---|---|---|---|---|---|
| 343 | (R)-1-(3-(3-(5-((1,3-dimethylazetidin-3-yl)(hydroxy)(4-isopropylphenyl)methyl)pyridin-3-yl)-1,2,4-oxadiazol-5-yl)azetidin-1-yl)ethan-1-one-2,2,2-d3 | 0.7 | 479.07 | D3.6 | (IX) then (V) |
| 344 | (R)-1-(3-(3-(5-((1,3-dimethylazetidin-3-yl)(hydroxy)(4-isopropylphenyl)methyl)pyridin-3-yl)-1,2,4-oxadiazol-5-yl)-3-methylazetidin-1-yl)ethan-1-one-2,2,2-d3 | 0.73 | 493.09 | D3.7 | (IX) then (V) |
| 345 | (R)-1-(3-(3-(5-((1,3-dimethylazetidin-3-yl)(hydroxy)(4-isopropylphenyl)methyl)pyridin-3-yl)-1,2,4-oxadiazol-5-yl)-3-fluoroazetidin-1-yl)ethan-1-one-2,2,2-d3 | 0.73 | 496.97 | D3.8 | (IX) then (V) |
| 346 | (R)-(1,3-Dimethyl-azetidin-3-yl)-(4-isopropyl-phenyl)-{5-[5-(1-methyl-1-morpholin-4-yl-ethyl)-[1,2,4]oxadiazol-3-yl]-pyridin-3-yl}-methanol | 0.66 | 506.1 | — | (IX) then (VI) |
| 347 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-piperidin-2-one | 0.69 | 490.09 | — | (IX) then (V) |
| 348 | 1-[(S)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-1-yl]-ethanone | 0.72 | 490.07 | D3.9 | (IX) then (V) |
| 349 | 1-[(R)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-1-yl]-ethanone | 0.72 | 490.06 | D3.10 | (IX) then (V) |
| 350 | N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-ethyl]-acetamide | 0.69 | 478.09 | D3.11 | (IX) then (V) |
| 351 | 1-Benzyl-3-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-pyrrolidin-2-one | 0.81 | 552.1 | — | (XIV) then (VI) |
| 352 | 3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,3-dimethyl-pyrrolidin-2-one | 0.71 | 490.01 | — | (IX) then (VI) |
| 353 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-isobutyl-pyrrolidin-2-one | 0.76 | 518.09 | — | (IX) then (VI) |
| 354 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-furan-2-ylmethyl-pyrrolidin-2-one | 0.75 | 542.03 | — | (IX) then (VI) |
| 355 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-phenyl-pyrrolidin-2-one | 0.78 | 538.06 | — | (XIV) then (VI) |
| 356 | 1-Benzyl-4-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-pyrrolidin-2-one | 0.78 | 552.06 | — | (XIV) then (VI) |
| 357 | 5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-phenyl-pyrrolidin-2-one | 0.77 | 538.07 | — | (IX) then (VI) |
| 358 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-2-one | 0.64 | 462.08 | — | (IX) then (V) |
| 359 | (S)-5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-2-one | 0.65 | 462.09 | — | (IX) then (V) |
| 360 | (R)-5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-2-one | 0.65 | 462.1 | — | (IX) then (V) |
| 361 | (S)-6-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one | 0.67 | 476.08 | — | (IX) then (V) |
| 362 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one | 0.66 | 476.1 | — | (IX) then (V) |
| 363 | (S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-azetidin-2-one | 0.65 | 448.09 | — | (IX) then (V) |
| 364 | (S)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-azetidin-2-one | 0.65 | 448.1 | — | (IX) then (V) |

Example 365 and Example 366 were synthesized starting from Example D2.1 and 1,3-Dimethyl-5-Oxopyrrolidine-3-carboxylic acid, and following the procedure described in Example 134. Prep LC-MS and Chiral Prep (HPLC) conditions, Chiral HPLC and LC-MS data are listed in the table below. The LC-MS conditions used were LC-MS (A).

| Example N° | Name | LC-MS $t_R$ | $[M+H]^+$ | Prep LC-MS | Chiral Prep | Chiral HPLC $t_R$ (method) |
|---|---|---|---|---|---|---|
| 365 | (S)- or (R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,4-dimethyl-pyrrolidin-2-one | 0.71 | 490.12 | (V) | XXVI | 6.68 (Y) |
| 366 | (R)- or (S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,4-dimethyl-pyrrolidin-2-one | 0.71 | 490.11 | (V) | XXVI | 8.54 (Y) |

Example 367 to Example 369 were synthesized starting from Example D2.1 and the appropriate commercially available acid following the two-step procedure described in Example 332 steps 332.1 to 332.2. Prep LC-MS conditions and LC-MS data are listed in the table below. The LC-MS conditions used were LC-MS (A).

| Example N° | Name | $t_R$ | $[M+H]^+$ | Prep LC-MS |
|---|---|---|---|---|
| 367 | (R)-(1,3-Dimethyl-azetidin-3-yl)-(4-isopropyl-phenyl)-[5-(5-piperidin-4-yl-[1,2,4]oxadiazol-3-yl)-pyridin-3-yl]-methanol | 0.56 | 462.1 | (VI) |
| 368 | (R)-(1,3-Dimethyl-azetidin-3-yl)-(4-isopropyl-phenyl)-{5-[5-(4-methyl-piperidin-4-yl)-[1,2,4]oxadiazol-3-yl]-pyridin-3-yl}-methanol | 0.58 | 476.03 | (VI) |
| 369 | (R)-(1,3-Dimethyl-azetidin-3-yl)-{5-[5-(4-fluoro-piperidin-4-yl)-[1,2,4]oxadiazol-3-yl]-pyridin-3-yl}-(4-isopropyl-phenyl)-methanol | 0.58 | 480.1 | (VI) |

Example 370 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-butan-1-one To a solution of Example 367 (29.8 mg) in DCM (1 ml) placed at 0° C. were added DIPEA (38.2 µL) and butyryl chloride (5.84 µL), resulting mixture was left warmed to rt and stirred overnight. Solvent was evaporated and residue was purified by Prep LC-MS (IX) and (VI). LC-MS (A): $t_R$=0.8 min; $[M+H]^+$: 532.09.

Example 371 to Example 388 were synthesized starting from Example 367 and the appropriate commercially available acid chloride, chloroformate or sulfonyl chloride following the procedure described in Example 370. Prep LC-MS conditions and LC-MS data are listed in the table below. The LC-MS conditions used were LC-MS (A).

| Example N° | Name | $t_R$ | $[M+H]^+$ | Prep LC-MS |
|---|---|---|---|---|
| 371 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2,2-dimethyl-propan-1-one | 0.83 | 545.86 | (XIV) then (VII) |
| 372 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2-methoxy-ethanone | 0.73 | 534.07 | (IX) then (V) |
| 373 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-3-methoxy-propan-1-one | 0.75 | 548.07 | (IX) then (V) |
| 374 | Cyclopropyl-[4-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-piperidin-1-yl]-methanone | 0.78 | 529.83 | (IX) then (VI) |
| 375 | Cyclopentyl-[4-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-piperidin-1-yl]-methanone | 0.84 | 558.11 | (XIV) then (VII) |

-continued

| Example N° | Name | $t_R$ | [M + H]$^+$ | Prep LC-MS |
|---|---|---|---|---|
| 376 | [4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-(tetrahydro-pyran-4-yl)-methanone | 0.75 | 574.1 | (IX) then (V) |
| 377 | [4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-phenyl-methanone | 0.82 | 566.06 | (XIV) then (VI) |
| 378 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-carboxylic acid methyl ester | 0.8 | 520.04 | (XIV) then (VI) |
| 379 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-carboxylic acid ethyl ester | 0.83 | 534.07 | (XIV) then (VII) |
| 380 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-carboxylic acid 2-methoxy-ethyl ester | 0.79 | 564.09 | (XIV) then (VI) |
| 381 | (R)-(1,3-Dimethyl-azetidin-3-yl)-(4-isopropyl-phenyl)-{5-[5-(1-methanesulfonyl-piperidin-4-yl)-[1,2,4]oxadiazol-3-yl]-pyridin-3-yl}-methanol | 0.76 | 540.02 | (IX) then (VI) |
| 382 | (R)-(1,3-Dimethyl-azetidin-3-yl)-(4-isopropyl-phenyl)-(5-{5-[1-(propane-2-sulfonyl)-piperidin-4-yl]-[1,2,4]oxadiazol-3-yl}-pyridin-3-yl)-methanol | 0.82 | 568.06 | (XIV) then (VI) |
| 383 | (R)-(1,3-Dimethyl-azetidin-3-yl)-(4-isopropyl-phenyl)-(5-{5-[1-(propane-1-sulfonyl)-piperidin-4-yl]-[1,2,4]oxadiazol-3-yl}-pyridin-3-yl)-methanol | 0.82 | 568.07 | (XIV) then (VI) |
| 384 | (R)-(1,3-Dimethyl-azetidin-3-yl)-(4-isopropyl-phenyl)-(5-{5-[1-(2-methoxy-ethanesulfonyl)-piperidin-4-yl]-[1,2,4]oxadiazol-3-yl}-pyridin-3-yl)-methanol | 0.78 | 584.04 | (IX) then (VI) |
| 385 | 2-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-sulfonyl]-ethanol | 0.72 | 570.02 | (IX) then (V) |
| 386 | (R)-{5-[5-(1-Cyclopentanesulfonyl-piperidin-4-yl)-[1,2,4]oxadiazol-3-yl]-pyridin-3-yl}-(1,3-dimethyl-azetidin-3-yl)-(4-isopropyl-phenyl)-methanol | 0.86 | 593.88 | (XIV) then (VII) |
| 387 | (R)-(1,3-Dimethyl-azetidin-3-yl)-(4-isopropyl-phenyl)-(5-{5-[1-(tetrahydro-pyran-4-sulfonyl)-piperidin-4-yl]-[1,2,4]oxadiazol-3-yl}-pyridin-3-yl)-methanol | 0.79 | 609.89 | (XIV) then (VI) |
| 388 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-sulfonicacid methylamide | 0.76 | 555.02 | (IX) then (VI) |

Example 389: (R)-(1,3-Dimethyl-azetidin-3-yl)-(4-isopropyl-phenyl)-{5-[5-(1-methylamino-cyclopropyl)-[1,2,4]oxadiazol-3-yl]-pyridin-3-yl}-methanol A solution of Example 333 (220 mg) in MeCN (2 ml) and HCl (1M, 2 mL) was stirred 48 h at 100° C. The crude was evaporated and placed under HV. The residue was purified by Prep LC-MS (IX) and (VI). LC-MS (A): $t_R$=0.59 min; [M+H]$^+$: 448.25.

Example 390 and Example 391 were synthesized starting from Example 389 and the appropriate commercially available acid chloride or sulfonyl chloride following the procedure described in Example 370. Prep LC-MS conditions and LC-MS data are listed in the table below. The LC-MS conditions used were LC-MS (A).

| Example N° | Name | $t_R$ | [M + H]$^+$ | Prep LC-MS |
|---|---|---|---|---|
| 390 | [1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclopropyl]-methyl-carbamic acid ethyl ester | 0.65 | 520.24 | (IX) then (VI) |
| 391 | N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclopropyl]-N-methyl-methanesulfonamide | 0.78 | 526.2 | (IX) then (VI) |

Example 392: (R)-(1,3-Dimethyl-azetidin-3-yl)-[6-(2,2-dimethyl-cyclopentyloxy)-pyridazin-4-yl]-(4-isopropyl-phenyl)-methanol 392.1 3-[(R)-[6-(2,2-Dimethyl-cyclopentyloxy)-pyridazin-4-yl]-hydroxy-(4-isopropyl-phenyl)-methyl]-3-methyl-azetidine-1-carboxylic acid tert-butyl ester To a solution of Example F1.6.2 (35 mg) in dioxane (1 mL) were added 2,2-dimethylcyclopentanol (27.8 mg) and NaH (60% in mineral oil, 12.4 mg), resulting mixture was stirred 22 h at 65° C. The resulting crude was cooled down to rt, diluted with MeCN, filtered through a syringe filter and purified by Prep LC-MS (VIII) to afford 18.1 mg of the title compound as white powder. LC-MS (A): $t_R$=1.16 min; $[M+H]^+$: 510.16.

392.2 (R)-[6-(2,2-Dimethyl-cyclopentyloxy)-pyridazin-4-yl]-(4-isopropyl-phenyl)-(3-methyl-azetidin-3-yl)-methanol A solution of Example 392.1 (18.1 mg) solved in HCl in dioxane (4M, 0.5 mL) was stirred 2 h at RT. The reaction mixture was cooled at 0° C., basified to pH=8 with aq. sat. $NaHCO_3$, diluted with water and extracted with DCM. The combined org. layers were dried ($MgSO_4$), filtrated off, evaporated and dried under HV to afford 13.8 mg of the title compound as beige solid. LC-MS (A): $t_R$=0.84 min; $[M+H]^+$: 410.19.

392.3 (R)-(1,3-Dimethyl-azetidin-3-yl)-[6-(2,2-dimethyl-cyclopentyloxy)-pyridazin-4-yl]-(4-isopropyl-phenyl)-methanol The title compound (6.3 mg, white powder) was synthesized starting from Example 392.2 (13.8 mg) and following the procedure described in Example F1.1 step F1.1.2. Resulting crude was purified by Prep LC-MS (V). LC-MS (A): $t_R$=0.85 min; $[M+H]^+$: 424.20.

Example 393: (R)-[6-(3,3-Difluoro-cyclopentyloxy)-pyridazin-4-yl]-(1,3-dimethyl-azetidin-3-yl)-(4-isopropyl-phenyl)-methanol The title compound (7 mg, white solid) was synthesized starting from Example F1.6.2 (35 mg) and 3,3-difluorocyclopentan-1-ol (30.6 mg) following the three-step procedure described in Example 392. Resulting crude was purified by Prep LC-MS (VII). LC-MS (A): $t_R$=0.78 min; $[M+H]^+$: 432.12.

Example 394: 2-(2-{5-[(R)-(1,3-Dimethyl-azetidin-3-yl)-hydroxy-(4-isopropyl-phenyl)-methyl]-pyridazin-3-yloxy}-phenyl)-ethanol 394.1 3-[(R)-Hydroxy-{6-[2-(2-hydroxy-ethyl)-phenoxy]-pyridazin-4-yl}-(4-isopropyl-phenyl)-methyl]-3-methyl-azetidine-1-carboxylic acid tert-butyl ester To a solution of Example F1.6.2 (200 mg) in NMP (2.3 mL) were added 2-hydroxyphenethyl alcohol (67 μL), molecular sieves (3A powder, 200 mg) and $Cs_2CO_3$ (366 mg). The resulting mixture was stirred at 65° C. for 2.5 days, cooled down to RT, diluted with MeCN, filtered through a syringe filter and purified by Prep LC-MS (XX) to afford 53 mg of the title compound as white solid. LC-MS (A): $t_R$=1.03 min; $[M+H]^+$: 534.14.

394.2 2-(2-{5-[(R)-(1,3-Dimethyl-azetidin-3-yl)-hydroxy-(4-isopropyl-phenyl)-methyl]-pyridazin-3-yloxy}-phenyl)-ethanol The title compound (13.8 mg, white solid) was synthesized starting from Example 394.1 (47.5 mg) and following the procedure described in Example 82 step 82.2 and 82.3. Resulting crude was purified by Prep LC-MS (V). LC-MS (A): $t_R$=0.71 min; $[M+H]^+$: 448.18.

Example 395 to Example 397 were synthesized starting from Example F1.6.2 and the appropriate commercially available alcohol following the procedure described in Example 394. Prep LC-MS conditions and LC-MS data are listed in the table below. The LC-MS conditions used were LC-MS (A).

| Example N° | Name | $t_R$ | $[M+H]^+$ | Prep LC-MS |
|---|---|---|---|---|
| 395 | 2-(4-{5-[(R)-(1,3-Dimethyl-azetidin-3-yl)-hydroxy-(4-isopropyl-phenyl)-methyl]-pyridazin-3-yloxy}-phenyl)-ethanol | 0.71 | 448.23 | (V) |
| 396 | (R)-[6-(Chroman-6-yloxy)-pyridazin-4-yl]-(1,3-dimethyl-azetidin-3-yl)-(4-isopropyl-phenyl)-methanol | 0.81 | 460.21 | (VII) |
| 397 | 6-{5-[(R)-(1,3-Dimethyl-azetidin-3-yl)-hydroxy-(4-isopropyl-phenyl)-methyl]-pyridazin-3-yloxy}-3H-benzooxazol-2-one | 0.69 | 461.17 | (XV) then (IX) |

Example 398 to 407 were synthesized starting from the corresponding Example of formula (F1) and the appropriate alkyne of formula (F5), and following the procedure described in Example 15. The precursors of formula (F1) and (F5) are indicated in the table below unless commercially available. Prep LC-MS conditions and LC-MS data are listed in the table below. The LC-MS conditions used were LC-MS (A).

| Example N° | Name | $t_R$ | $[M + H]^+$ | (F1) | (F5) | Prep LC-MS |
|---|---|---|---|---|---|---|
| 398 | 1-{5-[(R)-(1,3-Dimethyl-azetidin-3-yl)-hydroxy-(4-isopropyl-phenyl)-methyl]-pyridin-3-yl}-3-(6-methyl-pyrimidin-4-yl)-pent-1-yn-3-ol | 0.76 | 485.21 | F1.2 | F5.19 | (VI) then (IX) |
| 399 | (S)-4-5-(R)-(1,3-Dimethyl-azetidin-3-yl)-hydroxy-(4-isopropyl-phenyl)-methyl]-pyridin-3-yl}-2-(6-methyl-pyrimidin-4-yl)-but-3-yn-2-ol | 0.72 | 471.27 | F1.2 | F5.20 | (IX) then (V) |
| 400 | (R)-4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-but-3-yn-2-ol | 0.71 | 471.35 | F1.2 | F5.21 | (V) then (IX) |
| 401 | (S)- or (R)-4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-but-3-yn-2-ol | 0.7 | 473.28 | F1.2 | F5.22 | (IX) then (V) |
| 402 | (R)- or (S)-4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-but-3-yn-2-ol | 0.7 | 473.28 | F1.2 | F5.23 | (IX) then (V) |
| 403 | (R)-(1,3-Dimethyl-azetidin-3-yl)-{5-[1-(4-fluoro-phenyl)-cyclopropylethynyl]-pyridin-3-yl}-(4-isopropyl-phenyl)-methanol | 0.91 | 469.27 | F1.2 | — | (VIII) then (XIV) |
| 404 | (S)- or (R)-4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-but-3-yn-2-ol | 0.68 | 459.26 | F1.2 | F5.24 | (V) then (IX) |
| 405 | (R)- or (S)-4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-but-3-yn-2-ol | 0.68 | 459.26 | F1.2 | F5.25 | (V) then (IX) |
| 406 | 3-{5-[(R)-(1,3-Dimethyl-azetidin-3-yl)-hydroxy-(4-isopropyl-phenyl)-methyl]-pyridin-3-ylethynyl}-3-hydroxy-pyrrolidine-1-carboxylic acid tert-butyl ester | 0.79 | 520.15 | F1.2 | — | (VI) then (IX) |
| 407 | 4-{5-[(R)-(1,3-Dimethyl-azetidin-3-yl)-hydroxy-(4-isopropyl-phenyl)-methyl]-pyridin-3-ylethynyl}-piperidine-1-carboxylic acid tert-butyl ester | 0.86 | 518.15 | F1.2 | — | — |

Example 408: 1-{5-[(R)-(1,3-Dimethyl-azetidin-3-yl)-hydroxy-(4-isopropyl-phenyl)-methyl]-pyridin-3-yl}-3-(6-methyl-pyrimidin-4-yl)-pentan-3-ol A solution of Example 398 (15 mg) was dissolved in MeOH (0.3 mL), Pd/C (10% w/w, 50% water, 3 mg) was added and resulting mixture was stirred for 17 h under hydrogen. The reaction mixture was filtered off and evaporated to dryness to afford 12 mg of the title compound as white solid. LC-MS (A): $t_R$=0.64 min; $[M+H]^+$: 489.21.

Example 409 to Example 412 were synthesized starting from Example F1.2 and the appropriate alkyne of formula (F5), according to a two-step procedure described in Example 15 (Prep LC-MS conditions for the purification described in the table below) followed by Example 408 (no purification performed). The alkyne precursors of formula (F5) are indicated in the table below unless commercially available. LC-MS data are listed in the table below. The LC-MS conditions used were LC-MS (A).

| Example N° | Name | $t_R$ | $[M + H]^+$ | (F5) | Prep LC-MS step 1 |
|---|---|---|---|---|---|
| 409 | 2-(2-5-[(R)-(1,3-Dimethyl-azetidin-3-yl)-hydroxy-(4-isopropyl-phenyl)-methyl]-pyridin-3-yl}-ethyl)-benzoic acid methyl ester | 0.73 | 473.21 | — | (VIII) |
| 410 | (R)-(1,3-Dimethyl-azetidin-3-yl)-{5-[2-(2-hydroxymethyl-phenyl)-ethyl]-pyridin-3-yl}-(4-isopropyl-phenyl)-methanol | 0.65 | 445.21 | — | (VII) then (IX) |

-continued

| Example N° | Name | $t_R$ | [M + H]$^+$ | (F5) | Prep LC-MS step 1 |
|---|---|---|---|---|---|
| 411 | 4-{5-[(R)-(1,3-Dimethyl-azetidin-3-yl)-hydroxy-(4-isopropyl-phenyl)-methyl]-pyridin-3-yl}-2-(6-methoxy-pyrimidin-4-yl)-butan-2-ol | 0.62 | 491.2 | F5.26 | (VI) then (IX) |
| 412 | 3-(2-{5-[(R)-(1,3-Dimethyl-azetidin-3-yl)-hydroxy-(4-isopropyl-phenyl)-methyl]-pyridin-3-yl}-ethyl)-3-hydroxy-pyrrolidine-1-carboxylic acid tert-butyl ester | 0.67 | 524.29 | — | (VI) then (IX) |

Example 413: (R)-(1,3-Dimethyl-azetidin-3-yl)-(4-isopropyl-phenyl)-{5-[2-(1H-pyrrolo[2,3-b]pyridin-2-yl)-ethyl]-pyridin-3-yl}-methanol

413.1 (R)-(1,3-Dimethyl-azetidin-3-yl)-(4-isopropyl-phenyl)-(5-trimethylsilanylethynyl-pyridin-3-yl)-methanol The title compound (21 mg, white powder) was synthesized from Example F1.2 (200 mg) and trimethyl acetylene (97.3 μL), and following the procedure described in Example 15. Resulting crude was purified by Prep LC-MS (VII) then (XIV). LC-MS (A): $t_R$=0.88 min; [M+H]$^+$: 407.20.

413.2 (R)-(1,3-Dimethyl-azetidin-3-yl)-(5-ethynyl-pyridin-3-yl)-(4-isopropyl-phenyl)-methanol The title compound (18 mg, yellow oil) was synthesized from Example 413.1 (20 mg) following the procedure described in Example F5.1 step F5.1.2. LC-MS (A): $t_R$=0.73 min; [M+H]$^+$: 335.17.

413.3 (R)-(1,3-Dimethyl-azetidin-3-yl)-(4-isopropyl-phenyl)-[5-(1H-pyrrolo[2,3-b]pyridin-2-ylethynyl)-pyridin-3-yl]-methanol The title compound (12 mg, yellow powder) was synthesized from Example 413.2 (18 mg) and 2-Iodo-1H-pyrrolo [2,3-B]pyridine (18 mg), and following the procedure described in Example 15. Resulting crude was purified by Prep LC-MS (VII). LC-MS (A): $t_R$=0.77 min; [M+H]$^+$: 451.03.

413.4 (R)-(1,3-Dimethyl-azetidin-3-yl)-(4-isopropyl-phenyl)-{5-[2-(1H-pyrrolo[2,3-b]pyridin-2-yl)-ethyl]-pyridin-3-yl}-methanol The title compound (8 mg, light yellow solid) was synthesized from Example 413.3 (11 mg) following the procedure described in Example 1119-7775. LC-MS (A): $t_R$=0.57 min; [M+H]$^+$: 455.19.

Example 414: 4-(2-{5-[(R)-(1,3-Dimethyl-azetidin-3-yl)-hydroxy-(4-isopropyl-phenyl)-methyl]-pyridin-3-yl}-ethyl)-piperidine-1-carboxylic acid tert-butyl ester The title compound (28 mg, rose resin) was synthesized from Example 407 (52 mg) following the procedure described in Example 48. Resulting crude was basified with aq. sat. $NaHCO_3$ solution and extracted with DCM over phase separator and solvent was evaporated to dryness. LC-MS (A): $t_R$=0.73 min; [M+H]$^+$: 522.18.

Example 415 to Example 417 were synthesized starting from Example F1.2 and the appropriate alkyne of formula (F5), according to a two-step procedure described in Example 15 followed by Example 48. The alkyne precursors of formula (F5) are indicated in the table below. Prep LC-MS conditions from both steps and LC-MS data are listed in the table below. The LC-MS conditions used were LC-MS (A).

| Example N° | Name | $t_R$ | [M + H]$^+$ | (F5) | Prep LC-MS step 1 | Prep LC-MS step 2 |
|---|---|---|---|---|---|---|
| 415 | 4-{5-[(R)-(1,3-Dimethyl-azetidin-3-yl)-hydroxy-(4-isopropyl-phenyl)-methyl]-pyridin-3-yl}-2-pyridin-2-yl-butan-2-ol | 0.51 | 460.21 | F5.28 | (XV) then (IX) | (IX) |
| 416 | 1-Cyclopropyl-3-{5-[(R)-(1,3-dimethyl-azetidin-3-yl)-hydroxy-(4-isopropyl-phenyl)-methyl]-pyridin-3-yl}-1-pyridin-2-yl-propan-1-ol | 0.56 | 486.17 | F5.29 | (IX) | (IX) |
| 417 | 4-{5-[(R)-(1,3-Dimethyl-azetidin-3-yl)-hydroxy-(4-isopropyl-phenyl)-methyl]-pyridin-3-yl}-2-(5-methyl-pyridin-3-yl)-butan-2-ol | 0.48 | 474.17 | F5.30 | (V) then (XIV) | — |

Example 418: 8-(2-{5-[(R)-(1,3-Dimethyl-azetidin-3-yl)-hydroxy-(4-isopropyl-phenyl)-methyl]-pyridazin-3-yl}-ethyl)-5,6,7,8-tetrahydro-quinolin-8-ol 418.1 8-{5-[(R)-(1,3-Dimethyl-azetidin-3-yl)-hydroxy-(4-isopropyl-phenyl)-methyl]-pyridazin-3-ylethynyl}-5,6,7,8-tetrahydro-quinolin-8-ol The title compound (27 mg, brown solid) was synthesized from Example F1.6 (50 mg) and Example F5.14 (33.8 mg), and following the procedure described in Example 15. Resulting crude was purified by Prep LC-MS (IX) LC-MS (A): $t_R$=0.63 min; $[M+H]^+$: 483.16.

418.2 8-(2-{5-[(R)-(1,3-Dimethyl-azetidin-3-yl)-hydroxy-(4-isopropyl-phenyl)-methyl]-pyridazin-3-yl}-ethyl)-5,6,7,8-tetrahydro-quinolin-8-ol The title compound (2 mg, white solid) was synthesized from Example 418.1 (27 mg) following the procedure described in Example 48. Resulting crude was purified by Prep LC-M (IX) LC-MS (A): $t_R$=0.58 min; $[M+H]^+$: 487.2.

Example 419: 4-{5-[(R)-(1,3-Dimethyl-azetidin-3-yl)-hydroxy-(4-isopropyl-phenyl)-methyl]-pyridazin-3-yl}-2-(6-methoxy-pyridin-2-yl)-butan-2-ol 419.1 3-[Hydroxy-{6-[(R)-3-hydroxy-3-(6-methoxy-pyridin-2-yl)-but-1-ynyl]-pyridazin-4-yl}-(4-isopropyl-phenyl)-methyl]-3-methyl-azetidine-1-carboxylic acid tert-butyl ester The title compound (154 mg, pale rose powder) was synthesized from Example F1.6.2 (200 mg) and Example F5.9 (89 mg), and following the procedure described in Example 15. Resulting crude was purified by Prep LC-MS (VII). LC-MS (A): $t_R$=1.07 min; $[M+H]^+$: 573.09.

419.2 3-[Hydroxy-{6-[(R)-3-hydroxy-3-(6-methoxy-pyridin-2-yl)-butyl]-pyridazin-4-yl}-(4-isopropyl-phenyl)-methyl]-3-methyl-azetidine-1-carboxylic acid tert-butyl ester The title compound (126 mg, yellow solid) was synthesized from Example 419.1 (152 mg) following the procedure described in Example 408. LC-MS (A): $t_R$=1.04 min; $[M+H]^+$: 578.05.

419.3 4-{5-[(R)-Hydroxy-(4-isopropyl-phenyl)-(3-methyl-azetidin-3-yl)-methyl]-pyridazin-3-yl}-2-(6-methoxy-pyridin-2-yl)-butan-2-ol The title compound (25 mg, brown solid) was synthesized from Example 419.2 (54 mg) following the procedure described in Example 309 step 309.2. Resulting crude was purified by Prep LC-MS (VII). LC-MS (A): $t_R$=0.72 min; $[M+H]^+$: 477.03.

419.4 4-{5-[(R)-(1,3-Dimethyl-azetidin-3-yl)-hydroxy-(4-isopropyl-phenyl)-methyl]-pyridazin-3-yl}-2-(6-methoxy-pyridin-2-yl)-butan-2-ol The title compound (9 mg, white powder) was synthesized from Example 419.3 (23 mg) following the procedure described in Example F1.1 step F1.1.2. Resulting crude was purified by Prep LC-MS (VI). LC-MS (A): $t_R$=0.74 min; $[M+H]^+$: 491.01.

Example 420: 4-{5-[(R)-(1,3-Dimethyl-azetidin-3-yl)-hydroxy-(4-isopropyl-phenyl)-methyl]-pyridazin-3-yl}-2-(6-methyl-pyridin-2-yl)-butan-2-ol The title compound (10 mg, white powder) was synthesized from Example F1.6.2 and Example F5.27, and following the four-step procedure described in Example 419. Resulting crude was purified by Prep LC-MS (VI). LC-MS (A): $t_R$=0.57 min; $[M+H]^+$: 475.21.

Example 421: (1,3-Dimethyl-azetidin-3-yl)-(4-isopropyl-phenyl)-(6-pyrrolidin-1-yl-pyridin-2-yl)-methanol The title compound (0.7 mg, brown solid) was synthesized starting from Example A4.2 and 2-bromo-6-(pyrrolidine-1-yl)pyridine, following the procedure described in Example D1.1 but omitting the steps D1.1.2 and D1.1.3. Resulting crude was purified by Prep LC-MS (XIV) then (XVIII). LC-MS (A): $t_R$=0.85 min; $[M+H]^+$: 380.22.

Example 422 and Example 423 were synthesized starting from AcCl and the appropriate amine precursor, and following the procedure described in Example 370. The amine precursors are indicated in the table below. Prep LC-MS conditions and LC-MS data are listed in the table below. The LC-MS conditions used were LC-MS (A).

| Example N° | Name | $t_R$ | $[M+H]^+$ | Precursor | Prep LC-MS |
|---|---|---|---|---|---|
| 422 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-fluoro-piperidin-1-yl]-ethanone | 0.74 | 522.09 | Example 369 | (IX) then (VI) |
| 423 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-methyl-piperidin-1-yl]-ethanone | 0.75 | 518.11 | Example 368 | (IX) then (VI) |

Example 424: 4-{5-[(R)-(1,3-Dimethyl-azetidin-3-yl)-hydroxy-(4-isopropyl-phenyl)-methyl]-pyridin-3-yloxy}-cyclohexanone The title compound is Example 261.2 and was synthesized as described exactly in Example 261 steps 261.1 and 261.2. LC-MS (A): $t_R$=0.65 min; $[M+H]^+$: 423.23.

Example 425: 4-{5-[(R)-(1,3-Dimethyl-azetidin-3-yl)-hydroxy-(4-isopropyl-phenyl)-methyl]-pyridin-3-yl}-cyclohexanol Title compound (7 mg, white powder) was synthesized from Example 327 step 327.3 (41 mg) and following the procedure described in Example 261 step 261.3. Resulting crude was purified by Prep LC-MS (VI). LC-MS (A): $t_R$=0.55 min; $[M+H]^+$: 409.09.

Example 426 (R)-(5-Cyclopentyloxymethyl-pyridin-3-yl)-(1,3-dimethyl-azetidin-3-yl)-(4-isopropyl-phenyl)-methanol To a solution of Example F1.2 (30 mg) and potassium cyclopentoxymethyltrifluoroborate (15.9 mg) in a dioxane/water mixture (10:1, 1 mL) were added $Cs_2CO_3$ (75.4 mg), $Pd(OAc)_2$ (0.519 mg) and RuPhos (2.27 mg). The resulting mixture was stirred for 45 h at 95° C., allowed to cool down to RT, diluted with MeOH and water, filtered through a syringe filter and purified by Prep LC-MS (XIV) to give 6 mg of the title compound as colorless resin. LC-MS (A): $t_R$=0.69 min; $[M+H]^+$: 409.16.

Example 427 (1-(4-{5-[(R)-(1,3-Dimethyl-azetidin-3-yl)-hydroxy-(4-isopropyl-phenyl)-methyl]-pyridin-3-ylmethoxy}-piperidin-1-yl)-ethanone 427.1 (4-{5-[(R)-(1,3-Dimethyl-azetidin-3-yl)-hydroxy-(4-isopropyl-phenyl)-methyl]-pyridin-3-ylmethoxy}-piperidine-1-carboxylic acid tert-butyl ester The title compound (29 mg, off-white solid) was synthesized from Example F1.2 (100 mg) and potassium (1-Boc-4-piperidinyloxy)methyl trifluoroborate (82.5 mg), and following the procedure described in Example 426. The resulting crude was purified by Prep LC-MS (VII). LC-MS (A): $t_R$=0.79 min; $[M+H]^+$: 524.15.

427.2 (R)-(1,3-dim ethylazetidin-3-yl)(4-isopropylphenyl)(5-((piperidin-4-yloxy)methyl)pyridin-3-yl) methanol, hydrochloride salt The title compound (6 mg, yellow resin) was synthesized from Example 427.1 (9 mg) following the procedure described in Example 309 step 309.2. LC-MS (A): $t_R$=0.47 min; $[M+H]^+$: 424.28.

427.3 (1-(4-{5-[(R)-(1,3-Dimethyl-azetidin-3-yl)-hydroxy-(4-isopropyl-phenyl)-methyl]-pyridin-3-ylmethoxy}-piperidin-1-yl)-ethanone The title compound (0.7 mg, colorless resin) was synthesized from Example 427.2 (6 mg) and AcOH (2.07 µL), and following the procedure described in Example 140 step 140.3. The resulting crude was purified by Prep LC-MS (IX). LC-MS (A): $t_R$=0.58 min; $[M+H]^+$: 465.88.

Example 428: (R)-(1,3-Dimethyl-azetidin-3-yl)-(4-isopropyl-phenyl)-[6-(tetrahydro-pyran-4-yl)-pyridazin-4-yl]-methanol 428.1 (R)-[6-(3,6-Dihydro-2H-pyran-4-yl)-pyridazin-4-yl]-(1,3-dimethyl-azetidin-3-yl)-(4-isopropyl-phenyl)-methanol The title compound (27 mg, yellow solid) was synthesized from Example F1.6 (50 mg) and 3,6-dihydro-2H-pyran-4-boronic acid pinacol ester (62.6 mg), and following the procedure described in Example 303. The resulting crude was purified by Prep LC-MS (IX). LC-MS (A): $t_R$=0.69 min; $[M+H]^+$: 394.22.

428.2 (R)-(1,3-Dimethyl-azetidin-3-yl)-(4-isopropyl-phenyl)-[6-(tetrahydro-pyran-4-yl)-pyridazin-4-yl]-methanol The title compound (7 mg, white solid) was synthesized from Example 428.1 (27 mg) following the procedure described in Example 48. Resulting crude was purified by Prep LC-M (IX). LC-MS (A): $t_R$=0.68 min; $[M+H]^+$: 396.24.

Example 429: 4-{5-[(R)-(1,3-Dimethyl-azetidin-3-yl)-hydroxy-(4-isopropyl-phenyl)-methyl]-pyridazin-3-yl}-2-phenyl-butan-2-ol 429.1 3-[(R)-Hydroxy-[6-(3-hydroxy-3-phenyl-but-1-ynyl)-pyridazin-4-yl]-(4-isopropyl-phenyl)-methyl]-3-methyl-azetidine-1-carboxylic acid tert-butyl ester The title compound (52.5 mg, white powder) was synthesized from Example F1.6.2 (80 mg) and DL-2-phenyl-3-butyn-2-ol (41.4 mg), and following the procedure described in Example 165 step 165.1. The resulting crude was purified by Prep LC-MS (XII). LC-MS (A): $t_R$=1.07 min; $[M+H]^+$: 542.08.

429.2 3-chloro-4-(5-((R)-hydroxy(4-isopropylphenyl)(3-methylazetidin-3-yl)methyl)pyridazin-3-yl)-2-phenylbut-3-en-2-ol, hydrochloride salt The title compound (69 mg, yellow solid) was synthesized from Example 429.1 (52.5 mg) following the procedure described in Example 309 step 309.2. LC-MS (A): $t_R$=0.77 min; $[M+H]^+$: 478.10.

429.3. 3-Chloro-4-{5-[(R)-(1,3-dimethyl-azetidin-3-yl)-hydroxy-(4-isopropyl-phenyl)-methyl]-pyridazin-3-yl}-2-phenyl-but-3-en-2-ol The title compound (20.4 mg, beige solid) was synthesized starting from Example 429.2 (69 mg), and following the procedure described in Example F1.1 step F1.1.2. Resulting crude was purified by Prep LC-MS (IX). LC-MS (A): $t_R$=0.79 min; $[M+H]^+$: 492.13.

429.4. 4-{5-[(R)-(1,3-Dimethyl-azetidin-3-yl)-hydroxy-(4-isopropyl-phenyl)-methyl]-pyridazin-3-yl}-2-phenyl-butan-2-ol The title compound (5 mg, white powder) was synthesized from Example 429.3 (20.4 mg) following the procedure described in Example 48. Resulting crude was purified by Prep LC-MS (IX). LC-MS (A): $t_R$=0.74 min; $[M+H]^+$: 460.18.

Example 430 (R)-(1,3-Dimethyl-azetidin-3-yl)-(4-isopropyl-phenyl)-{6-[(S)-(tetrahydro-furan-3-yl)oxy]-pyridazin-4-yl}-methanol 430.1. 3—((R)-Hydroxy-(4-isopropyl-phenyl)-{6-[(S)-(tetrahydro-furan-3-yl)oxy]-pyridazin-4-yl}-methyl)-3-methyl-azetidine-1-carboxylic acid tert-butyl ester The title compound (25.3 mg, white powder) was synthesized from Example F1.6.2 (35 mg) and (S)-(±)-hydroxytetrahydrofuran (19.6 μL), and following the procedure described in Example 277 but heating the mixture at 65° C. for 1 h. The resulting crude was purified by Prep LC-MS (VI). LC-MS (A): $t_R$=1.03 min; $[M+H]^+$: 484.15.

430.2. (R)-(4-Isopropyl-phenyl)-(3-methyl-azetidin-3-yl)-{6-[(S)-(tetrahydro-furan-3-yl)oxy]-pyridazin-4-yl}-methanol The title compound (21.4 mg, beige solid) was synthesized from Example 430.1 (25.3 mg) following the procedure described in Example 309 step 309.2. LC-MS (A): $t_R$=0.66 min; $[M+H]^+$: 384.11.

430.3. (R)-(1,3-Dimethyl-azetidin-3-yl)-(4-isopropyl-phenyl)-{6-[(S)-(tetrahydro-furan-3-yl)oxy]-pyridazin-4-yl}-methanol The title compound (11.3 mg, white powder) was synthesized starting from Example 430.2 (21.4 mg), and following the procedure described in Example F1.1 step F1.1.2. Resulting crude was purified by Prep LC-MS (V). LC-MS (A): $t_R$=0.67 min; $[M+H]^+$: 398.16.

Example 431 (R)-(1,3-Dimethyl-azetidin-3-yl)-(4-isopropyl-phenyl)-{6-[(R)-(tetrahydro-furan-3-yl)oxy]-pyridazin-4-yl}-methanol The title compound (5.6 mg, white powder) was synthesized from Example F1.6.2 (35 mg) and (R)-(±)-hydroxytetrahydrofuran (19.6 μL), and following the three-step procedure described in Example 430. The resulting crude was purified by Prep LC-MS (V). LC-MS (A): $t_R$=0.67 min; $[M+H]^+$: 398.17.

Example 432 to 444 were synthesized starting from Example F1.6 and the appropriate commercially available carbamate (F4) or amide-containing reagent of Formula (F3), and following the procedure described in Example 167 step 167.1. Prep LC-MS conditions and LC-MS data are listed in the table below. The LC-MS conditions used were LC-MS (A).

| Example N° | Name | $t_R$ | $[M+H]^+$ | Prep LC-MS |
|---|---|---|---|---|
| 432 | 1-{5-[(R)-(1,3-Dimethyl-azetidin-3-yl)-hydroxy-(4-isopropyl-phenyl)-methyl]-pyridazin-3-yl}-4-methyl-pyrrolidin-2-one | 0.72 | 409.18 | (IX) |
| 433 | 1-{5-[(R)-(1,3-Dimethyl-azetidin-3-yl)-hydroxy-(4-isopropyl-phenyl)-methyl]-pyridazin-3-yl}-3-isopropyl-pyrrolidin-2-one | 0.80 | 437.19 | (XIV) |
| 434 | 1-{5-[(R)-(1,3-Dimethyl-azetidin-3-yl)-hydroxy-(4-isopropyl-phenyl)-methyl]-pyridazin-3-yl}-3,3-dimethyl-pyrrolidin-2-one | 0.75 | 423.18 | (IX) |
| 435 | 1-{5-[(R)-(1,3-Dimethyl-azetidin-3-yl)-hydroxy-(4-isopropyl-phenyl)-methyl]-pyridazin-3-yl}-4,4-dimethyl-pyrrolidin-2-one | 0.75 | 423.15 | (IX) |
| 436 | 5-{5-[(R)-(1,3-Dimethyl-azetidin-3-yl)-hydroxy-(4-isopropyl-phenyl)-methyl]-pyridazin-3-yl}-5-aza-spiro[2.4]heptan-6-one | 0.74 | 421.17 | (IX) |
| 437 | 1-{5-[(R)-(1,3-Dimethyl-azetidin-3-yl)-hydroxy-(4-isopropyl-phenyl)-methyl]-pyridazin-3-yl}-4-trifluoromethyl-pyrrolidin-2-one | 0.76 | 463.10 | (IX) |
| 438 | 4-Cyclopropyl-1-{5-[(R)-(1,3-dimethyl-azetidin-3-yl)-hydroxy-(4-isopropyl-phenyl)-methyl]-pyridazin-3-yl}-pyrrolidin-2-one | 0.79 | 435.18 | (IX) |
| 439 | 2-{5-[(R)-(1,3-Dimethyl-azetidin-3-yl)-hydroxy-(4-isopropyl-phenyl)-methyl]-pyridazin-3-yl}-8-oxa-2-aza-spiro[4.5]decan-3-one | 0.69 | 465.09 | (IX) |
| 440 | 3-{5-[(R)-(1,3-Dimethyl-azetidin-3-yl)-hydroxy-(4-isopropyl-phenyl)-methyl]-pyridazin-3-yl}-1-oxa-3-aza-spiro[4.5]decan-2-one | 0.82 | 465.04 | (XIV) |
| 441 | 1-{5-[(R)-(1,3-Dimethyl-azetidin-3-yl)-hydroxy-(4-isopropyl-phenyl)-methyl]-pyridazin-3-yl}-4-pyridin-2-yl-pyrrolidin-2-one | 0.62 | 472.13 | (IX) |
| 442 | 1-{5-[(R)-(1,3-Dimethyl-azetidin-3-yl)-hydroxy-(4-isopropyl-phenyl)-methyl]-pyridazin-3-yl}-3-(2-methoxy-ethyl)-pyrrolidin-2-one | 0.73 | 453.16 | (IX) then (VI) |
| 443 | 1-{5-[(R)-(1,3-Dimethyl-azetidin-3-yl)-hydroxy-(4-isopropyl-phenyl)-methyl]-pyridazin-3-yl}-4-phenyl-pyrrolidin-2-one | 0.82 | 471.15 | (XIV) then (VII) |
| 444 | 2-{5-[(R)-(1,3-Dimethyl-azetidin-3-yl)-hydroxy-(4-isopropyl-phenyl)-methyl]-pyridazin-3-yl}-2,3-dihydro-isoindol-1-one | 0.79 | 443.14 | (IX) then (VI) |

Example 445: 2-(3-{5-[(S)-(3-Fluoro-1-methyl-azetidin-3-yl)-hydroxy-(4-isopropyl-phenyl)-methyl]-pyridin-3-yl}-[1,2,4]oxadiazol-5-yl)-propan-2-ol 445.1 3-[(5-Cyano-pyridin-3-yl)-hydroxy-(4-isopropyl-phenyl)-methyl]-3-fluoro-azetidine-1-carboxylic acid tert-butyl ester To a solution of Example A4.13 (1.50 g) and 5-bromonicotinonitrile (1.08 g) in THF (30 mL) at −78° C., a solution of HexLi in THF (2.3 M, 1.3 mL) was added dropwise during 20 min. The reaction mixture was stirred at −78° C. for 20 min, before the cooling bath was removed and the reaction was quenched with aq. $NH_4Cl$. The mixture was extracted with EA twice, the combined organic layers were washed with brine, dried over $Na_2SO_4$, filtered and concentrated under vacuo. The residue was purified by CC (CombiFlash, RediSep 40 g, gradient n-Heptane/EA 90:10 to 60:40 over 25 min at 40 mL/min) to give the desired product as a yellow foam (1.49 g). It was further purified by prep LC-MS (XVII then XII) to give the title compound as white solid (1.04 g). LC-MS (A): $t_R$=1.09 min; $[M+H]^+$: 426.24.

445.2 3—[(S)-(5-Cyano-pyridin-3-yl)-hydroxy-(4-isopropyl-phenyl)-methyl]-3-fluoro-azetidine-1-carboxylic acid tert-butyl ester Example 445.1 (1.04 g) was purified by prep chiral HPLC (XL) to give the title compound as pure enantiomer (450 mg). Chiral SFC (F): $t_R$=1.86 min.

445.3 3-Fluoro-3-[(S)-hydroxy-[5-(N-hydroxycarbamimidoyl)-pyridin-3-yl]-(4-isopropyl-phenyl)-methyl]-azetidine-1-carboxylic acid tert-butyl ester Example 445.2 (150 mg) together with hydroxylamine hydrochloride (74 mg) and $K_2CO_3$ (195 mg) were suspended in EtOH (2.3 mL). The mixture was heated to 85° C. and stirred for 15 h. The reaction mixture was filtered, the residue was washed with more EtOH and the filtrate was concentrated under vacuo to give the title compound as off-white solid (149 mg), which was used in subsequent steps without further purification. LC-MS (A): $t_R$=0.80 min; $[M+H]^+$: 459.28.

445.4 3-Fluoro-3-[(S)-hydroxy-{5-[5-(1-hydroxy-1-methyl-ethyl)-[1,2,4]oxadiazol-3-yl]-pyridin-3-yl}-(4-isopropyl-phenyl)-methyl]-azetidine-1-carboxylic acid tert-butyl ester Example 445.3 (120 mg), alpha-hydroxyisobutyric acid (37 mg), PyBOP (423 mg) and $K_3PO_4$ (227 mg) were treated with DMF (2 mL) and $NEt_3$ (0.14 mL). The mixture was heated to 85° C. and stirred for 15 h. The reaction was cooled to room temperature, diluted with EA, washed with aq. $NaHCO_3$, aq. $NH_4Cl$ and brine, dried over $Na_2SO_4$, filtered and concentrated under vacuo to give an orange oil. The residue was purified by CC (CombiFlash, RediSep 12 g, gradient n-Heptane/EA 90:10 to 50:50 over 20 min at 30 mL/min) to afford the title compound as a colorless amorphous solid (90 mg). LC-MS (A): $t_R$=1.06 min; $[M+H]^+$: 527.28.

445.5 2-(3-{5-[(S)-(3-Fluoro-azetidin-3-yl)-hydroxy-(4-isopropyl-phenyl)-methyl]-pyridin-3-yl}-[1,2,4]oxadiazol-5-yl)-propan-2-ol, hydrochloride salt Example 445.4 (90 mg) was dissolved in a solution of HCl in dioxane (4 M, 0.43 mL) and stirred at RT for 1.5 h. A thick slurry resulted and to improve stirring, dioxane (0.5 mL) and little MeOH (0.15 mL) were added. After another 1.5 h at RT full conversion was achieved and the mixture was concentrated under vacuo to give the title compound as white solid (76 mg). It was used in the next steps without further purification. LC-MS (A): $t_R$=0.69 min; $[M+H]^+$: 427.26.

445.6 2-(3-{5-[(S)-(3-Fluoro-1-methyl-azetidin-3-yl)-hydroxy-(4-isopropyl-phenyl)-methyl]-pyridin-3-yl}-[1,2,4]oxadiazol-5-yl)-propan-2-ol To a solution of Example 445.5 (35 mg) in DCM (0.5 mL) at 0° C. was added a solution of formaldehyde in $H_2O$ (37 wt. %, 14 uL). After stirring for 5 min, $NaBH(OAc)_3$ (23 mg) was added, the suspension was stirred at 0° C. for 1 h. The mixture was treated with $NEt_3$ (0.01 mL) and additional aq. formaldehyde solution (37 wt %, 0.02 mL) and NaBH $(OAc)_3$ (18 mg). After stirring at 4° C. for 16 h, the reaction mixture was concentrated under vacuo, filtered through a syringe filter and purified by prep LC-MS (V) to give the title compound as a white solid (21 mg). LC-MS (A): $t_R$=0.70 min; $[M+H]^+$: 441.25.

Example 446: 2-(3-{5-[(S)-(1-Cyclopropyl-3-fluoro-azetidin-3-yl)-hydroxy-(4-isopropyl-phenyl)-methyl]-pyridin-3-yl}-[1,2,4]oxadiazol-5-yl)-propan-2-ol A solution of Example 445.5 (42 mg) in DCM (0.5 mL) and $NEt_3$ (0.01 mL) was cooled to 0° C., before (1-ethoxycyclopropoxy)trimethylsilane (0.05 mL) and AcOH (0.02 mL) were added. After stirring for 5 min, $NaBH(OAc)_3$ (28 mg) was added and the suspension was stirred at 0° C. for 1 h. Acetic acid (0.03 mL) was added and the mixture was allowed to warm to RT. After stirring for 2.5 h, the reaction mixture was heated to 40° C. and stirred for 2 h. The mixture was cooled to RT, quenched with sat. aq. $NaHCO_3$ and extracted with EA three times. The combined organic layers were dried over $Na_2SO_4$, filtered and concentrated under vacuo to give a yellow oil (being mostly reaction intermediate. The residue was taken up in MeOH (0.5 mL) and thereto was added $NaBH_3CN$ (18 mg). The mixture was heated to 65° C. and stirred for 1 h. The reaction mixture was concentrated under vacuo, redissolved in MeCN, filtered through a syringe filter and subjected to prep LC-MS (VI then IX) to give the title compound as a white solid (11 mg). LC-MS (A): $t_R$=0.73 min; $[M+H]^+$: 467.29.

Example 447: 1-[4-(3-{5-[(S)-(3-Fluoro-1-methyl-azetidin-3-yl)-hydroxy-(4-isopropyl-phenyl)-methyl]-pyridin-3-yl}-[1,2,4]oxadiazol-5-yl)-piperidin-1-yl]-ethanone 447.1 3—[(S)-{5-[5-(1-Acetyl-piperidin-4-yl)-[1,2,4]oxadiazol-3-yl]-pyridin-3-yl}-hydroxy-(4-isopropyl-phenyl)-methyl]-3-fluoro-azetidine-1-carboxylic acid tert-butyl ester A mixture of Example 445.3 (179 mg), 1-acetylpiperidine-4-carboxylic acid (84 mg), PyBOP (568 mg), $K_3PO_4$ (304 mg) and DIPEA (0.18 mL) in DMF (2.5 mL) was stirred at 85° C. for 15 h. The reaction mixture was cooled to RT, diluted with EA, washed with aq. $NaHCO_3$, aq. $NH_4Cl$ and brine, dried over $Na_2SO_4$, filtered and concentrated under vacuo to give an orange oil, which was purified by CC (CombiFlash, RediSep 12 g, gradient DCM to DCM/MeOH 90:10 over 20 min at 30 mL/min) to give a colorless amorphous solid (149 mg). LC-MS (A): $t_R$=1.10 min; $[M+H]^+$: 594.12.

447.2 1-[4-(3-{5-[(S)-(3-Fluoro-azetidin-3-yl)-hydroxy-(4-isopropyl-phenyl)-methyl]-pyridin-3-yl}-[1,2,4]oxadiazol-5-yl)-piperidin-1-yl]ethanone, hydrochloride salt Example 447.1 (145 mg) was treated with a solution of HCl in dioxane (4 M, 0.43 mL) and stirred for 1 h. The reaction mixture was concentrated under vacuo to give the desired product as slightly yellow solid (155 mg). The compound was used in the next step without further purification. LC-MS (A): $t_R$=0.70 min; $[M+H]^+$: 494.28.

447.3 1-[4-(3-{5-[(S)-(3-Fluoro-1-methyl-azetidin-3-yl)-hydroxy-(4-isopropyl-phenyl)-methyl]-pyridin-3-yl}-[1,2,4]oxadiazol-5-yl)-piperidin-1-yl]-ethanone A suspension of Example 447.2 in DCM (1.0 mL) was cooled to 0° C. Thereto was added a solution of formaldehyde in water (37 wt. %, 14 uL) and $NaBH(OAc)_3$ (68 mg). The mixture was stirred for 5 h at 0° C. and 1 h at RT. More formaldehyde solution (37 wt. %, 0.05 mL) and $NaBH(OAc)_3$ (65 mg) were added. The mixture was stirred at RT for 1 h. The reaction mixture was poured into aq. $NaHCO_3$ and extracted with DCM/MeOH (9:1) three times. The combined organic layers were passed through a phase separator and concentrated under vacuo to give a colourless oil, which was purified by prep LC-MS (V) to give a white solid (64 mg). LC-MS (A): $t_R$=0.71 min; $[M+H]^+$: 508.29.

Example 448: 1-[4-(3-{5-[(S)-(1-Cyclopropyl-3-fluoro-azetidin-3-yl)-hydroxy-(4-isopropyl-phenyl)-methyl]-pyridin-3-yl}-[1,2,4]oxadiazol-5-yl)-piperidin-1-yl]-ethanone 448.1 5—[(S)-(3-Fluoro-azetidin-3-yl)-hydroxy-(4-isopropyl-phenyl)-methyl]-nicotinonitrile Treatment of Example 445.2 (450 mg) with a solution of HCl in dioxane (4 M, 2.65 mL) led to a colourless solution that quickly turned into a thick suspension. To help stirring, MeOH (1.0 mL) was added and the mixture was stirred at RT for 1 h. The mixture was concentrated under vacuo, then purified by prep LC-MS (V) to give a white solid (160 mg). LC-MS (A): $t_R$=0.67 min; $[M+H]^+$: 326.20.

448.2 5—[(S)-(1-Cyclopropyl-3-fluoro-azetidin-3-yl)-hydroxy-(4-isopropyl-phenyl)-methyl]-nicotinonitrile To a solution of Example 448.1 (100 mg) in MeOH (5 mL) was added (1-ethoxycyclopropoxy)trimethylsilane (0.19 mL), acetic acid (0.04 mL) and $NaBH_3CN$ (41 mg). The suspension was heated to 55° C. and stirred for 90 min, then cooled to RT and stirred for 17 h. The reaction mixture was diluted with DCM and washed with aq. $NaHCO_3$. The aqueous phase was extracted once with DCM/MeOH (9:1). The combined organic layers were passed through a phase separator and concentrated under vacuo to give a colorless oil, which was purified by prep LC-MS (VI) to give the product as a white foam (74 mg). LC-MS (A): $t_R$=0.72 min; $[M+H]^+$: 366.24.

448.3 5—[(S)-(1-Cyclopropyl-3-fluoro-azetidin-3-A-hydroxy-(4-isopropyl-phenyl)-methyl]-N-hydroxy-nicotinamidine A suspension of Example 448.2 (74 mg), hydroxylamine hydrochloride (43 mg) and $K_2CO_3$ (112 mg) in EtOH (1.5 mL) was heated to 90° C. and stirred for 3 h. The reaction mixture was cooled to RT, filtered and concentrated under vacuo to give the desired product as a white solid (109 mg). The crude was used in the next step without further purification. LC-MS (A): $t_R$=0.55 min; $[M+H]^+$: 399.22.

448.4 1-[4-(3-{5-[(S)-(1-Cyclopropyl-3-fluoro-azetidin-3-yl)-hydroxy-(4-isopropyl-phenyl)-methyl]-pyridin-3-yl}-[1,2,4]oxadiazol-5-yl)-piperidin-1-yl]-ethanone A reaction vessel was charged with Example 448.3 (109 mg), PyBOP (326 mg), $K_3PO_4$ (175 mg) and 1-acetylpiperidine-4-carboxylic acid (48 mg), followed by DMF (1.0 mL) and DIPEA (0.11 mL). The mixture was stirred for 17 h at 80° C. and for 7 h at 95° C. More PyBOP (200 mg) was added and the reaction was stirred at 100° C. for 20 h. More 1-acetylpiperidine-4-carboxylic acid (30 mg), PyBOP (200 mg) and $K_3PO_4$ (100 mg) were added and the mixture was stirred at 100° C. for another 18 h. The reaction mixture was cooled to RT, diluted with EA, washed with aq. $NaHCO_3$ and with brine, dried over $Na_2SO_4$, filtered and concentrated under vacuo to give a yellow oil, which was purified with prep LC-MS (VI then IX) and CC (CombiFlash, RediSep 4 g, gradient DCM to DCM/MeOH/$NH_4OH$ 94.5:5.0:0.5 over 20 min at 18 mL/min) to give a white solid (5 mg). LC-MS (A): $t_R$=0.74 min; $[M+H]^+$: 534.31.

Example 449: 2-(3-{5-[(R)-(1-Cyclopropyl-3-methyl-azetidin-3-yl)-hydroxy-(4-isopropyl-phenyl)-methyl]-pyridin-3-yl}-[1,2,4]oxadiazol-5-yl)-propan-2-ol 449.1 5-[(R)-(1-Cyclopropyl-3-methyl-azetidin-3-yl)-hydroxy-(4-isopropyl-phenyl)-methyl]-nicotinonitrile To a solution of Example D1.1.4 (541 mg) in MeOH (6 mL) was added (1-ethoxypropoxy)trimethylsilane (0.73 mL), acetic acid (0.14 mL) and $NaBH_3CN$ (158 mg). The suspension was heated to 65° C. and stirred for 16 h. The reaction mixture was filtered, diluted with DCM and washed with aq. $NaHCO_3$. The aqueous phase was re-extracted with DCM/MeOH (9:1). The combined organic layers were passed through a phase separator and were concentrated under vacuo to give a colourless oil, which was purified by prep LC-MS (VI) to give the desired product as a white solid (174 mg). LC-MS (A): $t_R$=0.71 min; $[M+H]^+$: 362.20.

449.2 5-[(R)-(1-Cyclopropyl-3-methyl-azetidin-3-A-hydroxy-(4-isopropyl-phenyl)-methyl]-N-hydroxy-nicotinamidine A mixture of Example 449.1 (87 mg), hydroxylamine hydrochloride (49 mg) and $K_2CO_3$ (127 mg) in EtOH (1.5 mL) was heated to 85° C. and stirred for 1.5 h. The reaction mixture was cooled to RT, filtered, concentrated and dried under HV to give a white solid (101 mg), which was used in the next step without further purification. LC-MS (A): $t_R$=0.55 min; $[M+H]^+$: 395.26.

449.3 2-(3-{5-[(R)-(1-Cyclopropyl-3-methyl-azetidin-3-yl)-hydroxy-(4-isopropyl-phenyl)-methyl]-pyridin-3-yl}-[1,2,4]oxadiazol-5-yl)-propan-2-ol A mixture of Example 449.2 (43 mg), alpha-hydroxy-isobutyric acid (7 mg), PyBOP (35 mg) and $NEt_3$ (10 mg) in DMF (0.5 mL) was heated to 80° C. and stirred for 16 h. The reaction mixture was cooled to RT, diluted with $MeCN/H_2O$, filtered through a syringe filter and purified by prep LC-MS (2× VI) to give the title compound as a slightly yellow solid. LC-MS (A): $t_R$=0.72 min; $[M+H]^+$: 463.31.

Example 450 to Example 453 were prepared from Example 449.2 and the corresponding carboxylic acid according to the procedure described for Example 449.3. Prep LC-MS conditions and LC-MS data are listed in the table below. The LC-MS conditions used were LC-MS (A).

| Example N° | Name | $t_R$ (min) | [M + H]$^+$ | Prep LC-MS |
|---|---|---|---|---|
| 450 | 1-[4-(3-{5-[(R)-(1-Cyclopropyl-3-methyl-azetidin-3-yl)-hydroxy-(4-isopropyl-phenyl)-methyl]-pyridin-3-yl}-[1,2,4]oxadiazol-5-yl)-piperidin-1-yl]-ethanone | 0.74 | 530.15 | (VI) |
| 451 | (R)-(1-Cyclopropyl-3-methyl-azetidin-3-yl)-(4-isopropyl-phenyl)-{5-[5-(tetrahydro-pyran-4-yl)-[1,2,4]oxadiazol-3-yl]-pyridin-3-yl}-methanol | 0.77 | 489.34 | (VI) |
| 452 | trans-4-(3-{5-[(R)-(1-Cyclopropyl-3-methyl-azetidin-3-yl)-hydroxy-(4-isopropyl-phenyl)-methyl]-pyridin-3-yl}-[1,2,4]oxadiazol-5-yl)-cyclohexanol | 0.73 | 503.35 | (VI) |
| 453 | (R)-(1-Cyclopropyl-3-methyl-azetidin-3-yl)-(4-isopropyl-phenyl)-[5-(5-oxetan-3-yl-[1,2,4]oxadiazol-3-yl)-pyridin-3-yl]-methanol | 0.73 | 461.27 | (VI) |

Example 454: 1-[(R)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidin-1-yl]-ethanone 454.1 (R)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidine-1-carboxylic acid tert-butyl ester A mixture of Example D2.1 (39 mg), (R)-(1-Boc-pyrrolidin-3-yl)-acetic acid (36 mg), PyBOP (128 mg), $K_3PO_4$ (89 mg) and DIPEA (41 mg) in DMF (2 mL) was stirred at 85° C. for 64 h. The mixture was cooled to RT, diluted with $H_2O/MeCN$, passed through a syringe filter and purified by prep LC-MS (XIV) to give the desired product as a white solid. LC-MS (A): $t_R$=0.85 min; $[M+H]^+$: 562.21.

454.2 (R)-(1,3-dimethylazetidin-3-yl)(4-isopropylphenyl)(5-(5-(((R)-pyrrolidin-3-yl)methyl)-1,2,4-oxadiazol-3-yl)pyridin-3-yl)methanol hydrochloride salt Example 454.1 (76 mg) was treated with a solution of HCl in dioxane (4 M, 2 mL) and stirred at RT for 2 h. The reaction mixture was concentrated and dried under HV. The resulting white solid was used in the next step without further purification. LC-MS (A): $t_R$=0.55 min; $[M+H]^+$: 462.24.

454.3 1-[(R)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidin-1-yl]-ethanone To a solution of Example 454.2 (15 mg) in THF (1 mL) was added DIPEA (19 mg) and acetyl chloride (2.4 mg) at 0° C. The mixture was stirred at 0° C. for 45 min, before it was concentrated and dried under HV. The crude was purified by prep HPLC (IX) to give the title compound as a white solid (3 mg). LC-MS (A): $t_R$=0.71 min; $[M+H]^+$: 504.24.

Example 455 to Example 459 were synthesized according to the 3-step procedure described for Example 454, using the corresponding acids in the first step. Prep LC-MS conditions (first and third steps) and LC-MS data are listed in the table below. The LC-MS conditions used were LC-MS (A).

| Example N° | Name | $t_R$ (min) | [M + H]$^+$ | Prep LC-MS (Step 1) | Prep LC-MS (Step 3) |
|---|---|---|---|---|---|
| 455 | 1-[3-(3-5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-ethanone | 0.73 | 504.26 | (XIV) | (IX) |
| 456 | 1-[3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-3-hydroxy-piperidin-1-yl]-ethanone | 0.67 | 520.27 | (IX) | (IX) |

-continued

| Example N° | Name | $t_R$ (min) | [M + H]$^+$ | Prep LC-MS (Step 1) | Prep LC-MS (Step 3) |
|---|---|---|---|---|---|
| 457 | 1-[3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-3-methyl-piperidin-1-yl]-ethanone | 0.75 | 518.28 | (XIV) | (IX) |
| 458 | 1-[3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-piperidin-1-yl]-ethanone | 0.74 | 518.30 | (XIV) | (IX) |
| 459 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-4-hydroxy-piperidin-1-yl]-ethanone | 0.66 | 534.27 | (IX) | (IX) |

Example 460: N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclopropyl]-acetamide

460.1 [1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclopropyl]-carbamic acid tert-butyl ester A mixture of Example D2.1 (30 mg), 2-[1-({tert-butoxycarbonyl}amino)cyclopropyl]acetic acid (15 mg), PyBOP (60 mg), $K_3PO_4$ (59 mg) and DIPEA (27 mg) in DMF (0.75 mL) was heated to 90° C. and stirred for 3 h. After cooling to RT, the reaction mixture was filtered and directly purified by prep LC-MS (XIV) to give the desired product as a white solid (4 mg). LC-MS (A): $t_R$=0.82 min; [M+H]$^+$: 548.18.

460.2 (R)-{5-[5-(1-Amino-cyclopropylmethyl)-[1,2,4]oxadiazol-3-yl]-pyridin-3-yl}-(1,3-dimethyl-azetidin-3-yl)-(4-isopropyl-phenyl)-methanol, hydrochloride salt Example 460.1 (4 mg) was treated with a solution of HCl in dioxane (4 M, 1 mL) and stirred at RT for 1 h. The reaction mixture was concentrated under vacuo to give the desired product as a white solid (3 mg). LC-MS (A): $t_R$=0.57 min; [M+H]$^+$: 448.17.

460.3 N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclopropyl]-acetamide To a suspension of Example 460.2 (2 mg) and acetic acid (0.3 mg) in DMF (1 mL) was added HATU (1.9 mg) and DIPEA (1.7 mg). The reaction mixture was stirred at RT for 20 h, filtered and then directly purified by prep LC-MS (IX) to give the title compound as a white solid (0.5 mg). LC-MS (A): $t_R$=0.69 min; [M+H]$^+$: 490.04.

Examples 461 and 462 were prepared from Example 460.2, as described for Example 460, but using the corresponding acids. Prep LC-MS conditions and LC-MS data are listed in the table below. The LC-MS conditions used were LC-MS (A).

| Example N° | Name | $t_R$ | [M + H]$^+$ | Prep LC-MS |
|---|---|---|---|---|
| 461 | Tetrahydro-pyran-4-carboxylic acid [1-(3-{5-[(R)-(1,3-dimethyl-azetidin-3-yl)-hydroxy-(4-isopropyl-phenyl)-methyl]-pyridin-3-yl}-[1,2,4]oxadiazol-5-ylmethyl)-cyclopropyl]-amide | 0.71 | 560.12 | (IX) |
| 462 | N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclopropyl]-2-methoxy-acetamide | 0.71 | 520.12 | (IX) |

Example 463: N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclopropyl]-N-methyl-acetamide The title compound was prepared from Example D2.1, according to the 3-step procedure described for Example 460, but using the corresponding carboxylic acid in the first step. Prep LC-MS was used to purify the intermediate after step 1 (VII) and the final product (IX). LC-MS (A): $t_R$=0.72 min; $[M+H]^+$: 504.29.

Example 464: N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-propionamide hydrochloride464.1 [2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1-dimethyl-ethyl]carbamic acid tert-butyl ester A mixture of Example D2.1 (789 mg), N-Boc-3-amino-3-methylbutanoic acid (633 mg), PyBOP (3.00 g), $K_3PO_4$ (1.63 g) and DIPEA (738 mg) in DMF (12 mL) was heated to 80° C. and stirred for 16 h. The reaction mixture was cooled to RT, diluted with $H_2O$/MeCN, filtered through a syringe filter and purified by prep LC-MS (VII) to give a lightly yellow solid (516 mg). LC-MS (A): $t_R$=0.88 min; $[M+H]^+$: 550.31.

464.2 (R)-{5-[5-(2-Amino-2-methyl-propyl)-[1,2,4]oxadiazol-3-yl]pyridin-3-yl}-(1,3-dimethyl-azetidin-3-yl)-(4-isopropyl-phenyl)-methanol, hydrochloride salt Example 464.1 (516 mg) was treated with a solution of HCl in dioxane (4 M, 4.7 mL) and stirred at RT for 1.5 h. The reaction mixture was concentrated under vacuo to give the desired product as a white solid (577 mg). LC-MS (A): $t_R$=0.59 min; $[M+H]^+$: 450.08.

464.3 N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-propionamide To a solution of propionic acid (5 mg) in DMF (0.15 mL) were added DBU (32 mg) and HATU (32 mg). The solution was stirred at RT for 10 min and was then added to a solution of Example 464.2 (30 mg) and DBU (25 mg) in DMF (0.15 mL) at 0° C. The reaction mixture was stirred at 0° C. for 1 h, before more premixed (for 10 min) propionic acid (5 mg), DBU (32 mg) and HATU (32 mg) in DMF (0.15 mL) was added. The mixture was stirred for 1 h at 0° C., before it was diluted with MeCN/$H_2O$, filtered through a syringe filter and purified by prep LC-MS (IX) to give the title compound as white solid (5.5 mg). LC-MS (A): $t_R$=0.78 min; $[M+H]^+$: 506.31.

Examples 465 to Example 468 were synthesized starting from Example 464.2 according to the procedure described for Example 464, with the difference that the corresponding preactivated acid (1.2 equiv.) was only added once (since the conversion was sufficient). Prep LC-MS conditions and LC-MS data are listed in the table below. The LC-MS conditions used were LC-MS (A).

| Example N° | Name | $t_R$ (min) | $[M+H]^+$ | Prep LC-MS Method |
|---|---|---|---|---|
| 465 | N-[2-(3-5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-2-methoxy-acetamide | 0.77 | 522.31 | (IX) |
| 466 | Tetrahydro-pyran-4-carboxylic acid [2-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-amide | 0.74 | 562.14 | (IX) + (IX) |
| 467 | N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-isobutyramide | 0.80 | 520.32 | (IX) + (IX) |
| 468 | Cyclopropanecarboxylic acid [2-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-amide | 0.76 | 518.33 | (IX) |

Examples 469 to Example 472 were synthesized from Example D2.1 and the corresponding substituted 1-Boc-piperidine-4-carboxylic acids according to the 3-step procedure described for Example 464. In the last step, correspondingly different carboxylic acids were used. Prep LC-MS conditions (first and third steps) and LC-MS data are listed in the table below. The LC-MS conditions used were LC-MS (A).

| Example N° | Name | $t_R$ (min) | [M + H]$^+$ | Prep LC-MS Method (Step 1) | Prep LC-MS Method (Step 3) |
|---|---|---|---|---|---|
| 469 | 1-[cis-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-2-methyl-piperidin-1-yl]-ethanone | 0.73 | 518.20 | (XIV) | (IX) + (VI) |
| 470 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-hydroxy-piperidin-1-yl]-2-methyl-propan-1-one | 0.71 | 548.36 | (VII) | (IX) + (IX) |
| 471 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-hydroxy-piperidin-1-yl]-propan-1-one | 0.68 | 534.37 | (VII) | (IX) + (V) |
| 472 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-methoxy-piperidin-1-yl]-ethanone | 0.73 | 534.37 | (XIV) | (IX) + (IX) |

Example 473: 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-3,3,3-trifluoro-propan-1-one

473.1 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-carboxylic acid tert-butyl ester To a solution of N-Boc-piperidine-4-carboxylic acid (69 mg) in DMSO (0.25 mL) was added CDI (52 mg). The mixture was stirred at RT for 30 min. Thereto was added a solution of Example D2.1 (100 mg) in DMSO (0.25 mL). The resulting solution was stirred at 85° C. for 30 min and directly purified by prep LC-MS (IX) to give the title compound as white solid (83 mg). LC-MS (A): $t_R$=0.87 min; [M+H]$^+$: 562.43.

473.2 (R)-(1,3-Dimethyl-azetidin-3-yl)-(4-isopropyl-phenyl)-[5-(5-piperidin-4-yl-[1,2,4]oxadiazol-3-yl)-pyridin-3-yl]-methanol Example 473.1 (83 mg) was treated with a solution of HCl in dioxane (4 M, 1.11 mL) and stirred at RT for 2 h. The reaction mixture was concentrated and dried under HV. The residue was purified by prep LC-MS (VII) to give the desired product as white solid (31 mg). LC-MS (A): $t_R$=0.57 min; [M+H]$^+$: 462.38.

473.3 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-3,3,3-trifluoro-propan-1-one To a solution of 3,3,3-trifluoropropionic acid (3.4 mg) and HATU (10 mg) in DMF (0.5 mL) was added DIPEA (10 mg) and the mixture was stirred for 5 min before Example 473.2 (10 mg) in DMF (0.5 mL) was added. The reaction mixture was stirred for 2 h at RT, then it was diluted with MeCN/$H_2O$, filtered through a syringe filter and purified by prep LC-MS (VI) to give the title compound as white solid (2.5 mg). LC-MS (A): $t_R$=0.79 min; [M+H]$^+$: 572.37.

Example 474: 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2-oxetan-3-yl-ethanone

474.1 Oxetan-3-yl-acetic acid (R)-(1,3-dimethyl-azetidin-3-yl)-(4-isopropyl-phenyl)-(5-{5-[1-(2-oxetan-3-yl-acetyl)-piperidin-4-yl]-[1,2,4]oxadiazol-3-yl}-pyridin-3-yl)-methyl ester The compound was synthesized from Example D2.1 (100 mg) and N-Boc-piperidine-4-carboxylic acid (86 mg) according to the 3-step procedure described for Example 464. In the third step, the corresponding acid (3-oxetanacetic acid) was used. Prep LC-MS purification was used after the first step (XIV) and the third step (V). LC-MS (A): $t_R$=0.73 min; [M+H]$^+$: 658.39.

474.2 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2-oxetan-3-yl-ethanone To a solution of Example 474.1 (11 mg) in MeOH (1 mL) was added $K_2CO_3$ (22 mg) and the mixture was stirred at 45° C. for 5 h. The reaction was cooled to RT, diluted with EA and washed with water. The aqueous phase was reextracted with EA twice, the combined organic layers were dried over $Na_2SO_4$, filtered and concentrated under vacuo. The crude was purified by prep LC-MS (V) to give the title compound as a white solid (4.4 mg). LC-MS (A): $t_R$=0.72 min; [M+H]$^+$: 560.31.

Examples 475, 476 and 477 were synthesized from Example D2.1 and the corresponding piperidine carboxylic acids, according to the 4-step procedure described for Example 474 (in the first step of Example 475, molecular sieves instead of $K_3PO_4$ were used). In the third step the corresponding carboxylic acids were used. For Example 477, the reaction mixture in the first step was stirred at 100° C. for 41 h to reach full conversion. Prep LC-MS conditions (steps 1,3 and 4) and LC-MS data are listed in the table below. The LC-MS conditions used were LC-MS (A).

| Example N° | Name | $t_R$ (min) | [M + H]$^+$ | LC-MS Method (Step 1) | LC-MS Method (Step 3) | LC-MS Method (Step 4) |
|---|---|---|---|---|---|---|
| 475 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-ethyl-piperidin-1-yl]-ethanone | 0.80 | 532.43 | (XIV) | (VII) | (VI) |
| 476 | [4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-oxetan-3-yl-methanone | 0.71 | 546.33 | (XIV) | (V) | (V) |
| 477 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-isopropyl-piperidin-1-yl]-2-methoxy-ethanone | 0.78 | 576.41 | (VI) | (VII) | (VI) + (IX) |

Example 478: 1-[cis-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-3-methyl-piperidin-1-yl]-ethanone 478.1 cis-4-({{5-[(R)-(1,3-Dimethyl-azetidin-3-yl)-hydroxy-(4-isopropyl-phenyl)-methyl]-pyridin-3-yl}-[(E)-hydroxyimino]-methyl}-carbamoyl)-3-methyl piperidine-1-carboxylic acid tert-butyl ester A mixture of Example D2.1 (65 mg), cis-N-Boc-3-methylpiperidine-4-carboxylic acid (56 mg), PyBOP, molecular sieves (3A, 50 mg) and DIPEA (67 mg) in DMF (3 mL) was stirred at RT for 16 h. The reaction mixture was filtered, diluted with MeCN/$H_2O$, passed through a syringe filter and directly purified by prep LC-MS (IX) to give the desired compound as yellow oil (143 mg). LC-MS (A): $t_R$=0.78 min; [M+H]$^+$: 594.44.

478.2 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cis-3-methyl-piperidine-1-carboxylic acid tert-butyl ester A mixture of Example 478.1 (143 mg), molecular sieves (3A, 150 mg) and DIPEA (32 mg) in DMF (1 mL) was heated to 100° C. and stirred for 16 h. The reaction mixture was cooled to RT, diluted with MeCN/$H_2O$, passed through a syringe filter and purified by prep LC-MS (Method XIV) to give the desired product as brown powder (40 mg). LC-MS (A): $t_R$=0.90 min; [M+H]$^+$: 576.43.

478.3 (R)-(1,3-Dimethyl-azetidin-3-yl)-(4-isopropyl-phenyl)-{5-[5-(cis-3-methyl-piperidin-4-yl)-[1,2,4]oxadiazol-3-yl]-pyridin-3-yl}-methanol, hydrochloride salt Example 478.2 (40 mg) was treated with HCl in dioxane (4 M, 0.5 mL) and the mixture was stirred at RT for 30 min. The reaction was concentrated and dried under HV to give the desired product as a sticky solid (31 mg). LC-MS (A): $t_R$=0.59 min; [M+H]$^+$: 476.37.

478.4 Acetic acid (R)-{5-[5-(cis-1-acetyl-3-methyl-piperidin-4-yl)-[1,2,4]oxadiazol-3-yl]-pyridin-3-yl}-(1,3-dimethyl-azetidin-3-yl)-(4-isopropyl-phenyl)-methyl ester To a solution of Example 478.3 (31 mg) in DMF (0.5 mL) was added DBU (27 mg), before it was cooled to 0° C. Thereto was added a premixed (10 min) solution of acetic acid (5.1 mg), DBU (11 mg) and HATU (38 mg) in DMF (0.5 mL). The mixture was stirred at 0° C. for 1 h and 1 h at RT. The reaction was diluted with MeCN/$H_2O$, passed through a syringe filter and purified by prep LC-MS (IX) to give the bis-acylated product as a white solid (11 mg). LC-MS (A): $t_R$=0.79 min; [M+H]$^+$: 560.43.

478.5 1-[cis-4-(3-{5-[(R)-1,3-Dimethyl-azetidin-3-yl)-hydroxy-(4-isopropyl-phenyl)-methyl]-pyridin-3-yl}-[1,2,4]oxadiazol-5-yl)-3-methyl-piperidin-1-yl]-ethanone To a solution of Example 478.4 (11 mg) in MeOH (0.5 mL) was added $K_2CO_3$ (26 mg) and the mixture was stirred at RT for 16 h. The reaction was diluted with MeCN/$H_2O$ passed through a syringe filter and purified by prep LC-MS (Method VI) to give the title compound as white solid (6 mg). LC-MS (A): $t_R$=0.77 min; [M+H]$^+$: 518.24.

Example 479: 5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-piperidin-2-one A mixture of Example D2.1 (25 mg), 1-methyl-6-oxo-piperidine-3-carboxylic acid (16 mg), PyBOP (83 mg), $K_3PO_4$ (58 mg) and DIPEA (26 mg) in DMF (1 mL) was heated to 85° C. and stirred for 16 h. The reaction mixture was diluted with MeCN/$H_2O$, passed through a syringe filter and purified by prep LC-MS (IX then V) to give the title compound as white solid (7.6 mg). LC-MS (A): $t_R$=0.69 min; [M+H]$^+$: 490.11.

Example 480 to Example 497 were synthesized from Example D2.1 and the corresponding carboxylic acids according to the procedure described for Example 479. If necessary, to achieve full conversion the reaction mixture can be stirred up to 20 h, at slightly higher temperature (90° C.). Prep LC-MS conditions and LC-MS data are listed in the table below. The LC-MS conditions used were LC-MS (A).

| Example N° | Name | $t_R$ (min) | [M + H]$^+$ | prep LC-MS Method |
|---|---|---|---|---|
| 480 | 5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-5-methyl-piperidin-2-one | 0.69 | 490.15 | (IX) |
| 481 | 5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one | 0.66 | 476.16 | (IX) |
| 482 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-methyl-pyrrolidin-2-one | 0.68 | 476.15 | (IX) |
| 483 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-3,3-dimethyl-pyrrolidine-2,5-dione | 0.76 | 518.10 | (IX) |
| 484 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-imidazolidine-2,4-dione | 0.65 | 491.09 | (IX) |
| 485 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidin-2-one | 0.70 | 476.13 | (IX) |
| 486 | 3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-imidazolidine-2,4-dione | 0.66 | 491.09 | (IX) |
| 487 | 3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-1-methyl-imidazolidine-2,4-dione | 0.69 | 505.13 | (IX) |
| 488 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-3-methyl-imidazolidine-2,4-dione | 0.69 | 505.10 | (IX) |
| 489 | 3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-oxazolidin-2-one | 0.69 | 478.12 | (IX) |
| 490 | 1-Cyclopropyl-3-(3-{5-[(R)-(1,3-dimethyl-azetidin-3-yl)-hydroxy-(4-isopropyl-phenyl)-methyl]-pyridin-3-yl}-[1,2,4]oxadiazol-5-ylmethyl)-imidazolidin-2-one | 0.73 | 517.15 | (IX) |
| 491 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidine-2,5-dione | 0.70 | 490.13 | (IX) |
| 492 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-3-methyl-imidazolidin-2-one | 0.70 | 491.13 | (IX) |
| 493 | 1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-imidazolidin-2-one | 0.67 | 477.14 | (V) |
| 494 | 2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-propane-1,2-diol | 0.62 | 453.27 | (V) |
| 495 | (R)-(1,3-Dimethyl-azetidin-3-yl)-(4-isopropyl-phenyl)-[5-(5-pyridin-3-yl-[1,2,4]oxadiazol-3-yl)-pyridin-3-yl]-methanol | 0.76 | 456.32 | (IX) |
| 496 | 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-piperidin-1-yl]-ethanone | 0.74 | 518.12 | (IX) + (VI) |
| 497 | (3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-acetonitrile | 0.71 | 418.33 | (VI) + (IX) |

Example 498: 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-hydroxy-piperidin-1-yl]-ethanone The title compound was synthesized from Example D2.1 and Example D3.13 according to the procedure described for Example 479. The product was purified by prep LC-MS (IX then V) and prep chiral SFC (XXXII) to give the title compound as a yellow, sticky solid. LC-MS (A): $t_R$=0.66 min; $[M+H]^+$: 520.36.

Example 499: 3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-propionitrile To a solution of 3-cyanopropionic acid (33 mg) in DMSO (0.25 mL) was added CDI (55 mg) and the mixture was stirred at RT for 30 min. Thereto was added a solution of Example D2.1 (65 mg) in DMSO (0.25 mL). The mixture was stirred at 85° C. for 1 h. The reaction was cooled to RT, diluted with MeCN/$H_2O$, passed through a syringe filter and purified by prep LC-MS (XIV) to give the title compound as a white solid (25 mg). LC-MS (A): $t_R$=0.73 min; $[M+H]^+$: 432.35.

Example 500: 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-3-methoxy-piperidin-1-yl]-ethanone The title compound was synthesized from Example D2.1 and Example D3.14, according to the procedure described for Example 499. The product was purified by prep LC-MS (V—FIX) to yield to title compound as a white solid. LC-MS (A): $t_R$=0.73 min; $[M+H]^+$: 534.41.

Example 501: 1-[(R)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-ethanone

501.1 3-[(R)-{5-[5-((R)-1-Acetyl-piperidin-3-yl)-[1,2,4]oxadiazol-3-yl]-pyridin-3-yl}-hydroxy-(4-isopropyl-phenyl)-methyl]-3-methyl-azetidine-1-carboxylic acid tert-butyl ester A mixture of Example D2.2 (125 mg), (3R)-1-acetylpiperidine-3-carboxylic acid (74 mg), PyBOP (244 mg), $K_3PO_4$ (238 mg) and DIPEA (109 mg) in DMF (3 mL) was heated to 90° C. and stirred for 20 h. Due to incomplete conversion the same amounts of carboxylic acid and PyBOP were added again and the mixture was stirred for another 6 h at 90° C. The reaction mixture was cooled to RT, diluted with MeCN/$H_2O$, passed through a syringe filter and purified by prep LC-MS (XII) to give the desired product as an off-white solid (120 mg). LC-MS (A): $t_R$=1.08 min; $[M+H]^+$: 590.24.

501.2 1-[(R)-3-(3-{5-[(R)-Hydroxy-(4-isopropyl-phenyl)-(3-methyl-azetidin-3-yl)-methyl]-pyridin-3-yl}-[1,2,4]oxadiazol-5-yl)-piperidin-1-yl]-ethanone hydrochloride salt Example 501.1 (113 mg) was treated with a solution of HCl in dioxane (4 M, 1.5 mL) and stirred at RT for 1 h. The reaction mixture was concentrated under vacuo to give the desired product as an off-white solid (106 mg). LC-MS (A): $t_R$=0.72 min; $[M+H]^+$: 490.16.

501.3 1-[(R)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-ethanone To a solution of Example 501.2 (89 mg) in dioxane (4.7 mL) was added $NEt_3$ (55 mg), a solution of formaldehyde in $H_2O$ (37 wt. %, 52 mg) and $NaBH(OAc)_3$ (60 mg). The mixture was stirred at RT for 3 h, before it was diluted with MeCN/$H_2O$, filtered and purified by prep LC-MS (IX) to give the desired product as an off-white solid (49 mg). LC-MS (A): $t_R$=0.73 min; $[M+H]^+$: 504.14.

Examples 502 to Example 508 were prepared from D2.2 and the corresponding carboxylic acids, according to the 3-step procedure described for Example 501. In case of incomplete conversion in the first step, more carboxylic and PyBOP was added, or the reaction mixture was stirred at slightly higher temperatures (up to 100° C.). For Examples 507 and 508, $K_3PO_4$ was replaced by molecular sieves (3A). Example 504 was additionally purified by CC (CombiFlash, RediSep 4 g, gradient DCM to DCM/MeOH/$NH_4OH$ 90:10:1 over 20 min at 18 mL/min) after the prep LC-MS. Prep LC-MS conditions (steps 1,3) and LC-MS data are listed in the table below. The LC-MS conditions used were LC-MS (A).

| Example N° | Name | $t_R$ (min) | M + H)$^+$ | prep LC-MS (Step 1) | prep LC-MS (Step 3) |
|---|---|---|---|---|---|
| 502 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-tetrahydro-pyran-4-ol | 0.72 | 479.30 | (VI) | (VI) |
| 503 | (R)-(1,3-Dimethyl-azetidin-3-yl)-{5-[5-(3-hydroxymethyl-bicyclo[1.1.1]pent-1-yl)-[1,2,4]oxadiazol-3-yl]-pyridin-3-yl}-(4-isopropyl-phenyl)-methanol | 0.76 | 475.29 | (VI) | (VI) |
| 504 | 4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-piperidine-2,6-dione | 0.72 | 504.30 | (VI) | (VI) + (CC) |
| 505 | 2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-2,2-difluoro-ethanol | 0.72 | 459.32 | (VI) | (VI) |
| 506 | (R)-(1,3-Dimethyl-azetidin-3-yl)-(4-isopropyl-phenyl)-{5-[5-(3-methoxy-phenyl)-[1,2,4]oxadiazol-3-yl]-pyridin-3-yl}-methanol | 0.85 | 485.20 | (VIII) | (VI) |

-continued

| Example N° | Name | $t_R$ (min) | M + H)$^+$ | prep LC-MS (Step 1) | prep LC-MS (Step 3) |
|---|---|---|---|---|---|
| 507 | (R)-(1,3-Dimethyl-azetidin-3-yl)-[5-(5-isopropyl-[1,2,4]oxadiazol-3-yl)-pyridin-3-yl]-(4-isopropyl-phenyl)-methanol | 0.80 | 421.26 | (VIII) | (VIII) |
| 508 | (R)-(1,3-Dimethyl-azetidin-3-yl)-(4-isopropyl-phenyl)-{5-[5-(6-methyl-pyrimidin-4-yl)-[1,2,4]oxadiazol-3-yl]-pyridin-3-yl}-methanol | 0.76 | 471.35 | (XII) | (VI) |

Examples 509 to Example 514 were prepared according to the 3-step procedure described for Example 501, using Example D2.2 and the corresponding carboxylic acids indicated in the table below. Examples 510 and 511 were derived from the same carboxylic acid (Example D3.16), the corresponding epimeric mixture after step 1 was separated by prep chiral SFC (XXXIII). Prep LC-MS conditions (steps 1,3) and LC-MS data are listed in the table below. The LC-MS conditions used were LC-MS (A).

| Example N° | Name | carboxylic acid (Step 1) | $t_R$ (min) | [M + H]$^+$ | prep LC-MS (Step 1) | prep LC-MS (Step 3) |
|---|---|---|---|---|---|---|
| 509 | (R)- or (S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-pyrrolidin-2-one | D3.15 | 0.68 | 476.11 | (XX) | (IX) |
| 510 | (S)- or (R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-ethyl-pyrrolidin-2-one | D3.16 | 0.72 | 490.30 | (VI) + chiral SFC (2$^{nd}$ eluting) | (VI) |
| 511 | (R)- or (S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-ethyl-pyrrolidin-2-one | D3.16 | 0.72 | 490.32 | (I) + chiral SFC (1$^{st}$ eluting) | (VI) |
| 512 | (S)- or (R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-isopropyl-pyrrolidin-2-one | D3.17 | 0.73 | 504.12 | (XX) | (IX) |
| 513 | (R)- or (S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-isopropyl-pyrrolidin-2-one | D3.18 | 0.73 | 504.13 | (XX) | (IX) |
| 514 | 1-[(S)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidin-1-yl]-ethanone | D3.19 | 0.73 | 504.34 | (VI) | (V) |

Example 515 and Example 516 were synthesized according to the 3-step procedure described for Example 501, using Example D2.2 and 2-oxopiperidine-4-carboxylic acid. The epimeric mixture after step 1 was separated by prep chiral HPLC (XLIII). Prep LC-MS conditions (steps 1,3) and LC-MS data are listed in the table below. The LC-MS conditions used were LC-MS (A).

| Example N° | Name | $t_R$ (min) | M + H)$^+$ | prep LC-MS (Step 1) | prep LC-MS (Step 3) |
|---|---|---|---|---|---|
| 515 | (S)-or (R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one | 0.67 | 476.16 | (XX + chiral HPLC (1$^{st}$ eluting) | (IX) |
| 516 | (R)-or (S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one | 0.67 | 476.14 | (XX + chiral HPLC (2$^{nd}$ eluting) | (IX) + (IX) |

Example 517: (R)-(1,3-Dimethyl-azetidin-3-yl)-(4-isopropyl-phenyl)-[5-(5-methyl-[1,2,4]oxadiazol-3-yl)-pyridin-3-yl]-methanol 517.1 3—{(R)-Hydroxy-(4-isopropyl-phenyl)-[5-(5-methyl-[1,2,4]oxadiazol-3-yl)-pyridin-3-yl]-methyl}-3-methyl-azetidine-1-carboxylic acid tert-butyl ester To a solution of acetic acid (9.5 mg) in DMSO (0.25 mL) was added CDI (28 mg). The mixture was stirred at RT before a solution of Example D2.2 (60 mg) in DMSO (0.25 mL) was added. The reaction was stirred at 85° C. for 16 h. It was then purified by prep LC-MS (VII) to give the desired product as a white solid (43 mg). LC-MS (A): $t_R$=1.08 min; $[M+H]^+$: 479.38.

517.2 (R)-(4-Isopropyl-phenyl)-(3-methyl-azetidin-3-yl)-[5-(5-methyl-[1,2,4]oxadiazol-3-yl)-pyridin-3-yl]-methanol, hydrochloride salt Example 517.1 (43 mg) was treated with a solution of HCl in dioxane (4 M, 0.6 mL) and stirred at RT for 0.5 h. The reaction mixture was concentrated under vacuo to give the desired product as yellow amorphous solid (46 mg). LC-MS (A): $t_R$=0.71 min; $[M+H]^+$: 379.27.

517.3 (R)-(1,3-Dimethyl-azetidin-3-yl)-(4-isopropyl-phenyl)-[5-(5-methyl-[1,2,4]oxadiazol-3-yl)-pyridin-3-yl]-methanol To a solution of Example 517.2 (46 mg) in dioxane (1 mL) was added NEt3 (55 mg), a solution of formaldehyde in $H_2O$ (37 wt. %, 17 mg) and $NaBH(OAc)_3$ (35 mg). The mixture was stirred at RT for 1 h, before it was diluted with $MeCN/H_2O$, filtered and purified by prep LC-MS (VI) to give the desired product as a white solid (20 mg). LC-MS (A): $t_R$=0.73 min; $[M+H]^+$: 393.31.

Example 518: (R)-{5-[5-(1,1-Difluoro-ethyl)-[1,2,4]oxadiazol-3-yl]-pyridin-3-yl}-(1,3-dimethyl-azetidin-3-yl)-(4-isopropyl-phenyl)-methanol The title compound was synthesized from Example D2.2 and 2,2-difluoropropionic acid, according to the 3-step procedure described for Example 517. The crude material was purified by Prep LC-MS (VII) (step 1) and (VI) (step 3). LC-MS (A): $t_R$=0.81 min; $[M+H]^+$: 443.33.

Example 519: 4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-tetrahydro-pyran-4-ol 519.1 3-[(R)-Hydroxy-{5-[3-(4-hydroxy-tetrahydro-pyran-4-yl)-[1,2,4]oxadiazol-5-yl]-pyridin-3-yl}-(4-isopropyl-phenyl)-methyl]-3-methyl-azetidine-1-carboxylic acid tert-butyl ester To a solution of Example E1.1 (50 mg) in DMF (1 mL) was added CDI (23 mg). The mixture was stirred for 30 min before DIPEA (30 mg) was added. Then it was stirred at RT for 16 h. Example E2.16 (27 mg) was added and the reaction was heated to 90° C. for 3 h, after which molecular sieves (3A, 60 mg) were added and the mixture was heated again at 90° C. for 14 h. The reaction was cooled to RT, diluted with $MeCN/H_2O$, passed through a syringe filter and purified by prep LC-MS (VI) to give the desired compound as a white solid (12 mg). LC-MS (A): $t_R$=1.01 min; $[M+H]^+$: 565.40.

519.2 4-(5-{5-[(R)-Hydroxy-(4-isopropyl-phenyl)-(3-methyl-azetidin-3-yl)-methyl]-pyridin-3-yl}-[1,2,4]oxadiazol-3-yl)-tetrahydro-pyran-4-ol hydrochloride salt Example 519.1 (12 mg) was treated with a solution of HCl in dioxane (4 M, 1 mL), stirred at RT for 90 min, then concentrated under vacuo to give the desired product as a white solid (14 mg). LC-MS (A): $t_R$=0.67 min; $[M+H]^+$: 465.13.

519.3 4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-tetrahydro-pyran-4-ol To a suspension of Example 519.2 (14 mg) in dioxane (0.2 mL) was added $NEt_3$ (9 mg), a solution of formaldehyde in $H_2O$ (37 wt. %, 9 mg) and $NaBH(OAc)_3$ (10 mg). The mixture was stirred at RT for 90 min. The reaction was diluted with $MeCN/H_2O$, passed through a syringe filter and purified by prep LC-MS (IX then V) to give the title compound as a white solid (3 mg). LC-MS (A): $t_R$=0.67 min; $[M+H]^+$: 479.38.

Examples 520 to Example 523 were prepared from Example E1.1 and the corresponding hydroxyamidines (Examples indicated in the table below) according to the 3-step procedure described for Example 501, but using one equivalent of acid (Example E1.1) and 1.5-2.0 equivalents of hydroxyamidine. The applied hydroxyamidine of formula E2, the LC-MS retention times and observed masses, as well as the purification methods used after step 1 and 3 are shown in the table below. Examples 520 and 521 were generated from the same reaction sequence. Example 523 was prepared from Example E1.1 and the corresponding hydroxyamidine (indicated in the table) according to the procedure described for Example 519. The LC-MS conditions used were LC-MS (A).

| Example N° | Name | hydroxy-amidine | tR | [M + H]+ | prep LC-MS Method (Step 1) | prep LC-MS Method (Step 3) |
|---|---|---|---|---|---|---|
| 520 | (R)-[5-(3-tert-Butoxymethyl-[1,2,4]oxadiazol-5-yl)-pyridin-3-yl]-(1,3-dimethyl-azetidin-3-yl)-(4-isopropyl-phenyl)-methanol | E2.17 | 0.82 | 465.22 | (VII) | (VII) |
| 521 | (R)-(1,3-Dimethyl-azetidin-3-yl)-[5-(3-hydroxymethyl-[1,2,4]oxadiazol-5-yl)-pyridin-3-yl]-(4-isopropyl-phenyl)-methanol | E2.17 | 0.65 | 409.32 | (VII) | (VII) |
| 522 | 1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperazin-1-yl]-ethanone | E2.18 | 0.73 | 505.42 | (VI) | (IX) |

-continued

| Example N° | Name | hydroxy-amidine | tR | [M + H]+ | prep LC-MS Method (Step 1) | prep LC-MS Method (Step 3) |
|---|---|---|---|---|---|---|
| 523 | 1-[3-(5-{5-[(R)-(1,3-Dimethyl-azetidin-3-yl)-hydroxy-(4-isopropyl-phenyl)-methyl]-pyridin-3-yl}-[1,2,4]oxadiazol-3-ylmethyl)-azetidin-1-yl]-ethanone | E2.22 | 0.71 | 490.40 | (XV) | (V) |

Example 524: 4-(5-{5-[(R)-(1,3-Dimethyl-azetidin-3-yl)-hydroxy-(4-isopropyl-phenyl)-methyl]-pyridin-3-yl}-[1,2,4]oxadiazol-3-ylmethyl)-tetrahydro-pyran-4-ol The title compound was synthesized from Example E1.1 and the corresponding hydroxyamidine (Example E2.20) according to the 3-step procedure described for 517, but using 1 equivalent of acid and 1.5 equivalents of hydroxy-amidine. Prep LC-MS was used to purify the intermediate after step 1 (Method VI) and the final product after step 3 (Method V). LC-MS (A): $t_R$=0.68 min; $[M+H]^+$: 493.39.

Example 525: [4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-[1,4]dioxan-2-yl-methanone

525.1 5-[(R)-Hydroxy-(4-isopropyl-phenyl)-(3-methyl-azetidin-3-yl)-methyl]-nicotinic acid, hydrochloride salt Example E1.1 (1.20 g) was treated with a solution of HCl in dioxane (4 M, 14 mL). The mixture was stirred at RT for 1 h. The suspension was filtered, the residue was washed with dioxane, then dried under HV to give the desired compound as a white solid (1.13 g). LC-MS (A): $t_R$=0.67 min; $[M+H]^+$: 341.22.

525.2 5-[(R)-(1,3-Dimethyl-azetidin-3-yl)-hydroxy-(4-isopropyl-phenyl)-methyl]-nicotinic acid, formic acid salt To a suspension of Example 525.1 (1.13 g) in dioxane (27 mL) were added $NEt_3$ (1.14 mL), a solution of formaldehyde in $H_2O$ (37 wt. %, 0.32 mL) and $NaBH(OAc)_3$ (895 mg). The mixture was stirred at RT for 90 min, filtered and directly purified by prep LC-MS (IX) to give the title compound as a white solid (142 mg). LC-MS (A): $t_R$=0.59 min; $[M+H]^+$: 355.25.

525.3 4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidine-1-carboxylic acid tert-butyl ester To a solution of Example 525.2 (140 mg) in DMF (3.2 mL) were added DIPEA (0.17 mL) and PyBOP (236 mg). After stirring at RT for 15 min, a solution of E2.19 (170 mg) in DMF (0.9 mL) and $K_3PO_4$ (282 mg) were added. The mixture was stirred at 85° C. for 16 h. After cooling to RT, more PyBOP (259 mg), $K_3PO_4$ (282 mg) and DIPEA (0.17 mL) were added and the reaction was stirred at 85° C. for another 4 h. The mixture was cooled to RT, diluted with MeCN/$H_2O$, passed through a syringe filter and purified by prep LC-MS (Method VIII) to give the desired product as a white solid (88 mg). LC-MS (A): $t_R$=0.88 min; $[M+H]^+$: 562.35.

525.4 (R)-(1,3-Dimethyl-azetidin-3-yl)-(4-isopropyl-phenyl)-[5-(3-piperidin-4-yl-[1,2,4]oxadiazol-5-yl)-pyridin-3-yl]-methanol Example 525.3 (88 mg) was treated with a solution of HCl in dioxane (4 M, 1.2 mL) and stirred for 1 h. The reaction mixture was concentrated under vacuo to give the title compound as a pale yellow solid (102 mg). LC-MS (A): $t_R$=0.56 min; m/z $[M+2H+MeCN]^{2+}$: 252.35.

525.5 [4-(5-{5[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-[1,4]dioxan-2-yl-methanone To a solution of Example 525.4 (50 mg) in DMF (0.36 mL) was added DBU (51 mg) and a premixed (10 min) solution of 1,4-dioxane-2-carboxylic acid (23 mg), HATU (72 mg) and DBU (20 mg) in DMF (0.36 mL) at 0° C. The mixture was stirred at 0° C. for 1 h. The reaction was then diluted with MeCN/$H_2O$, passed through a syringe filter and purified by prep LC-MS (V then IX) to give the title compound as a white solid (25 mg). LC-MS (A): $t_R$=0.73 min; $[M+H]^+$: 576.41.

Example 526: 1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-2-methoxy-ethanone

526.1 Methoxy-acetic acid (R)-(1,3-dimethyl-azetidin-3-yl)-(4-isopropyl-phenyl)-(5-{3-[1-(2-methoxy-acetyl)-piperidin-4-yl][1,2,4]oxadiazol-5-yl}-pyridin-3-yl)-methyl ester The title compound was synthesized from Example 525.4 and methoxyacetic acid, according to the procedure described for Example 525 (step 5). LC-MS (A): $t_R$=0.74 min; $[M+H]^+$: 606.44.

526.2 1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-2-methoxy-ethanone, formic acid salt To a solution of Example 526.1 (59 mg) in MeOH was added $K_2CO_3$ (128 mg) and the mixture was stirred at 45° C. for 2 h. The reaction was cooled to RT, filtered, diluted with MeCN/$H_2O$, passed through a syringe filter and purified by prep LC-MS (V then IX) to give the title compound as a white solid (30 mg). LC-MS (A): $t_R$=0.72 min; $[M+H]^+$: 534.45.

Example 527: (R)-(1,3-Dimethyl-azetidin-3-yl)-(4-isopropyl-phenyl)-{5-[3-(1-methanesulfonyl-piperidin-4-yl)-[1,2,4]oxadiazol-5-yl]-pyridin-3-yl}-methanol To a solution of Example 525.4 (51 mg) and DIPEA (46 mg) in DCM (1.5 mL) at 0° C. was added methanesulfonyl chloride (10 mg). The mixture was stirred at 0° C. for 90 min. The solvent was then removed under vacuo, the residue was purified by prep LC-MS (IX) to give the desired product as a white solid (22 mg). LC-MS (A): $t_R$=0.75 min; $[M+H]^+$: 540.36.

Example 528: (R)-(1,3-Dimethyl-azetidin-3-yl)-(4-isopropyl-phenyl)-(5-{3-[1-(2-methoxy-ethanesulfonyl)-piperidin-4-yl]-[1,2,4]oxadiazol-5-yl}-pyridin-3-yl)-methanol Example 528 was synthesized from Example 525.4 and 2-methoxyethane-1-sulfonyl chloride according to the procedure described for Example 527. LC-MS (A): $t_R$=0.78 min; $[M+H]^+$: 584.38.

Example 529: 1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-2-hydroxy-ethanone 529.1 2-(tert-Butyl-diphenyl-silanyloxy)-1-[4-(5-{5-[(R)-(1,3-dimethyl-azetidin-3-yl)-hydroxy-(4-isopropyl-phenyl)-methyl]-pyridin-3-yl}-[1,2,4]oxadiazol-3-yl)-piperidin-1-yl]-ethanone To a solution of Example 525.2 (45 mg) in DMF (0.56 mL) were added DIPEA (44 mg) and PyBOP (182 mg). After stirring at RT for 15 min, a solution of E2.21 (74 mg) in DMF (0.5 mL) and $K_3PO_4$ (97 mg) were added and the reaction was stirred at 85° C. for 16 h. More PyBOP (91 mg), $K_3PO_4$ (50 mg) and DIPEA (44 mg) were added and the mixture was stirred at 100° C. for 5 h. The reaction was cooled to RT, diluted with MeCN/$H_2O$, passed through a syringe filter and purified by prep LC-MS (2× Method XX) to give the desired product as a white solid (10 mg). LC-MS (A): $t_R$=1.02 min; $[M+H]^+$: 758.52.

529.2 1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-2-hydroxy-ethanone To a solution of Example 529.1 (10 mg) in THF (0.2 mL) was added a solution of TBAF in THF (1.0 M, 0.02 mL). The reaction mixture was stirred at RT for 90 min, then diluted with MeCN/$H_2O$, passed through a syringe filter and purified by prep LC-MS (V then IX) to give the title compound as a white solid (1.5 mg). LC-MS (A): $t_R$=0.69 min; $[M+H]^+$: 520.39.

Example 530: (R)-(1,3-Dimethyl-azetidin-3-yl)-(4-isopropyl-phenyl)-(5-[1,2,4]oxadiazol-3-yl-pyridin-3-yl)-methanol 530.1 3-[(R)-Hydroxy-(4-isopropyl-phenyl)-(5-[1,2,4]oxadiazol-3-yl-pyridin-3-yl)-methyl]-3-methyl-azetidine-1-carboxylic acid tert-butyl ester To a solution of Example D2.2 (50 mg) in DMA (0.5 mL) was added trimethyl orthoformate (0.11 mL) and boron trifluoride diethyl etherate (4.6 mg). The reaction mixture was stirred at 50° C. for 2.5 h. MeCN was added and the mixture was passed through a syringe filter and purified by prep LC-MS (VII) to give the desired product as a white solid (32 mg). LC-MS (A): $t_R$=1.06 min; $[M+H]^+$: 465.34.

530.2 (R)-(4-Isopropyl-phenyl)-(3-methyl-azetidin-3-yl)-(5-[1,2,4]oxadiazol-3-yl-pyridin-3-yl)-methanol Example 530.1 (32 mg) was treated with a solution of HCl in dioxane (4 M, 0.3 mL) and stirred at RT for 30 min. The solvent was evaporated and the residue dried under HV to give the desired product as a white solid (39 mg). LC-MS (A): $t_R$=0.69 min; $[M+H]^+$: 365.18.

530.3 (R)-(1,3-Dimethyl-azetidin-3-yl)-(4-isopropyl-phenyl)-(5-[1,2,4]oxadiazol-3-yl-pyridin-3-yl)-methanol To a solution of Example 530.2 (39 mg) in dioxane (1 mL) was added $NEt_3$ (10 mg), a solution of formaldehyde in $H_2O$ (37 wt. %, 16 mg) and $NaBH(OAc)_3$ (32 mg). The reaction was stirred at RT for 1.5 h. The mixture was filtered and concentrated under vacuo, the crude was purified by prep LC-MS (VI) to give the title compound as a white solid (29 mg). LC-MS (A): $t_R$=0.71 min; $[M+H]^+$: 379.26.

Example 531: 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-ethanone 531.1 3-[(R)-{5-[5-(1-Acetyl-piperidin-4-yl)-[1,2,4]oxadiazol-3-yl-]pyridin-3-yl}-hydroxy-(4-isopropyl-phenyl)-methyl]-3-methyl-azetidine-1-carboxylic acid tert-butyl ester To a solution of Example D2.2 (1.7 g) in DMF (34 mL) were added 1-acetylpiperidine-4-carboxylic acid (967 mg), followed by PyBOP (4.57 g), DIPEA (1.96 mL) and $K_3PO_4$ (3.23 g). The resulting solution was stirred at 85° C. overnight. Additional 0.5 equivalent of reagents were added and the resulting mixture was stirred at 85° C. overnight. The reaction mixture was allowed to cool down to RT, filtered off, and evaporated in vacuo. The crude material was purified by Prep LC-MS (XXXV) to give the title compound as a white solid (1.76 g). LC-MS (A) $t_R$=1.08 min; $[M+H]^+$: 590.13.

531.2 1-[4-(3-{5-[(R)-Hydroxy-(4-isopropyl-phenyl)-(3-methyl-azetidin-3-yl)-methyl]-pyridin-3-yl}-[1,2,4]oxadiazol-5-yl)-piperidin-1-yl]-ethanone A solution of Example 531.1 (1.76 g) in HCl 4M in dioxane (35 mL) was stirred at RT for 1 h. The reaction mixture was evaporated in vacuo and dried in HV to afford 1.57 g as yellow solid. LC-MS (A) $t_R$=0.72 min; $[M+H]^+$: 490.2.

531.3 1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-ethanone The title compound was prepared starting from Example 531.2 (1.57 g), and following the procedure described in Example D1.1 step D1.1.5. The crude material was purified by Prep LC-MS (XXXVI) followed by Prep LC-MS (XXXVII) to give the title compound as a white solid (900 mg). LC-MS (A): $t_R$=0.72 min; $[M+H]^+$: 504.12. Example 532 to Example 566 were synthesized starting from the appropriate precursor of Formula (A7) or (D5) and following the procedure described in Example 1, except that TEA was used to neutralize the hydrochloride salt and DCM was replaced by dioxane. Prep LC-MS conditions and LC-MS data of Example 532 to Example 566 are listed in the table below. The LC-MS conditions used were LC-MS (A).

| Example N° | Name | $t_R$ | [M + H]$^+$ | Prep LC-MS | Precursor A7 or D5 |
|---|---|---|---|---|---|
| 532 | 2-(3-{5-[(R)-(4-Bromo-phenyl)-(1,3-dimethyl-azetidin-3-yl)-hydroxy-methyl]-pyridin-3-yl}-[1,2,4]oxadiazol-5-yl)-propan-2-ol | 0.65 | 472.96 | V | D5.1 |
| 533 | 2-(3-{5-[(R)-(1,3-Dimethyl-azetidin-3-yl)-hydroxy-naphthalen-2-yl-methyl]-pyridin-3-yl}-[1,2,4]oxadiazol-5-yl)-propan-2-ol | 0.67 | 445.10 | — | A7.4 |
| 534 | 2-[3-(5-{(R)-(1,3-Dimethyl-azetidin-3-yl)-hydroxy-[4-(1-trifluoromethyl-cyclopropyl)-phenyl]-methyl}-pyridin-3-yl)-[1,2,4]oxadiazol-5-yl]-propan-2-ol | 0.72 | 503.04 | VI | A7.5 |
| 535 | 2-[3-(5-{(R)-(1,3-Dimethyl-azetidin-3-yl)-hydroxy-[4-(2,2,2-trifluoro-1,1-dimethyl-ethyl)-phenyl]-methyl}-pyridin-3-yl)-[1,2,4]oxadiazol-5-yl]-propan-2-ol | 0.72 | 505.01 | VI | A7.6 |
| 536 | 2-(3-{5-[(R)-(1,3-Dimethyl-azetidin-3-yl)-hydroxy-(4-isopropoxy-phenyl)-methyl]-pyridin-3-yl}-[1,2,4]oxadiazol-5-yl)-propan-2-ol | 0.66 | 453.28 | V | A7.7 |
| 537 | 2-[3-(5-{(R)-(1,3-Dimethyl-azetidin-3-yl)-hydroxy-[4-(1,2,2,2-tetrafluoro-1-trifluoromethyl-ethyl)-phenyl]-methyl}-pyridin-3-yl)-[1,2,4]oxadiazol-5-yl]-propan-2-ol | 0.76 | 563.00 | VI | D5.2 |
| 538 | (R)-2-(3-(5-((1,3-dimethylazetidin-3-yl)(hydroxy)(4-(pentafluoro-λ6-sulfaneyl)phenyl) methyl)pyridin-3-yl)-1,2,4-oxadiazol-5-yl)propan-2-ol | 0.69 | 521.00 | V | D5.3 |
| 539 | 2-(3-{5-[(R)-(1,3-Dimethyl-azetidin-3-yl)-(3-fluoro-4-isopropyl-phenyl)-hydroxy-methyl]-pyridin-3-yl}-[1,2,4]oxadiazol-5-yl)-propan-2-ol | 0.71 | 455.00 | VI | A7.8 |
| 540 | 2-(3-{5-[(R)-(4-tert-Butyl-phenyl)-(1,3-dimethyl-azetidin-3-yl)-hydroxy-methyl]-pyridin-3-yl}-[1,2,4]oxadiazol-5-yl)-propan-2-ol | 0.70 | 451.17 | VI | A7.9 |
| 541 | 2-(3-{5-[(R)-Benzo[b]thiophen-5-yl-(1,3-dimethyl-azetidin-3-yl)-hydroxy-methyl]-pyridin-3-yl}-[1,2,4]oxadiazol-5-yl)-propan-2-ol | 0.64 | 451.09 | V | A7.10 |
| 542 | 2-(3-{5-[(R)-(1,3-Dimethyl-azetidin-3-yl)-hydroxy-(4-pentafluoroethyl-phenyl)-methyl]-pyridin-3-yl}-[1,2,4]oxadiazol-5-yl)-propan-2-ol | 0.71 | 512.91 | VI | A7.11 |
| 543 | 2-[3-(5-{(R)-(1,3-Dimethyl-azetidin-3-yl)-hydroxy-[4-(1-methyl-cyclopropyl)-phenyl]-methyl}-pyridin-3-yl)-[1,2,4]oxadiazol-5-yl]-propan-2-ol | 0.69 | 449.04 | V | A7.12 |
| 544 | 2-(3-{5-[(R)-(1,3-Dimethyl-azetidin-3-yl)-hydroxy-(4-isopropyl-3-methyl-phenyl)-methyl]-pyridin-3-yl}-[1,2,4]oxadiazol-5-yl)-propan-2-ol | 0.71 | 451.19 | VI | A7.13 |
| 545 | 2-(3-{5-[(R)-(1,3-Dimethyl-azetidin-3-yl)-hydroxy-(4-trifluoromethoxy-phenyl)-methyl]-pyridin-3-yl}-[1,2,4]oxadiazol-5-yl)-propan-2-ol | 0.67 | 479.10 | V | A7.14 |
| 546 | 1-[4-(3-{5-[(R)-(4-Bromo-phenyl)-(1,3-dimethyl-azetidin-3-yl)-hydroxy-methyl]-pyridin-3-yl}-[1,2,4]oxadiazol-5-yl)-piperidin-1-yl]-ethanone | 0.68 | 539.97 | V | D5.4 |
| 547 | 2-[3-(5-{(R)-(1,3-Dimethyl-azetidin-3-yl)-[4-(1-fluoro-1-methyl-ethyl)-phenyl]-hydroxy-methyl}-pyridin-3-yl)-[1,2,4]oxadiazol-5-yl]-propan-2-ol | 0.65 | 455.17 | V | A7.15 |
| 548 | 2-(3-{5-[(R)-[4-(1,1-Difluoro-ethyl)-phenyl]-(1,3-dimethyl-azetidin-3-yl)-hydroxy-methyl]-pyridin-3-yl}-[1,2,4]oxadiazol-5-yl)-propan-2-ol | 0.64 | 459.15 | V | A7.16 |
| 549 | 2-(3-{5-[(R)-(4-Bicyclo[1.1.1]pent-1-yl-phenyl)-(1,3-dimethyl-azetidin-3-yl)-hydroxy-methyl]-pyridin-3-yl}-[1,2,4]oxadiazol-5-yl)-propan-2-ol | 0.73 | 461.21 | VI | A7.17 |
| 550 | (R)-(1,3-Dimethyl-azetidin-3-yl)-{5-[5-(tetrahydro-pyran-4-yl)-[1,2,4]oxadiazol-3-yl]-pyridin-3-yl}-[4-(2,2,2-trifluoro-ethyl)-phenyl]-methanol | 0.71 | 503.14 | V | D5.5 |
| 551 | 2-[3-(5-{(R)-(1,3-Dimethyl-azetidin-3-yl)-[4-(1,1-dimethyl-propyl)-phenyl]-hydroxy-methyl}-pyridin-3-yl)-[1,2,4]oxadiazol-5-yl]-propan-2-ol | 0.77 | 465.07 | VII | A7.18 |
| 552 | 1-[4-(3-{5-[(R)-(1,3-Dimethyl-azetidin-3-yl)-(3-fluoro-4-isopropyl-phenyl)-hydroxy-methyl]-pyridin-3-yl}-[1,2,4]oxadiazol-5-yl)-piperidin-1-yl]-ethanone | 0.74 | 522.11 | VI | A7.19 |
| 553 | 1-{4-[3-(5-{(R)-(1,3-Dimethyl-azetidin-3-yl)-hydroxy-[4-(1-trifluoromethyl-cyclopropyl)-phenyl]-methyl}-pyridin-3-yl)-[1,2,4]oxadiazol-5-yl]-piperidin-1-yl}-ethanone | 0.75 | 570.12 | V | A7.20 |
| 554 | 1-[4-(3-{5-[(R)-(1,3-Dimethyl-azetidin-3-yl)-hydroxy-(4-trifluoromethoxy-phenyl)-methyl]-pyridin-3-yl}-[1,2,4]oxadiazol-5-yl)-piperidin-1-yl]-ethanone | 0.72 | 545.82 | V | A7.21 |

-continued

| Example N° | Name | $t_R$ | [M + H]$^+$ | Prep LC-MS | Precursor A7 or D5 |
|---|---|---|---|---|---|
| 555 | 1-[4-(3-{5-[(R)-(1,3-Dimethyl-azetidin-3-yl)-hydroxy-(4-isopropoxy-phenyl)-methyl]-pyridin-3-yl}-[1,2,4]oxadiazol-5-yl)-piperidin-1-yl]-ethanone | 0.70 | 520.10 | V | A7.22 |
| 556 | 2-(3-{5-[(R)-(3-Chloro-4-isopropyl-phenyl)-(1,3-dimethyl-azetidin-3-yl)-hydroxy-methyl]-pyridin-3-yl}-[1,2,4]oxadiazol-5-yl)-propan-2-ol | 0.75 | 471.16 | VI | A7.23 |
| 557 | 2-(3-{5-[(R)-(4-Cyclobutyl-phenyl)-(1,3-dimethyl-azetidin-3-yl)-hydroxy-methyl]-pyridin-3-yl}-[1,2,4]oxadiazol-5-yl)-propan-2-ol | 0.73 | 449.07 | VI | A7.24 |
| 558 | 1-[4-(3-{5-[(R)-(4-Cyclobutyl-phenyl)-(1,3-dimethyl-azetidin-3-yl)-hydroxy-methyl]-pyridin-3-yl}-[1,2,4]oxadiazol-5-yl)-piperidin-1-yl]-ethanone | 0.76 | 516.20 | VI | A7.25 |
| 559 | 1-[4-(3-{5-[(R)-(3,5-Difluoro-4-isopropyl-phenyl)-(1,3-dimethyl-azetidin-3-yl)-hydroxy-methyl]-pyridin-3-yl}-[1,2,4]oxadiazol-5-yl)-piperidin-1-yl]-ethanone | 0.76 | 540.18 | VI | A7.26 |
| 560 | 2-(3-{5-[(R)-(3,5-Difluoro-4-isopropyl-phenyl)-(1,3-dimethyl-azetidin-3-yl)-hydroxy-methyl]-pyridin-3-yl}-[1,2,4]oxadiazol-5-yl)-propan-2-ol | 0.74 | 473.18 | VI | A7.27 |
| 561 | 1-[4-(3-{5-[(R)-(4-Cyclobutoxy-phenyl)-(1,3-dimethyl-azetidin-3-yl)-hydroxy-methyl]-pyridin-3-yl}-[1,2,4]oxadiazol-5-yl)-piperidin-1-yl]-ethanone | 0.72 | 532.12 | VI | A7.28 |
| 562 | 2-[3-(5-{(1,3-Dimethyl-azetidin-3-yl)-[4-(1-ethyl-propyl)-phenyl]-hydroxy-methyl}-pyridin-3-yl)-[1,2,4]oxadiazol-5-yl]-propan-2-ol | 0.78 | 465.07 | VI | A7.29 |
| 563 | 1-{4-[3-(5-{(1,3-Dimethyl-azetidin-3-yl)-[4-(1-ethyl-propyl)-phenyl]-hydroxy-methyl}-pyridin-3-yl)-[1,2,4]oxadiazol-5-yl]-piperidin-1-yl}-ethanone | 0.81 | 532.23 | VI | A7.30 |
| 564 | 2-[3-(5-{(1,3-Dimethyl-azetidin-3-yl)-[4-(2,2-dimethyl-propyl)-phenyl]-hydroxy-methyl}-pyridin-3-yl)-[1,2,4]oxadiazol-5-yl]-propan-2-ol | 0.77 | 465.04 | VI | A7.31 |
| 565 | 1-{4-[3-(5-{(1,3-Dimethyl-azetidin-3-yl)-[4-(2,2-dimethyl-propyl)-phenyl]-hydroxy-methyl}-pyridin-3-yl)-[1,2,4]oxadiazol-5-yl]-piperidin-1-yl}-ethanone | 0.78 | 532.16 | VII | A7.32 |
| 566 | 1-{4-[3-(5-{(1,3-Dimethyl-azetidin-3-yl)-hydroxy-[4-(1-methyl-cyclopropyl)-phenyl]-methyl}-pyridin-3-yl)-[1,2,4]oxadiazol-5-yl]-piperidin-1-yl}-ethanone | 0.74 | 516.22 | VI | A7.33 |

Example 567 to Example 577 were synthesized starting from the appropriate precursor of Formula (J1), (J3) or (J5) and the appropriate precursor of Formula (J2), (J4) or (J6), respectively, following the method as indicated in the table below. Prep LC-MS conditions and LC-MS data of Example 567 to Example 577 are listed in the table below. The LC-MS conditions used were LC-MS (A).

Method A A mixture of compound (J1) (1 eq), boron species (J2) (1.3 to 1.6 eq), cataCXium A Pd G3 (0.05 to 0.1 eq) and $Cs_2CO_3$ (3 eq) in a mixture of toluene (5 mL/mmol) and water (0.5 mL/mmol) was flushed with argon, heated at 100° C. in a sealed vial and stirred for 18 h. It was filtered over Celite, the cake was washed with EA and the filtrate was concentrated in vacuo. The crude was purified by Prep LC-MS (see method in the Table below) and/or CC using SNAP KP-NH™ prepacked cartridges from Biotage and eluting with EA/MeOH or DCM/MeOH.

Method B

A mixture of boronic ester (J3) (1 eq), copper(I) reagent (J4) (1.2 eq) and KF (1 eq) in DMF (10 mL/mmol) was heated at 50° C. in a sealed vial and stirred for 18 h. It was filtered over Celite, the cake was washed with EA and the filtrate was concentrated in vacuo. The crude was purified by Prep LC-MS (see method in the Table below) and/or CC using SNAP KP-NH™ prepacked cartridges from Biotage and eluting with EA/MeOH or DCM/MeOH.

Method C

To a solution of phenol (J5) (1 eq) in DMF (20 mL/mmol) was added at RT, halide (J6) (5 eq) and $K_2CO_3$ (2.4 eq). The mixture was heated at 100° C. and stirred for 40 h. It was partitioned between EA and half sat. $NaHCO_3$. The aq. phase was extracted with EA/MeOH 95/5 and the combined org. phases were dried over $MgSO_4$ and concentrated in vacuo. The crude was purified by Prep LC-MS (see method in the Table below) and/or CC using SNAP KP-NH™ prepacked cartridges from Biotage and eluting with EA/MeOH or DCM/MeOH.

| Example N° | Name | $t_R$ | [M + H]$^+$ | Prep LC-MS | Precursor (J1), (J3) or (J5) | Precursor (J2), (J4) or (J6) | Method |
|---|---|---|---|---|---|---|---|
| 567 | 2-(3-{5-[(R)-(1,3-Dimethyl-azetidin-3-yl)-hydroxy-(4-propyl-phenyl)-methyl]-pyridin-3-yl}-[1,2,4]oxadiazol-5-yl)-propan-2-ol | 0.70 | 437.09 | V | Example 532 | Potassium propyl trifluoroborate | A |
| 568 | 2-(3-{5-[(R)-(4-Cyclopropyl-phenyl)-(1,3-dimethyl-azetidin-3-yl)-hydroxy-methyl]-pyridin-3-yl}-[1,2,4]oxadiazol-5-yl)-propan-2-ol | 0.66 | 435.10 | V | Example 532 | Potassium cyclopropyl trifluoroborate | A |

-continued

| Example N° | Name | $t_R$ | [M + H]$^+$ | Prep LC-MS | Precursor (J1), (J3) or (J5) | Precursor (J2), (J4) or (J6) | Method |
|---|---|---|---|---|---|---|---|
| 569 | 2-(3-{5-[(R)-(1,3-Dimethyl-azetidin-3-yl)-(4-ethyl-phenyl)-hydroxy-methyl]-pyridin-3-yl}-[1,2,4]oxadiazol-5-yl)-propan-2-ol | 0.66 | 423.11 | V | Example 532 | Ethylboronic acid | A |
| 570 | 2-(3-{5-[(R)-(4-Butyl-phenyl)-(1,3-dimethyl-azetidin-3-yl)-hydroxy-methyl]-pyridin-3-yl}-[1,2,4]oxadiazol-5-yl)-propan-2-ol | 0.74 | 451.13 | VI | Example 532 | Butylboronic acid | A |
| 571 | 2-(3-{5-[(R)-(1,3-Dimethyl-azetidin-3-yl)-hydroxy-(4-trifluoromethyl-phenyl)-methyl]-pyridin-3-yl)-[1,2,4]oxadiazol-5-yl)-propan-2-ol | 0.66 | 463.05 | V | J3.1 | (Phen)$CuCF_3$ | B |
| 572 | 2-[3-(5-{(R)-(1,3-Dimethyl-azetidin-3-yl)-hydroxy-[4-(2,2,2-trifluoro-ethyl)-phenyl]-methyl}-pyridin-3-yl)-[1,2,4]oxadiazol-5-yl]-propan-2-ol | 0.67 | 477.06 | V | Example 532 | 4,4,5,5-tetramethyl-2-(2,2,2-trifluoro ethyl)-1,3,2-dioxaborolane | A |
| 573 | 2-(3-{5-[(R)-(1,3-Dimethyl-azetidin-3-yl)-hydroxy-(4-isobutyl-phenyl)-methyl]-pyridin-3-yl}-[1,2,4]oxadiazol-5-yl)-propan-2-ol | 0.73 | 451.14 | VI | Example 532 | Isobutylboronic acid | A |
| 574 | 2-(3-{5-[(R)-(4-Cyclobutoxy-phenyl)-(1,3-dimethyl-azetidin-3-yl)-hydroxy-methyl]-pyridin-3-yl}-[1,2,4]oxadiazol-5-yl)-propan-2-ol | 0.69 | 464.99 | VI | J5.1 | Bromo cyclobutane | C |
| 575 | 2-(3-{5-[(R)-(1,3-Dimethyl-azetidin-3-yl)-hydroxy-(4-isopropenyl-phenyl)-methyl]-pyridin-3-yl}-[1,2,4]oxadiazol-5-yl)-propan-2-ol | 0.67 | 435.16 | V | Example 532 | (Prop-1-en-2-yl) boronic acid | A |
| 576 | 1-{4-[3-(5-{(R)-(1,3-Dimethyl-azetidin-3-yl)-hydroxy-[4-(2,2,2-trifluoro-ethyl)-phenyl]-methyl}-pyridin-3-yl)-[1,2,4]oxadiazol-5-yl]-piperidin-1-yl}-ethanone | 0.71 | 544.02 | V | Example 546 | 4,4,5,5-tetramethyl-2-(2,2,2-trifluoro ethyl)-1,3,2-dioxaborolane | A |
| 577 | 1-[4-(3-{5-[(R)-(1,3-Dimethyl-azetidin-3-yl)-hydroxy-(4-propyl-phenyl)-methyl]-pyridin-3-yl}-[1,2,4]oxadiazol-5-yl)-piperidin-1-yl]-ethanone | 0.73 | 504.21 | VI | 546 | Propylboronic acid | A |

Example 578 1-[4-(3-{5-[(R)-Hydroxy-(1-isopropyl-3-methyl-azetidin-3-yl)-(4-isopropyl-phenyl)-methyl]-pyridin-3-yl}-[1,2,4]oxadiazol-5-yl)-piperidin-1-yl]-ethanone Example 531.2 (40 mg) was dissolved in dioxane (881 μL), then acetone (23.5 μL) and sodium triacetoxyborohydride (35.7 mg) were added and the mixture was stirred at RT for 15 min. The reaction mixture was taken up in DCM, quenched with aq. sat. $NaHCO_3$. The phases were separated with a phase separator, evaporated and purified by prep LC-MS (VI), then by CC (Biotage, 11 g KP—NH, solvent A: Hept, solvent B: EA, gradient (in % B): 25 for 1 CV, 15 to 100 over 4 CV, 100 for 9 CV) to give 5 mg colorless glassy oil. LC-MS (A) $t_R$=0.78 min; [M+H]$^+$: 532.22.

Example 579 1-[4-(3-{5-[(R)-[1-(2,2-Difluoro-ethyl)-3-methyl-azetidin-3-yl]-hydroxy-(4-isopropyl-phenyl)-methyl]-pyridin-3-yl}-[1,2,4]oxadiazol-5-yl)-piperidin-1-yl]-ethanone Example 531.2 (32 mg) was dissolved in MeOH (0.256 μL), then TEA (44.6 μL) and 2-Iodo-1,1-difluoroethane (11.5 μL) were added. The mixture was shaken at 60° C. for 6 days, while 2× 2-iodo-1,1-difluoroethane (11.5 μL, 23 μL) were added after 4 h and 22 h. The mixture was filtrated through a syringe filter, diluted with MeOH and purified by prep LC-MS (VI) to give 20 mg off-white foam. LC-MS (A) $t_R$=0.76 min; [M+H]$^+$: 554.10

Example 580 1-[4-(3-{5-[(R)-Hydroxy-[1-(2-hydroxy-ethyl)-3-methyl-azetidin-3-yl]-(4-isopropyl-phenyl)-methyl]-pyridin-3-yl}[1,2,4]oxadiazol-5-yl)-piperidin-1-yl]-ethanone

580.1 1-[4-(3-{5-[(R)-{1-[2-(tert-Butyl-dimethyl-silanyloxy)-ethyl]-3-methyl-azetidin-3-yl}-hydroxy-(4-isopropyl-phenyl)-methyl]-pyridin-3-yl}-[1,2,4]oxadiazol-5-yl)-piperidin-1-yl]-ethanone Example 531.2 (50 mg) and $Cs_2CO_3$ (65.2 g) were taken up in DMF (500 μL), then (2-bromoethoxy)-tert-butyldimethylsilane (33.1 μL) was added. The mixture was shaken at 70° C. for 1 h40, filtrated through a syringe filter, diluted with DMF and purified by prep LC-MS (VIII) to give 29 mg off-white foam. LC-MS (A) $t_R$=0.97 min; [M+H]$^+$: 648.34.

580.2 1-[4-(3-{5-[(R)-Hydroxy-[1-(2-hydroxy-ethyl)-3-methyl-azetidin-3-yl]-(4-isopropyl-phenyl)-methyl]-pyridin-3-yl}-[1,2,4]oxadiazol-5-yl)-piperidin-1-yl]-ethanone Example 580.1 (29 mg) was dissolved in THF (500 μL), cooled to 0° C. and then TBAF 1M in THF (102 μL) was added, the mixture was stirred for 1 h at RT. The mixture was taken up in EA, washed with aq. sat. $NaHCO_3$ and water. The org. layer was washed with brine, dried over $MgSO_4$, filtrated, concentrated and purified by prep LC-MS (V) to give 11 mg beige glassy oil. LC-MS (A) $t_R$=0.72 min; [M+H]$^+$: 534.13.

Example 581 to Example 585 were synthesized following the procedure described in Example F1.1 step F1.1.2 starting from Example 531.2 and using the appropriate commercially available aldehyde and purified by prep LC-MS and CC (Biotage, 11 g SPHERE Amino, solvent A: Hept, solvent B: EA), if necessary. The purification conditions and the LC-MS (A) data are listed in the table below.

| Example N° | Name | Prep LC-MS | CC gradient (in % B) | $t_R$ | [M + H]$^+$ |
|---|---|---|---|---|---|
| 581 | 1-[4-(3-{5-[(R)-(1-Cyclopropylmethyl-3-methyl-azetidin-3-yl)-hydroxy-(4-isopropyl-phenyl)-methyl]-pyridin-3-yl}-[1,2,4]oxadiazol-5-yl)-piperidin-1-yl]-ethanone | (VI) | — | 0.79 | 544.15 |
| 582 | 1-{4-[3-(5-{(R)-Hydroxy-(4-isopropyl-phenyl)-[1-(2-methoxy-ethyl)-3-methyl-azetidin-3-yl]-methyl}-pyridin-3-yl)-[1,2,4]oxadiazol-5-yl]-piperidin-1-yl}-ethanone | (VI) | — | 0.76 | 548.13 |
| 583 | 1-{4-[3-(5-{(R)-Hydroxy-(4-isopropyl-phenyl)-[3-methyl-1-(3,3,3-trifluoro-propyl)-azetidin-3-yl]-methyl}-pyridin-3-yl)-[1,2,4]oxadiazol-5-yl]-piperidin-1-yl}-ethanone | (VI) | — | 0.82 | 586.24 |
| 584 | 1-[4-(3-{5-[(R)-Hydroxy-(4-isopropyl-phenyl)-(3-methyl-1-propyl-azetidin-3-yl)-methyl]-pyridin-3-yl}-[1,2,4]oxadiazol-5-yl)-piperidin-1-yl]-ethanone | (VI) | 25 for 1CV, 25 to 100 over 4CV, 100 for 4CV | 0.79 | 532.23 |
| 585 | 1-[4-(3-{5-[(R)-(1-Ethyl-3-methyl-azetidin-3-yl)-hydroxy-(4-isopropyl-phenyl)-methyl]-pyridin-3-yl}-[1,2,4]oxadiazol-5-yl)-piperidin-1-yl]-ethanone | (VI) | 25 for 1CV, 25 to 100 over 4CV, 100 for 19CV | 0.77 | 518.17 |

Example 586 to Example 635 were synthesized starting from the corresponding Example F1.2 and the appropriate alkyne, and following the procedure described in Example 15. The precursor alkyne is indicated in the table below unless commercially available. Prep LC-MS conditions and LC-MS data are listed in the table below. The LC-MS conditions used were LC-MS (A).

| Example N° | Name | $t_R$ | [M + H]$^+$ | Alkyne | Prep LC-MS |
|---|---|---|---|---|---|
| 586 | 1-(4-{5-[(R)-(1,3-Dimethyl-azetidin-3-yl)-hydroxy-(4-isopropyl-phenyl)-methyl]-pyridin-3-ylethynyl}-piperidin-1-yl)-ethanone | 0.72 | 460.18 | F5.54 | (VI) then (IX) |
| 587 | 4-{5-[(R)-(1,3-Dimethyl-azetidin-3-yl)-hydroxy-(4-isopropyl-phenyl)-methyl]-pyridin-3-yl}-1,1,1-trifluoro-2-methyl-but-3-yn-2-ol | 0.72 | 447.13 | F5.59 | (XIV) |
| 588 | Cyclopropanecarboxylic acid (3-{5-[(R)-(1,3-dimethyl-azetidin-3-yl)-hydroxy-(4-isopropyl-phenyl)-methyl]-pyridin-3-yl}-1,1-dimethyl-prop-2-ynyl)-amide | 0.71 | 460.16 | F5.60 | (XIV) then (VII) |
| 589 | N-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-isobutyramide | 0.73 | 462.18 | F5.61 | (IX) then (VII) |
| 590 | N-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-2-methoxy-acetamide | 0.69 | 464.14 | F5.62 | (XIV) then (VI) |
| 591 | 3-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-oxazolidin-2-one | 0.72 | 462.17 | F5.63 | (VI) then (VII) |
| 592 | 1-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-pyrrolidin-2-one | 0.73 | 460.18 | F5.64 | (VI) then (IX) |
| 593 | 1-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-3-methyl-imidazolidin-2-one | 0.72 | 475.17 | F5.66 | (XIV) then (VI) |
| 594 | 1-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-imidazolidin-2-one | 0.69 | 461.18 | F5.65 | (XIV) then (VI) |
| 595 | 3-(1-{5-[(R)-(1,3-Dimethyl-azetidin-3-yl)-hydroxy-(4-isopropyl-phenyl)-methyl]-pyridin-3-ylethynyl}-cyclopropyl)-oxazolidin-2-one | 0.69 | 460.14 | F5.67 | (XIV) then (VI) |
| 596 | 1-((R)-2-{5-[(R)-(1,3-Dimethyl-azetidin-3-yl)-hydroxy-(4-isopropyl-phenyl)-methyl]-pyridin-3-ylethynyl}-2-methyl-pyrrolidin-1-yl)-ethanone | 0.73 | 460.17 | F5.55 | (IX) then (VI) |

-continued

| Example N° | Name | $t_R$ | [M + H]$^+$ | Alkyne | Prep LC-MS |
|---|---|---|---|---|---|
| 597 | 1-(4-{5-[(R)-(1,3-Dimethyl-azetidin-3-yl)-hydroxy-(4-isopropyl-phenyl)-methyl]-pyridin-3-ylethynyl}-4-hydroxy-piperidin-1-yl)-ethanone | 0.65 | 476.16 | F5.31 | (V) then (IX) |
| 598 | 1-[4-(3-{5-[(R)-(1,3-Dimethyl-azetidin-3-yl)-hydroxy-(4-isopropyl-phenyl)-methyl]-pyridin-3-yl}-1-hydroxy-1-methyl-prop-2-ynyl)-piperidin-1-yl]-ethanone | 0.69 | 504.15 | F5.32 | (IX) then (V) |
| 599 | 1-[4-(3-{5-[(R)-(1,3-Dimethyl-azetidin-3-yl)-hydroxy-(4-isopropyl-phenyl)-methyl]-pyridin-3-yl}-1-hydroxy-prop-2-ynyl)-piperidin-1-yl]-ethanone | 0.67 | 490.16 | F5.33 | (IX) then (V) |
| 600 | 1-[4-(3-{5-[(R)-(1,3-Dimethyl-azetidin-3-yl)-hydroxy-(4-isopropyl-phenyl)-methyl]-pyridin-3-yl}-prop-2-ynyl)-piperidin-1-yl]-ethanone | 0.73 | 474.18 | F5.56 | (XIV) |
| 601 | 1-[4-(3-{5-[(R)-(1,3-Dimethyl-azetidin-3-yl)-hydroxy-(4-isopropyl-phenyl)-methyl]-pyridin-3-yl}-1-hydroxy-prop-2-ynyl)-4-methyl-piperidin-1-yl]-ethanone | 0.69 | 504.16 | F5.57 | (XIV) |
| 602 | 1-(4-{5-[(R)-(1,3-Dimethyl-azetidin-3-yl)-hydroxy-(4-isopropyl-phenyl)-methyl]-pyridin-3-ylethynyl}-4-methyl-piperidin-1-yl)-ethanone | 0.75 | 474.06 | F5.58 | (XIV) |
| 603 | (R)-(1,3-Dimethyl-azetidin-3-yl)-(4-isopropyl-phenyl)-[5-(1-methanesulfonyl-piperidin-4-ylethynyl)-pyridin-3-yl]-methanol | 0.73 | 496.09 | F5.70 | (XIV) then (VI) |
| 604 | 4-{5-[(R)-(1,3-Dimethyl-azetidin-3-yl)-hydroxy-(4-isopropyl-phenyl)-methyl]-pyridin-3-ylethynyl}-4-methyl-piperidine-1-sulfonic acid methylamide | 0.76 | 525.12 | F5.71 | (XIV) then (VI) |
| 605 | (R)-(1,3-Dimethyl-azetidin-3-yl)-(4-isopropyl-phenyl)-[5-(3-methanesulfonyl-3-methyl-but-1-ynyl)-pyridin-3-yl]-methanol | 0.70 | 455.12 | — | (XIV) then (VI) |
| 606 | 1-{5-[(R)-(1,3-Dimethyl-azetidin-3-yl)-hydroxy-(4-isopropyl-phenyl)-methyl]-pyridin-3-ylethynyl}-cyclopropanesulfonic acid dimethylamide | 0.74 | 481.90 | — | (XIV) |
| 607 | 1-{5-[(R)-(1,3-Dimethyl-azetidin-3-yl)-hydroxy-(4-isopropyl-phenyl)-methyl]-pyridin-3-ylethynyl}-cyclopropanesulfonic acid amide | 0.66 | 454.10 | — | (XIV) then (V) |
| 608 | (R)-[5-(3-Cyclopropanesulfonyl-3-methyl-but-1-ynyl)-pyridin-3-yl]-(1,3-dimethyl-azetidin-3-yl)-(4-isopropyl-phenyl)-methanol | 0.73 | 480.98 | F5.72 | (XIV) then (VI) |
| 609 | (R)-3-{5-[(R)-(1,3-Dimethyl-azetidin-3-yl)-hydroxy-(4-isopropyl-phenyl)-methyl]-pyridin-3-ylethynyl}-3-hydroxy-1-methyl-pyrrolidin-2-one | 0.63 | 448.17 | — | (XIV) |
| 610 | (S)-3-{5-[(R)-(1,3-Dimethyl-azetidin-3-yl)-hydroxy-(4-isopropyl-phenyl)-methyl]-pyridin-3-ylethynyl}-3-hydroxy-1-methyl-pyrrolidin-2-one | 0.63 | 448.15 | — | (XIV) |
| 611 | 4-{5-[(R)-(1,3-Dimethyl-azetidin-3-yl)-hydroxy-(4-isopropyl-phenyl)-methyl]-pyridin-3-ylethynyl}-3,4-dihydro-2H-pyrano[3,2-b]pyridin-4-ol | 0.68 | 484.06 | F5.35 | (XIV) |
| 612 | 3-{5-[(R)-(1,3-Dimethyl-azetidin-3-yl)-hydroxy-(4-isopropyl-phenyl)-methyl]-pyridin-3-ylethynyl}-3-hydroxy-1-methyl-1,3-dihydro-indol-2-one | 0.72 | 496.05 | F5.36 | (IX) then (VI) |
| 613 | 4-{5-[(R)-(1,3-Dimethyl-azetidin-3-yl)-hydroxy-(4-isopropyl-phenyl)-methyl]-pyridin-3-yl}-2-(1H-indazol-3-yl)-but-3-yn-2-ol | 0.72 | 495.10 | F5.37 | (VI) |
| 614 | 4-{5-[(R)-(1,3-Dimethyl-azetidin-3-yl)-hydroxy-(4-isopropyl-phenyl)-methyl]-pyridin-3-yl}-2-(1-methyl-1H-indazol-3-yl)-but-3-yn-2-ol | 0.76 | 509.06 | F5.38 | (VI) |
| 615 | 2-(1-Cyclopropyl-1H-pyrazol-3-yl)-4-{5-[(R)-(1,3-dimethyl-azetidin-3-yl)-hydroxy-(4-isopropyl-phenyl)-methyl]-pyridin-3-yl}-but-3-yn-2-ol | 0.89 | 585.16 | F5.73 | (VI) then (IX) |
| 616 | 4-{5-[(R)-(1,3-Dimethyl-azetidin-3-yl)-hydroxy-(4-isopropyl-phenyl)-methyl]-pyridin-3-yl}-2-(2-methyl-pyrimidin-4-yl)-but-3-yn-2-ol | 0.68 | 471.15 | F5.39 | (XIV) then (V) |
| 617 | 4-{5-[(R)-(1,3-Dimethyl-azetidin-3-yl)-hydroxy-(4-isopropyl-phenyl)-methyl]-pyridin-3-yl}-2-(5-methyl-pyrazin-2-yl)-but-3-yn-2-ol | 0.68 | 471.14 | F5.40 | (XIV) then (VI) |
| 618 | 4-{5-[(R)-(1,3-Dimethyl-azetidin-3-yl)-hydroxy-(4-isopropyl-phenyl)-methyl]-pyridin-3-yl}-2-(2-methyl-thiazol-5-yl)-but-3-yn-2-ol | 0.71 | 476.09 | F5.41 | (XIV) then (VI) |
| 619 | 2-(6-Cyclopropyl-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol | 0.73 | 497.04 | F5.42 | (XIV) then (VI) |
| 620 | (R)- or (S)-4-{5-[(R)-(1,3-Dimethyl-azetidin-3-yl)-hydroxy-(4-isopropyl-phenyl)-methyl]-pyridin-3-yl}-2-(6-methoxy-pyrimidin-4-yl)-but-3-yn-2-ol | 0.70 | 487.13 | F5.43 | (IX) then (V) |
| 621 | N-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-acetamide | 0.62 | 433.81 | — | (IX) |

-continued

| Example N° | Name | $t_R$ | [M + H]$^+$ | Alkyne | Prep LC-MS |
|---|---|---|---|---|---|
| 622 | (S)- or (R)-4-{5-[(R)-(1,3-Dimethyl-azetidin-3-yl)-hydroxy-(4-isopropyl-phenyl)-methyl]-pyridin-3-yl}-2-(6-methoxy-pyrimidin-4-yl)-but-3-yn-2-ol | 0.70 | 487.13 | F5.44 | (IX) then (V) |
| 623 | (R)- or (S)-4-{5-[(R)-(1,3-Dimethyl-azetidin-3-yl)-hydroxy-(4-isopropyl-phenyl)-methyl]-pyridin-3-yl}-2-(2-methoxy-pyrimidin-4-yl)-but-3-yn-2-ol | 0.70 | 487.13 | F5.45 | (IX) then (V) |
| 624 | (S)- or (R)-4-{5-[(R)-(1,3-Dimethyl-azetidin-3-yl)-hydroxy-(4-isopropyl-phenyl)-methyl]-pyridin-3-yl}-2-(2-methoxy-pyrimidin-4-yl)-but-3-yn-2-ol | 0.70 | 487.13 | F5.46 | (IX) then (V) |
| 625 | (R)- or (S)-4-{5-[(R)-(1,3-Dimethyl-azetidin-3-yl)-hydroxy-(4-isopropyl-phenyl)-methyl]-pyridin-3-yl}-2-(2,6-dimethyl-pyrimidin-4-yl)-but-3-yn-2-ol | 0.67 | 485.18 | F5.47 | (XIV) then (V) |
| 626 | (S)- or (R)-4-{5-[(R)-(1,3-Dimethyl-azetidin-3-yl)-hydroxy-(4-isopropyl-phenyl)-methyl]-pyridin-3-yl}-2-(2,6-dimethyl-pyrimidin-4-yl)-but-3-yn-2-ol | 0.67 | 485.16 | F5.48 | (XIV) then (V) |
| 627 | (R)- or (S)-2-(2,6-Dimethoxy-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol | 0.75 | 517.13 | F5.49 | (XIV) then (VI) |
| 628 | (S)- or (R)-2-(2,6-Dimethoxy-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol | 0.75 | 517.13 | F5.50 | (XIV) then (VI) |
| 629 | (S)- or (R)-4-{5-[(R)-(1,3-Dimethyl-azetidin-3-yl)-hydroxy-(4-isopropyl-phenyl)-methyl]-pyridin-3-yl}-2-(2-methoxy-6-methyl-pyrimidin-4-yl)-but-3-yn-2-ol | 0.74 | 501.15 | F5.51 | (XIV) then (VI) |
| 630 | (R)- or (S)-4-{5-[(R)-(1,3-Dimethyl-azetidin-3-yl)-hydroxy-(4-isopropyl-phenyl)-methyl]-pyridin-3-yl}-2-(6-methoxy-2-methyl-pyrimidin-4-yl)-but-3-yn-2-ol | 0.74 | 501.22 | F5.52 | (VI) |
| 631 | (S)- or (R)-4-{5-[(R)-(1,3-Dimethyl-azetidin-3-yl)-hydroxy-(4-isopropyl-phenyl)-methyl]-pyridin-3-yl}-2-(6-methoxy-2-methyl-pyrimidin-4-yl)-but-3-yn-2-ol | 0.74 | 501.19 | F5.53 | (VI) |
| 632 | 4-{5-[(R)-(1,3-Dimethyl-azetidin-3-yl)-hydroxy-(4-isopropyl-phenyl)-methyl]-pyridin-3-yl}-2-(6-trifluoromethyl-pyrimidin-4-yl)-but-3-yn-2-ol | 0.77 | 525.17 | F5.74 | (XIV) then (VI) |
| 633 | 2-(6-Difluoromethyl-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol | 0.75 | 507.17 | F5.75 | (XIV) then (VI) |
| 634 | (R)-(1,3-Dimethyl-azetidin-3-yl)-(4-isopropyl-phenyl)-[5-(1-pyridin-2-yl-cyclopropylethynyl)-pyridin-3-yl]-methanol | 0.74 | 452.18 | F5.68 | (VIII) then (XIV) |
| 635 | (R)-(1,3-Dimethyl-azetidin-3-yl)-(4-isopropyl-phenyl)-{5-[1-(6-methyl-pyrimidin-4-yl)-cyclopropylethynyl]-pyridin-3-yl}-methanol | 0.80 | 467.19 | F5.69 | (XIV) then (VI) |

Example 636 to Example 647 were synthesized from the appropriate alkyne following the procedure described in Example 408. LC-MS and prep LC-MS data are listed in the table below. The LC-MS conditions used were LC-MS (A).

| Example N° | Name | $t_R$ | [M + H]$^+$ | Prep LC-MS | Alkyne Example No |
|---|---|---|---|---|---|
| 636 | 1-[4-(2-{5-[(R)-(1,3-Dimethyl-azetidin-3-yl)-hydroxy-(4-isopropyl-phenyl)-methyl]-pyridin-3-yl}-ethyl)-piperidin-1-yl]-ethanone | 0.61 | 464.2 | — | 586 |
| 637 | 4-{5-[(R)-(1,3-Dimethyl-azetidin-3-yl)-hydroxy-(4-isopropyl-phenyl)-methyl]-pyridin-3-yl}-1,1,1-trifluoro-2-methyl-butan-2-ol | 0.62 | 451.07 | (IX) | 587 |
| 638 | 3-(3-{5-[(R)-(1,3-Dimethyl-azetidin-3-yl)-hydroxy-(4-isopropyl-phenyl)-methyl]-pyridin-3-yl}-1,1-dimethyl-propyl)-oxazolidin-2-one | 0.62 | 465.99 | — | 591 |
| 639 | 1-(3-{5-[(R)-(1,3-Dimethyl-azetidin-3-yl)-hydroxy-(4-isopropyl-phenyl)-methyl]-pyridin-3-yl}-1,1-dimethyl-propyl)-pyrrolidin-2-one | 0.62 | 464.12 | — | 592 |
| 640 | 1-(3-{5-[(R)-(1,3-Dimethyl-azetidin-3-yl)-hydroxy-(4-isopropyl-phenyl)-methyl]-pyridin-3-yl}-1,1-dimethyl-propyl)-3-methyl-imidazolidin-2-one | 0.62 | 479.16 | — | 593 |
| 641 | 1-(3-{5-[(R)-(1,3-Dimethyl-azetidin-3-yl)-hydroxy-(4-isopropyl-phenyl)-methyl]-pyridin-3-yl}-1,1-dimethyl-propyl)-imidazolidin-2-one | 0.60 | 465.08 | (VII) | 594 |
| 642 | 1-[(S)-2-(2-{5-[(R)-(1,3-Dimethyl-azetidin-3-yl)-hydroxy-(4-isopropyl-phenyl)-methyl]-pyridin-3-yl}-ethyl)-2-methyl-pyrrolidin-1-yl]-ethanone | 0.63 | 464.19 | — | 596 |

-continued

| Example N° | Name | $t_R$ | [M + H]$^+$ | Prep LC-MS | Alkyne Example No |
|---|---|---|---|---|---|
| 643 | 4-{5-[(R)-(1,3-Dimethyl-azetidin-3-yl)-hydroxy-(4-isopropyl-phenyl)-methyl]-pyridin-3-yl}-2-(1H-indazol-3-yl)-butan-2-ol | 0.60 | 499.10 | (XIV) | 613 |
| 644 | 2-(1-Cyclopropyl-1H-pyrazol-3-yl)-4-{5-[(R)-(1,3-dimethyl-azetidin-3-yl)-hydroxy-(4-isopropyl-phenyl)-methyl]-pyridin-3-yl}-butan-2-ol | 0.59 | 489.18 | — | 615 |
| 645 | 4-{5-[(R)-(1,3-Dimethyl-azetidin-3-yl)-hydroxy-(4-isopropyl-phenyl)-methyl]-pyridin-3-yl}-2-(2-methyl-pyrimidin-4-yl)-butan-2-ol | 0.57 | 475.15 | — | 616 |
| 646 | 4-{5-[(R)-(1,3-Dimethyl-azetidin-3-yl)-hydroxy-(4-isopropyl-phenyl)-methyl]-pyridin-3-yl}-2-(5-methyl-pyrazin-2-yl)-butan-2-ol | 0.58 | 475.16 | — | 617 |
| 647 | 4-{5-[(R)-(1,3-Dimethyl-azetidin-3-yl)-hydroxy-(4-isopropyl-phenyl)-methyl]-pyridin-3-yl}-2-(2-methyl-thiazol-5-yl)-butan-2-ol | 0.57 | 480.11 | — | 618 |

Example 648 to Example 653 were synthesized starting from the corresponding Example F1.2 and the appropriate alkyne, and following the procedure described in Example 15, where the amount of $Pd(PPh_3)_4$ was adjusted to 0.1 eq and the base was changed to pyrrolidine (3.5 eq). The precursor alkyne is indicated in the table below unless commercially available. Prep LC-MS conditions and LC-MS data are listed in the table below. The LC-MS conditions used were LC-MS (A).

| Example N° | Name | $t_R$ | [M + H]$^+$ | Alkyne | Prep LC-MS |
|---|---|---|---|---|---|
| 648 | 4-{5-[(R)-(1,3-Dimethyl-azetidin-3-yl)-hydroxy-(4-isopropyl-phenyl)-methyl]-pyridin-3-yl}-2-(3-methyl-isoxazol-5-yl)-but-3-yn-2-ol | 0.73 | 460.21 | F5.78 | (VI) |
| 649 | 4-{5-[(R)-(1,3-Dimethyl-azetidin-3-yl)-hydroxy-(4-isopropyl-phenyl)-methyl]-pyridin-3-yl}-2-(1-methyl-1H-imidazol-2-yl)-but-3-yn-2-ol | 0.56 | 459.21 | F5.79 | (V) |
| 650 | 4-{5-[(R)-(1,3-Dimethyl-azetidin-3-yl)-hydroxy-(4-isopropyl-phenyl)-methyl]-pyridin-3-yl}-2-(5-methyl-thiophen-2-yl)-but-3-yn-2-ol | 0.81 | 475.20 | F5.80 | (V) then (XIV) |
| 651 | 4-{5-[(R)-(1,3-Dimethyl-azetidin-3-yl)-hydroxy-(4-isopropyl-phenyl)-methyl]-pyridin-3-yl}-2-(1-methyl-1H-pyrrol-2-yl)-but-3-yn-2-ol | 0.76 | 458.24 | F5.81 | (VI) |
| 652 | (R)- or (S)-4-{5-[(R)-(1,3-Dimethyl-azetidin-3-yl)-hydroxy-(4-isopropyl-phenyl)-methyl]-pyridin-3-yl}-2-(2-trifluoromethyl-pyrimidin-4-yl)-but-3-yn-2-ol | 0.79 | 525.16 | F5.76 | (V) then (XIV) |
| 653 | (S)- or (R)-4-{5-[(R)-(1,3-Dimethyl-azetidin-3-yl)-hydroxy-(4-isopropyl-phenyl)-methyl]-pyridin-3-yl}-2-(2-trifluoromethyl-pyrimidin-4-yl)-but-3-yn-2-ol | 0.79 | 525.17 | F5.77 | (V) then (XIV) |

Example 654 to Example 661 were synthesized starting from the corresponding bromopyridine of structure F1 using Example F5.27, and following the procedure described in Example 15, where the amount of $Pd(PPh_3)_4$ was adjusted to 0.1 eq and the base was changed to pyrrolidine (3.5 eq). The precursor bromopyridine is indicated in the table below. Prep LC-MS conditions and LC-MS data are listed in the table below. The LC-MS conditions used were LC-MS (A).

| Example N° | Name | $t_R$ | [M + H]$^+$ | Bromopyridine | Prep LC-MS |
|---|---|---|---|---|---|
| 654 | 4-(5-{(R)-(1,3-Dimethyl-azetidin-3-yl)-hydroxy-[4-(1-trifluoromethyl-cyclopropyl)-phenyl]-methyl}-pyridin-3-yl)-2-(6-methyl-pyridin-2-yl)-but-3-yn-2-ol | 0.66 | 536.15 | F1.8 | (VI) then (XIV) |
| 655 | 4-(5-{(R)-(1,3-Dimethyl-azetidin-3-yl)-hydroxy-[4-(1-methyl-cyclopropyl)-phenyl]-methyl}-pyridin-3-yl)-2-(6-methyl-pyridin-2-yl)-but-3-yn-2-ol | 0.63 | 481.99 | F1.7 | (VI) |

-continued

| Example N° | Name | $t_R$ | [M + H]+ | Bromopyridine | Prep LC-MS |
|---|---|---|---|---|---|
| 656 | 4-{5-[(R)-(1,3-Dimethyl-azetidin-3-yl)-hydroxy-(4-trifluoromethyl-phenyl)-methyl]-pyridin-3-yl}-2-(6-methyl-pyridin-2-yl)-but-3-yn-2-ol | 0.60 | 496.14 | F1.15 | (VI) then (XIV) |
| 657 | 4-{5-[(R)-(1,3-Dimethyl-azetidin-3-yl)-(4-ethyl-phenyl)-hydroxy-methyl]-pyridin-3-yl}-2-(6-methyl-pyridin-2-yl)-but-3-yn-2-ol | 0.59 | 456.21 | F1.10 | (VI) then (XIV) |
| 658 | 4-{5-[(R)-(4-tert-Butyl-phenyl)-(1,3-dimethyl-azetidin-3-yl)-hydroxy-methyl]-pyridin-3-yl}-2-(6-methyl-pyridin-2-yl)-but-3-yn-2-ol | 0.65 | 484.26 | F1.9 | (XIV) |
| 659 | 4-{5-[(R)-(3-Ethyl-1-methyl-azetidin-3-yl)-hydroxy-(4-trifluoromethoxy-phenyl)-methyl]-pyridin-3-yl}-2-(6-methyl-pyridin-2-yl)-but-3-yn-2-ol | 0.65 | 526.13 | F1.13 | (VII) |
| 660 | 4-(5-{(R)-(1,3-Dimethyl-azetidin-3-yl)-hydroxy-[4-(2,2,2-trifluoro-ethyl)-phenyl]-methyl}-pyridin-3-yl)-2-(6-methyl-pyridin-2-yl)-but-3-yn-2-ol | 0.60 | 510.14 | F1.12 | (VI) then (XIV) |
| 661 | 4-{5-[(S)-(3-Fluoro-1-methyl-azetidin-3-yl)-hydroxy-(4-isopropyl-phenyl)-methyl]-pyridin-3-yl}-2-(6-methyl-pyridin-2-yl)-but-3-yn-2-ol | 0.63 | 474.22 | F1.14 | (VI) |

Example 662 to Example 664 were synthesized starting from Example F1.5 the appropriate alkyne, and following the procedure described in Example 15. The precursor alkyne is indicated in the table below unless commercially available. Prep LC-MS conditions and LC-MS data are listed in the table below. The LC-MS conditions used were LC-MS (A).

| Example N° | Name | $t_R$ | [M + H]+ | Alkyne | Prep LC-MS |
|---|---|---|---|---|---|
| 662 | 1-(4-{5-[(R)-(1,3-Dimethyl-azetidin-3-yl)-hydroxy-(4-isopropyl-phenyl)-methyl]-pyridazin-3-ylethynyl}-piperidin-1-yl)-ethanone | 0.66 | 461.18 | F5.54 | (XIV) then (V) |
| 663 | N-(3-{5-[(R)-(1,3-Dimethyl-azetidin-3-yl)-hydroxy-(4-isopropyl-phenyl)-methyl]-pyridazin-3-yl}-1,1-dimethyl-prop-2-ynyl)-acetamide | 0.58 | 435.18 | — | (XIV) then (V) |
| 664 | 1-(3-{5-[(R)-(1,3-Dimethyl-azetidin-3-yl)-hydroxy-(4-isopropyl-phenyl)-methyl]-pyridazin-3-yl}-1,1-dimethyl-prop-2-ynyl)-pyrrolidin-2-one | 0.68 | 461.19 | F5.64 | (XIV) then (VI) |

Example 665 and Example 666 were synthesized following the procedure described in Example D1.1 step D1.1.5 using the corresponding free azetidine A7.34 and the appropriate carbonyl reagent, purified (if necessary) by prep LC-MS. The LC-MS (A) data are listed in the table below.

| Example N° | Name | $t_R$ | [M + H]+ | Ketone/ formaldehyde | Prep LC-MS |
|---|---|---|---|---|---|
| 665 | 4-{5-[(R)-Hydroxy-(1-isopropyl-3-methyl-azetidin-3-yl)-(4-isopropyl-phenyl)-methyl]-pyridin-3-yl}-2-(6-methyl-pyridin-2-yl)-but-3-yn-2-ol | 0.67 | 497.97 | acetone | (V) |
| 666 | 4-{5-[(R)-(1,3-Dimethyl-azetidin-3-yl)-hydroxy-(4-isopropyl-phenyl)-methyl]-pyridin-3-yl}-2-(6-methyl-pyridin-2-yl)-but-3-yn-2-ol | 0.70 | 511.15 | formaldehyde | (XIV) |

Example 667 and Example 668 To a solution of A7.34 (30 mg) in MeOH (1 mL) were added at RT TEA (20.2 μL) followed by commercial available 2-iodoethanol (57.3 mg) for Example 667 and 1,1-difluoro-2-iodoethane (57 mg) for Example 668, respectively. The resulting mixture was shaken at reflux over weekend. The mixture was purified by prep LC-MS. Prep LC-MS data and LC-MS (A) data are listed in the table below.

| Example N° | Name | Prep LC-MS | $t_R$ | [M + H]$^+$ |
|---|---|---|---|---|
| 667 | 4-{5-[(R)-Hydroxy-[1-(2-hydroxy-ethyl)-3-methyl-azetidin-3-yl]-(4-isopropyl-phenyl)-methyl]-pyridin-3-yl}-2-(6-methyl-pyridin-2-yl)-but-3-yn-2-ol | (V) then (VI) | 0.61 | 500.24 |
| 668 | 4-{5-[(R)-[1-(2,2-Difluoro-ethyl)-3-methyl-azetidin-3-yl]-hydroxy-(4-isopropyl-phenyl)-methyl]-pyridin-3-yl}-2-(6-methyl-pyridin-2-yl)-but-3-yn-2-ol | (V) | 0.66 | 520.15 |

Example 669 1-(4-{5-[(R)-(1,3-Dimethyl-azetidin-3-yl)-hydroxy-(4-isopropyl-phenyl)-methyl]-pyridin-3-yloxymethyl}-piperidin-1-yl)-ethanone

669.1 4-{5-[(R)-(1,3-Dimethyl-azetidin-3-yl)-hydroxy-(4-isopropyl-phenyl)-methyl]-pyridin-3-yloxymethyl}-piperidine-1-carboxylic acid tert-butyl ester A flask was charged with G1.2 (11 mg), N-Boc-4-piperidinemethanol (22.4 mg), toluene abs. (300 μL) and cyanomethylenetributylphosphane (19.6 μL) at RT. The resulting suspension was stirred at 110° C. under argon overnight, then evaporated and purified by prep LC-MS (VIII) to give 25 mg off-white powder. LC-MS (A) $t_R$=0.77 min; [M+H]$^+$: 524.15.

669.2 (R)-(1,3-dimethylazetidin-3-yl)(4-isopropylphenyl)(5-(piperidin-4-ylmethoxy)pyridin-3-yl)methanol, hydrochloride salt The title compound was synthesized from Example 669.1 and following the procedure described in Example 309 step 309.2. LC-MS (A) $t_R$=0.49; [M+H]$^+$: 424.22.

669.3 1-(4-{5-[(R)-(1,3-Dimethyl-azetidin-3-yl)-hydroxy-(4-isopropyl-phenyl)-methyl]-pyridin-3-yloxymethyl}-piperidin-1-yl)-ethanone To a suspension of Example 669.2 (28 mg) in DCM (1 mL) were added DIPEA (48.3 μL), AcOH (9.7 μL), EDC·HCl (13 mg) and HOBt (9 mg) at RT. The resulting solution was stirred at RT for 1 h, then the mixture was evaporated and purified by prep LC-MS (IX) to give 1 mg white powder. LC-MS (A) $t_R$=0.63 min; [M+H]$^+$ 465.98.

Example 670 4-{5-[(R)-(1-Cyclopropyl-3-methyl-azetidin-3-yl)-hydroxy-(4-isopropyl-phenyl)-methyl]-pyridin-3-yl}-2-(6-methyl-pyridin-2-yl)-but-3-yn-2-ol The title compound was synthesized following the procedure described in Example B2.1, step 2 using (1-ethoxy-cyclopropoxy)trimethylsilane instead of formaldehyde and using sodium cyanoborohydride instead of $NaBH(OAc)_3$. The crude was purified by prep LC-MS (V). LC-MS (A) $t_R$=0.66 min; [M+H]$^+$: 496.21.

Example 671 to Example 679 were synthesized starting from the appropriate Example F3.2 to F3.10, and following procedure described in Example 167.1. LC-MS (A) data, prep LC-MS methods and the precursors are listed in the table below.

| Example N° | Name | $t_R$ | [M + H]$^+$ | Prep LC-MS 1 | Prep LC-MS 2 | Precursor |
|---|---|---|---|---|---|---|
| 671 | 1-{5-[(R)-(1,3-Dimethyl-azetidin-3-yl)-hydroxy-(4-isopropyl-phenyl)-methyl]-pyridin-3-yl}-4-(2-isopropyl-pyrimidin-4-yl)-pyrrolidin-2-one | 0.71 | 513.7 | (VII) | (XIV) | F3.2 |
| 672 | 1-{5-[(R)-(1,3-Dimethyl-azetidin-3-yl)-hydroxy-(4-isopropyl-phenyl)-methyl]-pyridin-3-yl}-4-(2-methyl-thiazol-5-yl)-pyrrolidin-2-one | 0.57 | 491.1 | (VII) | | F3.3 |
| 673 | 1-{5-[(R)-(1,3-Dimethyl-azetidin-3-yl)-hydroxy-(4-isopropyl-phenyl)-methyl]-pyridin-3-yl}-4-(6-methyl-pyridin-3-yl)-pyrrolidin-2-one | 0.52 | 485.13 | (VI) | (XIV) | F3.4 |
| 674 | 1-{5-[(R)-(1,3-Dimethyl-azetidin-3-yl)-hydroxy-(4-isopropyl-phenyl)-methyl]-pyridin-3-yl}-4-(6-isopropyl-pyridin-2-yl)-pyrrolidin-2-one | 0.64 | 512.99 | (VIII) | (IX) | F3.5 |
| 675 | 1-{5-[(R)-(1,3-Dimethyl-azetidin-3-yl)-hydroxy-(4-isopropyl-phenyl)-methyl]-pyridin-3-yl}-4-(6-trifluoromethyl-pyridin-3-yl)-pyrrolidin-2-one | 0.72 | 539.02 | (VII) | | F3.6 |
| 676 | 1-{5-[(R)-(1,3-Dimethyl-azetidin-3-yl)-hydroxy-(4-isopropyl-phenyl)-methyl]-pyridin-3-yl}-4-(1-methyl-1H-pyrazol-4-yl)-pyrrolidin-2-one | 0.63 | 474.12 | (IX) | | F3.7 |

-continued

| Example N° | Name | $t_R$ | [M + H]$^+$ | Prep LC-MS 1 | Prep LC-MS 2 | Precursor |
|---|---|---|---|---|---|---|
| 677 | 1-{5-[(R)-(1,3-Dimethyl-azetidin-3-yl)-hydroxy-(4-isopropyl-phenyl)-methyl]-pyridin-3-yl}-4-(1,3-dimethyl-1H-pyrazol-4-yl)-pyrrolidin-2-one | 0.64 | 488.15 | (IX) | | F3.8 |
| 678 | 4-(1-Difluoromethyl-1H-pyrazol-4-yl)-1-{5-[(R)-(1,3-dimethyl-azetidin-3-yl)-hydroxy-(4-isopropyl-phenyl)-methyl]-pyridin-3-yl}-pyrrolidin-2-one | 0.67 | 510.12 | (V) | | F3.9 |
| 679 | 1-{5-[(R)-(1,3-Dimethyl-azetidin-3-yl)-hydroxy-(4-isopropyl-phenyl)-methyl]-pyridin-3-yl}-4-(2-methyl-2H-[1,2,3]triazol-4-yl)-pyrrolidin-2-one | 0.63 | 475.15 | (IX) | | F3.10 |

Example 680: 4-(1-Acetyl-piperidin-4-yl)-1-{5-[(R)-(1,3-dimethyl-azetidin-3-yl)-hydroxy-(4-isopropyl-phenyl)-methyl]-pyridazin-3-yl}-pyrrolidin-2-one

680.1. 4-(1-Acetyl-piperidin-4-yl)-pyrrolidin-2-one

To a suspension of 4-(piperidin-4-yl)pyrrolidin-2-one (100 mg) in THF (2 mL) was added DIPEA (0.12 mL) followed by acetic anhydride (0.053 mL) at RT and the resulting suspension was stirred at RT for 3 h. The reaction mixture was diluted with water and extracted with DCM (3×). The combined org. layers were dried over $MgSO_4$ and concentrated to dryness to give the desired product (98 mg) as white solid. LC-MS (A): $t_R$=0.47 min; [M+H]$^+$: 211.2.

680.1. 4-(1-Acetyl-piperidin-4-yl)-1-{5-[(R)-(1,3-dimethyl-azetidin-3-yl)-hydroxy-(4-isopropyl-phenyl)-methyl]-pyridazin-3-yl}-pyrrolidin-2-one The title compound was synthesized starting from the Example F1.6 and Example 680.1, and following the procedure described in Example 167.1. The crude product was purified by described Prep LC-MS (IX)). LC-MS (A): $t_R$=0.68 min; [M+H]$^+$: 520.13.

Example 681: 5-{5-[(R)-(1,3-Dimethyl-azetidin-3-yl)-hydroxy-(4-isopropyl-phenyl)-methyl]-pyridazin-3-yl}-hexahydro-furo[2,3-c]pyrrol-4-one The title compound was synthesized starting from the Example F1.6 and rac-(3aR,6aS)-hexahydro-2H-furo[2,3-c]pyrrol-4-one, and following the procedure described in Example 167, step 1. The crude product was purified by described Prep LC-MS (IX). LC-MS (A): $t_R$=0.66 min; [M+H]$^+$: 437.1.

Example 682: 1-{5-[(R)-(1,3-Dimethyl-azetidin-3-yl)-hydroxy-(4-isopropyl-phenyl)-methyl]-pyridazin-3-yl}-4-(6-isopropyl-pyridin-2-yl)-pyrrolidin-2-one The title compound was synthesized starting from the Example F1.6 and Example F3.2, and following the procedure described in Example 167, step 1. The crude product was purified by described Prep LC-MS (V). LC-MS (A): $t_R$=0.63 min; [M+H]$^+$: 513.88.

Example 683: 1-(2-{5-[(R)-(1,3-Dimethyl-azetidin-3-yl)-hydroxy-(4-isopropyl-phenyl)-methyl]-pyridin-3-yl}-7,8-dihydro-5H-pyrido[4,3-d]pyrimidin-6-yl)-ethanone

683.1 1-(2-Chloro-7,8-dihydro-5H-pyrido[4,3-c]pyrimidin-6-yl)-ethanone

The title compound was synthesized from 2-chloro-5H,6H,7H,8H-pyrido[4,3-d]pyrimidine hydrochloride following the procedure in Example F5.54. LC-MS (A) $t_R$=0.53; [M+H]$^+$: 212.03

683.2 (R)-(5-((1,3-dimethylazetidin-3-yl)(hydroxy)(4-isopropylphenyl)methyl)pyridin-3-yl)boronic acid A heated-out vial was charged with F1.2 (200 mg), Bis(pinacolato)diboron (200 mg), [1,1'-Bis(diphenylphosphino)ferrocene]dichloropalladium(II) complex with dichloromethane (21 mg), potassium acetate (153 mg) and DMF (4 mL) at RT, sealed, 3× evacuated and backfilled with argon and shaken at 80° C. overnight. The reaction mixture was diluted with water and MeOH, filtrated off and purified by prep LC-MS, method (VIII) to give 107 mg pale purple powder. LC-MS (A) $t_R$=0.49 min; [M+H]$^+$: 355.07

683.3 1-(2-{5-[(R)-(1,3-Dimethyl-azetidin-3-yl)-hydroxy-(4-isopropyl-phenyl)-methyl]-pyridin-3-yl}-7,8-dihydro-5H-pyrido[4,3-d]pyrimidin-6-yl)-ethanone A vial was charged with the Example 683.1 (22 mg), Example 683.2 (44.4 mg), $Pd(PPh_3)_4$ (18.3 mg), $K_2CO_3$ 1 M (1 mL) and dioxane (1 mL) at RT, sealed degassed with argon in ultrasonic bath for 5 min and shaken at 100° C. for 1 h30 The resulting light brown susp was shaken at 100° C. The reaction mixture was allowed to cool down, diluted with water and MeOH, filtrated off and purified by prep LC-MS (IX) to give 22 mg white powder after lyophilization. LC-MS (A) $t_R$=0.65 min; [M+H]$^+$: 486.12.

Example 684: 1-(2-{5-[(R)-(1,3-Dimethyl-azetidin-3-yl)-hydroxy-(4-isopropyl-phenyl)-methyl]-pyridin-3-yl}-7,8-dihydro-5H-[1,6]naphthyridin-6-yl)-ethanone

684.1-(2-Chloro-7,8-dihydro-5H-[1,6]naphthyridin-6-yl)-ethanone

The title compound was synthesized from 2-chloro-5,6,7,8-tetrahydro-1,6-naphthyridine hydrochloride following the procedure in Example F5.54. LC-MS (A) $t_R$=0.63 min; [M+H]$^+$: 211.09

684.2 1-(2-{5-[(R)-(1,3-Dimethyl-azetidin-3-yl)-hydroxy-(4-isopropyl-phenyl)-methyl]-pyridin-3-yl}-7,8-dihydro-5H-[1,6]naphthyridin-6-yl)-ethanone The title compound was synthesized following the procedure in Example 683, step 3, Example 684.1 replacing Example 683.1. The crude product was purified by Prep LC-MS (XIV). LC-MS (A) $t_R$=0.64 min; $[M+H]^+$: 485.13

Example 685: 1-[4-(2-{5-[(R)-(1,3-Dimethyl-azetidin-3-yl)-hydroxy-(4-isopropyl-phenyl)-methyl]-pyridin-3-yl}-pyrimidin-5-yl)-piperidin-1-yl]-ethanone 685.1 4-(2-Chloro-pyrimidin-5-yl)-3,6-dihydro-2H-pyridine-1-carboxylic acid tert-butyl ester The title compound was synthesized following the procedure described in Example 280, step 1 using 5-bromo-2-chloropyrimidne and 3,6-dihydro-1H-pyridine-1-N-Boc-4-boronic acid, pinacol ester. Instead of direct purification via prep LC-MS the reaction mixture was extracted with 3×DCM. The combined org. layers were dried over $MgSO_4$, filtrated off, evaporated and purified by CC (Biotage, 10 g SNAP, solvent A: Hept, solvent B: EA, gradient (in % B): 10 for 2 CV, 10 to 30 over 5 CV, 30 for 2 CV) and by a second CC Biotage, 10 g SNAP, solvent A: Hept, solvent B: EA, gradient (in % B): 10 for 3 CV, 10 to 30 over 3 CV, 30 for 2 CV. LC-MS (A): $t_R$=0.94 min; $[M+H]^+$: 296.03

685.2 2-chloro-5-(1,2,3,6-tetrahydropyridin-4-yl) pyrimidine, hydrochloride salt The title compound was synthesized following the procedure described in Example F5.56.2 using Example 658.1. LC-MS (A) $t_R$=0.36 min; $[M+H]^+$:196.12

685.3 1-[4-(2-Chloro-pyrimidin-5-yl)-3,6-dihydro-2H-pyridin-1-yl]-ethanone

The title compound was synthesized following the procedure described in Example F5.54 using Example 685.2. LC-MS (A) $t_R$=0.63; $[M+H]^+$ 138.04

685.4 1-[4-(2-{5-[(R)-(1,3-Dimethyl-azetidin-3-yl)-hydroxy-(4-isopropyl-phenyl)-methyl]-pyridin-3-yl}-pyrimidin-5-yl)-3,6-dihydro-2H-pyridin-1-yl]-ethanone The title compound was synthesized like described in Example 683.3 using Example 685.3 and purified by prep LC-MS (VI) then (XX). LC-MS (A) $t_R$=70 min; $[M+H]^+$ 512.11

685.5 1-[4-(2-{5-[(R)-(1,3-Dimethyl-azetidin-3-yl)-hydroxy-(4-isopropyl-phenyl)-methyl]-pyridin-3-yl}-pyrimidin-5-yl)-piperidin-1-yl]-ethanone To a flask already containing Example 685.4 (8 mg) were added Pd/C (1.66 mg) and MeOH (300 μL) at RT under argon. The flask was 3× evacuated and backfilled with argon, then 3× evacuated and backfilled with H2. The resulting mixture was stirred at RT under $H_2$ overnight. The flask was 3× evacuated and backfilled with argon. The reaction mixture was filtrated through a syringe filter, the filter was washed with MeOH and the filtrate was evaporated and dried at HV to 6 mg white solid. LC-MS (A) $t_R$=0.69 min; $[M+H]^+$: 513.72

Example 686: 1-[4-(2-{5-[(R)-(1,3-Dimethyl-azetidin-3-yl)-hydroxy-(4-isopropyl-phenyl)-methyl]-pyridin-3-yl}-pyrimidin-4-yl)-piperidin-1-yl]-ethanone 686.1 4-(2-Chloro-pyrimidin-4-yl)-3,6-dihydro-2H-pyridine-1-carboxylic acid tert-butyl ester The title compound was synthesized following the procedure described in 280, step 1 using 4-bromo-2-chloropyrimidine and 3,6-dihydro-1H-pyridine-1-N-Boc-4-boronic acid, pinacol ester and purified with the adapted gradient (in % B): 30 for 3 CV, 30 to 50 over 3 CV, 50 for 2 CV, 50 to 70 over 2 CV, 70 for 1 CV. LC-MS (A) $t_R$=0.98 min; $[M+H]^+$: 296.06

686.2 2-chloro-4-(1,2,3,6-tetrahydropyridin-4-yl) pyrimidine hydrochloride salt

The title compound was synthesized following the procedure described in F5.56.2 using Example 686.1. LC-MS (A) $t_R$=0.38 min; $[M+H]^+$: 193.14

686.3 1-[4-(2-Chloro-pyrimidin-4-yl)-3,6-dihydro-2H-pyridin-1-yl]-ethanone

The title compound was synthesized following the procedure described in Example F5.54 using Example 686.2. LC-MS (A) $t_R$=0.67 min; $[M+H]^+$: 238.08

686.4 1-[4-(2-{5-[(R)-(1,3-Dimethyl-azetidin-3-yl)-hydroxy-(4-isopropyl-phenyl)-methyl]-pyridin-3-yl}-pyrimidin-4-yl)-3,6-dihydro-2H-pyridin-1-yl]-ethanone The title compound was synthesized like described in Example 683.3 using Example 686.3 and purified by prep LC-MS method (VI). LC-MS (A) $t_R$=0.72 min; $[M+H]^+$: 512.05

686.5 1-[4-(2-{5-[(R)-(1,3-Dimethyl-azetidin-3-yl)-hydroxy-(4-isopropyl-phenyl)-methyl]-pyridin-3-yl}-pyrimidin-4-yl)-piperidin-1-yl]-ethanone The title compound was synthesized following the procedure described in Example 685.5 using 686.4. LC-MS (A) $t_R$=0.71 min; $[M+H]^+$: 513.77.

Depending on the purification conditions, the title compounds/intermediates in Example 332 to 686 may be isolated as free bases or as salts such as formate salts, or hydrochloride salts. Whenever isolating a title compound/intermediate as a salt, formate salt or hydrochloride salt is indicated at the end of the chemical name and can refer to a mono-, di- or tri-formate salt, or mono-, di-, or tri-hydrochloride salt.

II. Biological Assays

FLIPR assay: The bioactivity of compounds is tested in a fluorometric imaging plate reader (FLIPR: Molecular Devices) using engineered HEK-293 cells expressing the human CCR6 (GenBank: AY242126). Frozen cells are plated on Poly-L-Lysine precoated 384-well plates 2 days prior to bioassay in DMEM medium supplemented with 10% FCS and 1% Penicillin-Streptomycin. At the day of bioassay, cell supernatant is discarded and cells are dye loaded for 30 minutes at room temperature in the dark with Fluo-8-AM (Focus Biomolecules) in Hanks Balanced Salt Solution (Gibco), buffered with 20 mM Hepes at pH 6.75 and supplemented with 0.05% BSA. This buffer, but lacking the dye, is also used for washing and compound dilution steps (assay buffer). Cells are washed free of excess dye with a wash-station (Biotek), leaving 40 microliter of assay buffer at the end. Cells were incubated for 15 minutes at room temperature in the dark, before adding compounds. Stock solutions of test compounds are made up at a concentration of 10 mM in DMSO, and serially diluted first in DMSO and then transferred in assay buffer to concentrations required for inhibition dose response curves. After a 45-minute incubation period in assay buffer at room temperature, 10 microliters of each compound dilution are transferred from a compound plate to the plate containing the recombinant cells in the FLIPR instrument according to the manufacturer's instructions. After cells and compounds were preincubated for 30 minutes at room temperature in the dark, 10 microliter agonist CCL20 (Peprotech) at a final concentration of 10 nM is added, again using the FLIPR instrument. Changes in fluorescence are monitored before and after addition of the test compounds and agonist. Emission peak values above base level after CCL20 addition are exported after base line subtraction.

The calculated $IC_{50}$ values may fluctuate depending on the daily assay performance. Fluctuations of this kind are known to those skilled in the art. In the case where $IC_{50}$ values have been determined several times for the same compound, mean values are given. Data are shown in Table 1.

| Example N° | FLIPR $IC_{50}$ (nM) |
|---|---|
| 1 | 114 |
| 2 | 147 |
| 3 | 28 |
| 4 | 36.2 |
| 5 | 33.3 |
| 6 | 47.2 |
| 7 | 54.3 |
| 8 | 110 |
| 9 | 74.7 |
| 10 | 64.1 |
| 11 | 130 |
| 12 | 73.5 |
| 13 | 43.5 |
| 14 | 70.6 |
| 15 | 80.8 |
| 16 | 52 |
| 17 | 53.5 |
| 18 | 33.5 |
| 19 | 44.9 |
| 20 | 23 |
| 21 | 47.9 |
| 22 | 126 |
| 23 | 46.8 |
| 24 | 6.44 |
| 25 | 7.69 |
| 26 | 13 |
| 27 | 43.7 |
| 28 | 44.6 |
| 29 | 85.5 |
| 30 | 33.9 |
| 31 | 81.2 |
| 32 | 18.7 |
| 33 | 20.8 |
| 34 | 21.1 |
| 35 | 141 |
| 36 | 61.7 |
| 37 | 20.7 |
| 38 | 130 |

-continued

| Example N° | FLIPR $IC_{50}$ (nM) |
|---|---|
| 39 | 76.5 |
| 40 | 92.5 |
| 41 | 133 |
| 42 | 41.5 |
| 43 | 55.9 |
| 44 | 63.3 |
| 45 | 32.8 |
| 46 | 145 |
| 47 | 35 |
| 48 | 100 |
| 49 | 219 |
| 50 | 90.2 |
| 51 | 134 |
| 52 | 200 |
| 53 | 46.3 |
| 54 | 66.9 |
| 55 | 65.8 |
| 56 | 61 |
| 57 | 349 |
| 58 | 440 |
| 59 | 7.1 |
| 60 | 9.06 |
| 61 | 19.4 |
| 62 | 242 |
| 63 | 601 |
| 64 | 441 |
| 65 | 44.7 |
| 66 | 223 |
| 67 | 11.8 |
| 68 | 17.9 |
| 69 | 16.1 |
| 70 | 434 |
| 71 | 147 |
| 72 | 15 |
| 73 | 112 |
| 74 | 154 |
| 75 | 184 |
| 76 | 627 |
| 77 | 52.1 |
| 78 | 80.6 |
| 79 | 30 |
| 80 | 10.5 |
| 81 | 19.1 |
| 82 | 185 |
| 83 | 128 |
| 84 | 52.8 |
| 85 | 89.9 |
| 86 | 75.3 |
| 87 | 61.5 |
| 88 | 98.4 |
| 89 | 231 |
| 90 | 163 |
| 91 | 46.2 |
| 92 | 81.5 |
| 93 | 86.8 |
| 94 | 71.1 |
| 95 | 196 |
| 96 | 130 |
| 97 | 71.3 |
| 98 | 60 |
| 99 | 111 |
| 100 | 69.9 |
| 101 | 41.8 |
| 102 | 103 |
| 103 | 110 |
| 104 | 42.2 |
| 105 | 43.4 |
| 106 | 46.7 |
| 107 | 54.3 |
| 108 | 21 |
| 109 | 21.2 |
| 110 | 39.1 |
| 111 | 43 |
| 112 | 38.5 |
| 113 | 29.8 |
| 114 | 38 |

-continued

| Example N° | FLIPR $IC_{50}$ (nM) |
|---|---|
| 115 | 41 |
| 116 | 40.8 |
| 117 | 20.1 |
| 118 | 43.1 |
| 119 | 20.5 |
| 120 | 59.2 |
| 121 | 57.7 |
| 122 | 42.1 |
| 123 | 46.9 |
| 124 | 35.9 |
| 125 | 46.9 |
| 126 | 84.9 |
| 127 | 32.4 |
| 128 | 40.3 |
| 129 | 35.9 |
| 130 | 74.7 |
| 131 | 60.8 |
| 132 | 50.1 |
| 133 | 74.5 |
| 134 | 62 |
| 135 | 74 |
| 136 | 123 |
| 137 | 60.3 |
| 138 | 45.8 |
| 139 | 66.6 |
| 140 | 681 |
| 141 | 211 |
| 142 | 274 |
| 143 | 188 |
| 144 | 376 |
| 145 | 274 |
| 146 | 309 |
| 147 | 63.5 |
| 148 | 138 |
| 149 | 149 |
| 150 | 35.8 |
| 151 | 336 |
| 152 | 60.2 |
| 153 | 214 |
| 154 | 36.8 |
| 155 | 28 |
| 156 | 147 |
| 157 | 27.7 |
| 158 | 222 |
| 159 | 91.6 |
| 160 | 82.9 |
| 161 | 202 |
| 162 | 43.4 |
| 163 | 24.6 |
| 164 | 18.9 |
| 165 | 677 |
| 166 | 85.3 |
| 167 | 66.9 |
| 168 | 109 |
| 169 | 101 |
| 170 | 133 |
| 171 | 34.7 |
| 172 | 205 |
| 173 | 77.9 |
| 174 | 75.2 |
| 175 | 183 |
| 176 | 39.2 |
| 177 | 284 |
| 178 | 47.5 |
| 179 | 64.5 |
| 180 | 55.7 |
| 181 | 295 |
| 182 | 86.5 |
| 183 | 31.7 |
| 184 | 16.5 |
| 185 | 27.9 |
| 186 | 43.5 |
| 187 | 15.8 |
| 188 | 23.4 |
| 189 | 19.1 |
| 190 | 38 |

-continued

| Example N° | FLIPR $IC_{50}$ (nM) |
|---|---|
| 191 | 317 |
| 192 | 85.4 |
| 193 | 184 |
| 194 | 20.5 |
| 195 | 29.3 |
| 196 | 67.6 |
| 197 | 106 |
| 198 | 70.8 |
| 199 | 487 |
| 200 | 407 |
| 201 | 159 |
| 202 | 29.9 |
| 203 | 64.9 |
| 204 | 48.2 |
| 205 | 26.9 |
| 206 | 89 |
| 207 | 52.5 |
| 208 | 38.4 |
| 209 | 205 |
| 210 | 326 |
| 211 | 50.1 |
| 212 | 70.8 |
| 213 | 459 |
| 214 | 184 |
| 215 | 50.9 |
| 216 | 476 |
| 217 | 43.3 |
| 218 | 60.4 |
| 219 | 135 |
| 220 | 214 |
| 221 | 350 |
| 222 | 164 |
| 223 | 29 |
| 224 | 48.5 |
| 225 | 83.3 |
| 226 | 26.6 |
| 227 | 26.1 |
| 228 | 44.6 |
| 229 | 59.1 |
| 230 | 36.7 |
| 231 | 14.9 |
| 232 | 46.7 |
| 233 | 29.7 |
| 234 | 123 |
| 235 | 23.4 |
| 236 | 210 |
| 237 | 217 |
| 238 | 22.4 |
| 239 | 283 |
| 240 | 82.9 |
| 241 | 128 |
| 242 | 22.1 |
| 243 | 211 |
| 244 | 274 |
| 245 | 26 |
| 246 | 33.3 |
| 247 | 250 |
| 248 | 247 |
| 249 | 78.4 |
| 250 | 10.9 |
| 251 | 8.25 |
| 252 | 238 |
| 253 | 13.1 |
| 254 | 19.3 |
| 255 | 774 |
| 256 | 57.8 |
| 257 | 87.4 |
| 258 | 15.5 |
| 259 | 56.7 |
| 260 | 324 |
| 261 | 206 |
| 262 | 72.6 |
| 263 | 162 |
| 264 | 167 |
| 265 | 90.6 |
| 266 | 79.1 |

-continued

| Example N° | FLIPR $IC_{50}$ (nM) |
|---|---|
| 267 | 103 |
| 268 | 99.3 |
| 269 | 224 |
| 270 | 27.4 |
| 271 | 36.5 |
| 272 | 485 |
| 273 | 32 |
| 274 | 252 |
| 275 | 67.1 |
| 276 | 413 |
| 277 | 42.2 |
| 278 | 48.9 |
| 279 | 166 |
| 280 | 37.4 |
| 281 | 82.2 |
| 282 | 44.3 |
| 283 | 61.6 |
| 284 | 222 |
| 285 | 78 |
| 286 | 36.3 |
| 287 | 42.8 |
| 288 | 33.9 |
| 289 | 82.4 |
| 290 | 100 |
| 291 | 24.8 |
| 292 | 748 |
| 293 | 246 |
| 294 | 49.4 |
| 295 | 61.1 |
| 296 | 118 |
| 297 | 93.5 |
| 298 | 65.2 |
| 299 | 80.6 |
| 300 | 40.8 |
| 301 | 60 |
| 302 | 44.5 |
| 303 | 30.7 |
| 304 | 385 |
| 305 | 121 |
| 306 | 101 |
| 307 | 567 |
| 308 | 515 |
| 309 | 58.6 |
| 310 | 48.6 |
| 311 | 140 |
| 312 | 23.9 |
| 313 | 158 |
| 314 | 111 |
| 315 | 23.6 |
| 316 | 23.4 |
| 317 | 15.2 |
| 318 | 154 |
| 319 | 94.4 |
| 320 | 86 |
| 321 | 273 |
| 322 | 49.9 |
| 323 | 67.8 |
| 324 | 15 |
| 325 | 595 |
| 326 | 83.3 |
| 327 | 168 |
| 328 | 187 |
| 329 | 485 |
| 330 | 143 |
| 331 | 50.1 |
| 332 | 290 |
| 333 | 112.8 |
| 334 | 216 |
| 335 | 337 |
| 336 | 207 |
| 337 | 95.1 |
| 338 | 93.8 |
| 339 | 100.4 |
| 340 | 79.4 |
| 341 | 66.6 |
| 342 | 154 |

-continued

| Example N° | FLIPR $IC_{50}$ (nM) |
|---|---|
| 343 | 532 |
| 344 | 441 |
| 345 | 252 |
| 346 | 62.5 |
| 347 | 120 |
| 348 | 135 |
| 349 | 113 |
| 350 | 242 |
| 351 | 27.6 |
| 352 | 110 |
| 353 | 40.3 |
| 354 | 29.0 |
| 355 | 24.8 |
| 356 | 12.7 |
| 357 | 26.1 |
| 358 | 131 |
| 359 | 234 |
| 360 | 292 |
| 361 | 164 |
| 362 | 90.0 |
| 363 | 178 |
| 364 | 142 |
| 365 | 147 |
| 366 | 165 |
| 367 | 321 |
| 368 | 271 |
| 369 | 187 |
| 370 | 65.9 |
| 371 | 49.7 |
| 372 | 102.8 |
| 373 | 88.9 |
| 374 | 39.0 |
| 375 | 39.7 |
| 376 | 102 |
| 377 | 39.5 |
| 378 | 54.9 |
| 379 | 41.2 |
| 380 | 71.5 |
| 381 | 53.4 |
| 382 | 43.7 |
| 383 | 53.8 |
| 384 | 42.1 |
| 385 | 117 |
| 386 | 41.0 |
| 387 | 55.1 |
| 388 | 28.2 |
| 389 | 58.1 |
| 390 | 175 |
| 391 | 58.8 |
| 392 | 24.2 |
| 393 | 25.1 |
| 394 | 1040 |
| 395 | 60.1 |
| 396 | 34.4 |
| 397 | 29.1 |
| 398 | 51.8 |
| 399 | 106.6 |
| 400 | 160 |
| 401 | 117 |
| 402 | 88.3 |
| 403 | 40.4 |
| 404 | 164 |
| 405 | 102 |
| 406 | 37.6 |
| 407 | 51.8 |
| 408 | 138 |
| 409 | 48.8 |
| 410 | 84.9 |
| 411 | 86.3 |
| 412 | 90.0 |
| 413 | 36.7 |
| 414 | 34.7 |
| 415 | 61.9 |
| 416 | 14.7 |
| 417 | 118 |
| 418 | 190 |

-continued

| Example N° | FLIPR $IC_{50}$ (nM) |
|---|---|
| 419 | 155 |
| 420 | 277 |
| 421 | 712 |
| 422 | 66.7 |
| 423 | 61.8 |
| 424 | 107 |
| 425 | 1730 |
| 426 | 17.7 |
| 427 | 292 |
| 428 | 598 |
| 429 | 103 |
| 430 | 209 |
| 431 | 197 |
| 432 | 146 |
| 433 | 58.5 |
| 434 | 147 |
| 435 | 175 |
| 436 | 114.7 |
| 437 | 95.2 |
| 438 | 53.6 |
| 439 | 265 |
| 440 | 50.7 |
| 441 | 118 |
| 442 | 177 |
| 443 | 35.3 |
| 444 | 33.4 |
| 445 | 44.8 |
| 446 | 48.4 |
| 447 | 43.2 |
| 448 | 35.2 |
| 449 | 40.8 |
| 450 | 57.8 |
| 451 | 43.5 |
| 452 | 33.6 |
| 453 | 58.1 |
| 454 | 103 |
| 455 | 83.1 |
| 456 | 201 |
| 457 | 56.4 |
| 458 | 99.0 |
| 459 | 440 |
| 460 | 469 |
| 461 | 384 |
| 462 | 286 |
| 463 | 122 |
| 464 | 129 |
| 465 | 87.5 |
| 466 | 143 |
| 467 | 129 |
| 468 | 62.3 |
| 469 | 137 |
| 470 | 131 |
| 471 | 125 |
| 472 | 79.8 |
| 473 | 77.6 |
| 474 | 121 |
| 475 | 54.7 |
| 476 | 112 |
| 477 | 33.9 |
| 478 | 88.9 |
| 479 | 111.8 |
| 480 | 128 |
| 481 | 184 |
| 482 | 92.3 |
| 483 | 73.1 |
| 484 | 593 |
| 485 | 259 |
| 486 | 287 |
| 487 | 248 |
| 488 | 382 |
| 489 | 135 |
| 490 | 143 |
| 491 | 172 |
| 492 | 267 |
| 493 | 185 |
| 494 | 240 |

-continued

| Example N° | FLIPR $IC_{50}$ (nM) |
|---|---|
| 495 | 20.9 |
| 496 | 69.7 |
| 497 | 74.3 |
| 498 | 234 |
| 499 | 53.8 |
| 500 | 149.5 |
| 501 | 108 |
| 502 | 65.8 |
| 503 | 51.1 |
| 504 | 143 |
| 505 | 35.9 |
| 506 | 24.0 |
| 507 | 32.7 |
| 508 | 49.1 |
| 509 | 208 |
| 510 | 184.5 |
| 511 | 133 |
| 512 | 61.1 |
| 513 | 101 |
| 514 | 142.5 |
| 515 | 181 |
| — | |
| 516 | 104 |
| 517 | 63.5 |
| 518 | 41.2 |
| 519 | 168 |
| 520 | 62.6 |
| 521 | 153 |
| 522 | 119 |
| 523 | 297 |
| 524 | 178 |
| 525 | 187 |
| 526 | 171 |
| 527 | 74.3 |
| 528 | 66.9 |
| 529 | 134 |
| 530 | 58.7 |
| 531 | 90 |
| 532 | 718 |
| 533 | 1020 |
| 534 | 47.0 |
| 535 | 331 |
| 536 | 2450 |
| 537 | 152 |
| 538 | 144.8 |
| 539 | 56.0 |
| 540 | 122 |
| 541 | 452 |
| 542 | 34.8 |
| 543 | 22.8 |
| 544 | 257 |
| 545 | 61.0 |
| 546 | 776 |
| 547 | 797 |
| 548 | 742 |
| 549 | 58.2 |
| 550 | 70.8 |
| 551 | 135 |
| 552 | 76.8 |
| 553 | 62.3 |
| 554 | 117 |
| 555 | 986 |
| 556 | 615 |
| 557 | 46.3 |
| 558 | 84.5 |
| 559 | 85.6 |
| 560 | 74.6 |
| 561 | 766 |
| 562 | 44.7 |
| 563 | 45.2 |
| 564 | 91.9 |
| 565 | 116 |
| 566 | 209 |
| 567 | 59.1 |
| 568 | 97.6 |
| 569 | 118 |

-continued

| Example N° | FLIPR $IC_{50}$ (nM) |
|---|---|
| 570 | 65.8 |
| 571 | 1190 |
| 572 | 149 |
| 573 | 75.9 |
| 574 | 1340 |
| 575 | 103 |
| 576 | 267 |
| 577 | 66.1 |
| 578 | 97.2 |
| 579 | 411 |
| 580 | 294 |
| 581 | 113 |
| 582 | 485 |
| 583 | 239 |
| 584 | 130 |
| 585 | 116 |
| 586 | 67.0 |
| 587 | 14.8 |
| 588 | 119 |
| 589 | 154 |
| 590 | 235 |
| 591 | 71.6 |
| 592 | 44.8 |
| 593 | 51.6 |
| 594 | 45.4 |
| 595 | 93.2 |
| 596 | 117 |
| 597 | 395 |
| 598 | 94.8 |
| 599 | 149 |
| 600 | 45.7 |
| 601 | 75.5 |
| 602 | 39.5 |
| 603 | 31.2 |
| 604 | 18.9 |
| 605 | 78.6 |
| 606 | 22.6 |
| 607 | 104 |
| 608 | 43.5 |
| 609 | 656 |
| 610 | 426 |
| 611 | 74.9 |
| 612 | 58.5 |
| 613 | 11.1 |
| 614 | 12.6 |
| 615 | 39.4 |
| 616 | 102 |
| 617 | 53.5 |
| 618 | 23.3 |
| 619 | 68.8 |
| 620 | 55.3 |
| 621 | 235 |
| 622 | 105 |
| 623 | 44.9 |
| 624 | 81.8 |
| 625 | 107 |
| 626 | 111 |
| 627 | 11.5 |
| 628 | 20.2 |
| 629 | 60.9 |
| 630 | 61.1 |
| 631 | 79.5 |
| 632 | 14.1 |
| 633 | 42.5 |
| 634 | 40.6 |
| 635 | 23.2 |
| 636 | 106.7 |
| 637 | 46.3 |
| 638 | 509 |
| 639 | 96.6 |
| 640 | 169 |
| 641 | 67.0 |
| 642 | 277 |
| 643 | 16.9 |
| 644 | 147 |
| 645 | 110 |

-continued

| Example N° | FLIPR $IC_{50}$ (nM) |
|---|---|
| 646 | 129 |
| 647 | 76.3 |
| 648 | 46.6 |
| 649 | 185 |
| 650 | 15.9 |
| 651 | 16.1 |
| 652 | 10.9 |
| 653 | 10.1 |
| 654 | 46.2 |
| 655 | 55.0 |
| 656 | 208 |
| 657 | 86.6 |
| 658 | 86.6 |
| 659 | 344 |
| 660 | 82.4 |
| 661 | 54.3 |
| 662 | 331 |
| 663 | 992 |
| 664 | 211 |
| 665 | 40.4 |
| 666 | 26.5 |
| 667 | 52.4 |
| 668 | 101 |
| 669 | 62.1 |
| 670 | 42.8 |
| 671 | 50.5 |
| 672 | 172 |
| 673 | 199 |
| 674 | 25.9 |
| 675 | 227 |
| 676 | 108 |
| 677 | 105 |
| 678 | 156 |
| 679 | 222 |
| 680 | 428 |
| 681 | 281 |
| 682 | 7.98 |
| 683 | 105 |
| 684 | 125 |
| 685 | 242 |
| 686 | 145 |
| — | |

The invention claimed is:

1. A compound according to Formula (I)

Formula (I)

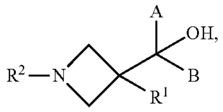

wherein

A represents a 6-membered heteroaryl containing from one to three ring nitrogen atom(s), wherein said 6-membered heteroaryl is unsubstituted, mono-, di- or tri-substituted, wherein the substituent(s), if any, is(are) independently selected from halogen;

cyano;

hydroxy-$C_{1-6}$-alkyl which is optionally substituted with one to three fluorine atoms;

$C_{1-5}$-alkyl which is unsubstituted or mono-substituted with $C_{1-3}$-alkoxy;

$C_{3-6}$-cycloalkyl which is optionally fused with a pyridine ring, wherein said $C_{3-6}$-cycloalkyl is unsubstituted or mono-substituted with hydroxy;

—O—$R^{O1}$, wherein $R^{O1}$ represents $C_{3-6}$-cycloalkyl or pyrrolidinyl which is independently unsubstituted or mono-substituted with $C_{1-3}$-alkyl or $C_{1-4}$-alkyl-carbonyl;

phenyl-$L^1$-, wherein said phenyl is unsubstituted or mono-substituted with fluorine, $C_{1-4}$-alkoxy-carbonyl, or hydroxy-$C_{1-4}$-alkyl; wherein -$L^1$- represents a bond, oxygen, or the group —$CH_2$—O—;

$C_{4-6}$-heterocyclyl containing one or two ring heteroatoms independently selected from nitrogen and oxygen, wherein said $C_{4-6}$-heterocyclyl is unsubstituted, mono-, or di-substituted with oxo, hydroxy, $C_{1-3}$-alkyl, $C_{1-4}$-alkyl-carbonyl, or $C_{1-4}$-alkoxy-carbonyl;

5-membered heteroaryl containing one or two ring nitrogen atoms, wherein said 5-membered heteroaryl is unsubstituted or mono-substituted with $C_{1-3}$-alkyl;

indolyl;

pyrrolopyridinyl;

N—($C_{1-3}$-alkyl)-amino-carbonyl-oxy; or 1-hydroxy-1-$C_{3-5}$-cycloalkyl-1-(pyridinyl)-methyl;

$C_{3-5}$-alkyl which is substituted with hydroxy and $R^{A1}$, wherein said substituents are both at position 3 with respect to the point of attachment of said $C_{3-5}$-alkyl to the rest of the molecule; wherein $R^{A1}$ represents tetrahydropyranyl;

phenyl which is unsubstituted or mono-substituted with fluorine or $C_{1-3}$-alkoxy;

5- or 6-membered heteroaryl containing one or two ring heteroatom(s) being independently selected from nitrogen or sulfur, wherein said 5- or 6-membered heteroaryl is independently unsubstituted, mono- or di-substituted, and wherein the substituent(s), if any, is(are) independently selected from $C_{1-3}$-alkyl, $C_{3-5}$-cycloalkyl, or $C_{1-3}$-alkoxy; or indazolyl;

$C_{3-5}$-alkenyl which is unsubstituted or mono-substituted with hydroxy;

$C_{4-6}$-cycloalkenyl which is unsubstituted, mono-, or di-substituted with $C_{1-3}$-alkyl, oxo, or hydroxy, wherein optionally one ring carbon atom of said $C_{4-6}$-cycloalkenyl is replaced by an oxygen atom;

$C_{3-6}$-cycloalkyl which is unsubstituted, mono-, or di-substituted with $C_{1-3}$-alkyl, hydroxy, or hydroxy-$C_{1-3}$ -alkyl, wherein optionally one ring carbon atom of said $C_{3-6}$-cycloalkyl is replaced by an oxygen atom;

—O—$RO^2$, wherein $RO^2$ represents $C_{1-4}$-alkyl;

$C_{2-5}$-alkyl which is mono-substituted with hydroxy or $C_{1-3}$-alkoxy;

-$L^2$-$CY^2$, wherein $L^2$- independently represents a bond, —$CH_2$—, or —$CH_2$—$CH_2$—; and $CY^2$ independently represents phenyl which is unsubstituted or mono-substituted with hydroxy-$C_{1-3}$-alkyl;

benzyl-oxy;

5- to 6-membered heteroaryl containing one to three ring heteroatom(s) being independently selected from nitrogen, oxygen, or sulfur, wherein said 5- or 6-membered heteroaryl is independently unsubstituted, mono- or di-substituted; wherein the substituent(s), if any, is(are) independently selected from $C_{1-3}$-alkyl or $C_{1-3}$-cycloalkyl;

$C_{3-6}$-cycloalkyl, wherein optionally one carbon ring atom is replaced by one heteroatom selected from oxygen and nitrogen; wherein said $C_{3-6}$-cycloalkyl is unsubstituted, mono-, or di-substituted, wherein the substituents are selected from $C_{1-3}$-alkyl, hydroxy, fluoro, oxo, $C_{1-3}$-alkyl-carbonyl and $C_{1-3}$-alkoxy;

benzooxazolonyl; or chromanyl;

—C≡C—$R^{T1}$, wherein $R^{T1}$ represents $C_{1-4}$-alkyl, wherein said $C_{1-4}$-alkyl independently is mono-substituted with hydroxy;

$C_{1-3}$-alkoxy;

-S(═O)$_2$—$R^{SOT}$, wherein $R^{SOT}$ represents $C_{1-3}$-alkyl, $C_{1-3}$-alkyl-amino, or $C_{3-5}$-cycloalkyl;

-$NR^{NT1}R^{NT2}$ wherein $R^{NT1}$ represents hydrogen and $R^{NT2}$ represents $C_{1-3}$-alkyl-carbonyl, $C_{1-3}$-alkoxy-$C_{1-3}$-alkyl-carbonyl, or $C_{3-5}$-cycloalkyl-carbonyl;

$C_{4-6}$-heterocyclyl containing one or two ring heteroatom(s) independently selected from nitrogen and oxygen; wherein said $C_{4-6}$-heterocyclyl is mono-substituted with oxo; or di-substituted with oxo and one $C_{1-3}$-alkyl; or N—($C_{1-3}$-alkyl-carbonyl)-piperidinyl-$C_{1-3}$-alkyl;

$C_{1-4}$-alkyl which is di-substituted, wherein one substituent is hydroxy, and a second substituent is trifluoromethyl;

$C_{3-6}$-cycloalkyl which is mono-substituted with hydroxy;

amino-sulfonyl which is optionally di-substituted with methyl;

phenyl which is mono-substituted with halogen;

pyridinyl;

pyrimidinyl which is mono-substituted with $C_{1-3}$-alkyl; or oxazolidinonyl;

$C_{3-6}$-cycloalkyl fused with a pyridine ring, wherein said $C_{3-6}$-cycloalkyl is mono-substituted with hydroxy; wherein optionally one ring carbon atom in said $C_{3-6}$-cycloalkyl is replaced by one oxygen atom;

$C_{4-6}$-heterocyclyl containing one ring heteroatom independently selected from nitrogen and oxygen; wherein said $C_{4-6}$-heterocyclyl is mono-, di-, or tri-substituted, wherein the substituent(s) is(are) independently selected from $C_{1-3}$-alkyl, hydroxy, oxo, $C_{1-3}$-alkyl-carbonyl, $C_{1-3}$-alkoxy-carbonyl, $C_{1-3}$-alkyl-sulfonyl, and $C_{1-3}$-alkyl-amino-sulfonyl;

pyrazolyl which is N-substituted with methyl;

indolyl;

3-hydroxy-1-methyl-1,3-dihydro-indol-2-on-3-yl; or 4-hydroxy-3,4-dihydro-2H-pyrano[3,2-b]pyridin-4-yl;

—C≡C—C(OH)($R^{T2}$)($R^{T3}$), wherein $R^{T2}$ represents hydrogen or $C_{1-3}$-alkyl;

$R^{T3}$ represents phenyl which is unsubstituted or mono-substituted, wherein the substituent, if any, is selected from $C_{1-3}$-alkoxy and halogen;

5- to 6-membered heteroaryl containing one or two ring heteroatom(s) being independently selected from nitrogen, oxygen, or sulfur; wherein said 5- or 6-membered heteroaryl is independently unsubstituted, mono- or di-substituted, and wherein the substituent(s), if any, is(are) independently selected from $C_{1-3}$-alkyl, $C_{1-3}$-cycloalkyl, $C_{1-3}$-fluoroalkyl, and $C_{1-3}$-alkoxy;

$C_{4-7}$-heterocyclyl containing one ring heteroatom selected from nitrogen and oxygen; wherein said $C_{4-7}$-heterocyclyl is unsubstituted, mono-, or di-substituted, wherein the substituent(s), if any, is(are) independently selected from $C_{1-3}$-alkyl or $C_{1-3}$-alkyl-carbonyl; or indazolyl;

—$NR^{N3}R^{N4}$ wherein $R^{N3}$ represents $C_{1-3}$-alkyl; and $R^{N4}$ represents hydroxy-$C_{1-3}$-alkyl or 2-(benzyloxy)-$C_{1-3}$-alkyl; or $R^{N3}$ and $R^{N4}$ form, together with the nitrogen to which they are attached, a heterocyclic ring of 4 to 6 members, wherein the members needed to complete said heterocyclic ring are each independently selected from —$CH_2$—, —O—, —(C=O)—, —$CHR^X$— and —$C(R^Y)_2$—; wherein said heterocyclic ring does not contain more than one member independently selected from the group consisting of —O— and —(C=O)—; wherein said heterocyclic ring does not contain more than two members selected from the group consisting of —$CHR^X$—; and wherein said heterocyclic ring does not contain more than two members selected from the group consisting of —$C(R^Y)_2$—; wherein $R^X$ independently represents fluorine, methyl, isopropyl, isobutyl, tert-butyl, hydroxy, trifluoromethyl, hydroxy-methyl, 1-hydroxy-ethyl, 1-hydroxy-1-methyl-ethyl, cyclopropyl, 2-methoxy-ethyl, 2-methyl-thiazol-5-yl, 4-methyl-thiazol-2-yl, phenyl, benzyl, tetrahydropyran-4-yl, N-acetyl-piperidin-4-yl, 1,2,4-oxadiazolyl, 3-methyl-1,2,4-oxadiazol-5-yl, 2-methyl-2H-[1,2,3]triazol-4-yl, 1-methyl-1H-pyrazol-4-yl, 1-difluoromethyl-1H-pyrazol-4-yl, 1,3-dimethyl-1H-pyrazol-4-yl, pyridin-2-yl, 6-methyl-pyridin-3-yl, 6-isopropyl-pyridin-2-yl, 6-trifluoromethyl-pyridin-3-yl, 2-isopropyl-pyrimidin-4-yl, or 1-methoxy-methyl; and wherein $R^Y$ independently represents fluorine, hydroxy, cyclopropyl, methyl, hydroxy-methyl, or trifluoromethyl;

—(C=O)—$N(R^{N5})(R^{N6})$, wherein $R^{N5}$ represents hydrogen; and $R^{N6}$ represents $C_{3-6}$-cycloalkyl or tetrahydropyranyl; or $R^{N5}$ and $R^{N6}$ form, together with the nitrogen to which they are attached, pyrrolidinyl;

piperidin-4-yl or pyrrolidin-3-yl which are mono-substituted at the nitrogen ring atom, wherein the substituent independently is selected from $C_{1-4}$-alkoxy-carbonyl, pyridinyl, phenyl, and 4-methylphenyl-sulfonyl;

5- or 6-membered heteroaryl containing from one to three ring heteroatom(s) independently selected from nitrogen, oxygen and sulfur; wherein said 5- or 6-membered heteroaryl is independently unsubstituted, mono-, di-, or tri-substituted, wherein the substituent(s), if any, is(are) independently selected from $C_{1-4}$-alkyl which is unsubstituted;

mono-substituted with hydroxy;

$C_{1-4}$-alkoxy; or

-$N(R^{N7})(R^{N8})$, wherein $R^{N7}$ represents hydrogen or $C_{1-3}$-alkyl; and $R^{N8}$ independently represent $C_{3-5}$-cycloalkyl-carbonyl, $C_{1-3}$-alkyl, $C_{1-3}$-alkyl-carbonyl including deuterated $C_{1-3}$-alkyl-carbonyl, $C_{1-3}$-alkoxy-$C_{1-3}$-alkyl-carbonyl, tetrahydropyranyl-carbonyl, or hydroxy-$C_{1-3}$-alkyl-carbonyl;

di-substituted, wherein one substituent is hydroxy, and another substituent is trifluoromethyl; or two substituents are hydroxy; or di- or tri-substituted, wherein two substituents are fluorine and, if present, one substituent is hydroxy;

-$L^3$-$CY^3$, wherein

-$L^3$- independently represents a bond, —$CH_2$—, —$CH_2$—$CH_2$—, —$C(CH_3)_2$—, —CH(OH)—, or —O—$CH_2$—, wherein when -$L^3$- is —O—$CH_2$—, said $CY^3$ is attached to the oxygen atom of said —O—$CH_2$—; and $CY^3$ independently represents $C_{4-6}$-heterocyclyl, said $C_{4-6}$-heterocyclyl containing one or two ring heteroatoms independently selected from nitrogen and oxygen; wherein said $CY^3$ independently is unsubstituted, mono-, di-, or tri-substituted, wherein the substituents are independently selected from halogen;

oxo;

hydroxy;

$C_{1-3}$-alkyl which is optionally mono-substituted with $C_{1-3}$-alkoxy;

$C_{1-3}$-alkoxy;

-(C=O)—$R^{CO}$, wherein $R^{CO}$ represents $C_{1-3}$-alkyl which is optionally mono-substituted with hydroxy or $C_{1-3}$-alkoxy;

$C_{1-3}$-fluoroalkyl;

$C_{1-3}$-alkoxy, wherein said $C_{1-3}$-alkoxy is optionally mono-substituted with $C_{1-3}$-alkoxy;

$C_{3-6}$-cycloalkyl-$(CH_2)n$-, wherein optionally one or two carbon ring atom(s) is/are replaced by one or two oxygen ring atom(s); wherein n represents the integer 0, 1, or 2; or phenyl;

-$N(R^{N9})(R^{N10})$, wherein $R^{N9}$ represents hydrogen or $C_{1-3}$-alkyl; and $R^{N10}$ represents $C_{1-3}$-alkyl, $C_{1-3}$-alkyl-carbonyl, $C_{1-3}$-alkyl-sulfonyl, $C_{1-3}$-alkoxy-carbonyl, $C_{1-3}$-alkoxy-$C_{1-3}$-alkyl-carbonyl, or tetrahydropyranyl-carbonyl;

-$S(=O)_2$—$R^{SO}$, wherein $R^{SO}$ represents $C_{1-3}$-alkyl which is optionally mono-substituted with hydroxy, $C_{1-3}$-alkoxy, or amino; or $C_{3-5}$-cycloalkyl, wherein optionally one carbon ring atom is replaced by one oxygen ring atom;

5-membered heteroaryl containing one ring heteroatom selected from nitrogen, oxygen, and sulfur; wherein said 5-membered heteroaryl is unsubstituted; and phenyl-$(CH_2)_p$—, wherein p represents the integer 0, 1, or 2;

phenyl or 6-membered heteroaryl containing one or two ring nitrogen atom(s); wherein said phenyl or 6-membered heteroaryl is independently unsubstituted or mono-substituted with $C_{1-3}$-alkyl or $C_{1-3}$-alkoxy;

pyrazolyl-$C_{1-3}$-alkyl;

$C_{1-3}$-alkyl-sulfonyl-$C_{1-3}$-alkyl;

3-hydroxymethyl-bicyclo[1.1.1]pent-1-yl;

7-oxa-bicyclo[2.2.1]hept-2-yl; and 6-oxa-spiro[2.5]oct-1-yl;

5-oxo-4-oxa-6-azaspiro[2.4]hept-6-yl, 5-aza-spiro[2.4]heptan-6-on-5yl, 2,2-dimethyl-6-oxo-5-oxa-7-azaspiro[3.4]oct-7-yl, 2-cyclopropyl-6-oxo-5-oxa-7-azaspiro[3.4]oct-7-yl, 2-oxo-1-oxa-3-azaspiro[4.4]non-3-yl, 8,8-difluoro-2-oxo-1-oxa-3-azaspiro[4.5]dec-3-yl, or 8-oxo-7-oxa-9-azadispiro[3.1.4.1]undec-9-yl;

7-aza-bicyclo[2.2.1]hept-7-yl, 2-oxa-5-aza-bicyclo[2.2.1]hept-5-yl, 6-oxa-3-aza-bicyclo[3.1.1]hept-3-yl, or 8-oxa-3-azabicyclo[3.2.1]oct-3-yl;

5-oxo-6-azaspiro[3.4]oct-6-yl, 3-oxo-2-azaspiro[4.4]non-2-yl, 1-oxa-3-aza-spiro[4.5]decan-2-on-3-yl, 1-oxo-2-azaspiro[4.5]dec-2-yl, 1-oxo-8-oxa-2-azaspiro[4.5]dec-2-yl, 3-oxo-8-oxa-2-azaspiro[4.5]dec-2-yl, or 4-oxo-hexahydro-5H-furo[2,3-c]pyrrol-5-yl;

3-(7-hydroxy-6,7-dihydro-5H-cyclopenta[b]pyridin-7-yl)propyl or 3-(8-hydroxy-5,6,7,8-tetrahydroquinolin-8-yl)propyl);

6-acetyl-5,6,7,8-tetrahydro-1,6-naphthyridine-2-yl;

2-(6,7-dihydro-5H-[1]pyrindin-7-ol)-ethyl;

2-(8-hydroxy-5,6,7,8-tetrahydro-quinolin-8-yl)-ethyl;

2,3-dihydro-isoindol-1-on-2-yl; and 6-acetyl-7,8-dihydro-5H-pyrido[4,3-d]pyrimidin-2-yl;

B represents phenyl, which is unsubstituted, mono-, di- or tri-substituted, wherein a first substituent, if present, is selected from halogen;

$C_{1-5}$-alkyl;

$C_{2-4}$-alkenyl;

$C_{1-3}$-alkoxy;

$C_{1-3}$-alkoxy-$C_{1-4}$-alkyl;

$C_{1-4}$-fluoroalkyl;

$C_{3-5}$-cycloalkyl which independently is unsubstituted or mono-substituted with $C_{1-3}$-alkyl or $C_{1-3}$-fluoroalkyl;

—$SF_5$;

bicyclo[1.1.1]pent-1-yl;

$C_{3-5}$-cycloalkoxy; and $C_{1-3}$-fluoroalkoxy;

and the remaining substituent/s of B, if present, independently is/are selected from halogen and $C_{1-3}$-alkyl;

or B represents benzothiophenyl or naphthalenyl;

$R^1$ represents $C_{1-3}$-alkyl, cyano, or halogen; and $R^2$ represents $C_{1-4}$-alkyl, $C_{3-5}$-cycloalkyl, $C_{3-5}$-cycloalkyl-$C_{1-3}$-alkyl, hydroxy-$C_{1-3}$-alkyl, $C_{1-3}$-alkoxy-$C_{1-3}$-alkyl, or $C_{1-3}$-fluoroalkyl;

or a pharmaceutically acceptable salt thereof.

2. A compound according to claim 1, wherein A represents pyridin-3-yl, wherein A is mono-substituted in meta-position of A with respect to the point of attachment of A to the rest of the molecule, wherein the substituent is as defined in claim 1; or a pharmaceutically acceptable salt thereof.

3. A compound according to claim 1, wherein said substituent of A or at least one of said substituents of A is 5- or 6-membered heteroaryl as defined in claim 1, wherein the substituent(s) of said 5- or 6-membered heteroaryl, if any, is(are) independently selected from the optionally substituted $C_{1-4}$-alkyl as defined in claim 1; or a pharmaceutically acceptable salt thereof.

4. A compound according to claim 3, wherein said substituent of A or at least one of said substituents of A is 5- or 6-membered heteroaryl containing from one to three ring heteroatom(s) independently selected from nitrogen, oxygen and sulfur; wherein said 5- or 6-membered heteroaryl is independently unsubstituted, mono-, di-, or tri-substituted, wherein the substituent(s), if any, is(are) independently selected from $C_{1-4}$-alkyl which is unsubstituted;

mono-substituted with hydroxy; or $C_{1-4}$-alkoxy;

di-substituted, wherein one substituent is hydroxy, and another substituent is trifluoromethyl; or two substituents are hydroxy; or di- or tri-substituted, wherein two substituents are fluorine and, if present, one substituent is hydroxy;

or a pharmaceutically acceptable salt thereof.

5. A compound according to claim 3, wherein said substituent of A or at least one of said substituents of A is 1,2,4-oxadiazol-5-yl or 1,2,4-oxadiazol-3-yl, wherein said oxadiazolyl groups are mono-substituted, wherein the substituent is independently selected from $C_{1-4}$-alkyl which is mono-substituted with hydroxy or $C_{1-4}$-alkoxy;

or a pharmaceutically acceptable salt thereof.

6. A compound according to claim 1, wherein B represents phenyl, which is mono-, di- or tri-substituted, wherein a first substituent is attached in para-position with respect to the point of attachment of B to the rest of molecule, wherein said substituent is selected from $C_{1-5}$-alkyl;

$C_{1-3}$-alkoxy-$C_{1-4}$-alkyl;

$C_{1-2}$-fluoroalkyl;

$C_{3-5}$-cycloalkyl which is unsubstituted or mono-substituted with $C_{1-3}$-alkyl or $C_{1-3}$-fluoroalkyl; and $C_1$-fluoroalkoxy;

and the remaining substituent(s) of B, if present, independently is/are selected from halogen;

or a pharmaceutically acceptable salt thereof.

7. A compound according to claim 1, wherein $R^1$ represents methyl; or a pharmaceutically acceptable salt thereof.

8. A compound according to claim 1, wherein $R^2$ represents $C_{1-4}$-alkyl, $C_{3-5}$-cycloalkyl, $C_{3-5}$-cycloalkyl-$C_{1-3}$-alkyl, or $C_{1-3}$-fluoroalkyl; or a pharmaceutically acceptable salt thereof.

9. A compound according to claim 1, which is also a compound of Formula (II)

Formula (II)

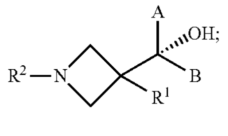

or a pharmaceutically acceptable salt thereof.

10. A compound according to claim 1 which is:

(3-Fluoro-1-methyl-azetidin-3-yl)-(5-pyrrolidin-1-yl-pyridin-3-yl)-(4-trifluoromethoxy-phenyl)-methanol;

3-[Hydroxy-(5-pyrrolidin-1-yl-pyridin-3-yl)-(4-trifluoromethoxy-phenyl)-methyl]-1-methyl-azetidine-3-carbonitrile;

(R)-(1-Ethyl-3-methyl-azetidin-3-yl)-(5-pyrrolidin-1-yl-pyridin-3-yl)-(4-trifluoromethoxy-phenyl)-methanol;

(R)-(3-Methyl-1-propyl-azetidin-3-yl)-(5-pyrrolidin-1-yl-pyridin-3-yl)-(4-trifluoromethoxy-phenyl)-methanol;

(R)-(1-Isopropyl-3-methyl-azetidin-3-yl)-(5-pyrrolidin-1-yl-pyridin-3-yl)-(4-trifluoromethoxy-phenyl)-methanol;

(R)-(1-Cyclopropylmethyl-3-methyl-azetidin-3-yl)-(5-pyrrolidin-1-yl-pyridin-3-yl)-(4-trifluoromethoxy-phenyl)-methanol;

(R)-(1-Cyclobutyl-3-methyl-azetidin-3-yl)-(5-pyrrolidin-1-yl-pyridin-3-yl)-(4-trifluoromethoxy-phenyl)-methanol;

(R)-(1-Isobutyl-3-methyl-azetidin-3-yl)-(5-pyrrolidin-1-yl-pyridin-3-yl)-(4-trifluoromethoxy-phenyl)-methanol;

(R)-(1-Cyclopropyl-3-methyl-azetidin-3-yl)-(5-pyrrolidin-1-yl-pyridin-3-yl)-(4-trifluoromethoxy-phenyl)-methanol;

(R)-[1-(2-Fluoro-ethyl)-3-methyl-azetidin-3-yl]-(5-pyrrolidin-1-yl-pyridin-3-yl)-(4-trifluoromethoxy-phenyl)-methanol;

(R)-[1-(2,2-Difluoro-ethyl)-3-methyl-azetidin-3-yl]-(5-pyrrolidin-1-yl-pyridin-3-yl)-(4-trifluoromethoxy-phenyl)-methanol;

(R)-(1-tert-Butyl-3-methyl-azetidin-3-yl)-(5-pyrrolidin-1-yl-pyridin-3-yl)-(4-trifluoromethoxy-phenyl)-methanol;

(1,3-Dimethyl-azetidin-3-yl)-(4-isopropyl-phenyl)-[5-(3-methoxy-prop-1-ynyl)-pyridin-3-yl]-methanol;

3-{5-[(R)-(1,3-Dimethyl-azetidin-3-yl)-hydroxy-(4-isopropyl-phenyl)-methyl]-pyridin-3-yl}-prop-1-yn-1-ol;

4-{5-[(R)-(1,3-Dimethyl-azetidin-3-yl)-hydroxy-(4-isopropyl-phenyl)-methyl]-pyridin-3-yl}-2-methyl-but-3-yn-2-ol;

(R)-4-{5-[(R)-(1,3-Dimethyl-azetidin-3-yl)-hydroxy-(4-isopropyl-phenyl)-methyl]-pyridin-3-yl}-but-3-yn-2-ol;

(S)-4-{5-[(R)-(1,3-Dimethyl-azetidin-3-yl)-hydroxy-(4-isopropyl-phenyl)-methyl]-pyridin-3-yl}-but-3-yn-2-ol;

1-{5-[(R)-(1,3-Dimethyl-azetidin-3-yl)-hydroxy-(4-isopropyl-phenyl)-methyl]-pyridin-3-ylethynyl}-cyclopentanol;

1-{5-[(R)-(1,3-Dimethyl-azetidin-3-yl)-hydroxy-(4-isopropyl-phenyl)-methyl]-pyridin-3-ylethynyl}-cyclopropanol;

3-{5-[(R)-(1,3-Dimethyl-azetidin-3-yl)-hydroxy-(4-isopropyl-phenyl)-methyl]-pyridin-3-ylethynyl}-3-hydroxy-azetidine-1-carboxylic acid tert-butyl ester;

1-{5-[(R)-(1,3-Dimethyl-azetidin-3-yl)-hydroxy-(4-isopropyl-phenyl)-methyl]-pyridin-3-ylethynyl}-cyclobutanol;

4-{5-[(R)-(1,3-Dimethyl-azetidin-3-yl)-hydroxy-(4-isopropyl-phenyl)-methyl]-pyridin-3-yl}-but-3-yn-1-ol;

(R)-(1,3-Dimethyl-azetidin-3-yl)-(4-isopropyl-phenyl)-[5-(1-methyl-1H-pyrazol-4-ylethynyl)-pyridin-3-yl]-methanol;

3-{5-[(R)-(1,3-Dimethyl-azetidin-3-yl)-hydroxy-(4-isopropyl-phenyl)-methyl]-pyridin-3-yl}-1-phenyl-prop-2-yn-1-ol;

4-{5-[(R)-(1,3-Dimethyl-azetidin-3-yl)-hydroxy-(4-isopropyl-phenyl)-methyl]-pyridin-3-yl}-2-phenyl-but-3-yn-2-ol;

1-{5-[(R)-(1,3-Dimethyl-azetidin-3-yl)-hydroxy-(4-isopropyl-phenyl)-methyl]-pyridin-3-yl}-4-methyl-pent-1-yn-3-ol;

4-{5-[(R)-(1,3-Dimethyl-azetidin-3-yl)-hydroxy-(4-isopropyl-phenyl)-methyl]-pyridin-3-ylethynyl}-tetrahydro-pyran-4-ol;

3-{5-[(R)-(1,3-Dimethyl-azetidin-3-yl)-hydroxy-(4-isopropyl-phenyl)-methyl]-pyridin-3-yl}-1-(tetrahydro-pyran-4-yl)-prop-2-yn-1-ol;

3-{5-[(R)-(1,3-Dimethyl-azetidin-3-yl)-hydroxy-(4-isopropyl-phenyl)-methyl]-pyridin-3-yl}-1-(1,3-dimethyl-1H-pyrazol-4-yl)-prop-2-yn-1-ol;

(R)-(1,3-Dimethyl-azetidin-3-yl)-(4-isopropyl-phenyl)-[5-(tetrahydro-pyran-4-ylethynyl)-pyridin-3-yl]-methanol;

3-{5-[(R)-(1,3-Dimethyl-azetidin-3-yl)-hydroxy-(4-isopropyl-phenyl)-methyl]-pyridin-3-yl}-1-(2-methyl-thiazol-4-yl)-prop-2-yn-1-ol;

4-{5-[(R)-(1,3-Dimethyl-azetidin-3-yl)-hydroxy-(4-isopropyl-phenyl)-methyl]-pyridin-3-yl}-2-(3-fluoro-phenyl)-but-3-yn-2-ol;

4-{5-[(R)-(1,3-Dimethyl-azetidin-3-yl)-hydroxy-(4-isopropyl-phenyl)-methyl]-pyridin-3-yl}-2-(4-methoxy-phenyl)-but-3-yn-2-ol;

4-{5-[(R)-(1,3-Dimethyl-azetidin-3-yl)-hydroxy-(4-isopropyl-phenyl)-methyl]-pyridin-3-yl}-2-(2-methoxy-phenyl)-but-3-yn-2-ol;

4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(2-methyl-thiazol-4-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(6-methoxy-pyridin-2-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-pyrimidin-2-yl-but-3-yn-2-ol;

4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-but-3-yn-2-ol;

3-{5-[(R)-(1,3-Dimethyl-azetidin-3-yl)-hydroxy-(4-isopropyl-phenyl)-methyl]-pyridin-3-yl}-1-(1,5-dimethyl-1H-pyrazol-3-yl)-prop-2-yn-1-ol;

8-{5-[(R)-(1,3-Dimethyl-azetidin-3-yl)-hydroxy-(4-isopropyl-phenyl)-methyl]-pyridin-3-ylethynyl}-5,6,7,8-tetrahydro-quinolin-8-ol;

7-{5-[(R)-(1,3-Dimethyl-azetidin-3-yl)-hydroxy-(4-isopropyl-phenyl)-methyl]-pyridin-3-ylethynyl}-6,7-dihydro-5H-[1]pyrindin-7-ol;

1-{5-[(R)-(1,3-Dimethyl-azetidin-3-yl)-hydroxy-(4-isopropyl-phenyl)-methyl]-pyridin-3-yl}-3-pyridin-2-yl-pent-1-yn-3-ol;

1-{5-[(R)-(1,3-Dimethyl-azetidin-3-yl)-hydroxy-(4-isopropyl-phenyl)-methyl]-pyridin-3-yl}-3-(6-methoxy-pyridin-2-yl)-pent-1-yn-3-ol;

1-(3-{5-[(R)-(1,3-Dimethyl-azetidin-3-yl)-hydroxy-(4-isopropyl-phenyl)-methyl]-pyridin-3-ylethynyl}-3-hydroxy-azetidin-1-yl)-2-methyl-propan-1-one;

(R)-(1,3-Dimethyl-azetidin-3-yl)-[5-(1H-indol-2-ylethynyl)-pyridin-3-yl]-(4-isopropyl-phenyl)-methanol;

(1,3-Dimethyl-azetidin-3-yl)-(4-isopropyl-phenyl)-[5-(3-methoxy-propyl)-pyridin-3-yl]-methanol;

3-{5-[(R)-(1,3-Dimethyl-azetidin-3-yl)-hydroxy-(4-isopropyl-phenyl)-methyl]-pyridin-3-yl}-propan-1-ol;

4-{5-[(R)-(1,3-Dimethyl-azetidin-3-yl)-hydroxy-(4-isopropyl-phenyl)-methyl]-pyridin-3-yl}-2-methyl-butan-2-ol;

(S)-4-{5-[(R)-(1,3-Dimethyl-azetidin-3-yl)-hydroxy-(4-isopropyl-phenyl)-methyl]-pyridin-3-yl}-butan-2-ol;

(R)-4-{5-[(R)-(1,3-Dimethyl-azetidin-3-yl)-hydroxy-(4-isopropyl-phenyl)-methyl]-pyridin-3-yl}-butan-2-ol;

1-(2-{5-[(R)-(1,3-Dimethyl-azetidin-3-yl)-hydroxy-(4-isopropyl-phenyl)-methyl]-pyridin-3-yl}-ethyl)-cyclopentanol;

1-(2-{5-[(R)-(1,3-Dimethyl-azetidin-3-yl)-hydroxy-(4-isopropyl-phenyl)-methyl]-pyridin-3-yl}-ethyl)-cyclopropanol;

3-(2-{5-[(R)-(1,3-Dimethyl-azetidin-3-yl)-hydroxy-(4-isopropyl-phenyl)-methyl]-pyridin-3-yl}-ethyl)-3-hydroxy-azetidine-1-carboxylic acid tert-butyl ester;

1-(2-{5-[(R)-(1,3-Dimethyl-azetidin-3-yl)-hydroxy-(4-isopropyl-phenyl)-methyl]-pyridin-3-yl}-ethyl)-cyclobutanol;

4-{5-[(R)-(1,3-Dimethyl-azetidin-3-yl)-hydroxy-(4-isopropyl-phenyl)-methyl]-pyridin-3-yl}-butan-1-ol;

(R)-(1,3-Dimethyl-azetidin-3-yl)-(4-isopropyl-phenyl)-{5-[2-(1-methyl-1H-pyrazol-4-yl)-ethyl]-pyridin-3-yl}-methanol;

3-{5-[(R)-(1,3-Dimethyl-azetidin-3-yl)-hydroxy-(4-isopropyl-phenyl)-methyl]-pyridin-3-yl}-1-phenyl-propan-1-ol;

4-{5-[(R)-(1,3-Dimethyl-azetidin-3-yl)-hydroxy-(4-isopropyl-phenyl)-methyl]-pyridin-3-yl}-2-phenyl-butan-2-ol;

1-{5-[(R)-(1,3-Dimethyl-azetidin-3-yl)-hydroxy-(4-isopropyl-phenyl)-methyl]-pyridin-3-yl}-4-methyl-pentan-3-ol;

4-(2-{5-[(R)-(1,3-Dimethyl-azetidin-3-yl)-hydroxy-(4-isopropyl-phenyl)-methyl]-pyridin-3-yl}-ethyl)-tetrahydro-pyran-4-ol;

3-{5-[(R)-(1,3-Dimethyl-azetidin-3-yl)-hydroxy-(4-isopropyl-phenyl)-methyl]-pyridin-3-yl}-1-(tetrahydro-pyran-4-yl)-propan-1-ol;

3-{5-[(R)-(1,3-Dimethyl-azetidin-3-yl)-hydroxy-(4-isopropyl-phenyl)-methyl]-pyridin-3-yl}-1-(1,3-dimethyl-1H-pyrazol-4-yl)-propan-1-ol;

(R)-(1,3-Dimethyl-azetidin-3-yl)-(4-isopropyl-phenyl)-{5-[2-(tetrahydro-pyran-4-yl)-ethyl]-pyridin-3-yl}-methanol;

3-{5-[(R)-(1,3-Dimethyl-azetidin-3-yl)-hydroxy-(4-isopropyl-phenyl)-methyl]-pyridin-3-yl}-1-(2-methyl-thiazol-4-yl)-propan-1-ol;

4-{5-[(R)-(1,3-Dimethyl-azetidin-3-yl)-hydroxy-(4-isopropyl-phenyl)-methyl]-pyridin-3-yl}-2-(3-fluoro-phenyl)-butan-2-ol;

4-{5-[(R)-(1,3-Dimethyl-azetidin-3-yl)-hydroxy-(4-isopropyl-phenyl)-methyl]-pyridin-3-yl}-2-(4-methoxy-phenyl)-butan-2-ol;

4-{5-[(R)-(1,3-Dimethyl-azetidin-3-yl)-hydroxy-(4-isopropyl-phenyl)-methyl]-pyridin-3-yl}-2-(2-methoxy-phenyl)-butan-2-ol;

4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-butan-2-ol;

4-{5-[(R)-(1,3-Dimethyl-azetidin-3-yl)-hydroxy-(4-isopropyl-phenyl)-methyl]-pyridin-3-yl}-2-(2-methyl-thiazol-4-yl)-butan-2-ol;

4-{5-[(R)-(1,3-Dimethyl-azetidin-3-yl)-hydroxy-(4-isopropyl-phenyl)-methyl]-pyridin-3-yl}-2-(6-methoxy-pyridin-2-yl)-butan-2-ol;

4-{5-[(R)-(1,3-Dimethyl-azetidin-3-yl)-hydroxy-(4-isopropyl-phenyl)-methyl]-pyridin-3-yl}-2-pyrimidin-2-yl-butan-2-ol;

4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-butan-2-ol;

4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-butan-2-ol;

3-{5-[(R)-(1,3-Dimethyl-azetidin-3-yl)-hydroxy-(4-isopropyl-phenyl)-methyl]-pyridin-3-yl}-1-(1,5-dimethyl-1H-pyrazol-3-yl)-propan-1-ol;

8-(2-{5-[(R)-(1,3-Dimethyl-azetidin-3-yl)-hydroxy-(4-isopropyl-phenyl)-methyl]-pyridin-3-yl}-ethyl)-5,6,7,8-tetrahydro-quinolin-8-ol;

7-(2-{5-[(R)-(1,3-Dimethyl-azetidin-3-yl)-hydroxy-(4-isopropyl-phenyl)-methyl]-pyridin-3-yl}-ethyl)-6,7-dihydro-5H-[1]pyrindin-7-ol;

1-{5-[(R)-(1,3-Dimethyl-azetidin-3-yl)-hydroxy-(4-isopropyl-phenyl)-methyl]-pyridin-3-yl}-3-pyridin-2-yl-pentan-3-ol;

1-{5-[(R)-(1,3-Dimethyl-azetidin-3-yl)-hydroxy-(4-isopropyl-phenyl)-methyl]-pyridin-3-yl}-3-(6-methoxy-pyridin-2-yl)-pentan-3-ol;

(R)-(1,3-Dimethyl-azetidin-3-yl)-{5-[2-(1H-indol-2-yl)-ethyl]-pyridin-3-yl}-(4-isopropyl-phenyl)-methanol;

(R)-(4-Cyclopropyl-phenyl)-(1,3-dimethyl-azetidin-3-yl)-{5-[3-(tetrahydro-pyran-4-yl)-[1,2,4]oxadiazol-5-yl]-pyridin-3-yl}-methanol;

(R)-(4-Cyclopropyl-phenyl)-(1,3-dimethyl-azetidin-3-yl)-{5-[3-(2-methoxy-1,1-dimethyl-ethyl)-[1,2,4]oxadiazol-5-yl]-pyridin-3-yl}-methanol;

(R)-[5-(3-Cyclobutoxymethyl-[1,2,4]oxadiazol-5-yl)-pyridin-3-yl]-(4-cyclopropyl-phenyl)-(1,3-dimethyl-azetidin-3-yl)-methanol;

(R)-(1,3-Dimethyl-azetidin-3-yl)-(4-propyl-phenyl)-{5-[3-(tetrahydro-pyran-4-yloxymethyl)-[1,2,4]oxadiazol-5-yl]-pyridin-3-yl}-methanol;

(R)-(1,3-Dimethyl-azetidin-3-yl)-(4-propyl-phenyl)-{5-[3-(tetrahydro-pyran-4-yl)-[1,2,4]oxadiazol-5-yl]-pyridin-3-yl}-methanol;

(R)-[5-(3-Cyclobutoxymethyl-[1,2,4]oxadiazol-5-yl)-pyridin-3-yl]-(1,3-dimethyl-azetidin-3-yl)-(4-propyl-phenyl)-methanol;

(R)-(1,3-Dimethyl-azetidin-3-yl)-(4-isopropyl-phenyl)-{5-[3-(tetrahydro-pyran-4-yl)-[1,2,4]oxadiazol-5-yl]-pyridin-3-yl}-methanol;

(R)-(1,3-Dimethyl-azetidin-3-yl)-(4-isopropyl-phenyl)-[5-(3-morpholin-4-ylmethyl-[1,2,4]oxadiazol-5-yl)-pyridin-3-yl]-methanol;

(R)-(1,3-Dimethyl-azetidin-3-yl)-{5-[3-(2,6-dimethyl-morpholin-4-ylmethyl)-[1,2,4]oxadiazol-5-yl]-pyridin-3-yl}-(4-isopropyl-phenyl)-methanol;

(R)-(1,3-Dimethyl-azetidin-3-yl)-(4-isopropyl-phenyl)-{5-[3-(4-methyl-tetrahydro-pyran-4-yl)-[1,2,4]oxadiazol-5-yl]-pyridin-3-yl}-methanol;

(R)-(1,3-Dimethyl-azetidin-3-yl)-(4-isopropyl-phenyl)-{5-[(1S,2S,4R)-3-(7-oxa-bicyclo[2.2.1]hept-2-yl)-[1,2,4]oxadiazol-5-yl]-pyridin-3-yl}-methanol;

(R)-(1,3-Dimethyl-azetidin-3-yl)-(4-isopropyl-phenyl)-{5-[3-(tetrahydro-pyran-4-yloxymethyl)-[1,2,4]oxadiazol-5-yl]-pyridin-3-yl}-methanol;

(R)-(1,3-Dimethyl-azetidin-3-yl)-(4-isopropyl-phenyl)-[5-(3-morpholin-4-yl-[1,2,4]oxadiazol-5-yl)-pyridin-3-yl]-methanol;

(R)-(4-Cyclopropyl-phenyl)-(1,3-dimethyl-azetidin-3-yl)-{5-[3-(4-methoxy-tetrahydro-pyran-4-yl)-[1,2,4]oxadiazol-5-yl]-pyridin-3-yl}-methanol;

(R)-(4-Cyclopropyl-phenyl)-(1,3-dimethyl-azetidin-3-yl)-{5-[3-(3-hydroxymethyl-bicyclo[1.1.1]pent-1-yl)-[1,2,4]oxadiazol-5-yl]-pyridin-3-yl}-methanol;

(R)-(1,3-Dimethyl-azetidin-3-yl)-{5-[3-(3-hydroxymethyl-bicyclo[1.1.1]pent-1-yl)-[1,2,4]oxadiazol-5-yl]-pyridin-3-yl}-(4-isopropyl-phenyl)-methanol;

2-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-2-methyl-propan-1-ol;

2-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-propan-2-ol;

(R)-(1,3-Dimethyl-azetidin-3-yl)-(4-isopropyl-phenyl)-{5-[3-(1-methoxy-1-methyl-ethyl)-[1,2,4]oxadiazol-5-yl]-pyridin-3-yl}-methanol;

(R)-(1,3-Dimethyl-azetidin-3-yl)-(4-isopropyl-phenyl)-{5-[3-(1-methoxy-cyclobutyl)-[1,2,4]oxadiazol-5-yl]-pyridin-3-yl}-methanol;

1-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-2-methyl-propan-2-ol;

(R)-(1,3-Dimethyl-azetidin-3-yl)-(4-isopropyl-phenyl)-[5-(5-methanesulfonylmethyl-[1,2,4]oxadiazol-3-yl)-pyridin-3-yl]-methanol;

(R)-(1,3-Dimethyl-azetidin-3-yl)-(4-isopropyl-phenyl)-{5-[5-(2-methoxy-ethyl)-[1,2,4]oxadiazol-3-yl]-pyridin-3-yl}-methanol;

(R)-(1,3-Dimethyl-azetidin-3-yl)-(4-isopropyl-phenyl)-[5-(5-methoxymethyl-[1,2,4]oxadiazol-3-yl)-pyridin-3-yl]-methanol;

(R)-(1,3-Dimethyl-azetidin-3-yl)-(4-isopropyl-phenyl)-{5-[5-(tetrahydro-furan-3-yl)-[1,2,4]oxadiazol-3-yl]-pyridin-3-yl}-methanol;

(R)-(1,3-Dimethyl-azetidin-3-yl)-(4-isopropyl-phenyl)-{5-[5-(tetrahydro-pyran-4-yl)-[1,2,4]oxadiazol-3-yl]-pyridin-3-yl}-methanol;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclohexanol;

(R)-[5-(5-tert-Butoxymethyl-[1,2,4]oxadiazol-3-yl)-pyridin-3-yl]-(1,3-dimethyl-azetidin-3-yl)-(4-isopropyl-phenyl)-methanol;

(R)-(1,3-Dimethyl-azetidin-3-yl)-(4-isopropyl-phenyl)-{5-[5-(tetrahydro-pyran-4-ylmethyl)-[1,2,4]oxadiazol-3-yl]-pyridin-3-yl}-methanol;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclohexanol;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclohexanol;

(R)-(1,3-Dimethyl-azetidin-3-yl)-(4-isopropyl-phenyl)-{5-[5-(1-methoxy-cyclobutyl)-[1,2,4]oxadiazol-3-yl]-pyridin-3-yl}-methanol;

(R)-(1,3-Dimethyl-azetidin-3-yl)-(4-isopropyl-phenyl)-{5-[5-(6-oxa-spiro[2.5]oct-1-yl)-[1,2,4]oxadiazol-3-yl]-pyridin-3-yl}-methanol;

(R)-(1,3-Dimethyl-azetidin-3-yl)-(4-isopropyl-phenyl)-{5-[5-(tetrahydro-pyran-3-yl)-[1,2,4]oxadiazol-3-yl]-pyridin-3-yl}-methanol;

(R)-(1,3-Dimethyl-azetidin-3-yl)-(4-isopropyl-phenyl)-(5-{5-[1-(tetrahydro-furan-2-yl)methyl]-[1,2,4]oxadiazol-3-yl}-pyridin-3-yl)-methanol;

(R)-2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1,1-trifluoro-propan-2-ol;

(R)-(1,3-Dimethyl-azetidin-3-yl)-(4-isopropyl-phenyl)-{5-[5-(1-methoxy-1-methyl-ethyl)-[1,2,4]oxadiazol-3-yl]-pyridin-3-yl}-methanol;

(R)-{5-[5-((R)-Cyclohexyl-hydroxy-methyl)-[1,2,4]oxadiazol-3-yl]-pyridin-3-yl}-(1,3-dimethyl-azetidin-3-yl)-(4-isopropyl-phenyl)-methanol;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclopropanol;

2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-propan-2-ol;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclopentanol;

3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclobutanol;

(R)-(1,3-Dimethyl-azetidin-3-yl)-{5-[5-(4-fluoro-tetrahydro-pyran-4-yl)-[1,2,4]oxadiazol-3-yl]-pyridin-3-yl}-(4-isopropyl-phenyl)-methanol;

(R)-(1,3-Dimethyl-azetidin-3-yl)-{5-[5-((2R,4R,6S)-2,6-dimethyl-tetrahydro-pyran-4-yl)-[1,2,4]oxadiazol-3-yl]-pyridin-3-yl}-(4-isopropyl-phenyl)-methanol;

(R)-(1,3-Dimethyl-azetidin-3-yl)-(4-isopropyl-phenyl)-{5-[5-(tetrahydro-pyran-4-yloxymethyl)-[1,2,4]oxadiazol-3-yl]-pyridin-3-yl}-methanol;

(R)-(1,3-Dimethyl-azetidin-3-yl)-(4-isopropyl-phenyl)-(5-{5-[1-methyl-1-(tetrahydro-pyran-4-yl)-ethyl]-[1,2,4]oxadiazol-3-yl}-pyridin-3-yl)-methanol;

(R)-(1,3-Dimethyl-azetidin-3-yl)-(4-isopropyl-phenyl)-(5-{5-[2-(tetrahydro-pyran-4-yl)-ethyl]-[1,2,4]oxadiazol-3-yl}-pyridin-3-yl)-methanol;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclobutanol;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-2-methyl-propan-2-ol;

(R)-(1,3-Dimethyl-azetidin-3-yl)-(4-isopropyl-phenyl)-{5-[5-(7-oxa-bicyclo[2.2.1]hept-2-yl)-[1,2,4]oxadiazol-3-yl]-pyridin-3-yl}-methanol;

(R)-(1,3-Dimethyl-azetidin-3-yl)-(4-isopropyl-phenyl)-{5-[5-(4-methyl-tetrahydro-pyran-4-yloxymethyl)-[1,2,4]oxadiazol-3-yl]-pyridin-3-yl}-methanol;

(R)-(1,3-Dimethyl-azetidin-3-yl)-(4-isopropyl-phenyl)-[5-(5-oxetan-3-yl-[1,2,4]oxadiazol-3-yl)-pyridin-3-yl]-methanol;

(R)-(1,3-Dimethyl-azetidin-3-yl)-(4-isopropyl-phenyl)-{5-[5-(2-methoxy-1,1-dimethyl-ethyl)-[1,2,4]oxadiazol-3-yl]-pyridin-3-yl}-methanol;

2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-2-methyl-propan-1-ol;

(R)-(1,3-Dimethyl-azetidin-3-yl)-(4-isopropyl-phenyl)-{5-[5-(2-methoxy-2-methyl-propyl)-[1,2,4]oxadiazol-3-yl]-pyridin-3-yl}-methanol;

1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclobutanol;

(R)-(1,3-Dimethyl-azetidin-3-yl)-(4-isopropyl-phenyl)-{5-[5-(1-methoxymethyl-cyclopropylmethyl)-[1,2,4]oxadiazol-3-yl]-pyridin-3-yl}-methanol;

(R)-(1,3-Dimethyl-azetidin-3-yl)-(4-isopropyl-phenyl)-{5-[5-(2-pyrazol-1-yl-ethyl)-[1,2,4]oxadiazol-3-yl]-pyridin-3-yl}-methanol;

(R)—N-(2-(3-(5-((1,3-dimethylazetidin-3-yl)(hydroxy)(4-isopropylphenyl)methyl)pyridin-3-yl)-1,2,4-oxadiazol-5-yl)ethyl)acetamide-2,2,2-$d_3$;

(R)—N-(1-(3-(5-((1,3-dimethylazetidin-3-yl)(hydroxy)(4-isopropylphenyl)methyl)pyridin-3-yl)-1,2,4-oxadiazol-5-yl)-2-methylpropan-2-yl)acetamide-2,2,2-$d_3$;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2-hydroxy-ethanone;

(R)-1-(4-(3-(5-((1,3-dimethylazetidin-3-yl)(hydroxy)(4-isopropylphenyl)methyl)pyridin-3-yl)-1,2,4-oxadiazol-5-yl)piperidin-1-yl)ethan-1-one-2,2,2-$d_3$;

N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-ethyl]-2-hydroxy-N-methyl-acetamide;

(R)—N-(2-(3-(5-((1,3-dimethylazetidin-3-yl)(hydroxy)(4-isopropylphenyl)methyl)pyridin-3-yl)-1,2,4-oxadiazol-5-yl)ethyl)-N-methylacetamide-$d_3$;

(1,3-Dimethyl-azetidin-3-yl)-(6-methoxy-pyridin-3-yl)-(4-trifluoromethoxy-phenyl)-methanol;

(1,3-Dimethyl-azetidin-3-yl)-(6-phenoxy-pyridin-3-yl)-(4-trifluoromethoxy-phenyl)-methanol;

(1,3-Dimethyl-azetidin-3-yl)-(6-ethoxy-pyridin-3-yl)-(4-trifluoromethoxy-phenyl)-methanol;

(1,3-Dimethyl-azetidin-3-yl)-(5-methyl-pyridin-3-yl)-(4-trifluoromethoxy-phenyl)-methanol;

(1,3-Dimethyl-azetidin-3-yl)-(4-propyl-phenyl)-(5-pyrrolidin-1-yl-pyridin-3-yl)-methanol;

(1,3-Dimethyl-azetidin-3-yl)-(4-methoxy-phenyl)-(5-pyrrolidin-1-yl-pyridin-3-yl)-methanol;

(1,3-Dimethyl-azetidin-3-yl)-(4-ethyl-phenyl)-(5-pyrrolidin-1-yl-pyridin-3-yl)-methanol;

(1,3-Dimethyl-azetidin-3-yl)-phenyl-(5-pyrrolidin-1-yl-pyridin-3-yl)-methanol;

(4-Cyclobutyl-phenyl)-(1,3-dimethyl-azetidin-3-yl)-(5-pyrrolidin-1-yl-pyridin-3-yl)-methanol;

(4-Cyclobutoxy-phenyl)-(1,3-dimethyl-azetidin-3-yl)-(5-pyrrolidin-1-yl-pyridin-3-yl)-methanol;

(1,3-Dimethyl-azetidin-3-yl)-(4-ethoxy-phenyl)-(5-pyrrolidin-1-yl-pyridin-3-yl)-methanol;

(4-tert-Butyl-phenyl)-(1,3-dimethyl-azetidin-3-yl)-(5-pyrrolidin-1-yl-pyridin-3-yl)-methanol;

(1,3-Dimethyl-azetidin-3-yl)-(4-isopropoxy-phenyl)-(5-pyrrolidin-1-yl-pyridin-3-yl)-methanol;

(1,3-Dimethyl-azetidin-3-yl)-(5-pyrrolidin-1-yl-pyridin-3-yl)-[4-(1-trifluoromethyl-cyclopropyl)-phenyl]-methanol;

(1,3-Dimethyl-azetidin-3-yl)-[4-(1-methyl-cyclopropyl)-phenyl]-(5-pyrrolidin-1-yl-pyridin-3-yl)-methanol;

(4-Cyclopropoxy-phenyl)-(1,3-dimethyl-azetidin-3-yl)-(5-pyrrolidin-1-yl-pyridin-3-yl)-methanol;

(S)-[2-(3,3-Difluoro-pyrrolidin-1-yl)-pyridin-4-yl]-(1,3-dimethyl-azetidin-3-yl)-(4-isopropyl-phenyl)-methanol;

(S)-[2-((3R,4S)-3,4-Difluoro-pyrrolidin-1-yl)-pyridin-4-yl]-(1,3-dimethyl-azetidin-3-yl)-(4-isopropyl-phenyl)-methanol;

(S)-(1,3-Dimethyl-azetidin-3-yl)-(2-isobutoxy-pyridin-4-yl)-(4-isopropyl-phenyl)-methanol;

4-{4-[(S)-(1,3-Dimethyl-azetidin-3-yl)-hydroxy-(4-isopropyl-phenyl)-methyl]-pyridin-2-yl}-2-methyl-butan-2-ol;

(R)-[6-(3,3-Difluoro-pyrrolidin-1-yl)-pyridazin-4-yl]-(1,3-dimethyl-azetidin-3-yl)-(4-isopropyl-phenyl)-methanol;

(S)-5-tert-Butyl-3-{5-[(R)-(1,3-dimethyl-azetidin-3-yl)-hydroxy-(4-isopropyl-phenyl)-methyl]-pyridin-3-yl}-oxazolidin-2-one;

(R)-1-{5-[(R)-(1,3-Dimethyl-azetidin-3-yl)-hydroxy-(4-isopropyl-phenyl)-methyl]-pyridin-3-yl}-pyrrolidin-3-ol;

(S)-1-{5-[(R)-(1,3-Dimethyl-azetidin-3-yl)-hydroxy-(4-isopropyl-phenyl)-methyl]-pyridin-3-yl}-pyrrolidin-3-ol;

(R)-(1,3-Dimethyl-azetidin-3-yl)-[5-((S)-3-hydroxymethyl-pyrrolidin-1-yl)-pyridin-3-yl]-(4-isopropyl-phenyl)-methanol;

(R)-(1,3-Dimethyl-azetidin-3-yl)-(4-isopropyl-phenyl)-(5-pyrrolidin-1-yl-pyridin-3-yl)-methanol;

(S)-1-{5-[(R)-(1,3-Dimethyl-azetidin-3-yl)-hydroxy-(4-isopropyl-phenyl)-methyl]-pyridin-3-yl}-3-methyl-pyrrolidin-3-ol;

3-Cyclopropyl-1-{5-[(R)-(1,3-dimethyl-azetidin-3-yl)-hydroxy-(4-isopropyl-phenyl)-methyl]-pyridin-3-yl}-pyrrolidin-3-ol;

2-((S)-1-{5-[(R)-(1,3-Dimethyl-azetidin-3-yl)-hydroxy-(4-isopropyl-phenyl)-methyl]-pyridin-3-yl}-pyrrolidin-3-yl)-propan-2-ol;

(R)-(1,3-Dimethyl-azetidin-3-yl)-(4-isopropyl-phenyl)-(5-morpholin-4-yl-pyridin-3-yl)-methanol;

(R)-(1,3-Dimethyl-azetidin-3-yl)-(4-isopropyl-phenyl)-(3,4,5,6-tetrahydro-2H-[1,3']bipyridinyl-5'-yl)-methanol;

(R)-[5-(7-Aza-bicyclo[2.2.1]hept-7-yl)-pyridin-3-yl]-(1,3-dimethyl-azetidin-3-yl)-(4-isopropyl-phenyl)-methanol;

(R)-(1,3-Dimethyl-azetidin-3-yl)-(4-isopropyl-phenyl)-[5-((S)-2-methyl-pyrrolidin-1-yl)-pyridin-3-yl]-methanol;

1-{5-[(R)-(1,3-Dimethyl-azetidin-3-yl)-hydroxy-(4-isopropyl-phenyl)-methyl]-pyridin-3-yl}-3-trifluoromethyl-pyrrolidin-3-ol;

(R)-[5-(3,3-Difluoro-pyrrolidin-1-yl)-pyridin-3-yl]-(1,3-dimethyl-azetidin-3-yl)-(4-isopropyl-phenyl)-methanol;

5'-[(R)-(1,3-Dimethyl-azetidin-3-yl)-hydroxy-(4-isopropyl-phenyl)-methyl]-3,4,5,6-tetrahydro-2H-[1,3']bipyridinyl-4-ol;

5'-[(R)-(1,3-Dimethyl-azetidin-3-yl)-hydroxy-(4-isopropyl-phenyl)-methyl]-3,4,5,6-tetrahydro-2H-[1,3']bipyridinyl-3-ol;

(R)-{5-[(2-Benzyloxy-ethyl)-methyl-amino]-pyridin-3-yl}-(1,3-dimethyl-azetidin-3-yl)-(4-isopropyl-phenyl)-methanol;

(R)-(1,3-Dimethyl-azetidin-3-yl)-[4-(1-methyl-cyclopropyl)-phenyl]-(5-pyrrolidin-1-yl-pyridin-3-yl)-methanol;

(R)-[5-((3R,4S)-3,4-Difluoro-pyrrolidin-1-yl)-pyridin-3-yl]-(1,3-dimethyl-azetidin-3-yl)-[4-(1-trifluoromethyl-cyclopropyl)-phenyl]-methanol;

2-[(S)-1-(5-{(R)-(1,3-Dimethyl-azetidin-3-yl)-hydroxy-[4-(1-trifluoromethyl-cyclopropyl)-phenyl]-methyl}-pyridin-3-yl)-pyrrolidin-3-yl]-propan-2-ol;

(R)-(1,3-Dimethyl-azetidin-3-yl)-(5-pyrrolidin-1-yl-pyridin-3-yl)-[4-(1-trifluoromethyl-cyclopropyl)-phenyl]-methanol;

(R)-(4-tert-Butyl-phenyl)-(1,3-dimethyl-azetidin-3-yl)-(3,4,5,6-tetrahydro-2H-[1,3']bipyridinyl-5'-yl)-methanol;

(R)-(1,3-Dimethyl-azetidin-3-yl)-(5-pyrrolidin-1-yl-pyridin-3-yl)-(4-trifluoromethoxy-phenyl)-methanol;

(R)-{5-[5-(1-Cyclopropanesulfonyl-piperidin-4-yl)-[1,2,4]oxadiazol-3-yl]-pyridin-3-yl}-(1,3-dimethyl-azetidin-3-yl)-(4-isopropyl-phenyl)-methanol;

2-({5-[(R)-(1,3-Dimethyl-azetidin-3-yl)-hydroxy-(4-isopropyl-phenyl)-methyl]-pyridin-3-yl}-methyl-amino)-ethanol;

(R)-1-((S)-1-{5-[(R)-(1,3-Dimethyl-azetidin-3-yl)-hydroxy-(4-isopropyl-phenyl)-methyl]-pyridin-3-yl}-pyrrolidin-3-yl)-ethanol;

3-{5-[(R)-(1,3-Dimethyl-azetidin-3-yl)-hydroxy-(4-isopropyl-phenyl)-methyl]-pyridin-3-yl}-oxazolidin-2-one;

3-{5-[(R)-(1,3-Dimethyl-azetidin-3-yl)-hydroxy-(4-isopropyl-phenyl)-methyl]-pyridin-3-yl}-5-phenyl-oxazolidin-2-one;

5-Benzyl-3-{5-[(R)-(1,3-dimethyl-azetidin-3-yl)-hydroxy-(4-isopropyl-phenyl)-methyl]-pyridin-3-yl}-oxazolidin-2-one;

3-{5-[(R)-(1,3-Dimethyl-azetidin-3-yl)-hydroxy-(4-isopropyl-phenyl)-methyl]-pyridin-3-yl}-5-isopropyl-oxazolidin-2-one;

6-{5-[(R)-(1,3-Dimethyl-azetidin-3-yl)-hydroxy-(4-isopropyl-phenyl)-methyl]-pyridin-3-yl}-4-oxa-6-aza-spiro[2.4]heptan-5-one;

3-{5-[(R)-(1,3-Dimethyl-azetidin-3-yl)-hydroxy-(4-isopropyl-phenyl)-methyl]-pyridin-3-yl}-1-oxa-3-aza-spiro[4.4]nonan-2-one;

3-{5-[(R)-(1,3-Dimethyl-azetidin-3-yl)-hydroxy-(4-isopropyl-phenyl)-methyl]-pyridin-3-yl}-5-(tetrahydro-pyran-4-yl)-oxazolidin-2-one;

3-{5-[(R)-(1,3-Dimethyl-azetidin-3-yl)-hydroxy-(4-isopropyl-phenyl)-methyl]-pyridin-3-yl}-5,5-dimethyl-oxazolidin-2-one;

3-{5-[(R)-(1,3-Dimethyl-azetidin-3-yl)-hydroxy-(4-isopropyl-phenyl)-methyl]-pyridin-3-yl}-8,8-difluoro-1-oxa-3-aza-spiro[4.5]decan-2-one;

9-{5-[(R)-(1,3-Dimethyl-azetidin-3-yl)-hydroxy-(4-isopropyl-phenyl)-methyl]-pyridin-3-yl}-7-oxa-9-aza-dispiro[3.1.4.1]undecan-8-one;

2-Cyclopropyl-7-{5-[(R)-(1,3-dimethyl-azetidin-3-yl)-hydroxy-(4-isopropyl-phenyl)-methyl]-pyridin-3-yl}-5-oxa-7-aza-spiro[3.4]octan-6-one;

7-{5-[(R)-(1,3-Dimethyl-azetidin-3-yl)-hydroxy-(4-isopropyl-phenyl)-methyl]-pyridin-3-yl}-2,2-dimethyl-5-oxa-7-aza-spiro[3.4]octan-6-one;

1-{5-[(R)-(1,3-Dimethyl-azetidin-3-yl)-hydroxy-(4-isopropyl-phenyl)-methyl]-pyridin-3-yl}-4-phenyl-pyrrolidin-2-one;

1-{5-[(R)-(1,3-Dimethyl-azetidin-3-yl)-hydroxy-(4-isopropyl-phenyl)-methyl]-pyridin-3-yl}-pyrrolidin-2-one;

1-{5-[(R)-(1,3-Dimethyl-azetidin-3-yl)-hydroxy-(4-isopropyl-phenyl)-methyl]-pyridin-3-yl}-4-isopropyl-pyrrolidin-2-one;

1-{5-[(R)-(1,3-Dimethyl-azetidin-3-yl)-hydroxy-(4-isopropyl-phenyl)-methyl]-pyridin-3-yl}-3-isopropyl-pyrrolidin-2-one;

1-{5-[(R)-(1,3-Dimethyl-azetidin-3-yl)-hydroxy-(4-isopropyl-phenyl)-methyl]-pyridin-3-yl}-4,4-dimethyl-pyrrolidin-2-one;

5-(5-((R)-(1,3-Dimethyl-azetidin-3-yl)(hydroxy)(4-isopropyl-phenyl)methyl)pyridin-3-yl)hexahydro-4H-furo[2,3-c]pyrrol-4-one;

2-{5-[(R)-(1,3-Dimethyl-azetidin-3-yl)-hydroxy-(4-isopropyl-phenyl)-methyl]-pyridin-3-yl}-2-aza-spiro[4.4]nonan-3-one;

6-{5-[(R)-(1,3-Dimethyl-azetidin-3-yl)-hydroxy-(4-isopropyl-phenyl)-methyl]-pyridin-3-yl}-6-aza-spiro[3.4]octan-5-one;

2-{5-[(R)-(1,3-Dimethyl-azetidin-3-yl)-hydroxy-(4-isopropyl-phenyl)-methyl]-pyridin-3-yl}-8-oxa-2-aza-spiro[4.5]decan-3-one;

1-{5-[(R)-(1,3-Dimethyl-azetidin-3-yl)-hydroxy-(4-isopropyl-phenyl)-methyl]-pyridin-3-yl}-3-(tetrahydro-pyran-4-yl)-pyrrolidin-2-one;

2-{5-[(R)-(1,3-Dimethyl-azetidin-3-yl)-hydroxy-(4-isopropyl-phenyl)-methyl]-pyridin-3-yl}-2-aza-spiro[4.5]decan-1-one;

2-{5-[(R)-(1,3-Dimethyl-azetidin-3-yl)-hydroxy-(4-isopropyl-phenyl)-methyl]-pyridin-3-yl}-8-oxa-2-aza-spiro[4.5]decan-1-one;

(S)-1-{5-[(R)-(1,3-Dimethyl-azetidin-3-yl)-hydroxy-(4-isopropyl-phenyl)-methyl]-pyridin-3-yl}-4-isobutyl-pyrrolidin-2-one;

4-Cyclopropyl-1-{5-[(R)-(1,3-dimethyl-azetidin-3-yl)-hydroxy-(4-isopropyl-phenyl)-methyl]-pyridin-3-yl}-pyrrolidin-2-one;

1-{5-[(R)-(1,3-Dimethyl-azetidin-3-yl)-hydroxy-(4-isopropyl-phenyl)-methyl]-pyridin-3-yl}-4-trifluoromethyl-pyrrolidin-2-one;

1-{5-[(R)-(1,3-Dimethyl-azetidin-3-yl)-hydroxy-(4-isopropyl-phenyl)-methyl]-pyridin-3-yl}-3-(2-methoxy-ethyl)-pyrrolidin-2-one;

1-{5-[(R)-(1,3-Dimethyl-azetidin-3-yl)-hydroxy-(4-isopropyl-phenyl)-methyl]-pyridin-3-yl}-4-(2-methoxy-ethyl)-pyrrolidin-2-one;

1-{5-[(R)-(1,3-Dimethyl-azetidin-3-yl)-hydroxy-(4-isopropyl-phenyl)-methyl]-pyridazin-3-yl}-pyrrolidin-2-one;

(1,3-Dimethyl-azetidin-3-yl)-(4-isopropyl-phenyl)-[5-((R)-3-isopropyl-pyrrolidin-1-yl)-pyridin-3-yl]-methanol;

(R)-(1,3-Dimethyl-azetidin-3-yl)-[5-((2R,6S)-2,6-dimethyl-morpholin-4-yl)-pyridin-3-yl]-(4-isopropyl-phenyl)-methanol;

(R)-(1,3-Dimethyl-azetidin-3-yl)-(4-isopropyl-phenyl)-[5-(6-oxa-3-aza-bicyclo[3.1.1]hept-3-yl)-pyridin-3-yl]-methanol;

(R)-[5-((3R,4S)-3,4-Difluoro-pyrrolidin-1-yl)-pyridin-3-yl]-(1,3-dimethyl-azetidin-3-yl)-(4-isopropyl-phenyl)-methanol;

(R)-[5-((3S,4S)-3,4-Difluoro-pyrrolidin-1-yl)-pyridin-3-yl]-(1,3-dimethyl-azetidin-3-yl)-(4-isopropyl-phenyl)-methanol;

(R)-(1,3-Dimethyl-azetidin-3-yl)-[5-((2S,6S)-2,6-dimethyl-morpholin-4-yl)-pyridin-3-yl]-(4-isopropyl-phenyl)-methanol;

(R)-(1,3-Dimethyl-azetidin-3-yl)-[5-((2R,6R)-2,6-dimethyl-morpholin-4-yl)-pyridin-3-yl]-(4-isopropyl-phenyl)-methanol;

(R)-(1,3-Dimethyl-azetidin-3-yl)-(4-isopropyl-phenyl)-{5-[3-(3-methyl-[1,2,4]oxadiazol-5-yl)-pyrrolidin-1-yl]-pyridin-3-yl}-methanol;

(R)-(1,3-Dimethyl-azetidin-3-yl)-(4-isopropyl-phenyl)-{5-[3-(4-methyl-thiazol-2-yl)-pyrrolidin-1-yl]-pyridin-3-yl}-methanol;
(R)-(1,3-Dimethyl-azetidin-3-yl)-(4-isopropyl-phenyl)-[5-(3-phenyl-pyrrolidin-1-yl)-pyridin-3-yl]-methanol;
(R)-(1,3-Dimethyl-azetidin-3-yl)-[5-(3,3-dimethyl-pyrrolidin-1-yl)-pyridin-3-yl]-(4-isopropyl-phenyl)-methanol;
(R)-(1,3-Dimethyl-azetidin-3-yl)-(4-isopropyl-phenyl)-[(1S,4S)-5-(2-oxa-5-aza-bicyclo[2.2.1]hept-5-yl)-pyridin-3-yl]-methanol;
(R)-(1,3-Dimethyl-azetidin-3-yl)-(4-isopropyl-phenyl)-[5-(2,2,6,6-tetrafluoro-morpholin-4-yl)-pyridin-3-yl]-methanol;
(R)-(1,3-Dimethyl-azetidin-3-yl)-(4-isopropyl-phenyl)-[5-((R)-2-methoxymethyl-morpholin-4-yl)-pyridin-3-yl]-methanol;
(R)-(1,3-Dimethyl-azetidin-3-yl)-(4-isopropyl-phenyl)-[5-((S)-2-methoxymethyl-morpholin-4-yl)-pyridin-3-yl]-methanol;
(R)-(1,3-Dimethyl-azetidin-3-yl)-(4-isopropyl-phenyl)-[5-(3-trifluoromethyl-pyrrolidin-1-yl)-pyridin-3-yl]-methanol;
(R)-(1,3-Dimethyl-azetidin-3-yl)-(4-isopropyl-phenyl)-[(1R,4R)-5-(2-oxa-5-aza-bicyclo[2.2.1]hept-5-yl)-pyridin-3-yl]-methanol;
(R)-(1,3-Dimethyl-azetidin-3-yl)-(4-isopropyl-phenyl)-[(1S,5R)-5-(8-oxa-3-aza-bicyclo[3.2.1]oct-3-yl)-pyridin-3-yl]-methanol;
(R)-(1,3-Dimethyl-azetidin-3-yl)-[(1S,4S)-5-(2-oxa-5-aza-bicyclo[2.2.1]hept-5-yl)-pyridin-3-yl]-[4-(1-trifluoromethyl-cyclopropyl)-phenyl]-methanol;
(R)-(1,3-Dimethyl-azetidin-3-yl)-(4-ethyl-phenyl)-(5-pyrrolidin-1-yl-pyridin-3-yl)-methanol;
(R)-(1,3-Dimethyl-azetidin-3-yl)-(4-ethyl-phenyl)-[5-(6-oxa-3-aza-bicyclo[3.1.1]hept-3-yl)-pyridin-3-yl]-methanol;
(R)-(1,3-Dimethyl-azetidin-3-yl)-(4-ethyl-phenyl)-[(1S,4S)-5-(2-oxa-5-aza-bicyclo[2.2.1]hept-5-yl)-pyridin-3-yl]-methanol;
(R)-(5-Benzyloxy-pyridin-3-yl)-(1,3-dimethyl-azetidin-3-yl)-(4-isopropyl-phenyl)-methanol;
(1,3-Dimethyl-azetidin-3-yl)-(4-isopropyl-phenyl)-[5-(2-pyridin-2-yl-ethoxy)-pyridin-3-yl]-methanol;
(1,3-Dimethyl-azetidin-3-yl)-(4-isopropyl-phenyl)-[5-(2-methoxy-ethoxy)-pyridin-3-yl]-methanol;
(1,3-Dimethyl-azetidin-3-yl)-(4-isopropyl-phenyl)-[5-(oxetan-3-ylmethoxy)-pyridin-3-yl]-methanol;
3-{5-[(R)-(1,3-Dimethyl-azetidin-3-yl)-hydroxy-(4-isopropyl-phenyl)-methyl]-pyridin-3-yloxy}-propan-1-ol;
(R)-(1,3-Dimethyl-azetidin-3-yl)-(5-isopropoxy-pyridin-3-yl)-(4-isopropyl-phenyl)-methanol;
(R)-(5-Cyclohexyloxy-pyridin-3-yl)-(1,3-dimethyl-azetidin-3-yl)-(4-isopropyl-phenyl)-methanol;
1-{5-[(R)-(1,3-Dimethyl-azetidin-3-yl)-hydroxy-(4-isopropyl-phenyl)-methyl]-pyridin-3-yloxy}-2-methyl-propan-2-ol;
(R)-(1,3-Dimethyl-azetidin-3-yl)-(4-isopropyl-phenyl)-[5-(3-methoxy-cyclopentyloxy)-pyridin-3-yl]-methanol;
(R)-[5-(3-Cyclopropyl-[1,2,4]oxadiazol-5-ylmethoxy)-pyridin-3-yl]-(1,3-dimethyl-azetidin-3-yl)-(4-isopropyl-phenyl)-methanol;
(R)-(1,3-Dimethyl-azetidin-3-yl)-{5-[2-(3,5-dimethyl-[1,2,4]triazol-1-yl)-ethoxy]-pyridin-3-yl}-(4-isopropyl-phenyl)-methanol;
4-{5-[(R)-(1,3-Dimethyl-azetidin-3-yl)-hydroxy-(4-isopropyl-phenyl)-methyl]-pyridin-3-yloxy}-2-methyl-butan-2-ol;
(R)-(1,3-Dimethyl-azetidin-3-yl)-(4-isopropyl-phenyl)-(5-methoxy-pyridin-3-yl)-methanol;
(R)-[5-(2-Benzyloxy-ethoxy)-pyridin-3-yl]-(1,3-dimethyl-azetidin-3-yl)-(4-isopropyl-phenyl)-methanol;
(R)-(1,3-Dimethyl-azetidin-3-yl)-(4-isopropyl-phenyl)-[5-(tetrahydro-pyran-4-yloxy)-pyridin-3-yl]-methanol;
2-{5-[(R)-(1,3-Dimethyl-azetidin-3-yl)-hydroxy-(4-isopropyl-phenyl)-methyl]-pyridin-3-yloxy}-ethanol;
4-{5-[(R)-(1,3-Dimethyl-azetidin-3-yl)-hydroxy-(4-isopropyl-phenyl)-methyl]-pyridin-3-yloxy}-cyclohexanol;
4-{5-[(R)-(1,3-Dimethyl-azetidin-3-yl)-hydroxy-(4-isopropyl-phenyl)-methyl]-pyridin-3-yloxy}-1-methyl-cyclohexanol;
(1,3-Dimethyl-azetidin-3-yl)-(2-phenoxy-pyrimidin-5-yl)-(4-trifluoromethoxy-phenyl)-methanol;
(6-Benzyloxy-pyridin-3-yl)-(1,3-dimethyl-azetidin-3-yl)-(4-trifluoromethoxy-phenyl)-methanol;
(1,3-Dimethyl-azetidin-3-yl)-(5-pyrazol-1-yl-pyridin-3-yl)-(4-trifluoromethoxy-phenyl)-methanol;
(1,3-Dimethyl-azetidin-3-yl)-(6-fluoro-5-pyrrolidin-1-yl-pyridin-3-yl)-(4-trifluoromethoxy-phenyl)-methanol;
5-[(1,3-Dimethyl-azetidin-3-yl)-hydroxy-(4-trifluoromethoxy-phenyl)-methyl]-3-pyrrolidin-1-yl-pyridine-2-carbonitrile;
(1,3-Dimethyl-azetidin-3-yl)-[6-(tetrahydro-pyran-4-yloxy)-pyridin-3-yl]-(4-trifluoromethoxy-phenyl)-methanol;
(1,3-Dimethyl-azetidin-3-yl)-[6-(oxetan-3-ylmethoxy)-pyridin-3-yl]-(4-trifluoromethoxy-phenyl)-methanol;
(1,3-Dimethyl-azetidin-3-yl)-(4-isopropyl-phenyl)-[5-(4-methyl-thiazol-2-yl)-pyridin-3-yl]-methanol;
(1,3-Dimethyl-azetidin-3-yl)-(4-isopropyl-phenyl)-[5-(5-methyl-thiazol-2-yl)-pyridin-3-yl]-methanol;
(1,3-Dimethyl-azetidin-3-yl)-(4-isopropyl-phenyl)-(2-methoxy-pyrimidin-5-yl)-methanol;
(S)-(1,3-Dimethyl-azetidin-3-yl)-(4-isopropyl-phenyl)-(2-pyrrolidin-1-yl-pyridin-4-yl)-methanol;
(1,3-Dimethyl-azetidin-3-yl)-[2-((R)-2-hydroxymethyl-pyrrolidin-1-yl)-pyridin-4-yl]-(4-isopropyl-phenyl)-methanol;
(1,3-Dimethyl-azetidin-3-yl)-(4-isopropyl-phenyl)-(3,4,5,6-tetrahydro-2H-[1,2']bipyridinyl-4'-yl)-methanol;
(1,3-Dimethyl-azetidin-3-yl)-(4-isopropyl-phenyl)-(2-morpholin-4-yl-pyridin-4-yl)-methanol;
(S)-(1,3-Dimethyl-azetidin-3-yl)-(2-ethyl-pyridin-4-yl)-(4-isopropyl-phenyl)-methanol;
(S)-(1,3-Dimethyl-azetidin-3-yl)-(4-isopropyl-phenyl)-[2-(tetrahydro-pyran-4-ylmethoxy)-pyridin-4-yl]-methanol;
(S)-(1,3-Dimethyl-azetidin-3-yl)-(4-isopropyl-phenyl)-[2-(2-methoxy-ethoxy)-pyridin-4-yl]-methanol;
(S)-(2-Cyclopentyl-pyridin-4-yl)-(1,3-dimethyl-azetidin-3-yl)-(4-isopropyl-phenyl)-methanol;
(R)-(1,3-Dimethyl-azetidin-3-yl)-(5-pyrrolidin-1-yl-pyridin-3-yl)-(4-trifluoromethyl-phenyl)-methanol;
(R)-(1,3-Dimethyl-azetidin-3-yl)-[5-((R)-3-hydroxymethyl-3-methyl-pyrrolidin-1-yl)-pyridin-3-yl]-(4-isopropyl-phenyl)-methanol;
(R)-(1,3-Dimethyl-azetidin-3-yl)-[5-((S)-3-fluoro-pyrrolidin-1-yl)-pyridin-3-yl]-(4-isopropyl-phenyl)-methanol;

(R)-(1,3-Dimethyl-azetidin-3-yl)-(4-isopropyl-phenyl)-{5-[4-(tetrahydro-pyran-4-yl)-[1,2,3]triazol-1-yl]-pyridin-3-yl}-methanol;
(1,3-Dimethyl-azetidin-3-yl)-(4-isopropyl-phenyl)-(5-methyl-pyridin-3-yl)-methanol;
(1,3-Dimethyl-azetidin-3-yl)-(5-isopropenyl-pyridin-3-yl)-(4-isopropyl-phenyl)-methanol;
(5-Cyclopropyl-pyridin-3-yl)-(1,3-dimethyl-azetidin-3-yl)-(4-isopropyl-phenyl)-methanol;
(5-Cyclopent-1-enyl-pyridin-3-yl)-(1,3-dimethyl-azetidin-3-yl)-(4-isopropyl-phenyl)-methanol;
3-{5-[(1,3-Dimethyl-azetidin-3-yl)-hydroxy-(4-isopropyl-phenyl)-methyl]-pyridin-3-yl}-cyclopent-2-enol;
(1,3-Dimethyl-azetidin-3-yl)-(4-isopropyl-phenyl)-(5-isopropyl-pyridin-3-yl)-methanol;
(5-Cyclopentyl-pyridin-3-yl)-(1,3-dimethyl-azetidin-3-yl)-(4-isopropyl-phenyl)-methanol;
3-{5-[(1,3-Dimethyl-azetidin-3-yl)-hydroxy-(4-isopropyl-phenyl)-methyl]-pyridin-3-yl}-cyclopentanol;
(R)-(1,3-Dimethyl-azetidin-3-yl)-(4-isopropyl-phenyl)-pyridin-3-yl-methanol;
3-{5-[(R)-(1,3-Dimethyl-azetidin-3-yl)-hydroxy-(4-isopropyl-phenyl)-methyl]-pyridin-3-yl}-cyclopent-2-enone;
3-{5-[(R)-(1,3-Dimethyl-azetidin-3-yl)-hydroxy-(4-isopropyl-phenyl)-methyl]-pyridin-3-yl}-1-methyl-cyclopent-2-enol;
(3S)-3-(5-((R)-(1,3-dimethylazetidin-3-yl)(hydroxy)(4-isopropylphenyl)methyl)pyridin-3-yl)-1-methylcyclopentan-1-ol;
(3R)-3-(5-((R)-(1,3-dimethylazetidin-3-yl)(hydroxy)(4-isopropylphenyl)methyl)pyridin-3-yl)-1-methylcyclopentan-1-ol;
3-{5-[(R)-(1,3-Dimethyl-azetidin-3-yl)-hydroxy-(4-isopropyl-phenyl)-methyl]-pyridin-3-yl}-1-ethyl-cyclopentanol;
3-{5-[(R)-(1,3-Dimethyl-azetidin-3-yl)-hydroxy-(4-isopropyl-phenyl)-methyl]-pyridin-3-yl}-1-isopropyl-cyclopentanol;
(R)-(1,3-Dimethyl-azetidin-3-yl)-(4-isopropyl-phenyl)-[5-(4-methyl-oxazol-2-yl)-pyridin-3-yl]-methanol;
(R)-(1,3-Dimethyl-azetidin-3-yl)-(5-ethyl-pyridin-3-yl)-(4-isopropyl-phenyl)-methanol;
(R)-(1,3-Dimethyl-azetidin-3-yl)-(4-isopropyl-phenyl)-(5-methyl-pyridin-3-yl)-methanol;
(R)-[5-(4,5-Dihydro-furan-3-yl)-pyridin-3-yl]-(1,3-dimethyl-azetidin-3-yl)-(4-isopropyl-phenyl)-methanol;
(R)-(1,3-Dimethyl-azetidin-3-yl)-(4-isopropyl-phenyl)-[5-(tetrahydro-furan-3-yl)-pyridin-3-yl]-methanol;
3-{5-[(R)-(1,3-Dimethyl-azetidin-3-yl)-hydroxy-(4-isopropyl-phenyl)-methyl]-pyridin-3-yl}-but-3-en-1-ol;
N-Cyclopentyl-5-[(R)-(1,3-dimethyl-azetidin-3-yl)-hydroxy-(4-isopropyl-phenyl)-methyl]-nicotinamide;
{5-[(R)-(1,3-Dimethyl-azetidin-3-yl)-hydroxy-(4-isopropyl-phenyl)-methyl]-pyridin-3-yl}-pyrrolidin-1-yl-methanone;
5-[(R)-(1,3-Dimethyl-azetidin-3-yl)-hydroxy-(4-isopropyl-phenyl)-methyl]-N-(tetrahydro-pyran-4-yl)-nicotinamide;
(1,3-Dimethyl-azetidin-3-yl)-[4-(3-methoxy-propyl)-phenyl]-(5-pyrrolidin-1-yl-pyridin-3-yl)-methanol;
(R)-(4-Cyclopropyl-phenyl)-(1,3-dimethyl-azetidin-3-yl)-(5-pyrrolidin-1-yl-pyridin-3-yl)-methanol;
(R)-(1,3-Dimethyl-azetidin-3-yl)-(5-pyrrolidin-1-yl-pyridin-3-yl)-p-tolyl-methanol;
5-[(R)-(1,3-Dimethyl-azetidin-3-yl)-hydroxy-(4-isopropyl-phenyl)-methyl]-3',4',5',6'-tetrahydro-2'H-[3,4']bipyridinyl-1'-carboxylic acid tert-butyl ester;
3-{5-[(R)-(1,3-Dimethyl-azetidin-3-yl)-hydroxy-(4-isopropyl-phenyl)-methyl]-pyridin-3-yl}-pyrrolidine-1-carboxylic acid tert-butyl ester;
(R)-(1,3-Dimethyl-azetidin-3-yl)-(4-isopropyl-phenyl)-[5-(tetrahydro-pyran-4-yl)-pyridin-3-yl]-methanol;
(R)-(1,3-Dimethyl-azetidin-3-yl)-(4-isopropyl-phenyl)-(3',4',5',6'-tetrahydro-2'H-[2,1';4',3"]terpyridin-5"-yl)-methanol;
(R)-(1,3-Dimethyl-azetidin-3-yl)-(4-isopropyl-phenyl)-(1'-phenyl-1',2',3',4',5',6'-hexahydro-[3,4']bipyridinyl-5-yl)-methanol;
(R)-(1,3-Dimethyl-azetidin-3-yl)-(4-isopropyl-phenyl)-[1'-(toluene-4-sulfonyl)-1',2',3',4',5',6'-hexahydro-[3,4']bipyridinyl-5-yl]-methanol;
(R)-(1,3-Dimethyl-azetidin-3-yl)-(4-isopropyl-phenyl)-[5-(tetrahydro-furan-2-yl)-pyridin-3-yl]-methanol;
(R)-(1,3-Dimethyl-azetidin-3-yl)-(4-isopropyl-phenyl)-[5-(5-methyl-tetrahydro-furan-2-yl)-pyridin-3-yl]-methanol;
(R)-(1,3-Dimethyl-azetidin-3-yl)-[5-(5,5-dimethyl-tetrahydro-furan-2-yl)-pyridin-3-yl]-(4-isopropyl-phenyl)-methanol;
3-{5-[(R)-(1,3-Dimethyl-azetidin-3-yl)-hydroxy-(4-isopropyl-phenyl)-methyl]-pyridin-3-yl}-2,2-difluoro-propan-1-ol;
(R)-(1,3-Dimethyl-azetidin-3-yl)-(4-isopropyl-phenyl)-[5-(5-methyl-oxazol-2-yl)-pyridin-3-yl]-methanol;
(R)-(1,3-Dimethyl-azetidin-3-yl)-(4-isopropyl-phenyl)-{5-[5-(tetrahydro-pyran-4-yl)-oxazol-2-yl]-pyridin-3-yl}-methanol;
(R)-(1,3-Dimethyl-azetidin-3-yl)-[5-(4-fluoro-phenoxymethyl)-pyridin-3-yl]-(4-isopropyl-phenyl)-methanol;
Isopropyl-carbamic acid 5-[(R)-(1,3-dimethyl-azetidin-3-yl)-hydroxy-(4-isopropyl-phenyl)-methyl]-pyridin-3-ylmethyl ester;
(R)-[5-(2-Benzyloxy-ethyl)-pyridin-3-yl]-(1,3-dimethyl-azetidin-3-yl)-(4-isopropyl-phenyl)-methanol;
4-{5-[(R)-(1,3-Dimethyl-azetidin-3-yl)-hydroxy-(4-isopropyl-phenyl)-methyl]-pyridin-3-yl}-1-methyl-cyclohexanol;
2-(2-{5-[(R)-(1,3-Dimethyl-azetidin-3-yl)-hydroxy-(4-isopropyl-phenyl)-methyl]-pyridin-3-yl}-cyclopropyl)-propan-2-ol;
(S)-(1,3-Dimethyl-azetidin-3-yl)-(4-isopropyl-phenyl)-{2-[5-(tetrahydro-pyran-4-yl)-[1,2,4]oxadiazol-3-yl]-pyridin-4-yl}-methanol;
(1,3-Dimethyl-azetidin-3-yl)-(4-isopropyl-phenyl)-(2-pyrrolidin-1-yl-pyrimidin-5-yl)-methanol;
(1,3-Dimethyl-azetidin-3-yl)-(4-isopropyl-phenyl)-(6-pyrrolidin-1-yl-pyrazin-2-yl)-methanol;
(R)—N-(1-(3-(5-((1,3-dimethylazetidin-3-yl)(hydroxy)(4-isopropylphenyl)methyl)pyridin-3-yl)-1,2,4-oxadiazol-5-yl)cyclopropyl)acetamide-2,2,2-$d_3$;
(R)—N-(1-(3-(5-((1,3-dimethylazetidin-3-yl)(hydroxy)(4-isopropylphenyl)methyl)pyridin-3-yl)-1,2,4-oxadiazol-5-yl)cyclopropyl)-N-methylacetamide-$d_3$;
(R)—N-((3-(5-((1,3-dimethylazetidin-3-yl)(hydroxy)(4-isopropylphenyl)methyl)pyridin-3-yl)-1,2,4-oxadiazol-5-yl)methyl)-N-methylacetamide-$d_3$;
N-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-2-hydroxy-acetamide;

(R)—N-((3-(5-((1,3-dimethylazetidin-3-yl)(hydroxy)(4-isopropylphenyl)methyl)pyridin-3-yl)-1,2,4-oxadiazol-5-yl)methyl)acetamide-2,2,2-$d_3$;

1-(3-{5-[(R)-Hydroxy-(1-isopropyl-3-methyl-azetidin-3-yl)-(4-isopropyl-phenyl)-methyl]-pyridin-3-yl}-[1,2,4]oxadiazol-5-yl)-2-methyl-propan-2-ol;

1-(3-{5-[(R)-(1-Ethyl-3-methyl-azetidin-3-yl)-hydroxy-(4-isopropyl-phenyl)-methyl]-pyridin-3-yl}-[1,2,4]oxadiazol-5-yl)-2-methyl-propan-2-ol;

2-(3-{5-[(R)-Hydroxy-(1-isopropyl-3-methyl-azetidin-3-yl)-(4-isopropyl-phenyl)-methyl]-pyridin-3-yl}-[1,2,4]oxadiazol-5-yl)-propan-2-ol;

2-(3-{5-[(R)-(1-Ethyl-3-methyl-azetidin-3-yl)-hydroxy-(4-isopropyl-phenyl)-methyl]-pyridin-3-yl}-[1,2,4]oxadiazol-5-yl)-propan-2-ol;

4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidine-1-carboxylic acid benzyl ester;

1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-ethanone;

(R)-1-(3-(3-(5-((1,3-dimethylazetidin-3-yl)(hydroxy)(4-isopropylphenyl)methyl)pyridin-3-yl)-1,2,4-oxadiazol-5-yl)azetidin-1-yl)ethan-1-one-2,2,2-$d_3$;

(R)-1-(3-(3-(5-((1,3-dimethylazetidin-3-yl)(hydroxy)(4-isopropylphenyl)methyl)pyridin-3-yl)-1,2,4-oxadiazol-5-yl)-3-methylazetidin-1-yl)ethan-1-one-2,2,2-$d_3$;

(R)-1-(3-(3-(5-((1,3-dimethylazetidin-3-yl)(hydroxy)(4-isopropylphenyl)methyl)pyridin-3-yl)-1,2,4-oxadiazol-5-yl)-3-fluoroazetidin-1-yl)ethan-1-one-2,2,2-$d_3$;

(R)-(1,3-Dimethyl-azetidin-3-yl)-(4-isopropyl-phenyl)-{5-[5-(1-methyl-1-morpholin-4-yl-ethyl)-[1,2,4]oxadiazol-3-yl]-pyridin-3-yl}-methanol;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-piperidin-2-one;

1-[(S)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-1-yl]-ethanone;

1-[(R)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-1-yl]-ethanone;

N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-ethyl]-acetamide;

1-Benzyl-3-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-pyrrolidin-2-one;

3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,3-dimethyl-pyrrolidin-2-one;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-isobutyl-pyrrolidin-2-one;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-furan-2-ylmethyl-pyrrolidin-2-one;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-phenyl-pyrrolidin-2-one;

1-Benzyl-4-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-pyrrolidin-2-one;

5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-phenyl-pyrrolidin-2-one;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-2-one;

(S)-5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-2-one;

(R)-5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-pyrrolidin-2-one;

(S)-6-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-azetidin-2-one;

(S)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-azetidin-2-one;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,4-dimethyl-pyrrolidin-2-one;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,4-dimethyl-pyrrolidin-2-one;

(R)-(1,3-Dimethyl-azetidin-3-yl)-(4-isopropyl-phenyl)-[5-(5-piperidin-4-yl-[1,2,4]oxadiazol-3-yl)-pyridin-3-yl]-methanol;

(R)-(1,3-Dimethyl-azetidin-3-yl)-(4-isopropyl-phenyl)-{5-[5-(4-methyl-piperidin-4-yl)-[1,2,4]oxadiazol-3-yl]-pyridin-3-yl}-methanol;

(R)-(1,3-Dimethyl-azetidin-3-yl)-{5-[5-(4-fluoro-piperidin-4-yl)-[1,2,4]oxadiazol-3-yl]-pyridin-3-yl}-(4-isopropyl-phenyl)-methanol;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-butan-1-one;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2,2-dimethyl-propan-1-one;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2-methoxy-ethanone;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-3-methoxy-propan-1-one;

Cyclopropyl-[4-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-piperidin-1-yl]-methanone;

Cyclopentyl-[4-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-piperidin-1-yl]-methanone;

[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-(tetrahydro-pyran-4-yl)-methanone;

[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-phenyl-methanone;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-carboxylic acid methyl ester;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-carboxylic acid ethyl ester;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-carboxylic acid 2-methoxy-ethyl ester;

(R)-(1,3-Dimethyl-azetidin-3-yl)-(4-isopropyl-phenyl)-{5-[5-(1-methanesulfonyl-piperidin-4-yl)-[1,2,4]oxadiazol-3-yl]-pyridin-3-yl}-methanol;

(R)-(1,3-Dimethyl-azetidin-3-yl)-(4-isopropyl-phenyl)-(5-{5-[1-(propane-2-sulfonyl)-piperidin-4-yl]-[1,2,4]oxadiazol-3-yl}-pyridin-3-yl)-methanol;

(R)-(1,3-Dimethyl-azetidin-3-yl)-(4-isopropyl-phenyl)-(5-{5-[1-(propane-1-sulfonyl)-piperidin-4-yl]-[1,2,4]oxadiazol-3-yl}-pyridin-3-yl)-methanol;

(R)-(1,3-Dimethyl-azetidin-3-yl)-(4-isopropyl-phenyl)-(5-{5-[1-(2-methoxy-ethanesulfonyl)-piperidin-4-yl]-[1,2,4]oxadiazol-3-yl}-pyridin-3-yl)-methanol;

2-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-sulfonyl]-ethanol;

(R)-{5-[5-(1-Cyclopentanesulfonyl-piperidin-4-yl)-[1,2,4]oxadiazol-3-yl]-pyridin-3-yl}-(1,3-dimethyl-azetidin-3-yl)-(4-isopropyl-phenyl)-methanol;

(R)-(1,3-Dimethyl-azetidin-3-yl)-(4-isopropyl-phenyl)-(5-{5-[1-(tetrahydro-pyran-4-sulfonyl)-piperidin-4-yl]-[1,2,4]oxadiazol-3-yl}-pyridin-3-yl)-methanol;

4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidine-1-sulfonic acid methylamide;

(R)-(1,3-Dimethyl-azetidin-3-yl)-(4-isopropyl-phenyl)-{5-[5-(1-methylamino-cyclopropyl)-[1,2,4]oxadiazol-3-yl]-pyridin-3-yl}-methanol;

[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclopropyl]-methyl-carbamic acid ethyl ester;

N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-cyclopropyl]-N-methyl-methanesulfonamide;

(R)-(1,3-Dimethyl-azetidin-3-yl)-[6-(2,2-dimethyl-cyclopentyloxy)-pyridazin-4-yl]-(4-isopropyl-phenyl)-methanol;

(R)-[6-(3,3-Difluoro-cyclopentyloxy)-pyridazin-4-yl]-(1,3-dimethyl-azetidin-3-yl)-(4-isopropyl-phenyl)-methanol;

2-(2-{5-[(R)-(1,3-Dimethyl-azetidin-3-yl)-hydroxy-(4-isopropyl-phenyl)-methyl]-pyridazin-3-yloxy}-phenyl)-ethanol;

2-(4-{5-[(R)-(1,3-Dimethyl-azetidin-3-yl)-hydroxy-(4-isopropyl-phenyl)-methyl]-pyridazin-3-yloxy}-phenyl)-ethanol;

(R)-[6-(Chroman-6-yloxy)-pyridazin-4-yl]-(1,3-dimethyl-azetidin-3-yl)-(4-isopropyl-phenyl)-methanol;

6-{5-[(R)-(1,3-Dimethyl-azetidin-3-yl)-hydroxy-(4-isopropyl-phenyl)-methyl]-pyridazin-3-yloxy}-3H-benzooxazol-2-one;

1-{5-[(R)-(1,3-Dimethyl-azetidin-3-yl)-hydroxy-(4-isopropyl-phenyl)-methyl]-pyridin-3-yl}-3-(6-methyl-pyrimidin-4-yl)-pent-1-yn-3-ol;

(S)-4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(1,5-dimethyl-1H-pyrazol-3-yl)-but-3-yn-2-ol;

(R)-(1,3-Dimethyl-azetidin-3-yl)-{5-[1-(4-fluoro-phenyl)-cyclopropylethynyl]-pyridin-3-yl)-(4-isopropyl-phenyl)-methanol;

(S)-4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(1-methyl-1H-pyrazol-3-yl)-but-3-yn-2-ol;

3-{5-[(R)-(1,3-Dimethyl-azetidin-3-yl)-hydroxy-(4-isopropyl-phenyl)-methyl]-pyridin-3-ylethynyl}-3-hydroxy-pyrrolidine-1-carboxylic acid tert-butyl ester;

4-{5-[(R)-(1,3-Dimethyl-azetidin-3-yl)-hydroxy-(4-isopropyl-phenyl)-methyl]-pyridin-3-ylethynyl}-piperidine-1-carboxylic acid tert-butyl ester;

1-{5-[(R)-(1,3-Dimethyl-azetidin-3-yl)-hydroxy-(4-isopropyl-phenyl)-methyl]-pyridin-3-yl}-3-(6-methyl-pyrimidin-4-yl)-pentan-3-ol;

2-(2-{5-[(R)-(1,3-Dimethyl-azetidin-3-yl)-hydroxy-(4-isopropyl-phenyl)-methyl]-pyridin-3-yl}-ethyl)-benzoic acid methyl ester;

(R)-(1,3-Dimethyl-azetidin-3-yl)-{5-[2-(2-hydroxymethyl-phenyl)-ethyl]-pyridin-3-yl}-(4-isopropyl-phenyl)-methanol;

4-{5-[(R)-(1,3-Dimethyl-azetidin-3-yl)-hydroxy-(4-isopropyl-phenyl)-methyl]-pyridin-3-yl}-2-(6-methoxy-pyrimidin-4-yl)-butan-2-ol;

3-(2-{5-[(R)-(1,3-Dimethyl-azetidin-3-yl)-hydroxy-(4-isopropyl-phenyl)-methyl]-pyridin-3-yl}-ethyl)-3-hydroxy-pyrrolidine-1-carboxylic acid tert-butyl ester;

(R)-(1,3-Dimethyl-azetidin-3-yl)-(4-isopropyl-phenyl)-{5-[2-(1H-pyrrolo[2,3-b]pyridin-2-yl)-ethyl]-pyridin-3-yl}-methanol;

4-(2-{5-[(R)-(1,3-Dimethyl-azetidin-3-yl)-hydroxy-(4-isopropyl-phenyl)-methyl]-pyridin-3-yl}-ethyl)-piperidine-1-carboxylic acid tert-butyl ester;

4-{5-[(R)-(1,3-Dimethyl-azetidin-3-yl)-hydroxy-(4-isopropyl-phenyl)-methyl]-pyridin-3-yl}-2-pyridin-2-yl-butan-2-ol;

1-Cyclopropyl-3-{5-[(R)-(1,3-dimethyl-azetidin-3-yl)-hydroxy-(4-isopropyl-phenyl)-methyl]-pyridin-3-yl}-1-pyridin-2-yl-propan-1-ol;

4-{5-[(R)-(1,3-Dimethyl-azetidin-3-yl)-hydroxy-(4-isopropyl-phenyl)-methyl]-pyridin-3-yl}-2-(5-methyl-pyridin-3-yl)-butan-2-ol;

8-(2-{5-[(R)-(1,3-Dimethyl-azetidin-3-yl)-hydroxy-(4-isopropyl-phenyl)-methyl]-pyridazin-3-yl}-ethyl)-5,6,7,8-tetrahydro-quinolin-8-ol;

4-{5-[(R)-(1,3-Dimethyl-azetidin-3-yl)-hydroxy-(4-isopropyl-phenyl)-methyl]-pyridazin-3-yl}-2-(6-methoxy-pyridin-2-yl)-butan-2-ol;

4-{5-[(R)-(1,3-Dimethyl-azetidin-3-yl)-hydroxy-(4-isopropyl-phenyl)-methyl]-pyridazin-3-yl}-2-(6-methyl-pyridin-2-yl)-butan-2-ol;

(1,3-Dimethyl-azetidin-3-yl)-(4-isopropyl-phenyl)-(6-pyrrolidin-1-yl-pyridin-2-yl)-methanol;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-fluoro-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-methyl-piperidin-1-yl]-ethanone;

4-{5-[(R)-(1,3-Dimethyl-azetidin-3-yl)-hydroxy-(4-isopropyl-phenyl)-methyl]-pyridin-3-yloxy}-cyclohexanone;

4-{5-[(R)-(1,3-Dimethyl-azetidin-3-yl)-hydroxy-(4-isopropyl-phenyl)-methyl]-pyridin-3-yl}-cyclohexanol;

(R)-(5-Cyclopentyloxymethyl-pyridin-3-yl)-(1,3-dimethyl-azetidin-3-yl)-(4-isopropyl-phenyl)-methanol;

1-(4-{5-[(R)-(1,3-Dimethyl-azetidin-3-yl)-hydroxy-(4-isopropyl-phenyl)-methyl]-pyridin-3-ylmethoxy}-piperidin-1-yl)-ethanone;

(R)-(1,3-Dimethyl-azetidin-3-yl)-(4-isopropyl-phenyl)-[6-(tetrahydro-pyran-4-yl)-pyridazin-4-yl]-methanol;

4-{5-[(R)-(1,3-Dimethyl-azetidin-3-yl)-hydroxy-(4-isopropyl-phenyl)-methyl]-pyridazin-3-yl}-2-phenyl-butan-2-ol;

(R)-(1,3-Dimethyl-azetidin-3-yl)-(4-isopropyl-phenyl)-{6-[(S)-(tetrahydro-furan-3-yl)oxy]-pyridazin-4-yl}-methanol;

(R)-(1,3-Dimethyl-azetidin-3-yl)-(4-isopropyl-phenyl)-{6-[(R)-(tetrahydro-furan-3-yl)oxy]-pyridazin-4-yl}-methanol;

1-{5-[(R)-(1,3-Dimethyl-azetidin-3-yl)-hydroxy-(4-isopropyl-phenyl)-methyl]-pyridazin-3-yl}-4-methyl-pyrrolidin-2-one;

1-{5-[(R)-(1,3-Dimethyl-azetidin-3-yl)-hydroxy-(4-isopropyl-phenyl)-methyl]-pyridazin-3-yl}-3-isopropyl-pyrrolidin-2-one;

1-{5-[(R)-(1,3-Dimethyl-azetidin-3-yl)-hydroxy-(4-isopropyl-phenyl)-methyl]-pyridazin-3-yl}-3,3-dimethyl-pyrrolidin-2-one;

1-{5-[(R)-(1,3-Dimethyl-azetidin-3-yl)-hydroxy-(4-isopropyl-phenyl)-methyl]-pyridazin-3-yl}-4,4-dimethyl-pyrrolidin-2-one;

5-{5-[(R)-(1,3-Dimethyl-azetidin-3-yl)-hydroxy-(4-isopropyl-phenyl)-methyl]-pyridazin-3-yl}-5-aza-spiro[2.4]heptan-6-one;

1-{5-[(R)-(1,3-Dimethyl-azetidin-3-yl)-hydroxy-(4-isopropyl-phenyl)-methyl]-pyridazin-3-yl}-4-trifluoromethyl-pyrrolidin-2-one;

4-Cyclopropyl-1-{5-[(R)-(1,3-dimethyl-azetidin-3-yl)-hydroxy-(4-isopropyl-phenyl)-methyl]-pyridazin-3-yl}-pyrrolidin-2-one;

2-{5-[(R)-(1,3-Dimethyl-azetidin-3-yl)-hydroxy-(4-isopropyl-phenyl)-methyl]-pyridazin-3-yl}-8-oxa-2-aza-spiro[4.5]decan-3-one;

3-{5-[(R)-(1,3-Dimethyl-azetidin-3-yl)-hydroxy-(4-isopropyl-phenyl)-methyl]-pyridazin-3-yl}-1-oxa-3-aza-spiro[4.5]decan-2-one;

1-{5-[(R)-(1,3-Dimethyl-azetidin-3-yl)-hydroxy-(4-isopropyl-phenyl)-methyl]-pyridazin-3-yl}-4-pyridin-2-yl-pyrrolidin-2-one;

1-{5-[(R)-(1,3-Dimethyl-azetidin-3-yl)-hydroxy-(4-isopropyl-phenyl)-methyl]-pyridazin-3-yl}-3-(2-methoxy-ethyl)-pyrrolidin-2-one;

1-{5-[(R)-(1,3-Dimethyl-azetidin-3-yl)-hydroxy-(4-isopropyl-phenyl)-methyl]-pyridazin-3-yl}-4-phenyl-pyrrolidin-2-one;

2-{5-[(R)-(1,3-Dimethyl-azetidin-3-yl)-hydroxy-(4-isopropyl-phenyl)-methyl]-pyridazin-3-yl}-2,3-dihydro-isoindol-1-one;

2-(3-{5-[(S)-(3-Fluoro-1-methyl-azetidin-3-yl)-hydroxy-(4-isopropyl-phenyl)-methyl]-pyridin-3-yl}-[1,2,4]oxadiazol-5-yl)-propan-2-ol;

2-(3-{5-[(S)-(1-Cyclopropyl-3-fluoro-azetidin-3-yl)-hydroxy-(4-isopropyl-phenyl)-methyl]-pyridin-3-yl}-[1,2,4]oxadiazol-5-yl)-propan-2-ol;

1-[4-(3-{5-[(S)-(3-Fluoro-1-methyl-azetidin-3-yl)-hydroxy-(4-isopropyl-phenyl)-methyl]-pyridin-3-yl}-[1,2,4]oxadiazol-5-yl)-piperidin-1-yl]-ethanone;

1-[4-(3-{5-[(S)-(1-Cyclopropyl-3-fluoro-azetidin-3-yl)-hydroxy-(4-isopropyl-phenyl)-methyl]-pyridin-3-yl}-[1,2,4]oxadiazol-5-yl)-piperidin-1-yl]-ethanone;

2-(3-{5-[(R)-(1-Cyclopropyl-3-methyl-azetidin-3-yl)-hydroxy-(4-isopropyl-phenyl)-methyl]-pyridin-3-yl}-[1,2,4]oxadiazol-5-yl)-propan-2-ol;

1-[4-(3-{5-[(R)-(1-Cyclopropyl-3-methyl-azetidin-3-yl)-hydroxy-(4-isopropyl-phenyl)-methyl]-pyridin-3-yl}-[1,2,4]oxadiazol-5-yl)-piperidin-1-yl]-ethanone;

(R)-(1-Cyclopropyl-3-methyl-azetidin-3-yl)-(4-isopropyl-phenyl)-{5-[5-(tetrahydro-pyran-4-yl)-[1,2,4]oxadiazol-3-yl]-pyridin-3-yl}-methanol;

trans-4-(3-{5-[(R)-(1-Cyclopropyl-3-methyl-azetidin-3-yl)-hydroxy-(4-isopropyl-phenyl)-methyl]-pyridin-3-yl}-[1,2,4]oxadiazol-5-yl)-cyclohexanol;

(R)-(1-Cyclopropyl-3-methyl-azetidin-3-yl)-(4-isopropyl-phenyl)-[5-(5-oxetan-3-yl-[1,2,4]oxadiazol-3-yl)-pyridin-3-yl]-methanol;

1-[(R)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidin-1-yl]-ethanone;

1-[3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-ethanone;

1-[3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-3-hydroxy-piperidin-1-yl]-ethanone;

1-[3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-3-methyl-piperidin-1-yl]-ethanone;

1-[3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-4-hydroxy-piperidin-1-yl]-ethanone;

N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclopropyl]-acetamide;

Tetrahydro-pyran-4-carboxylic acid [1-(3-{5-[(R)-(1,3-dimethyl-azetidin-3-yl)-hydroxy-(4-isopropyl-phenyl)-methyl]-pyridin-3-yl}-[1,2,4]oxadiazol-5-ylmethyl)-cyclopropyl]-amide;

N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclopropyl]-2-methoxy-acetamide;

N-[1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-cyclopropyl]-N-methyl-acetamide;

N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-propionamide;

N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-2-methoxy-acetamide;
Tetrahydro-pyran-4-carboxylic acid [2-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-amide;
N-[2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-isobutyramide;
Cyclopropanecarboxylic acid [2-(3-{5-[(R)-(1,3-dimethyl-azetidin-3-yl)-hydroxy-(4-isopropyl-phenyl)-methyl]-pyridin-3-yl}-[1,2,4]oxadiazol-5-yl)-1,1-dimethyl-ethyl]-amide;
1-[cis-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-2-methyl-piperidin-1-yl]-ethanone;
1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-hydroxy-piperidin-1-yl]-2-methyl-propan-1-one;
1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-hydroxy-piperidin-1-yl]-propan-1-one;
1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-methoxy-piperidin-1-yl]-ethanone;
1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-3,3,3-trifluoro-propan-1-one;
1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-2-oxetan-3-yl-ethanone;
1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-ethyl-piperidin-1-yl]-ethanone;
[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-oxetan-3-yl-methanone;
1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-isopropyl-piperidin-1-yl]-2-methoxy-ethanone;
1-[cis-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-3-methyl-piperidin-1-yl]-ethanone;
5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-piperidin-2-one;
5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-5-methyl-piperidin-2-one;
5-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one;
4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-methyl-pyrrolidin-2-one;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-3,3-dimethyl-pyrrolidine-2,5-dione;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-imidazolidine-2,4-dione;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidin-2-one;
3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-imidazolidine-2,4-dione;
3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-1-methyl-imidazolidine-2,4-dione;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-3-methyl-imidazolidine-2,4-dione;
3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-oxazolidin-2-one;
1-Cyclopropyl-3-(3-{5-[(R)-(1,3-dimethyl-azetidin-3-yl)-hydroxy-(4-isopropyl-phenyl)-methyl]-pyridin-3-yl}-[1,2,4]oxadiazol-5-ylmethyl)-imidazolidin-2-one;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidine-2,5-dione;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-3-methyl-imidazolidin-2-one;
1-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-imidazolidin-2-one;
2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-propane-1,2-diol;
(R)-(1,3-Dimethyl-azetidin-3-yl)-(4-isopropyl-phenyl)-[5-(5-pyridin-3-yl-[1,2,4]oxadiazol-3-yl)-pyridin-3-yl]-methanol;
1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-piperidin-1-yl]-ethanone;
(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-acetonitrile;
1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-4-hydroxy-piperidin-1-yl]-ethanone;
3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-propionitrile;
1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-3-methoxy-piperidin-1-yl]-ethanone;
1-[(R)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-ethanone;
4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-tetrahydro-pyran-4-ol;
(R)-(1,3-Dimethyl-azetidin-3-yl)-{5-[5-(3-hydroxymethyl-bicyclo[1.1.1]pent-1-yl)-[1,2,4]oxadiazol-3-yl]-pyridin-3-yl}-(4-isopropyl-phenyl)-methanol;
4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-piperidine-2,6-dione;
2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-2,2-difluoro-ethanol;

(R)-(1,3-Dimethyl-azetidin-3-yl)-(4-isopropyl-phenyl)-{5-[5-(3-methoxy-phenyl)-[1,2,4]oxadiazol-3-yl]-pyridin-3-yl}-methanol;

(R)-(1,3-Dimethyl-azetidin-3-yl)-[5-(5-isopropyl-[1,2,4]oxadiazol-3-yl)-pyridin-3-yl]-(4-isopropyl-phenyl)-methanol;

(R)-(1,3-Dimethyl-azetidin-3-yl)-(4-isopropyl-phenyl)-{5-[5-(6-methyl-pyrimidin-4-yl)-[1,2,4]oxadiazol-3-yl]-pyridin-3-yl}-methanol;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-pyrrolidin-2-one;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-methyl-pyrrolidin-2-one;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-ethyl-pyrrolidin-2-one;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-ethyl-pyrrolidin-2-one;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-isopropyl-pyrrolidin-2-one;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-1-isopropyl-pyrrolidin-2-one;

1-[(S)-3-(3-{5-[(R)-(1,3-Dimethyl-azetidin-3-yl)-hydroxy-(4-isopropyl-phenyl)-methyl]-pyridin-3-yl}-[1,2,4]oxadiazol-5-ylmethyl)-pyrrolidin-1-yl]-ethanone;

(S)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one;

(R)-4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-2-one;

(R)-(1,3-Dimethyl-azetidin-3-yl)-(4-isopropyl-phenyl)-[5-(5-methyl-[1,2,4]oxadiazol-3-yl)-pyridin-3-yl]-methanol;

(R)-{5-[5-(1,1-Difluoro-ethyl)-[1,2,4]oxadiazol-3-yl]-pyridin-3-yl}-(1,3-dimethyl-azetidin-3-yl)-(4-isopropyl-phenyl)-methanol;

4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-tetrahydro-pyran-4-ol;

(R)-[5-(3-tert-Butoxymethyl-[1,2,4]oxadiazol-5-yl)-pyridin-3-yl]-(1,3-dimethyl-azetidin-3-yl)-(4-isopropyl-phenyl)-methanol;

(R)-(1,3-Dimethyl-azetidin-3-yl)-[5-(3-hydroxymethyl-[1,2,4]oxadiazol-5-yl)-pyridin-3-yl]-(4-isopropyl-phenyl)-methanol;

1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperazin-1-yl]-ethanone;

1-[3-(5-{5-[(R)-(1,3-Dimethyl-azetidin-3-yl)-hydroxy-(4-isopropyl-phenyl)-methyl]-pyridin-3-yl}-[1,2,4]oxadiazol-3-ylmethyl)-azetidin-1-yl]-ethanone;

4-(5-{5-[(R)-(1,3-Dimethyl-azetidin-3-yl)-hydroxy-(4-isopropyl-phenyl)-methyl]-pyridin-3-yl}-[1,2,4]oxadiazol-3-ylmethyl)-tetrahydro-pyran-4-ol;

[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-[1,4]dioxan-2-yl-methanone;

1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-2-methoxy-ethanone;

(R)-(1,3-Dimethyl-azetidin-3-yl)-(4-isopropyl-phenyl)-{5-[3-(1-methanesulfonyl-piperidin-4-yl)-[1,2,4]oxadiazol-5-yl]-pyridin-3-yl}-methanol;

(R)-(1,3-Dimethyl-azetidin-3-yl)-(4-isopropyl-phenyl)-(5-{3-[1-(2-methoxy-ethanesulfonyl)-piperidin-4-yl]-[1,2,4]oxadiazol-5-yl}-pyridin-3-yl)-methanol;

1-[4-(5-{5-[(R)-(1,3-Dimethyl-azetidin-3-yl)-hydroxy-(4-isopropyl-phenyl)-methyl]-pyridin-3-yl}-[1,2,4]oxadiazol-3-yl)-piperidin-1-yl]-2-hydroxy-ethanone;

(R)-(1,3-Dimethyl-azetidin-3-yl)-(4-isopropyl-phenyl)-(5-[1,2,4]oxadiazol-3-yl-pyridin-3-yl)-methanol;

1-[4-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-piperidin-1-yl]-ethanone;

2-(3-{5-[(R)-(4-Bromo-phenyl)-(1,3-dimethyl-azetidin-3-yl)-hydroxy-methyl]-pyridin-3-yl}-[1,2,4]oxadiazol-5-yl)-propan-2-ol;

2-(3-{5-[(R)-(1,3-Dimethyl-azetidin-3-yl)-hydroxy-naphthalen-2-yl-methyl]-pyridin-3-yl}-[1,2,4]oxadiazol-5-yl)-propan-2-ol;

2-[3-(5-{(R)-(1,3-Dimethyl-azetidin-3-yl)-hydroxy-[4-(1-trifluoromethyl-cyclopropyl)-phenyl]-methyl}-pyridin-3-yl)-[1,2,4]oxadiazol-5-yl]-propan-2-ol;

2-[3-(5-{(R)-(1,3-Dimethyl-azetidin-3-yl)-hydroxy-[4-(2,2,2-trifluoro-1,1-dimethyl-ethyl)-phenyl]-methyl}-pyridin-3-yl)-[1,2,4]oxadiazol-5-yl]-propan-2-ol;

2-(3-{5-[(R)-(1,3-Dimethyl-azetidin-3-yl)-hydroxy-(4-isopropoxy-phenyl)-methyl]-pyridin-3-yl}-[1,2,4]oxadiazol-5-yl)-propan-2-ol;

2-[3-(5-{(R)-(1,3-Dimethyl-azetidin-3-yl)-hydroxy-[4-(1,2,2,2-tetrafluoro-1-trifluoromethyl-ethyl)-phenyl]-methyl}-pyridin-3-yl)-[1,2,4]oxadiazol-5-yl]-propan-2-ol;

(R)-2-(3-(5-((1,3-dimethylazetidin-3-yl)(hydroxy)(4-(pentafluoro-$\lambda^6$-sulfanyl)phenyl)methyl)pyridin-3-yl)-1,2,4-oxadiazol-5-yl)propan-2-ol;

2-(3-{5-[(R)-(1,3-Dimethyl-azetidin-3-yl)-(3-fluoro-4-isopropyl-phenyl)-hydroxy-methyl]-pyridin-3-yl}-[1,2,4]oxadiazol-5-yl)-propan-2-ol;

2-(3-{5-[(R)-(4-tert-Butyl-phenyl)-(1,3-dimethyl-azetidin-3-yl)-hydroxy-methyl]-pyridin-3-yl}-[1,2,4]oxadiazol-5-yl)-propan-2-ol;

2-(3-{5-[(R)-Benzo[b]thiophen-5-yl-(1,3-dimethyl-azetidin-3-yl)-hydroxy-methyl]-pyridin-3-yl}-[1,2,4]oxadiazol-5-yl)-propan-2-ol;

2-(3-{5-[(R)-(1,3-Dimethyl-azetidin-3-yl)-hydroxy-(4-pentafluoroethyl-phenyl)-methyl]-pyridin-3-yl}-[1,2,4]oxadiazol-5-yl)-propan-2-ol;

2-[3-(5-{(R)-(1,3-Dimethyl-azetidin-3-yl)-hydroxy-[4-(1-methyl-cyclopropyl)-phenyl]-methyl}-pyridin-3-yl)-[1,2,4]oxadiazol-5-yl]-propan-2-ol;

2-(3-{5-[(R)-(1,3-Dimethyl-azetidin-3-yl)-hydroxy-(4-isopropyl-3-methyl-phenyl)-methyl]-pyridin-3-yl}-[1,2,4]oxadiazol-5-yl)-propan-2-ol;

2-(3-{5-[(R)-(1,3-Dimethyl-azetidin-3-yl)-hydroxy-(4-trifluoromethoxy-phenyl)-methyl]-pyridin-3-yl}-[1,2,4]oxadiazol-5-yl)-propan-2-ol;

1-[4-(3-{5-[(R)-(4-Bromo-phenyl)-(1,3-dimethyl-azetidin-3-yl)-hydroxy-methyl]-pyridin-3-yl}-[1,2,4]oxadiazol-5-yl)-piperidin-1-yl]-ethanone;

2-[3-(5-{(R)-(1,3-Dimethyl-azetidin-3-yl)-[4-(1-fluoro-1-methyl-ethyl)-phenyl]-hydroxy-methyl}-pyridin-3-yl)-[1,2,4]oxadiazol-5-yl]-propan-2-ol;

2-(3-{5-[(R)-[4-(1,1-Difluoro-ethyl)-phenyl]-(1,3-dimethyl-azetidin-3-yl)-hydroxy-methyl]-pyridin-3-yl}-[1,2,4]oxadiazol-5-yl)-propan-2-ol;

2-(3-{5-[(R)-(4-Bicyclo[1.1.1]pent-1-yl-phenyl)-(1,3-dimethyl-azetidin-3-yl)-hydroxy-methyl]-pyridin-3-yl}-[1,2,4]oxadiazol-5-yl)-propan-2-ol;

(R)-(1,3-Dimethyl-azetidin-3-yl)-{5-[5-(tetrahydro-pyran-4-yl)-[1,2,4]oxadiazol-3-yl]-pyridin-3-yl}-[4-(2,2,2-trifluoro-ethyl)-phenyl]-methanol;

2-[3-(5-{(R)-(1,3-Dimethyl-azetidin-3-yl)-[4-(1,1-dimethyl-propyl)-phenyl]-hydroxy-methyl}-pyridin-3-yl)-[1,2,4]oxadiazol-5-yl]-propan-2-ol;

1-[4-(3-{5-[(R)-(1,3-Dimethyl-azetidin-3-yl)-(3-fluoro-4-isopropyl-phenyl)-hydroxy-methyl]-pyridin-3-yl}-[1,2,4]oxadiazol-5-yl)-piperidin-1-yl]-ethanone;

1-{4-[3-(5-{(R)-(1,3-Dimethyl-azetidin-3-yl)-hydroxy-[4-(1-trifluoromethyl-cyclopropyl)-phenyl]-methyl}-pyridin-3-yl)-[1,2,4]oxadiazol-5-yl]-piperidin-1-yl}-ethanone;

1-[4-(3-{5-[(R)-(1,3-Dimethyl-azetidin-3-yl)-hydroxy-(4-trifluoromethoxy-phenyl)-methyl]-pyridin-3-yl}-[1,2,4]oxadiazol-5-yl)-piperidin-1-yl]-ethanone;

1-[4-(3-{5-[(R)-(1,3-Dimethyl-azetidin-3-yl)-hydroxy-(4-isopropoxy-phenyl)-methyl]-pyridin-3-yl}-[1,2,4]oxadiazol-5-yl)-piperidin-1-yl]-ethanone;

2-(3-{5-[(R)-(3-Chloro-4-isopropyl-phenyl)-(1,3-dimethyl-azetidin-3-yl)-hydroxy-methyl]-pyridin-3-yl}-[1,2,4]oxadiazol-5-yl)-propan-2-ol;

2-(3-{5-[(R)-(4-Cyclobutyl-phenyl)-(1,3-dimethyl-azetidin-3-yl)-hydroxy-methyl]-pyridin-3-yl}-[1,2,4]oxadiazol-5-yl)-propan-2-ol;

1-[4-(3-{5-[(R)-(4-Cyclobutyl-phenyl)-(1,3-dimethyl-azetidin-3-yl)-hydroxy-methyl]-pyridin-3-yl}-[1,2,4]oxadiazol-5-yl)-piperidin-1-yl]-ethanone;

1-[4-(3-{5-[(R)-(3,5-Difluoro-4-isopropyl-phenyl)-(1,3-dimethyl-azetidin-3-yl)-hydroxy-methyl]-pyridin-3-yl}-[1,2,4]oxadiazol-5-yl)-piperidin-1-yl]-ethanone;

2-(3-{5-[(R)-(3,5-Difluoro-4-isopropyl-phenyl)-(1,3-dimethyl-azetidin-3-yl)-hydroxy-methyl]-pyridin-3-yl}-[1,2,4]oxadiazol-5-yl)-propan-2-ol;

1-[4-(3-{5-[(R)-(4-Cyclobutoxy-phenyl)-(1,3-dimethyl-azetidin-3-yl)-hydroxy-methyl]-pyridin-3-yl}-[1,2,4]oxadiazol-5-yl)-piperidin-1-yl]-ethanone;

2-[3-(5-{(1,3-Dimethyl-azetidin-3-yl)-[4-(1-ethyl-propyl)-phenyl]-hydroxy-methyl}-pyridin-3-yl)-[1,2,4]oxadiazol-5-yl]-propan-2-ol;

1-{4-[3-(5-{(1,3-Dimethyl-azetidin-3-yl)-[4-(2,2-dimethyl-propyl)-phenyl]-hydroxy-methyl}-pyridin-3-yl)-[1,2,4]oxadiazol-5-yl]-piperidin-1-yl}-ethanone;

2-[3-(5-{(1,3-Dimethyl-azetidin-3-yl)-[4-(2,2-dimethyl-propyl)-phenyl]-hydroxy-methyl}-pyridin-3-yl)-[1,2,4]oxadiazol-5-yl]-propan-2-ol;

1-{4-[3-(5-{(1,3-Dimethyl-azetidin-3-yl)-[4-(2,2-dimethyl-propyl)-phenyl]-hydroxy-methyl}-pyridin-3-yl)-[1,2,4]oxadiazol-5-yl]-piperidin-1-yl}-ethanone;

1-{4-[3-(5-{(1,3-Dimethyl-azetidin-3-yl)-hydroxy-[4-(1-methyl-cyclopropyl)-phenyl]-methyl}-pyridin-3-yl)-[1,2,4]oxadiazol-5-yl]-piperidin-1-yl}-ethanone;

2-(3-{5-[(R)-(1,3-Dimethyl-azetidin-3-yl)-hydroxy-(4-propyl-phenyl)-methyl]-pyridin-3-yl}-[1,2,4]oxadiazol-5-yl)-propan-2-ol;

2-(3-{5-[(R)-(4-Cyclopropyl-phenyl)-(1,3-dimethyl-azetidin-3-yl)-hydroxy-methyl]-pyridin-3-yl}-[1,2,4]oxadiazol-5-yl)-propan-2-ol;

2-(3-{5-[(R)-(1,3-Dimethyl-azetidin-3-yl)-(4-ethyl-phenyl)-hydroxy-methyl]-pyridin-3-yl}-[1,2,4]oxadiazol-5-yl)-propan-2-ol;

2-(3-{5-[(R)-(4-Butyl-phenyl)-(1,3-dimethyl-azetidin-3-yl)-hydroxy-methyl]-pyridin-3-yl}-[1,2,4]oxadiazol-5-yl)-propan-2-ol;

2-(3-{5-[(R)-(1,3-Dimethyl-azetidin-3-yl)-hydroxy-(4-trifluoromethyl-phenyl)-methyl]-pyridin-3-yl}-[1,2,4]oxadiazol-5-yl)-propan-2-ol;

2-[3-(5-{(R)-(1,3-Dimethyl-azetidin-3-yl)-hydroxy-[4-(2,2,2-trifluoro-ethyl)-phenyl]-methyl}-pyridin-3-yl)-[1,2,4]oxadiazol-5-yl]-propan-2-ol;

2-(3-{5-[(R)-(1,3-Dimethyl-azetidin-3-yl)-hydroxy-(4-isobutyl-phenyl)-methyl]-pyridin-3-yl}-[1,2,4]oxadiazol-5-yl)-propan-2-ol;

2-(3-{5-[(R)-(4-Cyclobutoxy-phenyl)-(1,3-dimethyl-azetidin-3-yl)-hydroxy-methyl]-pyridin-3-yl}-[1,2,4]oxadiazol-5-yl)-propan-2-ol;

2-(3-{5-[(R)-(1,3-Dimethyl-azetidin-3-yl)-hydroxy-(4-isopropenyl-phenyl)-methyl]-pyridin-3-yl}-[1,2,4]oxadiazol-5-yl)-propan-2-ol;

1-{4-[3-(5-{(R)-(1,3-Dimethyl-azetidin-3-yl)-hydroxy-[4-(2,2,2-trifluoro-ethyl)-phenyl]-methyl}-pyridin-3-yl)-[1,2,4]oxadiazol-5-yl]-piperidin-1-yl}-ethanone;

1-[4-(3-{5-[(R)-(1,3-Dimethyl-azetidin-3-yl)-hydroxy-(4-propyl-phenyl)-methyl]-pyridin-3-yl}-[1,2,4]oxadiazol-5-yl)-piperidin-1-yl]-ethanone;

1-[4-(3-{5-[(R)-Hydroxy-(1-isopropyl-3-methyl-azetidin-3-yl)-(4-isopropyl-phenyl)-methyl]-pyridin-3-yl}-[1,2,4]oxadiazol-5-yl)-piperidin-1-yl]-ethanone;

1-[4-(3-{5-[(R)-[1-(2,2-Difluoro-ethyl)-3-methyl-azetidin-3-yl]-hydroxy-(4-isopropyl-phenyl)-methyl]-pyridin-3-yl}-[1,2,4]oxadiazol-5-yl)-piperidin-1-yl]-ethanone;

1-[4-(3-{5-[(R)-Hydroxy-[1-(2-hydroxy-ethyl)-3-methyl-azetidin-3-yl]-(4-isopropyl-phenyl)-methyl]-pyridin-3-yl}-[1,2,4]oxadiazol-5-yl)-piperidin-1-yl]-ethanone;

1-[4-(3-{5-[(R)-(1-Cyclopropylmethyl-3-methyl-azetidin-3-yl)-hydroxy-(4-isopropyl-phenyl)-methyl]-pyridin-3-yl}-[1,2,4]oxadiazol-5-yl)-piperidin-1-yl]-ethanone;

1-{4-[3-(5-{(R)-Hydroxy-(4-isopropyl-phenyl)-[1-(2-methoxy-ethyl)-3-methyl-azetidin-3-yl]-methyl}-pyridin-3-yl)-[1,2,4]oxadiazol-5-yl]-piperidin-1-yl}-ethanone;

1-{4-[3-(5-{(R)-Hydroxy-(4-isopropyl-phenyl)-[3-methyl-1-(3,3,3-trifluoro-propyl)-azetidin-3-yl]-methyl}-pyridin-3-yl)-[1,2,4]oxadiazol-5-yl]-piperidin-1-yl}-ethanone;

1-[4-(3-{5-[(R)-Hydroxy-(4-isopropyl-phenyl)-(3-methyl-1-propyl-azetidin-3-yl)-methyl]-pyridin-3-yl}-[1,2,4]oxadiazol-5-yl)-piperidin-1-yl]-ethanone;

1-[4-(3-{5-[(R)-(1-Ethyl-3-methyl-azetidin-3-yl)-hydroxy-(4-isopropyl-phenyl)-methyl]-pyridin-3-yl}-[1,2,4]oxadiazol-5-yl)-piperidin-1-yl]-ethanone;

1-(4-{5-[(R)-(1,3-Dimethyl-azetidin-3-yl)-hydroxy-(4-isopropyl-phenyl)-methyl]-pyridin-3-ylethynyl}-piperidin-1-yl)-ethanone;

4-{5-[(R)-(1,3-Dimethyl-azetidin-3-yl)-hydroxy-(4-isopropyl-phenyl)-methyl]-pyridin-3-yl}-1,1,1-trifluoro-2-methyl-but-3-yn-2-ol;

Cyclopropanecarboxylic acid (3-{5-[(R)-(1,3-dimethyl-azetidin-3-yl)-hydroxy-(4-isopropyl-phenyl)-methyl]-pyridin-3-yl}-1,1-dimethyl-prop-2-ynyl)-amide;

N-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-isobutyramide;

N-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-2-methoxy-acetamide;

3-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-oxazolidin-2-one;

1-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-pyrrolidin-2-one;

1-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-3-methyl-imidazolidin-2-one;

1-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-imidazolidin-2-one;

3-(1-{5-[(R)-(1,3-Dimethyl-azetidin-3-yl)-hydroxy-(4-isopropyl-phenyl)-methyl]-pyridin-3-ylethynyl}-cyclopropyl)-oxazolidin-2-one;

1-((R)-2-{5-[(R)-(1,3-Dimethyl-azetidin-3-yl)-hydroxy-(4-isopropyl-phenyl)-methyl]-pyridin-3-ylethynyl}-2-methyl-pyrrolidin-1-yl)-ethanone;

1-(4-{5-[(R)-(1,3-Dimethyl-azetidin-3-yl)-hydroxy-(4-isopropyl-phenyl)-methyl]-pyridin-3-ylethynyl}-4-hydroxy-piperidin-1-yl)-ethanone;

1-[4-(3-{5-[(R)-(1,3-Dimethyl-azetidin-3-yl)-hydroxy-(4-isopropyl-phenyl)-methyl]-pyridin-3-yl}-1-hydroxy-1-methyl-prop-2-ynyl)-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}-1-hydroxy-prop-2-ynyl)-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}prop-2-ynyl)-piperidin-1-yl]-ethanone;

1-[4-(3-{5-[(R)-(1,3-Dimethyl-azetidin-3-yl)-hydroxy-(4-isopropyl-phenyl)-methyl]-pyridin-3-yl}-1-hydroxy-prop-2-ynyl)-4-methyl-piperidin-1-yl]-ethanone;

1-(4-{5-[(R)-(1,3-Dimethyl-azetidin-3-yl)-hydroxy-(4-isopropyl-phenyl)-methyl]-pyridin-3-ylethynyl}-4-methyl-piperidin-1-yl)-ethanone;

(R)-(1,3-Dimethyl-azetidin-3-yl)-(4-isopropyl-phenyl)-[5-(1-methanesulfonyl-piperidin-4-ylethynyl)-pyridin-3-yl]-methanol;

4-{5-[(R)-(1,3-Dimethyl-azetidin-3-yl)-hydroxy-(4-isopropyl-phenyl)-methyl]-pyridin-3-ylethynyl}-4-methyl-piperidine-1-sulfonic acid methylamide;

(R)-(1,3-Dimethyl-azetidin-3-yl)-(4-isopropyl-phenyl)-[5-(3-methanesulfonyl-3-methyl-but-1-ynyl)-pyridin-3-yl]-methanol;

1-{5-[(R)-(1,3-Dimethyl-azetidin-3-yl)-hydroxy-(4-isopropyl-phenyl)-methyl]-pyridin-3-ylethynyl}-cyclopropanesulfonic acid dimethylamide;

1-{5-[(R)-(1,3-Dimethyl-azetidin-3-yl)-hydroxy-(4-isopropyl-phenyl)-methyl]-pyridin-3-ylethynyl}-cyclopropanesulfonic acid amide;

(R)-[5-(3-Cyclopropanesulfonyl-3-methyl-but-1-ynyl)-pyridin-3-yl]-(1,3-dimethyl-azetidin-3-yl)-(4-isopropyl-phenyl)-methanol;

(R)-3-{5-[(R)-(1,3-Dimethyl-azetidin-3-yl)-hydroxy-(4-isopropyl-phenyl)-methyl]-pyridin-3-ylethynyl}-3-hydroxy-1-methyl-pyrrolidin-2-one;

(S)-3-{5-[(R)-(1,3-Dimethyl-azetidin-3-yl)-hydroxy-(4-isopropyl-phenyl)-methyl]-pyridin-3-ylethynyl}-3-hydroxy-1-methyl-pyrrolidin-2-one;

4-{5-[(R)-(1,3-Dimethyl-azetidin-3-yl)-hydroxy-(4-isopropyl-phenyl)-methyl]-pyridin-3-ylethynyl}-3,4-dihydro-2H-pyrano[3,2-b]pyridin-4-ol;

3-{5-[(R)-(1,3-Dimethyl-azetidin-3-yl)-hydroxy-(4-isopropyl-phenyl)-methyl]-pyridin-3-ylethynyl}-3-hydroxy-1-methyl-1,3-dihydro-indol-2-one;

4-{5-[(R)-(1,3-Dimethyl-azetidin-3-yl)-hydroxy-(4-isopropyl-phenyl)-methyl]-pyridin-3-yl}-2-(1H-indazol-3-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(1-methyl-1H-indazol-3-yl)-but-3-yn-2-ol;

2-(1-Cyclopropyl-1H-pyrazol-3-yl)-4-{5-[(R)-(1,3-dimethyl-azetidin-3-yl)-hydroxy-(4-isopropyl-phenyl)-methyl]-pyridin-3-yl}-but-3-yn-2-ol;

4-{5-[(R)-(1,3-Dimethyl-azetidin-3-yl)-hydroxy-(4-isopropyl-phenyl)-methyl]-pyridin-3-yl}-2-(2-methyl-pyrimidin-4-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(5-methyl-pyrazin-2-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(2-methyl-thiazol-5-yl)-but-3-yn-2-ol;

2-(6-Cyclopropyl-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol;

N-(3-{5-[(R)-(1,3-Dimethyl-azetidin-3-yl)-hydroxy-(4-isopropyl-phenyl)-methyl]-pyridin-3-yl}-1,1-dimethyl-prop-2-ynyl)-acetamide;

(S)-4-{5-[(R)-(1,3-Dimethyl-azetidin-3-yl)-hydroxy-(4-isopropyl-phenyl)-methyl]-pyridin-3-yl}-2-(6-methoxy-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(6-methoxy-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(2-methoxy-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(2-methoxy-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(2,6-dimethyl-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(2,6-dimethyl-pyrimidin-4-yl)-but-3-yn-2-ol;

(S)-2-(2,6-Dimethoxy-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol;

(R)-2-(2,6-Dimethoxy-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(2-methoxy-6-methyl-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(2-methoxy-6-methyl-pyrimidin-4-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(6-methoxy-2-methyl-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(6-methoxy-2-methyl-pyrimidin-4-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(6-trifluoromethyl-pyrimidin-4-yl)-but-3-yn-2-ol;

2-(6-Difluoromethyl-pyrimidin-4-yl)-4-{5-[(R)-(1,3-dimethyl-azetidin-3-yl)-hydroxy-(4-isopropyl-phenyl)-methyl]-pyridin-3-yl}-but-3-yn-2-ol;

(R)-(1,3-Dimethyl-azetidin-3-yl)-(4-isopropyl-phenyl)-[5-(1-pyridin-2-yl-cyclopropylethynyl)-pyridin-3-yl]-methanol;

(R)-(1,3-Dimethyl-azetidin-3-yl)-(4-isopropyl-phenyl)-{5-[1-(6-methyl-pyrimidin-4-yl)-cyclopropylethynyl]-pyridin-3-yl}-methanol;

1-[4-(2-{5-[(R)-(1,3-Dimethyl-azetidin-3-yl)-hydroxy-(4-isopropyl-phenyl)-methyl]-pyridin-3-yl}-ethyl)-piperidin-1-yl]-ethanone;

4-{5-[(R)-(1,3-Dimethyl-azetidin-3-yl)-hydroxy-(4-isopropyl-phenyl)-methyl]-pyridin-3-yl}-1,1,1-trifluoro-2-methyl-butan-2-ol;

3-(3-{5-[(R)-(1,3-Dimethyl-azetidin-3-yl)-hydroxy-(4-isopropyl-phenyl)-methyl]-pyridin-3-yl}-1,1-dimethyl-propyl)-oxazolidin-2-one;

1-(3-{5-[(R)-(1,3-Dimethyl-azetidin-3-yl)-hydroxy-(4-isopropyl-phenyl)-methyl]-pyridin-3-yl}-1,1-dimethyl-propyl)-pyrrolidin-2-one;

1-(3-{5-[(R)-(1,3-Dimethyl-azetidin-3-yl)-hydroxy-(4-isopropyl-phenyl)-methyl]-pyridin-3-yl}-1,1-dimethyl-propyl)-3-methyl-imidazolidin-2-one;

1-(3-{5-[(R)-(1,3-Dimethyl-azetidin-3-yl)-hydroxy-(4-isopropyl-phenyl)-methyl]-pyridin-3-yl}-1,1-dimethyl-propyl)-imidazolidin-2-one;

1-[(S)-2-(2-{5-[(R)-(1,3-Dimethyl-azetidin-3-yl)-hydroxy-(4-isopropyl-phenyl)-methyl]-pyridin-3-yl}-ethyl)-2-methyl-pyrrolidin-1-yl]-ethanone;

4-{5-[(R)-(1,3-Dimethyl-azetidin-3-yl)-hydroxy-(4-isopropyl-phenyl)-methyl]-pyridin-3-yl}-2-(1H-indazol-3-yl)-butan-2-ol;

2-(1-Cyclopropyl-1H-pyrazol-3-yl)-4-{5-[(R)-(1,3-dimethyl-azetidin-3-yl)-hydroxy-(4-isopropyl-phenyl)-methyl]-pyridin-3-yl}-butan-2-ol;

4-{5-[(R)-(1,3-Dimethyl-azetidin-3-yl)-hydroxy-(4-isopropyl-phenyl)-methyl]-pyridin-3-yl}-2-(2-methyl-pyrimidin-4-yl)-butan-2-ol;

4-{5-[(R)-(1,3-Dimethyl-azetidin-3-yl)-hydroxy-(4-isopropyl-phenyl)-methyl]-pyridin-3-yl}-2-(5-methyl-pyrazin-2-yl)-butan-2-ol;

4-{5-[(R)-(1,3-Dimethyl-azetidin-3-yl)-hydroxy-(4-isopropyl-phenyl)-methyl]-pyridin-3-yl}-2-(2-methyl-thiazol-5-yl)-butan-2-ol;

4-{5-[(R)-(1,3-Dimethyl-azetidin-3-yl)-hydroxy-(4-isopropyl-phenyl)-methyl]-pyridin-3-yl}-2-(3-methyl-isoxazol-5-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(1-methyl-1H-imidazol-2-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(5-methyl-thiophen-2-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(1-methyl-1H-pyrrol-2-yl)-but-3-yn-2-ol;

(R)-4-{5-[(R)-(1,3-Dimethyl-azetidin-3-yl)-hydroxy-(4-isopropyl-phenyl)-methyl]-pyridin-3-yl}-2-(2-trifluoromethyl-pyrimidin-4-yl)-but-3-yn-2-ol;

(S)-4-{5-[(R)-(1,3-Dimethyl-azetidin-3-yl)-hydroxy-(4-isopropyl-phenyl)-methyl]-pyridin-3-yl}-2-(2-trifluoromethyl-pyrimidin-4-yl)-but-3-yn-2-ol;

4-(5-{(R)-(1,3-Dimethyl-azetidin-3-yl)-hydroxy-[4-(1-trifluoromethyl-cyclopropyl)-phenyl]-methyl}-pyridin-3-yl)-2-(6-methyl-pyridin-2-yl)-but-3-yn-2-ol;

4-(5-{(R)-(1,3-Dimethyl-azetidin-3-yl)-hydroxy-[4-(1-methyl-cyclopropyl)-phenyl]-methyl}-pyridin-3-yl)-2-(6-methyl-pyridin-2-yl)-but-3-yn-2-ol;

4-{5-[(R)-(1,3-Dimethyl-azetidin-3-yl)-hydroxy-(4-trifluoromethyl-phenyl)-methyl]-pyridin-3-yl}-2-(6-methyl-pyridin-2-yl)-but-3-yn-2-ol;

4-{5-[(R)-(1,3-Dimethyl-azetidin-3-yl)-(4-ethyl-phenyl)-hydroxy-methyl]-pyridin-3-yl}-2-(6-methyl-pyridin-2-yl)-but-3-yn-2-ol;

4-{5-[(R)-(4-tert-Butyl-phenyl)-(1,3-dimethyl-azetidin-3-yl)-hydroxy-methyl]-pyridin-3-yl}-2-(6-methyl-pyridin-2-yl)-but-3-yn-2-ol;

4-{5-[(R)-(3-Ethyl-1-methyl-azetidin-3-yl)-hydroxy-(4-trifluoromethoxy-phenyl)-methyl]-pyridin-3-yl}-2-(6-methyl-pyridin-2-yl)-but-3-yn-2-ol;

4-(5-{(R)-(1,3-Dimethyl-azetidin-3-yl)-hydroxy-[4-(2,2,2-trifluoro-ethyl)-phenyl]-methyl}-pyridin-3-yl)-2-(6-methyl-pyridin-2-yl)-but-3-yn-2-ol;

4-{5-[(S)-(3-Fluoro-1-methyl-azetidin-3-yl)-hydroxy-(4-isopropyl-phenyl)-methyl]-pyridin-3-yl}-2-(6-methyl-pyridin-2-yl)-but-3-yn-2-ol;

1-(4-{5-[(R)-(1,3-Dimethyl-azetidin-3-yl)-hydroxy-(4-isopropyl-phenyl)-methyl]-pyridazin-3-ylethynyl}-piperidin-1-yl)-ethanone;

N-(3-{5-[(R)-(1,3-Dimethyl-azetidin-3-yl)-hydroxy-(4-isopropyl-phenyl)-methyl]-pyridazin-3-yl}-1,1-dimethyl-prop-2-ynyl)-acetamide;

1-(3-{5-[(R)-(1,3-Dimethyl-azetidin-3-yl)-hydroxy-(4-isopropyl-phenyl)-methyl]-pyridazin-3-yl}-1,1-dimethyl-prop-2-ynyl)-pyrrolidin-2-one;

4-{5-[(R)-Hydroxy-(1-isopropyl-3-methyl-azetidin-3-yl)-(4-isopropyl-phenyl)-methyl]-pyridin-3-yl}-2-(6-methyl-pyridin-2-yl)-but-3-yn-2-ol;

4-{5-[(R)-(1,3-Dimethyl-azetidin-3-yl)-hydroxy-(4-isopropyl-phenyl)-methyl]-pyridin-3-yl}-2-(6-methyl-pyridin-2-yl)-but-3-yn-2-ol;

4-{5-[(R)-Hydroxy-[1-(2-hydroxy-ethyl)-3-methyl-azetidin-3-yl]-(4-isopropyl-phenyl)-methyl]-pyridin-3-yl}-2-(6-methyl-pyridin-2-yl)-but-3-yn-2-ol;

4-{5-[(R)-[1-(2,2-Difluoro-ethyl)-3-methyl-azetidin-3-yl]-hydroxy-(4-isopropyl-phenyl)-methyl]-pyridin-3-yl}-2-(6-methyl-pyridin-2-yl)-but-3-yn-2-ol;

1-(4-{5-[(R)-(1,3-Dimethyl-azetidin-3-yl)-hydroxy-(4-isopropyl-phenyl)-methyl]-pyridin-3-yloxymethyl}-piperidin-1-yl)-ethanone;

4-{5-[(R)-(1-Cyclopropyl-3-methyl-azetidin-3-yl)-hydroxy-(4-isopropyl-phenyl)-methyl]-pyridin-3-yl}-2-(6-methyl-pyridin-2-yl)-but-3-yn-2-ol;

1-{5-[(R)-(1,3-Dimethyl-azetidin-3-yl)-hydroxy-(4-isopropyl-phenyl)-methyl]-pyridin-3-yl}-4-(2-isopropyl-pyrimidin-4-yl)-pyrrolidin-2-one;

1-{5-[(R)-(1,3-Dimethyl-azetidin-3-yl)-hydroxy-(4-isopropyl-phenyl)-methyl]-pyridin-3-yl}-4-(2-methyl-thiazol-5-yl)-pyrrolidin-2-one;

1-{5-[(R)-(1,3-Dimethyl-azetidin-3-yl)-hydroxy-(4-isopropyl-phenyl)-methyl]-pyridin-3-yl}-4-(6-methyl-pyridin-3-yl)-pyrrolidin-2-one;

1-{5-[(R)-(1,3-Dimethyl-azetidin-3-yl)-hydroxy-(4-isopropyl-phenyl)-methyl]-pyridin-3-yl}-4-(6-isopropyl-pyridin-2-yl)-pyrrolidin-2-one;

1-{5-[(R)-(1,3-Dimethyl-azetidin-3-yl)-hydroxy-(4-isopropyl-phenyl)-methyl]-pyridin-3-yl}-4-(6-trifluoromethyl-pyridin-3-yl)-pyrrolidin-2-one;

1-{5-[(R)-(1,3-Dimethyl-azetidin-3-yl)-hydroxy-(4-isopropyl-phenyl)-methyl]-pyridin-3-yl}-4-(1-methyl-1H-pyrazol-4-yl)-pyrrolidin-2-one;

1-{5-[(R)-(1,3-Dimethyl-azetidin-3-yl)-hydroxy-(4-isopropyl-phenyl)-methyl]-pyridin-3-yl}-4-(1,3-dimethyl-1H-pyrazol-4-yl)-pyrrolidin-2-one;

4-(1-Difluoromethyl-1H-pyrazol-4-yl)-1-{5-[(R)-(1,3-dimethyl-azetidin-3-yl)-hydroxy-(4-isopropyl-phenyl)-methyl]-pyridin-3-yl}-pyrrolidin-2-one;

1-{5-[(R)-(1,3-Dimethyl-azetidin-3-yl)-hydroxy-(4-isopropyl-phenyl)-methyl]-pyridin-3-yl}-4-(2-methyl-2H-[1,2,3]triazol-4-yl)-pyrrolidin-2-one;

4-(1-Acetyl-piperidin-4-yl)-1-{5-[(R)-(1,3-dimethyl-azetidin-3-yl)-hydroxy-(4-isopropyl-phenyl)-methyl]-pyridazin-3-yl}-pyrrolidin-2-one;

5-{5-[(R)-(1,3-Dimethyl-azetidin-3-yl)-hydroxy-(4-isopropyl-phenyl)-methyl]-pyridazin-3-yl}-hexahydro-furo[2,3-c]pyrrol-4-one;

1-{5-[(R)-(1,3-Dimethyl-azetidin-3-yl)-hydroxy-(4-isopropyl-phenyl)-methyl]-pyridazin-3-yl}-4-(6-isopropyl-pyridin-2-yl)-pyrrolidin-2-one;

1-(2-{5-[(R)-(1,3-Dimethyl-azetidin-3-yl)-hydroxy-(4-isopropyl-phenyl)-methyl]-pyridin-3-yl}-7,8-dihydro-5H-pyrido[4,3-d]pyrimidin-6-yl)-ethanone;

1-(2-{5-[(R)-(1,3-Dimethyl-azetidin-3-yl)-hydroxy-(4-isopropyl-phenyl)-methyl]-pyridin-3-yl}-7,8-dihydro-5H-[1,6]naphthyridin-6-yl)-ethanone;

1-[4-(2-{5-[(R)-(1,3-Dimethyl-azetidin-3-yl)-hydroxy-(4-isopropyl-phenyl)-methyl]-pyridin-3-yl}-pyrimidin-5-yl)-piperidin-1-yl]-ethanone; or 1-[4-(2-{5-[(R)-(1,3-Dimethyl-azetidin-3-yl)-hydroxy-(4-isopropyl-phenyl)-methyl]-pyridin-3-yl}-pyrimidin-4-yl)-piperidin-1-yl]-ethanone;

or a pharmaceutically acceptable salt thereof.

11. A compound according to claim 1 which is:

2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-propan-2-ol;

1-[4-(3-{5-[(R)-(1,3-Dimethyl-azetidin-3-yl)-hydroxy-(4-isopropyl-phenyl)-methyl]-pyridin-3-yl}-[1,2,4] oxadiazol-5-yl)-piperidin-1-yl]-ethanone; or (S)-4-{5-[(R)-(1,3-Dimethyl-azetidin-3-yl)-hydroxy-(4-isopropyl-phenyl)-methyl]-pyridin-3-yl}-2-(6-methyl-pyrimidin-4-yl)-but-3-yn-2-ol;

or a pharmaceutically acceptable salt thereof.

12. A compound which is:

2-(3-{5-[(R)-(1,3-Dimethyl-azetidin-3-yl)-hydroxy-(4-isopropyl-phenyl)-methyl]-pyridin-3-yl}-[1,2,4]oxadiazol-5-yl)-propan-2-ol; or a pharmaceutically acceptable salt thereof.

13. A pharmaceutical composition comprising a compound according to claim 1, or a pharmaceutically acceptable salt thereof, and at least one pharmaceutically acceptable carrier.

14. A method for the prevention or treatment of an inflammatory/autoimmune disease/disorder, or cancer; said method comprising administering to a subject a pharmaceutically active amount of a compound according to claim 1, or a pharmaceutically acceptable salt thereof, either alone or in combination with another pharmacologically active compounds and/or therapy.

15. A pharmaceutical composition comprising a compound according to claim 10, or a pharmaceutically acceptable salt thereof, and at least one pharmaceutically acceptable carrier.

16. A method for the prevention or treatment of an inflammatory/autoimmune disease/disorder, or cancer; said method comprising administering to a subject a pharmaceutically active amount of a compound according to claim 10, or a pharmaceutically acceptable salt thereof, either alone or in combination with another pharmacologically active compound and/or therapy.

17. A pharmaceutical composition comprising a compound according to claim 11, or a pharmaceutically acceptable salt thereof, and at least one pharmaceutically acceptable carrier.

18. A method for the prevention or treatment of an inflammatory/autoimmune disease/disorder, or cancer; said method comprising administering to a subject a pharmaceutically active amount of a compound according to claim 11, or a pharmaceutically acceptable salt thereof, either alone or in combination with another pharmacologically active compound and/or therapy.

19. A pharmaceutical composition comprising the compound according to claim 12, or a pharmaceutically acceptable salt thereof, and at least one pharmaceutically acceptable carrier.

20. A method for the prevention or treatment of an inflammatory/autoimmune disease/disorder, or cancer; said method comprising administering to a subject a pharmaceutically active amount of the compound according to claim 12, or a pharmaceutically acceptable salt thereof, either alone or in combination with another pharmacologically active compound and/or therapy.

21. A compound according to claim 1, wherein A represents pyridin-3-yl, wherein said pyridin-3-yl is mono-substituted in meta-position with respect to the point of attachment of said pyridin-3-yl to the rest of the molecule, wherein the substituent is 5-(hydroxy-methyl)-1,2,4-oxadiazol-3-yl, 5-(1-hydroxy-1-methyl-ethyl)-1,2,4-oxadiazol-3-yl, 5-(2-hydroxy-2-methyl-propyl)-1,2,4-oxadiazol-3-yl, or 5-(2-hydroxy-1,1-dimethyl-ethyl)-1,2,4-oxadiazol-3-yl; B represents 4-propyl-phenyl, 4-isopropyl-phenyl, 4-isobutyl-phenyl, 4-tert-butyl-phenyl, 3-fluoro-4-isopropyl-phenyl, 3,5-difluoro-4-isopropyl-phenyl, 4-cyclopropyl-phenyl, 4-trifluoromethyl-phenyl, 4-trifluoromethoxy-phenyl, 4-(2,2,2-trifluoro-ethyl)-phenyl, 4-cyclobutyl-phenyl, or 4-(1-trifluoromethyl-cyclopropyl)-phenyl; $R^1$ represents methyl; and $R^2$ represents methyl;

or a pharmaceutically acceptable salt thereof.

22. The compound according to claim 12, wherein said compound is in free form.

23. A compound which is 2-(3-{5- [(R)-(1,3-Dimethyl-azetidin-3-yl)-hydroxy-(4-isopropyl-phenyl)-methyl]-pyridin-3-yl}-[1,2,4] oxadiazol-5-yl)-propan-2-ol in pharmaceutically acceptable salt form.

24. The method according to claim 20, for the treatment of an inflammatory/autoimmune disease/disorder, said method comprising administering to a subject a pharmaceutically active amount of the compound according to claim 12, or a pharmaceutically acceptable salt thereof.

25. The method according to claim 24, wherein the inflammatory/autoimmune disease/disorder is selected from rheumatoid arthritis; ankylosing spondylitis; spondyloarthritis; psoriasis; psoriatic arthritis; inflammatory skin disorders; irritable bowel disease; inflammatory bowel disease; dry eye disease; multiple sclerosis; systemic lupus erythematosus; Sjögren's disease; autoimmune hepatitis; Primary Sclerosing Cholangitis; autoimmune keratitis; filamentary keratitis; autoimmune uveitis; allergic conjunctivitis; asthma; allergic disease of the gastrointestinal tract; type 1 diabetes (T1D); endometriosis; meibomian gland dysfunction; and graft-versus host disease.

26. The method according to claim 24, wherein the inflammatory/autoimmune disease/disorder is selected from psoriasis; psoriatic arthritis; rheumatoid arthritis; ankylosing spondylitis; spondyloarthritis;

inflammatory skin disorders; Crohn's disease; ulcerative colitis; irritable bowel disease; dry eye disease;

multiple sclerosis; systemic lupus erythematosus; Sjögren's disease; autoimmune hepatitis; and Primary Sclerosing Cholangitis.

27. The method according to claim 24, wherein the inflammatory/autoimmune disease/disorder is selected from psoriasis; psoriatic arthritis; rheumatoid arthritis; ankylosing spondylitis; spondyloarthritis; Crohn's disease; ulcerative colitis; and Primary Sclerosing Cholangitis.

28. The method according to claim 20, for the treatment of cancer; said method comprising administering to a subject a pharmaceutically active amount of the compound according to claim 27, or a pharmaceutically acceptable salt thereof, either alone or in combination with another pharmacologically active compound and/or therapy.

29. The method according to claim 28, for the treatment of cancer; said method comprising administering to a subject a pharmaceutically active amount of the compound according to claim 27, or a pharmaceutically acceptable salt thereof, either alone or in combination with another pharmacologically active compound and/or therapy, wherein the cancer is selected from lymphoma; brain cancer; breast cancer; colorectal cancer; hepatocarcinoma; renal cell carcinoma; lung cancer; gastric cancer; melanoma; bladder cancer; head and neck cancer; Hodgkin's lymphoma; cervical cancer; endometrial cancer; colon cancer; gastrointestinal stromal tumors; pancreatic cancer; prostatic cancer; leukemia; ovarian cancer; oesophageal carcinomas; mesothelioma; neuroblastoma; sarcoma; astrocytoma; myeloma; urothelial cancer; MSI-H or dMMR cancer; rectal cancer; laryngeal cancer; salivary adenocarcinoma; multiple myeloma; cholangiocarcinoma; oral squamous cell carcinoma; thyroid cancer; and esophagogastric junction cancer.

30. The method according to claim 28, for the treatment of cancer; said method comprising administering to a subject a pharmaceutically active amount of the compound according to claim 27, or a pharmaceutically acceptable salt thereof, either alone or in combination with another pharmacologically active compound and/or therapy, wherein the cancer is selected from lymphoma; brain cancer; breast cancer; colorectal cancer; hepatocarcinoma; renal cell carcinoma; lung cancer; and gastric cancer.

* * * * *